US012416034B2

(12) United States Patent
Houghton-Larsen et al.

(10) Patent No.: US 12,416,034 B2
(45) **Date of Patent: *Sep. 16, 2025**

(54) RECOMBINANT PRODUCTION OF STEVIOL GLYCOSIDES

(71) Applicant: EVOLVA SA, Reinach (CH)

(72) Inventors: Jens Houghton-Larsen, Birkerod (DK); Paula Hicks, Bend, OR (US); Michael Naesby, Huninque (FR); Thomas Tange Ostergaard, Reihen (CH); Jorgen Hansen, Frederiksberg (DK); Michael Mikkelsen Dalgaard, Vaerlose (DK); Esben Hansen-Halkjaer, Frederiksberg (DK); Ernesto Simon, Glostrup (DK); Sabina Tavares, Basel (CH)

(73) Assignee: Danstar Ferment AG, Schweiz (CH)

( * ) Notice: Subject to any disclaimer, the term of this patent is extended or adjusted under 35 U.S.C. 154(b) by 51 days.

This patent is subject to a terminal disclaimer.

(21) Appl. No.: 18/132,027

(22) Filed: Apr. 7, 2023

(65) Prior Publication Data

US 2023/0407360 A1 Dec. 21, 2023

Related U.S. Application Data

(60) Continuation of application No. 17/471,615, filed on Sep. 10, 2021, now abandoned, which is a continuation of application No. 16/535,373, filed on Aug. 8, 2019, now abandoned, which is a continuation of application No. 15/439,660, filed on Feb. 22, 2017, now Pat. No. 10,435,730, which is a division of application No. 14/237,540, filed as application No. PCT/US2012/050021 on Aug. 8, 2012, now Pat. No. 9,631,215.

(60) Provisional application No. 61/521,084, filed on Aug. 8, 2011, provisional application No. 61/521,203, filed on Aug. 8, 2011, provisional application No. 61/521,051, filed on Aug. 8, 2011, provisional application No. 61/523,487, filed on Aug. 15, 2011, provisional application No. 61/567,929, filed on Dec. 7, 2011, provisional application No. 61/603,639, filed on Feb. 27, 2012.

(51) Int. Cl.

| | |
|---|---|
| ***C12P 19/56*** | (2006.01) |
| ***C12N 1/21*** | (2006.01) |
| ***C12N 9/02*** | (2006.01) |
| ***C12N 9/06*** | (2006.01) |
| ***C12N 9/10*** | (2006.01) |
| ***C12N 9/88*** | (2006.01) |
| ***C12N 9/90*** | (2006.01) |
| ***C12N 15/63*** | (2006.01) |
| ***C12N 15/81*** | (2006.01) |
| ***C12N 15/82*** | (2006.01) |
| ***C12P 19/44*** | (2006.01) |

(52) U.S. Cl.

CPC ............ *C12P 19/56* (2013.01); *C12N 9/0032* (2013.01); *C12N 9/0071* (2013.01); *C12N 9/0073* (2013.01); *C12N 9/1051* (2013.01); *C12N 9/1085* (2013.01); *C12N 9/88* (2013.01); *C12N 9/90* (2013.01); *C12N 15/63* (2013.01); *C12N 15/81* (2013.01); *C12N 15/8243* (2013.01); *C12P 19/44* (2013.01); *Y02P 20/52* (2015.11)

(58) Field of Classification Search

None

See application file for complete search history.

(56) References Cited

U.S. PATENT DOCUMENTS

| | | | |
|---|---|---|---|
| 4,590,160 | A | 5/1986 | Nishihashi et al. |
| 5,198,360 | A | 3/1993 | Ballou |
| 5,204,253 | A | 4/1993 | Sanford et al. |
| 5,306,862 | A | 4/1994 | Chappell et al. |
| 5,460,949 | A | 10/1995 | Saunders et al. |
| 5,538,880 | A | 7/1996 | Lundquist et al. |
| 6,013,863 | A | 1/2000 | Lundquist et al. |
| 6,215,051 | B1 | 4/2001 | Yu et al. |
| 6,255,557 | B1 | 7/2001 | Brandle |
| 6,284,493 | B1 | 9/2001 | Roth |
| 6,284,506 | B1 | 9/2001 | Hoshino et al. |
| 6,329,571 | B1 | 12/2001 | Hiei |
| 6,586,202 | B2 | 7/2003 | Hoshino et al. |
| 6,660,507 | B2 | 12/2003 | Cheng et al. |
| 6,806,076 | B1 | 10/2004 | Miyake et al. |
| 6,969,595 | B2 | 11/2005 | Brzostowicz et al. |

(Continued)

FOREIGN PATENT DOCUMENTS

| | | |
|---|---|---|
| CN | 101720910 | 6/2010 |
| CN | 102216313 | 10/2011 |

(Continued)

OTHER PUBLICATIONS

Pace et al. (Contribution of Hydrophobic Interactions to Protein Stability, J. Mol. Biol. 408 (2011): 514-28. (Year: 2011).*

(Continued)

*Primary Examiner* — Todd M Epstein

(74) *Attorney, Agent, or Firm* — McDonnell Boehnen Hulbert & Berghoff LLP

(57) ABSTRACT

Recombinant microorganisms, plants, and plant cells are disclosed that have been engineered to express recombinant genes encoding UDP-glycosyltransferases (UGTs). Such microorganisms, plants, or plant cells can produce steviol glycosides, e.g., Rebaudioside A and/or Rebaudioside D, which can be used as natural sweeteners in food products and dietary supplements.

30 Claims, 44 Drawing Sheets

Specification includes a Sequence Listing.

(56) References Cited

U.S. PATENT DOCUMENTS

| | | | |
|---|---|---|---|
| 7,034,140 | B2 | 4/2006 | Bramucci et al. |
| 7,056,717 | B2 | 6/2006 | Cheng et al. |
| 7,098,000 | B2 | 8/2006 | Cheng et al. |
| 7,129,392 | B2 | 10/2006 | Hahn et al. |
| 7,132,268 | B2 | 11/2006 | Miyake et al. |
| 7,172,886 | B2 | 2/2007 | Keasling et al. |
| 7,183,089 | B2 | 2/2007 | Keasling et al. |
| 7,186,891 | B1 | 3/2007 | Chappell et al. |
| 7,208,298 | B2 | 4/2007 | Miyake et al. |
| 7,335,815 | B2 | 2/2008 | Boronat et al. |
| 7,364,885 | B2 | 4/2008 | Miyake et al. |
| 7,422,884 | B2 | 9/2008 | Bai et al. |
| 7,514,597 | B2 | 4/2009 | Nakamura et al. |
| 7,569,389 | B2 | 8/2009 | Feldmann et al. |
| 7,692,065 | B2 | 4/2010 | Harper et al. |
| 7,838,287 | B2 | 11/2010 | Goldsmith et al. |
| 7,923,541 | B2 | 4/2011 | Yang et al. |
| 7,927,851 | B2 | 4/2011 | Brandle et al. |
| 7,981,647 | B2 | 7/2011 | Berry et al. |
| 9,562,251 | B2 | 2/2017 | Kishore et al. |
| 10,435,730 | B2 * | 10/2019 | Houghton-Larsen ........................ C12N 15/63 |
| 10,815,514 | B2 | 10/2020 | Olsson et al. |
| 10,947,515 | B2 | 3/2021 | Boer et al. |
| 2002/0142408 | A1 | 10/2002 | DiCosimo et al. |
| 2003/0033626 | A1 | 2/2003 | Hahn et al. |
| 2003/0148416 | A1 | 8/2003 | Berry et al. |
| 2003/0148479 | A1 | 8/2003 | Keasling et al. |
| 2003/0190734 | A1 | 10/2003 | Hoshino et al. |
| 2003/0219798 | A1 | 11/2003 | Gokarn et al. |
| 2004/0010815 | A1 | 1/2004 | Lange et al. |
| 2004/0072311 | A1 | 4/2004 | DiCosimo et al. |
| 2004/0078846 | A1 | 4/2004 | Desouza et al. |
| 2004/0176570 | A1 | 9/2004 | Bacher et al. |
| 2004/0194162 | A1 | 9/2004 | Hahn et al. |
| 2005/0003474 | A1 | 1/2005 | Desouza et al. |
| 2005/0032169 | A1 | 2/2005 | Miyake et al. |
| 2006/0014264 | A1 | 1/2006 | Sauer et al. |
| 2006/0079476 | A1 | 4/2006 | Keasling et al. |
| 2006/0083838 | A1 | 4/2006 | Jackson et al. |
| 2007/0004000 | A1 | 1/2007 | Miyake et al. |
| 2007/0077616 | A1 | 4/2007 | Keasling et al. |
| 2007/0099261 | A1 | 5/2007 | Keasling et al. |
| 2007/0128311 | A1 | 6/2007 | Prakash et al. |
| 2007/0166782 | A1 | 7/2007 | Keasling et al. |
| 2007/0202579 | A1 | 8/2007 | Berry et al. |
| 2007/0238157 | A1 | 10/2007 | Millis et al. |
| 2007/0238159 | A1 | 10/2007 | Millis et al. |
| 2007/0238160 | A1 | 10/2007 | Millis et al. |
| 2007/0254354 | A1 | 11/2007 | Millis et al. |
| 2007/0269857 | A1 | 11/2007 | Miyake et al. |
| 2007/0286850 | A1 | 12/2007 | Bai et al. |
| 2008/0064063 | A1 | 3/2008 | Brandle et al. |
| 2008/0081358 | A1 | 4/2008 | Vittanen et al. |
| 2008/0131926 | A1 | 6/2008 | Miyake et al. |
| 2008/0216397 | A1 | 9/2008 | Busby et al. |
| 2008/0261280 | A1 | 10/2008 | Hahn et al. |
| 2008/0271205 | A1 * | 10/2008 | Yamaguchi ........ C12N 15/8245 800/278 |
| 2008/0286870 | A1 | 11/2008 | Vittanen et al. |
| 2008/0292775 | A1 | 11/2008 | Prakash et al. |
| 2008/0318227 | A1 | 12/2008 | Bacher et al. |
| 2009/0004724 | A1 | 1/2009 | Keasling et al. |
| 2009/0047718 | A1 | 2/2009 | Blaschek et al. |
| 2009/0055974 | A1 | 2/2009 | Tanksley et al. |
| 2009/0074935 | A1 | 3/2009 | Lee |
| 2009/0143308 | A1 | 6/2009 | Monk et al. |
| 2009/0286262 | A1 | 11/2009 | Slack |
| 2009/0298706 | A1 | 12/2009 | Lee et al. |
| 2010/0112156 | A1 | 5/2010 | Abelyan et al. |
| 2010/0120096 | A1 | 5/2010 | Kitaoka et al. |
| 2010/0221801 | A1 | 9/2010 | Van Dyk |
| 2010/0297722 | A1 | 11/2010 | Anterola et al. |
| 2010/0316782 | A1 | 12/2010 | Shi et al. |
| 2011/0087011 | A1 | 4/2011 | Chiang et al. |
| 2011/0092684 | A1 | 4/2011 | Abelyan et al. |
| 2011/0126318 | A1 | 5/2011 | Allen et al. |
| 2011/0160311 | A1 | 6/2011 | Prakash et al. |
| 2012/0021111 | A1 | 1/2012 | Pfister et al. |
| 2012/0083593 | A1 | 4/2012 | Liu et al. |
| 2012/0164678 | A1 | 6/2012 | Stephanopoulos et al. |
| 2012/0178169 | A1 | 7/2012 | Voytas et al. |
| 2013/0137138 | A1 | 5/2013 | Hansen |
| 2013/0171328 | A1 | 7/2013 | Kishore et al. |
| 2014/0329281 | A1 | 11/2014 | Houghton-Larsen et al. |
| 2015/0159188 | A1 | 6/2015 | Ono et al. |
| 2015/0342234 | A1 | 12/2015 | Hicks et al. |
| 2021/0147815 | A1 | 5/2021 | Boer et al. |

FOREIGN PATENT DOCUMENTS

| | | |
|---|---|---|
| CN | 103397064 | 11/2013 |
| EP | 0955363 | 11/1999 |
| EP | 1072683 | 1/2001 |
| EP | 1171610 | 4/2007 |
| EP | 1198575 | 9/2007 |
| EP | 1383864 | 1/2008 |
| EP | 1897951 | 3/2008 |
| EP | 1947189 | 7/2008 |
| EP | 1392824 | 8/2008 |
| EP | 2575432 | 4/2013 |
| EP | 2902410 | 8/2015 |
| JP | 59101408 | 6/1984 |
| JP | 3-277275 | 12/1991 |
| JP | 05-115298 | 5/1993 |
| JP | 2009034080 | 2/2009 |
| KR | 1020120088035 | 8/2012 |
| KR | 2015 0000258 | 1/2015 |
| WO | WO 1999/018224 | 4/1999 |
| WO | WO 2000/036081 | 6/2000 |
| WO | WO 2000/037663 | 6/2000 |
| WO | WO 2000/063400 | 10/2000 |
| WO | WO 2001/012828 | 2/2001 |
| WO | WO 2001/083769 | 11/2001 |
| WO | WO 2001/094561 | 12/2001 |
| WO | 2002/024865 | 3/2002 |
| WO | WO 2002/020728 | 3/2002 |
| WO | WO 2002/020815 | 3/2002 |
| WO | WO 2002/055709 | 7/2002 |
| WO | WO 2003/008540 | 1/2003 |
| WO | WO 2004/029255 | 4/2004 |
| WO | WO 2005/079183 | 9/2005 |
| WO | WO 2006/016395 | 2/2006 |
| WO | WO 2006069610 | 7/2006 |
| WO | WO 2006/093289 | 9/2006 |
| WO | WO 2006/096392 | 9/2006 |
| WO | WO 2007/136847 | 11/2007 |
| WO | WO 2008/008256 | 1/2008 |
| WO | WO 2008/034648 | 3/2008 |
| WO | WO 2008/039499 | 4/2008 |
| WO | WO 2008/051349 | 5/2008 |
| WO | WO 2008/091547 | 7/2008 |
| WO | WO 2009/005704 | 1/2009 |
| WO | WO 2009/037329 | 3/2009 |
| WO | WO 2009/071277 | 6/2009 |
| WO | WO 2009/086049 | 7/2009 |
| WO | WO 2009/105612 | 8/2009 |
| WO | WO 2009/108680 | 9/2009 |
| WO | WO 2009/111513 | 9/2009 |
| WO | 2009/140394 | 11/2009 |
| WO | WO 2010/021001 | 2/2010 |
| WO | WO 2010/038911 | 4/2010 |
| WO | WO 2010/044960 | 4/2010 |
| WO | 2010/142305 | 12/2010 |
| WO | WO 2010/146463 | 12/2010 |
| WO | WO 2011/028671 | 3/2011 |
| WO | WO 2011/037959 | 3/2011 |
| WO | WO 2011/046423 | 4/2011 |
| WO | WO 2011/056834 | 5/2011 |
| WO | 2011/140329 | 11/2011 |
| WO | 2011/151326 | 12/2011 |
| WO | 2011/153378 | 12/2011 |
| WO | WO 2011/153144 | 12/2011 |
| WO | WO 2012/075030 | 6/2012 |

(56) References Cited

FOREIGN PATENT DOCUMENTS

| | | |
|---|---|---|
| WO | WO 2013/019050 | 2/2013 |
| WO | WO 2013/022989 | 2/2013 |
| WO | WO 2013/076577 | 5/2013 |
| WO | WO 2013/096420 | 6/2013 |
| WO | WO 2013/102793 | 7/2013 |
| WO | WO 2013/110673 | 8/2013 |
| WO | WO 2013/176738 | 11/2013 |
| WO | WO 2014/086890 | 6/2014 |
| WO | WO 2014/122227 | 8/2014 |
| WO | WO 2014/122328 | 8/2014 |
| WO | 2014/191580 | 12/2014 |
| WO | 2015/011209 | 1/2015 |
| WO | 2015/014959 | 2/2015 |
| WO | 2015/016393 | 2/2015 |
| WO | WO 2015/014969 | 2/2015 |
| WO | WO 2015/028324 | 3/2015 |
| WO | WO 2015/132411 | 9/2015 |
| WO | 2016/023844 | 2/2016 |
| WO | WO 2016/038095 | 3/2016 |
| WO | WO 2016/120486 | 8/2016 |
| WO | WO 2017/025362 | 2/2017 |
| WO | WO 2018/083338 | 5/2018 |

OTHER PUBLICATIONS

Kovylyaeva et al., Glycosides from Stevia rebaudiana, Chem. Nat. Compounds 43, 2007, 81-85. (Year: 2007).*

Rellick et al., Comparison of van der Waals and semiempirical calculations of the molecular volumes of small molecules and proteins, Biopolymers: Original Research on Biomolecules 42.2, 1997, 191-202. (Year: 1997).*

Liu et al., "Functional and Biochemical Characterization of *Escherichia coli* Sugar Efflux Transporters," JBC, 274(33):22977-22984 (Aug. 1999).

Sun et al., "Regulation and Function of *Escherichia coli* Sugar Efflux Transporter A (Set A) during Glucose-Phosphate Stress," J of Bacteriology, 193(1):143-153 (Jan. 2011).

Bateman et al., "Pfam 3.1: 1313 multiple alignments and profile HMMs match the majority of proteins," Nucleic Acids Res. 27(1):260-2 (Jan. 1999).

Bay & Turner, "Diversity and evolution of the small multidrug resistance protein family," BMC Evol. Biol. 9:140 (Jun. 2009).

Brachmann et al., "Designer deletion strains derived from *Saccharomyces cerevisiae* S288C: a useful set of strains and plasmids for PCR-mediated gene disruption and other applications," Yeast 14:115-32 (1998).

Chen et al., "Transferring a biosynthetic cycle into a productive *Escherichia coli* strain: large-scale synthesis of galactosides," J. Am. Chem. Soc. 123(36):8866-7 (Sep. 2001).

Chenna et al., "Multiple sequence alignment with the Clustal series of programs," Nucleic Acids Res. 31(13):3497-500 (Jul. 2003).

Del Sorbo et al., "Fungal transporters involved in efflux of natural toxic compounds and fungicides," Fungal. Genet. Biol. 30(1):1-15 (Jun. 2000).

Diener et al., "*Arabidopsis* ALF5, a multidrug efflux transporter gene family member, confers resistance to toxins," Plant Cell 13(7):1625-38 (Jul. 2001).

GenBank Accession No. AAB62280, dated Jul. 2, 1997 (2 pages).

GenBank Accession No. AAB87091, dated Mar. 22, 2000 (2 pages).

GenBank Accession No. AAC28895.1, dated Aug. 6, 1998 (2 pages).

GenBank Accession No. AAC39505, dated Jul. 26, 1998 (1 page).

GenBank Accession No. AAD34294, dated Mar. 22, 2000 (2 pages).

GenBank Accession No. AAD34295, dated Mar. 22, 2000 (2 pages).

GenBank Accession No. AAD47596, dated Aug. 9, 1999 (2 pages).

GenBank Accession No. AAH69913, dated Jul. 15, 2006 (2 pages).

GenBank Accession No. AEE36246, dated Oct. 6, 2014 (3 pages).

GenBank Accession No. AAR06912, dated Dec. 28, 2004 (2 pages).

GenBank Accession No. AAR06916.1, dated Dec. 28, 2004 (2 pages).

GenBank Accession No. AAR06920.1, dated Dec. 28, 2004 (2 pages).

GenBank Accession No. ABA42921, dated Jun. 21, 2006 (1 page).

GenBank Accession No. ABB88839, dated May 28, 2008 (2 pages).

GenBank Accession No. ABC59076, dated Jun. 6, 2007 (1 page).

GenBank Accession No. ABC98596, dated Jan. 31, 2014 (2 pages).

GenBank Accession No. ABD60225, dated May 28, 2008 (2 pages).

GenBank Accession No. ABD92926, dated Oct. 10, 2007 (2 pages).

GenBank Accession No. AC133334, dated Jan. 31, 2004 (44 pages).

GenBank Accession No. ACD93722, dated Jun. 10, 2008 (1 page).

GenBank Accession No. AF034774, dated Apr. 17, 1998 (2 pages).

GenBank Accession No. AY562490, dated May 23, 2006 (3 pages).

GenBank Accession No. BAA43200, dated Mar. 13, 1999 (2 pages).

GenBank Accession No. BAB59027, dated Jan. 30, 2002 (1 page).

GenBank Accession No. BAF61135, dated May 9, 2007 (2 pages).

GenBank Accession No. BAG30962, dated Nov. 12, 2012 (2 pages).

GenBank Accession No. BC153262, dated Oct. 4, 2007 (3 pages).

GenBank Accession No. CAA75568, dated Nov. 14, 2006 (2 pages).

GenBank Accession No. CAA76703, dated Nov. 14, 2006 (1 page).

GenBank Accession No. CAE09055, dated Nov. 14, 2006 (2 pages).

GenBank Accession No. CAG41604, dated Feb. 6, 2015 (2 pages).

GenBank Accession No. DQ398871.3, dated May 28, 2008 (2 pages).

GenBank Accession No. EDY51667, dated Sep. 2, 2008 (2 pages).

GenBank Accession No. EU263989, dated Jun. 11, 2008 (2 pages).

GenBank Accession No. NM_116512, dated Jan. 22, 2014 (3 pages).

GenBank Accession No. NP_001105097, dated Aug. 4, 2015 (2 pages).

GenBank Accession No. NP_013636.1 (YML075C), dated Jul. 16, 2015 (3 pages).

GenBank Accession No. NP_194183, dated Jan. 22, 2014 (4 pages).

GenBank Accession No. NP_195399, dated Jan. 22, 2014 (3 pages).

GenBank Accession No. NP_197872.1, dated Jan. 22, 2014 (2 pages).

GenBank Accession No. Q9UVY5.1, dated Apr. 1, 2015 (3 pages).

Garber et al., "Computational methods for transcriptome annotation and quantification using RNA-seq," Nat Methods 8(6):469-77 (2011).

Kawai et al., "Transformation of *Saccharomyces cerevisiae* and other fungi: methods and possible underlying mechanism," Bioeng Bugs. 1(6):395-403 (2010).

Lin et al., "Arrestin-related ubiquitin-ligase adaptors regulate endocytosis and protein turnover at the cell surface," Cell 135(4):714-25 (2008).

Nagalakshmi et al., "The transcriptional landscape of the yeast genome defined by RNA sequencing," Science 320(5881 ): 1344-9 (2008).

Nikko & Pelham, "Arrestin-mediated endocytosis of yeast plasma membrane transporters," Traffic 10(12):1856-67 (2009).

Nikko et al. "Arrestin-like proteins mediate ubiquitination and endocytosis of the yeast metal transporter Smf1," EMBO Rep. 9(12):1216-21 (2008).

Olsson et al., "Microbial production of next-generation stevia sweeteners," Microbial Cell Factories, 15:11-14 (2016).

Partow et al., "Characterization of different promoters for designing a new expression vector in *Saccharomyces cerevisiae*," Yeast 27:955-64 (2010).

Robinson & Oshlack et al., "A scaling normalization method for differential expression analysis of RNA-seq data," Genome Bioi. 11(3):R25 (2010).

Saier Jr. et al., "The transporter classification database," Nucl. Acids Res., 42(1):D251-258 (2014).

Wang et al., "RNA-Seq: a revolutionary tool for transcriptomics," Nat Rev Genet. 10(1):57-63 (2009).

Wilhelm et al., "Defining transcribed regions using RNA-seq," Nature Protocols 5:255-66 (2010).

Yang Quanhua et.al., "Analysis of the Chemical constituents of Stevia rebaudiana and its sweetness," Journal of Beijing University of Chemical Technology, vol. 39, No. 2., p. 28-32 (2012) (English Abstract).

Ceunen & Geuns, "Steviol glycosides: chemical diversity, metabolism, and function," J. Nat. Prod. 76(6):1201-28 (Jun. 2013).

(56) References Cited

OTHER PUBLICATIONS

Olsson et al., "Microbial production of next-generation stevia sweeteners," Microbial Cell Factories, 15:1-14 (2016).
Song et al., "The Aspergillus fumigatus 1-29 damage resistance protein family coordinately regulates ergosterol biosynthesis and azole susceptibility," MBIO, 7:1-13 (2016).
Non-Final Office Action for U.S. Appl. No. 14/648,747, mailed Mar. 23, 2017, pp. 1-20.
Third Party Observation in EP Application No. 13801569.8; mailed Apr. 26, 2017, pp. 1-5.
Final Office Action for U.S. Appl. No. 14/648,747, mailed Sep. 6, 2017 (pp. 1-19).
Third Party Observation in EP Application No. 13801569.8; mailed Oct. 23, 2017, pp. 1-6.
International Preliminary Report on Patentability from the International Bureau for International Application PCT/EP2015/070620; mailed Mar. 14, 2017 (pp. 1-25).
Third Party Submission in U.S. Appl. No. 15/506,196; dated Mar. 9, 2018 pp. 1-68.
International Preliminary Report on Patentability from the International Bureau for International Application PCTEP2015/068314; mailed Feb. 14, 2017 (pp. 1-10).
International Search Report and Written Opinion of the International Searching Authority for International Application No. PCT/EP2015/052007; mailed Jul. 4, 2016, pp. 1-24.
International Preliminary Report on Patentability from the International Bureau for International Application PCT/EP2015/052007; mailed Aug. 1, 2017 (pp. 1-16).
International Search Report and Written Opinion of the International Searching Authority for International Application No. PCT/EP2016/068259; mailed Jan. 24, 2017, pp. 1-18.
International Preliminary Report on Patentability from the International Bureau for International Application PCT/EP2016/068259; mailed Feb. 13, 2018 (pp. 1-11).
International Search Report and Written Opinion of International Search Authority for International Application No. PCTEP2016/080516; mailed Mar. 15, 2017, pp. 1-22.
International Search Report and Written Opinion of the International Searching Authority for International Application No. PCT/EP2017/061775; mailed Sep. 6, 2017, pp. 1-17.
International Search Report and Written Opinion of International Search Authority for International Application No. PCTEP2017/059028; mailed Jun. 27, 2017, pp. 1-15.
International Search Report and Written Opinion of International Search Authority for International Application No. PCT/EP2017/055589; mailed May 12, 2017, pp. 1-18.
International Search Report and Written Opinion of the International Searching Authority for International Application No. PCT/EP2017/078473; mailed Jan. 25, 2018, pp. 1-16.
Mahe et al., "The ATP Binding Cassette Transporters Pdr5 and Snq2 of *Saccharomyces cerevisiae* Can Mediate Transport of Steriods via in Vivo", JBC, 271(41):25167-25172. (Oct. 1996).
Starratt et al., "Rebaudioside F, a diterpene glycoside from Stevia redaudiana", Phytochemistry, 59(4):367-370. (Feb. 2002). Abstract.
Uniprot Accession No. Q75183, dated Jul. 5, 2004 (pp. 1-2).
Uniprot Accession No. Q75183, dated Jul. 22, 2008 (pp. 1-4).
Ohta et al., MassBank Accession No. FU000299 (May 2016).
Ohta et al., MassBank Accession No. FU000332 (May 2016).
Communication pursuant to Rules 161(1) and 162 EPC for European Application No. 14702889.8, dated Oct. 14, 2015 (2 pages).
Communication pursuant to Article 94(3) EPC in European Application No. 14 702 889.8; dated Jul. 27, 2016, pp. 1-5.
Third Party Submission in U.S. Appl. No. 14/648,747; dated Mar. 28, 2016, pp. 1-231.
International Search Report of the International Searching Authority for International Application No. PCT/EP2017/061774; mailed Aug. 30, 2017, pp. 1-20.
Written Opinion of the International Searching Authority for International Application No. PCT/EP2017/061774; mailed Aug. 30, 2017, pp. 1-13.
Shao et al., "Crystal structures of a multifunctional triterpene/flavonoid glycosyltransferase from Medicago truncatula," Plant Cell 17(11):3141-54 (2005).
Shibata et al., "Glucosylation of Steviol and Steviol-Glucosides in Extracts from Stevia rebaudiana Bertoni" Plant Physiol. 95(1):152-56 (1991).
Singh et al., "Compendium of Transgenic Crop Plants: Transgenic Sugar, Tuber and Fiber," Ed. Kole & Hall, Blackwell Publishing Ltd. pp. 97-115 (2008).
U.S. Food and Drug Administration GRAS Notice 323, "GRAS Assessment of High Purity Steviol Glycosides; Food Usage Conditions for General Recognition of Safety for PureCircle USA, Inc.," pp. 1-262 (Feb. 2010).
U.S Food and Drug Administration GRAS Notice Notice 329, "Notice to the U.S. Food and Drug Administration that the use of RebpureTM (Rebaudioside A) derived from Stevia rebaudiana, as a Food Ingredient is Generally Recognized as Safe (GRAS)," pp. 1-275 (Mar. 2010).
Van Ooyen et al., "Heterologous protein production in the yeast *Kluyveromyces lactis*," FEMS Yeast Res. 6(3):381-92 (May 2006).
Vazquez De Aldana et al., "Nucleotide sequence of the exo-1,3-beta-glucanase-encoding gene, EXG1, of the yeast *Saccharomyces cerevisiae*," Gene 97(2):173-82 (1991).
Verwaal et al., "High-Level Production of Beta-Carotene in *Saccharomyces cerevisiae* by Successive Transformation with Carotenogenic Genes from Xanthophyllomyces dendrorhous," Appl Environ Microbiol. 73(13):4342-50 (2007).
Wallin, "Steviol Glycosides," Chem. Tech Assessment—63rd JECFA, pp. 1-5 (2004).
Wallin, "Steviol Glycosides," Chem. Tech Assessment—69th JECFA, pp. 1-7 (2007).
Wallner & Elofsson, "Can correct protein models be identified?," Protein Sci. 12(5):1073-86 (May 2003).
Wang, "Structure, mechanism and engineering of plant natural product glycosyltransferases," FEBS Letters 583(20):3303-9 (2009).
Xu et al., "Generation of hepatitis B virus PreS2-S antigen in Hansenula polymorpha," Virol Sin. 29(6):403-9 (Dec. 2014).
Yadav et al., "A review on the improvement of stevia [Stevia rebaudiana (Bertoni)]," Can J Plant Sci. 91:1-27 (2011).
Yao et al., "A genetic linkage map for Stevia rebaudiana," Genome 42:657-61 (1999).
Yazaki, "Abc transporters involved in the transport of plant secondary metabolites," FEBS Lett. 580(4):1183-91 (Feb. 2006).
Yu et al., "Bioconversion of ethyl 4-chloro-3-oxobutanoate by permeabilized fresh brewer's yeast cells in the presence of allyl bromide," J Ind Microbiol Biotechnol. 34(2)151-6 (2007).
Yuan et al., "Kinetics and activation parameters for oxidations of styrene by Compounds I from the cytochrome P450 (BM-3) (CYP102A1) heme domain and from CYP119," Biochemistry 48(38):9140-6 (Sep. 2009).
Zheng et al. "An efficient one-step site-directed and site-saturation mutagenesis protocol," Nucleic Acids Res. 32(14):e115 (Aug. 2004).
Zhu et al., "A multi-omic map of the lipid-producing yeast *Rhodosporidium toruloides*," Nature Commun. 3:1112 (Oct. 2012).
GenBank Accession No. AAF61439.1, dated Sep. 25, 2000 (2 pages).
GenBank Accession No. AAM53963.1, dated Jun. 17, 2002 (2 pages).
GenBank Accession No. AAR06918.1, dated Dec. 28, 2004 (2 pages).
GenBank Accession No. AAT93110.1, dated Apr. 24, 2007 (2 pages).
GenBank Accession No. ACE87855.1, dated Jun. 24, 2008 (1 page).
GenBank Accession No. ACM47734.1, dated Feb. 7, 2009 (1 page).
GenBank Accession No. ACT33422.1, dated Jul. 17, 2009 (1 page).
GenBank Accession No. AF515727.1, dated Jun. 17, 2002 (2 pages).
GenBank Accession No. AY345974.1, dated Dec. 28, 2004 (2 pages).
GenBank Accession No. AY345978.1, dated Dec. 28, 2004 (2 pages).
Genbank Accession No. AY345980.1, dated Dec. 28, 2004 (2 pages).

(56) References Cited

OTHER PUBLICATIONS

GenBank Accession No. AY345982.1, dated Dec. 28, 2004 (2 pages).
GenBank Accession No. BG521726.1, dated May 13, 2000 (2 pages).
GenBank Accession No. CAA23011.1, dated Oct. 23, 2008 (2 pages).
GenBank Accession No. CAA46815.1, dated Apr. 18, 2005 (2 pages).
GenBank Accession No. DQ269454.4, dated May 28, 2008 (2 pages).
GenBank Accession No. EU722415.1, dated Jun. 10, 2008 (2 pages).
GenBank Accession No. EU751291.1, dated Jun. 24, 2008 (2 pages).
EBI Accession No. AAY05902, "Jerusalem artichoke in-chain hydroxylase CYP81B1" (1 page), Jun. 15, 2009.
EBI Accession No. ABM86477, "Rice abiotic stress responsive polypeptide SEQ ID No. 4723" (1 page), dated Jun. 2, 2005.
UniProt Accession No. F2DG34, May 2011 (pp. 1-4).
UniProt Accession No. Q6VAA8, 2004 (pp. 1-6).
UniProt Accession No. Q7FPQ4, 2004 (pp. 1-6).
Jewett et al. "An integrated cell-free metabolic platform for protein production and synthetic biology," Mol Syst Biol. 4:220 (2008).
Johnstone et al., "Cloning an Aspergillus nidulans developmental gene by transformation," EMBO J. 4(5):1307-11 (1985).
Khoury et al., "Computational design of Candida boidinii xylose reductase for altered cofactor specificity," Protein Sci. 18(10):2125-38 (Oct. 2009).
Kim et al., "Hydroxylation of ent-Kaurenoic Acid to Steviol in Stevia rebaudiana Bertoni-Purification and Partial Characterization of the Enzyme," Arch Biochem Biophys. 332(2):223-30 (1996).
Kim & Shibata, "Characterization of ent-kaurenoic acid 13-hydroxylase in steviol biosynthesis of Stevia rebaudiana Bertoni," Journal of the Korean Agriculturalchemical Society 40(6):501-7 (1997).
Knowles et al., "Genetic Transformation and Plant Regeneration in Stevia rebaudiana Using Microprojectile Bombardment," In Vitro Cellular & Developmental Biology 39(abstract):23-A (2003).
Kohda et al., "New Sweet Diterpene glucoside from Stevia Rebaudiana," Phytochemistry 15(6):981-3 (1976).
Kondo et al., "Preparation of high activity whole cell biocatalyst by permeabilization of recombinant flocculent yeast with alcohol," Enzyme Microb Technol. 27(10), 806-11 (2000).
Kumar et al., "A comprehensive analysis of fifteen genes of steviol glycosides biosynthesis pathwayin Stevia rebaudiana (Bertoni)" Gene 492:276-84 (Epub Oct. 20, 2011).
Kusama et al., "Transglucosylation into stevioside by the enzyme system from *Streptomyces* sp.," Agric. Biol. Chem. 50(10):2445-51 (Oct. 1986).
Li et al., "Crystal structure of Medicago truncatula UGT85H2—insights into the structural basis of a multifunctional (iso) flavonoid glycosyltransferase," J Mol Biol. 370(5):951-63 (2007).
Li et al., "Systematic Mutational Analysis of Peptide Inhibition of the p53-MDM2/MDMX," J Mol Biol. 398(2):200-13 (2010).
Li et al., "High-density cultivation of oleaginous yeast *Rhodosporidium toruloides* Y4 in fed-batch culture," Enzyme and Microbial Technology 41(3):312-7 (Aug. 2007).
Liu et al., "Preparation of high-activity whole cell biocatalysts by permeabilization of recombinant yeasts with alcohol," J Biosci Bioeng. 89(6):554-8 (2000).
Ma et al., "Molecular cloning and characterization of Stevia Rebaudiana UDP-glucosyltransferase," Acta Biologiae Experimentalis Sinica 36(2):123-9 (2003).
Ma "Part 1. Molecular Cloning and Functional Analysis of UDPG Glucosyltransferase Gene. Part 2. Molecular Cloning, Sequence Analysis and Evolution of Actin and EF1a Genes in Stevia Rebaudiana." Chinese Doctor and Master Dissertations Full-Text Database, Agricultural Technology Part, vol. 2; pp. 1-74 (2004).
Madan et al., "Stevia rebaudiana (Bert.) Bertoni—A Review," Indian Journal of Natural Products and Resources 1(3):267-86 (2010).
Madhav et al., "Functional and structural variation of uridine diphosphate glycosyltransferase (UGT) gene of Stevia rebaudiana—UGTSr involved in the synthesis of rebaudioside A," Plant Physiol. Biochem. 63:245-53 (Feb. 2013).
Malonek et al., "The NADPH-cytochrome P450 Reductase Gene from Gibberalla fujikuroi is Essential for Gibberellin Biosynthesis," J Bio Chem. 279(24):25075-84 (2004).
Mantovaneli et al., "The effect of temperature and flow rate on the clarification of the aqueous stevia-extract in a fixed-bed column with zeolites," Braz J Chem Eng. 21(3):449-58 (2004).
Mattanovich et al., "Recombinant protein production in yeasts," Methods Mol Biol. 824:329-58 (2012).
Megeji et al., "Introducing Stevia rebaudiana, a natural zero-calorie sweetener," Current Science 88(5):801-4 (2005).
Mohamed et al., "UDP-dependent glycosyltransferases involved in the biosynthesis of steviol glycosides" Journal of Plant Physiology 168(10):1136-1141 (Jul. 2011; Epub Apr. 7, 2011).
Mumberg et al., "Yeast vectors for the controlled expression of heterologous proteins in different genetic backgrounds," Gene 156(1):119-22 (1995).
Naesby et al., "Yeast artificial chromosomes employed for random assembly of biosynthetic pathways and production of diverse compounds in *Saccharomyces cerevisiae*," Microb Cell Fact. 8:45 (2009).
Naglak & Wang, "Rapid protein release from *Escherichia coli* by chemical permeabilization under fermentation conditions," Biotechnol Bioeng. 39(7):732-40 (1991).
Nakagiri et al., "cDNA cloning, functional expression and characterization of ent-copalyl diphosphate synthase from *Scoparia dulcis* L.," Plant Sci. 169:760-7 (2005).
Nelson et al., "P450 superfamily: update on new sequences, gene mapping, accession numbers and nomenclature," Pharmacogenetics 6:1-42 (1996).
Newman et al., "High-level production of amorpha-4, 11-diene in a two-phase partitioning bioreactor of metabolically engineered *Escherichia coli*," Biotechnol Bioeng 95(4):684-91 (2006).
Nicaud, "Yarrowia lipolytica," Yeast 29(10):409-18 (Oct. 2012).
Nielsen et al., "Efficient PCR-based gene targeting with a recyclable marker for Aspergillus nidulans," Fungal Genet Biol. 43(1):54-64 (2006).
Nour-Eldin et al., "USER cloning and USER fusion: the ideal cloning techniques for small and big laboratories," Methods Mol Biol. 643:185-200 (2010).
Ohta et al., "Characterization of Novel Steviol Glycosides from Leaves of Stevia rebaudiana Morita," J. Applied Glycosides 57(3):199-209 (Mar. 2010).
Ohta et al., MassBank Accession No. FU000341 (May 2011).
Ohta et al., MassBank Accession No. FU000342 (May 2011).
Ohta et al., MassBank Accession No. FU000343 (May 2011).
Ohtani et al., "Further Study on the 1,4-alpha-Transglucosylation of Rubusoside, a Sweet Steviol-Bisglucoside from Rubus suavissimus," Agric Biol Chem. 55(2):449-53 (1991).
Oka & Jigami, "Reconstruction of de novo pathway for synthesis of UDP-glucuronic acid and UDP-xylose from intrinsic UDP-glucose in *Saccharomyces cerevisiae*," FEBS J. 273(12):2645-57 (2006).
Orihara et al., "Biotransformation of steviol by cultured cells of eucalyptus perriniana and Coffea Arabica," Phytochemistry 30(12):3989-92 (1991).
Paradise et al., "Redirection of flux through the FPP branch-point in *Saccharomyces cerevisiae* by down-regulating squalene synthase," Biotechnol Bioeng. 100(2):371-8 (2008).
Pearson & Lipman, "Improved tools for biological sequence comparison," Proc Natl Acad Sci. 85(8):2444-8 (1998).
Piirainen et al., "Glycoengineering of yeasts from the perspective of glycosylation efficiency," N Biotechnol. 31(6):532-7 (Dec. 2014).
Pompon et al., "Yeast Expression of Animal and Plant P450s in Optimized RedoxEnvironments," Methods Enzymol 272:51-64 (1996).
Prelich, "Gene overexpression: uses, mechanisms, and interpretation," Genetics 190(3):841-54 (Mar. 2012).

(56) References Cited

OTHER PUBLICATIONS

Presecki & Vasic-Racki, "Production of L-malic acid by permeabilized cells of commercial *Saccharomyces* sp. strains," Biotechnol Lett. 27(23-24):1835-9 (2005).
Ro et al., "Production of the antimalarial drug precursor artemisinic acid in engineered yeast," Nature 440(7086):940-3 (2006).
Saenge et al., "Potential use of oleaginous red yeast *Rhodotorula glutinis* for the bioconversion of crude glycerol from biodiesel plant to lipids and carotenoids," Process Biochemistry 46(1):210-8 (Jan. 2011).
Schwab et al., Poster, "Watchmaker®—Compound Generation by Combinatorial Genetics and Screening in Yeast," 141st Annual Conference in St. Louis, 2008, 1 page.
Sen et al., "Developments in Directed Evolution for Improving Enzyme Functions," Appl Biochem Biotechnol. 143(3):212-23 (2007).
Senthilraja et al., "RNA secondary structure prediction: Analysis of *Saccharomyces cerevisiae* RNAs," Int. J. Pharm. Rev. Res. 25(2):287-91 (Mar.-Apr. 2014).
Broun et al., "Catalytic plasticity of fatty acid modification enzymes underlying chemical diversity of plant lipids," Science, vol. 282: 1315-1317 (1998).
Cheng, "Food Biotechnology," Inner Mongolia Science and Technology Press (2008). (Book).
Devos et al., "Practical limits of function prediction," Proteins: Structure, Function, and Genetics, vol. 41: 98-107 (2000).
Seffernick et al., "Melamine deaminase and Atrazine chlorohydrolase: 98 percent identical but functionally different," J. Bacterial., vol. 183 (8): 2405-2410 (2001).
Whisstock et al., "Prediction of protein function from protein sequence," Q. Rev. Biophysics., vol. 36 (3): 307-340 (2003).
Witkowski et al., "Conversion of b-ketoacyl synthase to a Malonyl Decarboxylase by replacement of the active cysteine with glutamine," Biochemistry, vol. 38: 11643-11650 (1999).
Pearson, et al., "Improved tools for biological sequence comparison," Proc Natl Acad Sci. 85(8):2444-8 (1988).
GenBank Accession No. XM_001467423, dated Jul. 16, 2015 (2 pages).
GenBank Accession No. XP_002282091, dated Dec. 7, 2011 (1 page).
SenBank Accession No. XP_002288339, dated Jul. 15, 2009 (2 pages).
GenBank Accession No. XP_002311286, dated Dec. 31, 2013 (2 pages).
GenBank Accession No. ZP_05004570, dated Jun. 8, 2010 (2 pages).
Gossen & Bujard, "Studying gene function in eukaryotes by conditional gene inactivation," Annu. Rev. Genet. 36:153-73 (Jun. 2002).
Gritz & Davies, "Plasmid-encoded hygromycin B resistance: the sequence of hygromycin B phosphotransferase gene and its expression in *Escherichia coli* and *Saccharomyces cerevisiae*," Gene 25(2-3):179-88 (Nov. 1983).
Hallstrom & Moye-Rowley, "Divergent transcriptional control of multidrug resistance genes in *Saccharomyces cerevisiae*," J. Biol. Chem. 273(4):2098-104 (Jan. 1998).
Katzmann et al., "Expression of an ATP-binding cassette transporter-encoding gene (YOR1) is required for bligomycin resistance in *Saccharomyces cerevisiae*," Mol. Cell Biol. 15(12):6875-83 (Dec. 1995).
Li et al., "Phylogenetic analysis of the UDP-glycosyltransferase multigene family of *Arabidopsis thaliana*," J. Biol. Chem. 276(6):4338-43 (Oct. 2000).
Masada et al., "An efficient chemoenzymatic production of small molecule glucosides with in situ UDP-glucose recycling," FEBS Lett. 581(13):2562-6 (May 2007).
Morita et al., "Japanese morning glory dusky mutants displaying reddish-brown or purplish-gray flowers are deficient in a novel glycosylation enzyme for anthocyanin biosynthesis, UDP-glucose:anthocyanidin 3-O-glucoside-2"-O-glucosyltransferase, due to 4-bp insertions in the gene," Plant J. 42(3):353-63 (May 2005).
Nagy et al., "Role of the yeast ABC transporter Yor1p in cadmium detoxification," Biochimie 88(11):1665-71 (Jun. 2006).
Nikaido & Takatsuk, "Mechanisms of RND multidrug efflux pumps," Biochim. Biophys. Acta. 1794(5):769-81 (May 2009).
Osmani et al., "Catalytic key amino acids and UDP-sugar donor specificity of a plant glucuronosyltransferase, UGT94B1: molecular modeling substantiated by site-specific mutagenesis and biochemical analyses," Plant Physiol. 148(3):1295-308 (Nov. 2008).
Osmani et al., "Substrate specificity of plant UDP-dependent glycosyltransferases predicted from crystal structures and homology modeling," Phytochemistry 70(3):325-47 (Feb. 2009).
Richman et al., "Functional genomics uncovers three glucosyltransferases involved in the synthesis of the major sweet glucosides of Stevia rebaudiana," Plant J. 41(1):56-67 (Jan. 2005).
Riesmeier et al., "Isolation and characterization of a sucrose carrier cDNA from spinach by functional expression in yeast," Embo J. 11(13):4705-13 (Dec. 1992).
RodrÍguez-ConcepcióN & Boronat, "Elucidation of the methylerythritol phosphate pathway for isoprenoid biosynthesis in bacteria and plastids. A metabolic milestone achieved through genomics," Plant Physiol. 130(3):1079-89 (Nov. 2002).
Saier Jr et al., "The major facilitator superfamily," J. Mol. Microbiol. Biotechnol. 1(2):257-79 (Nov. 1999).
Saier Jr et al., "The Transporter Classification Database: recent advances," Nucleic Acids Res. 37:D274-8 (Jan. 2009).
Sauer et al., "The soluble and membrane-bound transhydrogenases UdhA and PntAB have divergent functions in NADPH metabolism of *Escherichia coli*," J. Biol. Chem. 279(8):6613-9 (Dec. 2003).
Sawada et al., "UDP-glucuronic acid:anthocyanin glucuronosyltransferase from red daisy (*Bellis perennis*) flowers. Enzymology and phylogenetics of a novel glucuronosyltransferase involved in flower pigment biosynthesis," J. Biol. Chem. 280(2):899-906 (Jan. 2005).
Shao et al., "Enhanced production of alpha-galactosyl epitopes by metabolically engineered Pichia pastoris," Appl. Environ. Microbiol. 69(9):5238-42 (Sep. 2003).
Son et al., "Production of flavonoid O-glucoside using sucrose synthase and flavonoid O-glucosyltransferase fusion protein," J. Microbiol. Biotechnol. 19(7):709-12 (Jul. 2009).
Sonnhammer et al., "Pfam: a comprehensive database of protein domain families based on seed alignments," Proteins 28(3):405-20 (Jul. 1997).
Sonnhammer et al., "Pfam: multiple sequence alignments and HMM-profiles of protein domains," Nucleic Acids Res. 26(1):320-2 (Jan. 1998).
Yadav et al., "Steviol Glycosides from Stevia: Biosynthesis Pathway Review and their Application in Foods and Medicine", Critical Reviews in Food Science and Nutrition, vol. 52, No. 11, pp. 988-998; (2012).
International Search Report by the International Searching Authority for International Application No. PCT/EP2014/052675, mailed Apr. 23, 2014 (5 pages).
Written Opinion of the International Searching Authority for International Application No. PCT/EP2014/052675, mailed Apr. 23, 2014 (7 pages).
Chen et al., "Sugar transporters for intercellular exchange and nutrition of pathogens," Nature 468(7323):527-32 (2010).
Daran et al., "Genetic and biochemical characterization of the UGP1 gene encoding the UDP-glucose byrophosphorylase from *Saccharomyces cerevisiae*," Eur J Biochem. 233(2):520-30 (Jul. 1995).
Gloster, "Advances in understanding glycosyltransferases from a structural perspective," Curr Opin Struct Biol. 28:131-41 (2014).
Husar et al., "Overexpression of the UGT73C6 alters brassinosteriod glucoside formation in *Arabidopsis thaliana*", BMC Plant Biology, 11:1-14 (2011).
Malonek et al., "The NADPH-cytochrome P450 Reductase Gene from Gibberalla fujikuroi is Essential for Gibberellin Biosynthesis", J Bio Chem. 279(24):25075-84 (Jun. 2004).
Nagatoshi et al., "UGT75L6 and UGT94E5 mediate sequential glucosylation of crocetin to crocin in Gardenia asminoides", FEBS Letters, 586:1055-1061 (2012).

(56) References Cited

OTHER PUBLICATIONS

Examination Report issued by the European Patent Office for European Application No. 12750513.9, dated Nov. 26, 2014.
Arnold, F. H. "Combinatorial and computational challenges for biocatalyst design," Nature 409(6817):253-257 (2001).
Duetz, "Microtiter plates as mini-bioreactors: miniaturization of fermentation methods," Trends Microbiol 15(10):469-75 (2007).
Franois et al., "Reserve carbohydrates metabolism in the yeast *Saccharomyces cerevisiae*," FEMS Microbiol Rev., 25(1):125-45 (2001).
Jones et al., "UGT73C6 and UGT78D1, Glycosyltransferases Involved in Flavonol Glycoside Biosynthesis in *Arabidopsis thaliana**," J. Biol. Chem., vol. 278, No. 45, pp. 43910-43918 (2003).
Popenberger et al., Heterologous Expression of *Arabidopsis* UDP-Glucosyltransferases in *Saccharomyces cerevisiae* for Production ofZearalenone-4-0-Glucoside, Appl. Environ. Microbial., vol. 72, pp. 4404-4410 (2006).
Rudinger et al., "Characteristics of the amino acids as components of a peptide hormone sequence," Peptide Hormones. Biol. Council. pp. 5-7 (1976).
Third-Party Submission under 37 CFR 1.290 for U.S. Appl. No. 15/439,660, dated Jul. 3, 2018 (88 pages).
Third Party Observation in EP Application No. 15193074.0; mailed Jul. 18, 2018, pp. 1-32.
Non-Final Office Action issued in U.S. Appl. No. 15/439,660; mailed Oct. 19, 2018, pp. 1-27.
GenBank Accession No. AAS07253.1, dated Jan. 31, 2004 (3 pages).
Guo et al., "Protein tolerance to random amino acid change", Proceedings of the National Academy of Sciences USA, vol. 101, No. 25, pp. 9205-9210 (2004).
Liu et al., "Biosynthesis of Rebaudioside A by Whole Cell of Recombinant *Saccharomyces cerevisiae*," Food and Fermentation Industries, 38(7) : 6-10 (2012) (Abstract translation).
Ni et al., "Outer membrane mutation effects on UDP-glucose permeability and whole-cell catalysis rate," Appl Microbiol Biotechnol. 73(2):384-93 (2006).
Prisic et al., "Synergistic substrate inhibition of ent-copalyl diphosphate synthase: a potential feed-forward inhibition mechanism limiting gibberellin metabolism," Plant Physiol. 144(1):445-54 (2007).
Ünligil et al., "Glycosyltransferase structure and mechanism," Curr Opin Struct Biol. 10(5):510-7 (2000).
Wanchao et al., "Advances on the Stevoil Glycoside Biosynthesis and Its Key Enzymes," Biotechnology Bulletin, Feb. 2008 (English Abstract translation).
lntemational Search Report by the International Searching Authority for lnternational Application No. PCT/EP2015l070620; mailed Mar. 29, 2016, pp. 1-10.
Written Opinion of the International Searching Authority for International Application No. PCT/EP2015/070620; mailed Mar. 29, 2016, pp. 1-24.
Boer, "Strain and process development for fermentative production of Rebaudiosides" Abstract of Offered Oral from 33rd International Specialised Symposium on Yeasts; Jun. 26-29, 2017 University of College Cork, Ireland; pp. 1-2.
Patent Examination Report No. 1 issued by IP Australia for Australian Application No. 2011261394, dated Jan. 15, 2015.
Response to Patent Examination Report No. 1 issued by IP Australia for Australian Application No. 2011261394, dated Feb. 5, 2015.
Patent Examination Report No. 2 issued by IP Australia for Australian Application No. 2011261394, dated Feb. 23, 2015.
Notice of Acceptance issued by IP Australia for Australian Application No. 2011261394, dated Aug. 13, 2015 (pp. 1-3).
Office Action for Canadian Patent Application No. 2,802,627, mailed Dec. 15, 2015 (pp. 1-5).
English Translation of First Office Action issued by the State Intellectual Property Office of People's Republic of China for CN Application No. 201180038475.4, dated Nov. 21, 2013.
English Translation on Response to First Office Action issued by the State Intellectual Property Office of People's Republic of China for CN Application No. 201180038475.4, dated Apr. 8, 2014.
English Translation of Second Office Action issued by the State Intellectual Property Office of People's Republic of China for Chinese Application No. 201180038475.4, dated Aug. 13, 2014.
English Translation of Response to Second Office Action issued by the State Intellectual Property Office of People's Republic of China for CN Application No. 201180038475.4, dated Oct. 28, 2014.
English Translation of Third Office Action issued by the State Intellectual Property Office of People's Republic of China for Chinese Application No. 201180038475.4, dated Mar. 3, 2015.
Notification of Grant of Patent Application issued by the State Intellectual Property Office of People's Republic of China for Chinese Application No. 201180038475.4, dated Dec. 1, 2015 (pp. 1-5). English translation included.
Response to Extended Search Report and Opinion issued by the European Patent Office for European Application No. 11790428.4, dated Jul. 16, 2014.
Communication pursuant to Rule 114(2) EPC for European Application No. 11790428.4, dated Nov. 28, 2014.
Examination Report issued by the European Patent Office for European Application No. 11790428.4, dated Dec. 1, 2014.
Response to Examination Report issued by the European Patent Office for European Application No. 11790428.4, dated Jun. 1, 2015 (16 pages).
Communication pursuant to Rule 114(2) EPC for European Application No. 11790428.4, dated Apr. 25, 2016 (19 pages).
Examination Report issued by the European Patent Office for European Application No. 11790428.4, dated May 13, 2016 (12 pages).
English Translation of Notification of Reasons for Refusal of Japanese Application No. 2013-513355, dated Aug. 4, 2015 (pp. 1-10).
Decision of Refusal in Japanese Patent Application No. 2013-513355; dispatch No. 304859, dispatch date Jul. 6, 2016, pp. 1-3. English translation submitted.
First Examination Report issued by the Intellectual Property Office of New Zealand for New Zealand Application No. 604915, dated Sep. 2, 2013.
Response to First Examination Report issued by the Intellectual Property Office of New Zealand for New Zealand Application No. 604915, dated Jan. 17, 2014.
Further Examination Report issued by the Intellectual Property Office of New Zealand for New Zealand Application No. 604915, dated Feb. 3, 2014.
Response to Further Examination Report issued by the Intellectual Property Office of New Zealand for New Zealand Application No. 604915, dated May 27, 2014.
Further Examination Report issued by the Intellectual Property Office of New Zealand for New Zealand Application No. 604915, dated Jun. 18, 2014.
Response to Further Examination Report issued by the Intellectual Property Office of New Zealand for New Zealand Application No. 604915, dated Sep. 15, 2014.
Notice of Acceptance issued by the Intellectual Property Office of New Zealand for New Zealand Application No. 604915, dated Oct. 7, 2014 (1 page).
First Examination Report issued by the Intellectual Property Office of New Zealand for New Zealand Application No. 700097, dated Oct. 6, 2014 (pp. 1-2).
Notice of Acceptance issued by the Intellectual Property Office of New Zealand for New Zealand Application No. 700097, dated Oct. 7, 2015 (1 page).
First Examination Report issued by the Intellectual Property Office of New Zealand for New Zealand Application No. 708078, dated May 28, 2015 (pp. 1-3).
Search Report issued by the Intellectual Property Office of Singapore for Singaporean Application No. 201208854-8, dated Nov. 3, 2014.
Written Opinion issued by the Intellectual Property Office of Singapore for Singaporean Application No. 201208854-8, dated Nov. 3, 2014.

(56) References Cited

OTHER PUBLICATIONS

Second Written Opinion in Singapore Patent Application No. 201208854-8; dated Apr. 18, 2016, pp. 1-12.
Final Office Action issued in U.S. Appl. No. 14/237,540; mailed Jul. 8, 2016, pp. 1-19.
English Translation of First Office Action and Search Report issued by the State Intellectual Property Office of People's Republic of China for Chinese Application No. 201280038853.3, dated Feb. 16, 2015.
English Translation of Second Office Action and Search Report issued by the State Intellectual Property Office of People's Republic of China for Chinese Application No. 201280038853.3, dated Jan. 11, 2016.
Communication pursuant to Rules 161(1) and 162 (EPC) issued by the European Patent Office for European Application No. 12750513.9, dated Mar. 14, 2014.
Response to Communication pursuant to Rules 161(1) and 162 (EPC) issued by the European Patent Office for European Application No. 12750513.9, dated Aug. 4, 2014.
Response to Examination Report issued by the European Patent Office for European Application No. 12750513.9, dated Mar. 25, 2015.
Statement of Facts and Arguments in Support of Opposition for EP Application No. 12750513.9; mailed Feb. 28, 2017. pp. 1-24.
Communication of Notice of Opposition against EP Application No. 12750513.9; mailed Mar. 6, 2017. pp. 1-8.
Sequence alignment between the sequence of Uniprot database entry Q75183 version 31, updated Jul. 22, 2008 and SEQ ID No. 152 (from European Patent No. 2742142) as cited in Notice of Opposition against EP Application No. 12750513.9; mailed Mar. 6, 2017; pp. 1-2.
Non-Final Office Action for U.S. Appl. No. 14/761,629, mailed Mar. 21, 2017 (pp. 1-19).
Final Office Action for U.S. Appl. No. 14/761,629, mailed Aug. 11, 2017 (pp. 1-16).
Communication pursuant to Rules 161(1) and 162 EPC for European Application No. 14704558.7, dated Sep. 18, 2015 (2 pages).
Response to Communication pursuant to Rules 161(1) and 162 EPC for European Application No. 14704558.7, dated Mar. 17, 2016 (pp. 1-24).
Non-Final Office Action for U.S. Appl. No. 14/764,898, mailed Mar. 30, 2017 (pp. 1-17).
Communication pursuant to Rules 161(1) and 162 EPC for European Application No. 13801569.8, dated Jul. 14, 2015 (2 pages).
Response to Communication pursuant to Rules 161(1) and 162 EPC for European Application No. 13801569.8, Jan. 13, 2016 (9 pages).
Abraham & Bhat, "Permeabilization of baker's yeast with N-lauroyl sarcosine," J Ind Microbial Biotechnol. 35(8):799-804 (2008).
Ageitos et al., "Oily yeasts as oleaginous cell factories," Appl Microbiol Biotechnol. 90(4):1219-27 (May 2011).
Agrawal, "NMR spectroscopy in the structural elucidation of oligosaccharides and glycosides," Phytochemistry 31(10):3307-30 (1992).
Ajikumar et al., "Terpenoids: opportunities for biosynthsis of natural product drugs using engineered microorganisms," Molecular Pharmaceuticals 5(2):167-90 (2008).
Alakomi et al., "Lactic acid permeabilizes gram-negative bacteria by disrupting the outer membrane," Appl Environ Microbiol. 66(5):2001-5 (2000).
Ali et al., "Biochemical investigation during different stages of in vitro propagation of Stevia rebaudiana," Pak J Bot. 42(4):2827-37 (2010).
Bankar et al., "Environmental and industrial applications of Yarrowia lipolytica," Appl Microbiol Biotechnol. 84(5):847-65 (Oct. 2009).
Baykov et al., "A malachite green procedure for orthophosphate determination and its use in alkaline phosphatase-based enzyme immunoassay," Anal Biochem. 171(2):266-70 (Jun. 1988).
Beopoulos et al., "Yarrowia lipolytica: A model and a tool to understand the mechanisms implicated in lipid accumulation," Biochimie 91(6):692-6 (Jun. 2009).
Brandle et al., "Leaf ESTs from Stevia rebaudiana: A Resource for Gene Discovery in Diterpene Synthesis," Plant Mol Biol. 50(4-5):613-22 (2002).
Brandle & Telmer, "Steviol glycoside biosynthesis," Phytochemistry 68(14):1855-63 (2007).
Brochado et al. "Improved vanillin production in baker's yeast through in silico design," Microb Cell Fact. 9:84-98 (2010).
Carretero-Paulet et al., "Expression and Molecular Analysis of the *Arabidopsis* DXR Gene Encoding 1-Deoxy-d-Xylulose 5-Phosphate Reductoisomerase, the First Committed Enzyme of the 2-C-Methyl-D-Erythritol 4-Phosphate Pathway," Plant Physiol. 129(4):1581-91 (2002).
Chemler et al., "Biosynthesis of isoprenoids, polyunsaturated fatty acids and flavonoids in *Saccharomyces cerevisiae*," Microb Cell Fact. 5:20 (2006).
Chen, "Summary on Study of Stevioside," China Pharmacist, 10(6):598-599 (2007).
Chen et al., "MolProbity: all-atom structure validation for macromolecular crystallography," Acta Crystallogr D Biol Crystallogr 66(Pt 1):12-21 (Jan. 2010).
Chica et al., "Semi-rational approaches to engineering enzyme activity: combining the benefits of directed evolution and rational design," Curr Opin Biotechnol. 16(4):378-84 (2005).
Chow & Palecek, "Enzyme encapsulation in permeabilized *Saccharomyces cerevisiae* cells," Biotechnol Prog. 20(2):449-56 (2004).
Correa et al., "Genetic mapping of 1,3-beta-glucanase-encoding genes in *Saccharomyces cerevisiae*," Current Genet. 22(4):283-8 (1992).
Darise et al., "Enzymic Transglucosylation of Rubusoside and the Structure-Sweetness Relationship of Steviol-Bisglycosides," Agric. Biol. Chem. 48(10):2483-8 (Jan. 1984).
Davis et al., "MolProbity: all-atom contacts and structure validation for proteins and nucleic acids," Nucleic Acids Res. 35:W375-83 (Apr. 2007).
Dodhia et al., "Engineering human cytochrome P450 enzymes into catalytically self-sufficient chimeras using molecular Lego," J Biol Inorg Chem. 11(7):903-16 (Oct. 2006).
Dubey, et al., An overview of the non-mevalonate pathway for terpenoid biosynthesis in plants, J. Biosci. 28(5):637-46 (2003).
Dubois & Stephenson, "Diterpenoid sweeteners. Synthesis and sensory evaluation of stevioside analogues with improved organoleptic properties," J. Med. Chem. 28(1):93-8 (Jan. 1985).
EFSA Panel on Food Additives and Nutrient Sources added to Food (ANS), "Scientific Opinion on the safety of steviol glycosides for the proposed uses as a food additive," EFSA Journal 8(4):1537 (2010).
Eisenreich et al., "Biosynthesis of isoprenoids via the non-mevalonate pathway," Cell Mol Life Sci. 61(12):1401-6 (2004).
Emboss Needle results for Pairwise Sequence Alignment of UGT91D1 and UGT91D2; dated Apr. 4, 2016, 2 pages.
Emmerstorfer et al., "Over-expression of ICE2 stabilizes cytochrome P450 reductase in *Saccharomyces cerevisiae*and Pichia pastoris," Biotechnol J. 10(4):623-35 (Apr. 2015).
Estrada De Martin et al., "Ice2p is important for the distribution and structure of the cortical ER network in *Saccharomyces cerevisiae*," J Cell Sci. 118(Pt 1):65-77 (Oct. 2006).
Fernandez et al., "Activation of chitin synthetase in permeabilized cells of a *Saccharomyces cerevisiae* mutant lacking proteinase B," J Bacteriol. 152(3):1255-64 (1982).
Flores et al., "Permeabilization of yeast cells (*Kluyveromyces lactis*) with organic solvents," Enzyme Microb Technol. 16(4):340-6 (1994).
Fowler & Zabin, "Effects of Dimethylsulfoxide on the Lactose Operon in *Escherichia coli*," J Bacteriol. 92(2):353-7 (1966).
Freire, "Differential scanning calorimetry," Methods Mol Biol. 40:191-218 (1995).
Fukunaga et al., "Enzymatic transglucosylation products of stevioside: separation and sweetness-evaluation," Agric. Biol. Chem. 53(6):1603-7 (Jan. 1989).
Geuns, "Stevioside," Phytochemistry 64(5):913-21 (2003).
Giaever & Nislow, "The yeast deletion collection: a decade of functional genomics," Genetics 197(2):451-65 (Jun. 2014).
Gietz & Schiestl, "High-efficiency yeast transformation using the LiAc/SS carrier DNA/PEG method," Nat Protoc. 2(1):31-4 (2007).

(56) References Cited

OTHER PUBLICATIONS

Girvan et al., "Flavocytochrome P450 BM3 mutant W1046A is a NADH-dependent fatty acid hydroxylase: implications for the mechanism of electron transfer in the P450 BM3 dimer," Arch Biochem Biophys. 507(1):75-85 (Mar. 2011).
Goralczyk, "Compounds from Stevia for Improving and Maintaining Mental Performance," Stevia World Forum, Feb. 24-25, 2010, 17 pages.
Guleria & Yadav, "Insights into Steviol Glycoside Biosynthesis Pathway Enzymes Through Structural Homology Modeling," Am. J. Biochem. Molec. Biol. 3(1):1-19 (2013).
Gunel et al., "Metabolic Engineering for Production of Geranylgeranyl Pyrophosphate Synthase in Non-Carotenogenic Yeast *Schizosaccharomyces pombe*," Biotechnol. & Biotechnol. Eq. 20(3):76-82 (2006).
Hansen et al., "De novo biosynthesis of vanillin in fission yeast (*Schizosaccharomyces pombe*) and baker's yeast (*Saccharomyces cerevisiae*)," Appl Environ Microbiol. 75(9):2765-74 (2009).
Hansen et al., "Versatile Enzyme Expression and Characterization System for Aspergillus nidulans, with the Penicillium brevicompactum Polyketide Synthase Gene from the Mycophenolic Acid Gene Cluster as a Test Case," Appl Environ Microbiol. 77(9):3044-51 (2011).
Hellfritsch et al., "Human psychometric and taste receptor responses to steviol glycosides," J. Agric. Food Chem. 60(27):6782-93 (Jul. 2012).
Humphrey et al., "Spatial organisation of four enzymes from Stevia rebaudiana that are involved in steviol glycoside synthesis," Plant Mol Bio. 61(1-2):47-62 (2006).
Iandolino et al., "High-Quality RNA, cDNA, and Derived EST Libraries From Grapevine (*Vitis vinifera* L.)," Plant Mol Biol Reporter 22:269-78 (2004).
Irmler et al., "Indole alkaloid biosynthesis in Catharanthus roseus: new enzyme activities and identification of cytochrome P450 CYP72A1 as secologanin synthase," Plant J. 24(6):797-804 (2000).
Jennewein et al., "Taxol biosythesis: baxane 13 alpha-hydroxylase is a cytochrome P450-dependent monooxygenase," Proc Natl Acad Sci U S A 98(24):13595-600 (2001).
Mikayama et al., "Molecular cloning and functional expression of a cDNA encoding glycosylation-inhibiting factor," Proc Natl Acad Sci U S A. 90(21):10056-60 (1993).
Rudinger et al., "Characteristics of the amino acids as components of a peptide hormone sequence," Peptide Hormones. Bioi. Council. pp. 5-7.
Gardana, et al., "Metabolism of stevioside and rebaudioside A from Stevia rebaudiana extracts by human micorflora", J. Argric Food Chem., 51:6618-22 (2003).
De Leon, et al., "Periplasmic penicillin G acylase activity in recombinantEscherichiacolicells permeabilized with organic solvents", Process Biochem, 29:301-05 (2003).
International Search Report issued by the International Searching Authority for International Application No. PCT/US2011/038967, dated Sep. 1, 2011 (10 pages).
Written Opinion of the International Searching Authority for International Application No. PCT/US2011/038967, dated Sep. 1, 2011 (12 pages).
International Preliminary Report on Patentability issued by the International Bureau for International Application No. PCT/US2011/038967, dated Dec. 4, 2012 (13 pages).
Third-Party Submission under 37 CFR 1.290 for U.S. Appl. No. 13/701,406, dated Mar. 7, 2014 (238 pages).
Extended European Search Report and Opinion issued by the European Patent Office for European Application No. 11790428.4, dated Dec. 20, 2013.
Non-Final Office Action for U.S. Appl. No. 14/237,540, mailed Dec. 30, 2015 (pp. 1-19).
International Search Report issued by the International Searching Authority for International Application No. PCT/US2012/050021, dated Apr. 12, 2013.
Written Opinion of the International Searching Authority for International Application No. PCT/US2012/050021, dated Apr. 12, 2013.
International Preliminary Report on Patentability issued by the International Bureau for International Application No. PCT/US2012/050021, dated Feb. 11, 2014.
Extended European Search Report issued in EP 15193074.0; dated Feb. 12, 2016, pp. 1-9.
International Search Report from the International Searching Authority for International Application No. PCT/EP2014/052363, mailed Sep. 22, 2014 (12 pages).
Written Opinion of the International Searching Authority for International Application No. PCT/EP2014/052363, mailed Sep. 22, 2014 (10 pages).
International Preliminary Report on Patentability issued by the International Bureau for International Application No. PCT/EP2014/052363, dated Aug. 11, 2015 (11 pages).
International Preliminary Report on Patentability issued by the International Bureau for International Application No. PCT/EP2014/052675, dated Aug. 11, 2015 (8 pages).
International Search Report of the International Searching Authority for International Application No. PCT/EP2013/075587, mailed Feb. 20, 2014 (pp. 1-5).
Written Opinion of the International Searching Authority for International Application No. PCT/EP2013/075587, mailed Feb. 20, 2014 (pp. 1-9).
International Preliminary Report on Patentability from the International Bureau for International Application No. PCT/EP2013/075587, dated Jun. 9, 2015 (pp. 1-10).
Invitation to Pay Additional Fees and, Where Applicable, Protest Fee by the International Searching Authority for International Application No. PCT/EP2015/070620, mailed Nov. 27, 2015 (pp. 1-14).
International Search Report and Written Opinion of the International Searching Authority for International Application No. PCT/EP2015/068314, dated Jan. 20, 2016 (pp. 1-7).
Written Opinion of the International Searching Authority for International Application No. PCT/EP2015/068314, dated Jan. 20, 2016 (pp. 1-9).

* cited by examiner

FIG. 1
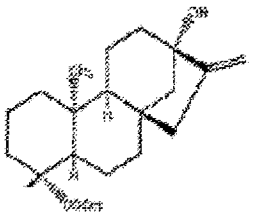
Steviol
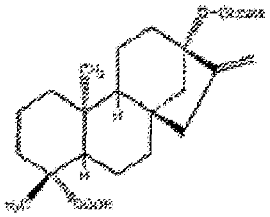
Steviolmonoside
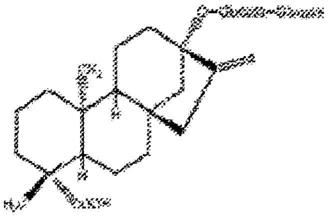
Steviolbioside
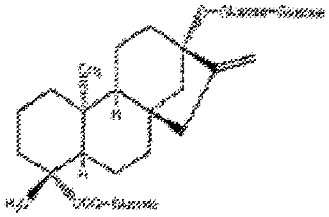
Stevioside
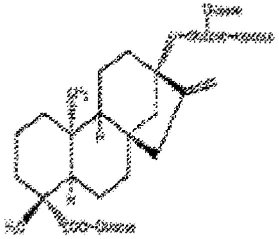
Rebaudioside A
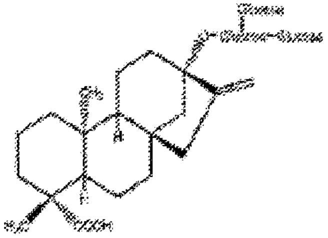
Rebaudioside B
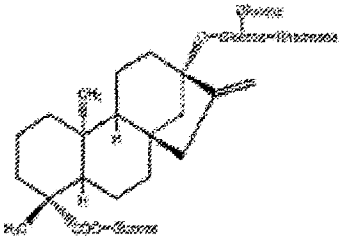
Rebaudioside C
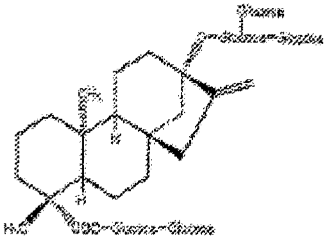
Rebaudioside D
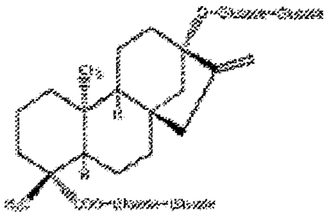
Rebaudioside E
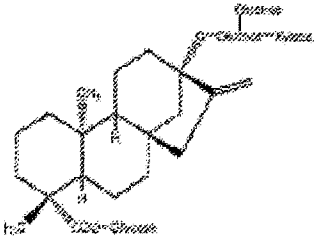
Rebaudioside F
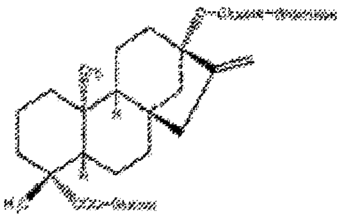
Dulcoside A Steviol Steviol-13-O-glucoside Steviol-19-O-Glucoside Steviol-1,2-xylobioside Rubusoside 1,2-Stevioxylobioside Rebaudioside F Steviol Steviol-19-*O*-Glucoside Rubusoside Stevioside Reb A

'1'

'2'

'3'

Reb D

FIG. 6

```
#fasta36-p-q-w80-m 6-m 6-z11-Z10000-f-10-g-2 TMP.q TMP.q2
FASTA searches a protein or DNA sequence data bank
version 36.3.5a Jun, 2011(preload8)
Please cite:
W.R. Pearson & D.J. Lipman PNAS (1988) 85:2444-2448

Query: TMP.g
  1>>>QUERY - 462 aa
Library: TMP.q2
    473 residues in 1 sequences
Statistics: (shuffled [128]) MLE statistics: Lambda= 0.1568; K=0.007058
statistics sampled from 1 (1) to 128 sequences
Algorithm: FASTA (3.7 Nov 2010) [optimized]
Parameters: BL50 matrix (15:-5), open/ext: -10/-2
 Ktup: 2, E-join: 1 (1), E-opt: 0.2 (1), width:  16
Scan time:  0.030

The best scores are:                                           opt bits E(10000)
QUERY                                                  (  473) 1003 236.0  2e-62 align

>>>QUERY, 462 aa vs TMP.q2 library
>>QUERY                                                             (473 aa)
 initn: 1037 init1:  443 opt: 1003  Z-score: 1225.1 bits: 236.0 E(10000): 2e-62
Smith-Waterman score: 1104; 42.7% identity (67.6% similar) in 457 aa overlap (15-457:14-460)

              10        20        30        40        50        60        70        80
QUERY  MDSGYSSSYARAAGMHVVICPWLAFGHLLPCLDLAQRLASRGHRVSFVSTPRNISRLPPVRPALAPLVAFVALPLPNVEG
        ::. :::::::::.::.:::.:::.:.:: ::.: .:::::::::::.:::::::::    ::: ::.::::.:::
QUERY  MATSDSIVDRXQLHVATPPWLAFGHILPYIQLSKLIAEKGHKVSFLSTTRNIQRLSS---HISPLINVVQJTLPRVQE
              10        20        30        40        50        60        70

              90       100       110       120       130       140       150
QUERY  LPDGAESTNDV-PHDRPDMVELHRRAFDGLAAPFSEFLGTACADWVIVDVFHHW--AAAAAL----EH---KVPCAMMLL
       ::.::::::::  : .::::  :::     : : :: :::::::: :: ::::  : :.::.  :.   :::: ...
QUERY  LPEDAEATYDVHPEDIPYL----KKASDGLQPEVTRFLEQHSPDWIIYDYTHYWLPSIAASLGISRAHPSVTTPWAIAYM
          80        90       100       110       120       130       140       150
```

FIG. 6 (cont'ed)

```
                 160       170       180       190       200       210       220
QUERY   G-SAHMIASIADRRLERAETESPAAAGQGRPAAAPTFEVARMKLIRTKGSSGMSLAERFSLTLSRSSLVVGRSCVEFEPE
        : ::  . . .: :     .  .:        :. .    .     .:.  : . :.: . :..:.:. :. ....    ::  .
QUERY   GPSADAMINGSDGRTTVEDLTTPPKWFP-FPTKVCWRKHDLARLVPYK-APGISDGYRMGLVLKGSDCLLSKCYHEFGTQ
              160       170       180       190       200       210       220       230

     230       240       250       260       270       280       290       300
QUERY   TVPLLSTLRGKPITFLGLMPPLHEGRREDGEDATVR-WLDAQPAKSVVYVALGSEVPLGVEKVHELALGLELAGTRFLWA
         .::: ::.  :..  .::.::     :  ..:      .... ::::..    :::::::::::: ..   .: :::::::::.:   :.::
QUERY   WLPLLETLHQVPVVPVGLLPPEIPGDEKDETWVSIKKWLDGKQKGSVVYVALGSEVLVSQTEVVELALGLELSGLPFVWA
              240       250       260       270       280       290       300       310

     310        320       330       340       350       360       370       380
QUERY   LRKPTGV--SDADLLPAGFEERTRGRGVVATRWVPQMSILAHAAVGAFLTHCGWNSTIEGLMFGHPLIMLPIFGDQGPNA
        ::: :    ::.  :: :: :::: ::.: : :.::. ::.: .: .:::::: .: .::::::::::::::::::  ::
QUERY   YRKPKGPAKSDSVELPDGFVERTRDRGLVWTSWAPQLRILSHESVCGFLTHCGSGSIVEGLMFGHPLIMLPIFGDQPLNA
              320       330       340       350       360       370       380       390

       390       400       410       420       430       440       450       460
QUERY   RLIEAKNAGLQVARNDGDGSFDREGVAAAIRAVAVEEESSKVFQAKAKKLQEIVADMACHERYIDGFIQQLRSYKD
        ::.: :..:...  ::. ::  .  .:.::  ..:.:.::.:.  ....:.:..:..:   :    ...:.. :.. :
QUERY   RLLEDKQVGIEIPRNEEDGCLTKESVARSLRSVVVEKEG-EIYKANARELSKIYNDTKVEKEYVSQFVDYLEKNARAVAI
              400       410       420       430       440       450       460

QUERY   DHES
     470


462 residues in 1 query   sequences
473 residues in 1 library sequences
 Tcomplib [36.3.5a Jun, 2011(preload8)] (16 proc in memory [0G])
 start: Thu Jul  7 13:19:40 2011 done: Thu Jul  7 13:19:40 2011
 Scan time:  0.030 Display time:  0.010

Function used was FASTA [36.3.5a Jun, 2011(preload8)]
```

FIG. 7

>EUGT-11 Protein. (SEQ ID NO: 152)
MDSGYSSSYAAAAGMHVVICPWLAFGHLLPCLDLAQRLASRGHRVSFVSTPRNISRLPPVRPALAPLVAFVALPLPRVEGLPDGAESTNDVPHDRPDMVELHRRAFDGLAAPFSEFLGTA
CADWVIVDVFHHWAAAAALEHKVPCAMMLLGSAHMIASIADRRLERAETESPAAAGQGRPAAAPTFEVARMKLIRTKGSSGMSLAERFSLTLSRSSLVVGRSCVEFEPETVPLLSTLRGK
PITFLGLMPPLHEGRREDGEDATVRWLDAQPAKSVVYVALGSEVPLGVEKVHELALGLELAGTRFLWALRKPTGVSDADLLPAGFEERTRGRGVVATRWVPQMSILAHAAVGAFLTHCG
WNSTIEGLMFGHPLIMLPIFGDQGPNARLIEAKNAGLQVARNDGDGSFDREGVAAAIRAVAVEEESSKVFQAKAKKLQEIVADMACHERYIDGFIQQLRSYKD >EUGT-11 Native gene. (SEQ ID NO: 153)
ATGGACTCCGGCTACTCCTCCTCCTACGCCGCCGCCGCCGGGATGCACGTCGTGATCTGCCCGTGGCTCGCCTTCGGCCACCTGCTCCCGTGCCTCGACCTCGCCCAGCGCCTCGC
GTCGCGGGGCCACCGCGTGTCGTTCGTCTCCACGCCGCGGAACATATCCCGCCTCCCGCCGGTGCGCCCCGCGCTCGCGCCGCTCGTCGCCTTCGTGGCGCTGCCGCTCCCGCGC
GTCGAGGGGCTCCCCGACGGCGCCGAGTCCACCAACGACGTCCCCCACGACAGGCCGGACATGGTCGAGCTCCACCGGAGGGCCTTCGACGGGCTCGCCGCGCCCTTCTCGGAG
TTCTTGGGCACCGCGTGCGCCGACTGGGTCATCGTCGACGTCTTCCACCACTGGGCCGCAGCCGCCGCTCTCGAGCACAAGGTGCCATGTGCAATGATGTTGTTGGGCTCTGCAC
ATATGATCGCTTCCATAGCAGACAGACGGCTCGAGCGCGCGGAGACAGAGTCGCCTGCGGCTGCCGGGCAGGGACGCCCAGCGGCGGCGCCAACGTTCGAGGTGGCGAGGAT
GAAGTTGATACGAACCAAAGGCTCATCGGGAATGTCCCTCGCCGAGCGCTTCTCCTTGACGCTCTCGAGGAGCAGCCTCGTCGTCGGGCGGAGCTGCGTGGAGTTCGAGCCGGA
GACCGTCCCGCTCCTGTCGACGCTCCGCGGTAAGCCTATTACCTTCCTTGGCCTTATGCCGCCGTTGCATGAAGGCCGCCGCGAGGACGGCGAGGATGCCACCGTCCGCTGGCTC
GACGCGCAGCCGGCCAAGTCCGTCGTGTACGTCGCGCTAGGCAGCGAGGTGCCACTGGGAGTGGAGAAGGTCCACGAGCTCGCGCTCGGGCTGGAGCTCGCCGGGACGCGCTT
CCTCTGGGCTCTTAGGAAGCCCACTGGCGTCTCCGACGCCGACCTCCTCCCCGCCGGCTTCGAGGAGCGCACGCGCGGCCGCGGCGTCGTGGCGACGAGATGGGTTCCTCAGAT
GAGCATACTGGCGCACGCCGCCGTGGGCGCGTTCCTGACCCACTGCGGCTGGAACTCGACCATCGAGGGGCTCATGTTCGGCCACCCGCTTATCATGCTGCCGATCTTCGGCGAC
CAGGGACCGAACGCGCGGCTAATCGAGGCGAAGAACGCCGGATTGCAGGTGGCAAGAAACGACGGCGATGGATCGTTCGACCGAGAAGGCGTCGCGGCGGCGATTCGTGCAG
TCGCGGTGGAGGAAGAAAGCAGCAAAGTGTTTCAAGCCAAAGCCAAGAAGCTGCAGGAGATCGTCGCGGACATGGCCTGCCATGAGAGGTACATCGACGGATTCATTCAGCAA
TTGAGATCTTACAAGGATTGA >EUGT-11 Optimized DNA. (SEQ ID NO: 154)
ATGGATAGTGGCTACTCCTCATCTTATGCTGCTGCCGCTGGTATGCACGTTGTGATCTGCCCTTGGTTGGCCTTTGGTCACCTGTTACCATGTCTGGATTTAGCCCAAAGACTGGCC
TCAAGAGGCCATAGAGTATCATTTGTGTCTACTCCTAGAAATATCTCTCGTTTACCACCAGTCAGACCTGCTCTAGCTCCTCTAGTTGCATTCGTTGCTCTTCCACTTCCAAGAGTAG
AAGGATTGCCAGACGGCGCTGAATCTACTAATGACGTACCACATGATAGACCTGACATGGTCGAATTGCATAGAAGAGCCTTTGATGGATTGGCAGCTCCATTTTCTGAGTTCCTG
GGCACAGCATGTGCAGACTGGGTTATAGTCGATGTATTTCATCACTGGGCTGCTGCAGCCGCATTGGAACATAAGGTGCCTTGTGCTATGATGTTGTTAGGGTCAGCACACATGA
TCGCATCCATAGCTGATAGAAGATTGGAAAGAGCTGAAACAGAATCCCCAGCCGCAGCAGGACAAGGTAGGCCAGCTGCCGCCCCAACCTTTGAAGTGGCTAGAATGAAATTGA
TTCGTACTAAAGGTAGTTCAGGGATGAGTCTTGCTGAAAGGTTTTCTCTGACATTATCTAGATCATCATTAGTTGTAGGTAGATCCTGCGTCGAGTTCGAACCTGAAACAGTACCTT
TACTATCTACTTTGAGAGGCAAACCTATTACTTTCCTTGGTCTAATGCCTCCATTACATGAAGGAAGGAGAGAAGATGGTGAAGATGCTACTGTTAGGTGGTTAGATGCCCAACCT
GCTAAGTCTGTTGTTTACGTTGCATTGGGTTCTGAGGTACCACTAGGGGTGGAAAAGGTGCATGAATTAGCATTAGGACTTGAGCTGGCCGGAACAAGATTCCTTTGGGCTTTGA
GAAAACCAACCGGTGTTTCTGACGCCGACTTGCTACCAGCTGGGTTCGAAGAGAGAACAAGAGGCCGTGGTGTCGTTGCTACTAGATGGGTCCCACAAATGAGTATTCTAGCTCA
TGCAGCTGTAGGGGCCTTTCTAACCCATTGCGGTTGGAACTCAACAATAGAAGGACTGATGTTTGGTCATCCACTTATTATGTTACCAATCTTTGGCGATCAGGGACCTAACGCAA
GATTGATTGAGGCAAAGAACGCAGGTCTGCAGGTTGCACGTAATGATGGTGATGGTTCCTTTGATAGAGAAGGCGTTGCAGCTGCCATCAGAGCAGTCGCCGTTGAGGAAGAGT
CATCTAAAGTTTTCCAAGCTAAGGCCAAAAAATTACAAGAGATTGTGGCTGACATGGCTTGTCACGAAAGATACATCGATGGTTTCATCCAACAATTGAGAAGTTATAAAGACTAA

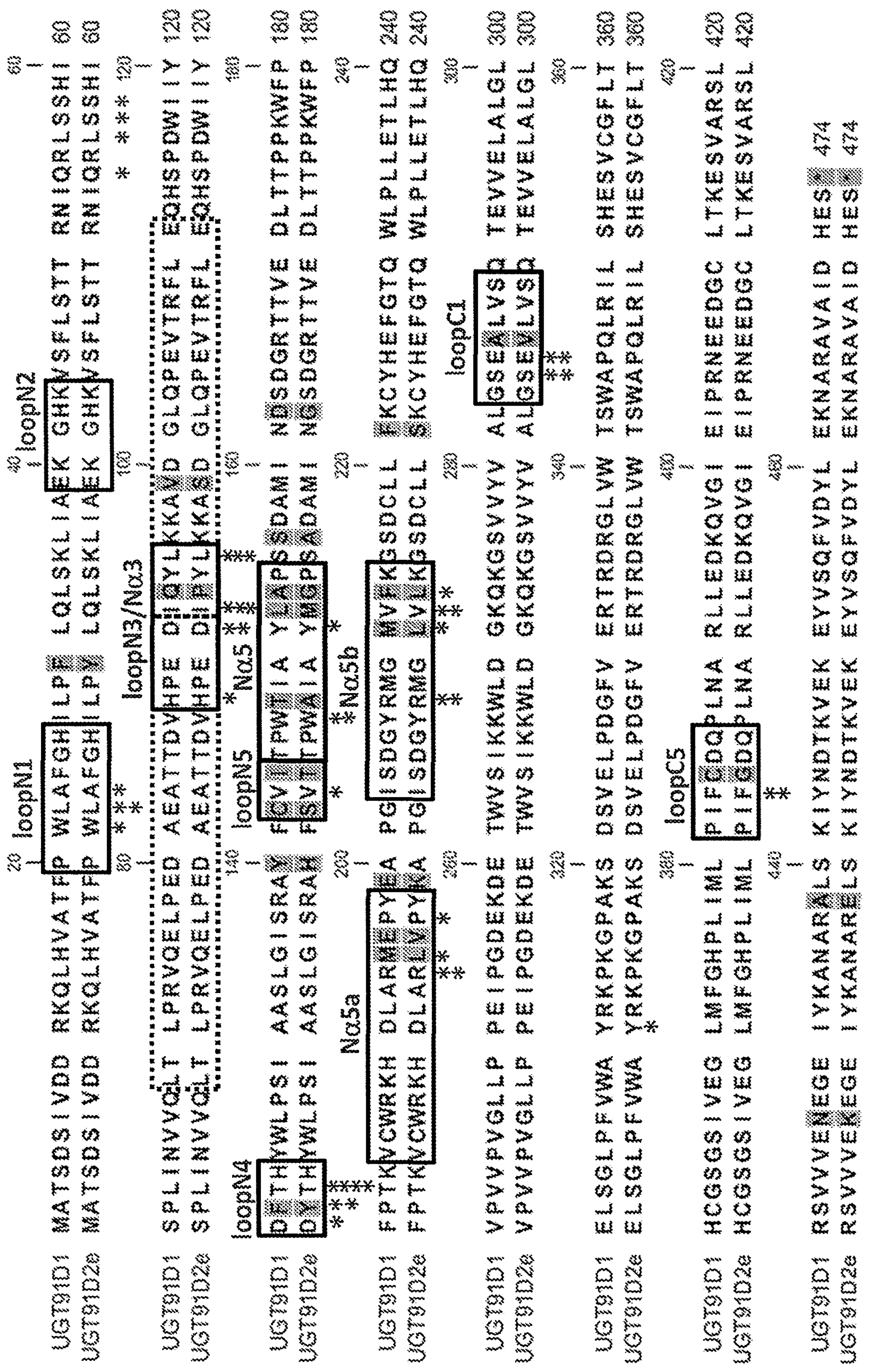

FIG. 9

```
UGT91D1  MATSDSIVDD RKQLHVATFP WLAFGHILPF LQLSKLIAEK GHKVSFLSTT RNIQRLSSHI  60
UGT91D2e MATSDSIVDD RKQLHVATFP WLAFGHILPW LQLSKLIAEK GHKVSFLSTT RNIQRLSSHI  60
                             loopN1                  loopN2
                              *          *           *    ****

UGT91D1  SPLINVVQLT LPRVQELPED AEATTDVHPE DIQYLKKAVD GLQPEVTRFL EQHSPDWIIY 120
UGT91D2e SPLINVVQLT LPRVQELPED AEATTDVHPE DIPYLKKASD GLQPEVTRFL EQHSPDWIIY 120
                                         loopN3/Nα3
                                          *  ***

UGT91D1  DETHYWLPSI AASLGISRAY FCVITPWTIA YLAPSSDAMI NDSDGRTTVE DLTTPPKWFP 180
UGT91D2e DTTHYWLPSI AASLGISRAH FSVITPWAIA YMGPSADAMI NGSDGRTTVE DLTTPPKWFP 180
         loopN4                loopN5                *
          ****                  *   ***    ***

UGT91D1  FPTKVCWRKH DLARMEPYEA PGISDGYRMG MVFKGSDCLL KCYHEFGTQ  WLPLLETLHQ 240
UGT91D2e FPTKVCWRKH DLARLMPYKA PGISDGYRMG LVLKGSDCLL SKCYHEFGTQ WLPLLETLHQ 240
                    Nα5a                  Nα5b
                       **  *                 **     *

UGT91D1  VPVVPVGLLP PEIPGDEKDE TWVSIKKWLD GKQKGSVVYV ALGSEALVSQ TEVVELALGL 300
UGT91D2e VPVVPVGLLP PEIPGDEKDE TWVSIKKWLD GKQKGSVVYV ALGSEMLVSQ TEVVELALGL 300
                   *                                 loopC1
                                                       **

UGT91D1  ELSGLPFVWA YRKPKGPAKS EIPRNEEDGC LTKESVARSL SHESVCGFLT 360
UGT91D2e ELSGLPFVWA YRKPKGPAKS EIPRNEEDGC LTKESVARSL SHESVCGFLT 360
                    *

UGT91D1  HCGSGSIVEG LMFGHPLIML PIFEDQPLNA RLLEDKQVGI EYVSQFVDYL 420
UGT91D2e HCGSGSIVEG LMFGHPLIML PIFSDQPLNA RLLEDKQVGI EYVSQFVDYL 420
                             loopC5
                              **

UGT91D1  RSVVVENEGE IYKANARALS KIYNDTKVEK EYVSQFVDYL EKNARAVAID HES  474
UGT91D2e RSVVVEKEGE IYKANARELS KIYNDTKVEK EYVSQFVDYL EKNARAVAID HES  474
```

FIG. 12A

*Stevia rebaudiana* KAH nucleotide (SEQ ID NO: 163)

ATGGAGGCTTCATATCTATACATTTCCATTCTTCTGCTTCTAGCTTCGTACCTCTTCACCACCCAACTTCGTCGTAAATCCGCCAATCT
ACCGCCGACGGTGTTCCCATCCATCCCCATAATCGGTCATCTCTACCTCCTCAAAAAACCACTCTATAGAACACTAGCCAAAATTGCCG
CCAAATACGGCCCTATCCTCCAACTCCAACTAGGGTACCGCCGTGTCCTCGTAATCTCCTCCCCTTCCGCCGCCGAAGAATGCTTCACC
AACAACGACGTTATCTTCGCCAACCGTCCGAAGACGCTATTCGGAAAAATTGTAGGGGGTACCAGCCTCGGGTCGCTGTCGTACGGCGA
CCAGTGGCGCAACCTCCGCCGCGTTGCATCCATCGAGATTCTATCAGTCCACCGGCTCAACGAGTTTCACGACATACGTGTTGACGAAA
ACCGGCTTCTGATCCGTAAACTAAGATCCAGTTCTTCTCCGGTGACTCTGATAACGGTGTTTTACGCACTAACGTTAAATGTGATTATG
AGAATGATCTCCGGAAAGAGGTATTTCGACTCGGGTGATCGGGAATTGGAGGAGGAAGGGAAGCGATTCCGGGAGATACTCGATGAGAC
ACTTTTGCTCGCGGGTGCTTCTAATGTTGGGGATTACTTGCCGATTCTGAATTGGTTGGGGGTGAAGAGCTTGGAGAAGAAGCTAATCG
CATTGCAGAAAAAGAGAGATGATTTCTTTCAGGGACTGATCGAGCAAGTTCGGAAATCTAGAGGGGCTAAAGTGGGAAAAGGAAGGAAG
ACGATGATCGAGTTGTTGTTATCCCTACAAGAATCTGAACCTGAGTATTACACTGACGCCATGATCCGATCATTTGTGCTGGGTTTATT
AGCAGCAGGGAGTGATACATCGGCTGGAACTATGGAATGGGCGATGTCTCTTTTGGTAAACCACCCGCACGTATTAAAAAGGCACAGG
CTGAAATTGATCGAGTCATCGGCAACAACCGTCTAATTGATGAGTCCGACATAGGGAATATACCTTACATTGGTTGCATCATAAACGAG
ACGCTCAGATTGTACCCTGCGGGCCCGTTGCTATTTCCCCATGAGTCATCAGCGGACTGTGTTATCAGCGGGTACAACATCCCTCGTGG
GACGATGCTTATTGTCAACCAATGGGCGATACATCATGACCCAAAGGTGTGGGACGACCCTGAGACATTCAAACCGGAAAGATTCCAAG
GGCTTGAAGGGACACGAGACGGGTTTAAGCTGATGCCTTTTGGGTCCGGAAGGAGGGGTTGTCCAGGGGAGGGATTGGCGATTCGTTTG
CTTGGGATGACTCTCGGGTCGGTTATCCAATGCTTTGATTGGGAACGAGTCGGTGACGAGATGGTTGATATGACCGAAGGTCTTGGGGT
CACGTTGCCTAAAGCTGTACCATTAGTCGCCAAGTGCAAGCCGCGTTCCGAAATGACGAATCTACTCTCTGAGCTATGA

FIG. 12B

*Stevia rebaudiana* KAHe1 nucleotide (SEQ ID NO: 165)

ATGGAAGCCTCTTACCTATACATTTCTATTTTGCTTTTACTGGCATCATACCTGTTCACCACTCAACTTAGAAGGAAGAGCGCTAATCT
ACCACCAACCGTGTTTCCATCAATACCAATCATTGGACACTTATACTTACTCAAAAAGCCTCTTTATAGAACTTTAGCAAAAATTGCCG
CTAAGTACGGACCAATACTGCAATTACAACTCGGCTACAGACGTGTTCTGGTGATTTCCTCACCATCAGCAGCAGAAGAGTGCTTTACC
AATAACGATGTAATCTTCGCAAATAGACCTAAGACATTGTTTGGCAAAATAGTGGGTGGAACATCCCTTGGCAGTTTATCCTACGGCGA
TCAATGGCGTAATCTAAGGAGAGTAGCTTCTATCGAAATCCTATCAGTTCATAGGTTGAACGAATTTCATGATATCAGAGTGGATGAGA
ACAGATTGTTAATTAGAAAACTTAGAAGTTCATCTTCTCCTGTTACTCTTATAACAGTCTTTTATGCTCTAACATTGAACGTCATTATG
AGAATGATCTCTGGCAAAAGATATTTCGACAGTGGGGATAGAGAATTGGAGGAGGAAGGTAAGAGATTTCGAGAAATCTTAGACGAAAC
GTTGCTTCTAGCCGGTGCTTCTAATGTTGGCGACTACTTACCAATATTGAACTGGTTGGGAGTTAAGTCTCTTGAAAAGAAATTGATCG
CTTTGCAGAAAAAGAGAGATGACTTTTTCCAGGGTTTGATTGAACAGGTTAGAAAATCTCGTGGTGCTAAAGTAGGCAAAGGTAGAAAA
ACGATGATCGAACTCTTATTATCTTTGCAAGAGTCAGAACCTGAGTACTATACAGATGCTATGATAAGATCTTTTGTCCTAGGTCTGCT
GGCTGCAGGTAGTGATACTTCAGCGGGCACTATGGAATGGGCCATGAGCTTACTGGTCAATCACCCACATGTATTGAAGAAAGCTCAAG
CTGAAATCGATAGAGTTATCGGTAATAACAGATTGATTGACGAGTCAGACATTGGAAATATCCCTTACATCGGGTGTATTATCAATGAA
ACTCTAAGACTCTATCCAGCAGGGCCATTGTTGTTCCCACATGAAAGTTCTGCCGACTGCGTTATTTCCGGTTACAATATACCTAGAGG
TACAATGTTAATCGTAAACCAATGGGCGATTCATCACGATCCTAAAGTCTGGGATGATCCTGAAACCTTTAAACCTGAAAGATTTCAAG
GATTAGAAGGAACTAGAGATGGTTTCAAACTTATGCCATTCGGTTCTGGGAGAAGAGGATGTCCAGGTGAAGGTTTGGCAATAAGGCTG
TTAGGGATGACACTAGGCTCAGTGATCCAATGTTTTGATTGGGAGAGAGTAGGAGATGAGATGGTTGACATGACAGAAGGTTTGGGTGT
CACACTTCCTAAGGCCGTTCCATTAGTTGCCAAATGTAAGCCACGTTCCGAAATGACTAATCTCCTATCCGAACTTTAA

FIG. 12C

*Stevia rebaudiana* KAHe1 polypeptide (SEQ ID NO:164)

MEASYLYISILLLLASYLFTTQLRRKSANLPPTVFPSIPIIGHLYLLKKPLYRTLAKIAA
KYGPILQLQLGYRRVLVISSPSAAEECFTNNDVIFANRPKTLFGKIVGGTSLGSLSYGDQ
WRNLRRVASIEILSVHRLNEFHDIRVDENRLLIRKLRSSSSPVTLITVFYALTLNVIMRM
ISGKRYFDSGDRELEEEGKRFREILDETLLLAGASNVGDYLPILNWLGVKSLEKKLIALQ
KKRDDFFQGLIEQVRKSRGAKVGKGRKTMIELLLSLQESEPEYYTDAMIRSFVLGLLAAG
SDTSAGTMEWAMSLLVNHPHVLKKAQAEIDRVIGNNRLIDESDIGNIPYIGCIINETLRL
YPAGPLLFPHESSADCVISGYNIPRGTMLIVNQWAIHHDPKVWDDPETFKPERFQGLEGT
RDGFKLMPFGSGRRGCPGEGLAIRLLGMTLGSVIQCFDWERVGDEMVDMTEGLGVTLPKA
VPLVAKCKPRSEMTNLLSEL

FIG. 13A

*S. cerevisiae* CPR polypeptide encoded by NCP1 (SEQ ID NO: 166)

MPFGIDNTDFTVLAGLVLAVLLYVKRNSIKELLMSDDGDITAVSSGNRDIAQVVTENNKNYLVLYASQTGTAEDYAKKFSKELVAKFNL
NVMCADVENYDFESLNDVPVIVSIFISTYGEGDFPDGAVNFEDFICNAEAGALSNLRYNMFGLGNSTYEFFNGAAKKAEKHLSAAGAIR
LGKLGEADDGAGTTDEDYMAWKDSILEVLKDELHLDEQEAKFTSQFQYTVLNEITDSMSLGEPSAHYLPSHQLNRNADGIQLGPFDLSQ
PYIAPIVKSRELFSSNDRNCIHSEFDLSGSNIKYSTGDHLAVWPSNPLEKVEQFLSIFNLDPETIFDLKPLDPTVKVPFPTPTTIGAAI
KHYLEITGPVSRQLFSSLIQFAPNADVKEKLTLLSKDKDQFAVEITSKYFNIADALKYLSDGAKWDTVPMQFLVESVPQMTPRYYSISS
SSLSEKQTVHVTSIVENFPNPELPDAPPVVGVTTNLLRNIQLAQNNVNIAETNLPVHYDLNGPRKLFANYKLPVHVRRSNFRLPSNPST
PVIMIGPGTGVAPFRGFIRERVAFLESQKKGGNNVSLGKHILFYGSRNTDDFLYQDEWPEYAKKLDGSFEMVVAHSRLPNTKKVYVQDK
LKDYEDQVFEMINNGAFIYVCGDAKGMAKGVSTALVGILSRGKSITTDEATELIKMLKTSGRYQEDVW

*Arabidopsis thaliana* CPR polypeptide encoded by ATR1 (SEQ ID NO: 148)

1 mtsalyasdl fkqlksimgt dslsddvvlv iattslalva gfvvllwkkt tadrsgelkp
61 lmipkslmak dedddldlgs gktrvsiffg tqtgtaegfa kalseeikar yekaavkvid
121 lddyaadddq yeeklkketl affcvatygd geptdnaarf ykwfteener diklqqlayg
181 vfalgnrqye hfnkigivld eelckkgakr lievglgddd qsieddfnaw keslwseldk
241 llkdeddksv atpytavipe yrvvthdprf ttqksmesnv angnttidih hpcrvdvavq
301 kelhthesdr scihlefdis rtgityetgd hvgvyaenhv eiveeagkll ghsldlvfsi
361 hadkedgspl esavpppfpq pctlgtglar yadllnpprk salvalaaya tepseaeklk
421 hltspdgkde ysqwivasqr sllevmaafp sakpplgvff aaiaprlqpr yysissspr1
481 apsrvhvtsa lvygptptgr ihkgvcstwm knavpaeksh ecsgapifir asnfklpsnp
541 stpivmvgpg tglapfrgfl qermalkedg eelgssllff gcrnrqmdfi yedelnnfvd
601 qgviselima fsregaqkey vqhkmmekaa qvwdlikeeg ylyvcgdakg mardvhrtlh
661 tivqeqegvs sseaeaivkk lqtegrylrd vw

*A. thaliana* CPR polypeptide encoded by ATR2 (SEQ ID NO: 168)

1 msssssssts midlmaaiik gepvivsdpa nasayesvaa elssmlienr qfamivttsi
61 avligcivml vwrrsgsgns krveplkplv ikpreeeidd grkkvtiffg tqtgtaegfa

FIG. 13A (cont'ed)

121 kalgeeakar yektrfkivd lddyaaddde yeeklkkedv affflatygd geptdnaarf
181 ykwftegndr gewlknlkyg vfglgnrqye hfnkvakvvd dilveqgaqr lvqvglgddd
241 qcieddftaw realwpeldt ilreegdtav atpytaavle yrvsihdsed akfnditlan
301 gnqytvfdaq hpykanvavk relhtpesdr scihlefdia gsqltmklgd hvgvlcdnls
361 etvdealrll dmspdtyfsl haekedgtpi ssslpppfpp cnlrtaltry acllsspkks
421 alvalaahas dpteaerlkh laspagkdey skwvvesqrs llevmaefps akpplgvffa
481 gvaprlqprf ysisssspkia etrihvtcal vyekmptgri hkgvcstwmk navpyeksek
541 lflgrpifvr qsnfklpsds kvpiimigpg tglapfrgfl qerlalvesg velgpsvlff
601 gcrnrrmdfi yeeelqrfve sgalaelsva fsregptkey vqhkmmdkas diwnmisqga
661 ylyvcgdakg mardvhrslh tiaqeqgsmd stkaegfvkn lqtsgrylrd vw

*Stevia rebaudiana* CPR7 (SEQ ID NO: 169)

MQSESVEASTIDLMTAVLKDTVIDTANASDNGDSKMPPALAMMFEIRDLLLILTTSVAVLVGCFVVLVWKRSSGKKSGKELEPPKIVVP
KRRLEQEVDDGKKKVTIFFGTQTGTAEGFAKALFEEAKARYEKAAFKVIDLDDYAADLDEYAEKLKKETYAFFFLATYGDGEPTDNAAK
FYKWFTEGDEKGVWLQKLQYGVFGLGNRQYEHFNKIGIVVDDGLTEQGAKRIVPVGLGDDDQSIEDDFSAWKELVWPELDLLLRDEDDK
AAATPYTAAIPEYRVVFHDKPDAFSDDHTQTNGHAVHDAQHPCRSNVAVKKELHTPESDRSCTHLEFDISHTGLSYETGDHVGVYCENL
IEVVEEAGKLLGLSTDTYFSLHIDNEDGSPLGGPSLQPPFPPCTLRKALTNYADLLSSPKKSTLLALAAHASDPTEADRLRFLASREGK
DEYAEWVVANQRSLLEVMEAFPSARPPLGVFFAAVAPRLQPRYYSISSSPKMEPNRIHVTCALVYEKTPAGRIHKGICSTWMKNAVPLT
ESQDCSWAPIFVRTSNFRLPIDPKVPVIMIGPGTGLAPFRGFLQERLALKESGTELGSSILFFGCRNRKVDYIYENELNNFVENGALSE
LDVAFSRDGPTKEYVQHKMTQKASEIWNMLSEGAYLYVCGDAKGMAKDVHRTLHTIVQEQGSLDSSKAELYVKNLQMSGRYLRDVW

*Stevia rebaudiana* CPR8 (SEQ ID NO: 170)

MQSNSVKISPLDLVTALFSGKVLDTSNASESGESAMLPTIAMIMENRELLMILTTSVAVLIGCVVVLVWRRSSTKKSALEPPVIVVPKR
VQEEEVDDGKKKVTVFFGTQTGTAEGFAKALVEEAKARYEKAVFKVIDLDDYAADDDEYEEKLKKESLAFFFLATYGDGEPTDNAARFY
KWFTEGDAKGEWLNKLQYGVFGLGNRQYEHFNKIAKVVDDGLVEQGAKRLVPVGLGDDDQCIEDDFTAWKELVWPELDQLLRDEDDTTV
ATPYTAAVAEYRVVFHEKPDALSEDYSYTNGHAVHDAQHPCRSNVAVKKELHSPESDRSCTHLEFDISNTGLSYETGDHVGVYCENLSE
VVNDAERLVGLPPDTYSSIHTDSEDGSPLGGASLPPPFPPCTLRKALTCYADVLSSPKKSALLALAAHATDPSEADRLKFLASPAGKDE
YSQWIVASQRSLLEVMEAFPSAKPSLGVFFASVAPRLQPRYYSISSSPKMAPDRIHVTCALVYEKTPAGRIHKGVCSTWMKNAVPMTES
QDCSWAPIYVRTSNFRLPSDPKVPVIMIGPGTGLAPFRGFLQERLALKEAGTDLGLSILFFGCRNRKVDFIYENELNNFVETGALSELI
VAFSREGPTKEYVQHKMSEKASDIWNLLSEGAYLYVCGDAKGMAKDVHRTLHTIVQEQGSLDSSKAELYVKNLQMSGRYLRDVW

FIG. 13B

>ATR1 codon optimized by DNA2.0. (SEQ ID NO: 171)

ATGACTTCTGCACTTTATGCCTCCGATCTTTTCAAACAATTGAAAAGTATCATGGGAACGGATTCTTTGTCCGATGATGTTGTATTAGT
TATTGCTACAACTTCTCTGGCACTGGTTGCTGGTTTCGTTGTCTTATTGTGGAAAAAGACCACGGCAGATCGTTCCGGCGAGCTAAAGC
CACTAATGATCCCTAAGTCTCTGATGGCGAAAGATGAGGATGATGACTTAGATCTAGGTTCTGGAAAAACGAGAGTCTCTATCTTCTTC
GGCACACAAACCGGAACAGCCGAAGGATTCGCTAAAGCACTTTCAGAAGAGATCAAAGCAAGATACGAAAAGGCGGCTGTAAAAGTAAT
CGATTTGGATGATTACGCTGCCGATGATGACCAATATGAGGAAAAGTTGAAAAAGGAAACATTGGCTTTCTTTTGTGTAGCCACGTATG
GTGATGGTGAACCAACCGATAACGCCGCAAGATTCTACAAGTGGTTTACTGAAGAGAACGAAAGAGATATCAAGTTGCAGCAACTTGCT
TACGGCGTTTTTGCCTTAGGTAACAGACAATACGAGCACTTTAACAAGATAGGTATTGTCTTAGATGAAGAGTTATGCAAAAAGGGTGC
GAAGAGATTGATTGAAGTCGGTTTAGGAGATGATGATCAATCTATCGAGGATGACTTTAATGCATGGAAGGAATCTTTGTGGTCTGAAT
TAGATAAGTTACTTAAGGACGAAGATGATAAATCCGTTGCCACTCCATACACAGCCGTCATTCCAGAATATAGAGTAGTTACTCATGAT
CCAAGATTCACAACACAGAAATCAATGGAAAGTAATGTGGCTAATGGTAATACTACCATCGATATTCATCATCCATGTAGAGTAGACGT
TGCAGTTCAAAAGGAATTGCACACTCATGAATCAGACAGATCTTGCATACATCTTGAATTTGATATATCACGTACTGGTATCACTTACG
AAACAGGTGATCACGTGGGTGTCTACGCTGAAAACCATGTTGAAATTGTAGAGGAAGCTGGAAAGTTGTTGGGCCATAGTTTAGATCTT
GTTTTCTCAATTCATGCCGATAAAGAGGATGGCTCACCACTAGAAAGTGCAGTGCCTCCACCATTTCCAGGACCATGCACCCTAGGTAC
CGGTTTAGCTCGTTACGCGGATCTGTTAAATCCTCCACGTAAATCAGCTCTAGTGGCCTTGGCTGCGTACGCCACAGAACCTTCTGAGG
CAGAAAAACTGAAACATCTAACTTCACCAGATGGTAAGGATGAATACTCACAATGGATAGTAGCTAGTCAACGTTCTTTACTAGAAGTT
ATGGCTGCTTTCCCATCCGCTAAACCTCCTTTGGGTGTTTTCTTCGCCGCAATAGCGCCTAGACTGCAACCAAGATACTATTCAATTTC
ATCCTCACCTAGACTGGCACCATCAAGAGTTCATGTCACATCCGCTTTAGTGTACGGTCCAACTCCTACTGGTAGAATCCATAAGGGCG
TTTGTTCAACATGGATGAAAAACGCGGTTCCAGCAGAGAAGTCTCACGAATGTTCTGGTGCTCCAATCTTTATCAGAGCCTCCAACTTC
AAACTGCCTTCCAATCCTTCTACTCCTATTGTCATGGTCGGTCCTGGTACAGGTCTTGCTCCATTCAGAGGTTTCTTACAAGAGAGAAT
GGCCTTAAAGGAGGATGGTGAAGAGTTGGGATCTTCTTTGTTGTTTTTCGGCTGTAGAAACAGACAAATGGATTTCATCTACGAAGATG
AACTGAATAACTTTGTAGATCAAGGAGTTATTTCAGAGTTGATAATGGCTTTTTCTAGAGAAGGTGCTCAGAAGGAGTACGTCCAACAC
AAAATGATGGAAAAGGCCGCACAAGTTTGGGACTTAATCAAAGAGGAAGGCTATCTATATGTCTGTGGTGATGCAAAGGGTATGGCAAG
AGATGTTCACAGAACACTTCATACTATAGTCCAGGAACAGGAAGGCGTTAGTTCTTCTGAAGCGGAAGCAATTGTGAAAAAGTTACAAA
CAGAGGGAAGATACTTGAGAGATGTGTGGTAA

FIG. 13B (cont'ed)

>ATR2 codon optimized by Genscript (SEQ ID NO: 172)
ATGTCTTCCTCTTCCTCTTCCAGTACCTCTATGATTGATTTGATGGCTGCTATTATTAAAGGTGAACCAGTTATCGTCTCCGACCCAGC
AAATGCCTCTGCTTATGAATCAGTTGCTGCAGAATTGTCTTCAATGTTGATCGAAAACAGACAATTCGCCATGATCGTAACTACATCAA
TCGCTGTTTTGATCGGTTGTATTGTCATGTTGGTATGGAGAAGATCCGGTAGTGGTAATTCTAAAAGAGTCGAACCTTTGAAACCATTA
GTAATTAAGCCAAGAGAAGAAGAAATAGATGACGGTAGAAAGAAAGTTACAATATTTTTCGGTACCCAAACTGGTACAGCTGAAGGTTT
TGCAAAAGCCTTAGGTGAAGAAGCTAAGGCAAGATACGAAAAGACTAGATTCAAGATAGTCGATTTGGATGACTATGCCGCTGATGACG
ATGAATACGAAGAAAAGTTGAAGAAAGAAGATGTTGCATTTTTCTTTTTGGCAACCTATGGTGACGGTGAACCAACTGACAATGCAGCC
AGATTCTACAAATGGTTTACAGAGGGTAATGATCGTGGTGAATGGTTGAAAAACTTAAAGTACGGTGTTTTCGGTTTGGGTAACAGACA
ATACGAACATTTCAACAAAGTTGCAAAGGTTGTCGACGATATTTTGGTCGAACAAGGTGCTCAAAGATTAGTCCAAGTAGGTTTGGGTG
ACGATGACCAATGTATAGAAGATGACTTTACTGCCTGGAGAGAAGCTTTGTGGCCTGAATTAGACACAATCTTGAGAGAAGAAGGTGAC
ACCGCCGTTGCTACCCCATATACTGCTGCAGTATTAGAATACAGAGTTTCCATCCATGATAGTGAAGACGCAAAGTTTAATGATATCAC
TTTGGCCAATGGTAACGGTTATACAGTTTTCGATGCACAACACCCTTACAAAGCTAACGTTGCAGTCAAGAGAGAATTACATACACCAG
AATCCGACAGAAGTTGTATACACTTGGAATTTGATATCGCTGGTTCCGGTTTAACCATGAAGTTGGGTGACCATGTAGGTGTTTTATGC
GACAATTTGTCTGAAACTGTTGATGAAGCATTGAGATTGTTGGATATGTCCCCTGACACTTATTTTAGTTTGCACGCTGAAAAAGAAGA
TGGTACACCAATTTCCAGTTCTTTACCACCTCCATTCCCTCCATGTAACTTAAGAACAGCCTTGACCAGATACGCTTGCTTGTTATCAT
CCCCTAAAAAGTCCGCCTTGGTTGCTTTAGCCGCTCATGCTAGTGATCCTACTGAAGCAGAAAGATTGAAACACTTAGCATCTCCAGCC
GGTAAAGATGAATATTCAAAGTGGGTAGTTGAATCTCAAAGATCATTGTTAGAAGTTATGGCAGAATTTCCATCTGCCAAGCCTCCATT
AGGTGTCTTCTTTGCTGGTGTAGCACCTAGATTGCAACCAAGATTCTACTCAATCAGTTCTTCACCTAAGATCGCTGAAACTAGAATTC
ATGTTACATGTGCATTAGTCTACGAAAAGATGCCAACCGGTAGAATTCACAAGGGTGTATGCTCTACTTGGATGAAAAATGCTGTTCCT
TACGAAAAATCAGAAAAGTTGTTCTTAGGTAGACCAATCTTCGTAAGACAATCAAACTTCAAGTTGCCTTCTGATTCAAAGGTTCCAAT
AATCATGATAGGTCCTGGTACAGGTTTAGCCCCATTCAGAGGTTTCTTGCAAGAAAGATTGGCTTTAGTTGAATCTGGTGTCGAATTAG
GTCCTTCAGTTTTGTTCTTTGGTTGTAGAAACAGAAGAATGGATTTCATCTATGAAGAAGAATTGCAAAGATTCGTCGAATCTGGTGCA
TTGGCCGAATTATCTGTAGCTTTTTCAAGAGAAGGTCCAACTAAGGAATACGTTCAACATAAGATGATGGATAAGGCATCCGACATATG
GAACATGATCAGTCAAGGTGCTTATTTGTACGTTTGCGGTGACGCAAAGGGTATGGCCAGAGATGTCCATAGATCTTTGCACACAATTG
CTCAAGAACAAGGTTCCATGGATAGTACCAAAGCTGAAGGTTTCGTAAAGAACTTACAAACTTCCGGTAGATACTTGAGAGATGTCTGG
TGA

FIG. 13B (cont'ed)

*Stevia rebaudiana* CPR7 (SEQ ID NO: 173; cloned from *S. rebaudiana* cDNA)

ATGCAATCGGAATCCGTTGAAGCATCGACGATTGATTTGATGACTGCTGTTTTGAAGGACACAGTGATCGATACAGCGAACGCATCTGA
TAACGGAGACTCAAAGATGCCGCCGGCGTTGGCGATGATGTTCGAAATTCGTGATCTGTTGCTGATTTTGACTACGTCAGTTGCTGTTT
TGGTCGGATGTTTCGTTGTTTTGGTGTGGAAGAGATCGTCCGGGAAGAAGTCCGGCAAGGAATTGGAGCCGCCGAAGATCGTTGTGCCG
AAGAGGCGGCTGGAGCAGGAGGTTGATGATGGTAAGAAGAAGGTTACGATTTTCTTCGGAACACAAACTGGAACGGCTGAAGGTTTCGC
TAAGGCACTTTTCGAAGAAGCGAAAGCGCGATATGAAAAGGCAGCGTTTAAAGTGATTGATTTGGATGATTATGCTGCTGATTTGGATG
AGTATGCAGAGAAGCTGAAGAAGGAAACATATGCTTTCTTCTTCTTGGCTACATATGGAGATGGTGAGCCAACTGATAATGCTGCCAAA
TTTTATAAATGGTTTACTGAGGGAGACGAGAAAGGCGTTTGGCTTCAAAAACTTCAATATGGAGTATTTGGTCTTGGCAACAGACAATA
TGAACATTTCAACAAGATTGGAATAGTGGTTGATGATGGTCTCACCGAGCAGGGTGCAAAACGCATTGTTCCCGTTGGTCTTGGAGACG
ACGATCAATCAATTGAAGACGATTTTTCGGCATGGAAAGAGTTAGTGTGGCCCGAATTGGATCTATTGCTTCGCGATGAAGATGACAAA
GCTGCTGCAACTCCTTACACAGCTGCAATCCCTGAATACCGCGTCGTATTTCATGACAAACCCGATGCGTTTTCTGATGATCATACTCA
AACCAATGGTCATGCTGTTCATGATGCTCAACATCCATGCAGATCCAATGTGGCTGTTAAAAAAGAGCTTCATACTCCTGAATCCGATC
GTTCATGCACACATCTTGAATTTGACATTTCTCACACTGGATTATCTTATGAAACTGGGGATCATGTTGGTGTATACTGTGAAAACCTA
ATTGAAGTAGTGGAAGAAGCTGGGAAATTGTTAGGATTATCAACAGATACTTATTTCTCGTTACATATTGATAACGAAGATGGTTCACC
ACTTGGTGGACCTTCATTACAACCTCCTTTTCCTCCTTGTACTTTAAGAAAAGCATTGACTAATTATGCAGATCTGTTAAGCTCTCCCA
AAAAGTCAACTTTGCTTGCTCTAGCTGCTCATGCTTCCGATCCCACTGAAGCTGATCGTTTAAGATTTCTTGCATCTCGCGAGGGCAAG
GATGAATATGCTGAATGGGTTGTTGCAAACCAAAGAAGTCTTCTTGAAGTCATGGAAGCTTTCCCGTCAGCTAGACCGCCACTTGGTGT
TTTCTTTGCAGCGGTTGCACCGCGTTTACAGCCTCGTTACTACTCTATTTCTTCCTCCCCAAAGATGGAACCAAACAGGATTCATGTTA
CTTGCGCGTTGGTTTATGAAAAAACTCCCGCAGGTCGTATCCACAAAGGAATCTGCTCAACCTGGATGAAGAACGCTGTACCTTTGACC
GAAAGTCAAGATTGCAGTTGGGCACCGATTTTTGTTAGAACATCAAACTTCAGACTTCCAATTGACCCGAAAGTCCCGGTTATCATGAT
TGGTCCTGGAACCGGGTTGGCTCCATTTAGGGGTTTTCTTCAAGAAAGATTGGCTCTTAAAGAATCCGGAACCGAACTCGGGTCATCTA
TTTTATTCTTCGGTTGTAGAAACCGCAAAGTGGATTACATATATGAGAATGAACTCAACAACTTTGTTGAAAATGGTGCGCTTTCTGAG
CTTGATGTTGCTTTCTCCCGCGATGGCCCGACGAAAGAATACGTGCAACATAAAATGACCCAAAAGGCTTCTGAAATATGGAATATGCT
TTCTGAGGGAGCATATTTATATGTATGTGGTGATGCTAAAGGCATGGCTAAAGATGTACACCGTACACTTCACACCATTGTGCAAGAAC
AGGGAAGTTTGGACTCGTCTAAAGCGGAGTTGTATGTGAAGAATCTACAAATGTCAGGAAGATACCTCCGTGATGTTTGGTAA

FIG. 13B (cont'ed)

*Stevia rebaudiana* CPR8 (SEQ ID NO: 174; CPR cloned from *S. rebaudiana* cDNA)

ATGCAATCTAACTCCGTGAAGATTTCGCCGCTTGATCTGGTAACTGCGCTGTTTAGCGGCAAGGTTTTGGACACATCGAACGCATCGGA
ATCGGGAGAATCTGCTATGCTGCCGACTATAGCGATGATTATGGAGAATCGTGAGCTGTTGATGATACTCACAACGTCGGTTGCTGTAT
TGATCGGATGCGTTGTCGTTTTGGTGTGGCGGAGATCGTCTACGAAGAAGTCGGCGTTGGAGCCACCGGTGATTGTGGTTCCGAAGAGA
GTGCAAGAGGAGGAAGTTGATGATGGTAAGAAGAAAGTTACGGTTTTCTTCGGCACCCAAACTGGAACAGCTGAAGGCTTCGCTAAGGC
ACTTGTTGAGGAAGCTAAAGCTCGATATGAAAAGGCTGTCTTTAAAGTAATTGATTTGGATGATTATGCTGCTGATGACGATGAGTATG
AGGAGAAACTAAAGAAAGAATCTTTGGCCTTTTTCTTTTTGGCTACGTATGGAGATGGTGAGCCAACAGATAATGCTGCCAGATTTTAT
AAATGGTTTACTGAGGGAGATGCGAAAGGAGAATGGCTTAATAAGCTTCAATATGGAGTATTTGGTTTGGGTAACAGACAATATGAACA
TTTTAACAAGATCGCAAAAGTGGTTGATGATGGTCTTGTAGAACAGGGTGCAAAGCGTCTTGTTCCTGTTGGACTTGGAGATGATGATC
AATGTATTGAAGATGACTTCACCGCATGGAAAGAGTTAGTATGGCCGGAGTTGGATCAATTACTTCGTGATGAGGATGACACAACTGTT
GCTACTCCATACACAGCTGCTGTTGCAGAATATCGCGTTGTTTTTCATGAAAAACCAGACGCGCTTTCTGAAGATTATAGTTATACAAA
TGGCCATGCTGTTCATGATGCTCAACATCCATGCAGATCCAACGTGGCTGTCAAAAAGGAACTTCATAGTCCTGAATCTGACCGGTCTT
GCACTCATCTTGAATTTGACATCTCGAACACCGGACTATCATATGAAACTGGGGACCATGTTGGAGTTTACTGTGAAAACTTGAGTGAA
GTTGTGAATGATGCTGAAAGATTAGTAGGATTACCACCAGACACTTACTCCTCCATCCACACTGATAGTGAAGACGGGTCGCCACTTGG
CGGAGCCTCATTGCCGCCTCCTTTCCCGCCATGCACTTTAAGGAAAGCATTGACGTGTTATGCTGATGTTTTGAGTTCTCCCAAGAAGT
CGGCTTTGCTTGCACTAGCTGCTCATGCCACCGATCCCAGTGAAGCTGATAGATTGAAATTTCTTGCATCCCCCGCCGGAAAGGATGAA
TATTCTCAATGGATAGTTGCAAGCCAAAGAAGTCTCCTTGAAGTCATGGAAGCATTCCCGTCAGCTAAGCCTTCACTTGGTGTTTTCTT
TGCATCTGTTGCCCCGCGCTTACAACCAAGATACTACTCTATTTCTTCCTCACCCAAGATGGCACCGGATAGGATTCATGTTACATGTG
CATTAGTCTATGAGAAAACACCTGCAGGCCGCATCCACAAAGGAGTTTGTTCAACTTGGATGAAGAACGCAGTGCCTATGACCGAGAGT
CAAGATTGCAGTTGGGCCCCAATATACGTCCGAACATCCAATTTCAGACTACCATCTGACCCTAAGGTCCCGGTTATCATGATTGGACC
TGGCACTGGTTTGGCTCCTTTTAGAGGTTTCCTTCAAGAGCGGTTAGCTTTAAAGGAAGCCGGAACTGACCTCGGTTTATCCATTTTAT
TCTTCGGATGTAGGAATCGCAAAGTGGATTTCATATATGAAAACGAGCTTAACAACTTTGTGGAGACTGGTGCTCTTTCTGAGCTTATT
GTTGCTTTCTCCCGTGAAGGCCCGACTAAGGAATATGTGCAACACAAGATGAGTGAGAAGGCTTCGGATATCTGGAACTTGCTTTCTGA
AGGAGCATATTTATACGTATGTGGTGATGCCAAAGGCATGGCCAAAGATGTACATCGAACCCTCCACACAATTGTGCAAGAACAGGGAT
CTCTTGACTCGTCAAAGGCAGAACTCTACGTGAAGAATCTACAAATGTCAGGAAGATACCTCCGTGACGTTTGGTAA

FIG. 14A

***Zea mays* CDPS nucleotide ( SEQ ID NO: 157)**

```
atggttttgt cttcttcttg tactacagta ccacacttat cttcattagc tgtcgtgcaa      60
cttggtcctt ggagcagtag gattaaaaag aaaaccgata ctgttgcagt accagccgct     120
gcaggaaggt ggagaagggc cttggctaga gcacagcaca catcagaatc cgcagctgtc     180
gcaaagggca gcagtttgac ccctatagtg agaactgacg ctgagtcaag gagaacaaga     240
tggccaaccg atgacgatga cgccgaacct ttagtggatg agatcagggc aatgcttact     300
tccatgtctg atggtgacat ttccgtgagc gcatacgata cagcctgggt cggattggtt     360
ccaagattag acggcggtga aggtcctcaa tttccagcag ctgtgagatg gataagaaat     420
aaccagttgc ctgacggaag ttggggcgat gccgcattat tctctgccta tgacaggctt     480
atcaataccc ttgcctgcgt tgtaactttg acaaggtggt ccctagaacc agagatgaga     540
ggtagaggac tatctttttt gggtaggaac atgtggaaat tagcaactga agatgaagag     600
tcaatgccta ttggcttcga attagcattt ccatctttga tagagcttgc taagagccta     660
ggtgtccatg acttccctta tgatcaccag gccctacaag gaatctactc ttcaagagag     720
atcaaaatga agaggattcc aaaagaagtg atgcataccg ttccaacatc aatattgcac     780
agtttggagg gtatgcctgg cctagattgg gctaaactac ttaaactaca gagcagcgac     840
ggaagttttt tgttctcacc agctgccact gcatatgctt taatgaatac cggagatgac     900
aggtgtttta gctacatcga tagaacagta aagaaattca acggcggcgt ccctaatgtt     960
tatccagtgg atctatttga acatatttgg gccgttgata gacttgaaag attaggaatc    1020
tccaggtact tccaaaagga gatcgaacaa tgcatggatt atgtaaacag gcattggact    1080
gaggacggta tttgttgggc aaggaactct gatgtcaaag aggtggacga cacagctatg    1140
gcctttagac ttcttaggtt gcacggctac agcgtcagtc ctgatgtgtt taaaaacttc    1200
gaaaaggacg gtgaattttt cgcatttgtc ggacagtcta atcaagctgt taccggtatg    1260
tacaacttaa acagagcaag ccagatatcc ttcccaggcg aggatgtgct tcatagagct    1320
ggtgccttct catatgagtt cttgaggaga aaagaagcag agggagcttt gagggacaag    1380
tggatcattt ctaaagatct acctggtgaa gttgtgtata ctttggattt tccatggtac    1440
ggcaacttac ctagagtcga ggccagagac tacctagagc aatacggagg tggtgatgac    1500
gtttggattg gcaagacatt gtataggatg ccacttgtaa acaatgatgt atatttggaa    1560
ttggcaagaa tggatttcaa ccactgccag gctttgcatc agttagagtg gcaaggacta    1620
aaaagatggt atactgaaaa taggttgatg gactttggtg tcgcccaaga agatgccctt    1680
agagcttatt ttcttgcagc cgcatctgtt tacgagcctt gtagagctgc cgagaggctt    1740
gcatgggcta gagccgcaat actagctaac gccgtgagca cccacttaag aaatagccca    1800
tcattcagag aaaggttaga gcattctctt aggtgtagac ctagtgaaga gacagatggc    1860
tcctggttta actcctcaag tggctctgat gcagttttag taaaggctgt cttaagactt    1920
actgattcat tagccaggga agcacagcca atccatggag gtgacccaga agatattata    1980
cacaagttgt taagatctgc ttgggccgag tgggttaggg aaaaggcaga cgctgccgat    2040
agcgtgtgca atggtagttc tgcagtagaa caagagggat caagaatggt ccatgataaa    2100
cagacctgtc tattattggc tagaatgatc gaaatttctg ccggtagggc agctggtgaa    2160
gcagccagtg aggacggcga tagaagaata attcaattaa caggctccat ctgcgacagt    2220
cttaagcaaa aaatgctagt ttcacaggac cctgaaaaaa atgaagagat gatgtctcac    2280
gtggatgacg aattgaagtt gaggattaga gagttcgttc aatatttgct tagactaggt    2340
gaaaaaaaga ctggatctag cgaaaccagg caaacatttt taagtatagt gaaatcatgt    2400
tactatgctg ctcattgccc acctcatgtc gttgatagac acattagtag agtgattttc    2460
gagccagtaa gtgccgcaaa gtaaccgcgg                                     2490
```

FIG. 14B

*Zea mays* CDPS polypeptide ( SEQ ID NO: 158)

Met Val Leu Ser Ser Ser Cys Thr Thr Val Pro His Leu Ser Ser Leu Ala Val
Val Gln Leu Gly Pro Trp Ser Ser Arg Ile Lys Lys Lys Thr Asp Thr Val Ala
Val Pro Ala Ala Ala Gly Arg Trp Arg Arg Ala Leu Ala Arg Ala Gln His Thr
Ser Glu Ser Ala Ala Val Ala Lys Gly Ser Ser Leu Thr Pro Ile Val Arg Thr
Asp Ala Glu Ser Arg Arg Thr Arg Trp Pro Thr Asp Asp Asp Ala Glu Pro
Leu Val Asp Glu Ile Arg Ala Met Leu Thr Ser Met Ser Asp Gly Asp Ile Ser
Val Ser Ala Tyr Asp Thr Ala Trp Val Gly Leu Val Pro Arg Leu Asp Gly Gly
Glu Gly Pro Gln Phe Pro Ala Ala Val Arg Trp Ile Arg Asn Asn Gln Leu Pro
Asp Gly Ser Trp Gly Asp Ala Ala Leu Phe Ser Ala Tyr Asp Arg Leu Ile Asn
Thr Leu Ala Cys Val Val Thr Leu Thr Arg Trp Ser Leu Glu Pro Glu Met Arg
Gly Arg Gly Leu Ser Phe Leu Gly Arg Asn Met Trp Lys Leu Ala Thr Glu Asp
Glu Glu Ser Met Pro Ile Gly Phe Glu Leu Ala Phe Pro Ser Leu Ile Glu Leu
Ala Lys Ser Leu Gly Val His Asp Phe Pro Tyr Asp His Gln Ala Leu Gln Gly
Ile Tyr Ser Ser Arg Glu Ile Lys Met Lys Arg Ile Pro Lys Glu Val Met His
Thr Val Pro Thr Ser Ile Leu His Ser Leu Glu Gly Met Pro Gly Leu Asp Trp
Ala Lys Leu Leu Lys Leu Gln Ser Ser Asp Gly Ser Phe Leu Phe Ser Pro Ala
Ala Thr Ala Tyr Ala Leu Met Asn Thr Gly Asp Asp Arg Cys Phe Ser Tyr Ile
Asp Arg Thr Val Lys Lys Phe Asn Gly Gly Val Pro Asn Val Tyr Pro Val Asp
Leu Phe Glu His Ile Trp Ala Val Asp Arg Leu Glu Arg Leu Gly Ile Ser Arg
Tyr Phe Gln Lys Glu Ile Glu Gln Cys Met Asp Tyr Val Asn Arg His Trp Thr
Glu Asp Gly Ile Cys Trp Ala Arg Asn Ser Asp Val Lys Glu Val Asp Asp Thr
Ala Met Ala Phe Arg Leu Leu Arg Leu His Gly Tyr Ser Val Ser Pro Asp Val
Phe Lys Asn Phe Glu Lys Asp Gly Glu Phe Phe Ala Phe Val Gly Gln Ser Asn
Gln Ala Val Thr Gly Met Tyr Asn Leu Asn Arg Ala Ser Gln Ile Ser Phe Pro
Gly Glu Asp Val Leu His Arg Ala Gly Ala Phe Ser Tyr Glu Phe Leu Arg Arg
Lys Glu Ala Glu Gly Ala Leu Arg Asp Lys Trp Ile Ile Ser Lys Asp Leu Pro
Gly Glu Val Val Tyr Thr Leu Asp Phe Pro Trp Tyr Gly Asn Leu Pro Arg Val
Glu Ala Arg Asp Tyr Leu Glu Gln Tyr Gly Gly Gly Asp Asp Val Trp Ile Gly
Lys Thr Leu Tyr Arg Met Pro Leu Val Asn Asn Asp Val Tyr Leu Glu Leu Ala
Arg Met Asp Phe Asn His Cys Gln Ala Leu His Gln Leu Glu Trp Gln Gly Leu
Lys Arg Trp Tyr Thr Glu Asn Arg Leu Met Asp Phe Gly Val Ala Gln Glu Asp
Ala Leu Arg Ala Tyr Phe Leu Ala Ala Ala Ser Val Tyr Glu Pro Cys Arg Ala
Ala Glu Arg Leu Ala Trp Ala Arg Ala Ala Ile Leu Ala Asn Ala Val Ser Thr
His Leu Arg Asn Ser Pro Ser Phe Arg Glu Arg Leu Glu His Ser Leu Arg Cys
Arg Pro Ser Glu Glu Thr Asp Gly Ser Trp Phe Asn Ser Ser Ser Gly Ser Asp
Ala Val Leu Val Lys Ala Val Leu Arg Leu Thr Asp Ser Leu Ala Arg Glu Ala
Gln Pro Ile His Gly Gly Asp Pro Glu Asp Ile Ile His Lys Leu Leu Arg Ser
Ala Trp Ala Glu Trp Val Arg Glu Lys Ala Asp Ala Ala Asp Ser Val Cys Asn
Gly Ser Ser Ala Val Glu Gln Glu Gly Ser Arg Met Val His Asp Lys Gln Thr
Cys Leu Leu Leu Ala Arg Met Ile Glu Ile Ser Ala Gly Arg Ala Ala Gly Glu
Ala Ala Ser Glu Asp Gly Asp Arg Arg Ile Ile Gln Leu Thr Gly Ser Ile Cys
Asp Ser Leu Lys Gln Lys Met Leu Val Ser Gln Asp Pro Glu Lys Asn Glu Glu
Met Met Ser His Val Asp Asp Glu Leu Lys Leu Arg Ile Arg Glu Phe Val Gln
Tyr Leu Leu Arg Leu Gly Glu Lys Lys Thr Gly Ser Ser Glu Thr Arg Gln Thr
Phe Leu Ser Ile Val Lys Ser Cys Tyr Tyr Ala Ala His Cys Pro Pro His Val
Val Asp Arg His Ile Ser Arg Val Ile Phe Glu Pro Val Ser Ala Ala Lys

FIG. 15A

Codon-optimized nucleotide sequence for CDPS-KS (SEQ ID NO:161)

ATGCCTGGTAAAATTGAAAATGGTACCCCAAAGGACCTCAAGACTGGAAATGATTTTGTTTCTGCTGCTAAGAGTTTACTAGATCGAGC
TTTCAAAAGTCATCATTCCTACTACGGATTATGCTCAACTTCATGTCAAGTTTATGATACAGCTTGGGTTGCAATGATTCCAAAAACAA
GAGATAATGTAAAACAGTGGTTGTTTCCAGAATGTTTCCATTACCTCTTAAAAACACAAGCCGCAGATGGCTCATGGGGTTCATTGCCT
ACAACACAGACAGCGGGTATCCTAGATACAGCCTCAGCTGTGCTGGCATTATTGTGCCACGCACAAGAGCCTTTACAAATATTGGATGT
ATCTCCAGATGAAATGGGGTTGAGAATAGAACACGGTGTCACATCCTTGAAACGTCAATTAGCAGTTTGGAATGATGTGGAGGACACCA
ACCATATTGGCGTCGAGTTTATCATACCAGCCTTACTTTCCATGCTAGAAAAGGAATTAGATGTTCCATCTTTTGAATTTCCATGTAGG
TCCATCTTAGAGAGAATGCACGGGGAGAAATTAGGTCATTTCGACCTGGAACAAGTTTACGGCAAGCCAAGCTCATTGTTGCACTCATT
GGAAGCATTTCTCGGTAAGCTAGATTTTGATCGACTATCACATCACCTATACCACGGCAGTATGATGGCATCTCCATCTTCAACGGCTG
CTTATCTTATTGGGGCTACAAAATGGGATGACGAAGCCGAAGATTACCTAAGACATGTAATGCGTAATGGTGCAGGACATGGGAATGGA
GGTATTTCTGGTACATTTCCAACTACTCATTTCGAATGTAGCTGGATTATAGCAACGTTGTTAAAGGTTGGCTTTACTTTGAAGCAAAT
TGACGGCGATGGCTTAAGAGGTTTATCAACCATCTTACTTGAGGCGCTTCGTGATGAGAATGGTGTCATAGGCTTTGCCCCTAGAACAG
CAGATGTAGATGACACAGCCAAAGCTCTATTGGCCTTGTCATTGGTAAACCAGCCAGTGTCACCTGATATCATGATTAAGGTCTTTGAG
GGCAAAGACCATTTTACCACTTTTGGTTCAGAAAGAGATCCATCATTGACTTCCAACCTGCACGTCCTTTTATCTTTACTTAAACAATC
TAACTTGTCTCAATACCATCCTCAAATCCTCAAAACAACATTATTCACTTGTAGATGGTGGTGGGGTTCCGATCATTGTGTCAAAGACA
AATGGAATTTGAGTCACCTATATCCAACTATGTTGTTGGTTGAAGCCTTCACTGAAGTGCTCCATCTCATTGACGGTGGTGAATTGTCT
AGTCTGTTTGATGAATCCTTTAAGTGTAAGATTGGTCTTAGCATCTTTCAAGCGGTACTTAGAATAATCCTCACCCAAGACAACGACGG
CTCTTGGAGAGGATACAGAGAACAGACGTGTTACGCAATATTGGCTTTAGTTCAAGCGAGACATGTATGCTTTTTCACTCACATGGTTG
ACAGACTGCAATCATGTGTTGATCGAGGTTTCTCATGGTTGAAATCTTGCTCTTTTCATTCTCAAGACCTGACTTGGACCTCTAAAACA
GCTTATGAAGTGGGTTTCGTAGCTGAAGCATATAAACTAGCTGCTTTACAATCTGCTTCCCTGGAGGTTCCTGCTGCCACCATTGGACA
TTCTGTCACGTCTGCCGTTCCATCAAGTGATCTTGAAAAATACATGAGATTGGTGAGAAAAACTGCGTTATTCTCTCCACTGGATGAGT
GGGGTCTAATGGCTTCTATCATCGAATCTTCATTTTTCGTACCATTACTGCAGGCACAAAGAGTTGAAATATACCCTAGAGATAATATC
AAGGTGGACGAAGATAAGTACTTGTCTATTATCCCATTCACATGGGTCGGATGCAATAATAGGTCTAGAACTTTCGCAAGTAACAGATG
GCTATACGATATGATGTACCTTTCATTACTCGGCTATCAAACCGACGAGTACATGGAAGCTGTAGCTGGGCCAGTGTTTGGGGATGTTT
CCTTGTTACATCAAACAATTGATAAGGTGATTGATAATACAATGGGTAACCTTGCGAGAGCCAATGGAACAGTACACAGTGGTAATGGA
CATCAGCACGAATCTCCTAATATAGGTCAAGTCGAGGACACCTTGACTCGTTTCACAAATTCAGTCTTGAATCACAAAGACGTCCTTAA
CTCTAGCTCATCTGATCAAGATACTTTGAGAAGAGAGTTTAGAACATTCATGCACGCTCATATAACACAAATCGAAGATAACTCACGAT
TCAGTAAGCAAGCCTCATCCGATGCGTTTTCCTCTCCTGAACAATCTTACTTTCAATGGGTGAACTCAACTGGTGGCTCACATGTCGCT
TGCGCCTATTCATTTGCCTTCTCTAATTGCCTCATGTCTGCAAATTTGTTGCAGGGTAAAGACGCATTTCCAAGCGGAACGCAAAAGTA
CTTAATCTCCTCTGTTATGAGACATGCCACAAACATGTGTAGAATGTATAACGACTTTGGCTCTATTGCCAGAGACAACGCTGAGAGAA
ATGTTAATAGTATTCATTTTCCTGAGTTTACTCTCTGTAACGGAACTTCTCAAAACCTAGATGAAAGGAAGGAAAGACTTCTGAAAATC
GCAACTTACGAACAAGGGTATTTGGATAGAGCACTAGAGGCCTTGGAAAGACAGAGTAGAGATGATGCCGGAGACAGAGCTGGATCTAA
AGATATGAGAAAGTTGAAAATCGTTAAGTTATTCTGTGATGTTACGGACTTATACGATCAGCTCTACGTTATCAAAGATTTGTCATCCT
CTATGAAGTAA

FIG. 15B

*Gibberella fujikuroi* CDPS-KS polypeptide(SEQ ID NO:162)

MPGKIENGTPKDLKTGNDFVSAAKSLLDRAFKSHHSYYGLCSTSCQVYDTAWVAMIPKTR
DNVKQWLFPECFHYLLKTQAADGSWGSLPTTQTAGILDTASAVLALLCHAQEPLQILDVS
PDEMGLRIEHGVTSLKRQLAVWNDVEDTNHIGVEFIIPALLSMLEKELDVPSFEFPCRSI
LERMHGEKLGHFDLEQVYGKPSSLLHSLEAFLGKLDFDRLSHHLYHGSMMASPSSTAAYL
IGATKWDDEAEDYLRHVMRNGAGHGNGGISGTFPTTHFECSWIIATLLKVGFTLKQIDGD
GLRGLSTILLEALRDENGVIGFAPRTADVDDTAKALLALSLVNQPVSPDIMIKVFEGKDH
FTTFGSERDPSLTSNLHVLLSLLKQSNLSQYHPQILKTTLFTCRWWWGSDHCVKDKWNLS
HLYPTMLLVEAFTEVLHLIDGGELSSLFDESFKCKIGLSIFQAVLRIILTQDNDGSWRGY
REQTCYAILALVQARHVCFFTHMVDRLQSCVDRGFSWLKSCSFHSQDLTWTSKTAYEVGF
VAEAYKLAALQSASLEVPAATIGHSVTSAVPSSDLEKYMRLVRKTALFSPLDEWGLMASI
IESSFFVPLLQAQRVEIYPRDNIKVDEDKYLSIIPFTWVGCNNRSRTFASNRWLYDMMYL
SLLGYQTDEYMEAVAGPVFGDVSLLHQTIDKVIDNTMGNLARANGTVHSGNGHQHESPNI
GQVEDTLTRFTNSVLNHKDVLNSSSSDQDTLRREFRTFMHAHITQIEDNSRFSKQASSDA
FSSPEQSYFQWVNSTGGSHVACAYSFAFSNCLMSANLLQGKDAFPSGTQKYLISSVMRHA
TNMCRMYNDFGSIARDNAERNVNSIHFPEFTLCNGTSQNLDERKERLLKIATYEQGYLDR
ALEALERQSRDDAGDRAGSKDMRKLKIVKLFCDVTDLYDQLYVIKDLSSSMK

FIG. 17A

Native *A. thaliana* SUS1 nucleotide (SEQ ID NO: 175)

ATGGCAAACGCTGAACGTATGATAACGCGCGTCCACAGCCAACGTGAGCGTTTGAACGAAACGCTTGTTTCTGAGAGAAACGAAGTCCT
TGCCTTGCTTTCCAGGGTTGAAGCCAAAGGTAAAGGTATTTTACAACAAAACCAGATCATTGCTGAATTCGAAGCTTTGCCTGAACAAA
CCCGGAAGAAACTTGAAGGTGGTCCTTTCTTTGACCTTCTCAAATCCACTCAGGAAGCAATTGTGTTGCCACCATGGGTTGCTCTAGCT
GTGAGGCCAAGGCCTGGTGTTTGGGAATACTTACGAGTCAATCTCCATGCTCTTGTCGTTGAAGAACTCCAACCTGCTGAGTTTCTTCA
TTTCAAGGAAGAACTCGTTGATGGAGTTAAGAATGGTAATTTCACTCTTGAGCTTGATTTCGAGCCATTCAATGCGTCTATCCCTCGTC
CAACACTCCACAAATACATTGGAAATGGTGTTGACTTCCTTAACCGTCATTTATCGGCTAAGCTCTTCCATGACAAGGAGAGTTTGCTT
CCATTGCTTAAGTTCCTTCGTCTTCACAGCCACCAGGGCAAGAACCTGATGTTGAGCGAGAAGATTCAGAACCTCAACACTCTGCAACA
CACCTTGAGGAAAGCAGAAGAGTATCTAGCAGAGCTTAAGTCCGAAACACTGTATGAAGAGTTTGAGGCCAAGTTTGAGGAGATTGGTC
TTGAGAGGGGATGGGGAGACAATGCAGAGCGTGTCCTTGACATGATACGTCTTCTTTTGGACCTTCTTGAGGCGCCTGATCCTTGCACT
CTTGAGACTTTTCTTGGAAGAGTACCAATGGTGTTCAACGTTGTGATCCTCTCTCCACATGGTTACTTTGCTCAGGACAATGTTCTTGG
TTACCCTGACACTGGTGGACAGGTTGTTTACATTCTTGATCAAGTTCGTGCTCTGGAGATAGAGATGCTTCAACGTATTAAGCAACAAG
GACTCAACATTAAACCAAGGATTCTCATTCTAACTCGACTTCTACCTGATGCGGTAGGAACTACATGCGGTGAACGTCTCGAGAGAGTT
TATGATTCTGAGTACTGTGATATTCTTCGTGTGCCCTTCAGAACAGAGAAGGGTATTGTTCGCAAATGGATCTCAAGGTTCGAAGTCTG
GCCATATCTAGAGACTTACACCGAGGATGCTGCGGTTGAGCTATCGAAAGAATTGAATGGCAAGCCTGACCTTATCATTGGTAACTACA
GTGATGGAAATCTTGTTGCTTCTTTATTGGCTCACAAACTTGGTGTCACTCAGTGTACCATTGCTCATGCTCTTGAGAAAACAAAGTAC
CCGGATTCTGATATCTACTGGAAGAAGCTTGACGACAAGTACCATTTCTCATGCCAGTTCACTGCGGATATTTTCGCAATGAACCACAC
TGATTTCATCATCACTAGTACTTTCCAAGAAATTGCTGGAAGCAAAGAAACTGTTGGGCAGTATGAAAGCCACACAGCCTTTACTCTTC
CCGGATTGTATCGAGTTGTTCACGGGATTGATGTGTTTGATCCCAAGTTCAACATTGTCTCTCCTGGTGCTGATATGAGCATCTACTTC
CCTTACACAGAGGAGAAGCGTAGATTGACTAAGTTCCACTCTGAGATCGAGGAGCTCCTCTACAGCGATGTTGAGAACAAAGAGCACTT
ATGTGTGCTCAAGGACAAGAAGAAGCCGATTCTCTTCACAATGGCTAGGCTTGATCGTGTCAAGAACTTGTCAGGTCTTGTTGAGTGGT
ACGGGAAGAACACCCGCTTGCGTGAGCTAGCTAACTTGGTTGTTGTTGGAGGAGACAGGAGGAAAGAGTCAAAGGACAATGAAGAGAAA
GCAGAGATGAAGAAAATGTATGATCTCATTGAGGAATACAAGCTAAACGGTCAGTTCAGGTGGATCTCCTCTCAGATGGACCGGGTAAG
GAACGGTGAGCTGTACCGGTACATCTGTGACACCAAGGGTGCTTTTGTCCAACCTGCATTATATGAAGCCTTTGGGTTAACTGTTGTGG
AGGCTATGACTTGTGGTTTACCGACTTTCGCCACTTGCAAAGGTGGTCCAGCTGAGATCATTGTGCACGGTAAATCGGGTTTCCACATT
GACCCTTACCATGGTGATCAGGCTGCTGATACTCTTGCTGATTTCTTCACCAAGTGTAAGGAGGATCCATCTCACTGGGATGAGATCTC
AAAAGGAGGGCTTCAGAGGATTGAGGAGAAATACACTTGGCAAATCTATTCACAGAGGCTCTTGACATTGACTGGTGTGTATGGATTCT
GGAAGCATGTCTCGAACCTTGACCGTCTTGAGGCTCGCCGTTACCTTGAAATGTTCTATGCATTGAAGTATCGCCCATTGGCTCAGGCT
GTTCCTCTTGCACAAGATGATTGA

FIG. 17B

*S. rebaudiana* SUS nucleotide (SEQ ID NO: 176) with the mutation that changes S11 to glutamate (E) in bold, lowercase letters

ATGGCGGAACGTGTACTCACTCGTGTTCACgaaCTTCGTGAGCGTCTCGATTCAACTCTCGCAACTCATCGTAATGAAATCCTCTTGTT
TCTTTCAAGGATTGAAAGCCATGGAAAAGGAATATTGAAGCCTCATCAAGTTATGACTGAATTTGAAGCTATCTGCAAAGAAGATCAGA
GCAAACTCTCTGATGGTGCTTTTTATGAAGTTCTTAAATGCACACAGGAAGCAATAGTGCAACCTCCATGGGTTGCACTCGCGATCCGT
CTTCGACCCGGTGTTTGGGAATATGTTAGAGTCAATGTTAATGTTTTGGTGGTTGAAGAATTAAGTGTTCCTGAATATCTTCACTTCAA
AGAAGAATTGGTTAATGGAACATCGAATGGCAACTTCGTGTTGGAACTGGATTTTGAACCTTTTACCGCATCGTTTCCTCGACCAACTT
TAACCAAGTCTATTGGTAATGGTGTTGAGTTTCTAAACAGACATTTATCTGCTAAAATGTTTCATGATAAGGATAGCATGCACCCTCTT
CTTGATTTCCTACGGACTCACCACTATAAGGGAAAGACAATGATGTTGAATGATAGAATCCAAAACCTCAATGCTCTACAATCGGTGTT
GCGAAAGGCGTCAGAGTACTTATCAACACTCGACGCGGCAACACCGTACTCTCAGTTTGAACATAAGTTTCAAGAAATCGGGTTGGAGA
GAGGTTGGGGTGATAAAGCGGAGGTCGTAATGGAGATGATCCACATGCTTCTAGACCTTCTAGAAGCACCCGACGCATGCACACTCGAG
AAGTTTCTCGGAAGAATCCCAATGGTTTTCAATGTTGTCATTCTTTCGCCTCATGGCTACTTCGCGCAAGAAAATGTGTTGGGATATCC
CGACACTGGCGGTCAGGTTGTTTACATCTTGGATCAAGTTCCCGCTCTGGAACGCGAGATGCTCAAAAGGATTAAGGAGCAAGGACTCG
ATATCATTCCTCGTATATTGATTGTTACGAGGCTTCTTCCTGACGCGGTTGGGACCACATGCGGGCAACGTTTAGAGAAAGTGTTTGGA
GCCGAACACTCGCATATTCTTCGGGTCCCGTTTAGAACCGAAAAGGGTATTCTTCGTAAATGGATCTCTCGTTTTGAGGTGTGGCCTTA
CATCGAGACTTTCACCGAGGATGTTGCTAAAGAAGTTACAGCAGAGTTGCAAGCAAAACCAGATTTGATCATTGGAAACTATAGTGAAG
GAAATTTGGTTGCATCTTTGCTAGCTCACAAGTTGGGTGTCACTCAGTGTACCATTGCTCATGCTTTGGAGAAAACTAAATACCCGGAT
TCTGATATCTACTGGAAGAACTTTGAGGAGAAATATCATTTCTCTTCGCAGTTTACCGCTGATCTTATCGCTATGAACCATACCGACTT
CATCATCACCAGTACTTTCCAAGAAATTGCTGGAAGTAAGGACACGGTTGGACAGTACGAGAGTCATACCGCGTTCACAATGCCGGGAT
TGTATCGGGTGGTTCACGGGATCGATGTTTTTGACCCCAAATTCAATATTGTTTCACCCGGGGCCGATATGGGAATTTACTACTCGTAT
ACCGAGAAAGAAAAGAGGCTCACTGCGCTTCACCCTGAAATCGATGAACTTCTCTTTAGTTCCGTCGAAAACGAAGAACACTTATGTGT
GTTGAAGGATAAGAGTAAACCAATCTTGTTCACAATGGCGCGATTGGATAATGTGAAGAATTTAACCGGACTGGTTGAATGGTACGCTA
AAAACGACCGCCTTCGTGAGCTCGTGAACCTCGTGGTCGTCGGTGGTGACCGAAGGAAAGAGTCGAAAGATCTTGAAGAGCAAGCTCAG
ATGAAGAAGATGCATGAACTTATCGAAACCTACAAACTCAACGGTCAGTTCAGGTGGATATCCTCACAAATGAACCGCGTGAGGAACGG
TGAGTTGTATCGCGTTATTGCTGACACGCGAGGTGCGTTTATCCAGCCTGCGTTTTACGAGGCGTTTGGGTTGACGGTTGTGGAGGCCA
TGACTTGTGGCCTGCCGACATTCGCGACACTTCATGGTGGGCCCGCTGAGATTATTGTTCACGGGAAATCCGGGTTCCATATTGACCCG
TATCACGGTGACCAGGTCACCGAGTTGCTGGTCAATTTCTTTGAGAAAACTAAACAAGACCCGGGTCATTGGGAGGCCATTTCCAAGGG
TGGTCTGCAACGTATTCAGGAGAAATACACGTGGCAGATTTATTCAGATAGGTTGTTGACGCTTGCCGGAGTTTATGGATTCTGGAAGC
ATGTGTCGAAGCTTGACAGGCTCGAGATCCGTCGTTATCTTGAAATGTTTTACGCGCTCAAGTATCGCAAACTGGCTGAATCTGTTCCA
TTGGCTGTTGATGAGTGA

FIG. 17C

*Coffea arabica* sus1 nucleotide (SEQ ID NO: 177)

ATGGCCGAACGTGTTCTGACCCGTGTTCACAGCCTCCGCGAACGCCTTGATGCTACTTTGGCTGCCCACCGCAACGATGTTTTGCTGTT
TATGTCGAGGCTTGAAACCCATGGGAAAGGGATCCTGAAACCCCACCAACTTTTGGCTGAGTTTGAAGAAATTAACAAGGATGGTAAAC
AAAAAATTCATGATCATGCCTTTGAAGAAGTCCTGAAGTCCACACAGGAAGCAATTGTGTTGCCCCCCTGGGTTGCACTTGCTATTCGT
CTCAGACCTGGTGTCTGGGAGTATGTTCGAGTCAATGTCCATGCACTCGTTGTTGAGGAGTTAACCGTGCCAGAGTACCTGCATTTCAA
GGAAGAACTCGTTGATGGAAGCAAAAATGGGAATTTTGTTTTGGAACTGGACTTCGAACCATTTACAGCCTCTTTTCCCAAGCCAACTC
TAACTAAGTACATAGGCGACGGAGTTGAGTTCCTCAACAGGCACCTCTCTGCCAAAATGTTCCATGACAAGGAGAGCATGGCCCCTCTC
CTTGATTTTCTCCGTGTTCACCAATACAAGGGCAAGACAATGATGCTTAACGACAGGATCAAGGACCTTAACACTCTCCAAGCAGTTCT
GAGGAAGGCAGAGGAGTACCTAACAACACTCTCTGCAGATACACCATACTCTGAATTCGAGCACAAATTCCAAGAAATTGGACTGGAGA
GAGGTTGGGGTGATACTGCTGAGCGTGTCTTGGAAATGATCTGCATGCTTCTGGATCTTCTGGGGGCTCCTGACTCGTGCACACTAGAG
AAATTCCTAGGGAGAATCCCTATGGTATTCAATGTTGTTATTCTTTCCCCCATGGATACTTTGCCCAGGAAAACGTATTGGGTTATCC
TGATACCGGTGGCCAGGTTGTTTACATATTGGATCAAGTTCCTGCCTTGGAGCGTGAGATGCTGAAGAGGATAAAGGAACAAGGACTTG
ATGTCAAGCCACGCATTCTAATTATAACTAGGCTGCTTCCTGATGCCCCTGGAACCACTTGTGGTCAACGGCTTGAGAAAGTATATGGA
TCAGAGTACTCCCATATACTCAGAGTCCCCTTCAGAACTGAGAAGGGAGTTGTTCGCAAATGGATCTCTCGCTTTGAAGTTTGGCCCTA
CATGGAAACATTTACTGAGGATGTTGCAAAAGAAGTCACTGCAGAATTACAGGCAAAGCCAGATTTGGTTATTGGTAACTACAGTGAGG
GTAACCTTGTTGCCTCCTTGCTTGCTCACAAGTTAGGTGTAACACAGTGTACCATTGCTCATGCTTTGGAAAAAACCAAGTATCCTGAT
TCTGATATTTATTTGAGCAAATTTGATGAAAAGTACCACTTCTCATGTCAGTTCACTGCGGATCTTATCGCAATGAACCATACAGATTT
CATTATCACTAGCACTTTCCAAGAAATAGCTGGAAGCAAGGACACTGTTGGGCAATATGAAAGCCATATGGCCTTCACAATGCCAGGAT
TATACAGAGTTGTACATGGCATTGATGTTTTTGATCCAAAATTCAACATTGTCTCACCTGGAGCTGATACAAACCTCTACTTCCCACAC
ACAGAGAAGGAAAAGAGATTGACATCTTTCCATCCTGAAATTGAGGAGTTGCTTTTCAGCGATGTGGAGAATGAGGAACACCTATGTGT
GCTAAAAGACAAAAAGAAGCCTATCTTATTCACCATGGCAAGACTGGATCGCGTAAAGAATTTGACAGGGCTTGTTGAATTGTATGCTA
AGAACCCAAAACTAAGGGAATTGGTCAATCTTGTCGTGGTTGGTGGAGACCGAAGGAAGGAATCCAAAGATTTGGAAGAACAAGCTGAG
ATGAAGAAAATGTATTCATTGATAGAAACTTACAACTTGAACGGCCAATTCAGATGGATTTCTTCTCAGATGAACAGGGTTAGAAATGG
TGAACTCTATCGGTACATTGCTGACACCAGGGGAGCATTCGTGCAACCTGCATTTTATGAGGCATTTGGGTTGACTGTGGTCGAGGCCA
TGACATGTGGTTTGCCAACATTTGCAACCAACCATGGTGGTCCTGCTGAGATCATTATTCATGGGAAATCTGGTTTCCACATTGATCCA
TACCATGGTGAGCAGGTCAGCGAGCTCCTTGCCAATTTCTTTGAAAGGTGCAAGAAAGAGCCTTCTTACTGGGACACCATTTCAGCCGG
TGGCTTGAAGCGTATCCAGGAAAAGTACACCTGGCAAATTTACTCAGATCGGTTGCTGACGCTGGCTGGAGTTTATGGATTCTGGAAAT
GTGTTTCCAAGCTTGATCGCCAGGAGATCCGCCGTTATCTGGAAATGTTTTATGCTCTCAAGTATCGCAAGTTGGCTGAAGCTGTT**CCA
TTGGCTGTTGATCAGTAA**

FIG. 19A

*A. thaliana* UDP-glycosyltransferase UGT72E2 polypeptide (SEQ ID NO: 178)

MHITKPHAAMFSSPGMGHVIPVIELGKRLSANNGFHVTVFVLETDAASAQSKFLNSTGVDIVKLPSPDIYGLVDPDDHVVTKIGVIMRA
AVPALRSKIAAMHQKPTALIVDLFGTDALCLAKEFNMLSYVFIPTNARFLGVSIYYPNLDKDIKEEHTVQRNPLAIPGCEPVRFEDTLD
AYLVPDEPVYRDFVRHGLAYPKADGILVNTWEEMEPKSLKSLLNPKLLGRVARVPVYPIGPLCRPIQSSETDHPVLDWLNEQPNESVLY
ISFGSGGCLSAKQLTELAWGLEQSQQRFVWVVRPPVDGSCCSEYVSANGGGTEDNTPEYLPEGFVSRTSDRGFVVPSWAPQAEILSHRA
VGGFLTHCGWSSTLESVVGGVPMIAWPLFAEQNMNAALLSDELGIAVRLDDPKEDISRWKIEALVRKVMTEKEGEAMRRKVKKLRDSAE
MSLSIDGGGLAHESLCRVTKECQRFLERVVDLSRGA

FIG. 19B

*A. thaliana* sucrose transporter SUC1 from (SEQ ID NO: 179)

MGAYETEKPTKDAAALETQSPEDFDQPSPLRKIISVASIAAGVQFGWALQLSLLTPYVQLLGIPHKWSSLIWLCGPVSGMIVQPIVGFH
SDRCRSKFGRRRPFIATGAALVAVAVFLIGYAADFGYKMGDKLEEKVKVRAIGIFALGFWILDVANNTLQGPCRAFLADLAAGDAKRTR
VANAFFSFFMAVGNVLGYAAGSYTNLHKMFPFTMTKACDIYCANLKTCFFLSITLLLIVTVTSLWYVNDKQWSPPPRNADDDEKTSSVP
LFGEIFGAFKVMKRPMWMLLIVTALNWIAWFPFLLFDTDWMGREVFGGDSDGNERSKKLYSLGVQSGAMGLMFNSIVLGFMSLGVEWIG
RKLGGAKRLWGIVNFILAAGLAMTVLVTKFAEDHRKTAGDLAGPSASVKAGALSLFAVLGIPLAITFSTPFALASIFSSCSGAGQGLSL
GVLNLAIVIPQMIVSLGGGPFDALFGGGNLPAFIVAAIAAAISGVLALTVLPSPPPDAPKATTMGGFH

FIG. 19C

*Coffea arabica* sucrose synthase polypeptide (SEQ ID NO: 180)

MAERVLTRVHSLRERLDATLAAHRNDVLLFMSRLETHGKGILKPHQLLAEFEEINKDGKQKIHDHAFEEVLKSTQEAIVLPPWVALAIR
LRPGVWEYVRVNVHALVVEELTVPEYLHFKEELVDGSKNGNFVLELDFEPFTASFPKPTLTKYIGDGVEFLNRHLSAKMFHDKESMAPL
LDFLRVHQYKGKTMMLNDRIKDLNTLQAVLRKAEEYLTTLSADTPYSEFEHKFQEIGLERGWGDTAERVLEMICMLLDLLGAPDSCTLE
KFLGRIPMVFNVVILSPHGYFAQENVLGYPDTGGQVVYILDQVPALEREMLKRIKEQGLDVKPRILIITRLLPDAPGTTCGQRLEKVYG
SEYSHILRVPFRTEKGVVRKWISRFEVWPYMETFTEDVAKEVTAELQAKPDLVIGNYSEGNLVASLLAHKLGVTQCTIAHALEKTKYPD
SDIYLSKFDEKYHFSCQFTADLIAMNHTDFIITSTFQEIAGSKDTVGQYESHMAFTMPGLYRVVHGIDVFDPKFNIVSPGADTNLYFPH
TEKEKRLTSFHPEIEELLFSDVENEEHLCVLKDKKKPILFTMARLDRVKNLTGLVELYAKNPKLRELVNLVVVGGDRRKESKDLEEQAE
MKKMYSLIETYNLNGQFRWISSQMNRVRNGELYRYIADTRGAFVQPAFYEAFGLTVVEAMTCGLPTFATNHGGPAEIIIHGKSGFHIDP
YHGEQVSELLANFFERCKKEPSYWDTISAGGLKRIQEKYTWQIYSDRLLTLAGVYGFWKCVSKLDRQEIRRYLEMFYALKYRKLAEAVP
LAVDQ

FIG. 21

SEQ ID NO: 185 (*Saccharomyces cerevisiae* Cycl promoter)

gcgttggttggtggatcaagcccacgcgtaggcaatcctcgagcagatccgccaggcgtgtatatatagcgtggatggccaggcaactt
tagtgctgacacatacaggcatatatatatgtgtgcgacgacacatgatcatatggcatgcatgtgctctgtatgtatataaaactctt
gttttcttcttttctctaaatattctttccttatacattaggacctttgcagcataaattactatacttctatagacacacaaacacaa
atacacacactaaattaata SEQ ID NO: 186 (*Saccharomyces cerevisiae* Kex2 promoter)
ggtcagcagctctgatgtagatacacgtatctcgacatgttttatttttactatacatacataaaagaaataaaaaatgataacgtgta
tattattattcatataatcaatgagggtcattttctgaaacgcaaaaaacggtaaatggaaaaaaaataaagatagaaaaagaaaacaa
acaaaggaaaggttagcatattaaataactgagctgatacttcaacagcatcgctgaagagaacagtattgaaaccgaaacattttcta
aaggcaaacaaggtactccatatttgctggacgtgttctttctctcgtttcatatgcataattctgtcataagcctgttctttttcctg
gcttaaacatcccgttttgtaaaagagaaatctattccacatatttcattcattcggctaccatactaaggataaactaatcccgttgt
tttttggcctcgtcacataattataaactactaacccattatcaga

FIG. 25

>sp|P29704|FDFT_YEAST Squalene synthase OS=*Saccharomyces cerevisiae* (strain ATCC 204508 / S288c) GN=ERG9 PE=1 SV=2 (SEQ ID NO: 192)
MGKLLQLALHPVEMKAALKLKFCRTPLFSIYDQSTSPYLLHCFELLNLTSRSFAAVIREL
HPELRNCVTLFYLILRALDTIEDDMSIEHDLKIDLLRHFHEKLLLTKWSFDGNAPDVKDR
AVLTDFESILIEFHKLKPEYQEVIKEITEKMGNGMADYILDENYNLNGLQTVHDYDVYCH
YVAGLVGDGLTRLIVIAKFANESLYSNEQLYESMGLFLQKTNIIRDYNEDLVDGRSFWPK
EIWSQYAPQLKDFMKPENEQLGLDCINHLVLNALSHVIDVLTYLAGIHEQSTFQFCAIPQ
VMAIATLALVFNNREVLHGNVKIRKGTTCYLILKSRTLRGCVEIFDYYLRDIKSKLAVQD
PNFLKLNIQISKIEQFMEEMYQDKLPPNVKPNETPIFLKVKERSRYDDELVPTQQEEEYK
FNMVLSIILSVLLGFYYIYTLHRA >sp|P36596|FDFT_SCHPO Squalene synthase OS=*Schizosaccharomyces pombe* (strain ATCC 38366 / 972) GN=erg9 PE=1 SV=1 (SEQ ID NO: 193)
MSLANRIEEIRCLCQYKLWNDLPSYGEDENVPQNIRRCYQLLDMTSRSFAVVIKELPNGI
REAVMIFYLVLRGLDTVEDDMTLPLDKKLPILRDFYKTIEVEGWTFNESGPNEKDRQLLV
EFDVVIKEYLNLSEGYRNVISNITKEMGDGMAYYASLAEKNDGFSVETIEDFNKYCHYVA
GLVGIGLSRLFAQSKLEDPDLAHSQAISNSLGLFLQKVNIIRDYREDFDDNRHFWPREIW
SKYTSSFGDLCLPDNSEKALECLSDMTANALTHATDALVYLSQLKTQEIFNFCAIPQVMA
IATLAAVFRNPDVFQTNVKIRKGQAVQIILHSVNLKNVCDLFLRYTRDIHYKNTPKDPNF
LKISIECGKIEQVSESLFPRRFREMYEKAYVSKLSEQKKGNGTQKAILNDEQKELYRKDL
QKLGISILFVFFIILVCLAVIFYVFNIRIHWSDFKELNLF >sp|Q9Y753|FDFT_YARLI Squalene synthase OS=*Yarrowia lipolytica* (strain CLIB 122 / E 150) GN=SQS1 PE=3 SV=1 (SEQ ID NO: 194)
MGKLIELLLHPSELSAAIHYKLWRQPLHPRDLSKESTELRRCYELLDVCSRSFAAVIREL
HPEVRDAVMLFYLILRALDTIEDDMTLSRDIKIPILRDFTKCMKTPGWKFTDSDPNERDR
VVLQEFPVVMTEFNKLKPKYQEVIYDITDRMGNGMADYVIDDDFNNNGVDTIAAYDLYCH
HVAGIVGEGLTRITILAGFGTDVLHENPRLQESMGLFLQKVNIIRDYREDIDVNRAFWPR
EIWHKYAEEMRDFKDPKYSKKALHCTSDLVANALGHATDCLDYLDNVTDPSTFTFCAIPQ

FIG. 25 (cont'ed)

VMAIATLQLVYRNPDVFQKNVKLRKGTTVSLILEASNVSGVCDIFTRYARKVYKKSDPND
PNYFRVSVLCGKIEQHAALIKRQRGPPAKTIAQLEGERKEMALSLIVCLAVIFSMSGLMA
YIAYVSGFRWSPREIFDSKMFFLRD

>sp|Q9HGZ6|FDFT_CANGA Squalene synthase OS=*Candida glabrata* (strain ATCC 2001 / CBS 138 / JCM 3761 / NBRC 0622 / NRRL Y-65) GN=ERG9 PE=3 SV=2 (SEQ ID NO: 195)
MGKVLDLALHPLELRAALKLKFIRQPLFSTNDTRATPQLERCYELLNLTSRSFAAVIMEL
HPELRNVIMVFYLILRALDTVEDDMTIDPQLKVKVLREFDSKLDTTDWSFDGNDLKEKDR
VVLTEFPCILGEYHKLKPEYQKVIKRITGLMGNGMADYILDENFNLNGVQTVKDYDKYCH
YVAGLVGDGLTELIVLAGFGSDDLYHGKNSFQLYESMGLFLQKTNIIRDYAEDLDDGRSF
WPKEIWSEYATKLTDFRDPKNTQKGVDCINHLVLNALTHVIDVLTYLSSIHEQSSFQFCA
IPQVMAIATLAKVFNNPEVLRKNVKIRKGTTCDLILNSRTLKGCVDIFQYYLRDMKQRLP
VEDPNYLKFNIQVAKIEQFIEEMFQDNLPAGVEPRETMIYLKVQERLKWDTQVIPRVQEE
DYKFNMALSVVFCVLLSFYFFTK >sp|Q752X9|FDFT_ASHGO Squalene synthase OS=*Ashbya gossypii* (strain ATCC 10895 / CBS 109.51 / FGSC 9923 / NRRL Y-1056) GN=ERG9 PE=3 SV=1 (SEQ ID NO: 196)
MGKVVQLFTHPLELKAALKLKFLREPLYPADDTQGSAELKRCYQLLQRTSRSFAAVIMEL
HPELRNAVMLFYLILRALDTVEDDMTISPKVKVPLLREFDQKLKLDTWSFDGNAKTEKDR
DVLVEFSTILAEFHKLKPEYQQVIADITHKMGNGMADYILDEKFNLSGLETIQDYDRYCH
YVAGLVGDGLTHLIMLAKFSSPGLYYDSPDLYESMGLFLQKTNIIRDYAEDLADGRSFWP
KEIWSHYADDLASFSKPENATAGVYCINHLVLNALGHVQHVLTYLASLREQSSFQFCAIP
QVMAIATLALVFGNERVLQTSVKIRKGTTCYLILKSRTFQGCVEIFEHYLRDIRKRLTVA
DPNYLKLNIEIAKLDKFIEEMYQDKLPVGAKPQETEIYKKVRERSAYDLEVLPREQEEEF
KFNVLLSILFTVFGALYWYAK >sp|O74165|FDFT_CYBJA Squalene synthase OS=*Cyberlindnera jadinii* GN=ERG9 PE=3 SV=1 (SEQ ID NO: 197)
MGKLLQLALHPDELASIVQFKLFRKNENARNPATESAELIRCYELLNLTSRSFAAVIEEL
HPELRNVIMVFYLVLRALDTVEVDMSIENSVKLPVLRQFHEKLDTKDWTFDGNSPNEKDR
CVLVEFDRILGQYHELKPQYQKVIKEITEKMGNGMADYIENENFNSNGLLTIEDYDLYCY

FIG. 25 (cont'ed)

YVAGLVGDGLTQLIVLAKFGNSELSVNKQLFKSMGLFLQKTNIIRDYEEDQVDGRAFWPK
EIWGKYANELSDFMKPENQSQGLWCISELVCNALDHVIDVLQYLALVEEQTSFNFCAIPQ
VMAIATLELVFQNPQVLTQHVKIRKGTTVSLILESRTLEGCARIFRRYLRKIHHKSHPSD
PNYLRLGITIGKIEQFLDGMYPHYVPKGITPQTTSIRTQVVKRLQLDEPMKRDIDEEILK
TRILLLSLGVAVFGVVYGVVRII

>sp|P78589|FDFT_CANAL Squalene synthase OS=*Candida albicans* GN=ERG9 PE=3 SV=1
(SEQ ID NO: 198)
MGKFLQLLSHPTELKAVIQLFGFRQPLHPGKRDVNDKELGRCYELLNLTSRSFAAVIEEL
HPELRDAVMIFYLVLRALDTIEDDMTIKSSIKIPLLREFDTKLNTKNWTFDGYGPNEKDR
TVLVEFDKILNVYHRLKPQYQDIIKSITFKMGNGMADYILDEEFNVYGVATVEDYNLYCH
YVAGLVGEGLTNLFVLANFGDKTLTENNFAKADSMGLFLQKTNIIRDYHEDLQDGRSFWP
REIWSKYTENLQDFHKVKTPAKEFAGVSCINELVLNALGHVTDCLDYLSLVKDPSSFSFC
AIPQVMAVATLAEVYNNPKVLHGVVKIRKGTTCRLILESRTLPGVVKIFKEYIQVINHKS
SVRDPNYLKIGIKCGEIEQYCEMIYPNKQALPPSMKSLPENKFTKIVASRESIDLSVQRR
IEPGNFNCNVVLFGIGALILSLIYFVLY >sp|P38604|ERG7_YEAST Lanosterol synthase OS=*Saccharomyces cerevisiae* (strain ATCC 204508 / S288c) GN=ERG7 PE=1 SV=6 (SEQ ID NO: 199)
MTEFYSDTIGLPKTDPRLWRLRTDELGRESWEYLTPQQAANDPPSTFTQWLLQDPKFPQP
HPERNKHSPDFSAFDACHNGASFFKLLQEPDSGIFPCQYKGPMFMIIGYVAVNYIAGIEI
PEHERIELIRYIVNTAHPVDGGWGLHSVDKSTVFGTVLNYVILRLLGLPKDHPVCAKARS
TLLRLGGAIGSPHWGKIWLSALNLYKWEGVNPAPPETWLLPYSLPMHPGRWWVHTRGVYI
PVSYLSLVKFSCPMTPLLEELRNEIYTKPFDKINFSKNRNTVCGVDLYYPHSTTLNIANS
LVVFYEKYLRNRFIYSLSKKKVYDLIKTELQNTDSLCIAPVNQAFCALVTLIEEGVDSEA
FQRLQYRFKDALFHGPQGMTIMGTNGVQTWDCAFAIQYFFVAGLAERPEFYNTIVSAYKF
LCHAQFDTECVPGSYRDKRKGAWGFSTKTQGYTVADCTAEAIKAIIMVKNSPVFSEVHHM
ISSERLFEGIDVLLNLQNIGSFEYGSFATYEKIKAPLAMETLNPAEVFGNIMVEYPYVEC
TDSSVLGLTYFHKYFDYRKEEIRTRIRIAIEFIKKSQLPDGSWYGSWGICFTYAGMFALE
ALHTVGETYENSSTVRKGCDFLVSKQMKDGGWGESMKSSELHSYVDSEKSLVVQTAWALI
ALLFAEYPNKEVIDRGIDLLKNRQEESGEWKFESVEGVFNHSCAIEYPSYRFLFPIKALGMYSRAYETHTL

FIG. 25 (cont'd)

>sp|P37268|FDFT_HUMAN Squalene synthase OS=*Homo sapiens* GN=FDFT1 PE=1 SV=1
(SEQ ID NO: 200)
MEFVKCLGHPEEFYNLVRFRIGGKRKVMPKMDQDSLSSSLKTCYKYLNQTSRSFAAVIQA
LDGEMRNAVCIFYLVLRALDTLEDDMTISVEKKVPLLHNFHSFLYQPDWRFMESKEKDRQ
VLEDFPTISLEFRNLAEKYQTVIADICRRMGIGMAEFLDKHVTSEQEWDKYCHYVAGLVG
IGLSRLFSASEFEDPLVGEDTERANSMGLFLQKTNIIRDYLEDQQGGREFWPQEVWSRYV
KKLGDFAKPENIDLAVQCLNELITNALHHIPDVITYLSRLRNQSVFNFCAIPQVMAIATL
AACYNNQQVFKGAVKIRKGQAVTLMMDATNMPAVKAIIYQYMEEIYHRIPDSDPSSSKTR
QIISTIRTQNLPNCQLISRSHYSPIYLSFVMLLAALSWQYLTTLSQVTEDYVQTGEH >sp|P53798|FDFT_MOUSE Squalene synthase OS=*Mus musculus* GN=Fdft1 PE=2 SV=2
(SEQ ID NO: 201)
MEFVKCLGHPEEFYNLLRFRMGGRRNFIPKMDQDSLSSSLKTCYKYLNQTSRSFAAVIQA
LDGDIRHAICVFYLVLRALDTVEDDMSISVEKKIPLLCNFHTFLYDPEWRFTESKEKDRQ
VLEDFPTISLEFRNLAEKYQTVIDDICHRMGCGMAEFVDKDVTSKQDWDKYCHYVAGLVG
IGLSRLFSASEFEDPIVGEDIECANSMGLFLQKTNIIRDYLEDQQEGRKFWPQEVWGRYI
KKLEDFAKPENVDVAVQCLNELITNTLQHIPDVLTYLSRLRNQSVFNFCAIPQVMAIATL
AACYNNQQVFKGVVKIRKGQAVTLMMDATNMPAVKAIIYQYIEEIYHRIPNSDPSSSKTK
QVISKIRTQNLPNCQLISRSHYSPIYLSFIMLLAALSWQYLSTLSQVTEDYVQREH >sp|Q02769|FDFT_RAT Squalene synthase OS=*Rattus norvegicus* GN=Fdft1 PE=2 SV=1
(SEQ ID NO: 202)
MEFVKCLGHPEEFYNLLRFRMGGRRNFIPKMDRNSLSNSLKTCYKYLDQTSRSFAAVIQA
LDGDIRHAVCVFYLILRAMDTVEDDMAISVEKKIPLLRNFHTFLYEPEWRFTESKEKHRV
VLEDFPTISLEFRNLAEKYQTVIADICHRMGCGMAEFLNKDVTSKQDWDKYCHYVAGLVG
IGLSRLFSASEFEDPIVGEDTECANSMGLFLQKTNIIRDYLEDQQEGRQFWPQEVWGKYV
KKLEDFVKPENVDVAVKCLNELITNALQHIPDVITYLSRLRNQSVFNFCAIPQVMAIATL
AACYNNHQVFKGVVKIRKGQAVTLMMDATNMPAVKAIIYQYIEEIYHRVPNSDPSASKAK
QLISNIRTQSLPNCQLISRSHYSPIYLSFIMLLAALSWQYLSTLSQVTEDYVQREH

FIG. 25 (cont'ed)

*Aspergilus nidulans* GGPPS-2 polypeptide (SEQ ID NO: 203)
MTSDSHFHPPHAIPPRISSNRMSGASTRDKAALMGNFEKDWLSKGDKLQTNTDLSKRHTR
NQSSLDGTKYKDGKWSQENEEVIMGPYDYMLQHPGKDLRRQMINAFNVWLKVPSESLAII
TKVVAMLHTASLLIDDVEDNSLLRRGIPVAHSIYGTAQTINSANYVYFLALQEVQKLKSP
AAIDIYVQELLNLHRGQGMDLFWRDTLTCPSEDEYLEMVGNKTGGLFRLAVKLMQAESST
GKDCVALVNVLGLVFQICDDYLNLSDTTYTQNKGLCEDLTEGKFSFPIIHSIRSNPGNHQ
LINILRQRTKDEEVKRYALQYMESTGSFKHTQDVVRQLRARALQLIEEIENSENGEQPEE
HNDGTMVRAILDKITESTLADENTTTRDINGNCATR

*Saccharomyces cerevisiae* GGPPS-3 polypeptide (SEQ ID NO: 167)
MEAKIDELINNDPVWSSQNESLISKPYNHILLKPGKNFRLNLIVQINRVMNLPKDQLAIV
SQIVELLHNSSLLIDDIEDNAPLRRGQTTSHLIFGVPSTINTANYMYFRAMQLVSQLTTK
EPLYHNLITIFNEELINLHRGQGLDIYWRDFLPEIIPTQEMYLNMVMNKTGGLFRLTLRL
MEALSPSSHHGHSLVPFINLLGIIYQIRDDYLNLKDFQMSSEKGFAEDITEGKLSFPIVH
ALNFTKTKGQTEQHNEILRILLLRTSDKDIKLKLIQILEFDTNSLAYTKNFINQLVNMIK
NDNENKYLPDLASHSDTATNLHDELLYIIDHLSEL

```
                          SEQUENCE LISTING


Sequence total quantity: 205
SEQ ID NO: 1            moltype = AA  length = 460
FEATURE                 Location/Qualifiers
source                  1..460
                        mol_type = protein
                        organism = Stevia rebaudiana
SEQUENCE: 1
MAEQQKIKKS PHVLLIPFPL QGHINPFIQF GKRLISKGVK TTLVTTIHTL NSTLNHSNTT  60
TTSIEIQAIS DGCDEGGFMS AGESYLETFK QVGSKSLADL IKKLQSEGTT IDAIIYDSMT  120
EWVLDVAIEF GIDGGSFFTQ ACVVNSLYYH VHKGLISLPL GETVSVPGFP VLQRWETPLI  180
LQNHEQIQSP WSQMLFGQFA NIDQARWVFT NSFYKLEEEV IEWTRKIWNL KVIGPTLPSM  240
YLDKRLDDDK DNGFNLYKAN HHECMNWLDD KPKESVVYVA FGSLVKHGPE QVEEITRALI  300
DSDVNFLWVI KHKEEGKLPE NLSEVIKTGK GLIVAWCKQL DVLAHESVGC FVTHCGFNST  360
LEAISLGVPV VAMPQFSDQT TNAKLLDEIL GVGVRVKADE NGIVRRGNLA SCIKMIMEEE  420
RGVIIRKNAV KWKDLAKVAV HEGGSSDNDI VEFVSELIKA                      460

SEQ ID NO: 2            moltype = DNA  length = 1383
FEATURE                 Location/Qualifiers
source                  1..1383
                        mol_type = other DNA
                        organism = Stevia rebaudiana
SEQUENCE: 2
atggcagagc aacaaaagat caaaaagtca cctcacgtct tacttattcc atttcctctg  60
caaggacata tcaacccatt catacaattt gggaaaagat tgattagtaa gggtgtaaag  120
acaacactgg taaccactat ccacactttg aattctactc tgaaccactc aaatactact  180
actacaagta tagaaattca agctatatca gacggatgcg atgagggtgg ctttatgtct  240
gccggtgaat cttacttgga aacattcaag caagtgggat ccaagtctct ggccgatcta  300
atcaaaaagt tacagagtga aggcaccaca attgacgcca taatctacga ttctatgaca  360
gagtgggttt tagacgttgc tatcgaattt ggtattgatg gaggttcctt tttcacacaa  420
gcatgtgttg tgaattctct atactaccat gtgcataaag ggttaatctc tttaccattg  480
ggtgaaactg tttcagttcc aggttttcca gtgttacaac gttgggaaac cccattgatc  540
ttacaaaatc atgaacaaat acaatcacct tggtcccaga tgttgtttgg tcaattcgct  600
aacatcgatc aagcaagatg ggtctttact aattcattct ataagttaga ggaagaggta  660
attgaatgga ctaggaagat ctggaatttg aaagtcattg gtccaacatt gccatcaatg  720
tatttggaca aaagacttga tgatgataaa gataatggtt tcaatttgta caaggctaat  780
catcacgaat gtatgaattg gctggatgac aaaccaaagg aatcagttgt atatgttgct  840
ttcggctctc ttgttaaaca tggtccagaa caagttgagg agattacaag agcacttata  900
gactctgacg taaacttttt gtgggtcatt aagcacaaag aggaggggaa actgccagaa  960
aacctttctg aagtgataaa gaccggaaaa ggtctaatcg ttgcttggtg taaacaattg  1020
gatgttttag ctcatgaatc tgtaggctgt tttgtaacac attgcggatt caactctaca  1080
```

```
ctagaagcca tttccttagg cgtacctgtc gttgcaatgc ctcagttctc cgatcagaca  1140
accaacgcta aacttttgga cgaaatacta ggggtgggtg tcagagttaa agcagacgag  1200
aatggtatcg tcagaagagg gaacctagct tcatgtatca aaatgatcat ggaagaggaa  1260
agaggagtta tcataaggaa aaacgcagtt aagtggaagg atcttgcaaa ggttgccgtc  1320
catgaaggcg gctcttcaga taatgatatt gttgaatttg tgtccgaact aatcaaagcc  1380
taa                                                                1383

SEQ ID NO: 3           moltype = AA  length = 481
FEATURE                Location/Qualifiers
source                 1..481
                       mol_type = protein
                       organism = Stevia rebaudiana
SEQUENCE: 3
MDAMATTEKK PHVIFIPFPA QSHIKAMLKL AQLLHHKGLQ ITFVNTDFIH NQFLESSGPH  60
CLDGAPGFRF ETIPDGVSHS PEASIPIRES LLRSIETNFL DRFIDLVTKL PDPPTCIISD  120
GFLSVFTIDA AKKLGIPVMM YWTLAACGFM GFYHIHSLIE KGFAPLKDAS YLTNGYLDTV  180
IDWVPGMEGI RLKDFPLDWS TDLNDKVLMF TTEAPQRSHK VSHHIFHTFD ELEPSIIKTL  240
SLRYNHIYTI GPLQLLLDQI PEEKKQTGIT SLHGYSLVKE EPECFQWLQS KEPNSVVYVN  300
FGSTTVMSLE DMTEFGWGLA NSNHYFLWII RSNLVIGENA VLPPELEEHI KKRGFIASWC  360
SQEKVLKHPS VGGFLTHCGW GSTIESLSAG VPMICWPYSW DQLTNCRYIC KEWEVGLEMG  420
TKVKRDEVKR LVQELMGEGG HKMRNKAKDW KEKARIAIAP NGSSSLNIDK MVKEITVLAR  480
N                                                                  481

SEQ ID NO: 4           moltype = DNA  length = 1446
FEATURE                Location/Qualifiers
source                 1..1446
                       mol_type = other DNA
                       organism = Stevia rebaudiana
SEQUENCE: 4
atggatgcaa tggcaactac tgagaaaaag cctcatgtga tcttcattcc atttcctgca  60
caatctcaca taaaggcaat gctaaagtta gcacaactat tacaccataa gggattacag  120
ataactttcg tgaataccga cttcatccat aatcaatttc tggaatctag tggccctcat  180
tgtttggacg gagccccagg gtttagattc gaaacaattc ctgacggtgt ttcacattcc  240
ccagaggcct ccatcccaat aagagagagt ttactgaggt caatagaaac caactttttg  300
gatcgtttca ttgacttggt cacaaaactt ccagacccac caacttgcat aatctctgat  360
ggctttctgt cagtgtttac tatcgacgct gccaaaaagt tgggtatccc agttatgatg  420
tactggactc ttgctgcatg cggtttcatg ggtttctatc acatccattc tcttatcgaa  480
aagggttttg ctccactgaa agatgcatca tacttaacca acggctacct ggatactgtt  540
attgactggg taccaggtat ggaaggtata agacttaaag atttcctttt ggattggtct  600
acagacctta atgataaagt attgatgttt actacagaag ctccacaaag atctcataag  660
gtttcacatc atatctttca cacctttgat gaattggaac catcaatcat caaaaccttg  720
tctctaagat acaatcatat ctacactatt ggtccattac aattacttct agatcaaatt  780
cctgaagaga aaaagcaaac tggtattaca tccttacacg gctactcttt agtgaaagag  840
gaaccagaat gttttcaatg gctacaaagt aaagagccta attctgtggt ctacgtcaac  900
ttcggaagta caacagtcat gtccttggaa gatatgactg aatttggttg gggccttgct  960
aattcaaatc attactttct atggattatc aggtccaatt tggtaatagg ggaaaacgcc  1020
gtattacctc cagaattgga ggaacacatc aaaaagagag gtttcattgc ttcctggtgt  1080
tctcaggaaa aggtattgaa acatccttct gttggtggtt tccttactca ttgcggttgg  1140
ggctctacaa tcgaatcact aagtgcagga gttccaatga tttgttggcc atattcatgg  1200
gaccaactta caaattgtag gtatatctgt aaagagtggg aagttggatt agaaatggga  1260
acaaaggtta aacgtgatga agtgaaaaga ttggttcagg agttgatggg ggaaggtggc  1320
cacaagatga gaaacaaggc caaagattgg aaggaaaaag ccagaattgc tattgctcct  1380
aacgggtcat cctctctaaa cattgataag atggtcaaag agattacagt cttagccaga  1440
aactaa                                                             1446

SEQ ID NO: 5           moltype = AA  length = 473
FEATURE                Location/Qualifiers
source                 1..473
                       mol_type = protein
                       organism = Stevia rebaudiana
SEQUENCE: 5
MATSDSIVDD RKQLHVATFP WLAFGHILPY LQLSKLIAEK GHKVSFLSTT RNIQRLSSHI  60
SPLINVVQLT LPRVQELPED AEATTDVHPE DIPYLKKASD GLQPEVTRFL EQHSPDWIIY  120
DYTHYWLPSI AASLGISRAH FSVTTPWAIA YMGPSADAMI NGSDGRTTVE DLTTPPKWFP  180
FPTKVCWRKH DLARLVPYKA PGISDGYRMG LVLKGSDCLL SKCYHEFGTQ WLPLLETLHQ  240
VPVVPVGLLP PEIPGDEKDE TWVSIKKWLD GKQKGSVVYV ALGSEVLVSQ TEVVELALGL  300
ELSGLPFVWA YRKPKGPAKS DSVELPDGFV ERTRDRGLVW TSWAPQLRIL SHESVCGFLT  360
HCGSGSIVEG LMFGHPLIML PIFGDQPLNA RLLEDKQVGI EIPRNEEDGC LTKESVARSL  420
RSVVVEKEGE IYKANARELS KIYNDTKVEK EYVSQFVDYL EKNARAVAID HES         473

SEQ ID NO: 6           moltype = DNA  length = 1422
FEATURE                Location/Qualifiers
source                 1..1422
                       mol_type = other DNA
                       organism = Stevia rebaudiana
SEQUENCE: 6
atggctacat ctgattctat tgttgatgac aggaagcagt tgcatgtggc tactttccct  60
tggcttgctt tcggtcatat actgccttac ctacaactat caaaactgat agctgaaaaa  120
ggacataaag tgtcattcct ttcaacaact agaaacattc aaagattatc ttcccacata  180
```

```
tcaccattga ttaacgtcgt tcaattgaca cttccaagag tacaggaatt accagaagat  240
gctgaagcta caacagatgt gcatcctgaa gatatccctt acttgaaaaa ggcatccgat  300
ggattacagc ctgaggtcac tagattcctt gagcaacaca gtccagattg gatcatatac  360
gactacactc actattggtt gccttcaatt gcagcatcac taggcatttc tagggcacat  420
ttcagtgtaa ccacaccttg ggccattgct tacatgggtc catccgctga tgctatgatt  480
aacggcagtg atggtagaac taccgttgaa gatttgacaa ccccaccaaa gtggtttcca  540
tttccaacta aagtctgttg gagaaaacac gacttagcaa gactggttcc atacaaggca  600
ccaggaatct cagacggcta tagaatgggt ttagtcctta aagggtctga ctgcctattg  660
tctaagtgtt accatgagtt tgggacacaa tggctaccac ttttggaaac attacaccaa  720
gttcctgtcg taccagttgg tctattacct ccagaaatcc ctggtgatga gaaggacgag  780
acttgggttt caatcaaaaa gtggttagac gggaagcaaa aaggctcagt ggtatatgtg  840
gcactgggtt ccgaagtttt agtatctcaa acagaagttg tggaacttgc cttaggtttg  900
gaactatctg gattgccatt tgtctgggcc tacagaaaac caaaaggccc tgcaaagtcc  960
gattcagttg aattgccaga cggctttgtc gagagaacta gagatagagg gttggtatgg  1020
acttcatggg ctccacaatt gagaatcctg agtcacgaat ctgtgtgcgg tttcctaaca  1080
cattgtggtt ctggttctat agttgaagga ctgatgtttg gtcatccact tatcatgttg  1140
ccaatctttg gtgaccagcc tttgaatgca cgtctgttag aagataaaca agttggaatt  1200
gaaatcccac gtaatgagga agatggatgt ttaaccaagg agtctgtggc cagatcatta  1260
cgttccgttg tcgttgaaaa ggaaggcgaa atctacaagg ccaatgcccg tgaactttca  1320
aagatctaca atgacacaaa agtagagaag gaatatgttt ctcaatttgt agattaccta  1380
gagaaaaacg ctagagccgt agctattgat catgaatcct aa                    1422

SEQ ID NO: 7            moltype = AA  length = 458
FEATURE                 Location/Qualifiers
source                  1..458
                        mol_type = protein
                        organism = Stevia rebaudiana
SEQUENCE: 7
MENKTETTVR RRRRIILFPV PFQGHINPIL QLANVLYSKG FSITIFHTNF NKPKTSNYPH  60
FTFRFILDND PQDERISNLP THGPLAGMRI PIINEHGADE LRRELELLML ASEEDEEVSC  120
LITDALWYFA QSVADSLNLR RLVLMTSSLF NFHAHVSLPQ FDELGYLDPD DKTRLEEQAS  180
GFPMLKVKDI KSAYSNWQIL KEILGKMIKQ TKASSGVIWN SFKELEESEL ETVIREIPAP  240
SFLIPLPKHL TASSSSLLDH DRTVFQWLDQ QPPSSVLYVS FGSTSEVDEK DFLEIARGLV  300
DSKQSFLWVV RPGFVKGSTW VEPLPDGFLG ERGRIVKWVP QQEVLAHGAI GAFWTHSGWN  360
STLESVCEGV PMIFSDFGLD QPLNARYMSD VLKVGVYLEN GWERGEIANA IRRVMVDEEG  420
EYIRQNARVL KQKADVSLMK GGSSYESLES LVSYISSL                          458

SEQ ID NO: 8            moltype = DNA  length = 1377
FEATURE                 Location/Qualifiers
source                  1..1377
                        mol_type = other DNA
                        organism = Stevia rebaudiana
SEQUENCE: 8
atggaaaaca agaccgaaac aacagttaga cgtaggcgta gaatcattct gtttccagta  60
ccttttcaag ggcacatcaa tccaatacta caactagcca acgttttgta ctctaaaggt  120
ttttctatta caatctttca caccaatttc aacaaaccaa aaacatccaa ttacccacat  180
ttcacattca gattcatact tgataatgat ccacaagatg aacgtatttc aaacttacct  240
acccacggtc ctttagctgg aatgagaatt ccaatcatca atgaacatgg tgccgatgag  300
cttagaagag aattagagtt acttatgttg gcatccgaag aggacgagga agtctcttgt  360
ctgattactg acgctctatg gtactttgcc caatctgtgg ctgatagttt gaatttgagg  420
agattggtac taatgacatc cagtctgttt aactttcacg ctcatgttag tttaccacaa  480
tttgacgaat tgggatactt ggaccctgat gacaagacta ggttagagga acaggcctct  540
ggttttccta tgttgaaagt caaagatatc aagtctgcct attctaattg gcaaatcttg  600
aaagagatct taggaaagat gatcaaacag acaaaggctt catctggagt gatttggaac  660
agtttcaaag agttagaaga gtctgaattg gagactgtaa tcagagaaat tccagcacct  720
tcattcctga taccattacc aaaacatttg actgcttcct cttcctcttt gttggatcat  780
gacagaacag tttttcaatg gttggaccaa caaccaccta gttctgtttt gtacgtgtca  840
tttggtagta cttctgaagt cgatgaaaag gacttccttg aaatcgcaag aggcttagtc  900
gatagtaagc agtcattcct ttgggtcgtg cgtccaggtt tcgtgaaagg ctcaacatgg  960
gtcgaaccac ttccagatgg ttttctaggc gaaagaggta gaatagtcaa atgggttcct  1020
caacaggaag ttttagctca tggcgctatt ggggcattct ggactcattc cggatggaat  1080
tcaactttag aatcagtatg cgaaggggta cctatgatct tttcagattt tggtcttgat  1140
caaccactga acgcaagata catgtctgat gttttgaaag tgggtgtata tctagaaaat  1200
ggctgggaaa ggggtgaaat agctaatgca ataagacgtg ttatggttga tgaagagggg  1260
gagtatatca gacaaaacgc aagagtgctg aagcaaaagg ccgacgtttc tctaatgaag  1320
ggaggctctt catacgaatc cttagaatct cttgtttcct acatttcatc actgtaa     1377

SEQ ID NO: 9            moltype = DNA  length = 1422
FEATURE                 Location/Qualifiers
source                  1..1422
                        mol_type = other DNA
                        organism = Stevia rebaudiana
SEQUENCE: 9
atggctacca gtgactccat agttgacgac cgtaagcagc ttcatgttgc gacgttccca  60
tggcttgctt tcggtcacat cctcccttac cttcagcttt cgaaattgat agctgaaaag  120
ggtcacaaag tctcgtttct ttctaccacc agaaacattc aacgtctctc ttctcatatc  180
tcgccactca taaatgttgt tcaactcaca cttccacgtg tccaagagct gccggaggat  240
gcagaggcga ccactgacgt ccaccctgaa gatattccat atctcaagaa ggcttctgat  300
ggtcttcaac cggaggtcac ccggtttcta gaacaacact ctccggactg gattatttat  360
```

-continued

```
gattatactc actactggtt gccatccatc gcggctagcc tcggtatctc acgagcccac  420
ttctccgtca ccactccatg ggccattgct tatatgggac cctcagctga cgccatgata  480
aatggttcag atggtcgaac cacggttgag gatctcacga caccgcccaa gtggtttccc  540
tttccgacca aagtatgctg gcggaagcat gatcttgccc gactggtgcc ttacaaagct  600
ccggggatat ctgatggata ccgtatgggg ctggttctta agggatctga ttgtttgctt  660
tccaaatgtt accatgagtt tggaactcaa tggctacctc ttttggagac actacaccaa  720
gtaccggtgg ttccggtggg attactgcca ccggaaatac ccggagacga gaaagatgaa  780
acatgggtgt caatcaagaa atggctcgat ggtaaacaaa aaggcagtgt ggtgtacgtt  840
gcattaggaa gcgaggtttt ggtgagccaa accgaggttg ttgagttagc attgggtctc  900
gagctttctg ggttgccatt tgtttgggct tatagaaaac caaaaggtcc cgcgaagtca  960
gactcggtgg agttgccaga cgggttcgtg gaacgaactc gtgaccgtgg gttggtctgg  1020
acgagttggg cacctcagtt acgaatactg agccatgagt cggtttgtgg tttcttgact  1080
cattgtggtt ctggatcaat tgtggaaggg ctaatgtttg gtcaccctct aatcatgcta  1140
ccgatttttg ggaccaacc tctgaatgct cgattactgg aggacaaaca ggtgggaatc  1200
gagataccaa gaaatgagga agatggttgc ttgaccaagg agtcggttgc tagatcactg  1260
aggtccgttg ttgtggaaaa agaaggggag atctacaagg cgaacgcgag ggagctgagt  1320
aaaatctata acgacactaa ggttgaaaaa gaatatgtaa gccaattcgt agactatttg  1380
gaaaagaatg cgcgtgcggt tgccatcgat catgagagtt aa                    1422

SEQ ID NO: 10          moltype = AA  length = 473
FEATURE                Location/Qualifiers
source                 1..473
                       mol_type = protein
                       organism = Stevia rebaudiana
SEQUENCE: 10
MATSDSIVDD RKQLHVATFP WLAFGHILPY LQLSKLIAEK GHKVSFLSTT RNIQRLSSHI  60
SPLINVVQLT LPRVQELPED AEATTDVHPE DIPYLKKASD GLQPEVTRFL EQHSPDWIIY  120
DYTHYWLPSI AASLGISRAH FSVTTPWAIA YMGPSADAMI NGSDGRTTVE DLTTPPKWFP  180
FPTKVCWRKH DLARLVPYKA PGISDGYRMG LVLKGSDCLL SKCYHEFGTQ WLPLLETLHQ  240
VPVVPVGLLP PEVPGDEKDE TWVSIKKWLD GKQKGSVVYV ALGSEVLVSQ TEVVELALGL  300
ELSGLPFVWA YRKPKGPAKS DSVELPDGFV ERTRDRGLVW TSWAPQLRIL SHESVCGFLT  360
HCGSGSIVEG LMFGHPLIML PIFGDQPLNA RLLEDKQVGI EIPRNEEDGC LTKESVARSL  420
RSVVVEKEGE IYKANARELS KIYNDTKVEK EYVSQFVDYL EKNTRAVAID HES         473

SEQ ID NO: 11          moltype = DNA  length = 1422
FEATURE                Location/Qualifiers
source                 1..1422
                       mol_type = other DNA
                       organism = Stevia rebaudiana
SEQUENCE: 11
atggctacca gtgactccat agttgacgac cgtaagcagc ttcatgttgc gacgttccca  60
tggcttgctt tcggtcacat cctcccttac cttcagcttt cgaaattgat agctgaaaag  120
ggtcacaaag tctcgtttct ttctaccacc agaaacattc aacgtctctc ttctcatatc  180
tcgccactca taaatgttgt tcaactcaca cttccacgtg tccaagagct gccggaggat  240
gcagaggcga ccactgacgt ccaccctgaa gatattccat atctcaagaa ggcttctgat  300
ggtcttcaac cggaggtcac ccggtttcta gaacaacact ctccggactg gattatttat  360
gattatactc actactggtt gccatccatc gcggctagcc tcggtatctc acgagcccac  420
ttctccgtca ccactccatg ggccattgct tatatgggac cctcagctga cgccatgata  480
aatggttcag atggtcgaac cacggttgag gatctcacga caccgcccaa gtggtttccc  540
tttccgacca aagtatgctg gcggaagcat gatcttgccc gactggtgcc ttacaaagct  600
ccggggatat ctgatggata ccgtatgggg ctggttctta agggatctga ttgtttgctt  660
tccaaatgtt accatgagtt tggaactcaa tggctacctc ttttggagac actacaccaa  720
gtaccggtgg ttccggtggg attactgcca ccggaagtac ccggagacga gaaagatgaa  780
acatgggtgt caatcaagaa atggctcgat ggtaaacaaa aaggcagtgt ggtgtacgtt  840
gcattaggaa gcgaggtttt ggtgagccaa accgaggttg ttgagttagc attgggtctc  900
gagctttctg ggttgccatt tgtttgggct tatagaaaac caaaaggtcc cgcgaagtca  960
gactcggtgg agttgccaga cgggttcgtg gaacgaactc gtgaccgtgg gttggtctgg  1020
acgagttggg cacctcagtt acgaatactg agccatgagt cggtttgtgg tttcttgact  1080
cattgtggtt ctggatcaat tgtggaaggg ctaatgtttg gtcaccctct aatcatgcta  1140
ccgatttttg ggaccaacc tctgaatgct cgattactgg aggacaaaca ggtgggaatc  1200
gagataccaa gaaatgagga agatggttgc ttgaccaagg agtcggttgc tagatcactg  1260
aggtccgttg ttgtggaaaa agaaggggag atctacaagg cgaacgcgag ggagctgagt  1320
aaaatctata acgacactaa ggttgaaaaa gaatatgtaa gccaattcgt agactatttg  1380
gaaaagaata cgcgtgcggt tgccatcgat catgagagtt aa                    1422

SEQ ID NO: 12          moltype = AA  length = 473
FEATURE                Location/Qualifiers
source                 1..473
                       mol_type = protein
                       organism = Stevia rebaudiana
SEQUENCE: 12
MATSDSIVDD RKQLHVATFP WLAFGHILPF LQLSKLIAEK GHKVSFLSTT RNIQRLSSHI  60
SPLINVVQLT LPRVQELPED AEATTDVHPE DIQYLKKAVD GLQPEVTRFL EQHSPDWIIY  120
DFTHYWLPSI AASLGISRAY FCVITPWTIA YLAPSSDAMI NDSDGRTTVE DLTTPPKWFP  180
FPTKVCWRKH DLARMEPYEA PGISDGYRMG MVFKGSDCLL FKCYHEFGTQ WLPLLETLHQ  240
VPVVPVGLLP PEIPGDEKDE TWVSIKKWLD GKQKGSVVYV ALGSEALVSQ TEVVELALGL  300
ELSGLPFVWA YRKPKGPAKS DSVELPDGFV ERTRDRGLVW TSWAPQLRIL SHESVCGFLT  360
HCGSGSIVEG LMFGHPLIML PLFGDQPLNA RLLEDKQVGI EIPRNEEDGC LTKESVARSL  420
RSVVVENEGE IYKANARELS KIYNDTKVEK EYVSQFVDYL EKNARAVAID HES         473
```

```
SEQ ID NO: 13          moltype = DNA  length = 1422
FEATURE                Location/Qualifiers
source                 1..1422
                       mol_type = other DNA
                       organism = Stevia rebaudiana
SEQUENCE: 13
atggctacca gtgactccat agttgacgac cgtaagcagc ttcatgttgc gacgttccca  60
tggcttgctt tcggtcacat cctccctttc cttcagcttt cgaaattgat agctgaaaag  120
ggtcacaaag tctcgtttct ttctaccacc agaaacattc aacgtctctc ttctcatatc  180
tcgccactca taaatgttgt tcaactcaca cttccacgtg tccaagagct gccggaggat  240
gcagaggcga ccactgacgt ccaccctgaa gatattcaat atctcaagaa ggctgttgat  300
ggtcttcaac cggaggtcac ccggtttcta gaacaacact ctccggactg gattatttat  360
gattttactc actactggtt gccatccatc gcggctagcc tcggtatctc acgagcctac  420
ttctgcgtca tcactccatg gaccattgct tatttggcac cctcatctga cgccatgata  480
aatgattcag atggtcgaac cacggttgag gatctcacga caccgcccaa gtggtttccc  540
tttccgacca aagtatgctg gcggaagcat gatcttgccc gaatggagcc ttacgaagct  600
ccagggatat ctgatggata ccgtatgggg atggttttta agggatctga ttgtttgctt  660
ttcaaatgtt accatgagtt tggaactcaa tggctacctc ttttggagac actacaccaa  720
gtaccggtgg ttccggtggg attactgccg ccggaaatac ccggagacga gaaagatgaa  780
acatgggtgt caatcaagaa atggctcgat ggtaaacaaa aaggcagtgt ggtgtacgtt  840
gcattaggaa gcgaggcttt ggtgagccaa accgaggttg ttgagttagc attgggtctc  900
gagctttctg ggttgccatt tgtttgggct tatagaaaac caaaaggtcc cgcgaagtca  960
gactcggtgg agttgccaga cggttcgtg gaacgaactc gtgaccgtgg gttggtctgg  1020
acgagttggg cacctcagtt acgaatactg agccatgagt cggtttgtgg tttcttgact  1080
cattgtggtt ctggatcaat tgtggaaggg ctaatgtttg gtcaccctct aatcatgcta  1140
ccgctttttg gggaccaacc tctgaatgct cgattactgg aggacaaaca ggtgggaatc  1200
gagataccaa gaaatgagga agatggttgc ttgaccaagg agtcggttgc tagatcactg  1260
aggtccgttg ttgtggaaaa cgaaggggag atctacaagg cgaacgcgag ggagctgagt  1320
aaaatctata acgacactaa ggtggaaaaa gaatatgtaa gccaattcgt agactatttg  1380
gaaaagaatg cgcgtgcggt tgccatcgat catgagagtt aa                      1422

SEQ ID NO: 14          moltype = AA  length = 485
FEATURE                Location/Qualifiers
source                 1..485
                       mol_type = protein
                       organism = Stevia rebaudiana
SEQUENCE: 14
MYNVTYHQNS KAMATSDSIV DDRKQLHVAT FPWLAFGHIL PFLQLSKLIA EKGHKVSFLS  60
TTRNIQRLSS HISPLINVVQ LTLPRVQELP EDAEATTDVH PEDIQYLKKA VDGLQPEVTR  120
FLEQHSPDWI IYDFTHYWLP SIAASLGISR AYFCVITPWT IAYLAPSSDA MINDSDGRTT  180
VEDLTTPPKW FPFPTKVCWR KHDLARMEPY EAPGISDGYR MGMVFKGSDC LLFKCYHEFG  240
TQWLPLLETL HQVPVVPVGL LPPEIPGDEK DETWVSIKKW LDGKQKGSVV YVALGSEALV  300
SQTEVVELAL GLELSGLPFV WAYRKPKGPA KSDSVELPDG FVERTRDRGL VWTSWAPQLR  360
ILSHESVCGF LTHCGSGSIV EGLMFGHPLI MLPIFCDQPL NARLLEDKQV GIEIPRNEED  420
GCLTKESVAR SLRSVVVENE GEIYKANARA LSKIYNDTKV EKEYVSQFVD YLEKNARAVA  480
IDHES                                                               485

SEQ ID NO: 15          moltype = DNA  length = 1458
FEATURE                Location/Qualifiers
source                 1..1458
                       mol_type = other DNA
                       organism = Stevia rebaudiana
SEQUENCE: 15
atgtacaacg ttacttatca tcaaaattca aaagcaatgg ctaccagtga ctccatagtt  60
gacgaccgta agcagcttca tgttgcgacg ttcccatggc ttgctttcgg tcacatcctc  120
cctttccttc agctttcgaa attgatagct gaaaagggtc acaaagtctc gtttctttct  180
accaccagaa acattcaacg tctctcttct catatctcgc cactcataaa tgttgttcaa  240
ctcacacttc cacgtgtcca agagctgccg gaggatgcag aggcgaccac tgacgtccac  300
cctgaagata ttcaatatct caagaaggct gttgatggtc ttcaaccgga ggtcacccgg  360
tttctagaac aacactctcc ggactggatt atttatgatt ttactcacta ctggttgcca  420
tccatcgcgg ctagcctcgg tatctcacga gcctacttct gcgtcatcac tccatggacc  480
attgcttatt tggcaccctc atctgacgcc atgataaatg attcagatgg tcgaaccacg  540
gttgaggatc tcacgacacc gcccaagtgg tttccctttc cgaccaaagt atgctggcgg  600
aagcatgatc ttgcccgaat ggagccttac gaagctccgg ggatatctga tggataccgt  660
atggggatgg tttttaaggg atctgattgt ttgcttttca aatgttacca tgagtttgga  720
actcaatggc tacctctttt ggagacacta caccaagtac cggtggttcc ggtgggatta  780
ctgccgccgg aaatacccgg agacgagaaa gatgaaacat gggtgtcaat caagaaatgg  840
ctcgatggta aacaaaaagg cagtgtggtg tacgttgcat taggaagcga ggctttggtg  900
agccaaaccg aggttgttga gttagcattg ggtctcgagc tttctgggtt gccatttgtt  960
tgggcttata gaaaaccaaa aggtcccgcg aagtcagact cggtggagtt gccagacggg  1020
ttcgtggaac gaactcgtga ccgtgggttg gtctggacga gttgggcacc tcagttacga  1080
atactgagcc acgagtcagt ttgtggtttc ttgactcatt gtggttctgg atcaattgtg  1140
gaagggctaa tgtttggtca ccctctaatc atgctaccga tttttgtga ccaacctctg  1200
aatgctcgat tactggagga caaacaggtg ggaatcgaga taccaagaaa tgaggaagat  1260
ggttgcttga ccaaggagtc ggttgctaga tcactgaggt ccgttgttgt ggaaaacgaa  1320
ggggagatct acaaggcgaa cgcgagggcg ctgagtaaaa tctataacga cactaaggtg  1380
gaaaaagaat atgtaagcca attcgtagac tatttggaaa agaatgcgcg tgcggttgcc  1440
atcgatcatg agagttaa                                                 1458
```

-continued

```
SEQ ID NO: 16          moltype = AA  length = 473
FEATURE                Location/Qualifiers
source                 1..473
                       mol_type = protein
                       organism = Stevia rebaudiana
SEQUENCE: 16
MATSDSIVDD RKQLHVATFP WLAFGHILPF LQLSKLIAEK GHKVSFLSTT RNIQRLSSHI  60
SPLINVVQLT LPRVQELPED AEATTDVHPE DIQYLKKAVD GLQPEVTRFL EQHSPDWIIY  120
DFTHYWLPSI AASLGISRAY FCVITPWTIA YLAPSSDAMI NDSDGRTTVE DLTTPPKWFP  180
FPTKVCWRKH DLARMEPYEA PGISDGYRMG MVFKGSDCLL FKCYHEFGTQ WLPLLETLHQ  240
VPVVPVGLLP PEIPGDEKDE TWVSIKKWLD GKQKGSVVYV ALGSEALVSQ TEVVELALGL  300
ELSGLPFVWA YRKPKGPAKS DSVELPDGFV ERTRDRGLVW TSWAPQLRIL SHESVCGFLT  360
HCGSGSIVEG LMFGHPLIML PIFCDQPLNA RLLEDKQVGI EIPRNEEDGC LTKESVARSL  420
RSVVVENEGE IYKANARALS KIYNDTKVEK EYVSQFVDYL EKNARAVAID HES         473

SEQ ID NO: 17          moltype = DNA  length = 1422
FEATURE                Location/Qualifiers
source                 1..1422
                       mol_type = other DNA
                       organism = Stevia rebaudiana
SEQUENCE: 17
atggctacca gtgactccat agttgacgac cgtaagcagc ttcatgttgc gacgttccca  60
tggcttgctt tcggtcacat cctcccttc cttcagcttt cgaaattgat agctgaaaag  120
ggtcacaaag tctcgtttct ttctaccacc agaaacattc aacgtctctc ttctcatatc  180
tcgccactca taaatgttgt tcaactcaca cttccacgtg tccaagagct gccggaggat  240
gcagaggcga ccactgacgt ccaccctgaa gatattcaat atctcaagaa ggctgttgat  300
ggtcttcaac cggaggtcac ccggtttcta gaacaacact ctccggactg gattatttat  360
gattttactc actactggtt gccatccatc gcggctagcc tcggtatctc acgagcctac  420
ttctgcgtca tcactccatg gaccattgct tatttggcac cctcatctga cgccatgata  480
aatgattcag atggtcgaac cacggttgag gatctcacga caccgcccaa gtggtttccc  540
tttccgacca aagtatgctg gcggaagcat gatcttgccc gaatggagcc ttacgaagct  600
ccggggatat ctgatggata ccgtatgggg atggttttta agggatctga ttgtttgctt  660
ttcaaatgtt accatgagtt tggaactcaa tggctacctc ttttggagac actacaccaa  720
gtaccggtgg ttccggtggg attactgccg ccggaaatac ccggagacga gaaagatgaa  780
acatgggtgt caatcaagaa atggctcgat ggtaaacaaa aaggcagtgt ggtgtacgtt  840
gcattaggaa gcgaggcttt ggtgagccaa accgaggttg ttgagttagc attgggtctc  900
gagctttctg ggttgccatt tgtttgggct tatagaaaac caaaaggtcc cgcgaagtca  960
gactcggtgg agttgccaga cggttcgtg gaacgaactc gtgaccgtgg gttggtctgg  1020
acgagttggg cacctcagtt acgaatactg agccacgagt cagtttgtgg tttcttgact  1080
cattgtggtt ctggatcaat tgtggaaggg ctaatgtttg gtcaccctct aatcatgcta  1140
ccgatttttt gtgaccaacc tctgaatgct cgattactgg aggacaaaca ggtgggaatc  1200
gagataccaa gaaatgagga agatggttgc ttgaccaagg agtcggttgc tagatcactg  1260
aggtccgttg ttgtggaaaa cgaaggggag atctacaagg cgaacgcgag ggcgctgagt  1320
aaaatctata acgacactaa ggtggaaaaa gaatatgtaa gccaattcgt agactatttg  1380
gaaaagaatg cgcgtgcggt tgccatcgat catgagagtt aa                     1422

SEQ ID NO: 18          moltype = DNA  length = 1086
FEATURE                Location/Qualifiers
misc_feature           1..1086
                       note = Description of Artificial Sequence: Synthetic
                        polynucleotide
source                 1..1086
                       mol_type = other DNA
                       organism = synthetic construct
SEQUENCE: 18
atggctttgg taaacccaac cgctcttttc tatggtacct ctatcagaac aagacctaca  60
aacttactaa atccaactca aaagctaaga ccagtttcat catcttcctt accttctttc  120
tcatcagtta gtgcgattct tactgaaaaa catcaatcta atccttctga gaacaacaat  180
ttgcaaactc atctagaaac tcctttcaac tttgatagtt atatgttgga aaaagtcaac  240
atggttaacg aggcgcttga tgcatctgtc ccactaaaag acccaatcaa aatccatgaa  300
tccatgagat actctttatt ggcaggcggt aagagaatca gaccaatgat gtgtattgca  360
gcctgcgaaa tagtcggagg taatatcctt aacgccatgc cagccgcatg tgccgtggaa  420
atgattcata ctatgtcttt ggtgcatgac gatcttccat gtatggataa tgatgacttc  480
agaagaggta aacctatttc acacaaggtc tacggggagg aaatggcagt attgaccggc  540
gatgctttac taagtttatc tttcgaacat atagctactg ctacaaaggg tgtatcaaag  600
gatagaatcg tcagagctat aggggagttg gcccgttcag ttggctccga aggtttagtg  660
gctggacaag ttgtagatat cttgtcagag ggtgctgatg ttggattaga tcacctagaa  720
tacattcaca tccacaaaac agcaatgttg cttgagtcct cagtagttat tggcgctatc  780
atgggaggag gatctgatca gcagatcgaa aagttgagaa aattcgctag atctattggt  840
ctactattcc aagttgtgga tgacattttg gatgttacaa aatctaccga agagttgggg  900
aaaacagctg gtaaggattt gttgacagat aagacaactt acccaaagtt gttaggtata  960
gaaaagtcca gagaatttgc cgaaaaactt aacaaggaag cacaagagca attaagtggc  1020
tttgatagac gtaaggcagc tcctttgatc gcgttagcca actacaatgc gtaccgtcaa  1080
aattga                                                             1086

SEQ ID NO: 19          moltype = DNA  length = 1029
FEATURE                Location/Qualifiers
misc_feature           1..1029
```

```
                      note = Description of Artificial Sequence: Synthetic
                       polynucleotide
source                1..1029
                      mol_type = other DNA
                      organism = synthetic construct
SEQUENCE: 19
atggctgagc aacaaatatc taacttgctg tctatgtttg atgcttcaca tgctagtcag  60
aaattagaaa ttactgtcca aatgatggac acataccatt acagagaaac gcctccagat  120
tcctcatctt ctgaaggcgg ttcattgtct agatacgacg agagaagagt ctctttgcct  180
ctcagtcata atgctgcctc tccagatatt gtatcacaac tatgttttc cactgcaatg  240
tcttcagagt tgaatcacag atggaaatct caaagattaa aggtggccga ttctccttac  300
aactatatcc taacattacc atcaaaagga attagaggtg cctttatcga ttccctgaac  360
gtatggttgg aggttccaga ggatgaaaca tcagtcatca aggaagttat tggtatgctc  420
cacaactctt cattaatcat tgatgacttc caagataatt ctccacttag aagaggaaag  480
ccatctaccc atacagtctt cggccctgcc caggctatca atactgctac ttacgttata  540
gttaaagcaa tcgaaaagat acaagacata gtgggacacg atgcattggc agatgttacg  600
ggtactatta caactatttt ccaaggtcag gccatggact tgtggtggac agcaaatgca  660
atcgttccat caatacagga atacttactt atggtaaacg ataaaaccgg tgctctcttt  720
agactgagtt tggagttgtt agctctgaat tccgaagcca gtatttctga ctctgcttta  780
gaaagtttat ctagtgctgt ttccttgcta ggtcaatact tccaaatcag agacgactat  840
atgaacttga tcgataacaa gtatacagat cagaaaggct tctgcgaaga tcttgatgaa  900
ggcaagtact cactaacact tattcatgcc ctccaaactg attcatccga tctactgacc  960
aacatccttt caatgagaag agtgcaagga aagttaacgg cacaaaagag atgttggttc  1020
tggaaatga                                                         1029

SEQ ID NO: 20         moltype = DNA  length = 903
FEATURE               Location/Qualifiers
misc_feature          1..903
                      note = Description of Artificial Sequence: Synthetic
                       polynucleotide
source                1..903
                      mol_type = other DNA
                      organism = synthetic construct
SEQUENCE: 20
atggaaaaga ctaaggagaa agcagaacgt atcttgctgg agccatacag atacttatta  60
caactaccag gaaagcaagt ccgttctaaa ctatcacaag cgttcaatca ctggttaaaa  120
gttcctgaag ataagttaca aatcattatt gaagtcacag aaatgctaca caatgcttct  180
ttactgatcg atgatataga ggattcttcc aaactgagaa gaggttttcc tgtcgctcat  240
tccatatacg ggtaccaag tgtaatcaac tcagctaatt acgtctactt cttgggattg  300
gaaaaagtat tgacattaga tcatccagac gctgtaaagc tattcaccag acaacttctt  360
gaattgcatc aaggtcaagg tttggatatc tattggagag acacttatac ttgcccaaca  420
gaagaggagt acaaagcaat ggttctacaa aagactggcg gtttgttcgg acttgccgtt  480
ggtctgatgc aacttttctc tgattacaag gaggacttaa agcctctgtt ggataccttg  540
ggcttgtttt tccagattag agatgactac gctaacttac attcaaagga atattcagaa  600
aacaaatcat tctgtgaaga tttgactgaa gggaagttta gttttccaac aatccacgcc  660
atttggtcaa gaccagaatc tactcaagtg caaaacattc tgcgtcagag aacagagaat  720
attgacatca aaaagtattg tgttcagtac ttggaagatg ttggttcttt tgcttacaca  780
agacatacac ttagagaatt agaggcaaaa gcatacaagc aaatagaagc ctgtggaggc  840
aatccttctc tagtggcatt ggttaaacat ttgtccaaaa tgttcaccga ggaaaacaag  900
taa                                                               903

SEQ ID NO: 21         moltype = DNA  length = 1020
FEATURE               Location/Qualifiers
misc_feature          1..1020
                      note = Description of Artificial Sequence: Synthetic
                       polynucleotide
source                1..1020
                      mol_type = other DNA
                      organism = synthetic construct
SEQUENCE: 21
atggcaagat tctattttct taacgcacta ttgatggtta tctcattaca atcaactaca  60
gccttcactc cagctaaact tgcttatcca acaacaacaa cagctctaaa tgtcgcctcc  120
gccgaaactt ctttcagtct agatgaatac ttggcctcta agataggacc tatagagtct  180
gccttggaag catcagtcaa atccagaatt ccacagaccg ataagatctg cgaatctatg  240
gcctactctt tgatggcagg aggcaagaga attagaccag tgttgtgtat cgctgcatgt  300
gagatgttcg gtggatccca agatgtcgct atgcctactg ctgtggcatt agaaatgata  360
cacacaatgt ctttgattca tgatgatttg ccatccatgg ataacgatga cttgagaaga  420
ggtaaaccaa caaaccatgt cgttttcggc gaagatgtag ctattcttgc aggtgactct  480
ttattgtcaa cttccttcga gcacgtcgct agagaaacaa aaggagtgtc agcagaaaag  540
atcgtggatg ttatcgctag attaggcaaa tctgttggtg ccgagggcct tgctggcggt  600
caagttatgg acttagaatg tgaagctaaa ccaggtacca cattagacga cttgaaatgg  660
attcatatcc ataaaaccgc tacattgtta caagttgctg tagcttctgg tgcagttcta  720
ggtggtgcaa ctcctgaaga ggttgctgca tgcgagttgt ttgctatgaa tataggtctt  780
gcctttcaag ttgccgacga tatccttgat gtaaccgctt catcagaaga tttgggtaaa  840
actgcaggca aagatgaagc tactgataag acaacttacc caaagttatt aggattagaa  900
gagagtaagg catacgcaag acaactaatc gatgaagcca aggaaagttt ggctcctttt  960
ggagatagag ctgccccttt attggccatt gcagatttca ttattgatag aaagaattga  1020

SEQ ID NO: 22         moltype = DNA  length = 1068
```

-continued

```
FEATURE                Location/Qualifiers
misc_feature           1..1068
                       note = Description of Artificial Sequence: Synthetic
                        polynucleotide
source                 1..1068
                       mol_type = other DNA
                       organism = synthetic construct
SEQUENCE: 22
atgcacttag caccacgtag agtccctaga ggtagaagat caccacctga cagagttcct  60
gaaagacaag gtgccttggg tagaagacgt ggagctggct ctactggctg tgcccgtgct  120
gctgctggtg ttcaccgtag aagaggagga ggcgaggctg atccatcagc tgctgtgcat  180
agaggctggc aagccggtgg tggcaccggt ttgcctgatg aggtggtgtc taccgcagcc  240
gccttagaaa tgtttcatgc ttttgcttta atccatgatg atatcatgga tgatagtgca  300
actagaagag gctccccaac tgttcacaga gccctagctg atcgtttagg cgctgctctg  360
gacccagatc aggccggtca actaggagtt tctactgcta tcttggttgg agatctggct  420
ttgacatggt ccgatgaatt gttatacgct ccattgactc cacatagact ggcagcagta  480
ctaccattgg taacagctat gagagctgaa accgttcatg gccaatatct tgatataact  540
agtgctagaa gacctgggac cgatacttct cttgcattga gaatagccag atataagaca  600
gcagcttaca caatggaacg tccactgcac attggtgcag ccctggctgg ggcaagacca  660
gaactattag cagggctttc agcatacgcc ttgccagctg gagaagcctt ccaattggca  720
gatgacctgc taggcgtctt cggtgatcca agacgtacag ggaaacctga cctagatgat  780
cttagaggtg gaaagcatac tgtcttagtc gccttggcaa gagaacatgc cactccagaa  840
cagagacaca cattggatac attattgggt acaccaggtc ttgatagaca aggcgcttca  900
agactaagat gcgtattggt agcaactggt gcaagagccg aagccgaaag acttattaca  960
gagagaagag atcaagcatt aactgcattg aacgcattaa cactgccacc tcctttagct  1020
gaggcattag caagattgac attagggtct acagctcatc ctgcctaa              1068

SEQ ID NO: 23          moltype = DNA  length = 993
FEATURE                Location/Qualifiers
misc_feature           1..993
                       note = Description of Artificial Sequence: Synthetic
                        polynucleotide
source                 1..993
                       mol_type = other DNA
                       organism = synthetic construct
SEQUENCE: 23
atgtcatatt tcgataacta cttcaatgag atagttaatt ccgtgaacga catcattaag  60
tcttacatct ctggcgacgt accaaaacta tacgaagcct cctaccattt gtttacatca  120
ggaggaaaga gactaagacc attgatcctt acaatttctt ctgatctttt cggtggacag  180
agagaaagag catactatgc tggcgcagca atcgaagttt tgcacacatt cactttggtt  240
cacgatgata tcatggatca agataacatt cgtagaggtc ttcctactgt acatgtcaag  300
tatggcctac ctttggccat tttagctggt gacttattgc atgcaaaagc ctttcaattg  360
ttgactcagg cattgagagg tctaccatct gaaactatca tcaaggcgtt tgatatcttt  420
acaagatcta tcattatcat atcagaaggt caagctgtcg atatggaatt cgaagataga  480
attgatatca aggaacaaga gtatttggat atgatatctc gtaaaaccgc tgccttattc  540
tcagcttctt cttccattgg ggcgttgata gctggagcta atgataacga tgtgagatta  600
atgtccgatt tcggtacaaa tcttgggatc gcatttcaaa ttgtagatga tatacttggt  660
ttaacagctg atgaaaaaga gctaggaaaa cctgttttca gtgatatcag agaaggtaaa  720
aagaccatat tagtcattaa gactttagaa ttgtgtaagg aagacgagaa aaagattgtg  780
ttaaaagcgc taggcaacaa gtcagcatca aaggaagagt tgatgagttc tgctgacata  840
atcaaaaagt actcattgga ttacgcctac aacttagctg agaaatacta caaaaacgcc  900
atcgattctc taaatcaagt ttcaagtaaa agtgatattc cagggaaggc attgaaatat  960
cttgctgaat tcaccatcag aagacgtaag taa                               993

SEQ ID NO: 24          moltype = DNA  length = 894
FEATURE                Location/Qualifiers
misc_feature           1..894
                       note = Description of Artificial Sequence: Synthetic
                        polynucleotide
source                 1..894
                       mol_type = other DNA
                       organism = synthetic construct
SEQUENCE: 24
atggtcgcac aaactttcaa cctggatacc tacttatccc aaagacaaca acaagttgaa  60
gaggccctaa gtgctgctct tgtgccagct tatcctgaga gaatatacga agctatgaga  120
tactccctcc tggcaggtgg caaaagatta agacctatct tatgtttagc tgcttgcgaa  180
ttggcaggtg gttctgttga acaagccatg ccaactgcgt gtgcacttga aatgatccat  240
acaatgtcac taattcatga tgacctgcca gccatggata acgatgattt cagaagagga  300
aagccaacta atcacaaggt gttcggggaa gatatagcca tcttagcggg tgatgcgctt  360
ttagcttacg cttttgaaca tattgcttct caaacaagag gagtaccacc tcaattggtg  420
ctacaagtta ttgctagaat cggacacgcc gttgctgcaa caggcctcgt tggaggccaa  480
gtcgtagacc ttgaatctga aggtaaagct atttccttag aaacattgga gtatattcac  540
tcacataaga ctggagcctt gctggaagca tcagttgtct caggcggtat tctcgcaggg  600
gcagatgaag agcttttggc cagattgtct cattacgcta gagatatagg cttggctttt  660
caaatcgtcg atgatatcct ggatgttact gctacatctg aacagttggg gaaaaccgct  720
ggtaaagacc aggcagccgc aaaggcaact tatccaagtc tattgggttt agaagcctct  780
agacagaaag cggaagagtt gattcaatct gctaaggaag ccttaagacc ttacggttca  840
caagcagagc cactcctagc gctggcagac ttcatcacac gtcgtcagca ttaa        894
```

-continued

```
SEQ ID NO: 25          moltype = DNA  length = 1116
FEATURE                Location/Qualifiers
misc_feature           1..1116
                       note = Description of Artificial Sequence: Synthetic
                        polynucleotide
source                 1..1116
                       mol_type = other DNA
                       organism = synthetic construct
SEQUENCE: 25
atggcctctg ttactttggg ttcctggatc gtcgtccacc accataacca tcaccatcca  60
tcatctatcc taactaaatc tcgttcaaga tcctgtccta ttacactaac caaaccaatc  120
tcttttcgtt caaagagaac agtttcctct agtagttcta tcgtgtcctc tagtgtcgtc  180
actaaggaag acaatctgag acagtctgaa ccttcttcct ttgatttcat gtcatatatc  240
attactaagg cagaactagt gaataaggct cttgattcag cagttccatt aagagagcca  300
ttgaaaatcc atgaagcaat gagatactct cttctagctg gcgggaagag agtcagacct  360
gtactctgca tagcagcgtg cgaattagtt ggtggcgagg aatcaaccgc tatgcctgcc  420
gcttgtgctg tagaaatgat tcatacaatg tcactgatac acgatgattt gccatgtatg  480
gataacgatg atctgagaag ggtaagcca actaaccata aggttttcgg cgaagatgtt  540
gccgtcttag ctggtgatgc tttgttatct ttcgcgttcg aacatttggc atccgcaaca  600
tcaagtgatg ttgtgtcacc agtaagagta gttagagcag ttggagaact ggctaaagct  660
attggaactg agggtttagt tgcaggtcaa gtcgtcgata tctcttccga aggtcttgat  720
ttgaatgatg taggtcttga acatctcgaa ttcatccatc ttcacaagac agctgcactt  780
ttagaagcca gtgcggttct cggcgcaatt gttggcggag ggagtgatga cgaaattgag  840
agattgagga agtttgctag atgtatagga ttactgttcc aagtagtaga cgatatacta  900
gatgtgacaa agtcttccaa agagttggga aaaacagctg gtaaagattt gattgccgac  960
aaattgacct accctaagat tatggggcta gaaaaatcaa gagaatttgc cgagaaactc  1020
aatagagagg cgcgtgatca actgttgggt ttcgattctg ataaagttgc accactctta  1080
gccttagcca actacatcgc ttacagacaa aactaa                           1116

SEQ ID NO: 26          moltype = DNA  length = 1086
FEATURE                Location/Qualifiers
source                 1..1086
                       mol_type = other DNA
                       organism = Stevia rebaudiana
SEQUENCE: 26
atggctcttg taaatcccac agctttgttc tatggaacct ccataagaac cagacccaca  60
aacttgctca acccgaccca aaaacttcga cccgtttcct cgtcttcttt gccttccttc  120
tcttcagttt ctgcaatctt gacggaaaaa caccaatcaa acccatcaga aaacaataac  180
ttgcaaaccc atctcgaaac accattcaat ttcgactctt acatgctgga gaaagtaaac  240
atggtgaatg aagctctgga cgcctcggtt ccactcaaag acccgataaa gatccatgaa  300
tccatgcggt actcccttct agctggcggg aaacgcatcc gaccgatgat gtgcatcgcc  360
gcttgcgaaa tagtcggagg caacatatta aacgccatgc cagctgcatg cgcggtcgag  420
atgattcaca ccatgtcact agttcatgac gaccttccat gcatggataa cgacgacttc  480
cgacgtggaa aaccaataag ccacaaggtg tacggtgaag aaatggcggt tctaaccggg  540
gacgcgttac tctcattatc cttcgaacat atcgcgaccg cgacaaaagg cgtatccaaa  600
gacaggatcg tccgagccat tggtgaactc gcaaggtccg ttggctcgga gggtttggtc  660
gccggtcagg tggttgatat tttatccgaa ggggctgatg ttgggttaga ccacttggag  720
tatattcata tacacaagac tgcaatgttg cttgagagct cggtcgtgat cggcgcgatc  780
atgggcggtg ggtctgacca acagatcgaa aagttgcgaa agtttgcgag atcgattggt  840
ttgttgtttc aggtggtaga tgatattctt gatgtcacaa agtcgactga ggaattgggg  900
aaaacggcgg gaaaagattt gctgacggac aagacaacgt atccgaagtt gttggggatc  960
gaaaaatcga gagaatttgc ggagaaatta aacaaggaag cgcaagaaca attgtcgggg  1020
tttgatcgcc gcaaggcggc tccgttaatt gcccttgcta attacaatgc ttataggcaa  1080
aactga                                                            1086

SEQ ID NO: 27          moltype = DNA  length = 1029
FEATURE                Location/Qualifiers
source                 1..1029
                       mol_type = other DNA
                       organism = Gibberella fujikuroi
SEQUENCE: 27
atggctgaac aacagatctc caaccttctt tcaatgtttg atgcttctca cgcaagccag  60
aagttggaga ttacggttca gatgatggat acctaccatt acagagaaac tcctccagac  120
tcttcctctt cagaaggcgg ttccttatct cgctatgatg agcgacgggt ctcccttccg  180
ctctctcaca atgcagcctc cccagacata gtctcccagt tatgcttctc aacagctatg  240
agctcggagc tcaatcacag gtggaagtca cagcgcctca aggttgctga ctctccctac  300
aactacatcc tgactcttcc atctaaaggt attcgtgggg ctttcattga ctcactgaat  360
gtctggctcg aggtccccga agacgagacc tcggtgatca aagaggtgat tggcatgctc  420
cacaactcgt ctctcataat cgatgacttc caagacaact ccccacttcg gcggggcaag  480
ccatctacac atactgtctt cggtccagca caagcaatca acacagcaac atatgtcatc  540
gtcaaggcca tcgagaaaat acaggatatc gtcggtcacg atgcattggc agatgtaact  600
ggcactataa cccacaatctt ccagggtcag gcaatggatc tgtggtggac tgctaatgcc  660
attgttccgt ctatccaaga atatctcctg atggtcaatg acaagactgg tgccctgttc  720
aggttatcgc ttgaactact ggcgctgaac tctgaagcat ccatcagtga cagcgcgctt  780
gaatctctca gcagcgctgt ctcactgctc gggcagtatt tccagataag agatgattac  840
atgaatctca ttgacaacaa gtatactgat cagaaaggat tttgcgagga tctggacgag  900
gggaaatact cgttgactct aatccatgct ctgcagaccg actccagcga ccttctcacc  960
aacatcttat cgatgagaag agtccaagga aaacttacgg cgcagaaaag atgctggttt  1020
tggaagtga                                                         1029
```

```
SEQ ID NO: 28          moltype = DNA  length = 903
FEATURE                Location/Qualifiers
source                 1..903
                       mol_type = other DNA
                       organism = Mus musculus
SEQUENCE: 28
atggagaaaa ctaaagagaa agctgagagg attcttctag agccctatag gtacttactt  60
cagttaccag gtaaacaggt gagaagcaaa ctttcacagg catttaatca ctggctgaaa  120
gttccagaag acaagctaca gattatcatt gaagtgactg aaatgttgca taatgccagt  180
ttactcattg atgatattga agacagttca aagctccgac gtggtttccc agtggctcac  240
agcatctatg gtgtcccatc tgtcattaat tctgccaatt acgtctactt ccttggactg  300
gaaaaagtct taacccttga tcacccggat gcggtgaagc ttttcacacg ccagcttctg  360
gaacttcatc agggacaagg cctcgatatt tactggaggg acacctacac ttgtccaact  420
gaagaagaat ataaagccat ggtgttgcag aagacaggtg gtttgtttgg attagcagta  480
ggtcttatgc agctgttctc tgattacaaa gaagatctaa agccactgct tgacacactt  540
gggctctttt tccagattag agatgattat gccaatctac actccaaaga atacagtgaa  600
aacaaaagtt tctgtgaaga cttgacagaa gggaagttct cattccccac tatccatgcc  660
atttggtcaa ggccagaaag cacccaggta cagaacatcc tgcgccagag aacagagaat  720
atagatatta aaaagtattg tgtgcagtac ctggaggatg taggttcttt tgcatacact  780
cgacacactc ttagagagct tgaagctaaa gcctacaaac aaattgaggc ctgtggtggg  840
aacccttcac tagtggcttt agtcaagcac ttaagtaaga tgttcacaga agaaaataaa  900
taa                                                                903

SEQ ID NO: 29          moltype = DNA  length = 1020
FEATURE                Location/Qualifiers
source                 1..1020
                       mol_type = other DNA
                       organism = Thalassiosira pseudonana
SEQUENCE: 29
atggctcgtt tctacttcct gaacgctctc ctcatggtga tttctttaca aagcaccacg  60
gcattcaccc cggcaaaact cgcctaccca acaaccacca ctgcattaaa cgttgcctct  120
gccgaaacat catttagcct cgatgaatac ctagcctcca aaatcggacc cattgaatca  180
gctctcgagg catctgtcaa atctcgcatt cctcaaactg acaagatatg cgagtctatg  240
gcatactcac tcatggctgg aggaaagcgt atccgtcccg ttttgtgcat tgctgcttgt  300
gaaatgtttg ggggaagtca agatgtggct atgccgacgg ctgtggcttt ggagatgatt  360
catactatga gtcttattca tgacgatttg ccttcaatgg acaacgatga tctccgacga  420
ggaaagccaa ctaatcatgt tgtctttgga gaggatgttg ctattcttgc tggggattct  480
cttctcagta cgtcttttga acatgttgcc cgtgaaacca aaggagtgtc agctgaaaag  540
attgtagatg ttatcgctcg cctcgggaag tctgtgggtg cagagggtct tgctggtgga  600
caggttatgg atcttgagtg tgaggcgaag ccaggaacta ccctcgacga tctcaagtgg  660
attcacattc acaaaactgc cactcttctt caagtggcag tggcatcagg tgctgttctt  720
ggaggggcca caccagagga ggttgctgct tgtgaactgt tcgcaatgaa tattggactt  780
gccttccagg tcgctgatga tattttggac gtgacggcat cgagtgagga tcttggcaaa  840
actgctggaa aggatgaagc cacagataag acaacttatc ctaagctttt gggattggag  900
gagagtaagg catacgctcg acaactcata gacgaagcaa aggaatcttt ggctcctttc  960
ggtgatcgtg ctgctccatt gttggcaatt gccgacttta tcattgatcg aaagaactag  1020

SEQ ID NO: 30          moltype = DNA  length = 1068
FEATURE                Location/Qualifiers
source                 1..1068
                       mol_type = other DNA
                       organism = Streptomyces clavuligerus
SEQUENCE: 30
atgcacctgg ctccccgccg agtaccgcgc ggccgtcgaa gcccacctga ccgcgttcct  60
gaacgccaag gagcgctcgg ccgccgccgg ggggccggtt ccacaggatg tgcccgcgct  120
gctgcgggag ttcatcggcg ccgggggggg ggggaagcgg atccgtccgc tgctgtgcat  180
cgcggctggc aggccggcgg cggaacagga ctgccggacg aggtggtgtc cacagcggcg  240
gcgctggaga tgttccacgc gttcgcgctg atccacgacg acatcatgga tgactccgcg  300
accaggcgcg gcagcccgac ggtgcaccgg gcactcgccg accggctcgg cgccgctctc  360
gaccccgacc aagccggaca actgggggtg agcacggcga tcctcgtcgg ggacctcgcc  420
ctgacctggt cggacgaact gctgtacgct cccctgaccc cccaccggct ggccgcggta  480
ctgcccctgg tcacggccat gcgcgcggaa acggtccacg gccagtacct ggacatcacc  540
tccgcccgcc ggcccggcac ggacacctca ctggcgctgc gaatcgcgcg ctacaaaacc  600
gctgcttaca ccatggaacg cccccctgcac atcggagcag cgctcgccgg cgcacgaccg  660
gaactcctgg cagggctcag cgcctacgcg ctgccggcgg gcgaggcatt ccagctcgcc  720
gacgacctcc tgggagtgtt cggcgatcca cggagaaccg gcaaacccga cctcgacgac  780
ctccgcggcg gcaagcacac cgtcctcgtg gccctcgccc gggaacacgc cacacctgaa  840
cagcggcaca ccctggacac cctgctcggc acaccaggcc tcgaccggca gggcgcgtcc  900
cggctgcgct gcgtcctcgt cgccaccggg gcccgggcgg aagccgaacg cctgatcacc  960
gaacggcgcg accaggccct caccgcgctc aacgccctga cactgccccc accgctcgcc  1020
gaggcactcg cccgcctcac cctcgggagt accgcacacc cggcctga              1068

SEQ ID NO: 31          moltype = DNA  length = 993
FEATURE                Location/Qualifiers
source                 1..993
                       mol_type = other DNA
                       organism = Sulfulobus acidicaldarius
SEQUENCE: 31
```

-continued

```
atgagttact ttgacaacta ttttaatgag attgttaatt ctgtaaacga cattattaag  60
agctatatat ctggagatgt tcctaaacta tatgaagcct catatcattt gtttacatct  120
ggaggtaaga ggttaagacc attaatctta actatatcat cagatttatt cggaggacag  180
agagaaagag cttattatgc aggtgcagct attgaagttc ttcatacttt tacgcttgtg  240
catgatgata ttatggatca agataaatatc agaagagggt tacccacagt ccacgtgaaa  300
tacggcttac ccttagcaat attagctggg gatttactac atgcaaaggc ttttcagctc  360
ttaacccagg ctcttagagg tttgccaagt gaaaccataa ttaaggcttt cgatattttc  420
actcgttcaa taataattat atccgaagga caggcagtag atatggaatt tgaggacaga  480
attgatataa aggagcagga ataccttgac atgatctcac gtaagacagc tgcattattc  540
tcggcatcct caagtatagg cgcacttatt gctggtgcta atgataatga tgtaagactg  600
atgtctgatt tcggtacgaa tctaggtatt gcatttcaga ttgttgacga tatcttaggt  660
ctaacagcag acgaaaagga acttggaaag cctgttttta gtgatattag ggagggtaaa  720
aagactatac ttgtaataaa aacactggag ctttgtaaag aggacgagaa gaagattgtc  780
ctaaaggcgt taggtaataa gtcagcctca aaagaagaat taatgagctc agcagatata  840
attaagaaat actctttaga ttatgcatac aatttagcag agaaatatta taaaaatgct  900
atagactctt taaatcaagt ctcctctaag agtgatatac ctggaaaggc tttaaaatat  960
ctagctgaat ttacgataag aaggagaaaa taa                              993

SEQ ID NO: 32          moltype = DNA  length = 894
FEATURE                Location/Qualifiers
source                 1..894
                       mol_type = other DNA
                       organism = Synechococcus sp.
SEQUENCE: 32
ttggttgccc aaaccttcaa cctggacacc tacttgagcc aacgccagca acaggtggaa  60
gaggcgcttt ctgcggcatt ggttcccgcc tatccggagc gcatttacga ggcgatgcgc  120
tacagcctgc tggcgggggg gaaacgcctg aggccgatcc tctgtctggc ggcctgtgag  180
ttggccggcg gctctgtgga gcaggccatg cccaccgcct gcgccctgga gatgatccac  240
accatgtcgc tgatccacga cgatctgccg gcgatggaca acgacgattt tcgccgcggc  300
aagcccacca atcacaaggt attcggcgag gatatcgcca ttttggcagg agatgccctg  360
ttggcctatg cctttgagca tatcgccagc caaacgcggg gggtgccgcc gcagttggtg  420
ctgcaagtca ttgcccgcat tggccatgct gtggcggcaa ccggcttggt agggggccag  480
gtggtggatc tggagtccga aggcaaagcc atttccctag aaactttgga gtacatccac  540
agtcacaaga cgggtgctct gctggaggcc tcggtggttt cgggagggat cctggcaggg  600
gccgatgagg agctgctggc gcggctgagc cactacgctc gggacatcgg cctggctttt  660
cagatcgtgg acgacatttt ggatgttact gccaccagcg agcaactggg caaaacggca  720
ggcaaggatc aagctgccgc caaagccacc taccccagct tgttgggcct agaggcttcc  780
cggcagaaag ctgaggaact gatccaatcg gccaaggagg cgttgcgccc ctacggatcc  840
caggccgagc ccctgttggc tctggccgat ttcatcaccc gccgccagca ttga        894

SEQ ID NO: 33          moltype = DNA  length = 1116
FEATURE                Location/Qualifiers
source                 1..1116
                       mol_type = other DNA
                       organism = Arabidopsis thaliana
SEQUENCE: 33
atggcttcag tgactctagg ttcatggatt gttgttcacc accacaatca tcatcatcca  60
tcttcaatcc ttaccaaatc cagatccaga tcttgtccta taactcttac taaacccatc  120
tcctttcgat caaaacgcac cgtttcatca tcttcttcaa tcgtttcttc ttccgttgtt  180
acaaaagaag acaatctacg ccaatctgaa ccatcctctt tcgatttcat gtcgtacatc  240
atcaccaaag ccgaattagt caacaaagct ttagattcag ctgttcctct ccgtgagcca  300
ctcaagatcc acgaagcgat gcgttactct cttctcgccg gtggcaaaag agttagacca  360
gttctctgca tcgctgcttg tgaactcgtc ggaggtgaag aatcaaccgc tatgccagca  420
gcttgcgccg tcgagatgat tcacaccatg tcgttgatcc acgacgatct cccttgtatg  480
gataacgacg atctccgccg tggaaaaccg accaaccaca aagtgtttgg tgaagacgtc  540
gctgttttag ccggagacgc gcttctctct ttcgctttcg agcatttagc ttcggcgacg  600
agttctgatg ttgtttctcc ggtgagagtg gttcgagccg ttggagaatt ggctaaagcg  660
ataggaacag aagggttagt ggcgggtcaa gtcgtggata ttagtagtga agggttagat  720
ttaaacgacg tcggtttaga gcatttggag tttatccatt tgcataaaac ggcggcgttg  780
cttgaagctt ctgctgtttt gggagctatt gttggtggag gaagtgatga tgagattgag  840
aggttaagaa agtttgcgag atgtattggt ttgttgtttc aggtggttga tgatatcttg  900
gatgtgacga aatcgtcgaa agagttaggg aaaactgctg ggaaagattt gattgctgat  960
aagttgacgt atcctaagat tatgggtttg gagaaatcga gagagtttgc tgagaaattg  1020
aatagagagg ctcgtgatca gcttttaggg tttgattctg ataaggttgc tcctttgttg  1080
gctttggcta attacattgc ctatagacag aactga                            1116

SEQ ID NO: 34          moltype = DNA  length = 2364
FEATURE                Location/Qualifiers
misc_feature           1..2364
                       note = Description of Artificial Sequence: Synthetic
                        polynucleotide
source                 1..2364
                       mol_type = other DNA
                       organism = synthetic construct
SEQUENCE: 34
atgaaaaccg ggtttatctc accagcaaca gtatttcatc acagaatctc accagcgacc  60
actttcagac atcacttatc acctgctact acaaactcta caggcattgt cgccttaaga  120
gacatcaact tcagatgtaa agcagtttct aaagagtact ctgatctgtt gcagaaagat  180
gaggcttctt tcacaaaatg ggacgatgac aaggtgaaag atcatcttga taccaacaaa  240
```

-continued

```
aacttatacc caaatgatga gattaaggaa tttgttgaat cagtaaaggc tatgttcggt  300
agtatgaatg acggggagat aaacgtctct gcatacgata ctgcatgggt tgctttggtt  360
caagatgtcg atggatcagg tagtcctcag ttcccttctt ctttagaatg gattgccaac  420
aatcaattgt cagatggatc atggggagat catttgctgt tctcagctca cgatagaatc  480
atcaacacat tagcatgcgt tattgcactt acaagttgga atgttcatcc ttctaagtgt  540
gaaaaaggtt tgaattttct gagagaaaac atttgcaaat tagaagatga aaacgcagaa  600
catatgccaa ttggttttga agtaacattc ccatcactaa ttgatatcgc gaaaaagttg  660
aacattgaag tacctgagga tactccagca cttaaagaga tctacgcacg tagagatatc  720
aagttaacta agatcccaat ggaagttctt cacaaggtac ctactacttt gttacattct  780
ttggaaggaa tgcctgattt ggagtgggaa aaactgttaa agctacaatg taaagatggt  840
agtttcttgt tttccccatc tagtaccgca ttcgccctaa tgcaaacaaa agatgagaaa  900
tgcttacagt atctaacaaa tatcgtcact aagttcaacg gtggcgtgcc taatgtgtac  960
ccagtcgatt tgtttgaaca tatttgggtt gttgatagac tgcagagatt ggggattgcc  1020
agatacttca aatcagagat aaaagattgt gtagagtata tcaataagta ctggaccaaa  1080
aatggaattt gttgggctag aaatactcac gttcaagata tcgatgatac agccatggga  1140
ttcagagtgt tgagagcgca cggttatgac gtcactccag atgtttttag acaatttgaa  1200
aaagatggta aattcgtttg ctttgcaggg caatcaacac aagccgtgac aggaatgttt  1260
aacgtttaca gagcctctca aatgttgttc ccaggggaga gaattttgga agatgccaaa  1320
aagttctctt acaattactt aaaggaaaag caaagtacca acgaattgct ggataaatgg  1380
ataatcgcta aagatctacc tggtgaagtt ggttatgctc tggatatccc atggtatgct  1440
tccttaccaa gattggaaac tcgttattac cttgaacaat acggcggtga agatgatgtc  1500
tggataggca agacattata cagaatgggt tacgtgtcca ataacacata tctagaaatg  1560
gcaaagctgg attacaataa ctatgttgca gtccttcaat tagaatggta cacaatacaa  1620
caatggtacg tcgatattgg tatagagaag ttcgaatctg acaacatcaa gtcagtcctg  1680
gtttcttact acttggctgc ggcttcaata ttcgaacctg agagatctaa ggagagaatc  1740
gcttgggcaa agacaacaat cttagtcgat aagatcacat caattttcga ttcctctcag  1800
tcaagtaagg aagatattac tgcctttatt gacaagtttc gtaacaagtc ctcctctaaa  1860
aagcactcta tcaacggtga accatggcat gaagttatgg tagctttgaa aaagacctta  1920
cacggctttg ctctggatgc tcttatgact cattctcaag atatacatcc acagttacat  1980
caagcctggg aaatgtggtt gactaaacta caagacggcg tagatgttac tgctgagcta  2040
atggtccaaa tgatcaacat gactgctggc agatgggtat caaaggaatt acttactcat  2100
ccacaatatc aaagattgtc tactgtgaca aattctgtgt gtcacgatat taccaaactt  2160
cacaatttca aggagaattc caccacagtg gattcaaagg ttcaggaact agtccagttg  2220
gtttttagtg acacaccaga tgatttggat caagatatga aacaaacatt cctgacagtg  2280
atgaagacat tctactacaa ggcgtggtgt gatccaaaca ctataaacga tcatatatct  2340
aaagttttcg aaatcgtaat ttga                                     2364
```

```
SEQ ID NO: 35          moltype = DNA  length = 1584
FEATURE                Location/Qualifiers
misc_feature           1..1584
                       note = Description of Artificial Sequence: Synthetic
                        polynucleotide
source                 1..1584
                       mol_type = other DNA
                       organism = synthetic construct
SEQUENCE: 35
atgcctgatg cacacgatgc tccacctcca caaataagac agagaacact agtagatgag  60
gctacccaac tgctaactga gtccgcagaa gatgcatggg gtgaagtcag tgtgtcagaa  120
tacgaaacag caaggctagt tgcccatgct acatggttag gtggacacgc cacaagagtg  180
gccttccttc tggagagaca acacgaagac gggtcatggg gtccaccagg tggatatagg  240
ttagtcccta cattatctgc tgttcacgca ttattgacat gtcttgcctc tcctgctcag  300
gatcatggcg ttccacatga tagacttta agagctgttg acgcaggctt gactgccttg  360
agaagattgg ggacatctga ctccccacct gatactatag cagttgagct ggttatccca  420
tctttgctag agggcattca acacttactg gaccctgctc atcctcatag tagaccagcc  480
ttctctcaac atagaggctc tcttgtttgt cctggtggac tagatgggag aactctagga  540
gctttgagat cacacgccgc agcaggtaca ccagtaccag gaaaagtctg gcacgcttcc  600
gagactttgg gcttgagtac cgaagctgct tctcacttgc aaccagccca aggtataatc  660
ggtggctctg ctgctgccac agcaacatgg ctaaccaggg ttgcaccatc tcaacagtca  720
gattctgcca gaagatacct tgaggaatta caacacagat actctggccc agttccttcc  780
attaccccta tcacatactt cgaaagagca tggttattga acaattttgc agcagccggt  840
gttccttgtg aggctccagc tgctttgttg gattccttag aagcagcact tacaccacaa  900
ggtgctcctg ctggagcagg attgcctcca gatgctgatg atacagccgc tgtgttgctt  960
gcattggcaa cacatgggag aggtagaaga ccagaagtac tgatggatta caggactgac  1020
gggtatttcc aatgctttat tggggaaagg actccatcaa tttcaacaaa cgctcacgta  1080
ttggaaacat tagggcatca tgtggcccaa catccacaag atagagccag atacggatca  1140
gccatggata ccgcatcagc ttggctgctg gcagctcaaa agcaagatgg ctcttggtta  1200
gataaatggc atgcctcacc atactacgct actgtttgtt gcacacaagc cctagccgct  1260
catgcaagtc ctgcaactgc accagctaga cagagagctg tcagatgggt tttagccaca  1320
caaagatccg atggcggttg gggtctatgg cattcaactg ttgaagagac tgcttatgcc  1380
ttacagatct tggccccacc ttctggtggt ggcaatatcc cagtccaaca agcacttact  1440
agaggcagag caagattgtg tggagccttg ccactgactc ctttatggca tgataaggat  1500
ttgtatactc cagtaagagt agtcagagct gccagagctg ctgctctgta cactaccaga  1560
gatctattgt taccaccatt gtaa                                     1584
```

```
SEQ ID NO: 36          moltype = DNA  length = 1551
FEATURE                Location/Qualifiers
misc_feature           1..1551
                       note = Description of Artificial Sequence: Synthetic
                        polynucleotide
```

```
source                 1..1551
                       mol_type = other DNA
                       organism = synthetic construct
SEQUENCE: 36
atgaacgccc tatccgaaca cattttgtct gaattgagaa gattattgtc tgaaatgagt  60
gatggcggat ctgttggtcc atctgtgtat gatacggccc aggccctaag attccacggt  120
aacgtaacag gtagacaaga tgcatatgct tggttgatcg cccagcaaca agcagatgga  180
ggttggggct ctgccgactt tccactcttt agacatgctc caacatgggc tgcacttctc  240
gcattacaaa gagctgatcc acttcctggc gcagcagacg cagttcagac cgcaacaaga  300
ttcttgcaaa gacaaccaga tccatacgct catgccgttc ctgaggatgc ccctattggt  360
gctgaactga tcttgcctca gttttgtgga gaggctgctt ggttgttggg aggtgtggcc  420
ttccctagac acccagccct attaccatta agacaggctt gtttagtcaa actgggtgca  480
gtcgccatgt tgccttcagg acacccattg ctccactcct gggaggcatg gggtacttct  540
ccaacaacag cctgtccaga cgatgatggt tctataggta tctcaccagc agctacagcc  600
gcctggagag cccaggctgt gaccagaggc tcaactcctc aagtgggcag agctgacgca  660
tacttacaaa tggcttcaag agcaacgaga tcaggcatag aaggagtctt ccctaatgtt  720
tggcctataa acgtattcga accatgctgg tcactgtaca ctctccatct tgccggtctg  780
ttcgcccatc cagcactggc tgaggctgta agagttatcg ttgctcaact tgaagcaaga  840
ttgggagtgc atggcctcgg accagcttta cattttgctg ccgacgctga tgatactgca  900
gttgccttat gcgttctgca tttggctggc agagatcctg cagttgacgc attgagacat  960
tttgaaattg gtgagctctt tgttacattc ccaggagaga gaaatgctag tgtctctacg  1020
aacattcacg ctcttcatgc tttgagattg ttaggtaaac cagctgccgg agcaagtgca  1080
tacgtcgaag caaatagaaa tccacatggt ttgtgggaca acgaaaaatg gcacgtttca  1140
tggctttatc caactgcaca cgccgttgca gctctagctc aaggcaagcc tcaatggaga  1200
gatgaaagag cactagccgc tctactacaa gctcaaagag atgatggtgg ttggggagct  1260
ggtagaggat ccactttcga ggaaaccgcc tacgctcttt tcgctttaca cgttatggac  1320
ggatctgagg aagccacagg cagaagaaga atcgctcaag tcgtcgcaag agccttagaa  1380
tggatgctag ctagacatgc cgcacatgga ttaccacaaa caccactctg gattggtaag  1440
gaattgtact gtcctactag agtcgtaaga gtagctgagc tagctggcct gtggttagca  1500
ttaagatggg gtagaagagt attagctgaa ggtgctggtg ctgcacctta a           1551

SEQ ID NO: 37          moltype = DNA  length = 2364
FEATURE                Location/Qualifiers
source                 1..2364
                       mol_type = other DNA
                       organism = Stevia rebaudiana
SEQUENCE: 37
atgaagaccg gcttcatctc tcccgccacc gtcttccacc accgtatttc tccggcaacc  60
accttccgcc accacctttc tccggcgacc accaactcca ctggaattgt agctcttaga  120
gacatcaact tccggtgtaa agcggtatcc aaagagtact ctgatttact acaaaaagat  180
gaggcttcat ttaccaagtg ggacgatgac aaagtgaagg accatttgga cacaaataag  240
aatttgtatc caaacgatga gatcaaggag tttgttgaga gcgtgaaagc aatgtttggt  300
tctatgaatg acggagaaat aaatgtgtca gcgtatgata cggcttgggt tgcactcgtg  360
caagatgttg atggaagtgg ttcccctcaa tttccatcaa gtttggagtg gatcgcgaac  420
aatcaactct cagatgggtc ttggggcgat catttgttat ttcggctcca tgataggatc  480
attaacacgt tggcatgtgt tatagcgctt acttcttgga acgtccatcc aagtaaatgt  540
gaaaaaggac tgaattttct tagagaaaac atatgtaaac tcgaagacga gaacgcggaa  600
catatgccaa ttggttttga agtcacgttc ccgtcgctaa tagatatcgc aaagaagcta  660
aatattgaag ttcctgagga tactcctgcc ttaaaagaaa tttatgcaag aagagacata  720
aaactcacaa agataccaat ggaagtattg cacaaagtgc ccacaacttt acttcatagt  780
ttggaaggaa tgccagattt ggaatgggaa aaacttctga aattgcaatg caaagatgga  840
tcatttctgt tttctccatc atctactgct tttgcactca tgcaaacaaa agatgaaaag  900
tgtcttcagt atttgacaaa tattgttacc aaattcaatg gtggagttcc gaatgtgtac  960
ccggtggatc tattcgaaca tatttgggta gttgatcgac ttcaacgact tgggattgct  1020
cgttatttca aatcagagat caaagattgc gttgaatata ttaacaagta ttggacaaag  1080
aatgggattt gttgggcaag aaacacgcac gtacaagata ttgatgatac cgcaatggga  1140
tttagggttt taagagcaca tggttatgat gttactccag atgtatttcg acaatttgag  1200
aaggatggta aattcgtatg tttcgctgga cagtcaacac aagccgtcac cggaatgttc  1260
aatgtgtata gagcgtcaca aatgctcttt cccggagaaa gaattcttga agatgcaaag  1320
aaattttcat ataattattt gaaagaaaaa caatcgacaa atgagcttct tgataaatgg  1380
atcatcgcca aagacttacc tggagaggtt ggatatgcgc tagacatacc atggtatgca  1440
agcttaccgc gactcgagac aagatattac ttagagcaat acgggggcga ggatgatgtt  1500
tggattggaa aaactctata caggatggga tatgtgagca ataatacgta ccttgaaatg  1560
gccaaattgg actacaataa ctatgtggcc gtgcttcaac tcgaatggta cactatccag  1620
caatggtatg ttgatatcgg tatcgaaaag tttgaaagtg acaatatcaa aagcgtatta  1680
gtgtcgtatt acttggctgc agccagcata ttcgagccgg aaaggtccaa ggaacgaatc  1740
gcgtgggcta aaaccaccat attagttgac aagatcacct caatttttga ttcatcacaa  1800
tcctcaaaag aggacataac agcctttata gacaaattta ggaacaaatc gtcttctaag  1860
aagcattcaa taaatggaga accatggcac gaggtgatgg ttgcactgaa aaagacccta  1920
cacggcttcg ctttggatgc actcatgact catagtcaag acatccaccc gcaactccat  1980
caagcttggg agatgtggtt gacgaaattg caagatggag tagatgtgac agcggaatta  2040
atggtacaaa tgataaatat gacagctggt cgttgggtat ccaaagaact tttaactcat  2100
cctcaatacc aacgcctctc aaccgtcaca aatagtgtgt gtcacgatat aactaagctc  2160
cataacttca aggagaattc cacgacggta gactcgaaag ttcaagaact agtgcaactt  2220
gtgtttagcg acacgcccga tgatcttgat caggatatga aacagacgtt tctaaccgtc  2280
atgaaaacct tctactacaa ggcgtggtgt gatccgaaca cgataaatga ccatatctcc  2340
aaggtgttcg agattgtaat atga                                         2364

SEQ ID NO: 38          moltype = DNA  length = 1584
```

-continued

```
FEATURE                Location/Qualifiers
source                 1..1584
                       mol_type = other DNA
                       organism = Streptomyces clavuligerus
SEQUENCE: 38
ttgcccgacg cgcatgatgc ccctccgcct cagatacgac agcggaccct tgtcgatgag  60
gcgacgcaac tcctcacgga gtcggccgag gacgcctggg gtgaggtgtc cgtgtccgag  120
tacgaaacgg cgcggctggt ggcccacgcc acctggctcg gcggtcacgc cacacgggtg  180
gccttcctgc tggagcggca gcatgaggac ggctcgtggg gcccgcccgg cgggtaccgt  240
ctcgtaccca cgctgagtgc cgtacacgcc ctgctcacct gtctggcgtc tcccgcgcag  300
gaccacggag tgcctcatga ccggctcctg cgcgcagttg acgcgggcct gacggcactg  360
cgtcgtcttg ggacgagcga cagcccgccg gacaccattg cggtcgaact ggtcataccc  420
tcgctccttg agggcatcca gcacctcctg gacccggcgc acccgcattc ccgacccgct  480
ttttcgcaac accgcggcag cctcgtctgc cccgggggcc tcgacggccg cacgctgggg  540
gccttgcgct cccacgccgc agccggcaca cctgtcccgg gcaaggtgtg gcacgcctcg  600
gaaaccttgg ggctatcgac cgaggcagcc tcccaccttc aacccgccca gggcatcatc  660
ggtggctccg ccgccgcgac agcaacatgg ctcaccaggg tcgccccgtc gcaacagagc  720
gacagcgcac ggcgctacct ggaagaactc cagcaccgat acagcggccc ggtgccctcc  780
atcaccccga tcacctattt cgaacgggcc tggctgctca acaacttcgc tgccgcgggg  840
gttccatgcg aggctccggc agcccttctc gacagcctgg aggcagcgct cacaccacag  900
ggcgctccag cgggtgcggg actgccgccg gacgcggatg acaccgccgc cgttctgctg  960
gcgcttgcca cgcacggccg cgggcgccgt cccgaggtcc tcatggacta ccgcacggac  1020
ggctacttcc agtgcttcat cggcgaacgc accccttcca tcagcaccaa tgcccatgtc  1080
ctggagacgc tcggtcacca cgtcgcccaa caccctcagg acagggcccg atacggctca  1140
gccatggaca ccgcatcagc gtggctcctc gcggctcaga agcaggatgg cagctggctc  1200
gacaagtggc acgcctcccc ctactacgcc accgtctgct gcacccaggc actggcagcc  1260
cacgcttccc ctgccaccgc ccccgcacgg cagcgtgctg tgcggtgggt gctggcaaca  1320
caacgctcgg acggcggctg ggcctgtggg cactccacgg tcgaggagac cgcctacgcc  1380
ctgcagatcc tcgccccacc ttccggcggc gggaacatcc ccgtgcaaca ggcgctcacc  1440
agggggcgcg cccgcctctg cggcgctttg ccgctgactc ccctatggca tgacaaggac  1500
ctgtacacgc cggtacgtgt cgtccgcgcc gcccgtgccg ccgccctgta caccacccgt  1560
gacctgcttc tgccgcccct gtga                                        1584

SEQ ID NO: 39          moltype = DNA  length = 1551
FEATURE                Location/Qualifiers
source                 1..1551
                       mol_type = other DNA
                       organism = Bradyrhizobium japonicum
SEQUENCE: 39
gtgaacgcgc tgtccgaaca tatcctttcc gaattgcgcc gcctgctgag cgaaatgagc  60
gatggcggca gcgtcggtcc gtccgtctac gacacggcgc aggcgctgcg cttccacggc  120
aacgtcaccg gtcggcagga cgcatacgcg tggctcatcg cgcagcaaca ggccgacggc  180
ggatggggaa gcgcggactt cccgctgttc cgccatgcgc ccacgtgggc ggcgttactg  240
gcattgcagc gtgccgatcc tcttcccgga gctgcggacg cagtccagac tgcaacgagg  300
ttcctccagc gccagcccga tccctacgca catgcggtgc cagaagacgc gccgatcggc  360
gcggagctga tcctgccgca gttttgcggt gaggccgcat ggttgctggg tggcgtagcg  420
tttccgcgcc atcctgcgct gttgccattg cggcaagcgt gcctggtcaa gctgggggcg  480
gtggcgatgt tgccgagcgg ccatccgttg ctacactcct gggaagcctg ggggacgtcg  540
ccgaccaccg catgcccgga tgacgacggc agcatcggca tcagtccggc ggccaccgcc  600
gcgtggcgtg cccaggccgt gacacggggg agcacgccgc aggtcgggcg cgccgatgcg  660
tatctgcaga tggcatcgcg ggcgacgcgc agcggcatcg aaggtgtctt tcccaacgtc  720
tggccgatca atgtgttcga gccatgctgg tcgctgtaca ccctgcatct ggccgggctt  780
ttcgcgcatc ccgcgctcgc ggaggcggtt cgcgtgatcg tcgcgcagct cgaggcccgt  840
ctgggcgtgc acggtctggg cccggccttg cacttcgcgg ctgatgcgga cgacaccgcc  900
gttgcgttgt gcgtcctgca ccttgcaggc cgtgacccgg cggtcgatgc gttgcgccat  960
ttcgaaatcg gcgagctgtt cgtcaccttc cccggcgaac gcaatgcctc ggtgtcgacc  1020
aacattcatg ccctgcatgc gttgcgactg ttgggaaagc ccgccgcggg cgccagcgcg  1080
tacgtcgagg ccaatcgcaa cccgcacggt ctatgggaca acgaaaaatg gcacgtttcg  1140
tggctgtatc ccaccgcgca tgcggtcgct gcgctggcgc aaggcaagcc ccagtggcga  1200
gatgagcgcg cgctggcggc gctgctgcag gcgcagcgcg acgacggtgg ctggggcgcg  1260
ggtcgcgggt ccacgttcga ggaaaccgcc tatgcgctgt ttgcgttgca cgtgatggat  1320
gggagcgaag aggcgacagg gcgccggcgc atcgcgcagg tggtggcgcg tgcgctggag  1380
tggatgctcg cccgccatgc ggcgcatgga ttgccgcaga cgccgctgtg gatcggcaag  1440
gaactgtatt gccccactcg ggtcgtgcgc gtggccgaac tcgccgggtt gtggctggcg  1500
cttcgttggg ggcggcgcgt cctggccgag ggggcaggag cggcgccatg a           1551

SEQ ID NO: 40          moltype = DNA  length = 2355
FEATURE                Location/Qualifiers
misc_feature           1..2355
                       note = Description of Artificial Sequence: Synthetic
                        polynucleotide
source                 1..2355
                       mol_type = other DNA
                       organism = synthetic construct
SEQUENCE: 40
atgaatttga gtttgtgtat agcatctcca ctattgacca aatctaatag accagctgct  60
ttatcagcaa ttcatacagc tagtacatcc catggtggcc aaaccaaccc tacgaatctg  120
ataatcgata cgaccaagga gagaatacaa aaacaattca aaaatgttga aatttcagtt  180
tcttcttatg atactgcgtg ggttgccatg gttccatcac ctaattctcc aaagtctcca  240
```

-continued

```
tgtttcccag aatgtttgaa ttggctgatt aacaaccagt tgaatgatgg atcttggggt  300
ttagtcaatc acacgcacaa tcacaaccat ccacttttga aagattcttt atcctcaact  360
ttggcttgca tcgtggccct aaagagatgg aacgtaggtg aggatcagat taacaagggg  420
cttagtttca ttgaatctaa cttggcttcc gcgactgaaa aatctcaacc atctccaata  480
ggattcgata tcatctttcc aggtctgtta gagtacgcca aaaatctaga tatcaactta  540
ctgtctaagc aaactgattt ctcactaatg ttacacaaga gagaattaga acaaaagaga  600
tgtcattcaa acgaaatgga tggttaccta gcttatatct ctgaaggtct tggtaatctt  660
tacgattgga atatggtgaa aaagtaccag atgaaaaatg gctcagtttt caattcccct  720
tctgcaactg cggcagcatt cattaaccat caaaatccag gatgcctgaa ctatttgaat  780
tcactactag acaaattcgg caacgcagtt ccaactgtat accctcacga tttgtttatc  840
agattgagta tggtggatac aattgaaaga cttggtatat cccaccactt tagagtcgag  900
atcaaaaatg ttttggatga gacataccgt tgttgggtgg agagagatga acaaatcttt  960
atggatgttg tgacgtgcgc gttggccttt agattgttgc gtattaacgg ttacgaagtt  1020
agtccagatc cacttgccga aattacaaac gaattagctt taaaggatga atacgccgct  1080
cttgaaacat atcatgcgtc acatatcctt taccaagagg acttatcatc tggaaaacaa  1140
attcttaaat ctgctgattt cctgaaggaa atcatatcca ctgatagtaa tagactgtcc  1200
aaactgatcc ataaagaggt tgaaaatgca cttaagttcc ctattaacac cggcttagaa  1260
cgtattaaca caagacgtaa catccagctt tacaacgtag acaatactag aatcttgaaa  1320
accacttacc attcttccaa catatcaaac actgattacc taagattagc tgttgaagat  1380
ttctacacat gtcagtctat ctatagagaa gagctgaaag gattagagag atgggtcgtt  1440
gagaataagc tagatcaatt gaaatttgcc agacaaaaga cagcttattg ttacttctca  1500
gttgccgcca ctttatcaag tccagaattg tcagatgcac gtatttcttg ggctaaaaac  1560
ggaattttga caactgttgt tgatgatttc tttgatattg gcgggacaat cgacgaattg  1620
acaaacctga ttcaatgcgt tgaaaagtgg aatgtcgatg tcgataaaga ctgttgctca  1680
gaacatgtta gaatactgtt cttggctctg aaagatgcta tctgttggat cggggatgag  1740
gctttcaaat ggcaagctag agatgtgacg tctcacgtca ttcaaacctg gctagaactg  1800
atgaactcta tgttgagaga agcaatttgg actagagatg catacgttcc tacattaaac  1860
gagtatatgg aaaacgctta tgtctccttt gctttgggtc ctatcgttaa gcctgccata  1920
tactttgtag gaccaaagct atccgaggaa atcgtcgaat catcagaata ccataacttg  1980
ttcaagttaa tgtccacaca aggcagatta cttaatgata ttcattcttt caaaagagag  2040
tttaaggaag gaaagttaaa tgctgttgct ctgcatcttt ctaatggcga aagtggtaaa  2100
gtcgaagagg aagtagttga ggaaatgatg atgatgatca aaaacaagag aaaggagttg  2160
atgaaactaa tcttcgaaga gaacggttca attgttccta gagcatgtaa ggatgcattt  2220
tggaacatgt gtcatgtgct aaactttttc tacgcaaacg acgatggttt tactgggaac  2280
acaatactag atacagtaaa agacatcata tacaaccctt tggtcttagt aaacgaaaac  2340
gaggagcaaa gataa                                                  2355
```

```
SEQ ID NO: 41          moltype = DNA  length = 2355
FEATURE                Location/Qualifiers
misc_feature           1..2355
                       note = Description of Artificial Sequence: Synthetic
                        polynucleotide
source                 1..2355
                       mol_type = other DNA
                       organism = synthetic construct
SEQUENCE: 41
atgaatctgt ccctttgtat agctagtcca ctgttgacaa aatcttctag accaactgct  60
ctttctgcaa ttcatactgc cagtactagt catggaggtc aaacaaaccc aacaaatttg  120
ataatcgata ctactaagga gagaatccaa aagctattca aaaatgttga aatctcagta  180
tcatcttatg acaccgcatg ggttgcaatg gtgccatcac ctaattcccc aaaaagtcca  240
tgttttccag agtgcttgaa ttggttaatc aataatcagt taaacgatgg ttcttggggt  300
ttagtcaacc acactcataa ccacaatcat ccattattga aggactcttt atcatcaaca  360
ttagcctgta ttgttgcatt gaaaagatgg aatgtaggtg aagatcaaat caacaagggt  420
ttatcattca tagaatccaa tctagcttct gctaccgaca aatcacaacc atctccaatc  480
gggttcgaca taatcttccc tggtttgctg gagtatgcca aaaaccttga tatcaactta  540
ctgtctaaac aaacagattt ctctttgatg ctacacaaaa gagagttaga gcagaaaaga  600
tgccattcta acgaaattga cgggtactta gcatatatct cagaaggttt gggtaatttg  660
tatgactgga acatggtcaa aaagtatcag atgaaaaatg gatccgtatt caattctcct  720
tctgcaactg ccgcagcatt cattaatcat caaaaccctg ggtgtcttaa ctacttgaac  780
tcactattag ataagtttgg aaatgcagtt ccaacagtct atcctttgga cttgtacatc  840
agattatcta tggttgacac tatagagaga ttaggtattt ctcatcattt cagagttgag  900
atcaaaaatg ttttggacga gacatacaga tgttgggtcg aaagagatga gcaaatcttt  960
atggatgtcg tgacctgcgc tctggctttt agattgctaa ggatacacgg atacaaagta  1020
tctcctgatc aactggctga gattacaaac gaactggctt tcaaagacga atacgccgca  1080
ttagaaacat accatgcatc ccaaatactt taccaggaag acctaagttc aggaaaacaa  1140
atcttgaagt ctgcagattt cctgaaaggc attctgtcta cagatagtaa taggttgtct  1200
aaattgatac acaaggaagt agaaaacgca ctaaagtttc ctattaacac tggtttagag  1260
agaatcaata ctaggagaaa cattcagctg tacaacgtag ataatacaag gattcttaag  1320
accacctacc atagttcaaa catttccaac acctattact taagattagc tgtcgaagac  1380
ttttacactt gtcaatcaat ctacagagag gagttaaagg gcctagaaag atgggtagtt  1440
caaaacaagt tggatcaact gaagtttgct agacagaaga cagcatactg ttatttctct  1500
gttgctgcta ccctttcatc cccagaattg tctgatgcca gaataagttg ggccaaaaat  1560
ggtattctta caactgtagt cgatgatttc tttgatattg gaggtactat tgatgaactg  1620
acaaatctta ttcaatgtgt tgaaaagtgg aacgtggatg tagataagga ttgctgcagt  1680
gaacatgtga gaatactttt cctggctcta aaagatgcaa tatgttggat tggcgacgag  1740
gccttcaagt ggcaagctag agatgttaca tctcatgtca tccaaacttg gcttgaactg  1800
atgaactcaa tgctaagaga agcaatctgg acaagagatg catacgttcc aacattgaac  1860
gaatacatgg aaaacgctta cgtctcattt gccttgggtc ctattgttaa gccagccata  1920
tactttgttg ggccaaagtt atccgaagag attgttgagt cttccgaata tcataaccta  1980
```

-continued

```
ttcaagttaa tgtcaacaca aggcagactt ctgaacgata tccactcctt caaaagagaa  2040
ttcaaggaag gtaagctaaa cgctgttgct ttgcacttgt ctaatggtga atctggcaaa  2100
gtggaagagg aagtcgttga ggaaatgatg atgatgatca aaaacaagag aaaggaattg  2160
atgaaattga ttttcgagga aaatggttca atcgtaccta gagcttgtaa agatgctttt  2220
tggaatatgt gccatgttct taacttcttt tacgctaatg atgatggctt cactggaaat  2280
acaatattgg atacagttaa agatatcatc tacaacccac ttgttttggt caatgagaac  2340
gaggaacaaa gataa                                                   2355

SEQ ID NO: 42          moltype = DNA  length = 1773
FEATURE                Location/Qualifiers
misc_feature           1..1773
                       note = Description of Artificial Sequence: Synthetic
                        polynucleotide
source                 1..1773
                       mol_type = other DNA
                       organism = synthetic construct
SEQUENCE: 42
atggctatgc cagtgaagct aacacctgcg tcattatcct taaaagctgt gtgctgcaga  60
ttctcatccg gtggccatgc tttgagattc gggagtagtc tgccatgttg gagaaggacc  120
cctacccaaa gatctacttc ttcctctact actagaccag ctgccgaagt gtcatcaggt  180
aagagtaaac aacatgatca ggaagctagt gaagcgacta tcagacaaca attacaactt  240
gtggatgtcc tggagaatat gggaatatcc agacatttg ctgcagagat aaagtgcata  300
ctagacagaa cttacagatc ttggttacaa agacacgagg aaatcatgct ggacactatg  360
acatgtgcta tggcttttag aatcctaaga ttgaacggat acaacgtttc atcagatgaa  420
ctataccacg ttgtagaggc atctggtctg cataattctt tgggtgggta tcttaacgat  480
accagaacac tacttgaatt acacaaggct tcaacagtta gtatctctga ggatgaatct  540
atcttagatt caattggctc tagatccaga acattgctta gagaacaatt ggagtctggt  600
ggcgcactga gaaagccttc tttattcaaa gaggttgaac atgcactgga tggacctttt  660
tacaccacac ttgatagact tcatcatagg tggaatattg aaaacttcaa cattattgag  720
caacacatgt tggagactcc atacttatct aaccagcata catcaaggga tatcctagca  780
ttgtcaatta gagattttc ctcctcacaa ttcacttatc aacaagagct acagcatctg  840
gagagttggg ttaaggaatg tagattagat caactacagt tcgcaagaca gaaattagcg  900
tacttttacc tatcagccgc aggcaccatg ttttctcctg agctttctga tgcgagaaca  960
ttatgggcca aaaacggggt gttgacaact attgttgatg atttctttga tgttgccggt  1020
tctaaagagg aattggaaaa cttagtcatg ctggtcgaaa tgtgggatga acatcacaaa  1080
gttgaattct attctgagca ggtcgaaatc atcttctctt ccatctacga ttctgtcaac  1140
caattgggtg agaaggcctc tttggttcaa gacagatcaa ttacaaaaca ccttgttgaa  1200
atatggttag acttgttaaa gtccatgatg acggaagttg aatggagact gtcaaaatac  1260
gtgcctacag aaaaggaata catgattaat gcctctctta tcttcggcct aggtccaatc  1320
gttttaccag ctttgtattt cgttggtcca aagatttcag aaagtatagt aaaggaccca  1380
gaatatgatg aattgttcaa actaatgtca acatgtggta gattgttgaa tgacgtgcaa  1440
acgttcgaaa gagaatacaa tgagggtaaa ctgaattctg tcagtctatt ggttcttcac  1500
ggaggcccaa tgtctatttc agacgcaaag aggaaattac aaaagcctat tgatacgtgt  1560
agaagagatc ttctttcttt ggtccttaga gaagagtctg tagtaccaag accatgtaag  1620
gaactattct ggaaaatgtg taaagtgtgc tatttctttt actcaacaac tgatgggttt  1680
tctagtcaag tcgaaagagc aaaagaggta gacgctgtca taaatgagcc actgaagttg  1740
caaggttctc atacactggt atctgatgtt taa                               1773

SEQ ID NO: 43          moltype = DNA  length = 2232
FEATURE                Location/Qualifiers
misc_feature           1..2232
                       note = Description of Artificial Sequence: Synthetic
                        polynucleotide
source                 1..2232
                       mol_type = other DNA
                       organism = synthetic construct
SEQUENCE: 43
atgcagaact tccatggtac aaaggaaagg atcaaaaaga tgtttgacaa gattgaattg  60
tccgtttctt cttatgatac agcctgggtt gcaatggtcc catcccctga ttgcccagaa  120
acaccttgtt ttccagaatg tactaaatgg atcctagaaa atcagttggg tgatggtagt  180
tggtcacttc ctcatggcaa tccacttcta gttaaagatg cattatcttc cactcttgct  240
tgtattctgg ctcttaaaag atggggaatc ggtgaggaac agattaacaa aggactgaga  300
ttcatagaac tcaactctgc tagtgtaacc gataacgaac aacacaaacc aattggattt  360
gacattatct ttccaggtat gattgaatac gctatagact tagacctgaa tctaccacta  420
aaaccaactg acattaactc catgttgcat cgtagagccc ttgaattgac atcaggtgga  480
ggcaaaaatc tagaaggtag aagagcttac ttggcctacg tctctgaagg aatcggtaag  540
ctgcaagatt gggaaatggc tatgaaatac caacgtaaaa acggatctct gttcaatagt  600
ccatcaacaa ctgcagctgc attcatccat atacaagatg ctgaatgcct ccactatatt  660
cgttctcttc tccagaaatt tggaaacgca gtccctacaa tataccctct cgatatctat  720
gccagacttt caatggtaga tgccctggaa cgtcttggta ttgatagaca tttcagaaag  780
gagagaaagt tcgttctgga tgaaacatac agattttggt tgcaaggaga agaggagatt  840
ttctccgata acgcaacctg tgctttggcc ttcagaatat tgagacttaa tggttacgat  900
gtctctcttg aagatcactt ctctaactct ctgggcggtt acttaaagga ctcaggagca  960
gctttagaac tgtacagagc cctccaattg tcttacccag acgagtccct cctggaaaag  1020
caaaattcta gaacttctta cttcttaaaa caaggtttat ccaatgtctc cctctgtggt  1080
gacagattgc gtaaaaacat aattggagag gtgcatgatg ctttaaactt ttccgaccac  1140
gctaacttac aaagattagc tattcgtaga aggattaagc attacgctac tgacgataca  1200
aggattctaa aaacttccta cagatgctca acaatcggta accaagattt tctaaaactt  1260
gcagtggaag atttcaatat ctgtcaatca atacaaagag aggaattcaa gcatattgaa  1320
```

-continued

```
agatgggtcg ttgaaagacg tctagacaag ttaaagttcg ctagacaaaa agaggcctat  1380
tgctatttct cagccgcagc aacattgttt gcccctgaat tgtctgatgc tagaatgtct  1440
tgggccaaaa atggtgtatt gacaactgtg gttgatgatt tcttcgatgt cggaggctct  1500
gaagaggaat tagttaactt gatagaattg atcgagcgtt gggatgtgaa tggcagtgca  1560
gatttttgta gtgaggaagt tgagattatc tattctgcta tccactcaac tatctctgaa  1620
ataggtgata agtcatttgg ctggcaaggt agagatgtaa agtctcaagt tatcaagatc  1680
tggctggact tattgaaatc aatgttaact gaagctcaat ggtcttcaaa caagtctgtt  1740
cctaccctag atgagtatat gacaaccgcc catgtttcat tcgcacttgg tccaattgta  1800
cttccagcct tatacttcgt tggcccaaag ttgtcagaag aggttgcagg tcatcctgaa  1860
ctactaaacc tctacaaagt cacatctact tgtggcagac tactgaatga ttggagaagt  1920
tttaagagag aatccgagga aggtaagctc aacgctatta gtttatacat gatccactcc  1980
ggtggtgctt ctacagaaga ggaaacaatc gaacatttca aaggtttgat tgattctcag  2040
agaaggcaac tgttacaatt ggtgttgcaa gagaaggata gtatcatacc tagaccatgt  2100
aaagatctat tttggaatat gattaagtta ttacacactt tctacatgaa agatgatggc  2160
ttcacctcaa atgagatgag gaatgtagtt aaggcaatca ttaacgaacc aatctcactg  2220
gatgaattat ga                                                     2232

SEQ ID NO: 44          moltype = DNA  length = 2355
FEATURE                Location/Qualifiers
source                 1..2355
                       mol_type = other DNA
                       organism = Stevia rebaudiana
SEQUENCE: 44
atgaatcttt cactatgcat cgcgtcccct ttgttaacca aatcaaatcg acccgcggct  60
ctgtcagcta ttcatacagc atcaacttca catggtggac aaactaatcc cactaatctg  120
atcattgata caaccaaaga acggatccaa aaacagttta aaaatgtaga aatttctgtt  180
tcttcatatg acacagcatg ggtagccatg gtcccttctc caaactcacc caaatcgcct  240
tgtttccctg agtgtctcaa ttggttaatt aataatcagc ttaatgatgg ttcatggggt  300
cttgttaatc acactcataa tcataatcac ccgttgctta aagattctct atcttcaaca  360
ttagcatgta ttgttgcatt aaaaagatgg aatgttgggg aagatcaaat aaataaaggt  420
ctaagtttta ttgagtcaaa tcttgcttca gctactgaaa aaagtcaacc atctcccatt  480
ggttttgaca tcatatttcc tggtttgctt gagtatgcga aaaacttgga cataaacctc  540
ctttcaaaac aaacagattt tagtttgatg ctacataaga gggaattgga gcaaaaaaga  600
tgccattcaa atgagatgga tggatacttg gcgtatatct ctgaaggact cggtaattta  660
tatgattgga atatggtgaa gaaatatcag atgaaaaatg gttctgtttt caactcacca  720
tcagcaacag ctgctgcttt cattaatcat caaaatcctg gttgtcttaa ttatttaaat  780
tcacttttgg acaagtttgg taatgcagtc ccaacagttt atcctcatga tttatttatc  840
cgactttcta tggttgacac aattgaaaga ttaggaattt cacaccattt cagagtggaa  900
attaaaaatg ttttagatga aacatacaga tgttgggtgg aacgagatga gcaaatattc  960
atggatgttg taacatgtgc tttagccttt cggttattaa ggatcaatgg gtatgaagtt  1020
tccccagatc cattggctga aattactaat gaattagctt tgaaagacga atatgcagct  1080
cttgaaacat atcatgcgtc acatatatta taccaagagg atttatcttc tggaaaacaa  1140
atcttgaagt cagctgattt cctcaaagag ataatatcca ctgattcaaa caggctttct  1200
aaattaattc acaaagaggt ggaaaatgct cttaagttcc ctatcaatac cggtttagaa  1260
cgcataaaca ctagacgaaa tatacagctt tacaatgtag acaatacaag aattctgaaa  1320
actacatatc actcatcaaa tattagtaac actgattacc taaggttggc tgttgaagat  1380
ttctacacct gccaatctat ttatcgtgaa gaattaaaag gtcttgaaag gtgggtggta  1440
gagaataagt tggaccagct caagtttgct aggcaaaaga ccgcctactg ttatttctct  1500
gttgctgcaa cactttcgtc tcccgaatta tcagatgcgc gtatttcatg ggccaaaaat  1560
ggcatattaa ctacagtagt tgatgacttt tttgatatcg gtggtacaat cgatgaattg  1620
accaacctga ttcaatgtgt tgaaaaatgg aatgtagatg tcgacaagga ttgttgttca  1680
gagcatgttc ggattttatt tttagcatta aaagatgcaa tctgttggat tggagatgaa  1740
gcttttaaat ggcaagcgcg cgatgtaact agccatgtta ttcaaacttg gttggaacta  1800
atgaatagta tgttgagaga agctatatgg acaagagatg cttatgtgcc aacattaaat  1860
gaatatatgg aaaacgctta cgtgtcattt gcattaggcc cgattgtcaa gccggctatt  1920
tactttgtgg ggcccaaatt atcagaggag attgttgaaa gctctgaata tcataatcta  1980
tttaagctaa tgagcacgca gggtcgactt ctaaacgata tccatagctt caagagggaa  2040
tttaaggaag gcaaattaaa cgcggtagca ttgcatttga gtaacggaga aagtgggaaa  2100
gtggaagaag aggttgtgga ggagatgatg atgatgatta aaaacaagag gaaagaatta  2160
atgaaattaa tttttgaaga aaatggtagc attgttccta gagcttgtaa agatgcattt  2220
tggaacatgt gtcacgtgtt gaattttttt tacgcaaacg atgacgggtt tactggaaac  2280
acgattcttg atactgtgaa ggacatcatt tacaacccgt tggtgcttgt gaatgaaaat  2340
gaagaacaaa ggtaa                                                  2355

SEQ ID NO: 45          moltype = DNA  length = 2355
FEATURE                Location/Qualifiers
source                 1..2355
                       mol_type = other DNA
                       organism = Stevia rebaudiana
SEQUENCE: 45
atgaatcttt cactatgcat tgcgtcccct ttgttaacca aatcaagtcg acccacggct  60
ctgtcagcta ttcatacagc atcaacttca catggtggac aaactaatcc cactaatctg  120
atcattgata caaccaaaga acggatccaa aaactgttta aaaatgtaga aatttctgtt  180
tcttcatatg acacagcatg ggtagccatg gtcccttctc caaactcacc caaatcgcct  240
tgtttccctg agtgtctcaa ttggttaatt aataatcagc ttaatgatgg ttcatggggt  300
cttgttaatc acactcataa tcataatcac ccgttgctta aagattctct atcttcaaca  360
ttagcatgta ttgttgcatt aaaaagatgg aatgttgggg aagatcaaat aaataaaggt  420
ctaagtttta ttgagtcaaa tcttgcttca gcaactgaca aaagtcaacc atctcccatt  480
ggttttgata tcatatttcc tggtttgctt gagtatgcga aaaacttgga cataaacctc  540
```

-continued

```
ctttcaaaac aaacagattt tagtttgatg ctacataaga gggaattgga gcaaaaaaga  600
tgccattcaa atgagattga tggatacttg gcgtatatct ctgaaggact cggtaattta  660
tatgattgga atatggtgaa gaaatatcag atgaaaaatg gttctgtttt caactcacca  720
tcagcaacag cagctgcttt cattaatcat caaaatcccg gttgtcttaa ttatttaaat  780
tcacttttgg acaagtttgg taatgcagtc ccaacagttt atcctcttga tttatatatc  840
cggctttcta tggttgacac aattgaaaga ttaggaattt cacaccattt cagagtggaa  900
attaaaaatg ttttagatga aacatacaga tgttgggtgg aacgagatga gcaaatattc  960
atggatgttg taacatgtgc tttagccttt cggttattaa ggatccacgg gtataaagtc  1020
tccccagatc aattggctga aattactaat gaattagctt tcaaagacga atacgcagct  1080
cttgaaacat atcatgcatc acagatatta taccaagagg atttatcttc tggaaaacaa  1140
atcttgaagt cagctgattt cctcaaaggg atattatcca ctgattcaaa caggctttct  1200
aaattaattc acaaagaggt ggaaaatgct cttaagttcc ctatcaatac cggtttagaa  1260
cgcataaaca ctagacgaaa tatacagctt tacaatgtag acaatacaag aattctgaaa  1320
actacatatc actcatcaaa tattagtaac acttattacc taaggttggc tgttgaagat  1380
ttctacacct gccaatctat ttatcgtgaa gaattaaaag gtcttgaaag gtgggtggta  1440
cagaataagt tggaccagct caagtttgct aggcaaaaga ccgcctactg ttatttctct  1500
gttgctgcaa cactttcgtc tcccgaatta tcagatgcgc gtatttcatg ggccaaaaat  1560
ggcatattaa ctacagtagt tgatgacttt tttgatatcg gtggtacaat cgatgaattg  1620
accaacctga ttcaatgtgt tgaaaaatgg aatgtagatg tcgacaagga ttgttgttca  1680
gagcatgttc ggattttatt tttagcatta aaagatgcaa tctgttggat tggagatgaa  1740
gcttttaaat ggcaagcgcg cgatgtaact agccatgtta ttcaaacttg gttggaacta  1800
atgaatagta tgttgagaga agctatatgg acaagagatg cttatgtgcc aacattaaat  1860
gaatatatgg aaaacgctta cgtgtcattt gcattaggcc cgattgtcaa gccggctatt  1920
tactttgtgg ggcccaaatt atcagaggag attgttgaaa gctctgaata tcataatcta  1980
tttaagctaa tgagcacgca gggtcgactt ctaaacgata tccatagctt caagagggaa  2040
tttaaggaag gcaaattaaa cgcggtagca ttgcatttga gtaacggaga aagtgggaaa  2100
gtggaagaag aggttgtgga ggagatgatg atgatgatta aaaacaagag gaaagaatta  2160
atgaaattaa tttttgaaga aaatggtagc attgttccta gagcttgtaa agatgcattt  2220
tggaacatgt gtcacgtgtt gaattttttt tacgcaaacg atgacgggtt tactggaaac  2280
acgattcttg atactgtgaa ggacatcatt tacaacccgt tggtgcttgt gaatgaaaat  2340
gaagaacaaa ggtaa                                                   2355
```

SEQ ID NO: 46 moltype = DNA length = 1773
FEATURE Location/Qualifiers
source 1..1773
mol_type = other DNA
organism = Zea mays
SEQUENCE: 46

```
atggccatgc cagtgaagct gactcctgcc tccctctcgc tgaaggcggt ctgctgccgc  60
ttcagctccg gagggcatgc gctgcgcttc ggctcgtcgc taccgtgctg gaggaggacg  120
ccgacgcaac ggagcacgtc gtcgtctacg acgcgccctg cggctgaggt tagctctggc  180
aaaagcaagc agcacgatca agaagcatcg gaggctacga taagacagca gctccagcta  240
gtcgatgtgc ttgagaacat ggggatttct cggcattttg ctgctgaaat caaatgcatc  300
cttgacagga catacagaag ttggttacag agacatgagg aaattatgct ggacacaatg  360
acctgtgcga tggcatttcg tattctaagg ttgaatggat acaatgtctc ttctgatgag  420
ttgtatcatg ttgttgaagc ttccggactc cataattcac ttggaggata tctcaatgat  480
acaagaacct tgttagaatt acacaaggcc tcgacagtta gtatctctga agatgagtct  540
atcctggata gcataggctc aaggtcacgt accttactga gggaacaact agagtctggt  600
ggtgctctac gaaaaccttc actctttaaa gaggtggaac atgctctgga cggtcccttc  660
tacaccacat tggaccgtct acaccatagg tggaacatcg aaaatttcaa tattatagag  720
cagcacatgc tagagacacc atacttgtca aatcaacata ccagtagaga tattctagcg  780
ttgagtatta gagacttcag ttcctctcag tttacttacc agcaagaact tcaacatctt  840
gaaagctggg tgaaagagtg caggttagac cagctacaat ttgcgcgaca gaagttggca  900
tacttctact tgtctgctgc tggcaccatg ttctctcctg agctgtctga tgctcgaact  960
ttgtgggcca aaaatggtgt gctcacaact attgttgacg acttctttga tgttgcggga  1020
tcaaaagaag aacttgaaaa ccttgtcatg ttggttgaga tgtgggacga gcatcacaaa  1080
gttgagttct actcagaaca agtagagatt atattttctt caatttatga ctcagttaac  1140
caacttggtg aaaaggcttc tttggtacaa gaccgcagta ttaccaaaca cctagtagaa  1200
atatggttgg atttgctaaa gtctatgatg acagaggtag agtggcgttt gagcaaatat  1260
gtgccaacag agaaggaata catgataaat gcatctttaa tatttggact aggccccatt  1320
gtattgccag cattatattt tgttgggcca aagatctcag agtctattgt taaagatcca  1380
gaatatgatg aattgttcaa actgatgagc acatgtggtc gcctcttgaa tgatgttcag  1440
acttttgaga gggagtacaa cgagggcaag ttgaatagtg tttctctcct cgttcttcat  1500
ggtggcccca tgtccatatc agacgccaaa aggaaattac agaagcccat agacacatgc  1560
agaagagacc tcctaagttt agttcttcgt gaagaaagtg ttgttcctag gccctgcaag  1620
gaattatttt ggaaaatgtg caaggtgtgc tacttcttct actcgacgac ggatgggttt  1680
agctcacaag tggagagggc taaagaagtg gatgcggtga tcaatgagcc actaaagcta  1740
caaggaagtc atacgctggt gtctgatgtg tga                               1773
```

SEQ ID NO: 47 moltype = DNA length = 2232
FEATURE Location/Qualifiers
source 1..2232
mol_type = other DNA
organism = Populus trichocarpa
SEQUENCE: 47

```
atgcagaact ttcatggaac taaggaaagg atcaagaaga tgtttgataa gattgaattg  60
tcagtgtctt catatgacac tgcttgggtg gcaatggtcc catctccaga ttgtccggaa  120
actccttgtt ttccagagtg cacaaaatgg attttggaaa atcaacttgg tgatggctcc  180
tggagtcttc ctcatggcaa tccattatta gttaaggatg ctctttcatc tacattagcg  240
```

```
tgcatccttg cattgaagcg atggggtatc ggtgaagaac aaataaataa aggccttcga  300
tttattgagt tgaattccgc ttcagttacg gataacgagc aacataaacc aattggattt  360
gatataatat ttcctggcat gattgaatat gccatagatt tggatttgaa cctccctttg  420
aagccgacag atataaattc catgctccac aggagggctt tggagcttac aagtggcggt  480
ggcaagaact tggagggaag aagagcctac ttagcatatg tttcggaagg aattggaaaa  540
ttacaggatt gggaaatggc catgaaatat caaagaaaga atggatcact gttcaattca  600
ccatccacca cagcagctgc ctttattcat attcaagatg ctgagtgtct ccattatatt  660
cgttcactct tacagaagtt tgggaatgca gttccaacca tttatccttt ggatatatat  720
gctcgtcttt ctatggttga tgctcttgaa aggttgggaa tcgatcggca ttttaggaag  780
gaaagaaaat ttgttttgga cgaaacatac cgattttggt tgcaggggga ggaagagata  840
ttttctgata atgccacttg tgctttggca tttaggatat tacgtttgaa cggatatgat  900
gtctctctag aagatcattt ctctaattca ctgggaggat atttgaagga ttcgggagct  960
gccttagagt tgtacagagc tctgcagcta agttatccag atgaatcact tctggaaaaa  1020
caaaattctc ggacaagcta tttcctgaaa cagggattat ccaacgtttc actttgtgga  1080
gataggcttc gtaaaaatat tatcggagag gtgcatgatg ctctcaattt ttctgaccat  1140
gcaaatttgc aacgcttagc tatcagaaga agaattaaac attatgctac agatgatacg  1200
aggattttga aaacttcgta tcgttgttcg actattggta accaggattt tctcaaattg  1260
gctgtagaag acttcaatat ctgtcaatca atacagcgtg aagaatttaa acatatcgag  1320
aggtgggttg tagagaggag actggacaag ctaaagtttg ctaggcagaa ggaggcctac  1380
tgttacttct ctgctgcagc aactctcttc gctccagaac tatctgatgc acgcatgtca  1440
tgggcaaaaa atggtgtgct tactactgtt gttgatgact tctttgatgt tggtggttct  1500
gaagaagaac tggtaaacct tattgaattg attgagaggt gggatgtcaa tggcagtgct  1560
gatttttgtt ctgaggaagt tgagatcata tattcggcaa ttcacagcac tataagtgag  1620
ataggagaca aatctttcgg atggcaagga cgcgatgtga aaagtcaggt tatcaagatt  1680
tggttggatt tgctcaaatc catgttgaca gaagcacaat ggtcaagtaa caaatcagtg  1740
ccgacccttg atgaatatat gacaactgca catgtatcgt tcgctctagg gcctattgtt  1800
cttccagctc tgtattttgt ggggcctaag ctttcagagg aggttgctgg acatcctgaa  1860
ttgcttaatc tatacaaggt tacgagcact tgcgggcgtc tgctcaatga ctggagaagc  1920
tttaagagag aatctgaaga agggaaattg aatgccatct cattgtacat gattcacagc  1980
ggtggtgctt caactgaaga agagaccatc gaacatttta aaggattgat cgacagccag  2040
agaagacaat tgcttcaatt agttttgcag gaaaaggata gtataattcc tagaccctgc  2100
aaggatttgt tttggaacat gataaaatta ttgcacacgt tctacatgaa ggatgatgga  2160
ttcacttcaa acgagatgag aaatgttgtc aaggcaataa taaatgaacc catctctcta  2220
gatgaattat aa                                                     2232
```

```
SEQ ID NO: 48          moltype = DNA  length = 2952
FEATURE                Location/Qualifiers
misc_feature           1..2952
                       note = Description of Artificial Sequence: Synthetic
                        polynucleotide
source                 1..2952
                       mol_type = other DNA
                       organism = synthetic construct
SEQUENCE: 48
atggaatttg atgaaccatt ggttgacgaa gcaagatctt tagtgcagcg tactttacaa  60
gattatgatg acagatacgg cttcggtact atgtcatgtg ctgcttatga tacagcctgg  120
gtgtctttag ttacaaaaac agtcgatggg agaaaacaat ggcttttccc agagtgtttt  180
gaatttctac tagaaacaca atctgatgcc ggaggatggg aaatcgggaa ttcagcacca  240
atcgacggta tattgaatac agctgcatcc ttacttgctc taaaacgtca cgttcaaact  300
gagcaaatca tccaacctca acatgaccat aaggatctag caggtagagc tgaacgtgcc  360
gctgcatctt tgagagcaca attggctgca ttggatgtgt ctacaactga acacgtcggt  420
tttgagataa ttgttcctgc aatgctagac ccattagaag ccgaagatcc atctctagtt  480
ttcgattttc cagctaggaa acctttgatg aagattcatg atgctaagat gagtagattc  540
aggccagaat acttgtatgg caaacaacca atgaccgcct tacattcatt agaggctttc  600
ataggcaaaa tcgacttcga taaggtaaga caccaccgta cccatgggtc tatgatgggt  660
tctccttcat ctaccgcagc ctacttaatg cacgcttcac aatgggatgg tgactcagag  720
gcttacctta gacacgtgat taaacacgca gcagggcagg gaactggtgc tgtaccatct  780
gctttcccat caacacattt tgagtcatct tggattctta ccacattgtt tagagctgga  840
ttttcagctt ctcatcttgc ctgtgatgag ttgaacaagt tggtcgagat acttgagggc  900
tcattcgaga aggaaggtgg ggcaatcggt tacgctccag ggtttcaagc agatgttgat  960
gatactgcta aacaataaag tacattagca gtccttggaa gagatgctac accaagacaa  1020
atgatcaagg tatttgaagc taatacacat tttagaacat accctggtga aagagatcct  1080
tctttgacag ctaattgtaa tgctctatca gccttactac accaaccaga tgcagcaatg  1140
tatggatctc aaattcaaaa gattaccaaa tttgtctgtg actattggtg gaagtctgat  1200
ggtaagatta aagataagtg gaacacttgc tacttgtacc catctgtctt attagttgag  1260
gttttggttg atcttgttag tttattggag cagggtaaat tgcctgatgt tttggatcaa  1320
gagcttcaat acagagtcgc catcacattg ttccaagcat gtttaaggcc attactagac  1380
caagatgccg aaggatcatg gaacaagtct atcgaagcca cagcctacgg catccttatc  1440
ctaactgaag ctaggagagt ttgtttcttc gacagattgt ctgagccatt gaatgaggca  1500
atccgtagag gtatcgcttt cgccgactct atgtctggaa ctgaagctca gttgaactac  1560
atttggatcg aaaaggttag ttacgcacct gcattattga ctaaatccta tttgttagca  1620
gcaagatggg ctgctaagtc tcctttaggc gcttccgtag gctcttcttt gtggactcca  1680
ccaagagaag gattggataa gcatgtcaga ttattccatc aagctgagtt attcagatcc  1740
cttccagaat gggaattaag agcctccatg attgaagcag ctttgttcac accacttcta  1800
agagcacata gactagacgt tttccctaga caagatgtag gtgaagacaa atatcttgat  1860
gtagttccat tcttttggac tgccgctaac aacagagata gaacttacgc ttccactcta  1920
ttcctttacg atatgtgttt tatcgcaatg ttaaacttcc agttagacga attcatggag  1980
gccacagccg gtatcttatt cagagatcat atggatgatt tgaggcaatt gattcatgat  2040
cttttggcag agaaaacttc cccaaagagt tctggtagaa gtagtcaggg cacaaaagat  2100
```

-continued

```
gctgactcag gtatagagga agacgtgtca atgtccgatt cagcttcaga ttcccaggat  2160
agaagtccag aatacgactt ggttttcagt gcattgagta cctttacaaa acatgtcttg  2220
caacacccat ctatacaaag tgcctctgta tgggatagaa aactacttgc tagagagatg  2280
aaggcttact tacttgctca tatccaacaa gcagaagatt caactccatt gtctgaattg  2340
aaagatgtgc ctcaaaagac tgatgtaaca agagtttcta catctactac taccttcttt  2400
aactgggtta gaacaacttc cgcagaccat atatcctgcc catactcctt ccactttgta  2460
gcatgccatc taggcgcagc attgtcacct aaagggtcta acggtgattg ctatccttca  2520
gctggtgaga agttcttggc agctgcagtc tgcagacatt tggccaccat gtgtagaatg  2580
tacaacgatc ttggatcagc tgaacgtgat tctgatgaag gtaatttgaa ctccttggac  2640
ttccctgaat tcgccgattc cgcaggaaac ggagggatag aaattcagaa ggccgctcta  2700
ttaaggttag ctgagtttga gagagattca tacttagagg ccttccgtcg tttacaagat  2760
gaatccaata gagttcacgg tccagccggt ggtgatgaag ccagattgtc cagaaggaga  2820
atggcaatcc ttgaattctt cgcccagcag gtagatttgt acggtcaagt atacgtcatt  2880
agggatattt ccgctcgtat tcctaaaaac gaggttgaga aaaagagaaa attggatgat  2940
gctttcaatt ga                                                     2952
```

```
SEQ ID NO: 49          moltype = DNA  length = 2646
FEATURE                Location/Qualifiers
misc_feature           1..2646
                       note = Description of Artificial Sequence: Synthetic
                        polynucleotide
source                 1..2646
                       mol_type = other DNA
                       organism = synthetic construct
SEQUENCE: 49
atggcttcta gtacacttat ccaaaacaga tcatgtggcg tcacatcatc tatgtcaagt  60
tttcaaatct tcagaggtca accactaaga tttcctggca ctagaacccc agctgcagtt  120
caatgcttga aaaagaggag atgccttagg ccaaccgaat ccgtactaga atcatctcct  180
ggctctggtt catatagaat agtaactggc ccttctggaa ttaaccctag ttctaacggg  240
cacttgcaag agggttcctt gactcacagg ttaccaatac caatggaaaa atctatcgat  300
aacttccaat ctactctata tgtgtcagat atttggtctg aaacactaca gagaactgaa  360
tgtttgctac aagtaactga aaacgtccag atgaatgagt ggattgagga aattagaatg  420
tactttagaa atatgacttt aggtgaaatt tccatgtccc cttacgacac tgcttgggtg  480
gctagagttc cagcgttgga cggttctcat gggcctcaat tccacagatc tttgcaatgg  540
attatcgaca accaattacc agatggggac tggggcgaac cttctctttt cttgggttac  600
gatagagttt gtaatacttt agcctgtgtg attgcgttga aaacatgggg tgttggggca  660
caaaacgttg aaagaggaat tcagttccta caatctaaca tatacaagat ggaggaagat  720
gacgctaatc atatgccaat aggattcgaa atcgtattcc ctgctatgat ggaagatgcc  780
aaagcattag gtttggattt gccatacgat gctactattt tgcaacagat ttcagccgaa  840
agagagaaaa agatgaaaaa gatcccaatg gcaatggtgt acaaataccc aaccacttta  900
cttcactcct tagaaggctt gcatagagaa gttgattgga ataagttgtt acaattacaa  960
tctgaaaatg gtagttttct ttattcacct gcttcaaccg catgcgcctt aatgtacact  1020
aaggacgtta aatgttttga ttacttaaac cagttgttga tcaagttcga ccacgcatgc  1080
ccaaatgtat atccagtcga tctattcgaa agattatgga tggttgacag attgcagaga  1140
ttagggatct ccagatactt tgaaagagag attagagatt gtttacaata cgtctacaga  1200
tattggaaag attgtggaat cggatgggct tctaactctt ccgtacaaga tgttgatgat  1260
acagccatgg cgtttagact tttaaggact catggtttcg acgtaaagga agattgcttt  1320
agacagtttt tcaaggacgg agaattcttc tgcttcgcag gccaatcatc tcaagcagtt  1380
acaggcatgt ttaatctttc aagagccagt caaacattgt ttccaggaga atctttattg  1440
aaaaaggcta gaaccttctc tagaaacttc ttgagaacaa agcatgagaa caacgaatgt  1500
ttcgataaat ggatcattac taaagatttg gctggtgaag tcgagtataa cttgaccttc  1560
ccatggtatg cctctttgcc tagattagaa cataggacat acttagatca atatggaatc  1620
gatgatatct ggataggcaa atctttatac aaaatgcctg ctgttaccaa cgaagttttc  1680
ctaaagttgg caaaggcaga ctttaacatg tgtcaagctc tacacaaaaa ggaattggaa  1740
caagtgataa agtggaacgc gtcctgtcaa ttcagagatc ttgaattcgc cagacaaaaa  1800
tcagtagaat gctattttgc tggtgcagcc acaatgttcg aaccagaaat ggttcaagct  1860
agattagtct gggcaagatg ttgtgtattg acaactgtct tagacgatta ctttgaccac  1920
gggacacctg ttgaggaact tagagtgttt gttcaagctg tcagaacatg gaatccagag  1980
ttgatcaacg gtttgccaga gcaagctaaa atcttgttta tgggcttata caaaacagtt  2040
aacacaattg cagaggaagc attcatggca cagaaaagag acgtccatca tcatttgaaa  2100
cactattggg acaagttgat aacaagtgcc ctaaaggagg ccgaatgggc agagtcaggt  2160
tacgtcccaa catttgatga atacatggaa gtagctgaaa tttctgttgc tctagaacca  2220
attgtctgta gtaccttgtt ctttgcgggt catagactag atgaggatgt tctagatagt  2280
tacgattacc atctagttat gcatttggta aacagagtcg gtagaatctt gaatgatata  2340
caaggcatga agagggaggc ttcacaaggt aagatctcat cagttcaaat ctacatggag  2400
gaacatccat ctgttccatc tgaggccatg gcgatcgctc atcttcaaga gttagttgat  2460
aattcaatgc agcaattgac atacgaagtt cttaggttca ctgcggttcc aaaaagttgt  2520
aagagaatcc acttgaatat ggctaaaatc atgcatgcct tctacaagga tactgatgga  2580
ttctcatccc ttactgcaat gacaggattc gtcaaaaagg ttcttttcga acctgtgcct  2640
gagtaa                                                            2646
```

```
SEQ ID NO: 50          moltype = DNA  length = 2952
FEATURE                Location/Qualifiers
source                 1..2952
                       mol_type = other DNA
                       organism = Phomopsis amygdali
SEQUENCE: 50
atggagttcg atgaaccact tgtggacgag gcgaggtcct tggtccaaag aaccctgcaa  60
gattatgacg accgctatgg ctttggcact atgagctgtg cggcctatga cacagcatgg  120
```

-continued

```
gtatcgctgg tgactaaaac agtcgatggg cgtaaacaat ggttgttccc tgagtgcttc  180
gaatttctcc tagaaacgca gtccgatgct ggcggctggg aaatcggcaa cagcgcaccc  240
atcgatggga tccttaacac tgctgcttca ctgctggcat tgaagcgcca cgtccaaaca  300
gagcagatta ttcagccgca acacgaccat aaagacctgg ccgggcgtgc ggaaagagcg  360
gcggcgtctt tgcgagcaca gttggcggct ctggatgtgt cgacaacgga gcatgtgggc  420
ttcgaaatca tcgtcccggc catgctcgac cctctcgagg ccgaagaccc gtctttggtg  480
ttcgactttc cagcacgcaa accactgatg aagatccacg acgctaagat gtcgcgattc  540
cgaccagagt acctctacgg taaacagccg atgacggcat tgcattcgct cgaggccttt  600
atcgggaaaa tagacttcga caaagtacgg catcacagga cacacggttc gatgatgggg  660
tcgccctcgt cgacggctgc atacctgatg catgcttctc agtgggacgg cgactctgag  720
gcctatctac gccatgtcat caagcacgca gctggccagg gcaccggagc tgttccgagt  780
gcatttcctt cgacgcattt cgagtcttct tggattttga caacattgtt tcgagctggg  840
ttctcagcct ctcatctagc atgcgacgaa ttaaacaagc tggtagagat cctcgaaggc  900
tcatttgaga aagaaggggg agccatcggt tatgctcctg ggtttcaagc agatgtggat  960
gataccgcaa agaccatctc cactttggct gtgcttggga gagatgccac tccccggcaa  1020
atgatcaagg tttttgaagc caatacacac tttcggactt accctggtga aagagatcca  1080
agcttgactg ccaattgcaa cgcgctctcg gctcttcttc accagccaga cgcagcaatg  1140
tacggcagcc agatccagaa gatcacaaag tttgtttgtg actactggtg gaaaagtgac  1200
ggcaaaatca aggacaagtg gaatacctgc tacttgtatc catcggtcct cctcgtcgag  1260
gtgttagtag accttgtgtc cctgttggag caaggaaagc tacccgacgt gctggatcag  1320
gagctgcaat acagggtcgc cattacgtta ttccaggcct gcttgcgacc gctacttgat  1380
caagatgctg aaggttcatg gaacaaatcc attgaagcca cagcctacgg cattctaatc  1440
cttacggagg cgcggcgagt atgctttttt gaccgtctga gtgagcctct gaatgaggct  1500
attcgacgcg ggattgcgtt tgcagattcg atgagcggta ctgaagctca gctgaattat  1560
atatggatcg agaaagtgag ctacgcacct gctcttctga ccaaatcata cctcctcgca  1620
gctcggtggg cggcaaagtc cccgcttggc gcttccgttg gatccagcct ttggacgcct  1680
ccaagagaag gcttggataa gcacgtccgt ctattccacc aggcagagct cttcaggtcg  1740
ttgccggagt gggagctgcg cgcgtccatg atcgaggcag ccctgttcac tcctttgctg  1800
cgtgcgcata ggctggatgt atttccacgc caagacgtcg gcgaggacaa gtacctggac  1860
gttgtgccgt tcttctggac ggccgccaat aaccgcgatc gcacgtacgc atccactctg  1920
tttctgtatg acatgtgctt tatcgccatg cttaacttcc agctggatga gttcatggag  1980
gctacagcgg gaatcctctt ccgggaccat atggatgatt tgcgccaact catccacgac  2040
ctgcttgccg aaaagacgag ccccaagtca tcgggcagaa gtagccaagg aaccaaagac  2100
gcggactcgg gcatcgaaga agacgtttct atgagcgact cagcgtcaga ctcccaggac  2160
cgcagccctg aatacgacct ggtcttctct gcgctctcta ccttcaccaa acatgtcctg  2220
cagcacccctt caatccagtc agccagtgtc tgggatagga aactactcgc tcgcgagatg  2280
aaagcatacc tcctagctca tattcaacag gctgaggaca gcacgccctt gagtgagctc  2340
aaggacgtcc ctcaaaaaac tgacgtgaca cgcgtctcaa cgtccacaac gactttcttc  2400
aactgggtac gcacaacatc cgcagaccac atatcctgcc catattcatt ccatttcgtg  2460
gcgtgtcacc tcggcgccgc gctgagcccc aagggcagca acggcgactg ttacccgtca  2520
gccggtgaaa agttcctcgc ggccgccgta tgccgccatt tggccacgat gtgccgcatg  2580
tacaatgact tgggatcggc ggagcgcgac agtgacgagg gaaatttgaa ttcactcgac  2640
tttcccgagt tcgccgactc agcggggaat ggtgggattg agatccagaa agctgccttg  2700
ctcaggctgg ccgagttcga acgcgactcg tatctcgagg ctttccggcg acttcaggat  2760
gaaagcaacc gcgttcacgg accggctggt ggggatgaag ccagactcag caggcggcgc  2820
atggccatcc ttgagttctt tgcccagcag gtggacttgt atggccaggt ctacgttatt  2880
cgcgatatct cggccaggat tccaaagaac gaggttgaga agaaaaggaa actagatgat  2940
gctttcaatt ag                                                       2952
```

```
SEQ ID NO: 51          moltype = DNA  length = 2646
FEATURE                Location/Qualifiers
source                 1..2646
                       mol_type = other DNA
                       organism = Physcomitrella patens
SEQUENCE: 51
atggcttcca gcaccttgat acagaatcgc tcttgtggcg ttacgtcaag catgtcttcc  60
tttcagattt ttcgagggca acctctacgt tttccaggca ctagaactcc tgctgcagtt  120
caatgcctaa agaagcgtcg atgtttgcga cctactgaat cagtcctcga gagctctcct  180
ggtagcggat cttacaggat tgtaactgga ccctccggca tcaatccttc ttcaaacggc  240
cacttgcaag aggggtccct tactcacaga cttccgatac ccatggaaaa atccattgat  300
aacttccagt ctactttgta cgtatcagac atatggtcag aaaccttgca aagaacggaa  360
tgtttgttgc aggtgactga gaatgtacag atgaacgagt ggattgagga aatcagaatg  420
tacttccgaa atatgacact gggggaaata tccatgtctc catacgacac agcttgggta  480
gcgcgagtgc cagcgctgga tggctcacat ggccctcagt tccatcggtc tttgcagtgg  540
attattgata atcagctccc ggatggcgat tggggtgaac cgtctctttt ccttggatac  600
gatcgcgttt gcaacactct cgcctgtgta attgccctga aacttggggg tgttggggct  660
cagaacgtag agcgtggaat ccagtttctg caatctaaca tctacaaaat ggaggaagat  720
gacgccaatc atatgccgat tggatttgag attgtcttcc cagcgatgat ggaagatgcc  780
aaggcactgg gactggattt accatacgat gccactatct tgcaacaaat ctcggctgaa  840
agagagaaga aaatgaaaaa gattcctatg gcgatggtgt acaagtaccc cactactttg  900
ctgcattctc tggaaggcct gcaccgggaa gtggactgga acaagctcct ccagctacag  960
tccgagaatg gctcctttct gtattcaccc gcatccactg catgcgcact tatgtacaca  1020
aaagatgtga agtgcttcga ctacttgaac cagctcctca tcaagttcga ccacgcttgt  1080
ccaaacgtgt accccgttga tctcttcgag cgtttgtgga tggtagaccg cctacaaagg  1140
ctgggaatat cccgctactt cgagcgagaa atcagagact gtctacaata tgtataccga  1200
tactggaagg attgtggtat tggctgggca agcaattcgt ccgtgcagga cgtggacgac  1260
acggccatgg ccttccgcct tctccgcaca cacggattcg acgtcaagga ggactgcttc  1320
agacagtttt tcaaagatgg tgagttcttc tgcttcgccg gccagtccag ccaagccgtc  1380
acgggaatgt tcaacctcag cagagcatcg caaacgctct tcccagggga atcactccta  1440
```

-continued

```
aaaaaggcca gaacctttc cagaaacttt ttgagaacca agcatgaaaa caatgaatgc  1500
ttcgacaagt ggataatcac gaaggatcta gcgggcgagg tggaatacaa tctcacattc  1560
ccctggtatg ctagccttcc tcgtcttgag catcgcacct acttggacca atatgggatt  1620
gatgatatct ggattggcaa gtcgctctac aaaatgccgg ccgtcaccaa cgaagtgttt  1680
ctcaaattgg ccaaagccga cttcaacatg tgccaagctc ttcacaagaa ggaactcgag  1740
caggtcatca aatggaatgc cagctgccaa tttagagacc tcgagtttgc tagacagaaa  1800
tccgtggagt gctacttcgc aggcgctgca accatgtttg agcccgaaat ggtgcaggcg  1860
aggctcgttt gggcacgctg ttgcgtgctc accaccgttc tagacgatta cttcgatcac  1920
ggtacacctg tggaagagct tcgggttttt gtgcaggccg taaggacttg gaatcccgag  1980
ctcatcaacg gactacctga gcaagccaag attctcttta tgggactgta caagactgtg  2040
aacactatcg ccgaggaggc attcatggca cagaaacgag acgtacatca tcatctcaag  2100
cattactggg acaaattgat cacttcagct ttgaaagaag ccgaatgggc agagtccggc  2160
tacgtcccca ccttcgacga gtatatggaa gtcgctgaaa tctccgtcgc actagagccc  2220
attgtatgta gcactctctt cttcgccggc cataggctcg atgaggatgt gcttgacagt  2280
tatgactacc atcttgtcat gcatctcgtc aaccgcgtag gtcgcatcct caacgacatc  2340
caaggaatga agagggaagc cagccaaggg aagatatcga gcgtgcagat ctacatggag  2400
gagcatccaa gtgtgccttc agaggccatg gccatcgctc atctgcagga attggtcgac  2460
aactccatgc aacagctgac atacgaagtg ctgcgcttca ctgcagtccc gaagtcctgt  2520
aagagaatcc atttaaacat ggcgaagatc atgcacgctt tctacaagga cactgatggg  2580
ttttcgtcac tgacagccat gacagggttt gtgaagaagg tgctcttcga gccagtacct  2640
gaatag                                                            2646
```

```
SEQ ID NO: 52          moltype = DNA  length = 1542
FEATURE                Location/Qualifiers
misc_feature           1..1542
                       note = Description of Artificial Sequence: Synthetic
                        polynucleotide
source                 1..1542
                       mol_type = other DNA
                       organism = synthetic construct
SEQUENCE: 52
atggatgctg tgacgggttt gttaactgtc ccagcaaccg ctataactat tggtggaact  60
gctgtagcat tggcggtagc gctaatcttt tggtacctga aatcctacac atcagctaga  120
agatcccaat caaatcatct tccaagagtg cctgaagtcc caggtgttcc attgttagga  180
aatctgttac aattgaagga gaaaaagcca tacatgactt ttacgagatg ggcagcgaca  240
tatggaccta tctatagtat caaaactggg gctacaagta tggttgtggt atcatctaat  300
gagatagcca aggaggcatt ggtgaccaga ttccaatcca tatctacaag gaacttatct  360
aaagccctga aagtacttac agcagataag acaatggtcg caatgtcaga ttatgatgat  420
tatcataaaa cagttaagag acacatactg accgccgtct tgggtcctaa tgcacagaaa  480
aagcatagaa ttcacagaga tatcatgatg gataacatat ctactcaact tcatgaattc  540
gtgaaaaaca acccagaaca ggaagaggta gaccttagaa aaatctttca atctgagtta  600
ttcggcttag ctatgagaca agccttagga aaggatgttg aaagtttgta cgttgaagac  660
ctgaaaatca ctatgaatag agacgaaatc tttcaagtcc ttgttgttga tccaatgatg  720
ggagcaatcg atgttgattg gagagacttc tttccatacc taaagtgggt cccaaacaaa  780
aagttcgaaa atactattca acaaatgtac atcagaagag aagctgttat gaaatcttta  840
atcaaagagc acaaaaagag aatagcgtca ggcgaaaagc taaatagtta tatcgattac  900
cttttatctg aagctcaaac tttaaccgat cagcaactat tgatgtcctt gtgggaacca  960
atcattgaat cttcagatac aacaatggtc acaacagaat gggcaatgta cgaattagct  1020
aaaaacccta aattgcaaga taggttgtac agagacatta agtccgtctg tggatctgaa  1080
aagataaccg aagagcatct atcacagctg ccttacatta cagctatttt ccacgaaaca  1140
ctgagaagac actcaccagt tcctatcatt cctctaagac atgtacatga agataccgtt  1200
ctaggcggct accatgttcc tgctggcaca gaacttgccg ttaacatcta cggttgcaac  1260
atggacaaaa acgtttggga aaatccagag gaatggaacc cagaaagatt catgaaagag  1320
aatgagacaa ttgattttca aaagacgatg gccttcggtg gtggtaagag agtttgtgct  1380
ggttccttgc aagccctttt aactgcatct attgggattg ggagaatggt tcaagagttc  1440
gaatggaaac tgaaggatat gactcaagag gaagtgaaca cgataggcct aactacacaa  1500
atgttaagac cattgagagc tattatcaaa cctaggatct aa                    1542
```

```
SEQ ID NO: 53          moltype = DNA  length = 1530
FEATURE                Location/Qualifiers
misc_feature           1..1530
                       note = Description of Artificial Sequence: Synthetic
                        polynucleotide
source                 1..1530
                       mol_type = other DNA
                       organism = synthetic construct
SEQUENCE: 53
atggcatttt tctctatgat ttcaattttg ttgggatttg ttatttcttc tttcatcttc  60
atctttttct tcaaaaagtt acttagtttt agtaggaaaa acatgtcaga agtttctact  120
ttgccaagtg ttccagtagt gcctggtttt ccagttattg ggaatttgtt gcaactaaag  180
gagaaaaagc ctcataaaac tttcactaga tggtcagaga tatatggacc tatctactct  240
ataaagatgg gttcttcatc tcttattgta ttgaacagta cagaaactgc taaggaagca  300
atggtcacta gatttcatc aatatctacc agaaaattgt caaacgccct aacagttcta  360
acctgcgata agtctatggt cgccacttct gattatgatg acttccacaa attagttaag  420
agatgtttgc taaatggact tcttggtgct aatgctcaaa agagaaaaag acactacaga  480
gatgctttga ttgaaaatgt gagttccaag ctacatgcac acgctagaga tcatccacaa  540
gagccagtta actttagagc aattttcgaa cacgaattgt ttggtgtagc attaaagcaa  600
gccttcggta aagacgtaga atccatatac gtcaaggagt taggcgtaac attatcaaaa  660
gatgaaatct ttaaggtgct tgtacatgat atgatggagg gtgcaattga tgtagattgg  720
```

-continued

```
agagatttct tcccatattt gaaatggatc cctaataagt cttttgaagc taggatacaa  780
caaaagcaca agagaagact agctgttatg aacgcactta tacaggacag attgaagcaa  840
aatgggtctg aatcagatga tgattgttac cttaacttct taatgtctga ggctaaaaca  900
ttgactaagg aacagatcgc aatccttgtc tgggaaacaa tcattgaaac agcagatact  960
accttagtca caactgaatg ggccatatac gagctagcca aacatccatc tgtgcaagat  1020
aggttgtgta aggagatcca gaacgtgtgt ggtggagaga aattcaagga agagcagttg  1080
tcacaagttc cttaccttaa cggcgttttc catgaaacct tgagaaaata ctcacctgca  1140
ccattagttc ctattagata cgcccacgaa gatacacaaa tcggtggcta ccatgttcca  1200
gctgggtccg aaattgctat aaacatctac gggtgcaaca tggacaaaaa gagatgggaa  1260
agaccagaag attggtggcc agaaagattc ttagatgatg gcaaatatga aacatctgat  1320
ttgcataaaa caatggcttt cggagctggc aaaagagtgt gtgccggtgc tctacaagcc  1380
tccctaatgg ctggtatcgc tattggtaga ttggtccaag agttcgaatg gaaacttaga  1440
gatggtgaag aggaaaatgt cgatacttat gggttaacat ctcaaaagtt atacccacta  1500
atggcaatca tcaatcctag aagatcctaa                                  1530
```

```
SEQ ID NO: 54          moltype = DNA  length = 1578
FEATURE                Location/Qualifiers
misc_feature           1..1578
                       note = Description of Artificial Sequence: Synthetic
                        polynucleotide
source                 1..1578
                       mol_type = other DNA
                       organism = synthetic construct
SEQUENCE: 54
atgagtaagt ctaatagtat gaattctaca tcacacgaaa cccttttca acaattggtc  60
ttgggtttgg accgtatgcc attgatggat gttcactggt tgatctacgt tgctttcggc  120
gcatggttat gttcttatgt gatacatgtt ttatcatctt cctctacagt aaaagtgcca  180
gttgttggat acaggtctgt attcgaacct acatggttgc ttagacttag attcgtctgg  240
gaaggtggct ctatcatagg tcaagggtac aataagttta aagactctat tttccaagtt  300
aggaaattgg gaactgatat tgtcattata ccacctaact atattgatga agtgagaaaa  360
ttgtcacagg acaagactag atcagttgaa cctttcatta atgattttgc aggtcaatac  420
acaagaggca tggttttctt gcaatctgac ttacaaaacc gtgttataca acaaagacta  480
actccaaaat tggtttcctt gaccaaggtc atgaaggaag agttggatta tgctttaaca  540
aaagagatgc ctgatatgaa aaatgacgaa tgggtagaag tagatatcag tagtataatg  600
gtgagattga tttccaggat ctccgccaga gtctttctag ggcctgaaca ctgtcgtaac  660
caggaatggt tgactactac agcagaatat tcagaatcac ttttcattac agggtttatc  720
ttaagagttg tacctcatat cttaagacca ttcatcgccc ctctattacc ttcatacagg  780
actctactta gaaacgtttc aagtggtaga agagtcatcg gtgacatcat aagatctcag  840
caaggggatg gtaacgaaga tatactttcc tggatgagag atgctgccac aggagaggaa  900
aagcaaatcg ataacattgc tcagagaatg ttaattcttt ctttagcatc aatccacact  960
actgcgatga ccatgacaca tgccatgtac gatctatgtg cttgccctga gtacattgaa  1020
ccattaagag atgaagttaa atctgttgtt ggggcttctg gctgggacaa gacagcgtta  1080
aacagatttc ataagttgga ctccttccta aaagagtcac aaagattcaa cccagtattc  1140
ttattgacat tcaatagaat ctaccatcaa tctatgacct tatcagatgg cactaacatt  1200
ccatctggaa cacgtattgc tgttccatca cacgcaatgt tgcaagattc tgcacatgtc  1260
ccaggtccaa ccccacctac tgaatttgat ggattcagat atagtaagat acgttctgat  1320
agtaactacg cacaaaagta cctattctcc atgaccgatt cttcaaacat ggctttcgga  1380
tacggcaagt atgcttgtcc aggtagattt tacgcgtcta atgagatgaa actaacatta  1440
gccattttgt tgctacaatt tgagttcaaa ctaccagatg gtaaaggtcg tcctagaaat  1500
atcactatcg attctgatat gattccagac ccaagagcta gactttgcgt cagaaaaaga  1560
tcacttagag atgaatga                                                1578
```

```
SEQ ID NO: 55          moltype = DNA  length = 1500
FEATURE                Location/Qualifiers
misc_feature           1..1500
                       note = Description of Artificial Sequence: Synthetic
                        polynucleotide
source                 1..1500
                       mol_type = other DNA
                       organism = synthetic construct
SEQUENCE: 55
atggaagatc ctactgtctt atatgcttgt cttgccattg cagttgcaac tttcgttgtt  60
agatggtaca gagatccatt gagatccatc ccaacagttg gtggttccga tttgcctatt  120
ctatcttaca tcggcgcact aagatggaca agacgtggca gagagatact tcaagaggga  180
tatgatggct acagaggatc tacattcaaa atcgcgatgt tagaccgttg gatcgtgatc  240
gcaaatggtc ctaaactagc tgatgaagtc agacgtagac cagatgaaga gttaaacttt  300
atggacggat taggagcatt cgtccaaact aagtacacct taggtgaagc tattcataac  360
gatccatacc atgtcgatat cataagagaa aaactaacaa gaggccttcc agccgtgctt  420
cctgatgtca ttgaagagtt gacacttgcg gttagacagt acattccaac agaaggtgat  480
gaatgggtgt ccgtaaactg ttcaaaggcc gcaagagata ttgttgctag agcttctaat  540
agagtctttg taggtttgcc tgcttgcaga aaccaaggtt acttagattt ggcaatagac  600
tttacattgt ctgttgtcaa ggatagagcc atcatcaata tgtttccaga attgttgaag  660
ccaatagttg gcagagttgt aggtaacgcc accagaaatg ttcgtagagc tgttcctttt  720
gttgctccat tggtggagga aagacgtaga cttatggaag agtacggtga agactggtct  780
gaaaaaccta atgatatgtt acagtggata atggatgaag ctgcatccag agatagttca  840
gtgaaggcaa tcgcagagag attgttaatg gtgaacttcg cggctattca tacctcatca  900
aacactatca ctcatgcttt gtaccacctt gccgaaatgc ctgaaacttt gcaaccactt  960
agagaagaga tcgaaccatt agtcaaagag gagggctgga ccaaggctgc tatgggaaaa  1020
atgtggtggt tagattcatt tctaagagaa tctcaaagat acaatggcat taacatcgta  1080
```

```
tctttaacta gaatggctga caaagatatt acattgagtg atggcacatt tttgccaaaa  1140
ggtactctag tggccgttcc agcgtattct actcatagag atgatgctgt ctacgctgat  1200
gccttagtat tcgatccttt cagattctca cgtatgagag cgagagaagg tgaaggtaca  1260
aagcaccagt tcgttaatac ttcagtcgag tacgttccat ttggtcacgg aaagcatgct  1320
tgtccaggaa gattcttcgc cgcaaacgaa ttgaaagcaa tgttggctta cattgttcta  1380
aactatgatg taaagttgcc tggtgacggt aaacgtccat tgaacatgta ttggggtcca  1440
acagttttgc ctgcaccagc aggccaagta ttgttcagaa agagacaagt tagtctataa  1500

SEQ ID NO: 56          moltype = DNA  length = 1542
FEATURE                Location/Qualifiers
source                 1..1542
                       mol_type = other DNA
                       organism = Stevia rebaudiana
SEQUENCE: 56
atggatgccg tcaccggttt gctgacagtt ccggcaaccg caataaccat cggcggtacg  60
gccgtcgcac tcgccgtcgc tctgatattc tggtacctca aaagctacac atctgcacgc  120
aggagccaat caaaccatct ccctcgggtt cccgaggtac ctggtgtgcc attattgggg  180
aatttattgc agttgaagga gaagaaacct tacatgactt ttacaagatg ggcggcaact  240
tatggtccga tttattcgat taaaaccgga gcaacttcta tggtggtcgt cagttcaaat  300
gaaattgcaa aggaggcatt ggttaccaga tttcaatcta tctcaaccag aaacctatca  360
aaggcattaa aggttctcac agcagataaa accatggtgg cgatgagtga ttatgatgat  420
tatcataaga ctgtcaaacg ccatatactg accgctgttt tgggaccaaa tgctcagaag  480
aaacaccgca tccataggga catcatgatg gataatatat caacccaact tcatgaattt  540
gttaaaaata atcctgaaca agaggaagtg gatctaagga aaatattcca atccgaactt  600
tttggattag ctatgagaca agcattggga aaggatgtgg agagcttata tgttgaggat  660
cttaaaatca ccatgaaccg agacgagata tttcaggtat tggttgttga cccgatgatg  720
ggtgcaattg acgtcgactg gagagatttc ttcccgtatc taaagtgggt cccgaataaa  780
aagtttgaaa acacgatcca acaaatgtat atccggagag aagctgtgat gaagtctctt  840
attaaagaac ataaaaaacg tattgcatcc ggagagaaat taaacagcta cattgattac  900
ttgctatcgg aagcacaaac gttaaccgat caacaactac ttatgtctct atgggaacct  960
attattgaat catcagacac cactatggtt acaactgaat gggctatgta tgaacttgca  1020
aaaaacccca aacttcagga tcgtttgtat cgggatatca aaagtgtttg cgggtcagag  1080
aagattacag aagaacactt gtctcaactg ccatacataa ctgccatttt tcatgaaacc  1140
ttgagaaggc atagtccagt tcctataatt ccattaagac acgtgcatga agacacagtg  1200
ttaggagggt accatgtgcc agctggaacc gagctagcgg taaacattta tggatgtaac  1260
atggataaga atgtgtggga gaatcctgaa gaatggaatc cagagagatt catgaaggaa  1320
aatgaaacga tagatttcca gaaaacaatg gcgtttggag gtggaaagcg cgtatgtgct  1380
ggttcgcttc aagcattgtt gactgcttcc attggaattg gaagaatggt gcaagagttt  1440
gagtggaaac tgaaagayat gacccaagaa gaagttaata cgattgggct tacgacccag  1500
atgcttcgtc cactgcgggc cataataaag cccaggatat ga                    1542

SEQ ID NO: 57          moltype = DNA  length = 1530
FEATURE                Location/Qualifiers
source                 1..1530
                       mol_type = other DNA
                       organism = Arabidopsis thaliana
SEQUENCE: 57
atggccttct tctccatgat ctccattctc cttggctttg ttatctcctc cttcatcttc  60
atcttcttct tcaagaaact tctctccttc tccagaaaga acatgtctga agtctccact  120
ctcccctctg ttccagtggt accagggttt cctgttattg ggaacttgct gcaactaaaa  180
gagaagaaac ctcacaagac tttcactaga tggtcagaga tttatggtcc tatttactct  240
ataaagatgg gttcttcttc tcttattgtc ctcaattcta ctgagactgc caaagaggcc  300
atggtgacgc ggttttcgtc tatctcaacg aggaagttgt caaatgcgtt gacagtcctt  360
acttgtgaca aatctatggt tgctactagt gattatgatg atttccacaa gttggtgaaa  420
cggtgtctct tgaacggtct tttgggtgct aatgcacaga aacgaaaaag acattacaga  480
gatgcactca ttgaaaatgt gtcttccaag ttgcatgccc atgctaggga ccatccacaa  540
gaacctgtaa acttcagagc tatatttgag catgagcttt tcggtgtagc attgaagcaa  600
gcttttggga aagatgtgga atccatttat gttaaagaac tcggtgtgac tttgtcgaaa  660
gacgagatct tcaaggtttt agtacatgac atgatggaag gtgcaattga tgttgattgg  720
agagacttct tcccatactt gaaatggatt ccaaataaaa gttttgaagc aagaatccag  780
caaaagcata aacgtagact cgcggtgatg aatgctctga ttcaagatcg actgaagcag  840
aatggttcag aatcggatga tgattgctat ctcaacttct tgatgtcgga agcgaaaaca  900
ctaaccaagg agcaaattgc tatcttggtt tgggagacga ttatcgagac agctgacact  960
actttggtta caactgaatg ggccatctat gagctcgcta agcatccaag tgtccaagat  1020
cgtctgtgta aagaaatcca aaatgtctgc ggaggagaaa agttcaaaga agagcaattg  1080
tctcaagttc cttatctcaa tggagtattc catgaaacgc ttaggaaata cagtcctgct  1140
cctctagtcc ccattcgcta tgcccacgaa gatacgcaaa tcggaggcta tcatgtccct  1200
gcaggaagtg agattgcaat aaacatctat ggatgcaaca tggataagaa gcgttgggag  1260
agaccagagg actggtggcc ggagcggttt cttgatgatg gcaaatacga aacgtcggat  1320
cttcacaaga caatggcgtt tggagcggga aagagggttt gtgctggtgc tcttcaagca  1380
tctctcatgg caggcattgc cattgggagg ttagtgcaag aattcgagtg gaagcttaga  1440
gacggtgaag aagagaatgt ggatacatat ggcttgacct ctcagaagct ttatcctctt  1500
atggctatta tcaatccaag gcgttcttaa                                  1530

SEQ ID NO: 58          moltype = DNA  length = 1578
FEATURE                Location/Qualifiers
source                 1..1578
                       mol_type = other DNA
                       organism = Gibberella fujikoroi
```

```
SEQUENCE: 58
atgagtaagt ccaacagcat gaacagtacc agccatgaaa cgttattcca gcagctcgtc  60
ttaggtcttg acagaatgcc gctaatggac gttcactggc tgatctacgt ggcctttggc  120
gcttggttat gctcttatgt catccatgtc ctatcgtcct cttctacagt caaagtgccc  180
gtcgtaggct accgcagcgt ctttgagcct acatggcttc tccgtttgcg ctttgtttgg  240
gaagggggat ctatcatcgg ccaaggctac aacaaattta aagactctat cttccaggtg  300
cgaaagcttg gtaccgatat cgtcatcatc ccgccaaact acatcgatga ggtcagaaag  360
ctgtcccaag acaagactcg ctcggtcgag cccttcatca atgactttgc gggacagtat  420
acacggggca tggtctttct gcaaagtgat ttgcagaacc gtgtgattca gcagcggttg  480
acgccaaaac tcgtatcgtt gacaaaggta atgaaggagg agcttgacta tgccttgacc  540
aaagagatgc ctgacatgaa gaatgatgaa tgggttgaag tcgacatttc ttccatcatg  600
gtcaggctca tatcacgcat ctcagccaga gtgtttctcg gtccagagca ctgccgcaac  660
caagaatggt tgacgaccac tgcagagtac agcgagagcc tgttcataac tggctttatt  720
ctccgcgttg tcccccatat tctaagacca ttcatagccc cgctgctacc ctcctacaga  780
acactacttc gcaacgtctc gtcaggtcga agagttattg gagacatcat tcgctcccag  840
caaggtgatg gcaacgagga catcctgtca tggatgaggg atgctgcgac aggggaagaa  900
aagcaaattg acaacattgc ccagcggatg cttatcctga gtctcgcgtc tattcacact  960
acggcaatga cgatgacgca tgctatgtat gacttatgtg cttgccctga gtacatagag  1020
cctcttagag atgaggtcaa aagtgtcgtt ggcgctagtg gttgggacaa gacggcgttg  1080
aatcgattcc acaaactcga cagctttctc aaagagtcac aacgcttcaa ccccgtgttc  1140
ctcttaacgt tcaatcgcat ttatcaccaa tccatgacac tctcagatgg caccaacatc  1200
ccatcaggca ctcgcatcgc ggttccctct cacgcgatgc ttcaggactc agcgcatgtc  1260
ccaggcccga cgccaccaac cgagtttgat ggatttagat actcaaagat tcgctcagac  1320
tcaaactatg cacagaaata tctcttctcc atgactgatt ctagtaacat ggcgtttggg  1380
tatgggaaat acgcctgccc agggcggttc tatgcatcta atgagatgaa gctgactttg  1440
gcgatactcc ttttacaatt tgagttcaag ttgccagatg ggaaaggaag accacgaaat  1500
atcactattg atagtgacat gatacctgat ccgagagcta ggctgtgcgt taggaagcga  1560
tcactgagag atgaatga                                                1578

SEQ ID NO: 59           moltype = DNA  length = 1500
FEATURE                 Location/Qualifiers
source                  1..1500
                        mol_type = other DNA
                        organism = Trametes versicolor
SEQUENCE: 59
atggaggatc ccaccgtact ctacgcttgc ctcgccatcg ctgtcgctac tttcgttgtc  60
agatggtaca gagacccgct tcggtccatt cctacggttg ggggctctga ccttcccatc  120
ctctcataca tcggggcgct caggtggacc cgccgcggaa gagagatact gcaagaaggt  180
tatgatgggt atcgcggatc cacgttcaag atcgcgatgc tcgaccggtg gatcgtcatc  240
gccaacggcc caaagctcgc cgacgaggtg aggaggcgtc ctgacgaaga gctaaacttc  300
atggacggac tgggagcgtt cgtgcagacg aagtataccc ttggggaagc aatccacaat  360
gacccgtacc acgtggacat tattcgtgag aagctgacgc gaggcctccc ggcagtcctg  420
ccggacgtca tcgaggaact cacgctagcc gttcgccagt acatcccgac ggaaggagat  480
gaatgggtca gcgtgaactg ctccaaagca gcgcgggaca tcgtcgcccg ggcaagcaac  540
cgcgtctttg tcgggttgcc cgcttgccgc aaccagggtt atctcgacct cgccattgac  600
ttcaccctga gcgttgtcaa agacagggcg atcatcaata tgttcccgga gttgctgaaa  660
cctatcgtcg gacgcgtggt tggaaatgcc actaggaacg tgcgccgcgc ggtcccattc  720
gtagcgccgt tggtggagga acgtcgccgc ctcatggagg agtacggtga ggattggtcg  780
gagaaaccga acgacatgct ccagtggatc atggacgagg cagcctcgcg ggactcctcc  840
gtcaaagcga tcgctgagcg tcttctcatg gtcaactttg ccgcaattca cacgtcgtcg  900
aacaccatca cccacgctct ttaccacctc gccgagatgc cggagaccct acagccgctg  960
cgggaagaga tcgagccgct cgtcaaggaa gaaggctgga cgaaggccgc catgggcaag  1020
atgtggtggc tcgacagctt cctgcgggag tcacagcgct acaatggcat caacatcgtc  1080
tccctgacgc gcatggccga caaggacata acgctcagcg acggcacgtt cctcccgaag  1140
ggcacgctcg tcgcggtccc cgcgtactcg acgcaccgcg acgacgcggt gtacgcggac  1200
gcgctggtct tcgacccgtt ccgcttctcc cgcatgcgcg cccgcgaggg cgagggcacg  1260
aagcaccagt tcgtcaacac ctccgtggag tacgtgccct tcggccacgg gaagcacgcc  1320
tgccccgggc ggttcttcgc ggccaacgag ctgaaggcga tgctcgcgta catcgtgctc  1380
aactacgacg tgaagctgcc cggcgatggc aagcgccccc tgaacatgta ctggggcccg  1440
acggtcttgc ctgctccggc tgggcaggtg ctcttccgca agaggcaggt gtcgctgtag  1500

SEQ ID NO: 60           moltype = DNA  length = 1578
FEATURE                 Location/Qualifiers
misc_feature            1..1578
                        note = Description of Artificial Sequence: Synthetic
                         polynucleotide
source                  1..1578
                        mol_type = other DNA
                        organism = synthetic construct
SEQUENCE: 60
atgggtttgt tcccattaga ggattcctac gcgctggtct ttgaaggact agcaataaca  60
ctggctttgt actatctact gtctttcatc tacaaaacat ctaaaaagac atgtacacct  120
cctaaagcat ctggtgaaat cattccaatt acaggaatca tattgaatct gctatctggc  180
tcaagtggtc tacctattat cttagcactt gcctctttag cagacagatg tggtcctatt  240
ttcaccatta ggctgggtat taggagagtg ctagtagtat caaattggga aatcgctaag  300
gagattttca ctacccacga tttgatagtt tctaatagac caaaatactt agccgctaag  360
attcttggtt tcaattatgt ttcattctct ttcgctccat acggcccata ttgggtcgga  420
atcagaaaga ttattgctac aaaactaatg tcttcttcca gacttcagaa gttgcaattt  480
gtaagagttt ttgaactaga aaactctatg aaatctatca gagaatcatg gaaggagaaa  540
```

-continued

```
aaggatgaag agggaaaggt attagttgag atgaaaaagt ggttctggga actgaatatg  600
aacatagtgt taaggacagt tgctggtaaa caatacactg gtacagttga tgatgccgat  660
gcaaagcgta tctccgagtt attcagagaa tggtttcact acactggcag atttgtcgtt  720
ggagacgctt ttccttttct aggttggttg gacctgggcg gatacaaaaa gacaatggaa  780
ttagttgcta gtagattgga ctcaatggtc agtaaatggt tagatgagca tcgtaaaaag  840
caagctaacg atgacaaaaa ggaggatatg gatttcatgg atatcatgat ctccatgaca  900
gaagcaaatt caccacttga aggatacggc actgatacta ttatcaagac cacatgtatg  960
actttgattg tttcaggagt tgatacaacc tcaatcgtac ttacttgggc cttatcactt  1020
ttgttaaaca acagagatac tttgaaaaag gcacaagagg aattagatat gtgcgtaggt  1080
aaaggaagac aagtcaacga gtctgatctt gttaacttga tatacttgga agcagtgctt  1140
aaagaggctt taagacttta cccagcagcg ttcttaggcg gaccaagagc attcttggaa  1200
gattgtactg ttgctggtta tagaattcca aagggcacct gcttgttgat taacatgtgg  1260
aaactgcata gagatccaaa catttggagt gatccttgcg aattcaagcc agaaagattt  1320
ttgacaccta atcaaaagga tgttgatgtg atcggtatgg atttcgaatt gataccattt  1380
ggtgccggca gaagatattg tccaggtact agattggctt tacagatgtt gcatatcgta  1440
ttagcgacat tgctgcaaaa cttcgaaatg tcaacaccaa acgatgcgcc agtcgatatg  1500
actgcttctg ttggcatgac aaatgccaaa gcatcacctt tagaagtctt gctatcacct  1560
cgtgttaaat ggtcctaa                                                1578
```

```
SEQ ID NO: 61          moltype = DNA  length = 1431
FEATURE                Location/Qualifiers
misc_feature           1..1431
                       note = Description of Artificial Sequence: Synthetic
                        polynucleotide
source                 1..1431
                       mol_type = other DNA
                       organism = synthetic construct
SEQUENCE: 61
atgatacaag ttttaactcc aattctactc ttcctcatct tcttcgtttt ctggaaagtc  60
tacaaacatc aaaagactaa aatcaatcta ccaccaggtt ccttcggctg gccatttttg  120
ggtgaaacct tagccttact tagagcaggc tgggattctg agccagaaag attcgtaaga  180
gagcgtatca aaaagcatgg atctccactt gttttcaaga catcactatt tggagacaga  240
ttcgctgttc tttgcggtcc agctggtaat aagtttttgt tctgcaacga aaacaaatta  300
gtggcatctt ggtggccagt ccctgtaagg aagttgttcg gtaaaagttt actcacaata  360
agaggagatg aagcaaaatg gatgagaaaa atgctattgt cttacttggg tccagatgca  420
tttgccacac attatgccgt tactatggat gttgtaacac gtagacatat tgatgtccat  480
tggaggggca aggaggaagt taatgtattt caaacagtta agttgtacgc attcgaatta  540
gcttgtagat tattcatgaa cctagatgac ccaaaccaca tcgcgaaact cggtagtctt  600
ttcaacattt tcctcaaagg gatcatcgag cttcctatag acgttcctgg aactagattt  660
tactccagta aaaaggccgc agctgccatt agaattgaat tgaaaaagct cattaaagct  720
agaaaactcg aattgaagga gggtaaggcg tcttcttcac aggacttgct ttctcatcta  780
ttaacatcac ctgatgagaa tggatgttc ttgacagaag aggaaatagt cgataacatt  840
ctacttttgt tattcgctgg tcacgatacc tctgcactat caataacact tttgatgaaa  900
accttaggtg aacacagtga tgtgtacgac aaggttttga aggaacaatt agaaatttcc  960
aaaacaaagg aggcttggga atcactaaag tgggaagata tccagaagat gaagtactca  1020
tggtcagtaa tctgtgaagt catgagattg aatcctcctg tcatagggac atacagagag  1080
gcgttggttg atatcgacta tgctggttac actatcccaa aaggatggaa gttgcattgg  1140
tcagctgttt ctactcaaag agacgaagcc aatttcgaag atgtaactag attcgatcca  1200
tccagatttg aaggggcagg ccctactcca ttcacatttg tgcctttcgg tggaggtcct  1260
agaatgtgtt taggcaaaga gtttgccagg ttagaagtgt tagcatttct ccacaacatt  1320
gttaccaact ttaagtggga tcttctaatc cctgatgaga agatcgaata tgatccaatg  1380
gctactccag ctaagggctt gccaattaga cttcatccac accaagtcta a           1431
```

```
SEQ ID NO: 62          moltype = DNA  length = 1578
FEATURE                Location/Qualifiers
misc_feature           1..1578
                       note = Description of Artificial Sequence: Synthetic
                        polynucleotide
source                 1..1578
                       mol_type = other DNA
                       organism = synthetic construct
SEQUENCE: 62
atggagtctt tagtggttca tacagtaaat gctatctggt gtattgtaat cgtcgggatt  60
ttctcagttg gttatcacgt ttacggtaga gctgtggtcg aacaatggag aatgagaaga  120
tcactgaagc tacaaggtgt taaaggccca ccaccatcca tcttcaatgg taacgtctca  180
gaaatgcaac gtatccaatc cgaagctaaa cactgctctg gcgataacat tatctcacat  240
gattattctt cttcattatt cccacacttc gatcactgga gaaaacagta cggcagaatc  300
tacacatact ctactggatt aaagcaacac ttgtacatca atcatccaga aatggtgaag  360
gagctatctc agactaacac attgaacttg ggtagaatca cccatataac caaaagattg  420
aatcctatct taggtaacgg aatcataacc tctaatggtc ctcattgggc ccatcagcgt  480
agaattatcg cctacgagtt tactcatgat aagatcaagg gtatggttgg tttgatggtt  540
gagtctgcta tgcctatgtt gaataagtgg gaggagatgg taaagagagg cggagaaatg  600
ggatgcgaca taagagttga tgaggacttg aaagatgttt cagcagatgt gattgcaaaa  660
gcctgtttcg gatcctcatt ttctaaaggt aaggctattt tctctatgat aagagatttg  720
cttacagcta tcacaaagag aagtgttcta ttcagattca acggattcac tgatatggtc  780
tttgggagta aaaagcatgg tgacgttgat atagacgctt tagaaatgga attggaatca  840
tccatttggg aaactgtcaa ggaacgtgaa atagaatgta aagatactca caaaaaggat  900
ctgatgcaat tgattttgga aggggcaatg cgttcatgtg acggtaacct ttgggataaa  960
tcagcatata gaagatttgt tgtagataat tgtaaatcta tctacttcgc agggcatgat  1020
```

-continued

```
agtacagctg tctcagtgtc atggtgtttg atgttactgg ccctaaaccc atcatggcaa  1080
gttaagatcc gtgatgaaat tctgtcttct tgcaaaaatg gtattccaga tgccgaaagt  1140
atcccaaacc ttaaaacagt gactatggtt attcaagaga caatgagatt ataccctcca  1200
gcaccaatcg tcgggagaga agcctctaaa gatatcagat tgggcgatct agttgttcct  1260
aaaggcgtct gtatatggac actaatacca gctttacaca gagatcctga gatttgggga  1320
ccagatgcaa acgatttcaa accagaaaga ttttctgaag gaatttcaaa ggcttgtaag  1380
tatcctcaaa gttacattcc atttggtctg ggtcctagaa catgcgttgg taaaaacttt  1440
ggcatgatgg aagtaaaggt tcttgtttcc ctgattgtct ccaagttctc tttcactcta  1500
tctcctacct accaacatag tcctagtcac aaacttttag tagaaccaca acatggggtg  1560
gtaattagag tggtttaa                                                1578
```

```
SEQ ID NO: 63          moltype = DNA  length = 1590
FEATURE                Location/Qualifiers
misc_feature           1..1590
                       note = Description of Artificial Sequence: Synthetic
                        polynucleotide
source                 1..1590
                       mol_type = other DNA
                       organism = synthetic construct
SEQUENCE: 63
atgtacttcc tactacaata cctcaacatc acaaccgttg gtgtctttgc cacattgttt  60
ctctcttatt gtttacttct ctggagaagt agagcgggta acaaaaagat tgccccagaa  120
gctgccgctg catggcctat tatcggccac ctccacttac ttgcaggtgg atcccatcaa  180
ctaccacata ttacattggg taacatggca gataagtacg gtcctgtatt cacaatcaga  240
ataggcttgc atagagctgt agttgtctca tcttgggaaa tggcaaagga atgttcaaca  300
gctaatgatc aagtgtcttc ttcaagacct gaactattag cttctaagtt gttgggttat  360
aactacgcca tgtttggttt ttcaccatac ggttcatact ggagagaaat gagaaagatc  420
atctctctcg aattactatc taattccaga ttggaactat tgaaagatgt tagagcctca  480
gaagttgtca catctattaa ggaactatac aaattgtggg cggaaaagaa gaatgagtca  540
ggattggttt ctgtcgagat gaaacaatgg ttcggagatt tgactttaaa cgtgatcttg  600
agaatggtgg ctggtaaaag atacttctcc gcgagtgacg cttcagaaaa caaacaggcc  660
cagcgttgta gaagagtctt cagagaattc ttccatctct ccggcttgtt tgtggttgct  720
gatgctatac cttttcttgg atggctcgat tggggaagac acgagaagac cttgaaaaag  780
accgccatag aaatggattc catcgcccag gagtggcttg aggaacatag acgtagaaaa  840
gattctggag atgataattc tacccaagat ttcatggacg ttatgcaatc tgtgctagat  900
ggcaaaaatc taggcggata cgatgctgat acgattaaca aggctacatg cttaactctt  960
atatcaggtg gcagtgatac tactgtagtt tctttgacat gggctcttag tcttgtgtta  1020
aacaatagag atactttgaa aaaggcacag gaagagttag acatccaagt cggtaaggaa  1080
agattggtta acgagcaaga catcagtaag ttagtttact tgcaagcaat agtaaaagag  1140
acactcagac tttatccacc aggtcctttg ggtggtttga gacaattcac tgaagattgt  1200
acactaggtg gctatcacgt ttcaaaagga actagattaa tcatgaactt atccaagatt  1260
caaaaagatc cacgtatttg gtctgatcct actgaattcc aaccagagag attccttacg  1320
actcataaag atgtcgatcc acgtggtaaa cactttgaat tcattccatt cggtgcagga  1380
agacgtgcat gtcctggtat cacattcgga ttacaagtac tacatctaac attggcatct  1440
ttcttgcatg cgtttgaatt ttcaacacca tcaaatgagc aggttaacat gagagaatca  1500
ttaggtctta cgaatatgaa atctacccca ttagaagttt tgatttctcc aagactatcc  1560
cttaattgct tcaaccttat gaaaatttga                                  1590
```

```
SEQ ID NO: 64          moltype = DNA  length = 1440
FEATURE                Location/Qualifiers
misc_feature           1..1440
                       note = Description of Artificial Sequence: Synthetic
                        polynucleotide
source                 1..1440
                       mol_type = other DNA
                       organism = synthetic construct
SEQUENCE: 64
atggaaccta acttttactt gtcattacta ttgttgttcg tgaccttcat ttctttaagt  60
ctgtttttca tcttttacaa acaaaagtcc ccattgaatt tgccaccagg gaaaatgggt  120
taccctatca taggtgaaag tttagaattc ctatccacag gctggaaggg acatcctgaa  180
aagttcatat ttgatagaat gcgtaagtac agtagtgagt tattcaagac ttctattgta  240
ggcgaatcca cagttgtttg ctgtggggca gctagtaaca aattcctatt ctctaacgaa  300
aacaaactgg taactgcctg gtggccagat tctgttaaca aaatcttccc aacaacttca  360
ctggattcta atttgaagga ggaatctata aagatgagaa agttgctgcc acagttcttc  420
aaaccagaag cacttcaaag atacgtcggc gttatggatg taatcgcaca aagacatttt  480
gtcactcact gggacaacaa aaatgagatc acagtttatc cacttgctaa aagatacact  540
ttcttgcttg cgtgtagact gttcatgtct gttgaggatg aaaatcatgt ggcgaaattc  600
tcagacccat tccaactaat cgctgcaggc atcatttcac ttcctatcga tcttcctggt  660
actccattca acaaggccat aaaggcttca aatttcatta gaaaagagct gataaagatt  720
atcaaacaaa gacgtgttga tctggcagag ggtacagcat ctccaaccca ggatatcttg  780
tcacatatgc tattaacatc tgatgaaaac ggtaaatcta tgaacgagtt gaacattgcc  840
gacaagattc ttggactatt gataggaggc cacgatacag cttcagtagc ttgcacattt  900
ctagtgaagt acttaggaga attaccacat atctacgata aagtctacca agagcaaatg  960
gaaattgcca agtccaaacc tgctggggaa ttgttgaatt gggatgactt gaaaaagatg  1020
aagtattcat ggaatgtggc atgtgaggta atgagattgt caccaccttt acaaggtggt  1080
tttagagagg ctataactga ctttatgttt aacggtttct ctattccaaa agggtggaag  1140
ttatactggt ccgccaactc tacacacaaa aatgcagaat gtttcccaat gcctgagaaa  1200
ttcgatccta ccagatttga aggtaatggt ccagcgcctt atacatttgt accattcggt  1260
ggaggcccta gaatgtgtcc tggaaaggaa tacgctagat tagaaatctt ggttttcatg  1320
```

-continued

```
cataatctgg tcaaacgttt taagtgggaa aaggttattc cagacgaaaa gattattgtc  1380
gatccattcc caatcccagc taaagatctt ccaatccgtt tgtatcctca caaagcttaa  1440

SEQ ID NO: 65          moltype = DNA  length = 1572
FEATURE                Location/Qualifiers
source                 1..1572
                       mol_type = other DNA
                       organism = Stevia rebaudiana
SEQUENCE: 65
atgggtctct tccctttgga agatagttac gcactcgtct ttgaaggttt agcaataact  60
actctagctc tctactactt attatccttc atctataaaa cctctaaaaa gacttgtact  120
ccacctaaag caagcggtga gcaccctata acaggccact taaaccttct tagtggttca  180
tccggtcttc cccatctagc cttagcatct ttggctgacc gatgtgggcc catattcacc  240
atccgacttg gcatacgtag agttttggtg gttagtaatt gggaaattgc taaggagatc  300
ttcactaccc atgatttgat tgtttcaaac cgtcccaaat acctcgctgc aaagattttg  360
ggattcaact atgtgtcctt ttcgtttgct ccatatggcc cctattgggt tggaatccgt  420
aagatcatcg ccacaaaact gatgtcaagt agcaggctcc agaagcttca gtttgtccga  480
gttttcgaac tagaaaactc catgaaaagc atacgcgagt cttggaaaga gaaaaaagac  540
gaagaaggta aagtgttggt ggagatgaaa aaatggtttt gggaattgaa tatgaatata  600
gttcttagaa ctgttgctgg taaacagtac actggaactg ttgatgatgc ggatgcgaag  660
aggattagtg aattgtttag agaatggttt cattacacag gaaggtttgt tgtgggagat  720
gcttttcctt ttcttgggtg gttggatttg ggtggatata agaagaccat ggaactagtg  780
gcttccagac tagattccat ggtctcaaaa tggttagacg agcatcgcaa aaagcaggct  840
aacgacgaca aaaaagagga catggatttc atggacatca tgatatcgat gactgaagcc  900
aattcccctt tggagggtta tggtacggat acaataatta aaaccacttg catgactctt  960
attgtcagtg gtgtagatac aacctccatc gtgctaactt gggcactctc gttactactg  1020
aacaaccgtg acactcttaa gaaagctcaa gaagagctag acatgtgtgt gggaaaaggt  1080
cgacaagtaa acgaatcaga tctagtaaac ctaatctacc ttgaagccgt attaaaagaa  1140
gcattgcgac tataccagc  agcattcctt ggaggtccta gagccttttt agaagactgc  1200
accgtggcag ggtaccgtat cccaaaaggc acatgtctac ttattaacat gtggaaactt  1260
catcgtgatc caaacatatg gtcagaccca tgtgagttta aaccagagag gttcttaacc  1320
ccaaaccaaa aggacgtaga tgttattgga atggattttg agttaatccc atttggtgcg  1380
ggaagaaggt attgtccagg gacacgtttg gcattacaaa tgttacacat agttctggcc  1440
actctactac aaaactttga gatgtcaact ccaaatgatg cacccgttga tatgaccgcg  1500
agtgttggaa tgacaaatgc gaaggcaagt ccacttgaag ttctactttc gccacgtgtt  1560
aagtggtcat ag                                                      1572

SEQ ID NO: 66          moltype = DNA  length = 1431
FEATURE                Location/Qualifiers
source                 1..1431
                       mol_type = other DNA
                       organism = Stevia rebaudiana
SEQUENCE: 66
atgattcaag ttctaacacc gatccttctc ttcctcattt tcttcgtttt ctggaaggtt  60
tacaagcacc agaaaaccaa aatcaatctt ccaccgggaa gcttcggatg gccatttctg  120
ggcgaaactc tggcactcct acgtgcaggt tgggactcag agccggagag atttgttcgt  180
gaacggatca agaaacacgg aagtcctcta gtgtttaaga cgtcgttgtt tggcgaccgt  240
tttgcggtgt tgtgtggacc tgccggaaac aagttcctgt tctgcaacga gaacaagctg  300
gtggcgtcgt ggtggccggt tccggtgagg aagcttttcg gcaagtctct gctcacgatt  360
cgtggtgatg aagctaagtg gatgaggaag atgttgttat cgtatctcgg tcctgatgct  420
ttcgcaactc attatgccgt caccatggac gtcgtcaccc gtcggcatat cgacgttcat  480
tggcgaggga aggaagaggt gaacgtattc caaaccgtta agttatatgc ctttgagctt  540
gcatgtcgtt tattcatgaa cctagacgac cccaaaccaca ttgcaaaact cggttccttg  600
ttcaacattt tcttgaaagg catcattgag cttccaatcg acgtcccagg gacacgattt  660
tatagctcca aaaaagcagc agcagctatc aggattgaac taaaaaaatt gattaaagca  720
agaaaactgg aactgaaaga agggaaggca tcatcttcac aagacctctt atcacatttg  780
cttacatctc cagatgaaaa tggtatgttt ctaaccgaag aagagattgt agacaacatc  840
ttgttactac tctttgcggg tcatgatacc tcggctcttt caatcacttt gctcatgaag  900
actcttggcg aacattctga tgtttatgac aaggtgttaa aagagcaact agagatatcg  960
aagacgaaag aagcatggga gtccctgaaa tgggaggaca tacaaaagat gaaatactcc  1020
tggagtgtta tatgtgaagt catgagacta aatccacctg ttataggaac ctatagagag  1080
gcccttgtgg atattgatta tgcgggttat accatcccca aaggatggaa gctgcactgg  1140
agtgctgtat cgacacaaag ggacgaggct aactttgaag acgtaacacg ttttgaccca  1200
tcacggtttg aaggcgcagg accgactcca ttcacctttg ttccgtttgg agggggggcct  1260
agaatgtgtt tagggaaaga atttgctcga ttggaagtac ttgcgtttct tcacaatatt  1320
gtcaccaatt tcaaatggga cctgttgata cctgatgaga aaatagaata tgatcccatg  1380
gctaccccag caaaggggct tccaattcgt cttcatcccc atcaagtttg a           1431

SEQ ID NO: 67          moltype = DNA  length = 1578
FEATURE                Location/Qualifiers
source                 1..1578
                       mol_type = other DNA
                       organism = Arabidopsis thaliana
SEQUENCE: 67
atggagagtt tggttgttca tacggtaaat gcaatttggt gcatagttat tgtcggaatc  60
ttcagcgtag gttatcatgt gtatggaaga gcggtggtgg agcagtggag gatgcggagg  120
agtttaaagt tgcaaggcgt gaagggtcct ccaccgtcga tctttaacgg caatgtgtcg  180
gagatgcaac ggattcagtc ggaggctaaa cactgttccg gcgataacat catttctcat  240
gactattctt cttctctatt tcctcatttc gatcactggc gaaaacaata cggaaggatt  300
```

```
tacacatact caacggggtt aaagcagcac ctttacataa accacccgga aatggtgaag  360
gagcttagcc aaaccaacac acttaacctt ggtagaatca ctcacatcac caaacgcctt  420
aaccccattc tcggcaatgg catcatcacc tctaatgggc ctcattgggc ccatcaacgt  480
cgtatcattg cctatgagtt tacccacgac aaaatcaagg gaatggttgg tttaatggtg  540
gaatctgcca tgccaatgtt gaacaaatgg gaagagatgg tgaaaagagg aggagaaatg  600
ggttgtgaca taagagtgga cgaagacctt aaggatgtct cagctgatgt catcgctaag  660
gcttgctttg ggagctcttt ttcaaaaggc aaagcaatat tctctatgat tagggatctt  720
ttaaccgcca ttactaaacg aagcgtcctc ttcagattca atggcttcac tgatatggtg  780
tttggaagta agaagcatgg tgatgtggat attgatgcgc ttgagatgga attagaatct  840
tctatatggg aaacggttaa ggagagggaa attgaatgta aggatactca caagaaggat  900
ctaatgcagt tgatactcga gggagcgatg cgaagctgcg atggtaactt gtgggacaag  960
tcagcctata gacggtttgt ggtggacaat tgcaagagca tctatttcgc cggacatgat  1020
tcaaccgcag tctcagtgtc ttggtgcctt atgctcctcg ctctcaatcc tagttggcag  1080
gttaaaattc gcgatgaaat cttgagttct tgcaagaatg gcattcccga cgcagaatca  1140
attcctaatc tcaaaacggt gacaatggta atacaagaaa caatgagact atacccacca  1200
gcaccaatcg tgggaagaga agcatccaaa gacataagac ttggagacct tgtggtgcca  1260
aaaggagtgt gcatttggac actcattcct gccttacacc gagaccccga gatctgggga  1320
ccagacgcaa acgacttcaa gccagagagg tttagtgagg gaatctctaa ggcttgcaaa  1380
taccctcagt catacatccc atttggcctt ggaccaagaa catgcgtagg caaaaacttt  1440
ggtatgatgg aagtgaaagt gcttgtttca cttattgtct caaagttcag ttttactctt  1500
tccccgactt atcagcactc tccaagccat aaactccttg tagagcctca acatggtgtt  1560
gtcattaggg ttgtttga                                                1578

SEQ ID NO: 68          moltype = DNA  length = 1590
FEATURE                Location/Qualifiers
source                 1..1590
                       mol_type = other DNA
                       organism = Vitis vinifera
SEQUENCE: 68
atgtatttcc ttctccaata cctaaacatc accacggtcg gagtctttgc cacacttttc  60
ctttcctact gtctattatt atggaggtct agagctggta acaaaaaaat agcacctgaa  120
gctgctgctg catggcccat aatcggtcac ctacacctgt tagctggtgg ttctcatcag  180
cttccccaca taaccttggg aaacatggcc gacaaatatg gaccggtctt cacaattcgg  240
attgggttgc atcgagctgt ggtggtaagt tcttgggaga tggctaaaga atgctcgacc  300
gccaatgacc aggtttcatc ctcgcgtccc gaacttttag cctcaaaact tttgggctac  360
aactacgcca tgtttggttt ctctccatac ggttcttact ggcgtgaaat gcgcaagata  420
atcagcctag agctactctc taacagccgc ttagagctgc tgaaggacgt ccgagcttca  480
gaagtggtga catccataaa agagctatac aagctctggg cagagaaaaa aaatgaatcg  540
ggccttgtct cggtggagat gaagcagtgg tttggagact tgactctgaa cgtaattctt  600
aggatggtgg cagggaagcg ttatttcagt gcttcagatg caagtgaaaa taaacaggcg  660
cagaggtgcc ggagagtgtt cagggaattc tttcatttgt cagggctctt tgtggtggcg  720
gacgctattc catttcttgg atggctcgac tgggggagac atgagaaaac cctaaagaag  780
acagcaatag aaatggacag tattgctcaa gaatggttag aggagcaccg tcggaggaaa  840
gactccggtg atgataatag tacgcaagac ttcatggatg tgatgcagtc agttcttgat  900
ggcaaaaacc ttggtggtta cgacgctgat accatcaata aagccacatg cctgactcta  960
atctccggag gtagcgacac aactgttgtc tctctaacat gggcactctc tcttgtacta  1020
aacaaccgtg acaccttaaa aaaagctcaa gaagaattag acatccaagt tggtaaggaa  1080
agattagtga atgaacaaga tataagtaag ttggtctatc tccaagccat tgttaaagag  1140
acattacggt tatatccacc aggaccactt ggaggactac gccaatttac cgaggattgc  1200
accttgggtg gataccatgt ctctaaaggc acccgtttaa taatgaacct ttcgaagatc  1260
caaaaggatc caagaatttg gtcagatccg acagaattcc aaccagagag gtttctcacc  1320
acccataaag atgttgatcc tcggggaaaa cattttgagt ttataccatt tggagctggt  1380
cgaagagcat gtccaggaat aacttttggt cttcaagtat tacatttaac attggctagt  1440
ttcttacatg cgtttgaatt ttcaactcca tcaaatgaac aggtcaatat gcgcgagagc  1500
cttggactta caaatatgaa atctacccca cttgaagttc tcatttctcc acgcttatca  1560
ttgaattgtt ttaacctaat gaagatataa                                    1590

SEQ ID NO: 69          moltype = DNA  length = 1440
FEATURE                Location/Qualifiers
source                 1..1440
                       mol_type = other DNA
                       organism = Medicago truncalata
SEQUENCE: 69
atggagccta atttctatct ctcccttctc cttctctttg tcactttcat atctctctct  60
cttttttca tattctacaa acagaaatct ccattaaatt tgccacctgg taaaatgggt  120
tacccaatca taggtgaaag ccttgagttc ttatcaacag gatggaaagg acatcctgaa  180
aaattcattt tcgaccgtat gcgtaaatat tcctcagaac tctttaaaac atcaatcgta  240
ggagaatcta cggtggtttg ttgcggagca gcaagtaaca agtttttgtt ttcaaacgag  300
aataaacttg tgactgcatg gtggccagat agtgtaaaca aaatcttccc tactacttct  360
cttgactcta acttgaagga agaatccatc aagatgagaa aattgcttcc acaattcttt  420
aaacccgaag ctctacaacg ttatgttggt gtcatggatg ttattgctca aagacatttt  480
gttactcatt gggataataa aaatgaaatc accgtctacc ccttggccaa gaggtacacc  540
tttttgttag cttgtcggtt gttcatgagc gttgaagacg agaatcatgt agcaaaattt  600
agtgatccat ttcagttaat tgcggccgga atcatatctc taccaattga tttgccagga  660
acaccattca acaaagctat aaaggcctca aactttataa gaaaggagtt gattaagatc  720
ataaagcaaa ggagggtaga tttggcagaa gggacagcat caccaacaca agatatattg  780
tctcacatgt tgttgacaag tgatgaaaat ggaaagagta tgaatgaact taatattgct  840
gataagattc ttggcctttt gatcggagga catgacactg ctagcgtcgc atgcactttc  900
cttgtcaaat atctcggcga gttacctcac atttatgata aagtctatca agagcaaatg  960
```

```
gaaattgcaa aatcgaaacc agcaggagaa ttgttgaatt gggatgacct gaagaaaatg  1020
aaatactctt ggaacgtagc ttgtgaagta atgagacttt cccctccact ccaaggaggt  1080
ttcagggaag ccatcactga ctttatgttc aatggattct caattcctaa gggatggaag  1140
ctttattgga gtgcaaattc aacacataag aacgcagaat gttttcccat gccagagaaa  1200
tttgacccaa caagatttga aggaaatgga ccagctcctt atacttttgt tccctttggt  1260
ggaggaccaa ggatgtgtcc tggaaaagag tatgcaagat tagaaatact tgttttcatg  1320
cacaatttgg tgaaaaggtt taagtgggaa aaggtgattc cagatgagaa gattattgtt  1380
gatccattcc ccatccctgc aaaggatctt ccaattcgcc tttatccaca caaagcttaa  1440

SEQ ID NO: 70          moltype = DNA  length = 2133
FEATURE                Location/Qualifiers
misc_feature           1..2133
                       note = Description of Artificial Sequence: Synthetic
                        polynucleotide
source                 1..2133
                       mol_type = other DNA
                       organism = synthetic construct
SEQUENCE: 70
atgcaatcag attcagtcaa agtctctcca tttgatttgg tttccgctgc tatgaatggc  60
aaggcaatgg aaaagttgaa cgctagtgaa tctgaagatc caacaacatt gcctgcacta  120
aagatgctag ttgaaaatag agaattgttg acactgttca caacttcctt cgcagttctt  180
attgggtgtc ttgtatttct aatgtggaga cgttcatcct ctaaaaagct ggtacaagat  240
ccagttccac aagttatcgt tgtaaagaag aaagagaagg agtcagaggt tgatgacggg  300
aaaaagaaag tttctatttt ctacggcaca caaacaggaa ctgccgaagg ttttgctaaa  360
gcattagtcg aggaagcaaa agtgagatat gaaaagacct ctttcaaggt tatcgatcta  420
gatgactacg ctgcagatga tgatgaatat gaggaaaaac tgaaaaagga atccttagcc  480
ttcttcttct tggccacata cggtgatggt gaacctactg ataatgctgc taacttctac  540
aagtggttca cagaaggcga cgataaaggt gaatggctga aaaagttaca atacggagta  600
tttggtttag gtaacagaca atatgaacat ttcaacaaga tcgctattgt agttgatgat  660
aaacttactg aaatgggagc caaaagatta gtaccagtag gattagggga tgatgatcag  720
tgtatagaag atgacttcac cgcctggaag gaattggtat ggccagaatt ggatcaactt  780
ttaagggacg aagatgatac ttctgtgact accccataca ctgcagccgt attggagtac  840
agagtggttt accatgataa accagcagac tcatatgctg aagatcaaac ccatacaaac  900
ggtcatgttg ttcatgatgc acagcatcct tcaagatcta atgtggcttt caaaaaggaa  960
ctacacacct ctcaatcaga taggtcttgt actcacttag aattcgatat ttctcacaca  1020
ggactgtctt acgaaactgg cgatcacgtt ggcgtttatt ccgagaactt gtccgaagtt  1080
gtcgatgaag cactaaaact gttagggtta tcaccagaca catacttctc agtccatgct  1140
gataaggagg atgggacacc tatcggtggt gcttcactac caccaccttt tcctccttgc  1200
acattgagag acgctctaac cagatacgca gatgtcttat cctcacctaa aaaggtagct  1260
ttgctggcat tggctgctca tgctagtgat cctagtgaag ccgataggtt aaagttcctg  1320
gcttcaccag ccggaaaaga tgaatatgca caatggatcg tcgccaacca acgttctttg  1380
ctagaagtga tgcaaagttt tccatctgcc aagcctccat taggtgtgtt cttcgcagca  1440
gtagctccac gtttacaacc aagatactac tctatcagtt catctcctaa gatgtctcct  1500
aacagaatac atgttacatg tgctttggtg tacgagacta ctccagcagg cagaattcac  1560
agaggattgt gttcaacctg gatgaaaaat gctgtccctt taacagagtc acctgattgc  1620
tctcaagcat ccattttcgt tagaacatca aatttcagac ttccagtgga tccaaaagtt  1680
ccagtcatta tgataggacc aggcactggt cttgccccat tcaggggctt tcttcaagag  1740
agattggcct tgaaggaatc tggtacagaa ttgggttctt ctatcttttt ctttggttgc  1800
cgtaatagaa aagttgactt tatctacgag gacgagctta acaattttgt tgagacagga  1860
gcattgtcag aattgatcgt cgcattttca agagaaggga ctgccaaaga gtacgttcag  1920
cacaagatga gtcaaaaagc ctccgatata tggaaacttc taagtgaagg tgcctatctt  1980
tatgtctgtg gcgatgcaaa gggcatggcc aaggatgtcc atagaactct gcatacaatt  2040
gttcaggaac aagggagtct ggattcttcc aaggctgaat tgtacgtcaa aaacttacag  2100
atgtctggaa gatacttaag agatgtttgg taa                               2133

SEQ ID NO: 71          moltype = DNA  length = 2079
FEATURE                Location/Qualifiers
misc_feature           1..2079
                       note = Description of Artificial Sequence: Synthetic
                        polynucleotide
source                 1..2079
                       mol_type = other DNA
                       organism = synthetic construct
SEQUENCE: 71
atgacttctg cactttatgc ctccgatctt ttcaaacaat tgaaaagtat catgggaacg  60
gattctttgt ccgatgatgt tgtattagtt attgctacaa cttctctggc actggttgct  120
ggtttcgttg tcttattgtg gaaaaagacc acggcagatc gttccggcga gctaaagcca  180
ctaatgatcc ctaagtctct gatggcgaaa gatgaggatg atgacttaga tctaggttct  240
ggaaaaacga gagtctctat cttcttcggc acacaaaccg gaacagccga aggattcgct  300
aaagcacttt cagaagagat caaagcaaga tacgaaaagg cggctgtaaa agtaatcgat  360
ttggatgatt acgctgccga tgatgaccaa tatgaggaaa agttgaaaaa ggaaacattg  420
gctttctttt gtgtagccac gtatggtgat ggtgaaccaa ccgataacgc cgcaagattc  480
tacaagtggt ttactgaaga gaacgaaaga gatatcaagt tgcagcaact tgcttacggc  540
gtttttgcct taggtaacag acaatacgag cactttaaca agataggtat tgtcttagat  600
gaagagttat gcaaaaaggg tgcgaagaga ttgattgaag tcggtttagg agatgatgat  660
caatctatcg aggatgactt taatgcatgg aaggaatctt tgtggtctga attagataag  720
ttacttaagg acgaagatga taaatccgtt gccactccat acacagccgt cattccagaa  780
tatagagtag ttactcatga tccaagattc acaacacaga aatcaatgga aagtaatgtg  840
gctaatggta atactaccat cgatattcat catccatgta gagtagacgt tgcagttcaa  900
```

-continued

```
aaggaattgc acactcatga atcagacaga tcttgcatac atcttgaatt tgatatatca  960
cgtactggta tcacttacga aacaggtgat cacgtgggtg tctacgctga aaaccatgtt  1020
gaaattgtag aggaagctgg aaagttgttg ggccatagtt tagatcttgt tttctcaatt  1080
catgccgata aagaggatgg ctcaccacta gaaagtgcag tgcctccacc atttccagga  1140
ccatgcaccc taggtaccgg tttagctcgt tacgcggatc tgttaaatcc tccacgtaaa  1200
tcagctctag tggccttggc tgcgtacgcc acagaacctt ctgaggcaga aaaactgaaa  1260
catctaactt caccagatgg taaggatgaa tactcacaat ggatagtagc tagtcaacgt  1320
tctttactag aagttatggc tgctttccca tccgctaaac ctcctttggg tgttttcttc  1380
gccgcaatag cgcctagact gcaaccaaga tactattcaa tttcatcctc acctagactg  1440
gcaccatcaa gagttcatgt cacatccgct ttagtgtacg gtccaactcc tactggtaga  1500
atccataagg gcgtttgttc aacatggatg aaaaacgcgg ttccagcaga gaagtctcac  1560
gaatgttctg gtgctccaat ctttatcaga gcctccaact tcaaactgcc ttccaatcct  1620
tctactccta ttgtcatggt cggtcctggt acaggtcttg ctccattcag aggtttctta  1680
caagagagaa tggccttaaa ggaggatggt gaagagttgg gatcttcttt gttgttttc   1740
ggctgtagaa acagacaaat ggatttcatc tacgaagatg aactgaataa ctttgtagat  1800
caaggagtta tttcagagtt gataatggct ttttctagag aaggtgctca gaaggagtac  1860
gtccaacaca aaatgatgga aaaggccgca caagtttggg acttaatcaa agaggaaggc  1920
tatctatatg tctgtggtga tgcaaagggt atggcaagag atgttcacag aacacttcat  1980
actatagtcc aggaacagga aggcgttagt tcttctgaag cggaagcaat tgtgaaaaag  2040
ttacaaacag agggaagata cttgagagat gtgtggtaa                         2079
```

```
SEQ ID NO: 72          moltype = DNA  length = 2142
FEATURE                Location/Qualifiers
misc_feature           1..2142
                       note = Description of Artificial Sequence: Synthetic
                        polynucleotide
source                 1..2142
                       mol_type = other DNA
                       organism = synthetic construct
SEQUENCE: 72
atggcagaat tagatacact tgatatagta gtattaggtg ttatcttttt gggtactgtg  60
gcatacttta ctaagggtaa attgtggggt gttaccaagg atccatacgc taacggattc  120
gctgcaggtg gtgcttccaa gcctggcaga actagaaaca tcgtcgaagc tatggaggaa  180
tcaggtaaaa actgtgttgt tttctacggc agtcaaacag gtacagcgga ggattacgca  240
tcaagacttg caaaggaagg aaagtccaga ttcggtttga acactatgat cgccgatcta  300
gaagattatg acttcgataa cttagacact gttccatctg ataacatcgt tatgtttgta  360
ttggctactt acggtgaagg cgaaccaaca gataacgccg tggatttcta tgagttcatt  420
actggcgaag atgcctcttt caatgagggc aacgatcctc cactaggtaa cttgaattac  480
gttgcgttcg gtctgggcaa caatacctac gaacactaca actcaatggt caggaacgtt  540
aacaaggctc tagaaaagtt aggagctcat agaattggag aagcaggtga gggtgacgac  600
ggagctggaa ctatggaaga ggactttttta gcttggaaag atccaatgtg ggaagccttg  660
gctaaaaaga tgggcttgga ggaaagagaa gctgtatatg aacctatttt cgctatcaat  720
gagagagatg atttgacccc tgaagcgaat gaggtatact tgggagaacc taataagcta  780
cacttggaag gtacagcgaa aggtccattc aactcccaca acccatatat cgcaccaatt  840
gcagaatcat acgaactttt ctcagctaag gatagaaatt gtctgcatat ggaaattgat  900
atttctggta gtaatctaaa gtatgaaaca ggcgaccata tcgcgatctg gcctaccaac  960
ccaggtgaag aggtcaacaa atttcttgac attctagatc tgtctggtaa gcaacattcc  1020
gtcgtaacag tgaaagcctt agaacctaca gccaaagttc cttttccaaa tccaactacc  1080
tacgatgcta tattgagata ccatctggaa atatgcgctc cagtttctag acagtttgtc  1140
tcaactttag cagcattcgc ccctaatgat gatatcaaag ctgagatgaa ccgtttggga  1200
tcagacaaag attacttcca cgaaaagaca ggaccacatt actacaatat cgctagattt  1260
ttggcctcag tctctaaagg tgaaaaatgg acaaagatac cattttctgc tttcatagaa  1320
ggccttacaa aactacaacc aagatactat tctatctctt cctctagttt agttcagcct  1380
aaaaagatta gtattactgc tgttgtcgaa tctcagcaaa ttccaggtag agatgaccca  1440
ttcagaggtg tagcgactaa ctacttgttc gctttgaagc agaaacaaaa cggtgatcca  1500
aatccagctc cttttggcca atcatacgag ttgacaggac caaggaataa gtatgatggt  1560
atacatgttc cagtccatgt aagacattct aactttaagc taccatctga tccaggcaaa  1620
cctattatca tgatcggtcc aggtaccggt gttgcccctt ttagaggctt cgtccaagag  1680
agggcaaaac aagccagaga tggtgtagaa gttggtaaaa cactgctgtt ctttggatgt  1740
agaaagagta cagaagattt catgtatcaa aaagagtggc aagagtacaa ggaagctctt  1800
ggcgacaaat tcgaaatgat tacagctttt tcaagagaag gatctaaaaa ggtttatgtt  1860
caacacagac tgaaggaaag atcaaaggaa gtttctgatc ttctatccca aaaagcatac  1920
ttctacgttt gcggagacgc cgcacatatg gcacgtgaag tgaacactgt gttagcacag  1980
atcatagcag aaggccgtgg tgtatcagaa gccaagggtg aggaaattgt caaaaacatg  2040
agatcagcaa atcaatacca agtgtgttct gatttcgtaa ctttacactg taaagagaca  2100
acatacgcga attcagaatt gcaagaggat gtctggagtt aa                     2142
```

```
SEQ ID NO: 73          moltype = DNA  length = 2133
FEATURE                Location/Qualifiers
source                 1..2133
                       mol_type = other DNA
                       organism = Stevia rebaudiana
SEQUENCE: 73
atgcaatcag attccgtaaa agtgtcgccg ttcgatctcg tatctgcagc tatgaacgga  60
aaagcaatgg agaaattgaa cgcatcggaa tcggaagatc cgacgacgct accggcgttg  120
aagatgctgg tggagaatcg cgagctgctg acactgttta cgacgtcgtt tgctgtattg  180
atcggatgtc tcgtgttttt gatgtggcgg agatcgtcct cgaagaaact ggttcaggat  240
ccggtgccgc aggtaatcgt tgttaagaag aaagagaagg agtctgaggt tgatgatggc  300
aagaagaaag tttcgatatt ctacggaact caaacaggaa ccgctgaagg ttttgccaag  360
```

-continued

```
gcacttgtag aggaagctaa agttcgatat gaaaagacat cctttaaagt tattgatctg  420
gatgattatg ctgctgatga cgatgagtat gaggagaagc ttaagaaaga atctttggcg  480
tttttctttt tggcaacgta tggagatggt gaaccaacag ataatgcagc caatttttac  540
aaatggttta cagagggaga tgacaaaggc gaatggctga agaaacttca atatggcgtg  600
tttggcctcg gtaacagaca atatgagcat ttcaataaga ttgcaatagt ggttgatgac  660
aaactcacag aaatgggcgc aaaacgcctt gttcctgtgg gtcttggaga tgacgatcaa  720
tgtatagaag atgactttac agcatggaaa gagttagtgt ggcccgagtt ggatcaattg  780
ttgcgtgatg aggatgacac gagtgttacg actccttaca ctgctgcggt tttggaatac  840
cgagttgtat atcatgataa acctgcagac tcgtatgcag aagatcaaac tcatacaaat  900
ggtcatgttg ttcatgatgc tcaacatcca tctagatcca atgtggcatt taaaaaggaa  960
ttgcacacct ctcaatctga ccggtcttgc actcatttgg aatttgatat ctctcacacc  1020
gggctatcat acgagacggg ggatcatgtt ggtgtctaca gtgagaatct aagtgaagtt  1080
gtagatgaag ctttaaaatt actcggtttg tcacccgaca cttatttctc agtccatgct  1140
gacaaggaag acggaacacc tattggcggc gcctccttgc cgccaccttt ccctccatgc  1200
actttaagag atgcattaac gcgctacgca gatgttttga gttctcctaa aaaggttgct  1260
ttgcttgctc tggctgctca tgcttctgat cctagcgaag ccgatcgatt aaaatttcta  1320
gcatctccgg ctggcaagga tgaatatgct caatggatag ttgcaaacca aagaagtctt  1380
cttgaagtta tgcagtcatt tccgtcagct aaaccgccac ttggtgtttt cttcgcagct  1440
gtcgccccac gtttacaacc tcgatattac tcgatttctt cttctccaaa gatgtcacca  1500
aacagaattc atgtgacttg tgcattagtt tatgagacaa cacctgcagg acgtattcac  1560
agaggattgt gttcaacatg gatgaagaat gctgtgcctt tgaccgaaag tccagattgt  1620
agtcaggcgt cgatttttgt tagaacgtct aacttccgac ttccggttga cccgaaagtc  1680
ccggtcatca tgatcggtcc cgggactggg ttagcccctt tcagaggttt tcttcaagaa  1740
cggttagctt tgaaggaatc tggaaccgaa ctcgggtcat ctattttctt tttcggatgc  1800
agaaaccgca aagtggattt tatatacgaa gacgaactaa acaactttgt ggagaccggt  1860
gctttatcgg agcttattgt tgcattctcc cgtgaaggaa ccgcaaagga gtatgtgcaa  1920
cataaaatga gccagaaggc ttcagatatc tggaagttgc tttcagaggg agcatattta  1980
tatgtatgtg gtgatgctaa aggcatggct aaagatgtac acagaaccct tcacacaatt  2040
gtacaagaac agggatctct agattcttcc aaggcagaat tgtatgtaaa gaacctacaa  2100
atgtcgggaa gatatcttcg tgatgtttgg taa                               2133
```

```
SEQ ID NO: 74          moltype = DNA  length = 2079
FEATURE                Location/Qualifiers
source                 1..2079
                       mol_type = other DNA
                       organism = Arabidopsis thaliana
SEQUENCE: 74
atgacttctg ctttgtatgc ttccgatttg tttaagcagc tcaagtcaat tatggggaca  60
gattcgttat ccgacgatgt tgtacttgtg attgcaacga cgtctttggc actagtagct  120
ggatttgtgg tgttgttatg gaagaaaacg acggcggatc ggagcgggga gctgaagcct  180
ttgatgatcc ctaagtctct tatggctaag gacgaggatg atgatttgga tttgggatcc  240
gggaagacta gagtctctat cttcttcggt acgcagactg gaacagctga gggatttgct  300
aaggcattat ccgaagaaat caaagcgaga tatgaaaaag cagcagtcaa agtcattgac  360
ttggatgact atgctgccga tgatgaccag tatgaagaga aattgaagaa ggaaactttg  420
gcattttttct gtgttgctac ttatggagat ggagagccta ctgacaatgc tgccagattt  480
tacaaatggt ttacggagga aaatgaacgg gatataaagc ttcaacaact agcatatggt  540
gtgtttgctc ttggtaatcg ccaatatgaa cattttaata agatcgggat agttcttgat  600
gaagagttat gtaagaaagg tgcaaagcgt cttattgaag tcggtctagg agatgatgat  660
cagagcattg aggatgattt taatgcctgg aaagaatcac tatggtctga gctagacaag  720
ctcctcaaag acgaggatga taaaagtgtg gcaactcctt atacagctgt tattcctgaa  780
taccgggtgg tgactcatga tcctcggttt acaactcaaa aatcaatgga atcaaatgtg  840
gccaatggaa atactactat tgacattcat catccctgca gagttgatgt tgctgtgcag  900
aaggagcttc acacacatga atctgatcgg tcttgcattc atctcgagtt cgacatatcc  960
aggacgggta ttacatatga aacaggtgac catgtaggtg tatatgctga aaatcatgtt  1020
gaaatagttg aagaagctgg aaaattgctt ggccactctt tagatttagt attttccata  1080
catgctgaca aggaagatgg ctccccattg gaaagcgcag tgccgcctcc tttccctggt  1140
ccatgcacac ttgggactgg tttggcaaga tacgcagacc ttttgaaccc tcctcgaaag  1200
tctgcgttag ttgccttggc ggcctatgcc actgaaccaa gtgaagccga gaaacttaag  1260
cacctgacat cacctgatgg aaaggatgag tactcacaat ggattgttgc aagtcagaga  1320
agtcttttag aggtgatggc tgcttttcca tctgcaaaac ccccactagg tgtatttttt  1380
gctgcaatag ctcctcgtct acaacctcgt tactactcca tctcatcctc gccaagattg  1440
gcgccaagta gagttcatgt tacatccgca ctagtatatg gtccaactcc tactggtaga  1500
atccacaagg gtgtgtgttc tacgtggatg aagaatgcag ttcctgcgga gaaaagtcat  1560
gaatgtagtg gagccccaat ctttattcga gcatctaatt tcaagttacc atccaaccct  1620
tcaactccaa tcgttatggt gggacctggg actgggctgg caccttttag aggttttctg  1680
caggaaagga tggcactaaa agaagatgga gaagaactag gttcatcttt gctcttcttt  1740
gggtgtagaa atcgacagat ggactttata tacgaggatg agctcaataa ttttgttgat  1800
caaggcgtaa tatctgagct catcatggca ttctcccgtg aaggagctca gaaggagtat  1860
gttcaacata agatgatgga gaaggcagca caagtttggg atctaataaa ggaagaagga  1920
tatctctatg tatgcggtga tgctaagggc atggcgaggg acgtccaccg aactctacac  1980
accattgttc aggagcagga aggtgtgagt tcgtcagagg cagaggctat agttaagaaa  2040
cttcaaaccg aaggaagata cctcagagat gtctggtga                          2079
```

```
SEQ ID NO: 75          moltype = DNA  length = 2142
FEATURE                Location/Qualifiers
source                 1..2142
                       mol_type = other DNA
                       organism = Giberella fujikuroi
SEQUENCE: 75
```

-continued

```
atggctgaac tcgacactct ggacatcgtc gtcctcggcg ttatcttcct cggaacggtt  60
gcatacttta caaagggcaa gctatggggt gttaccaagg atccctacgc gaatggcttc  120
gctgccggcg gcgcttctaa gccgggtcgc acgaggaaca tcgtcgaggc aatggaagaa  180
tccggcaaga actgtgttgt cttctatggt tctcagaccg gtactgctga agattatgct  240
tctcgcctcg ccaaggaggg taagagtcga ttcggactaa acaccatgat tgccgatctt  300
gaggactacg atttcgacaa cctggatacc gttcccagtg acaacattgt catgttcgtt  360
ctcgcaactt atggtgaagg tgagcctacc gataacgcgg tcgacttcta tgaattcatt  420
accggcgagg atgccagctt caatgagggc aatgatcctc cgctgggcaa cctcaactac  480
gttgctttcg gtctcggaaa caacacgtac gagcactaca actctatggt ccgcaatgtt  540
aacaaggctc tcgagaagct tggcgctcac cgcatcggtg aagctggtga gggtgatgat  600
ggtgctggta ccatggaaga ggacttcttg gcctggaagg atcccatgtg ggaagccctc  660
gctaagaaaa tgggactgga agagcgtgaa gcagtctacg agcctatttt tgccattaac  720
gaacgcgacg acctgactcc tgaagccaat gaagtgtatc tcggtgagcc caacaagctg  780
catctcgaag gcaccgccaa gggaccattc aactctcaca acccctacat tgcccctatc  840
gctgaatctt atgagttgtt ctccgccaag gacagaaact gcctccacat ggaaattgac  900
atcagcggtt ctaacctcaa gtacgaaact ggagaccata ttgctatctg gcctaccaac  960
cctggtgagg aggtcaacaa attcctggat attctcgacc tctctggaaa gcagcacagc  1020
gttgtcactg tcaaggctct cgagcctacc gccaaggttc ctttccccaa ccctacaacc  1080
tacgatgcca ttctgcgata ccacctcgag atctgcgctc ctgtttcacg tcaattcgtc  1140
tctactctcg ccgcatttgc tcccaacgat gatatcaagg ctgagatgaa ccgccttggc  1200
agcgataagg attatttcca cgagaagact ggcccgcatt actacaacat tgcccgtttc  1260
cttgccagcg tcagcaaggg cgagaagtgg accaaaatcc cgttctctgc cttcatcgag  1320
ggtctcacca agctccagcc ccgttactac tccatttctt cctcgtctct ggttcagccc  1380
aagaaaatct cgatcactgc cgtcgttgaa tcccagcaga ttcctggccg ggatgatcct  1440
ttccgtggtg ttgctacaaa ctatcttttt gccctaaagc aaaagcagaa cggtgacccc  1500
aaccctgcac cttttggtca gagctacgag cttacaggcc cccgcaataa gtatgatggc  1560
atccacgttc ctgtccatgt tcgtcactcc aacttcaagc tcccctcgga ccccggtaag  1620
cccatcatca tgattggtcc tggtactggt gtcgctccct tccgcggttt cgtgcaggag  1680
cgtgctaagc aagcccgtga tggtgttgag gttggaaaga cactcttgtt ctttggttgc  1740
cgaaagtcaa ccgaggattt catgtaccaa aaggagtggc aggaatacaa ggaggctctt  1800
ggcgataagt ttgaaatgat caccgccttt tctcgagagg gctccaagaa ggtttatgtt  1860
cagcaccgac ttaaggagcg atctaaggag gtcagcgatc tgctctccca gaaggcttat  1920
ttctatgtct gcggtgatgc agcccacatg gcccgcgagg tcaataccgt cttggcacaa  1980
atcattgccg agggacgtgg ggtgtctgag gccaagggcg aggagatcgt gaagaacatg  2040
agatcagcga accaatacca ggtatgtagt gactttgtta ctcttcactg caaagaaacc  2100
acatatgcta actcagaatt acaggaggat gtttggtcat ag                    2142

SEQ ID NO: 76          moltype = AA  length = 459
FEATURE                Location/Qualifiers
source                 1..459
                       mol_type = protein
                       organism = Ipomoea purpurea
SEQUENCE: 76
MGSQATTYHM AMYPWFGVGH LTGFFRLANK LAGKGHRISF LIPKNTQSKL ESFNLHPHLI  60
SFVPIVVPSI PGLPPGAETT SDVPFPSTHL LMEAMDKTQN DIEIILKDLK VDVVFYDFTH  120
WLPSLARKIG IKSVFYSTIS PLMHGYALSP ERRVVGKQLT EADMMKAPAS FPDPSIKLHA  180
HEARGFTART VMKFGGDITF FDRIFTAVSE SDGLAYSTCR EIEGQFCDYI ETQFQKPVLL  240
AGPALPVPSK STMEQKWSDW LGKFKEGSVI YCAFGSECTL RKDKFQELLW GLELTGMPFF  300
AALKPPFETE SVEAAIPEEL KEKIQGRGIV HGEWVQQQLF LQHPSVGCFV SHCGWASLSE  360
ALVNDCQIVL LPQVGDQIIN ARIMSVSLKV GVEVEKGEED GVFSRESVCK AVKAVMDEKS  420
EIGREVRGNH DKLRGFLMNA DLDSKYMDSF NQKLQDLLG                        459

SEQ ID NO: 77          moltype = DNA  length = 1380
FEATURE                Location/Qualifiers
source                 1..1380
                       mol_type = other DNA
                       organism = Ipomoea purpurea
SEQUENCE: 77
atgggttctc aagctacaac ttaccatatg gccatgtatc catggtttgg ggttggacat  60
ttgactggtt tcttccgttt ggcaaacaaa ttagctggca aaggacatag aatctcattt  120
ctaattccta aaaacactca atctaagtta gaatctttca accttcatcc acacttaatc  180
tcttttgtgc ctatcgttgt cccaagtata ccaggcctgc cacctggtgc agagactaca  240
tcagatgttc ctttcccaag tacacatttg ctaatggaag caatggacaa gactcaaaac  300
gatatagaga ttatcctgaa ggatcttaaa gtagatgttg ttttctatga ttttactcac  360
tggttgcctt ctctggccag aaagattggc attaagagtg tcttttactc caccatttct  420
cctttaatgc atggatatgc tttatcacca gaaagacgtg tagttggtaa gcaattgaca  480
gaggcagata tgatgaaggc cccagcttct ttcccagacc catccattaa gctacatgca  540
catgaagcta ggggttttac agccagaacc gttatgaaat tcggtggtga catcaccttt  600
ttcgatagaa tattcacagc agtttccgaa agtgatggcc tggcctactc tacttgtaga  660
gagatcgagg gacaattctg tgattacatt gaaacacaat tccagaagcc agtcttgtta  720
gccggtccag ctttgccagt cccatccaaa tccactatgg aacaaaagtg gtcagattgg  780
ttggggaaat tcaaggaagg ctccgtcatc tactgtgctt tcgggtctga atgtacattg  840
agaaaggaca aatttcagga acttttatgg ggtttggaat tgacaggaat gcctttcttc  900
gctgctctga agccaccttt tgagactgag tctgttgagg ctgctatccc tgaggaacta  960
aaggaaaaga ttcagggaag aggtatagta catggagaat gggtacaaca acaattgttt  1020
cttcaacacc catctgtcgg gtgcttcgtt tctcactgcg gctgggcaag tttatctgaa  1080
gcccttgtta atgattgtca aatcgtgtta cttccacaag ttggcgatca gattatcaac  1140
gccagaataa tgtcagtatc acttaaagtg ggcgtggaag ttgaaaaggg tgaggaggac  1200
ggtgtctttt caagagaatc tgtgtgcaag gctgttaaag cagtaatgga tgaaaaatct  1260
```

```
gaaatcggta gagaagtcag aggtaatcat gataaactga ggggtttctt gatgaatgca  1320
gacttagatt caaagtacat ggattcattc aatcaaaagc tacaagattt gctaggttaa  1380

SEQ ID NO: 78          moltype = AA  length = 438
FEATURE                Location/Qualifiers
source                 1..438
                       mol_type = protein
                       organism = Bellis perennis
SEQUENCE: 78
MDSKIDSKTF RVVMLPWLAY SHISSFLVFA KRLTNHNFHI YICSSQTNMQ YLKNNLTSQY  60
SKSIQLIELN LPSSSELPLQ YHTTHGLPPH LTKTLSDDYQ KSGPDFETIL IKLNPHLVIY  120
DFNQLWAPEV ASTLHIPSIQ LLSGCVALYA LDAHLYTKPL DENLAKFPFP EIYPKNRDIP  180
KGGSKYIERF VDCMRRSCEI ILVRSTMELE GKYIDYLSKT LGKKVLPVGP LVQEASLLQD  240
DHIWIMKWLD KKEESSVVFV CFGSEYILSD NEIEDIAYGL ELSQVSFVWA IRAKTSALNG  300
FIDRVGDKGL VIDKWVPQAN ILSHSSTGGF ISHCGWSSTM ESIRYGVPII AMPMQFDQPY  360
NARLMETVGA GIEVGRDGEG RLKREEIAAV VRKVVVEDSG ESIREKAKEL GEIMKKNMEA  420
EVDGIVIENL VKLCEMNN                                                438

SEQ ID NO: 79          moltype = DNA  length = 1317
FEATURE                Location/Qualifiers
source                 1..1317
                       mol_type = other DNA
                       organism = Bellis perennis
SEQUENCE: 79
atggattcta aaatcgattc aaagacattc agagtcgtta tgttgccttg gcttgcatac  60
tcacacattt catcattcct agtgtttgcc aagagactaa caaatcataa cttccacatc  120
tacatttgtt cctctcaaac aaatatgcaa tacctgaaaa acaacttgac gtctcagtat  180
tcaaaatcta tacaactgat tgagttgaat cttccatcta gttccgaatt gcctctgcag  240
tatcatacta ctcacggact accaccacac cttacgaaaa cattgtctga tgattatcaa  300
aagtccggac ctgactttga aaccattttg atcaaattga acccacatct ggtaatctac  360
gactttaatc aactttgggc tccagaggtt gctagtacac ttcatattcc atccatacag  420
ttactgtctg gttgcgtcgc cttatatgcc ttagacgccc atctgtacac aaagccacta  480
gacgaaaact tggctaagtt tcctttccca gaaatctatc ctaaaaacag agatattcct  540
aagggaggta gtaaatacat cgaaaggttc gtagactgta tgagaagatc ttgtgaaatc  600
atattagtca gaagtaccat ggaacttgaa ggaaaataca ttgattactt gtctaagaca  660
ttagggaaaa aggtgttgcc agtagggcct ctggtgcaag aggcttcttt gttgcaagat  720
gatcatatat ggattatgaa gtggttagac aaaaaggagg agtcatccgt cgtgtttgtt  780
tgttttggtt ctgagtacat cttatcagac aacgaaatag aagatattgc ttatggccta  840
gagttgtccc aagtaagttt cgtttgggca ataagagcta agacttctgc cttaaatggc  900
ttcattgata gagtgggtga taaaggctta gtcatcgata aatgggttcc acaggctaac  960
atcttatctc actcttctac tggtggattc attagtcatt gcggttggtc atcaacaatg  1020
gaatctatta gatatggggt tcctattatc gccatgccaa tgcaattcga tcaaccttac  1080
aatgctaggt tgatggaaac tgttggtgca ggtatcgaag ttggcagaga tggcgaaggt  1140
agattgaaaa gagaagagat tgctgccgtg gttagaaagg tcgttgttga agattctggg  1200
gaatccataa gggagaaggc aaaggaattg ggagaaatca tgaaaaaaaa catggaggcc  1260
gaagtagatg gtatagtgat tgaaaatcta gttaagctat gtgagatgaa caattaa     1317

SEQ ID NO: 80          moltype = DNA  length = 2490
FEATURE                Location/Qualifiers
source                 1..2490
                       mol_type = other DNA
                       organism = Zea mays
SEQUENCE: 80
atggttttgt cttcttcttg tactacagta ccacacttat cttcattagc tgtcgtgcaa  60
cttggtcctt ggagcagtag gattaaaaag aaaaccgata ctgttgcagt accagccgct  120
gcaggaaggt ggagaagggc cttggctaga gcacagcaca catcagaatc cgcagctgtc  180
gcaaagggca gcagtttgac ccctatagtg agaactgacg ctgagtcaag gagaacaaga  240
tggccaaccg atgacgatga cgccgaacct ttagtggatg agatcagggc aatgcttact  300
tccatgtctg atggtgacat ttccgtgagc gcatacgata cagcctgggt cggattggtt  360
ccaagattag acggcggtga aggtcctcaa tttccagcag ctgtgagatg gataagaaat  420
aaccagttgc ctgacggaag ttggggcgat gccgcattat tctctgccta tgacaggctt  480
atcaataccc ttgcctgcgt tgtaactttg acaaggtggt ccctagaacc agagatgaga  540
ggtagaggac tatctttttt gggtaggaac atgtggaaat tagcaactga agatgaagag  600
tcaatgccta ttggcttcga attagcattt ccatctttga tagagcttgc taagagccta  660
ggtgtccatg acttccctta tgatcaccag gccctacaag gaatctactc ttcaagagag  720
atcaaaatga agaggattcc aaaagaagtg atgcataccg ttccaacatc aatattgcac  780
agtttggagg gtatgcctgg cctagattgg gctaaactac ttaaactaca gagcagcgac  840
ggaagttttt tgttctcacc agctgccact gcatatgctt taatgaatac cggagatgac  900
aggtgtttta gctacatcga tagaacagta aagaaattca acggcggcgt ccctaatgtt  960
tatccagtgg atctatttga acatatttgg gccgttgata gacttgaaag attaggaatc  1020
tccaggtact tccaaaagga gatcgaacaa tgcatggatt atgtaaacag gcattggact  1080
gaggacggta tttgttgggc aaggaactct gatgtcaaag aggtggacga cacagctatg  1140
gcctttagac ttcttaggtt gcacggctac agcgtcagtc ctgatgtgtt taaaaacttc  1200
gaaaaggacg gtgaattttt cgcatttgtc ggacagtcta atcaagctgt taccggtatg  1260
tacaacttaa acagagcaag ccagatatcc ttcccaggcg aggatgtgct tcatagagct  1320
ggtgccttct catatgagtt cttgaggaga aaagaagcag agggagcttt gagggacaag  1380
tggatcattt ctaaagatct acctggtgaa gttgtgtata ctttggattt tccatggtac  1440
ggcaacttac ctagagtcga ggccagagac tacctagagc aatacggagg tggtgatgac  1500
gtttggattg gcaagacatt gtataggatg ccacttgtaa acaatgatgt atatttggaa  1560
```

-continued

```
ttggcaagaa tggatttcaa ccactgccag gctttgcatc agttagagtg gcaaggacta  1620
aaaagatggt atactgaaaa taggttgatg gactttggtg tcgcccaaga agatgccctt  1680
agagcttatt ttcttgcagc cgcatctgtt tacgagcctt gtagagctgc cgagaggctt  1740
gcatgggcta gagccgcaat actagctaac gccgtgagca cccacttaag aaatagccca  1800
tcattcagag aaaggttaga gcattctctt aggtgtagac ctagtgaaga gacagatggc  1860
tcctggttta actcctcaag tggctctgat gcagttttag taaaggctgt cttaagactt  1920
actgattcat tagccaggga agcacagcca atccatggag gtgacccaga agatattata  1980
cacaagttgt taagatctgc ttgggccgag tgggttaggg aaaaggcaga cgctgccgat  2040
agcgtgtgca atggtagttc tgcagtagaa caagagggat caagaatggt ccatgataaa  2100
cagacctgtc tattattggc tagaatgatc gaaatttctg ccggtagggc agctggtgaa  2160
gcagccagtg aggacggcga tagaagaata attcaattaa caggctccat ctgcgacagt  2220
cttaagcaaa aaatgctagt ttcacaggac cctgaaaaaa atgaagagat gatgtctcac  2280
gtggatgacg aattgaagtt gaggattaga gagttcgttc aatatttgct tagactaggt  2340
gaaaaaaaga ctggatctag cgaaaccagg caaacatttt taagtatagt gaaatcatgt  2400
tactatgctg ctcattgccc acctcatgtc gttgatagac acattagtag agtgattttc  2460
gagccagtaa gtgccgcaaa gtaaccgcgg                                  2490
```

```
SEQ ID NO: 81          moltype = AA  length = 827
FEATURE                Location/Qualifiers
source                 1..827
                       mol_type = protein
                       organism = Zea mays
SEQUENCE: 81
MVLSSSCTTV PHLSSLAVVQ LGPWSSRIKK KTDTVAVPAA AGRWRRALAR AQHTSESAAV  60
AKGSSLTPIV RTDAESRRTR WPTDDDDAEP LVDEIRAMLT SMSDGDISVS AYDTAWVGLV  120
PRLDGGEGPQ FPAAVRWIRN NQLPDGSWGD AALFSAYDRL INTLACVVTL TRWSLEPEMR  180
GRGLSFLGRN MWKLATEDEE SMPIGFELAF PSLIELAKSL GVHDFPYDHQ ALQGIYSSRE  240
IKMKRIPKEV MHTVPTSILH SLEGMPGLDW AKLLKLQSSD GSFLFSPAAT AYALMNTGDD  300
RCFSYIDRTV KKFNGGVPNV YPVDLFEHIW AVDRLERLGI SRYFQKEIEQ CMDYVNRHWT  360
EDGICWARNS DVKEVDDTAM AFRLLRLHGY SVSPDVFKNF EKDGEFFAFV GQSNQAVTGM  420
YNLNRASQIS FPGEDVLHRA GAFSYEFLRR KEAEGALRDK WIISKDLPGE VVYTLDFPWY  480
GNLPRVEARD YLEQYGGGDD VWIGKTLYRM PLVNNDVYLE LARMDFNHCQ ALHQLEWQGL  540
KRWYTENRLM DFGVAQEDAL RAYFLAAASV YEPCRAAERL AWARAAILAN AVSTHLRNSP  600
SFRERLEHSL RCRPSEETDG SWFNSSSGSD AVLVKAVLRL TDSLAREAQP IHGGDPEDII  660
HKLLRSAWAE WVREKADAAD SVCNGSSAVE QEGSRMVHDK QTCLLLARMI EISAGRAAGE  720
AASEDGDRRI IQLTGSICDS LKQKMLVSQD PEKNEEMMSH VDDELKLRIR EFVQYLLRLG  780
EKKTGSSETR QTFLSIVKSC YYAAHCPPHV VDRHISRVIF EPVSAAK               827
```

```
SEQ ID NO: 82          moltype = DNA  length = 1461
FEATURE                Location/Qualifiers
misc_feature           1..1461
                       note = Description of Artificial Sequence: Synthetic
                        polynucleotide
source                 1..1461
                       mol_type = other DNA
                       organism = synthetic construct
SEQUENCE: 82
actagtaaaa tggatgcaat ggcaactact gagaaaaagc ctcatgtgat cttcattcca  60
tttcctgcac aatctcacat aaaggcaatg ctaaagttag cacaactatt acaccataag  120
ggattacaga taactttcgt gaataccgac ttcatccata atcaatttct ggaatctagt  180
ggccctcatt gtttggacgg agccccaggg tttagattcg aaacaattcc tgacggtgtt  240
tcacattccc cagaggcctc catcccaata agagagagtt tactgaggtc aatagaaacc  300
aactttttgg atcgtttcat tgacttggtc acaaaacttc cagacccacc aacttgcata  360
atctctgatg gctttctgtc agtgtttact atcgacgctg ccaaaaagtt gggtatccca  420
gttatgatgt actggactct tgctgcatgc ggtttcatgg gtttctatca catccattct  480
cttatcgaaa agggttttgc tccactgaaa gatgcatcat acttaaccaa cggctacctg  540
gatactgtta ttgactgggt accaggtatg gaaggtataa gacttaaaga ttttcctttg  600
gattggtcta cagaccttaa tgataaagta ttgatgttta ctacagaagc tccacaaaga  660
tctcataagg tttcacatca tatctttcac acctttgatg aattggaacc atcaatcatc  720
aaaaccttgt ctctaagata caatcatatc tacactattg gtccattaca attacttcta  780
gatcaaattc ctgaagagaa aaagcaaact ggtattacat ccttacacgg ctactcttta  840
gtgaaagagg aaccagaatg ttttcaatgg ctacaaagta aagagcctaa ttctgtggtc  900
tacgtcaact tcggaagtac aacagtcatg tccttggaag atatgactga atttggttgg  960
ggccttgcta attcaaatca ttactttcta tggattatca ggtccaattt ggtaataggg  1020
gaaaacgccg tattacctcc agaattggag gaacacatca aaaagagagg tttcattgct  1080
tcctggtgtt ctcaggaaaa ggtattgaaa catccttctg ttggtggttt ccttactcat  1140
tgcggttggg gctctacaat cgaatcacta agtgcaggag ttccaatgat ttgttggcca  1200
tattcatggg accaacttac aaattgtagg tatatctgta aagagtggga agttggatta  1260
gaaatgggaa caaaggttaa acgtgatgaa gtgaaaagat tggttcagga gttgatgggg  1320
gaaggtggcc acaagatgag aaacaaggcc aaagattgga aggaaaaagc cagaattgct  1380
attgctccta acgggtcatc ctctctaaac attgataaga tggtcaaaga gattacagtc  1440
ttagccagaa actaagtcga c                                           1461
```

```
SEQ ID NO: 83          moltype = DNA  length = 1398
FEATURE                Location/Qualifiers
misc_feature           1..1398
                       note = Description of Artificial Sequence: Synthetic
                        polynucleotide
source                 1..1398
```

```
                         mol_type = other DNA
                         organism = synthetic construct
SEQUENCE: 83
actagtaaaa tggcagagca acaaaagatc aaaaagtcac ctcacgtctt acttattcca  60
tttcctctgc aaggacatat caacccattc atacaatttg ggaaaagatt gattagtaag  120
ggtgtaaaga caacactggt aaccactatc cacactttga attctactct gaaccactca  180
aatactacta ctacaagtat agaaattcaa gctatatcag acggatgcga tgagggtggc  240
tttatgtctg ccggtgaatc ttacttggaa acattcaagc aagtgggatc caagtctctg  300
gccgatctaa tcaaaaagtt acagagtgaa ggcaccacaa ttgacgccat aatctacgat  360
tctatgacag agtgggtttt agacgttgct atcgaatttg gtattgatgg aggttccttt  420
ttcacacaag catgtgttgt gaattctcta tactaccatg tgcataaagg gttaatctct  480
ttaccattgg gtgaaactgt ttcagttcca ggttttccag tgttacaacg ttgggaaacc  540
ccattgatct tacaaaatca tgaacaaata caatcacctt ggtcccagat gttgtttggt  600
caattcgcta acatcgatca agcaagatgg gtctttacta attcattcta taagttagag  660
gaagaggtaa ttgaatggac taggaagatc tggaatttga aagtcattgg tccaacattg  720
ccatcaatgt atttggacaa aagacttgat gatgataaag ataatggttt caatttgtac  780
aaggctaatc atcacgaatg tatgaattgg ctggatgaca aaccaaagga atcagttgta  840
tatgttgctt tcggctctct tgttaaacat ggtccagaac aagttgagga gattacaaga  900
gcacttatag actctgacgt aaactttttg tgggtcatta agcacaaaga ggaggggaaa  960
ctgccagaaa acctttctga agtgataaag accggaaaag gtctaatcgt tgcttggtgt  1020
aaacaattgg atgttttagc tcatgaatct gtaggctgtt ttgtaacaca ttgcggattc  1080
aactctacac tagaagccat ttccttaggc gtacctgtcg ttgcaatgcc tcagttctcc  1140
gatcagacaa ccaacgctaa acttttggac gaaatactag ggtgggtgt cagagttaaa  1200
gcagacgaga atggtatcgt cagaagaggg aacctagctt catgtatcaa aatgatcatg  1260
gaagaggaaa gaggagttat cataaggaaa aacgcagtta agtggaagga tcttgcaaag  1320
gttgccgtcc atgaaggcgg ctcttcagat aatgatattg ttgaatttgt gtccgaacta  1380
atcaaagcct aagtcgac                                                1398

SEQ ID NO: 84            moltype = DNA  length = 1437
FEATURE                  Location/Qualifiers
misc_feature             1..1437
                         note = Description of Artificial Sequence: Synthetic
                          polynucleotide
source                   1..1437
                         mol_type = other DNA
                         organism = synthetic construct
SEQUENCE: 84
actagtaaaa tggctacatc tgattctatt gttgatgaca ggaagcagtt gcatgtggct  60
actttccctt ggcttgcttt cggtcatata ctgccttacc tacaactatc aaaactgata  120
gctgaaaaag gacataaagt gtcattcctt tcaacaacta gaaacattca aagattatct  180
tcccacatat caccattgat taacgtcgtt caattgacac ttccaagagt acaggaatta  240
ccagaagatg ctgaagctac aacagatgtg catcctgaag atatccctta cttgaaaaag  300
gcatccgatg gattacagcc tgaggtcact agattccttg agcaacacag tccagattgg  360
atcatatacg actacactca ctattggttg ccttcaattg cagcatcact aggcatttct  420
agggcacatt tcagtgtaac cacaccttgg gccattgctt acatgggtcc atccgctgat  480
gctatgatta acggcagtga tggtagaact accgttgaag atttgacaac ccccaccaaag  540
tggtttccat ttccaactaa agtctgttgg agaaaacacg acttagcaag actggttcca  600
tacaaggcac caggaatctc agacggctat agaatgggtt tagtccttaa agggtctgac  660
tgcctattgt ctaagtgtta ccatgagttt gggacacaat ggctaccact tttggaaaca  720
ttacaccaag ttcctgtcgt accagttggt ctattacctc cagaaatccc tggtgatgag  780
aaggacgaga cttgggtttc aatcaaaaag tggttagacg ggaagcaaaa aggctcagtg  840
gtatatgtgg cactgggttc cgaagtttta gtatctcaaa cagaagttgt ggaacttgcc  900
ttaggtttgg aactatctgg attgccattt gtctgggcct acagaaaacc aaaaggccct  960
gcaaagtccg attcagttga attgccagac ggctttgtcg agagaactag agatagaggg  1020
ttggtatgga cttcatgggc tccacaattg agaatcctga gtcacgaatc tgtgtgcggt  1080
ttcctaacac attgtggttc tggttctata gttgaaggac tgatgtttgg tcatccactt  1140
atcatgttgc caatctttgg tgaccagcct ttgaatgcac gtctgttaga agataaacaa  1200
gttggaattg aaatcccacg taatgaggaa gatggatgtt taaccaagga gtctgtggcc  1260
agatcattac gttccgttgt cgttgaaaag gaaggcgaaa tctacaaggc caatgcccgt  1320
gaactttcaa agatctacaa tgacacaaaa gtagagaagg aatatgtttc tcaatttgta  1380
gattacctag agaaaaacgc tagagccgta gctattgatc atgaatccta agtcgac     1437

SEQ ID NO: 85            moltype = DNA  length = 1392
FEATURE                  Location/Qualifiers
misc_feature             1..1392
                         note = Description of Artificial Sequence: Synthetic
                          polynucleotide
source                   1..1392
                         mol_type = other DNA
                         organism = synthetic construct
SEQUENCE: 85
actagtaaaa tggaaaacaa gaccgaaaca acagttagac gtaggcgtag aatcattctg  60
tttccagtac cttttcaagg gcacatcaat ccaatactac aactagccaa cgttttgtac  120
tctaaaggtt tttctattac aatctttcac accaatttca acaaaccaaa aacatccaat  180
tacccacatt tcacattcag attcatactt gataatgatc cacaagatga acgtatttca  240
aacttaccta cccacggtcc tttagctgga atgagaattc caatcatcaa tgaacatggt  300
gccgatgagc ttagaagaga attagagtta cttatgttgg catccgaaga ggacgaggaa  360
gtctcttgtc tgattactga cgctctatgg tactttgccc aatctgtggc tgatagtttg  420
aatttgagga gattggtact aatgacatcc agtctgttta actttcacgc tcatgttagt  480
```

-continued

```
ttaccacaat ttgacgaatt gggatacttg gaccctgatg acaagactag gttagaggaa  540
caggcctctg gttttcctat gttgaaagtc aaagatatca agtctgccta ttctaattgg  600
caaatcttga aagagatctt aggaaagatg atcaaacaga caaaggcttc atctggagtg  660
atttggaaca gtttcaaaga gttagaagag tctgaattgg agactgtaat cagagaaatt  720
ccagcacctt cattcctgat accattacca aaacatttga ctgcttcctc ttcctctttg  780
ttggatcatg acagaacagt ttttcaatgg ttggaccaac aaccacctag ttctgttttg  840
tacgtgtcat ttggtagtac ttctgaagtc gatgaaaagg acttccttga aatcgcaaga  900
ggcttagtcg atagtaagca gtcattcctt tgggtcgtgc gtccaggttt cgtgaaaggc  960
tcaacatggg tcgaaccact tccagatggt tttctaggcg aaagaggtag aatagtcaaa  1020
tgggttcctc aacaggaagt tttagctcat ggcgctattg gggcattctg gactcattcc  1080
ggatggaatt caactttaga atcagtatgc gaaggggtac ctatgatctt ttcagatttt  1140
ggtcttgatc aaccactgaa cgcaagatac atgtctgatg ttttgaaagt gggtgtatat  1200
ctagaaaatg gctgggaaag gggtgaaata gctaatgcaa taagacgtgt tatggttgat  1260
gaagaggggg agtatatcag acaaaacgca agagtgctga agcaaaaggc cgacgtttct  1320
ctaatgaagg gaggctcttc atacgaatcc ttagaatctc ttgtttccta catttcatca  1380
ctgtaagtcg ac                                                      1392
```

```
SEQ ID NO: 86          moltype = AA  length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 86
TSFAEYWNLL SP                                                      12
```

```
SEQ ID NO: 87          moltype = DNA  length = 1602
FEATURE                Location/Qualifiers
misc_feature           1..1602
                       note = Description of Artificial Sequence: Synthetic
                        polynucleotide
source                 1..1602
                       mol_type = other DNA
                       organism = synthetic construct
SEQUENCE: 87
atgaccagct ttgccgagta ttggaatctg ttaagtccca cttcttttgc agaatattgg  60
aaccttctat caccgacgag tttcgcggag tactggaatt tgttttctcc aacatcgttc  120
gctgaatact ggaacttact cagccctgct agtaaaatgg atgcaatggc aactactgag  180
aaaaagcctc atgtgatctt cattccattt cctgcacaat ctcacataaa ggcaatgcta  240
aagttagcac aactattaca ccataaggga ttacagataa ctttcgtgaa taccgacttc  300
atccataatc aatttctgga atctagtggc cctcattgtt tggacggagc cccagggttt  360
agattcgaaa caattcctga cggtgtttca cattccccag aggcctccat cccaataaga  420
gagagtttac tgaggtcaat agaaaccaac tttttggatc gtttcattga cttggtcaca  480
aaacttccag acccaccaac ttgcataatc tctgatggct ttctgtcagt gtttactatc  540
gacgctgcca aaaagttggg tatcccagtt atgatgtact ggactcttgc tgcatgcggt  600
ttcatgggtt tctatcacat ccattctctt atcgaaaagg gttttgctcc actgaaagat  660
gcatcatact taaccaacgg ctacctggat actgttattg actgggtacc aggtatggaa  720
ggtataagac ttaaagattt tcctttggat tggtctacag accttaatga taaagtattg  780
atgtttacta cagaagctcc acaaagatct cataaggttt cacatcatat ctttcacacc  840
tttgatgaat tggaaccatc aatcatcaaa accttgtctc taagatacaa tcatatctac  900
actattggtc cattacaatt acttctagat caaattcctg aagagaaaaa gcaaactggt  960
attacatcct tacacggcta ctctttagtg aaagaggaac cagaatgttt tcaatggcta  1020
caaagtaaag agcctaattc tgtggtctac gtcaacttcg gaagtacaac agtcatgtcc  1080
ttggaagata tgactgaatt tggttggggc cttgctaatt caaatcatta ctttctatgg  1140
attatcaggt ccaatttggt aataggggaa aacgccgtat tacctccaga attggaggaa  1200
cacatcaaaa agagaggttt cattgcttcc tggtgttctc aggaaaaggt attgaaacat  1260
ccttctgttg gtggtttcct tactcattgc ggttggggct ctacaatcga atcactaagt  1320
gcaggagttc caatgatttg ttggccatat tcatgggacc aacttacaaa ttgtaggtat  1380
atctgtaaag agtgggaagt tggattagaa atgggaacaa aggttaaacg tgatgaagtg  1440
aaaagattgg ttcaggagtt gatgggggaa ggtggccaca agatgagaaa caaggccaaa  1500
gattggaagg aaaaagccag aattgctatt gctcctaacg ggtcatcctc tctaaacatt  1560
gataagatgg tcaaagagat tacagtctta gccagaaact aa                     1602
```

```
SEQ ID NO: 88          moltype = AA  length = 533
FEATURE                Location/Qualifiers
REGION                 1..533
                       note = Description of Artificial Sequence: Synthetic
                        polypeptide
source                 1..533
                       mol_type = protein
                       organism = synthetic construct
SEQUENCE: 88
MTSFAEYWNL LSPTSFAEYW NLLSPTSFAE YWNLFSPTSF AEYWNLLSPA SKMDAMATTE  60
KKPHVIFIPF PAQSHIKAML KLAQLLHHKG LQITFVNTDF IHNQFLESSG PHCLDGAPGF  120
RFETIPDGVS HSPEASIPIR ESLLRSIETN FLDRFIDLVT KLPDPPTCII SDGFLSVFTI  180
DAAKKLGIPV MMYWTLAACG FMGFYHIHSL IEKGFAPLKD ASYLTNGYLD TVIDWVPGME  240
GIRLKDFPLD WSTDLNDKVL MFTTEAPQRS HKVSHHIFHT FDELEPSIIK TLSLRYNHIY  300
TIGPLQLLLD QIPEEKKQTG ITSLHGYSLV KEEPECFQWL QSKEPNSVVY VNFGSTTVMS  360
```

-continued

```
LEDMTEFGWG LANSNHYFLW IIRSNLVIGE NAVLPPELEE HIKKRGFIAS WCSQEKVLKH  420
PSVGGFLTHC GWGSTIESLS AGVPMICWPY SWDQLTNCRY ICKEWEVGLE MGTKVKRDEV  480
KRLVQELMGE GGHKMRNKAK DWKEKARIAI APNGSSSLNI DKMVKEITVL ARN         533

SEQ ID NO: 89          moltype = DNA  length = 1893
FEATURE                Location/Qualifiers
misc_feature           1..1893
                       note = Description of Artificial Sequence: Synthetic
                        polynucleotide
source                 1..1893
                       mol_type = other DNA
                       organism = synthetic construct
SEQUENCE: 89
atgtgcaata ccaacatgtc tgtacctact gatggtgctg taaccacctc acagattcca  60
gcttcggaac aagagaccct ggttagacca aagccattgc ttttgaagtt attaaagtct  120
gttggtgcac aaaaagacac ttatactatg aaagaggttc ttttttatct tggccagtat  180
attatgacta aacgattata tgatgagaag caacaacata ttgtatattg ttcaaatgat  240
cttctaggag atttgtttgg cgtgccaagc ttctctgtga aagagcacag gaaaatatat  300
accatgatct acaggaactt ggtagtagtc aatcagcagg aatcatcgga ctcaggtaca  360
tctgtgagtg agaacaggtg tcaccttgaa ggtgggagtg atcaaaagga ccttgtacaa  420
gagcttcagg aagagaaacc ttcatcttca catttggttt ctagaccatc taccggtggt  480
agcggatcct ctggaggcag tgctagtaaa atggcagagc aacaaaagat caaaaagtca  540
cctcacgtct tacttattcc atttcctctg caaggacata tcaacccatt catacaattt  600
gggaaaagat tgattagtaa gggtgtaaag acaacactgg taaccactat ccacactttg  660
aattctactc tgaaccactc aaatactact actacaagta tagaaattca agctatatca  720
gacggatgcg atgagggtgg ctttatgtct gccggtgaat cttacttgga aacattcaag  780
caagtgggat ccaagtctct ggccgatcta atcaaaaagt tacagagtga aggcaccaca  840
attgacgcca taatctacga ttctatgaca gagtgggttt tagacgttgc tatcgaattt  900
ggtattgatg gaggttcctt tttcacacaa gcatgtgttg tgaattctct atactaccat  960
gtgcataaag ggttaatctc tttaccattg ggtgaaactg tttcagttcc aggttttcca  1020
gtgttacaac gttgggaaac cccattgatc ttacaaaatc atgaacaaat acaatcacct  1080
tggtcccaga tgttgtttgg tcaattcgct aacatcgatc aagcaagatg ggtctttact  1140
aattcattct ataagttaga ggaagaggta attgaatgga ctaggaagat ctggaatttg  1200
aaagtcattg gtccaacatt gccatcaatg tatttggaca aaagacttga tgatgataaa  1260
gataatggtt tcaatttgta caaggctaat catcacgaat gtatgaattg gctggatgac  1320
aaaccaaagg aatcagttgt atatgttgct ttcggctctc ttgttaaaca tggtccagaa  1380
caagttgagg agattacaag agcacttata gactctgacg taaacttttt gtgggtcatt  1440
aagcacaaag aggaggggaa actgccagaa aacctttctg aagtgataaa gaccggaaaa  1500
ggtctaatcg ttgcttggtg taaacaattg gatgttttag ctcatgaatc tgtaggctgt  1560
tttgtaacac attgcggatt caactctaca ctagaagcca tttccttagg cgtacctgtc  1620
gttgcaatgc ctcagttctc cgatcagaca accaacgcta aacttttgga cgaaatacta  1680
ggggtgggtg tcagagttaa agcagacgag aatggtatcg tcagaagagg gaacctagct  1740
tcatgtatca aaatgatcat ggaagaggaa agaggagtta tcataaggaa aaacgcagtt  1800
aagtggaagg atcttgcaaa ggttgccgtc catgaaggcg gctcttcaga taatgatatt  1860
gttgaatttg tgtccgaact aatcaaagcc taa                               1893

SEQ ID NO: 90          moltype = AA  length = 630
FEATURE                Location/Qualifiers
REGION                 1..630
                       note = Description of Artificial Sequence: Synthetic
                        polypeptide
source                 1..630
                       mol_type = protein
                       organism = synthetic construct
SEQUENCE: 90
MCNTNMSVPT DGAVTTSQIP ASEQETLVRP KPLLLKLLKS VGAQKDTYTM KEVLFYLGQY  60
IMTKRLYDEK QQHIVYCSND LLGDLFGVPS FSVKEHRKIY TMIYRNLVVV NQQESSDSGT  120
SVSENRCHLE GGSDQKDLVQ ELQEEKPSSS HLVSRPSTGG SGSSGGSASK MAEQQKIKKS  180
PHVLLIPFPL QGHINPFIQF GKRLISKGVK TTLVTTIHTL NSTLNHSNTT TTSIEIQAIS  240
DGCDEGGFMS AGESYLETFK QVGSKSLADL IKKLQSEGTT IDAIIYDSMT EWVLDVAIEF  300
GIDGGSFFTQ ACVVNSLYYH VHKGLISLPL GETVSVPGFP VLQRWETPLI LQNHEQIQSP  360
WSQMLFGQFA NIDQARWVFT NSFYKLEEEV IEWTRKIWNL KVIGPTLPSM YLDKRLDDDK  420
DNGFNLYKAN HHECMNWLDD KPKESVVYVA FGSLVKHGPE QVEEITRALI DSDVNFLWVI  480
KHKEEGKLPE NLSEVIKTGK GLIVAWCKQL DVLAHESVGC FVTHCGFNST LEAISLGVPV  540
VAMPQFSDQT TNAKLLDEIL GVGVRVKADE NGIVRRGNLA SCIKMIMEEE RGVIIRKNAV  600
KWKDLAKVAV HEGGSSDNDI VEFVSELIKA                                   630

SEQ ID NO: 91          moltype = DNA  length = 1932
FEATURE                Location/Qualifiers
misc_feature           1..1932
                       note = Description of Artificial Sequence: Synthetic
                        polynucleotide
source                 1..1932
                       mol_type = other DNA
                       organism = synthetic construct
SEQUENCE: 91
atgtgcaata ccaacatgtc tgtacctact gatggtgctg taaccacctc acagattcca  60
gcttcggaac aagagaccct ggttagacca aagccattgc ttttgaagtt attaaagtct  120
gttggtgcac aaaaagacac ttatactatg aaagaggttc ttttttatct tggccagtat  180
```

-continued

```
attatgacta aacgattata tgatgagaag caacaacata ttgtatattg ttcaaatgat  240
cttctaggag atttgtttgg cgtgccaagc ttctctgtga aagagcacag gaaaatatat  300
accatgatct acaggaactt ggtagtagtc aatcagcagg aatcatcgga ctcaggtaca  360
tctgtgagtg agaacaggtg tcaccttgaa ggtgggagtg atcaaaagga ccttgtacaa  420
gagcttcagg aagagaaacc ttcatcttca catttggttt ctagaccatc taccggtggt  480
agcggatcct ctggaggcag tgctagtaaa atggctacat ctgattctat tgttgatgac  540
aggaagcagt tgcatgtggc tactttccct tggcttgctt tcggtcatat actgccttac  600
ctacaactat caaaactgat agctgaaaaa ggacataaag tgtcattcct ttcaacaact  660
agaaacattc aaagattatc ttcccacata tcaccattga ttaacgtcgt tcaattgaca  720
cttccaagag tacaggaatt accagaagat gctgaagcta caacagatgt gcatcctgaa  780
gatatccctt acttgaaaaa ggcatccgat ggattacagc ctgaggtcac tagattcctt  840
gagcaacaca gtccagattg gatcatatac gactacactc actattggtt gccttcaatt  900
gcagcatcac taggcatttc tagggcacat ttcagtgtaa ccacaccttg ggccattgct  960
tacatgggtc catccgctga tgctatgatt aacggcagtg atggtagaac taccgttgaa  1020
gatttgacaa ccccaccaaa gtggtttcca tttccaacta aagtctgttg gagaaaacac  1080
gacttagcaa gactggttcc atacaaggca ccaggaatct cagacggcta tagaatgggt  1140
ttagtcctta aagggtctga ctgcctattg tctaagtgtt accatgagtt tgggacacaa  1200
tggctaccac ttttggaaac attacaccaa gttcctgtcg taccagttgg tctattacct  1260
ccagaaatcc ctggtgatga gaaggacgag acttgggttt caatcaaaaa gtggttagac  1320
gggaagcaaa aaggctcagt ggtatatgtg gcactgggtt ccgaagtttt agtatctcaa  1380
acagaagttg tggaacttgc cttaggtttg gaactatctg gattgccatt tgtctgggcc  1440
tacagaaaac caaaaggccc tgcaaagtcc gattcagttg aattgccaga cggctttgtc  1500
gagagaacta gagatagagg gttggtatgg acttcatggg ctccacaatt gagaatcctg  1560
agtcacgaat ctgtgtgcgg tttcctaaca cattgtggtt ctggttctat agttgaagga  1620
ctgatgtttg gtcatccact tatcatgttg ccaatctttg gtgaccagcc tttgaatgca  1680
cgtctgttag aagataaaca agttggaatt gaaatcccac gtaatgagga agatggatgt  1740
ttaaccaagg agtctgtggc cagatcatta cgttccgttg tcgttgaaaa ggaaggcgaa  1800
atctacaagg ccaatgcccg tgaactttca aagatctaca atgacacaaa agtagagaag  1860
gaatatgttt ctcaatttgt agattaccta gagaaaaacg ctagagccgt agctattgat  1920
catgaatcct aa                                                     1932
```

```
SEQ ID NO: 92           moltype = AA  length = 643
FEATURE                 Location/Qualifiers
REGION                  1..643
                        note = Description of Artificial Sequence: Synthetic
                         polypeptide
source                  1..643
                        mol_type = protein
                        organism = synthetic construct
SEQUENCE: 92
MCNTNMSVPT DGAVTTSQIP ASEQETLVRP KPLLLKLLKS VGAQKDTYTM KEVLFYLGQY  60
IMTKRLYDEK QQHIVYCSND LLGDLFGVPS FSVKEHRKIY TMIYRNLVVV NQQESSDSGT  120
SVSENRCHLE GGSDQKDLVQ ELQEEKPSSS HLVSRPSTGG SGSSGGSASK MATSDSIVDD  180
RKQLHVATFP WLAFGHILPY LQLSKLIAEK GHKVSFLSTT RNIQRLSSHI SPLINVVQLT  240
LPRVQELPED AEATTDVHPE DIPYLKKASD GLQPEVTRFL EQHSPDWIIY DYTHYWLPSI  300
AASLGISRAH FSVTTPWAIA YMGPSADAMI NGSDGRTTVE DLTTPPKWFP FPTKVCWRKH  360
DLARLVPYKA PGISDGYRMG LVLKGSDCLL SKCYHEFGTQ WLPLLETLHQ VPVVPVGLLP  420
PEIPGDEKDE TWVSIKKWLD GKQKGSVVYV ALGSEVLVSQ TEVVELALGL ELSGLPFVWA  480
YRKPKGPAKS DSVELPDGFV ERTRDRGLVW TSWAPQLRIL SHESVCGFLT HCGSGSIVEG  540
LMFGHPLIML PIFGDQPLNA RLLEDKQVGI EIPRNEEDGC LTKESVARSL RSVVVEKEGE  600
IYKANARELS KIYNDTKVEK EYVSQFVDYL EKNARAVAID HES                   643
```

```
SEQ ID NO: 93           moltype = DNA  length = 1887
FEATURE                 Location/Qualifiers
misc_feature            1..1887
                        note = Description of Artificial Sequence: Synthetic
                         polynucleotide
source                  1..1887
                        mol_type = other DNA
                        organism = synthetic construct
SEQUENCE: 93
atgtgcaata ccaacatgtc tgtacctact gatggtgctg taaccacctc acagattcca  60
gcttcggaac aagagaccct ggttagacca aagccattgc ttttgaagtt attaaagtct  120
gttggtgcac aaaaagacac ttatactatg aaagaggttc ttttttatct tggccagtat  180
attatgacta aacgattata tgatgagaag caacaacata ttgtatattg ttcaaatgat  240
cttctaggag atttgtttgg cgtgccaagc ttctctgtga aagagcacag gaaaatatat  300
accatgatct acaggaactt ggtagtagtc aatcagcagg aatcatcgga ctcaggtaca  360
tctgtgagtg agaacaggtg tcaccttgaa ggtgggagtg atcaaaagga ccttgtacaa  420
gagcttcagg aagagaaacc ttcatcttca catttggttt ctagaccatc taccggtggt  480
agcggatcct ctggaggcag tgctagtaaa atggaaaaca agaccgaaac aacagttaga  540
cgtaggcgta gaatcattct gtttccagta ccttttcaag ggcacatcaa tccaatacta  600
caactagcca acgttttgta ctctaaaggt tttctatta caatctttca caccaatttc  660
aacaaaccaa aaacatccaa ttacccacat ttcacattca gattcatact tgataatgat  720
ccacaagatg aacgtatttc aaacttacct acccacggtc ctttagctgg aatgagaatt  780
ccaatcatca atgaacatgg tgccgatgag cttagaagag aattagagtt acttatgttg  840
gcatccgaag aggacgagga agtctcttgt ctgattactg acgctctatg gtactttgcc  900
caatctgtgg ctgatagttt gaatttgagg agattggtac taatgacatc cagtctgttt  960
aactttcacg ctcatgttag tttaccacaa tttgacgaat tgggatactt ggaccctgat  1020
gacaagacta ggttagagga acaggcctct ggttttccta tgttgaaagt caaagatatc  1080
```

-continued

```
aagtctgcct attctaattg gcaaatcttg aaagagatct taggaaagat gatcaaacag  1140
acaaaggctt catctggagt gatttggaac agtttcaaag agttagaaga gtctgaattg  1200
gagactgtaa tcagagaaat tccagcacct tcattcctga taccattacc aaaacatttg  1260
actgcttcct cttcctcttt gttggatcat gacagaacag tttttcaatg gttggaccaa  1320
caaccaccta gttctgtttt gtacgtgtca tttggtagta cttctgaagt cgatgaaaag  1380
gacttccttg aaatcgcaag aggcttagtc gatagtaagc agtcattcct ttgggtcgtg  1440
cgtccaggtt tcgtgaaagg ctcaacatgg gtcgaaccac ttccagatgg ttttctaggc  1500
gaaagaggta gaatagtcaa atgggttcct caacaggaag ttttagctca tggcgctatt  1560
ggggcattct ggactcattc cggatggaat tcaactttag aatcagtatg cgaaggggta  1620
cctatgatct tttcagattt tggtcttgat caaccactga acgcaagata catgtctgat  1680
gttttgaaag tgggtgtata tctagaaaat ggctgggaaa ggggtgaaat agctaatgca  1740
ataagacgtg ttatggttga tgaagagggg gagtatatca gacaaaacgc aagagtgctg  1800
aagcaaaagg ccgacgtttc tctaatgaag ggaggctctt catacgaatc cttagaatct  1860
cttgtttcct acatttcatc actgtaa                                     1887

SEQ ID NO: 94          moltype = AA  length = 628
FEATURE                Location/Qualifiers
REGION                 1..628
                       note = Description of Artificial Sequence: Synthetic
                        polypeptide
source                 1..628
                       mol_type = protein
                       organism = synthetic construct
SEQUENCE: 94
MCNTNMSVPT DGAVTTSQIP ASEQETLVRP KPLLLKLLKS VGAQKDTYTM KEVLFYLGQY  60
IMTKRLYDEK QQHIVYCSND LLGDLFGVPS FSVKEHRKIY TMIYRNLVVV NQQESSDSGT  120
SVSENRCHLE GGSDQKDLVQ ELQEEKPSSS HLVSRPSTGG SGSSGGSASK MENKTETTVR  180
RRRRIILFPV PFQGHINPIL QLANVLYSKG FSITIFHTNF NKPKTSNYPH FTFRFILDND  240
PQDERISNLP THGPLAGMRI PIINEHGADE LRRELELLML ASEEDEEVSC LITDALWYFA  300
QSVADSLNLR RLVLMTSSLF NFHAHVSLPQ FDELGYLDPD DKTRLEEQAS GFPMLKVKDI  360
KSAYSNWQIL KEILGKMIKQ TKASSGVIWN SFKELEESEL ETVIREIPAP SFLIPLPKHL  420
TASSSSLLDH DRTVFQWLDQ QPPSSVLYVS FGSTSEVDEK DFLEIARGLV DSKQSFLWVV  480
RPGFVKGSTW VEPLPDGFLG ERGRIVKWVP QQEVLAHGAI GAFWTHSGWN STLESVCEGV  540
PMIFSDFGLD QPLNARYMSD VLKVGVYLEN GWERGEIANA IRRVMVDEEG EYIRQNARVL  600
KQKADVSLMK GGSSYESLES LVSYISSL                                    628

SEQ ID NO: 95          moltype = AA  length = 473
FEATURE                Location/Qualifiers
source                 1..473
                       mol_type = protein
                       organism = Stevia rebaudiana
SEQUENCE: 95
MATSDSIVDD RKQLHVATFP WLAFGHILPY LQLSKLIAEK GHKVSFLSTT RNIQRLSSHI  60
SPLINVVQLT LPRVQELPED AEATTDVHPE DIPYLKKASD GLQPEVTRFL EQHSPDWIIY  120
DYTHYWLPSI AASLGISRAH FSVTTPWAIA YMGPSADAMI NGSDGRTTVE DLTTPPKWFP  180
FPTKVCWRKH DLARLVPYKA PGISDRCRMG LVLKGSDCLL SKCYHEFGTQ WLPLLETLHQ  240
VPVVPVGLLP PEIPGDEKDE TWVSIKKWLD GKQKGSVVYV ALGSEVLVSQ TEVVELALGL  300
ELSGLPFVWA YRKPKGPAKS DSVELPDGFV ERTRDRGLVW TSRAPQLRIL SHESVCGFLT  360
HCGSGSIVEG LMFGHPLIML PIFGDQPLNA RLLEDKQVGI EIPRNEEDGC LTKESVARSL  420
RSVVVEKEGE IYKANARELS KIYNDTKVEK EYVSQFVDYL EKNARAVAID HES         473

SEQ ID NO: 96          moltype = DNA  length = 1422
FEATURE                Location/Qualifiers
source                 1..1422
                       mol_type = other DNA
                       organism = Stevia rebaudiana
SEQUENCE: 96
atggctacca gtgactccat agttgacgac cgtaagcagc ttcatgttgc gacgttccca  60
tggcttgctt tcggtcacat cctcccttac cttcagcttt cgaaattgat agctgaaaag  120
ggtcacaaag tctcgtttct ttctaccacc agaaacattc aacgtctctc ttctcatatc  180
tcgccactca taaatgttgt tcaactcaca cttccacgtg tccaagagct gccggaggat  240
gcagaggcga ccactgacgt ccaccctgaa gatattccat atctcaagaa ggcttctgat  300
ggtcttcaac cggaggtcac ccggtttcta gaacaacact ctccggactg gattatttat  360
gattatactc actactggtt gccatccatc gcggctagcc tcggtatctc acgagcccac  420
ttctccgtca ccactccatg ggccattgct tatatgggac cctcagctga cgccatgata  480
aatggttcag atggtcgaac cacggttgag gatctcacga caccgcccaa gtggtttccc  540
tttccgacca aagtatgctg gcggaagcat gatcttgccc gactggtgcc ttacaaagct  600
ccggggatat ctgatcgatg ccgtatgggg ctggttctta agggatctga ttgtttgctc  660
tccaaatgtt accatgagtt tggaactcaa tggctacctc ttttggagac actacaccaa  720
gtaccggtgg ttccggtggg attactgcca ccggaaatac ccggagacga gaaagatgaa  780
acatgggtgt caatcaagaa atggctcgat ggtaaacaaa aaggcagtgt ggtgtacgtt  840
gcattaggaa gcgaggtttt ggtgagccaa accgaggttg ttgagttagc attgggtctc  900
gagctttctg ggttgccatt tgtttgggct tatagaaaac caaaaggtcc cgcgaagtca  960
gactcggtgg agttgccaga cgggttcgtg gaacgaactc gtgaccgtgg gttggtctgg  1020
acgagtcggg cacctcagtt acgaatactg agccatgagt cggtttgtgg gttcttgacg  1080
cattgtggtt ctggatcaat tgtggaaggg ctaatgtttg gtcaccctct aatcatgcta  1140
ccgatttttg gggaccaacc tctgaatgct cgattactgg aggacaaaca ggtgggaatc  1200
gagataccaa gaaatgagga agatggttgc ttgaccaagg agtcggttgc tagatcactg  1260
aggtccgttg ttgtggaaaa agaaggggag atctacaagg cgaacgcgag ggagctgagt  1320
```

```
aaaatctata acgacactaa ggttgaaaaa gaatatgtaa gccaattcgt agactatttg  1380
gaaaagaatg cgcgtgcggt tgccatcgat catgagagtt aa                     1422

SEQ ID NO: 97          moltype = DNA  length = 1380
FEATURE                Location/Qualifiers
source                 1..1380
                       mol_type = other DNA
                       organism = Stevia rebaudiana
SEQUENCE: 97
atggaaaata aaacggagac caccgttcgc cggcgccgga gaataatatt attcccggta  60
ccatttcaag gccacattaa cccaattctt cagctagcca atgtgttgta ctctaaagga  120
ttcagtatca ccatctttca caccaacttc aacaaaccca aaacatctaa ttaccctcac  180
ttcactttca gattcatcct cgacaacgac ccacaagacg aacgcatttc caatctaccg  240
actcatggtc cgctcgctgg tatgcggatt ccgattatca acgaacacgg agctgacgaa  300
ttacgacgcg aactggaact gttgatgtta gcttctgaag aagatgaaga ggtatcgtgt  360
ttaatcacgg atgctctttg gtacttcgcg caatctgttg ctgacagtct taacctccga  420
cggcttgttt tgatgacaag cagcttgttt aattttcatg cacatgtttc acttcctcag  480
tttgatgagc ttggttacct cgatcctgat gacaaaaccc gtttggaaga acaagcgagt  540
gggtttccta tgctaaaagt gaaagacatc aagtctgcgt attcgaactg gcaaatactc  600
aaagagatat tagggaagat gataaaacaa acaaaagcat cttcaggagt catctggaac  660
tcatttaagg aactcgaaga gtctgagctc gaaactgtta tccgtgagat cccggctcca  720
agtttcttga taccactccc caagcatttg acagcctctt ccagcagctt actagaccac  780
gatcgaaccg tttttccatg gttagaccaa caaccgtcac gttcggtact gtatgttagt  840
tttggtagtg gtactgaagt actggatgag aaagatttct tggaaatagc tcgtgggttg  900
gttgatagca agcagtcgtt tttatgggtg gttcgacctg ggtttgtcaa gggttcgacg  960
tgggtcgaac cgttgccaga tgggttcttg ggtgaaagag gacgtattgt gaaatgggtt  1020
ccacagcaag aagtgctagc tcatggagca ataggcgcat tctggactca tagcggatgg  1080
aactctacgt tggaaagcgt ttgtgaaggt gttcctatga ttttctcgga ttttgggctc  1140
gatcaaccgt tgaatgctag atacatgagt gatgttttga aggtaggggt gtatttggaa  1200
aatgggtggg aaagaggaga gatagcaaat gcaataagaa gagttatggt ggatgaagaa  1260
ggagaataca ttagacagaa tgcaagagtt ttgaaacaaa aggcagatgt ttctttgatg  1320
aagggtggtt cgtcttacga atcattagag tctctagttt cttacatttc atcgttgtaa  1380

SEQ ID NO: 98          moltype = AA  length = 459
FEATURE                Location/Qualifiers
source                 1..459
                       mol_type = protein
                       organism = Stevia rebaudiana
SEQUENCE: 98
MENKTETTVR RRRRIILFPV PFQGHINPIL QLANVLYSKG FSITIFHTNF NKPKTSNYPH  60
FTFRFILDND PQDERISNLP THGPLAGMRI PIINEHGADE LRRELELLML ASEEDEEVSC  120
LITDALWYFA QSVADSLNLR RLVLMTSSLF NFHAHVSLPQ FDELGYLDPD DKTRLEEQAS  180
GFPMLKVKDI KSAYSNWQIL KEILGKMIKQ TKASSGVIWN SFKELEESEL ETVIREIPAP  240
SFLIPLPKHL TASSSSLLDH DRTVFPWLDQ QPSRSVLYVS FGSGTEVLDE KDFLEIARGL  300
VDSKQSFLWV VRPGFVKGST WVEPLPDGFL GERGRIVKWV PQQEVLAHGA IGAFWTHSGW  360
NSTLESVCEG VPMIFSDFGL DQPLNARYMS DVLKVGVYLE NGWERGEIAN AIRRVMVDEE  420
GEYIRQNARV LKQKADVSLM KGGSSYESLE SLVSYISSL                         459

SEQ ID NO: 99          moltype = DNA  length = 1380
FEATURE                Location/Qualifiers
modified_base          861..863
                       mod_base = OTHER
                       note = a, c, t, g, unknown or other
misc_feature           861..863
                       note = n is a, c, g, or t
source                 1..1380
                       mol_type = other DNA
                       organism = Stevia rebaudiana
SEQUENCE: 99
atggaaaata aaacggagac caccgttcgc cggcgccgga gaataatatt attcccggta  60
ccatttcaag gccacattaa cccaattctt cagctagcca atgtgttgta ctctaaagga  120
ttcagtatca ccatctttca caccaacttc aacaaaccca aaacatctaa ttaccctcac  180
ttcactttca gattcatcct cgacaacgac ccacaagacg aacgcatttc caatctaccg  240
actcatggtc cgctcgctgg tatgcggatt ccgattatca acgaacacgg agctgacgaa  300
ttacgacgcg aactggaact gttgatgtta gcttctgaag aagatgaaga ggtatcgtgt  360
ttaatcacgg atgctctttg gtacttcgcg caatctgttg ctgacagtct taacctccga  420
cggcttgttt tgatgacaag cagcttgttt aattttcatg cacatgtttc acttcctcag  480
tttgatgagc ttggttacct cgatcctgat gacaaaaccc gtttggaaga acaagcgagt  540
gggtttccta tgctaaaagt gaaagacatc aagtctgcgt attcgaactg gcaaatactc  600
aaagagatat tagggaagat gataaaacaa acaaaagcat cttcaggagt catctggaac  660
tcatttaagg aactcgaaga gtctgagctc gaaactgtta tccgtgagat cccggctcca  720
agtttcttga taccactccc caagcatttg acagcctctt ccagcagctt actagaccac  780
gatcgaaccg tttttcaatg gttagaccaa caaccgccaa gttcggtact gtatgttagt  840
tttggtagta ctagtgaagt nnnggatgag aaagatttct tggaaatagc tcgtgggttg  900
gttgatagca agcagtcgtt tttatgggtg gttcgacctg ggtttgtcaa gggttcgacg  960
tgggtcgaac cgttgccaga tgggttcgtg gccgaaagag ggcgtattgt gaaatgggtt  1020
ccgcaacagg aagtgatagc tcatggagca atcggtgcat tctggactca tagcggatgg  1080
aactctacat tggaaagcgt ttgtgaaggt gttcctatga ttttctcgga ttttgggctc  1140
gatcaaccgt tgaatgctag atacatgagt gatgttttga aggtaggggt gtatttggaa  1200
```

```
aatgggtggg aaagaggaga gatagcaaat gcaatacgaa gagttatggt ggatgaagaa  1260
ggagaataca ttagacagaa tgcaagagtt ttgaaacaaa aggcagatgt ttctttgatg  1320
aagggtggtt catcttacga atcattagag tctctagttt cttacatttc atcgttgtaa  1380

SEQ ID NO: 100         moltype = AA  length = 459
FEATURE                Location/Qualifiers
MOD_RES                288
                       note = Any amino acid
source                 1..459
                       mol_type = protein
                       organism = Stevia rebaudiana
SEQUENCE: 100
MENKTETTVR RRRRIILFPV PFQGHINPIL QLANVLYSKG FSITIFHTNF NKPKTSNYPH  60
FTFRFILDND PQDERISNLP THGPLAGMRI PIINEHGADE LRRELELLML ASEEDEEVSC  120
LITDALWYFA QSVADSLNLR RLVLMTSSLF NFHAHVSLPQ FDELGYLDPD DKTRLEEQAS  180
GFPMLKVKDI KSAYSNWQIL KEILGKMIKQ TKASSGVIWN SFKELEESEL ETVIREIPAP  240
SFLIPLPKHL TASSSSLLDH DRTVFQWLDQ QPPSSVLYVS FGSTSEVXDE KDFLEIARGL  300
VDSKQSFLWV VRPGFVKGST WVEPLPDGFV AERGRIVKWV PQQEVIAHGA IGAFWTHSGW  360
NSTLESVCEG VPMIFSDFGL DQPLNARYMS DVLKVGVYLE NGWERGEIAN AIRRVMVDEE  420
GEYIRQNARV LKQKADVSLM KGGSSYESLE SLVSYISSL                         459

SEQ ID NO: 101         moltype = DNA  length = 1380
FEATURE                Location/Qualifiers
modified_base          861..863
                       mod_base = OTHER
                       note = a, c, t, g, unknown or other
misc_feature           861..863
                       note = n is a, c, g, or t
source                 1..1380
                       mol_type = other DNA
                       organism = Stevia rebaudiana
SEQUENCE: 101
atggaaaata aaacggagac caccgttcgc cggcgccgga gaataatatt attcccggta  60
ccatttcaag gccacattaa cccaattctt cagctagcca atgtgttgta ctctaaagga  120
ttcagtatca ccatctttca caccaacttc aacaaaccca aaacatctaa ttaccctcac  180
ttcactttca gattcatcct cgacaacgac ccacaagacg aacgcatttc caatctaccg  240
actcatggtc cgctcgctgg tatgcggatt ccgattatca acgaacacgg agctgacgaa  300
ttacgacgcg aactggaact gttgatgtta gcttctgaag aagatgaaga ggtatcgtgt  360
ttaatcacgg atgctctttg gtacttcgcg caatctgttg ctgacagtct taacctccga  420
cggcttgttt tgatgacaag cagcttgttt aattttcatg cacatgtttc acttcctcag  480
tttgatgagc ttggttacct cgatcctgat gacaaaaccc gtttggaaga acaagcgagt  540
gggtttccta tgctaaaagt gaaagacatc aagtctgcgt attcgaactg gcaaatactc  600
aaagagatat tagggaagat gataaaacaa acaaaagcat cttcaggagt catctggaac  660
tcatttaagg aactcgaaga gtctgagctc gaaactgtta tccgtgagat cccggctcca  720
agtttcttga taccactccc caagcatttg acagcctctt ccagcagctt actagaccac  780
gatcgaaccg tttttcaatg gttagaccaa caaccgccaa gttcggtact gtatgttagt  840
tttggtagta ctagtgaagt nnnggatgag aaagatttct tggaaatagc tcgtgggttg  900
gttgatagca agcagtcgtt tttatgggtg gttcgacctg ggtttgtcaa gggttcgacg  960
tgggtcgaac cgttgccaga tgggttcttg ggtgaaagag gacgtattgt gaaatgggtt  1020
ccacagcaag aagtgctagc tcatggagca ataggcgcat tctggactca tagcggatgg  1080
aactctacgt tggaaagcgt ttgtgaaggt gttcctatga ttttctcgga ttttgggctc  1140
gatcaaccgt tgaatgctag atacatgagt gatgttttga aggtaggggt gtatttggaa  1200
aatgggtggg aaagaggaga gatagcaaat gcaataagaa gagttatggt ggatgaagaa  1260
ggagaataca ttagacagaa tgcaagagtt ttgaaacaaa aggcagatgt ttctttgatg  1320
aagggtggtt cgtcttacga atcattagag tctctagttt cttacatttc atcgttgtaa  1380

SEQ ID NO: 102         moltype = AA  length = 459
FEATURE                Location/Qualifiers
MOD_RES                288
                       note = Any amino acid
source                 1..459
                       mol_type = protein
                       organism = Stevia rebaudiana
SEQUENCE: 102
MENKTETTVR RRRRIILFPV PFQGHINPIL QLANVLYSKG FSITIFHTNF NKPKTSNYPH  60
FTFRFILDND PQDERISNLP THGPLAGMRI PIINEHGADE LRRELELLML ASEEDEEVSC  120
LITDALWYFA QSVADSLNLR RLVLMTSSLF NFHAHVSLPQ FDELGYLDPD DKTRLEEQAS  180
GFPMLKVKDI KSAYSNWQIL KEILGKMIKQ TKASSGVIWN SFKELEESEL ETVIREIPAP  240
SFLIPLPKHL TASSSSLLDH DRTVFQWLDQ QPPSSVLYVS FGSTSEVXDE KDFLEIARGL  300
VDSKQSFLWV VRPGFVKGST WVEPLPDGFL GERGRIVKWV PQQEVLAHGA IGAFWTHSGW  360
NSTLESVCEG VPMIFSDFGL DQPLNARYMS DVLKVGVYLE NGWERGEIAN AIRRVMVDEE  420
GEYIRQNARV LKQKADVSLM KGGSSYESLE SLVSYISSL                         459

SEQ ID NO: 103         moltype = DNA  length = 1323
FEATURE                Location/Qualifiers
misc_feature           1..1323
                       note = Description of Artificial Sequence: Synthetic
                        polynucleotide
source                 1..1323
```

```
                         mol_type = other DNA
                         organism = synthetic construct
SEQUENCE: 103
atgcattcta ccagacatat cttaagacaa agggccgtcc tagttacagg cgctagaaca  60
ccattcgtga aatcatttgg ggctcttatg aaagcagata ccttggaatt ggcatcagca  120
tcagtcgctg ggttgctgaa caagacctca ctggacccta gagatatcga tcatatcgtt  180
tggggtaatg ttgtacttca aggatcagct cataactgcg ccagagaaat agttatcgac  240
cttaacatgc ctaaaaagat catcggtaat ttgacatcta tggcctgtgc ttcaggctta  300
tcttctttgt cacaagcctg tatgctaata gagggtggtc atgccgatgt cgtcattgct  360
ggcggttctg attcagtctc caacactgaa gtgcctttgc caagatccgt cacttacggt  420
ctaatgatgg cccaaaggaa gggtgttatg ggcttcttta aggaagcagg atacaaccca  480
ttcaaatggt ttccaggcgg tattgcttta accgaacgta gtacaggaaa aactatgggt  540
tggcatggag acttaattgc tgagttaaac tctatatcta gagatgacca ggaagccctg  600
gctgtggctt ctcatgcaaa tgctgctaga gcagaaaaag ctgggtactt taaggaggaa  660
attgtacctg tgacaatcga caaaaagggc aaaaagactg aagtaacatg tgatgatgtt  720
atgcaaagag atacagaaaa gatgaaggcc aagatgccat cattgaagcc tgttttcaga  780
aaagagggag gtacaataac agcagccact tccagtactc tgactgatgg tggctctgca  840
atgttggtta tgtcagagga aaaggccaaa aagttgggtt atccaactga tgtctgcgtg  900
aagtcttggt atttcagtgg tatcgatcct tacccacaac ttttgttagc accagttcta  960
ggttggggtc cagctttgaa aaaggccgga ttaaccccta aagatatcga tttgtacgaa  1020
attcacgaag catttgctgc acaagttcta gccacaatta agtgtttgaa gtctcaggaa  1080
ttcttcgata ggtacgctaa cggtgcaaag ccagtattaa ctgaggatat tgatctttct  1140
aaactaaatg ttaatggcgg ttccttagca cttggccacc cattcgccgc tacaggaggt  1200
agaatcgtaa tctctctagc aaatgagttg agaagatccg gaaagagaca cgggctggtc  1260
agtatttgtg cagctggagg gttaggcgga gtagctatac ttgagcatac agcaagtaag  1320
taa                                                                1323

SEQ ID NO: 104           moltype = AA  length = 440
FEATURE                  Location/Qualifiers
source                   1..440
                         mol_type = protein
                         organism = Leishmania infantum
SEQUENCE: 104
MHSTRHILRQ RAVLVTGART PFVKSFGALM KADTLELASA SVAGLLNKTS LDPRDIDHIV  60
WGNVVLQGSA HNCAREIVID LNMPKKIIGN LTSMACASGL SSLSQACMLI EGGHADVVIA  120
GGSDSVSNTE VPLPRSVTYG LMMAQRKGVM GFFKEAGYNP FKWFPGGIAL TERSTGKTMG  180
WHGDLIAELN SISRDDQEAL AVASHANAAR AEKAGYFKEE IVPVTIDKKG KKTEVTCDDV  240
MQRDTEKMKA KMPSLKPVFR KEGGTITAAT SSTLTDGGSA MLVMSEEKAK KLGYPTDVCV  300
KSWYFSGIDP YPQLLLAPVL GWGPALKKAG LTPKDIDLYE IHEAFAAQVL ATIKCLKSQE  360
FFDRYANGAK PVLTEDIDLS KLNVNGGSLA LGHPFAATGG RIVISLANEL RRSGKRHGLV  420
SICAAGGLGG VAILEHTASK                                              440

SEQ ID NO: 105           moltype = DNA  length = 1584
FEATURE                  Location/Qualifiers
misc_feature             1..1584
                         note = Description of Artificial Sequence: Synthetic
                          polynucleotide
source                   1..1584
                         mol_type = other DNA
                         organism = synthetic construct
SEQUENCE: 105
atggcagctg accaattggt gaaaactgaa gtcaccaaga agtcttttac tgctcctgta  60
caaaaggctt ctacaccagt tttaaccaat aaaacagtca tttctggatc gaaagtcaaa  120
agtttatcat ctgcgcaatc gagctcatca ggaccttcat catctagtga ggaagatgat  180
tcccgcgata ttgaaagctt ggataagaaa atacgtcctt tagaagaatt agaagcatta  240
ttaagtagtg gaaatacaaa acaattgaag aacaaagagg tcgctgcctt ggttattcac  300
ggtaagttac ctttgtacgc tttggagaaa aaattaggtg atactacgag agcggttgcg  360
gtacgtagga aggctctttc aattttggca gaagctcctg tattagcatc tgatcgttta  420
ccatataaaa attatgacta cgaccgcgta tttggcgctt gttgtgaaaa tgttataggt  480
tacatgcctt tgcccgttgg tgttataggc cccttggtta tcgatggtac atcttatcat  540
ataccaatgg caactacaga gggttgtttg gtagcttctg ccatgcgtgg ctgtaaggca  600
atcaatgctg gcggtggtgc aacaactgtt ttaactaagg atggtatgac aagaggccca  660
gtagtccgtt tcccaacttt gaaaagatct ggtgcctgta agatatggtt agactcagaa  720
gagggacaaa acgcaattaa aaaagctttt aactctacat caagatttgc acgtctgcaa  780
catattcaaa cttgtctagc aggagattta ctcttcatga gatttagaac aactactggt  840
gacgcaatgg gtatgaatat gatttctaaa ggtgtcgaat actcattaaa gcaaatggta  900
gaagagtatg gctgggaaga tatggaggtt gtctccgttt ctggtaacta ctgtaccgac  960
aaaaaaccag ctgccatcaa ctggatcgaa ggtcgtggta agagtgtcgt cgcagaagct  1020
actattcctg gtgatgttgt cagaaaagtg ttaaaaagtg atgtttccgc attggttgag  1080
ttgaacattg ctaagaattt ggttggatct gcaatggctg ggtctgttgg tggatttaac  1140
gcacatgcag ctaatttagt gacagctgtt ttcttggcat taggacaaga tcctgcacaa  1200
aatgttgaaa gttccaactg tataacattg atgaaagaag tggacggtga tttgagaatt  1260
tccgtatcca tgccatccat cgaagtaggt accatcggtg gtggtactgt tctagaacca  1320
caaggtgcca tgttggactt attaggtgta agaggcccgc atgctaccgc tcctggtacc  1380
aacgcacgtc aattagcaag aatagttgcc tgtgccgtct tggcaggtga attatcctta  1440
tgtgctgccc tagcagccgg ccatttggtt caaagtcata tgacccacaa caggaaacct  1500
gctgaaccaa caaaacctaa caatttggac gccactgata taaatcgttt gaaagatggg  1560
tccgtcacct gcattaaatc ctaa                                         1584
```

```
SEQ ID NO: 106          moltype = AA  length = 527
FEATURE                 Location/Qualifiers
source                  1..527
                        mol_type = protein
                        organism = Saccharomyces cerevisiae
SEQUENCE: 106
MAADQLVKTE VTKKSFTAPV QKASTPVLTN KTVISGSKVK SLSSAQSSSS GPSSSSEEDD  60
SRDIESLDKK IRPLEELEAL LSSGNTKQLK NKEVAALVIH GKLPLYALEK KLGDTTRAVA  120
VRRKALSILA EAPVLASDRL PYKNYDYDRV FGACCENVIG YMPLPVGVIG PLVIDGTSYH  180
IPMATTEGCL VASAMRGCKA INAGGGATTV LTKDGMTRGP VVRFPTLKRS GACKIWLDSE  240
EGQNAIKKAF NSTSRFARLQ HIQTCLAGDL LFMRFRTTTG DAMGMNMISK GVEYSLKQMV  300
EEYGWEDMEV VSVSGNYCTD KKPAAINWIE GRGKSVVAEA TIPGDVVRKV LKSDVSALVE  360
LNIAKNLVGS AMAGSVGGFN AHAANLVTAV FLALGQDPAQ NVESSNCITL MKEVDGDLRI  420
SVSMPSIEVG TIGGGTVLEP QGAMLDLLGV RGPHATAPGT NARQLARIVA CAVLAGELSL  480
CAALAAGHLV QSHMTHNRKP AEPTKPNNLD ATDINRLKDG SVTCIKS             527

SEQ ID NO: 107          moltype = DNA  length = 3681
FEATURE                 Location/Qualifiers
misc_feature            1..3681
                        note = Description of Artificial Sequence: Synthetic
                         polynucleotide
source                  1..3681
                        mol_type = other DNA
                        organism = synthetic construct
SEQUENCE: 107
atgagagctg tccttagatt gttatcaaca catactgttt tctctcctat tgaaacaatt  60
gtatctgttt tcgtgttagc tacattagct tacttccaca tcttgtccgg aatcaagcac  120
tcaagtttct ttgcatcttc tcatcctcct gctatcagac ctgcttttgc acatctgacc  180
aacggggaat gggttgccgt ctcccaacat gattggactg aagcatggaa gcatcctggc  240
ggttcacttg atgcattaga acttcaacaa gtagttttca ctttagatga caagactcaa  300
ccatctgctg tgctagatgc atccgcaatt agtcagcact tagtttccaa tgttcctgca  360
ttatctggaa aagcctactc ttcattgtgc caccatccaa atgtatcagg cacctcctgt  420
tttacatcag tttctggtcc aggagcttca ccaatcttga cactgagttt taagcctgga  480
actagagacg attggttagg atcattaagg aaggagaaaa ctatcacact agatggggtt  540
aagtacgacg ttggagccgg aaaaagacaa gagtcaatcg gcgatatgga atcatctaag  600
tgggttgctt atgcattatc agctttggta cttagatttt gggaattaac aaaggcagat  660
tccttagata tactagtggt tctaactggg tacatcctaa tgcacgtaac attcatgaga  720
ttgttcttgg catccagagc acttggcagt aacttttggt tatcagctgg catattctcc  780
tccgcaacaa tttctttcct attcacttta ccaatgtgta gatctatgga tattccactt  840
gatccaattg ccttgacaga agccctgcca ttcttggtgt gtaccgtagg ttttgacaaa  900
ccacttagat tggcaagagc tgtgatggct catcctaata tccttaaacc tcaagatgat  960
ggtaggatga aagctgccgg agatgtcatt cttgaggcac tggacagagt tggtaacatg  1020
atattgagag attacgcttt agagatcgca gttctattcg ttggcgttaa ctccagagtt  1080
ggcggtctta aggaatttg tgctgtagct gcagcattac ttgctatgga cagattaatg  1140
acattcacac tttatacagc agtgttaacc atcatggttg aggtaaggcg tatcaaaaag  1200
gtcagagata tgactaaggc tagatctaga agttcttcta ttaccgccgt tacagccaac  1260
ggcaccgcca taagaggcgt tttgagtaga aaatcttcaa aacaatctgt gacagaacca  1320
gagacaacta aaaacctaag acaaagagcc actgattcag ccatcggtgt taagggttca  1380
ttgctgaaag atggaggcag attgcaggaa gccgaggaga atccaatggc aagattaaag  1440
ctattgttaa tcgcttcctt cttaacacta cacatcttga acttttgtac tactttgact  1500
tcagccacag ctaacgcaag acatcaaaga catcctttta gaaccgttca agaggtagta  1560
ccaattccta gagttgacat tactacccca gccatagcca atatcttgtc tcatctagct  1620
gtggctcagg aacctatgtt cactgttgtt ggcagtgaac ctatcgaact tcttgttaaa  1680
gtcgctgctc cagtctacgt ccatgctcta ccattggccc ctgctttaag agcttcaaac  1740
actaatactg gagaagctat tgaaaacttt atgagttcat ggtctagtct ggtaggtgac  1800
ccagttgtta gtaagtggat cgtagcattg ctagctgtct ctgttgcatt gaatggatac  1860
ttgttaaagg gtatagccgc aggttccggg ttggctgcca tgagagctgt tagatctcaa  1920
ggtgttcgtt tcagatctag agctagaagt atcgtaaaga tatctgatga acctgagcca  1980
gagccagaac actctatcga cccagcacca gtagtgttct tcgcttccgc agcaccagct  2040
gtagaggccc ctgctccagc tcctgcacct gaaccagaac caccagtcaa cagaccacca  2100
ccattgacta ttttctcaag accactgaac ttagaaacag tggacaaaaa gttacaagat  2160
gctctgccaa taagatcccc accacctgtt gaaccaatca ctccagaatc tagagaagtg  2220
gaaccaaccc aagtagaagt aagatctcta gctgaatgtg tggatgtgtt cgagaatggg  2280
ccaagaccag tctcagtggc tttaaagact ctgaatgatg aggaagttat cctgctttgc  2340
caaacaggta agatagctcc atatgcattg gttaagatgt tggctgattt cgatagggcc  2400
gtacgtgtca gaagagcact tattagtaga gcttcacgta caaaaacttt agaaaactca  2460
ctggttccta tgaaagatta tgattacgcc agagtcatgg gtgcctgttg tgaaaacgtt  2520
atcggataca tgccattacc actagggatt gcaggtccat tgaagattga tggcttgatg  2580
tatcctatac caatggcaac cgcagaaggt accttggttg catctacttc taggggctgt  2640
aaggccttaa atgctggtgg aggggtcaca actgtcttga cagcagatgg catgacaaga  2700
gggccagcta tagactttcc ttccatcgtc agagctgcag aggctaaggc cttcattgaa  2760
tcagaagatg gatacgctac aatcagggag gctttcgagt ctacttctag atttgccaag  2820
ttgcaaaaga tcaagtgtgc actagctggt cgtactcttt ttgtcagatt tgctactaga  2880
acaggagatg ccatgggtat gaacatgatt tctaaggcta ccgaaaaggc acttgatgtc  2940
ctgagtcacg agttccctga aatggtcgtc cttgctttgt ctggtaacta ctgcacagac  3000
aaaaagcctg cagctatttc atggatcgaa ggtaggggaa aatctattgt agcagaagca  3060
gttattcctg gtaaggtcgt taagtcagtc ctgaaaacaa cagtcgagtc tctttgcaat  3120
gtcaacacta agaaaaacct gattggttca gccatggcag gttctgttgg tggtttcaac  3180
gctcatgccg ccaacatcct aacagctgtg ttcctagcca caggtcagga tcctgctcaa  3240
```

```
aatgtcgaat cttctaattg catgacttta atggaaccaa caaacggcgg tgaggatttg  3300
ctaatgacaa tttcaatgcc atgtatagag gtaggaaccg ttggtggagg gacaattctg  3360
gaaccacaag gtgcagtttt ggatttgttg ggcgttagag gggctcaccc tactaatcct  3420
ggtcaaaacg ctcaacagtt agccagaatt atcgcatcag ctgtaatggc aggcgaattg  3480
tctttgataa gtgccttagc cgcaggtcat ttggttagag ctcatcttgc ccacaatcgt  3540
tctcaattga atacaccaat gccatccaga ccacatactc ctggccctga ggatgtctca  3600
catgtgcagc agctacctac accatctgca tctgatgata aaggtgttac agctcaaggt  3660
tacgttgtcg aagcaaaata a                                            3681

SEQ ID NO: 108         moltype = AA  length = 1226
FEATURE                Location/Qualifiers
source                 1..1226
                       mol_type = protein
                       organism = Ganoderma lucidum
SEQUENCE: 108
MRAVLRLLST HTVFSPIETI VSVFVLATLA YFHILSGIKH SSFFASSHPP AIRPAFAHLT  60
NGEWVAVSQH DWTEAWKHPG GSLDALELQQ VVFTLDDKTQ PSAVLDASAI SQHLVSNVPA  120
LSGKAYSSLC HHPNVSGTSC FTSVSGPGAS PILTLSFKPG TRDDWLGSLR KEKTITLDGV  180
KYDVGAGKRQ ESIGDMESSK WVAYALSALV LRFWELTKAD SLDILVVLTG YILMHVTFMR  240
LFLASRALGS NFWLSAGIFS SATISFLFTL PMCRSMDIPL DPIALTEALP FLVCTVGFDK  300
PLRLARAVMA HPNILKPQDD GRMKAAGDVI LEALDRVGNM ILRDYALEIA VLFVGVNSRV  360
GGLKEFCAVA AALLAMDRLM TFTLYTAVLT IMVEVRRIKK VRDMTKARSR SSSITAVTAN  420
GTAIRGVLSR KSSKQSVTEP ETTKNLRQRA TDSAIGVKGS LLKDGGRLQE AEENPMARLK  480
LLLIASFLTL HILNFCTTLT SATANARHQR HPFRTVQEVV PIPRVDITTP AIANILSHLA  540
VAQEPMFTVV GSEPIELLVK VAAPVYVHAL PLAPALRASN TNTGEAIENF MSSWSSLVGD  600
PVVSKWIVAL LAVSVALNGY LLKGIAAGSG LAAMRAVRSQ GVRFRSRARS IVKISDEPEP  660
EPEHSIDPAP VVFFASAAPA VEAPAPAPAP EPEPPVNRPP PLTIFSRPLN LETVDKKLQD  720
ALPIRSPPPV EPITPESREV EPTQVEVRSL AECVDVFENG PRPVSVALKT LNDEEVILLC  780
QTGKIAPYAL VKMLADFDRA VRVRRALISR ASRTKTLENS LVPMKDYDYA RVMGACCENV  840
IGYMPLPLGI AGPLKIDGLM YPIPMATAEG TLVASTSRGC KALNAGGGVT TVLTADGMTR  900
GPAIDFPSIV RAAEAKAFIE SEDGYATIRE AFESTSRFAK LQKIKCALAG RTLFVRFATR  960
TGDAMGMNMI SKATEKALDV LSHEFPEMVV LALSGNYCTD KKPAAISWIE GRGKSIVAEA  1020
VIPGKVVKSV LKTTVESLCN VNTKKNLIGS AMAGSVGGFN AHAANILTAV FLATGQDPAQ  1080
NVESSNCMTL MEPTNGGEDL LMTISMPCIE VGTVGGGTIL EPQGAVLDLL GVRGAHPTNP  1140
GQNAQQLARI IASAVMAGEL SLISALAAGH LVRAHLAHNR SQLNTPMPSR PHTPGPEDVS  1200
HVQQLPTPSA SDDKGVTAQG YVVEAK                                       1226

SEQ ID NO: 109         moltype = DNA  length = 2667
FEATURE                Location/Qualifiers
misc_feature           1..2667
                       note = Description of Artificial Sequence: Synthetic
                        polynucleotide
source                 1..2667
                       mol_type = other DNA
                       organism = synthetic construct
SEQUENCE: 109
atgttatcaa gattgttcag aatgcatggt ctatttgttg cttctcaccc ttgggaagta  60
atagttggta ctgtaacatt aacgatctgt atgatgtcta tgaacatgtt taccggaaac  120
aacaagattt gtggttggaa ttatgagtgt cctaagctgg aagaggatgt gttgagttca  180
gacatcatca tacttactat aacaagatgc attgcaatat tgtatatcta cttccaattt  240
caaaacctta gacaattggg tagtaaatac atcctaggca tcgccggatt gttcactatt  300
ttctctagtt ttgttttctc aaccgtcgtt attcactttt tggacaaaga gttaactggt  360
ttgaacgaag ctctaccatt cttcttgctg ctggtagatt tgtccagagc ttccgcttta  420
gctaaattcg ctctgtcctc taattctcaa gatgaagtta gagagaatat agcaagggga  480
atggccatac ttggacctac tttcacactt gatgcccttg tcgaatgttt ggttattggg  540
gttggcacaa tgtccggcgt tagacagtta gaaatcatgt gttgttttgg ctgtatgagt  600
gtcttggcta actactttgt ctttatgaca ttctttccag cttgcgtttc tttggtattg  660
gagctgtcaa gagaatcaag agaaggcaga ccaatatggc aactatcaca tttcgccaga  720
gtgttagaag aggaggaaaa caaacctaat cctgtcacac agagagtgaa aatgatcatg  780
tctttgggtt tagtcctagt gcatgctcat tctagatgga tcgcagatcc atcccctcag  840
aattctacag ctgataactc taaagttagt ttaggtttag atgaaaatgt aagtaagagg  900
attgaacctt ccgtgtcttt gtggcaattc tacttatcaa aaatgatttc catggatatt  960
gaacaagtga taacgttgtc tttggcttta ttgttagccg ttaagtacat tttctttgag  1020
caagccgaaa cggaatctac attatcactg aaaaacccaa ttacatcccc agtcgttacc  1080
cagaaaaaga taactgatga ttgctgtaga agagatccag tgttggtcag gaatgatcaa  1140
aagttccacg ccatggagga ggaaactagg aaaaacagag aaaggaaagt tgaagttatc  1200
aagcctctat tagcagaaaa tgacacttca catagggcca ctttcgttgt cggcaattca  1260
tctcttttag gtacgtcatt ggagctggaa acacaggaac cagaaatgga actaccagtt  1320
gaaccaagac caaatgagga atgtttgcaa atactagaga acgctgaaaa gggagccaag  1380
ttcctatctg atgccgagat tatccagctg gtcaatgcca agcacattcc tgcctacaag  1440
ttggaaaccc ttatggagac acatgagaga ggtgtgtcta ttaggagaca attactatct  1500
aaaaagttac ctgaaccaag ttccctacaa tacctgcctt atagagatta caattactcc  1560
ttggtaatgg gagcttgttg tgaaaatgtc attgggtaca tgccaattcc agtgggtgtc  1620
gccggtccac tatgtttgga cggtaaggaa tttcaagtac ctatggcaac gactgaaggc  1680
tgcttagttg catctacaaa cagaggttgt agagccattg gattaggtgg cggtgcttct  1740
tcaagagtct tggctgacgg tatgactaga ggtcctgttg tgagatttcc tagggcctgt  1800
gactctgcag aagttaaggc ttggttggaa actccagaag gtttcaccgt aatcaaagag  1860
gcctttgatt ccacatcaag ggtggccaga ttacaaaaac tacacatgtc tgtcgctggg  1920
agaaatctgt atatcagatt tcaatccaga tccggcgacg caatgggtat gaatatgatt  1980
```

-continued

```
tcaaaaggga cagaaaaggc tttgtcaaag ctgcaggagt atttcccaga gatgcaaatc  2040
ttggccgtat ctggcaacta ttgcacagac aaaaagcctg ccgccatcaa ctggattgaa  2100
ggaagaggca aatctgtggt ttgtgaagct gtaattccag ccaaagttgt tagagaagtg  2160
ttaaagacca caacagaagc tatgattgaa gtaaacataa acaaaaactt agtagggtct  2220
gccatggctg gttcaattgg aggatacaac gctcatgctg ccaatattgt aaccgctatc  2280
tacatcgcat gtggacaaga tgctgcccaa aatgtcggtt cctcaaattg catcacattg  2340
atggaagcat ctggccctac aaacgaggat ttgtatatca gttgcacaat gccatctata  2400
gaaataggga ctgtgggagg aggaactaac ttacttccac agcaagcctg cttacaaatg  2460
ctgggtgtac aaggagcctg tagagataat ccaggggaga acgctagaca acttgccaga  2520
attgtttgtg ggacagttat ggctggtgaa cttagtctaa tggcagcttt ggctgctggg  2580
cacctggtga gatctcatat gattcataat agaagtaaga ttaaccttca agatttgcaa  2640
ggtacgtgta cgaaaaaggc tgcctaa                                       2667

SEQ ID NO: 110          moltype = AA  length = 888
FEATURE                 Location/Qualifiers
source                  1..888
                        mol_type = protein
                        organism = Bos taurus
SEQUENCE: 110
MLSRLFRMHG LFVASHPWEV IVGTVTLTIC MMSMNMFTGN NKICGWNYEC PKLEEDVLSS  60
DIIILTITRC IAILYIYFQF QNLRQLGSKY ILGIAGLFTI FSSFVFSTVV IHFLDKELTG  120
LNEALPFFLL LVDLSRASAL AKFALSSNSQ DEVRENIARG MAILGPTFTL DALVECLVIG  180
VGTMSGVRQL EIMCCFGCMS VLANYFVFMT FFPACVSLVL ELSRESREGR PIWQLSHFAR  240
VLEEEENKPN PVTQRVKMIM SLGLVLVHAH SRWIADPSPQ NSTADNSKVS LGLDENVSKR  300
IEPSVSLWQF YLSKMISMDI EQVITLSLAL LLAVKYIFFE QAETESTLSL KNPITSPVVT  360
QKKITDDCCR RDPVLVRNDQ KFHAMEEETR KNRERKVEVI KPLLAENDTS HRATFVVGNS  420
SLLGTSLELE TQEPEMELPV EPRPNEECLQ ILENAEKGAK FLSDAEIIQL VNAKHIPAYK  480
LETLMETHER GVSIRRQLLS KKLPEPSSLQ YLPYRDYNYS LVMGACCENV IGYMPIPVGV  540
AGPLCLDGKE FQVPMATTEG CLVASTNRGC RAIGLGGGAS SRVLADGMTR GPVVRFPRAC  600
DSAEVKAWLE TPEGFTVIKE AFDSTSRVAR LQKLHMSVAG RNLYIRFQSR SGDAMGMNMI  660
SKGTEKALSK LQEYFPEMQI LAVSGNYCTD KKPAAINWIE GRGKSVVCEA VIPAKVVREV  720
LKTTTEAMIE VNINKNLVGS AMAGSIGGYN AHAANIVTAI YIACGQDAAQ NVGSSNCITL  780
MEASGPTNED LYISCTMPSI EIGTVGGGTN LLPQQACLQM LGVQGACRDN PGENARQLAR  840
IVCGTVMAGE LSLMAALAAG HLVRSHMIHN RSKINLQDLQ GTCTKKAA                888

SEQ ID NO: 111          moltype = DNA  length = 1704
FEATURE                 Location/Qualifiers
misc_feature            1..1704
                        note = Description of Artificial Sequence: Synthetic
                         polynucleotide
source                  1..1704
                        mol_type = other DNA
                        organism = synthetic construct
SEQUENCE: 111
atggatttga gaaggaaatt accacctaag cctccatctt caacaacaac aaaacagcca  60
agtcataggt cccattctcc tacgccaatt ccaaaggctt cagatgcatt gcctcttcca  120
ttgtacctga ccaatacgtt tttcttcact cttttctttt ccgtagcata ttacctgttg  180
cataggtgga gagacaagat tagatccgga acacctttac acgttgtgac actgactgaa  240
ctatccgcaa ttgtactgct gattgcttcc ttcatctatc ttttaggctt tttcggtatt  300
gattttgtgc aatctttcac atcaagagaa aatgagcaac taaacaacga tgatcacaac  360
gtcgtgtcaa caaacaatgt tttatctgat agaaggttag tttacgacta tggattcgat  420
gtgacaggag acaacgataa cgataatgat gacgatgtta ttgtgaaaag tgtcgtttct  480
ggggaagtta attcttatag tttggaggct tccctaggag attgttacag agccgcaaag  540
attagaaaga gagccgtcga gagaattgtc gggagagaag tattaggctt gggtttcgag  600
ggatttgatt atgaatctat cctggggcaa tgttgtgaaa tgcctatcgg gtacgtccaa  660
gtgccagtag gtgtcgctgg acctttattg ttaaatggtg gggaattcat ggttccaatg  720
gctacaactg aaggctgtct tgtagcttcc actaatagag gttgtaaagc catatgctta  780
tcaggtggtg ccactgccat attgctaaaa gatggtatga caagagcccc agtagtgaga  840
ttcgccacag ctgagagagc ttcacaacta aagttttact tggaagatgg tgtcaatttc  900
gatacattgt ctgttgtctt taacaaaagt tcaagatttg ccagattgca aaacatccaa  960
tgctcaattg ccggtaaaaa cttgtacatt aggtttactt gctccacagg cgacgccatg  1020
ggtatgaaca tggtttcaaa aggagtacaa aatgtattag actttttaca aaatgatttt  1080
cctgatatgg acgtaattgg gatctcttgg aagttctgct ctgacaaaaa gccaacagct  1140
gtcaactgga ttgagggcag aggaaagtct gtcgttttcc aggccgtaat taccaaaaag  1200
gtggttagaa agtctgcact gaaccctcaa acttgcacat gtagaacttt gacctgttta  1260
agaccattat tggttctgct acttctggtt ttgctagtgg acttaatgca tatgcttcat  1320
atcgtgtctg ccgtgttcat cgctaccggt caagatccag ctcagaatat cgaatctagt  1380
cactgtatca ctatgatgga ggctgtcaac aatggtaagg atttgcacgt taatgttacg  1440
atgccatcta tagaagttgg cacggtggga ggtggcactc agctagcctc tcaatcagcc  1500
tgtttgaact tgcttggtgt aaagggtgcc tgtatagaat ccccaggatc aaacgcccag  1560
ttgttagcta gaatcgttgc tggttctgtt ctggcaggcg aattaagttt gatgtcagct  1620
ataagtgctg ggcaactagt taaatctcat atgaaataca ataggtctag tagagatatg  1680
tcagcaatag cttctaaggt ctaa                                          1704

SEQ ID NO: 112          moltype = AA  length = 567
FEATURE                 Location/Qualifiers
source                  1..567
                        mol_type = protein
                        organism = Artemisia annua
```

SEQUENCE: 112
MDLRRKLPPK PPSSTTTKQP SHRSHSPTPI PKASDALPLP LYLTNTFFFT LFFSVAYYLL 60
HRWRDKIRSG TPLHVVTLTE LSAIVLLIAS FIYLLGFFGI DFVQSFTSRE NEQLNNDDHN 120
VVSTNNVLSD RRLVYDYGFD VTGDNDNDND DDVIVKSVVS GEVNSYSLEA SLGDCYRAAK 180
IRKRAVERIV GREVLGLGFE GFDYESILGQ CCEMPIGYVQ VPVGVAGPLL LNGGEFMVPM 240
ATTEGCLVAS TNRGCKAICL SGGATAILLK DGMTRAPVVR FATAERASQL KFYLEDGVNF 300
DTLSVVFNKS SRFARLQNIQ CSIAGKNLYI RFTCSTGDAM GMNMVSKGVQ NVLDFLQNDF 360
PDMDVIGISW KFCSDKKPTA VNWIEGRGKS VVFQAVITKK VVRKSALNPQ TCTCRTLTCL 420
RPLLVLLLLV LLVDLMHMLH IVSAVFIATG QDPAQNIESS HCITMMEAVN NGKDLHVNVT 480
MPSIEVGTVG GGTQLASQSA CLNLLGVKGA CIESPGSNAQ LLARIVAGSV LAGELSLMSA 540
ISAGQLVKSH MKYNRSSRDM SAIASKV 567

SEQ ID NO: 113 moltype = DNA length = 1308
FEATURE Location/Qualifiers
misc_feature 1..1308
note = Description of Artificial Sequence: Synthetic polynucleotide
source 1..1308
mol_type = other DNA
organism = synthetic construct
SEQUENCE: 113
atgtttagaa gagctatact gttaggatgc tctgctgcca agacaccatg gtctgagtgt 60
tctaacgctc aattagttga tgcagttaag tctagaaaga tctcattcta cggtcttgaa 120
caagccttgg aaccagatta tagaagggct atcgaagtaa ggagagaggt tgtctctgaa 180
atcgcctcac aacagccaga agcaaaaaag aagcaatccg cattgcacac aataccattt 240
gagaattatg attggaataa ggtcgttggc caaaactgtg aaaacattat tggatacgtc 300
ccaataccac tgggcgttgc tggccctatt ttgattgatg gtaaagagta cccaatacca 360
atggctacaa cagaaggcgc tttggtcgct agtactcata gaggtgctag agctattaca 420
agatccggag gttgtaagac attgttatta ggtgaaggta tgacaagagc accagtggtt 480
gaattgcctt cattagagga agctgggcgt ttgcacaagt actgtaatga gaacttctta 540
tctttaaagg aagcatttga atcaactacc caatatggaa aacttaattc tttaaagtgc 600
gtactagctg gtagaaaagc ataccttaga ttcagagcca ctacaggcga tgctatgggc 660
atgaacatga taacaaaggg tgtagacaaa gcactgtctg ttctacagca acatttccct 720
tcaatggaaa tcctagccct aagtggtaat tactgtaccg acaaaaagcc atctgctgta 780
aattggattg atggcagagg taaatcagtg gttgcagaag ccactttatt ggctgatgtt 840
gtcgaagata ctctgaaatg tacagtcgat tctttggtat ccttgaatat cgacaaaaac 900
cttgttgggt cagctatggc tggttctgtt ggaggtttta acgcccaggc tgcaaacgct 960
gtggcagcca ttttcattgc aaccggtcaa gatcctgctc aagtggtaga aagttcaatg 1020
tgtatcacta caatgtccaa ggtaggtaac gatctattga tctctgtgac catgccttct 1080
atcgaggtcg gggtcgtggg aggagggact ggtcttgctg cccaaagagg atgcttagag 1140
ttaatagggt gcggaggccc atctaaggag tctcctggta ctaatgccca acttctaagt 1200
agagttgttg cagctggcgt tttatcagcc gaactttcct tgatgtccgg actggcagca 1260
ggtcatctat tgtcagcaca tatgagattg aacagaaaga agaaataa 1308

SEQ ID NO: 114 moltype = AA length = 435
FEATURE Location/Qualifiers
source 1..435
mol_type = protein
organism = Trypanosoma cruzi
SEQUENCE: 114
MFRRAILLGC SAAKTPWSEC SNAQLVDAVK SRKISFYGLE QALEPDYRRA IEVRREVVSE 60
IASQQPEAKK KQSALHTIPF ENYDWNKVVG QNCENIIGYV PIPLGVAGPI LIDGKEYPIP 120
MATTEGALVA STHRGARAIT RSGGCKTLLL GEGMTRAPVV ELPSLEEAGR LHKYCNENFL 180
SLKEAFESTT QYGKLNSLKC VLAGRKAYLR FRATTGDAMG MNMITKGVDK ALSVLQQHFP 240
SMEILALSGN YCTDKKPSAV NWIDGRGKSV VAEATLLADV VEDTLKCTVD SLVSLNIDKN 300
LVGSAMAGSV GGFNAQAANA VAAIFIATGQ DPAQVVESSM CITTMSKVGN DLLISVTMPS 360
IEVGVVGGGT GLAAQRGCLE LIGCGGPSKE SPGTNAQLLS RVVAAGVLSA ELSLMSGLAA 420
GHLLSAHMRL NRKKK 435

SEQ ID NO: 115 moltype = DNA length = 1281
FEATURE Location/Qualifiers
misc_feature 1..1281
note = Description of Artificial Sequence: Synthetic polynucleotide
source 1..1281
mol_type = other DNA
organism = synthetic construct
SEQUENCE: 115
atgcaatccc tggacaaaaa ctttagacac ttatcaagac aacagaagtt acaacagcta 60
gttgataaac aatggctatc agaggaacaa ttcaatattc tacttaacca ccccacttatt 120
gatgaagagg tagcaaactc attgatagaa aatgtcatcg cacagggcgc actgcctgtt 180
ggtttactac caaatatcat cgttgatgac aaagcatacg tcgtgcctat gatggtggaa 240
gagccatctg ttgttgccgc tgcttcatac ggcgctaaat tggtgaacca aacaggtggt 300
ttcaaaaccg tgtcctcaga acgtatcatg ataggtcaaa tagtatttga tggagtcgat 360
gataccgaga aactgtctgc agatatcaag gctcttgaaa aacaaatcca tcagattgca 420
gatgaggctt acccttctat taaggccaga ggtggaggct atcaaaggat cgccatcgat 480
acattcccag aacaacagtt gctttcattg aaggttttcg ttgatactaa ggatgctatg 540
ggcgctaata tgttaaacac aatcctagaa gcaatcacag cctttttgaa aaacgaattc 600
ccacaatctg atatcttgat gtctatcctt tccaaccacg caacagccag tgttgtcaag 660

-continued

```
gtccagggtg aaatagacgt taaggatttg gcaagaggag aacgtactgg agaagaggtc  720
gctaagagaa tggaaagagc atctgtgtta gctcaagtgg acattcatag agcagcaaca  780
cacaataagg gtgttatgaa tggcattcat gctgtagtct tggctacagg taatgatact  840
agaggtgcag aagcctctgc tcacgcttac gcttccaaag acggtcaata tagagggata  900
gctacatgga gatacgatca agagagacaa aggttaatag gaactataga agttccaatg  960
actctggcca ttgttggtgg cggtaccaag gtactgccta ttgctaaggc ctctttagaa  1020
ctgttaaacg tagaaagtgc ccaagagttg ggacatgttg tcgctgccgt tggactagct  1080
caaaacttcg ctgcatgtag agctttggtt tccgaaggta ttcaacaagg gcatatgtct  1140
ttgcaataca agtctttagc catcgtagtc ggggctaagg gcgatgaaat tgctcaggta  1200
gccgaagcac taaagcaaga gccaagagca aacactcaag ttgcagagag aattttgcaa  1260
gatttgagaa gtcaacaata a                                            1281

SEQ ID NO: 116         moltype = AA  length = 426
FEATURE                Location/Qualifiers
source                 1..426
                       mol_type = protein
                       organism = Staphylococcus aureus
SEQUENCE: 116
MQSLDKNFRH LSRQQKLQQL VDKQWLSEEQ FNILLNHPLI DEEVANSLIE NVIAQGALPV  60
GLLPNIIVDD KAYVVPMMVE EPSVVAAASY GAKLVNQTGG FKTVSSERIM IGQIVFDGVD  120
DTEKLSADIK ALEKQIHQIA DEAYPSIKAR GGGYQRIAID TFPEQQLLSL KVFVDTKDAM  180
GANMLNTILE AITAFLKNEF PQSDILMSIL SNHATASVVK VQGEIDVKDL ARGERTGEEV  240
AKRMERASVL AQVDIHRAAT HNKGVMNGIH AVVLATGNDT RGAEASAHAY ASKDGQYRGI  300
ATWRYDQERQ RLIGTIEVPM TLAIVGGGTK VLPIAKASLE LLNVESAQEL GHVVAAVGLA  360
QNFAACRALV SEGIQQGHMS LQYKSLAIVV GAKGDEIAQV AEALKQEPRA NTQVAERILQ  420
DLRSQQ                                                             426

SEQ ID NO: 117         moltype = DNA  length = 1311
FEATURE                Location/Qualifiers
misc_feature           1..1311
                       note = Description of Artificial Sequence: Synthetic
                        polynucleotide
source                 1..1311
                       mol_type = other DNA
                       organism = synthetic construct
SEQUENCE: 117
atgcaggtct taagattgga taggagacat tacaaaagtg gcaagattag aagagcaatg  60
agttctagaa ttcctggttt ctacaaattg tcagtcgagg aaagactgaa aaaggttgct  120
gaatttgcag ggttatctga tgaggaagtg aaagctgttt tgtcacaagg tttacctttg  180
gacgtagctg atagaatgat cgaaaatgtg atcggtacat ttgaattacc acttggtata  240
gcaaccaatt tccttattga tggcaaggat tatctaatcc ctatggctat agaggaacca  300
tcagtagttg cagctgcttc taacgcagct agaatggcca gagagtctgg cgggtttaca  360
actgattaca cagggtccct gatgattggt caaattcaag tcacaaaact gttgaatcca  420
aatgcagcta agttcgaagt tctacgtcaa aaagacgaaa tcatagaaag agcaaatgag  480
tgtgatccaa tgttggtgaa tttgggcggt ggatgtaaag atatagaagc aagggtgatc  540
gatacaatca tgggtaagat gctaattgtt catctgatcg ttgatgttaa agacgctatg  600
ggtgcaaatg ctgtcaacac tatgtgtgaa aaagttgctc ctttcatcga acgtattact  660
gggggaaagg tctatcttag aatcatttcc aacttggctg catatagact tgctagagca  720
aaggccgttt ttgacaaaga cgttattggc ggagaggagg ttgtagaagg gatcatgctt  780
gcatacgcct tcgctgccgc tgacccattt cgttgcgcca cccacaataa gggtatcatg  840
aatggcatat cagccttaat gatcgctaca ggaaacgact ttagagccat tgaagcagga  900
gctcattcct atgctgcaat aggtggatac aaaccactaa ctacctacga agttgataga  960
aaaggtaatc tagtaggcac aattgaaata cctatggcag taggcgtgat tggtggtgca  1020
accaaagtca acccactagc caagatctct cttaagatac taggagtgaa cactgctgaa  1080
gagttagcca gagtcgcagc cgctctaggt ttggctcaaa actttgctgc cttaagagcc  1140
ttggccacag aaggtatcca aagaggtcac atggaattac atgccaggaa cttagcaatc  1200
atggctggag ctactggaga tgaggttgac agagttgtag agattatggt gagagatggc  1260
aaaatcagat tggactacgc taaggaagta ttggagagac tgcgttccta a           1311

SEQ ID NO: 118         moltype = AA  length = 436
FEATURE                Location/Qualifiers
source                 1..436
                       mol_type = protein
                       organism = Archaeoglobus fulgidus
SEQUENCE: 118
MQVLRLDRRH YKSGKIRRAM SSRIPGFYKL SVEERLKKVA EFAGLSDEEV KAVLSQGLPL  60
DVADRMIENV IGTFELPLGI ATNFLIDGKD YLIPMAIEEP SVVAAASNAA RMARESGGFT  120
TDYTGSLMIG QIQVTKLLNP NAAKFEVLRQ KDEIIERANE CDPMLVNLGG GCKDIEARVI  180
DTIMGKMLIV HLIVDVKDAM GANAVNTMCE KVAPFIERIT GGKVYLRIIS NLAAYRLARA  240
KAVFDKDVIG GEEVVEGIML AYAFAAADPF RCATHNKGIM NGISALMIAT GNDFRAIEAG  300
AHSYAAIGGY KPLTTYEVDR KGNLVGTIEI PMAVGVIGGA TKVNPLAKIS LKILGVNTAE  360
ELARVAAALG LAQNFAALRA LATEGIQRGH MELHARNLAI MAGATGDEVD RVVEIMVRDG  420
KIRLDYAKEV LERLRS                                                  436

SEQ ID NO: 119         moltype = DNA  length = 1287
FEATURE                Location/Qualifiers
misc_feature           1..1287
                       note = Description of Artificial Sequence: Synthetic
                        polynucleotide
```

```
source                 1..1287
                       mol_type = other DNA
                       organism = synthetic construct
SEQUENCE: 119
atgtccttag attcaagact gccagctttc agaaatctgt ctccagctgc aagactagat  60
cacattggcc aacttttggg actaagtcat gacgacgttt ccctttttagc aaacgccggt  120
gctttaccaa tggatatcgc taatggtatg attgaaaatg taatcgggac ctttgaactg  180
ccatatgcag tggccagtaa ctttcagatc aatggccgtg acgtcttagt accattagtt  240
gtggaggaac ctagtatcgt tgctgcagcc tcttacatgg caaagttagc tagagccaat  300
ggtgggttca ctacatcttc atctgctcca ctaatgcatg cacaagtaca aattgtcggc  360
attcaggatc cactaaacgc aagattgtct ttactgcgta gaaaggatga gatcatagaa  420
ttagccaata ggaaggacca acttctgaat tcattgggcg gtggttgcag agacatagag  480
gtgcatacat ttgccgatac tccaagagga ccaatgcttg tagcacacct tattgtcgat  540
gtgcgtgatg ccatgggagc taatactgtt aacactatgg ctgaagcagt agcacctctg  600
atggaagcca taacaggtgg ccaggtaaga ttgagaatcc tttccaattt ggctgatctt  660
agattggcca gagcccaagt gagaatcact cctcagcaat tggaaactgc cgaattctca  720
ggtgaggcag taattgaggg tatcttggac gcatatgctt ttgccgctgt ggacccttac  780
agagccgcta cccacaacaa aggcataatg aacggtatcg atcctttgat cgtcgctaca  840
ggaaatgatt ggagagctgt tgaggcagga gctcatgcat acgcttgtag atccggacat  900
tacggttcat taacaacatg ggaaaaagat aacaatggac acttggtcgg gacattggaa  960
atgcctatgc cagttggttt agttggggt gctacaaaaa cccatcctct tgctcaattg  1020
tctttgagga tacttggtgt caaaactgct caagcactag ccgaaattgc cgttgctgtt  1080
ggtttggcac aaaacttggg tgcaatgcgt gctttagcta cagaaggcat ccaaagagga  1140
catatggctc tacacgctag aaacattgca gttgttgcag gagccagagg tgatgaggtt  1200
gattgggtgg ctagacaact tgtcgaatat catgatgtca gagcagacag ggctgtggca  1260
ttactgaaac agaagagagg tcaataa                                    1287

SEQ ID NO: 120         moltype = AA  length = 428
FEATURE                Location/Qualifiers
source                 1..428
                       mol_type = protein
                       organism = Pseudomonas mevalonii
SEQUENCE: 120
MSLDSRLPAF RNLSPAARLD HIGQLLGLSH DDVSLLANAG ALPMDIANGM IENVIGTFEL  60
PYAVASNFQI NGRDVLVPLV VEEPSIVAAA SYMAKLARAN GGFTTSSSAP LMHAQVQIVG  120
IQDPLNARLS LLRRKDEIIE LANRKDQLLN SLGGGCRDIE VHTFADTPRG PMLVAHLIVD  180
VRDAMGANTV NTMAEAVAPL MEAITGGQVR LRILSNLADL RLARAQVRIT PQQLETAEFS  240
GEAVIEGILD AYAFAAVDPY RAATHNKGIM NGIDPLIVAT GNDWRAVEAG AHAYACRSGH  300
YGSLTTWEKD NNGHLVGTLE MPMPVGLVGG ATKTHPLAQL SLRILGVKTA QALAEIAVAV  360
GLAQNLGAMR ALATEGIQRG HMALHARNIA VVAGARGDEV DWVARQLVEY HDVRADRAVA  420
LLKQKRGQ                                                         428

SEQ ID NO: 121         moltype = AA  length = 361
FEATURE                Location/Qualifiers
source                 1..361
                       mol_type = protein
                       organism = Stevia rebaudiana
SEQUENCE: 121
MALVNPTALF YGTSIRTRPT NLLNPTQKLR PVSSSSLPSF SSVSAILTEK HQSNPSENNN  60
LQTHLETPFN FDSYMLEKVN MVNEALDASV PLKDPIKIHE SMRYSLLAGG KRIRPMMCIA  120
ACEIVGGNIL NAMPAACAVE MIHTMSLVHD DLPCMDNDDF RRGKPISHKV YGEEMAVLTG  180
DALLSLSFEH IATATKGVSK DRIVRAIGEL ARSVGSEGLV AGQVVDILSE GADVGLDHLE  240
YIHIHKTAML LESSVVIGAI MGGGSDQQIE KLRKFARSIG LLFQVVDDIL DVTKSTEELG  300
KTAGKDLLTD KTTYPKLLGI EKSREFAEKL NKEAQEQLSG FDRRKAAPLI ALANYNAYRQ  360
N                                                                361

SEQ ID NO: 122         moltype = AA  length = 342
FEATURE                Location/Qualifiers
source                 1..342
                       mol_type = protein
                       organism = Gibberella fujikuroi
SEQUENCE: 122
MAEQQISNLL SMFDASHASQ KLEITVQMMD TYHYRETPPD SSSSEGGSLS RYDERRVSLP  60
LSHNAASPDI VSQLCFSTAM SSELNHRWKS QRLKVADSPY NYILTLPSKG IRGAFIDSLN  120
VWLEVPEDET SVIKEVIGML HNSSLIIDDF QDNSPLRRGK PSTHTVFGPA QAINTATYVI  180
VKAIEKIQDI VGHDALADVT GTITTIFQGQ AMDLWWTANA IVPSIQEYLL MVNDKTGALF  240
RLSLELLALN SEASISDSAL ESLSSAVSLL GQYFQIRDDY MNLIDNKYTD QKGFCEDLDE  300
GKYSLTLIHA LQTDSSDLLT NILSMRRVQG KLTAQKRCWF WK                   342

SEQ ID NO: 123         moltype = AA  length = 300
FEATURE                Location/Qualifiers
source                 1..300
                       mol_type = protein
                       organism = Mus musculus
SEQUENCE: 123
MEKTKEKAER ILLEPYRYLL QLPGKQVRSK LSQAFNHWLK VPEDKLQIII EVTEMLHNAS  60
LLIDDIEDSS KLRRGFPVAH SIYGVPSVIN SANYVYFLGL EKVLTLDHPD AVKLFTRQLL  120
ELHQGQGLDI YWRDTYTCPT EEEYKAMVLQ KTGGLFGLAV GLMQLFSDYK EDLKPLLDTL  180
GLFFQIRDDY ANLHSKEYSE NKSFCEDLTE GKFSFPTIHA IWSRPESTQV QNILRQRTEN  240
```

-continued

```
IDIKKYCVQY LEDVGSFAYT RHTLRELEAK AYKQIEACGG NPSLVALVKH LSKMFTEENK  300

SEQ ID NO: 124         moltype = AA  length = 339
FEATURE                Location/Qualifiers
source                 1..339
                       mol_type = protein
                       organism = Thalassiosira pseudonana
SEQUENCE: 124
MARFYFLNAL LMVISLQSTT AFTPAKLAYP TTTTALNVAS AETSFSLDEY LASKIGPIES  60
ALEASVKSRI PQTDKICESM AYSLMAGGKR IRPVLCIAAC EMFGGSQDVA MPTAVALEMI  120
HTMSLIHDDL PSMDNDDLRR GKPTNHVVFG EDVAILAGDS LLSTSFEHVA RETKGVSAEK  180
IVDVIARLGK SVGAEGLAGG QVMDLECEAK PGTTLDDLKW IHIHKTATLL QVAVASGAVL  240
GGATPEEVAA CELFAMNIGL AFQVADDILD VTASSEDLGK TAGKDEATDK TTYPKLLGLE  300
ESKAYARQLI DEAKESLAPF GDRAAPLLAI ADFIIDRKN                        339

SEQ ID NO: 125         moltype = AA  length = 355
FEATURE                Location/Qualifiers
source                 1..355
                       mol_type = protein
                       organism = Streptomyces clavuligerus
SEQUENCE: 125
MHLAPRRVPR GRRSPPDRVP ERQGALGRRR GAGSTGCARA AAGVHRRRGG GEADPSAAVH  60
RGWQAGGGTG LPDEVVSTAA ALEMFHAFAL IHDDIMDDSA TRRGSPTVHR ALADRLGAAL  120
DPDQAGQLGV STAILVGDLA LTWSDELLYA PLTPHRLAAV LPLVTAMRAE TVHGQYLDIT  180
SARRPGTDTS LALRIARYKT AAYTMERPLH IGAALAGARP ELLAGLSAYA LPAGEAFQLA  240
DDLLGVFGDP RRTGKPDLDD LRGGKHTVLV ALAREHATPE QRHTLDTLLG TPGLDRQGAS  300
RLRCVLVATG ARAEAERLIT ERRDQALTAL NALTLPPPLA EALARLTLGS TAHPA       355

SEQ ID NO: 126         moltype = AA  length = 330
FEATURE                Location/Qualifiers
source                 1..330
                       mol_type = protein
                       organism = Sulfulobus acidicaldarius
SEQUENCE: 126
MSYFDNYFNE IVNSVNDIIK SYISGDVPKL YEASYHLFTS GGKRLRPLIL TISSDLFGGQ  60
RERAYYAGAA IEVLHTFTLV HDDIMDQDNI RRGLPTVHVK YGLPLAILAG DLLHAKAFQL  120
LTQALRGLPS ETIIKAFDIF TRSIIIISEG QAVDMEFEDR IDIKEQEYLD MISRKTAALF  180
SASSSIGALI AGANDNDVRL MSDFGTNLGI AFQIVDDILG LTADEKELGK PVFSDIREGK  240
KTILVIKTLE LCKEDEKKIV LKALGNKSAS KEELMSSADI IKKYSLDYAY NLAEKYYKNA  300
IDSLNQVSSK SDIPGKALKY LAEFTIRRRK                                  330

SEQ ID NO: 127         moltype = AA  length = 297
FEATURE                Location/Qualifiers
source                 1..297
                       mol_type = protein
                       organism = Synechococcus sp.
SEQUENCE: 127
MVAQTFNLDT YLSQRQQQVE EALSAALVPA YPERIYEAMR YSLLAGGKRL RPILCLAACE  60
LAGGSVEQAM PTACALEMIH TMSLIHDDLP AMDNDDFRRG KPTNHKVFGE DIAILAGDAL  120
LAYAFEHIAS QTRGVPPQLV LQVIARIGHA VAATGLVGGQ VVDLESEGKA ISLETLEYIH  180
SHKTGALLEA SVVSGGILAG ADEELLARLS HYARDIGLAF QIVDDILDVT ATSEQLGKTA  240
GKDQAAAKAT YPSLLGLEAS RQKAEELIQS AKEALRPYGS QAEPLLALAD FITRRQH     297

SEQ ID NO: 128         moltype = AA  length = 371
FEATURE                Location/Qualifiers
source                 1..371
                       mol_type = protein
                       organism = Arabidopsis thaliana
SEQUENCE: 128
MASVTLGSWI VVHHHNHHHP SSILTKSRSR SCPITLTKPI SFRSKRTVSS SSSIVSSSVV  60
TKEDNLRQSE PSSFDFMSYI ITKAELVNKA LDSAVPLREP LKIHEAMRYS LLAGGKRVRP  120
VLCIAACELV GGEESTAMPA ACAVEMIHTM SLIHDDLPCM DNDDLRRGKP TNHKVFGEDV  180
AVLAGDALLS FAFEHLASAT SSDVVSPVRV VRAVGELAKA IGTEGLVAGQ VVDISSEGLD  240
LNDVGLEHLE FIHLHKTAAL LEASAVLGAI VGGGSDDEIE RLRKFARCIG LLFQVVDDIL  300
DVTKSSKELG KTAGKDLIAD KLTYPKIMGL EKSREFAEKL NREARDQLLG FDSDKVAPLL  360
ALANYIAYRQ N                                                      371

SEQ ID NO: 129         moltype = AA  length = 787
FEATURE                Location/Qualifiers
source                 1..787
                       mol_type = protein
                       organism = Stevia rebaudiana
SEQUENCE: 129
MKTGFISPAT VFHHRISPAT TFRHHLSPAT TNSTGIVALR DINFRCKAVS KEYSDLLQKD  60
EASFTKWDDD KVKDHLDTNK NLYPNDEIKE FVESVKAMFG SMNDGEINVS AYDTAWVALV  120
QDVDGSGSPQ FPSSLEWIAN NQLSDGSWGD HLLFSAHDRI INTLACVIAL TSWNVHPSKC  180
EKGLNFLREN ICKLEDENAE HMPIGFEVTF PSLIDIAKKL NIEVPEDTPA LKEIYARRDI  240
KLTKIPMEVL HKVPTTLLHS LEGMPDLEWE KLLKLQCKDG SFLFSPSSTA FALMQTKDEK  300
CLQYLTNIVT KFNGGVPNVY PVDLFEHIWV VDRLQRLGIA RYFKSEIKDC VEYINKYWTK  360
```

-continued

```
NGICWARNTH VQDIDDTAMG FRVLRAHGYD VTPDVFRQFE KDGKFVCFAG QSTQAVTGMF  420
NVYRASQMLF PGERILEDAK KFSYNYLKEK QSTNELLDKW IIAKDLPGEV GYALDIPWYA  480
SLPRLETRYY LEQYGGEDDV WIGKTLYRMG YVSNNTYLEM AKLDYNNYVA VLQLEWYTIQ  540
QWYVDIGIEK FESDNIKSVL VSYYLAAASI FEPERSKERI AWAKTTILVD KITSIFDSSQ  600
SSKEDITAFI DKFRNKSSSK KHSINGEPWH EVMVALKKTL HGFALDALMT HSQDIHPQLH  660
QAWEMWLTKL QDGVDVTAEL MVQMINMTAG RWVSKELLTH PQYQRLSTVT NSVCHDITKL  720
HNFKENSTTV DSKVQELVQL VFSDTPDDLD QDMKQTFLTV MKTFYYKAWC DPNTINDHIS  780
KVFEIVI                                                            787

SEQ ID NO: 130         moltype = AA  length = 527
FEATURE                Location/Qualifiers
source                 1..527
                       mol_type = protein
                       organism = Streptomyces clavuligerus
SEQUENCE: 130
MPDAHDAPPP QIRQRTLVDE ATQLLTESAE DAWGEVSVSE YETARLVAHA TWLGGHATRV  60
AFLLERQHED GSWGPPGGYR LVPTLSAVHA LLTCLASPAQ DHGVPHDRLL RAVDAGLTAL  120
RRLGTSDSPP DTIAVELVIP SLLEGIQHLL DPAHPHSRPA FSQHRGSLVC PGGLDGRTLG  180
ALRSHAAAGT PVPGKVWHAS ETLGLSTEAA SHLQPAQGII GGSAAATATW LTRVAPSQQS  240
DSARRYLEEL QHRYSGPVPS ITPITYFERA WLLNNFAAAG VPCEAPAALL DSLEAALTPQ  300
GAPAGAGLPP DADDTAAVLL ALATHGRGRR PEVLMDYRTD GYFQCFIGER TPSISTNAHV  360
LETLGHHVAQ HPQDRARYGS AMDTASAWLL AAQKQDGSWL DKWHASPYYA TVCCTQALAA  420
HASPATAPAR QRAVRWVLAT QRSDGGWGLW HSTVEETAYA LQILAPPSGG GNIPVQQALT  480
RGRARLCGAL PLTPLWHDKD LYTPVRVVRA ARAAALYTTR DLLLPPL                527

SEQ ID NO: 131         moltype = AA  length = 516
FEATURE                Location/Qualifiers
source                 1..516
                       mol_type = protein
                       organism = Bradyrhizobium japonicum
SEQUENCE: 131
MNALSEHILS ELRRLLSEMS DGGSVGPSVY DTAQALRFHG NVTGRQDAYA WLIAQQQADG  60
GWGSADFPLF RHAPTWAALL ALQRADPLPG AADAVQTATR FLQRQPDPYA HAVPEDAPIG  120
AELILPQFCG EAAWLLGGVA FPRHPALLPL RQACLVKLGA VAMLPSGHPL LHSWEAWGTS  180
PTTACPDDDG SIGISPAATA AWRAQAVTRG STPQVGRADA YLQMASRATR SGIEGVFPNV  240
WPINVFEPCW SLYTLHLAGL FAHPALAEAV RVIVAQLEAR LGVHGLGPAL HFAADADDTA  300
VALCVLHLAG RDPAVDALRH FEIGELFVTF PGERNASVST NIHALHALRL LGKPAAGASA  360
YVEANRNPHG LWDNEKWHVS WLYPTAHAVA ALAQGKPQWR DERALAALLQ AQRDDGGWGA  420
GRGSTFEETA YALFALHVMD GSEEATGRRR IAQVVARALE WMLARHAAHG LPQTPLWIGK  480
ELYCPTRVVR VAELAGLWLA LRWGRRVLAE GAGAAP                            516

SEQ ID NO: 132         moltype = AA  length = 784
FEATURE                Location/Qualifiers
source                 1..784
                       mol_type = protein
                       organism = Stevia rebaudiana
SEQUENCE: 132
MNLSLCIASP LLTKSNRPAA LSAIHTASTS HGGQTNPTNL IIDTTKERIQ KQFKNVEISV  60
SSYDTAWVAM VPSPNSPKSP CFPECLNWLI NNQLNDGSWG LVNHTHNHNH PLLKDSLSST  120
LACIVALKRW NVGEDQINKG LSFIESNLAS ATEKSQPSPI GFDIIFPGLL EYAKNLDINL  180
LSKQTDFSLM LHKRELEQKR CHSNEMDGYL AYISEGLGNL YDWNMVKKYQ MKNGSVFNSP  240
SATAAAFINH QNPGCLNYLN SLLDKFGNAV PTVYPHDLFI RLSMVDTIER LGISHHFRVE  300
IKNVLDETYR CWVERDEQIF MDVVTCALAF RLLRINGYEV SPDPLAEITN ELALKDEYAA  360
LETYHASHIL YQEDLSSGKQ ILKSADFLKE IISTDSNRLS KLIHKEVENA LKFPINTGLE  420
RINTRRNIQL YNVDNTRILK TTYHSSNISN TDYLRLAVED FYTCQSIYRE ELKGLERWVV  480
ENKLDQLKFA RQKTAYCYFS VAATLSSPEL SDARISWAKN GILTTVVDDF FDIGGTIDEL  540
TNLIQCVEKW NVDVDKDCCS EHVRILFLAL KDAICWIGDE AFKWQARDVT SHVIQTWLEL  600
MNSMLREAIW TRDAYVPTLN EYMENAYVSF ALGPIVKPAI YFVGPKLSEE IVESSEYHNL  660
FKLMSTQGRL LNDIHSFKRE FKEGKLNAVA LHLSNGESGK VEEEVVEEMM MMIKNKRKEL  720
MKLIFEENGS IVPRACKDAF WNMCHVLNFF YANDDGFTGN TILDTVKDII YNPLVLVNEN  780
EEQR                                                               784

SEQ ID NO: 133         moltype = AA  length = 784
FEATURE                Location/Qualifiers
source                 1..784
                       mol_type = protein
                       organism = Stevia rebaudiana
SEQUENCE: 133
MNLSLCIASP LLTKSSRPTA LSAIHTASTS HGGQTNPTNL IIDTTKERIQ KLFKNVEISV  60
SSYDTAWVAM VPSPNSPKSP CFPECLNWLI NNQLNDGSWG LVNHTHNHNH PLLKDSLSST  120
LACIVALKRW NVGEDQINKG LSFIESNLAS ATDKSQPSPI GFDIIFPGLL EYAKNLDINL  180
LSKQTDFSLM LHKRELEQKR CHSNEIDGYL AYISEGLGNL YDWNMVKKYQ MKNGSVFNSP  240
SATAAAFINH QNPGCLNYLN SLLDKFGNAV PTVYPLDLYI RLSMVDTIER LGISHHFRVE  300
IKNVLDETYR CWVERDEQIF MDVVTCALAF RLLRIHGYKV SPDQLAEITN ELAFKDEYAA  360
LETYHASQIL YQEDLSSGKQ ILKSADFLKG ILSTDSNRLS KLIHKEVENA LKFPINTGLE  420
RINTRRNIQL YNVDNTRILK TTYHSSNISN TYYLRLAVED FYTCQSIYRE ELKGLERWVV  480
QNKLDQLKFA RQKTAYCYFS VAATLSSPEL SDARISWAKN GILTTVVDDF FDIGGTIDEL  540
TNLIQCVEKW NVDVDKDCCS EHVRILFLAL KDAICWIGDE AFKWQARDVT SHVIQTWLEL  600
MNSMLREAIW TRDAYVPTLN EYMENAYVSF ALGPIVKPAI YFVGPKLSEE IVESSEYHNL  660
```

-continued

```
FKLMSTQGRL LNDIHSFKRE FKEGKLNAVA LHLSNGESGK VEEEVVEEMM MMIKNKRKEL  720
MKLIFEENGS IVPRACKDAF WNMCHVLNFF YANDDGFTGN TILDTVKDII YNPLVLVNEN  780
EEQR                                                              784

SEQ ID NO: 134         moltype = AA  length = 590
FEATURE                Location/Qualifiers
source                 1..590
                       mol_type = protein
                       organism = Zea mays
SEQUENCE: 134
MAMPVKLTPA SLSLKAVCCR FSSGGHALRF GSSLPCWRRT PTQRSTSSST TRPAAEVSSG  60
KSKQHDQEAS EATIRQQLQL VDVLENMGIS RHFAAEIKCI LDRTYRSWLQ RHEEIMLDTM  120
TCAMAFRILR LNGYNVSSDE LYHVVEASGL HNSLGGYLND TRTLLELHKA STVSISEDES  180
ILDSIGSRSR TLLREQLESG GALRKPSLFK EVEHALDGPF YTTLDRLHHR WNIENFNIIE  240
QHMLETPYLS NQHTSRDILA LSIRDFSSSQ FTYQQELQHL ESWVKECRLD QLQFARQKLA  300
YFYLSAAGTM FSPELSDART LWAKNGVLTT IVDDFFDVAG SKEELENLVM LVEMWDEHHK  360
VEFYSEQVEI IFSSIYDSVN QLGEKASLVQ DRSITKHLVE IWLDLLKSMM TEVEWRLSKY  420
VPTEKEYMIN ASLIFGLGPI VLPALYFVGP KISESIVKDP EYDELFKLMS TCGRLLNDVQ  480
TFEREYNEGK LNSVSLLVLH GGPMSISDAK RKLQKPIDTC RRDLLSLVLR EESVVPRPCK  540
ELFWKMCKVC YFFYSTTDGF SSQVERAKEV DAVINEPLKL QGSHTLVSDV            590

SEQ ID NO: 135         moltype = AA  length = 743
FEATURE                Location/Qualifiers
source                 1..743
                       mol_type = protein
                       organism = Populus trichocarpa
SEQUENCE: 135
MQNFHGTKER IKKMFDKIEL SVSSYDTAWV AMVPSPDCPE TPCFPECTKW ILENQLGDGS  60
WSLPHGNPLL VKDALSSTLA CILALKRWGI GEEQINKGLR FIELNSASVT DNEQHKPIGF  120
DIIFPGMIEY AIDLDLNLPL KPTDINSMLH RRALELTSGG GKNLEGRRAY LAYVSEGIGK  180
LQDWEMAMKY QRKNGSLFNS PSTTAAAFIH IQDAECLHYI RSLLQKFGNA VPTIYPLDIY  240
ARLSMVDALE RLGIDRHFRK ERKFVLDETY RFWLQGEEEI FSDNATCALA FRILRLNGYD  300
VSLEDHFSNS LGGYLKDSGA ALELYRALQL SYPDESLLEK QNSRTSYFLK QGLSNVSLCG  360
DRLRKNIIGE VHDALNFSDH ANLQRLAIRR RIKHYATDDT RILKTSYRCS TIGNQDFLKL  420
AVEDFNICQS IQREEFKHIE RWVVERRLDK LKFARQKEAY CYFSAAATLF APELSDARMS  480
WAKNGVLTTV VDDFFDVGGS EEELVNLIEL IERWDVNGSA DFCSEEVEII YSAIHSTISE  540
IGDKSFGWQG RDVKSQVIKI WLDLLKSMLT EAQWSSNKSV PTLDEYMTTA HVSFALGPIV  600
LPALYFVGPK LSEEVAGHPE LLNLYKVTST CGRLLNDWRS FKRESEEGKL NAISLYMIHS  660
GGASTEEETI EHFKGLIDSQ RRQLLQLVLQ EKDSIIPRPC KDLFWNMIKL LHTFYMKDDG  720
FTSNEMRNVV KAIINEPISL DEL                                         743

SEQ ID NO: 136         moltype = AA  length = 983
FEATURE                Location/Qualifiers
source                 1..983
                       mol_type = protein
                       organism = Phomopsis amygdali
SEQUENCE: 136
MEFDEPLVDE ARSLVQRTLQ DYDDRYGFGT MSCAAYDTAW VSLVTKTVDG RKQWLFPECF  60
EFLLETQSDA GGWEIGNSAP IDGILNTAAS LLALKRHVQT EQIIQPQHDH KDLAGRAERA  120
AASLRAQLAA LDVSTTEHVG FEIIVPAMLD PLEAEDPSLV FDFPARKPLM KIHDAKMSRF  180
RPEYLYGKQP MTALHSLEAF IGKIDFDKVR HHRTHGSMMG SPSSTAAYLM HASQWDGDSE  240
AYLRHVIKHA AGQGTGAVPS AFPSTHFESS WILTTLFRAG FSASHLACDE LNKLVEILEG  300
SFEKEGGAIG YAPGFQADVD DTAKTISTLA VLGRDATPRQ MIKVFEANTH FRTYPGERDP  360
SLTANCNALS ALLHQPDAAM YGSQIQKITK FVCDYWWKSD GKIKDKWNTC YLYPSVLLVE  420
VLVDLVSLLE QGKLPDVLDQ ELQYRVAITL FQACLRPLLD QDAEGSWNKS IEATAYGILI  480
LTEARRVCFF DRLSEPLNEA IRRGIAFADS MSGTEAQLNY IWIEKVSYAP ALLTKSYLLA  540
ARWAAKSPLG ASVGSSLWTP PREGLDKHVR LFHQAELFRS LPEWELRASM IEAALFTPLL  600
RAHRLDVFPR QDVGEDKYLD VVPFFWTAAN NRDRTYASTL FLYDMCFIAM LNFQLDEFME  660
ATAGILFRDH MDDLRQLIHD LLAEKTSPKS SGRSSQGTKD ADSGIEEDVS MSDSASDSQD  720
RSPEYDLVFS ALSTFTKHVL QHPSIQSASV WDRKLLAREM KAYLLAHIQQ AEDSTPLSEL  780
KDVPQKTDVT RVSTSTTTFF NWVRTTSADH ISCPYSFHFV ACHLGAALSP KGSNGDCYPS  840
AGEKFLAAAV CRHLATMCRM YNDLGSAERD SDEGNLNSLD FPEFADSAGN GGIEIQKAAL  900
LRLAEFERDS YLEAFRRLQD ESNRVHGPAG GDEARLSRRR MAILEFFAQQ VDLYGQVYVI  960
RDISARIPKN EVEKKRKLDD AFN                                         983

SEQ ID NO: 137         moltype = AA  length = 881
FEATURE                Location/Qualifiers
source                 1..881
                       mol_type = protein
                       organism = Physcomitrella patens
SEQUENCE: 137
MASSTLIQNR SCGVTSSMSS FQIFRGQPLR FPGTRTPAAV QCLKKRRCLR PTESVLESSP  60
GSGSYRIVTG PSGINPSSNG HLQEGSLTHR LPIPMEKSID NFQSTLYVSD IWSETLQRTE  120
CLLQVTENVQ MNEWIEEIRM YFRNMTLGEI SMSPYDTAWV ARVPALDGSH GPQFHRSLQW  180
IIDNQLPDGD WGEPSLFLGY DRVCNTLACV IALKTWGVGA QNVERGIQFL QSNIYKMEED  240
DANHMPIGFE IVFPAMMEDA KALGLDLPYD ATILQQISAE REKKMKKIPM AMVYKYPTTL  300
LHSLEGLHRE VDWNKLLQLQ SENGSFLYSP ASTACALMYT KDVKCFDYLN QLLIKFDHAC  360
PNVYPVDLFE RLWMVDRLQR LGISRYFERE IRDCLQYVYR YWKDCGIGWA SNSSVQDVDD  420
TAMAFRLLRT HGFDVKEDCF RQFFKDGEFF CFAGQSSQAV TGMFNLSRAS QTLFPGESLL  480
```

-continued

```
KKARTFSRNF LRTKHENNEC FDKWIITKDL AGEVEYNLTF PWYASLPRLE HRTYLDQYGI  540
DDIWIGKSLY KMPAVTNEVF LKLAKADFNM CQALHKKELE QVIKWNASCQ FRDLEFARQK  600
SVECYFAGAA TMFEPEMVQA RLVWARCCVL TTVLDDYFDH GTPVEELRVF VQAVRTWNPE  660
LINGLPEQAK ILFMGLYKTV NTIAEEAFMA QKRDVHHHLK HYWDKLITSA LKEAEWAESG  720
YVPTFDEYME VAEISVALEP IVCSTLFFAG HRLDEDVLDS YDYHLVMHLV NRVGRILNDI  780
QGMKREASQG KISSVQIYME EHPSVPSEAM AIAHLQELVD NSMQQLTYEV LRFTAVPKSC  840
KRIHLNMAKI MHAFYKDTDG FSSLTAMTGF VKKVLFEPVP E                      881

SEQ ID NO: 138          moltype = AA  length = 513
FEATURE                 Location/Qualifiers
source                  1..513
                        mol_type = protein
                        organism = Stevia rebaudiana
SEQUENCE: 138
MDAVTGLLTV PATAITIGGT AVALAVALIF WYLKSYTSAR RSQSNHLPRV PEVPGVPLLG  60
NLLQLKEKKP YMTFTRWAAT YGPIYSIKTG ATSMVVVSSN EIAKEALVTR FQSISTRNLS  120
KALKVLTADK TMVAMSDYDD YHKTVKRHIL TAVLGPNAQK KHRIHRDIMM DNISTQLHEF  180
VKNNPEQEEV DLRKIFQSEL FGLAMRQALG KDVESLYVED LKITMNRDEI FQVLVVDPMM  240
GAIDVDWRDF FPYLKWVPNK KFENTIQQMY IRREAVMKSL IKEHKKRIAS GEKLNSYIDY  300
LLSEAQTLTD QQLLMSLWEP IIESSDTTMV TTEWAMYELA KNPKLQDRLY RDIKSVCGSE  360
KITEEHLSQL PYITAIFHET LRRHSPVPII PLRHVHEDTV LGGYHVPAGT ELAVNIYGCN  420
MDKNVWENPE EWNPERFMKE NETIDFQKTM AFGGGKRVCA GSLQALLTAS IGIGRMVQEF  480
EWKLKDMTQE EVNTIGLTTQ MLRPLRAIIK PRI                                513

SEQ ID NO: 139          moltype = AA  length = 509
FEATURE                 Location/Qualifiers
source                  1..509
                        mol_type = protein
                        organism = Arabidopsis thaliana
SEQUENCE: 139
MAFFSMISIL LGFVISSFIF IFFFKKLLSF SRKNMSEVST LPSVPVVPGF PVIGNLLQLK  60
EKKPHKTFTR WSEIYGPIYS IKMGSSSLIV LNSTETAKEA MVTRFSSIST RKLSNALTVL  120
TCDKSMVATS DYDDFHKLVK RCLLNGLLGA NAQKRKRHYR DALIENVSSK LHAHARDHPQ  180
EPVNFRAIFE HELFGVALKQ AFGKDVESIY VKELGVTLSK DEIFKVLVHD MMEGAIDVDW  240
RDFFPYLKWI PNKSFEARIQ QKHKRRLAVM NALIQDRLKQ NGSESDDDCY LNFLMSEAKT  300
LTKEQIAILV WETIIETADT TLVTTEWAIY ELAKHPSVQD RLCKEIQNVC GGEKFKEEQL  360
SQVPYLNGVF HETLRKYSPA PLVPIRYAHE DTQIGGYHVP AGSEIAINIY GCNMDKKRWE  420
RPEDWWPERF LDDGKYETSD LHKTMAFGAG KRVCAGALQA SLMAGIAIGR LVQEFEWKLR  480
DGEEENVDTY GLTSQKLYPL MAIINPRRS                                     509

SEQ ID NO: 140          moltype = AA  length = 525
FEATURE                 Location/Qualifiers
source                  1..525
                        mol_type = protein
                        organism = Gibberella fujikoroi
SEQUENCE: 140
MSKSNSMNST SHETLFQQLV LGLDRMPLMD VHWLIYVAFG AWLCSYVIHV LSSSSTVKVP  60
VVGYRSVFEP TWLLRLRFVW EGGSIIGQGY NKFKDSIFQV RKLGTDIVII PPNYIDEVRK  120
LSQDKTRSVE PFINDFAGQY TRGMVFLQSD LQNRVIQQRL TPKLVSLTKV MKEELDYALT  180
KEMPDMKNDE WVEVDISSIM VRLISRISAR VFLGPEHCRN QEWLTTTAEY SESLFITGFI  240
LRVVPHILRP FIAPLLPSYR TLLRNVSSGR RVIGDIIRSQ QGDGNEDILS WMRDAATGEE  300
KQIDNIAQRM LILSLASIHT TAMTMTHAMY DLCACPEYIE PLRDEVKSVV GASGWDKTAL  360
NRFHKLDSFL KESQRFNPVF LLTFNRIYHQ SMTLSDGTNI PSGTRIAVPS HAMLQDSAHV  420
PGPTPPTEFD GFRYSKIRSD SNYAQKYLFS MTDSSNMAFG YGKYACPGRF YASNEMKLTL  480
AILLLQFEFK LPDGKGRPRN ITIDSDMIPD PRARLCVRKR SLRDE                  525

SEQ ID NO: 141          moltype = AA  length = 499
FEATURE                 Location/Qualifiers
source                  1..499
                        mol_type = protein
                        organism = Trametes versicolor
SEQUENCE: 141
MEDPTVLYAC LAIAVATFVV RWYRDPLRSI PTVGGSDLPI LSYIGALRWT RRGREILQEG  60
YDGYRGSTFK IAMLDRWIVI ANGPKLADEV RRRPDEELNF MDGLGAFVQT KYTLGEAIHN  120
DPYHVDIIRE KLTRGLPAVL PDVIEELTLA VRQYIPTEGD EWVSVNCSKA ARDIVARASN  180
RVFVGLPACR NQGYLDLAID FTLSVVKDRA IINMFPELLK PIVGRVVGNA TRNVRRAVPF  240
VAPLVEERRR LMEEYGEDWS EKPNDMLQWI MDEAASRDSS VKAIAERLLM VNFAAIHTSS  300
NTITHALYHL AEMPETLQPL REEIEPLVKE EGWTKAAMGK MWWLDSFLRE SQRYNGINIV  360
SLTRMADKDI TLSDGTFLPK GTLVAVPAYS THRDDAVYAD ALVFDPFRFS RMRAREGEGT  420
KHQFVNTSVE YVPFGHGKHA CPGRFFAANE LKAMLAYIVL NYDVKLPGDG KRPLNMYWGP  480
TVLPAPAGQV LFRKRQVSL                                                499

SEQ ID NO: 142          moltype = AA  length = 525
FEATURE                 Location/Qualifiers
source                  1..525
                        mol_type = protein
                        organism = Stevia rebaudiana
SEQUENCE: 142
MGLFPLEDSY ALVFEGLAIT LALYYLLSFI YKTSKKTCTP PKASGEIIPI TGIILNLLSG  60
```

-continued

```
SSGLPIILAL ASLADRCGPI FTIRLGIRRV LVVSNWEIAK EIFTTHDLIV SNRPKYLAAK  120
ILGFNYVSFS FAPYGPYWVG IRKIIATKLM SSSRLQKLQF VRVFELENSM KSIRESWKEK  180
KDEEGKVLVE MKKWFWELNM NIVLRTVAGK QYTGTVDDAD AKRISELFRE WFHYTGRFVV  240
GDAFPFLGWL DLGGYKKTME LVASRLDSMV SKWLDEHRKK QANDDKKEDM DFMDIMISMT  300
EANSPLEGYG TDTIIKTTCM TLIVSGVDTT SIVLTWALSL LLNNRDTLKK AQEELDMCVG  360
KGRQVNESDL VNLIYLEAVL KEALRLYPAA FLGGPRAFLE DCTVAGYRIP KGTCLLINMW  420
KLHRDPNIWS DPCEFKPERF LTPNQKDVDV IGMDFELIPF GAGRRYCPGT RLALQMLHIV  480
LATLLQNFEM STPNDAPVDM TASVGMTNAK ASPLEVLLSP RVKWS                 525

SEQ ID NO: 143          moltype = AA  length = 476
FEATURE                 Location/Qualifiers
source                  1..476
                        mol_type = protein
                        organism = Stevia rebaudiana
SEQUENCE: 143
MIQVLTPILL FLIFFVFWKV YKHQKTKINL PPGSFGWPFL GETLALLRAG WDSEPERFVR  60
ERIKKHGSPL VFKTSLFGDR FAVLCGPAGN KFLFCNENKL VASWWPVPVR KLFGKSLLTI  120
RGDEAKWMRK MLLSYLGPDA FATHYAVTMD VVTRRHIDVH WRGKEEVNVF QTVKLYAFEL  180
ACRLFMNLDD PNHIAKLGSL FNIFLKGIIE LPIDVPGTRF YSSKKAAAAI RIELKKLIKA  240
RKLELKEGKA SSSQDLLSHL LTSPDENGMF LTEEEIVDNI LLLLFAGHDT SALSITLLMK  300
TLGEHSDVYD KVLKEQLEIS KTKEAWESLK WEDIQKMKYS WSVICEVMRL NPPVIGTYRE  360
ALVDIDYAGY TIPKGWKLHW SAVSTQRDEA NFEDVTRFDP SRFEGAGPTP FTFVPFGGGP  420
RMCLGKEFAR LEVLAFLHNI VTNFKWDLLI PDEKIEYDPM ATPAKGLPIR LHPHQV      476

SEQ ID NO: 144          moltype = AA  length = 525
FEATURE                 Location/Qualifiers
source                  1..525
                        mol_type = protein
                        organism = Arabidopsis thaliana
SEQUENCE: 144
MESLVVHTVN AIWCIVIVGI FSVGYHVYGR AVVEQWRMRR SLKLQGVKGP PPSIFNGNVS  60
EMQRIQSEAK HCSGDNIISH DYSSSLFPHF DHWRKQYGRI YTYSTGLKQH LYINHPEMVK  120
ELSQTNTLNL GRITHITKRL NPILGNGIIT SNGPHWAHQR RIIAYEFTHD KIKGMVGLMV  180
ESAMPMLNKW EEMVKRGGEM GCDIRVDEDL KDVSADVIAK ACFGSSFSKG KAIFSMIRDL  240
LTAITKRSVL FRFNGFTDMV FGSKKHGDVD IDALEMELES SIWETVKERE IECKDTHKKD  300
LMQLILEGAM RSCDGNLWDK SAYRRFVVDN CKSIYFAGHD STAVSVSWCL MLLALNPSWQ  360
VKIRDEILSS CKNGIPDAES IPNLKTVTMV IQETMRLYPP APIVGREASK DIRLGDLVVP  420
KGVCIWTLIP ALHRDPEIWG PDANDFKPER FSEGISKACK YPQSYIPFGL GPRTCVGKNF  480
GMMEVKVLVS LIVSKFSFTL SPTYQHSPSH KLLVEPQHGV VIRVV                 525

SEQ ID NO: 145          moltype = AA  length = 529
FEATURE                 Location/Qualifiers
source                  1..529
                        mol_type = protein
                        organism = Vitis vinifera
SEQUENCE: 145
MYFLLQYLNI TTVGVFATLF LSYCLLLWRS RAGNKKIAPE AAAAWPIIGH LHLLAGGSHQ  60
LPHITLGNMA DKYGPVFTIR IGLHRAVVVS SWEMAKECST ANDQVSSSRP ELLASKLLGY  120
NYAMFGFSPY GSYWREMRKI ISLELLSNSR LELLKDVRAS EVVTSIKELY KLWAEKKNES  180
GLVSVEMKQW FGDLTLNVIL RMVAGKRYFS ASDASENKQA QRCRRVFREF FHLSGLFVVA  240
DAIPFLGWLD WGRHEKTLKK TAIEMDSIAQ EWLEEHRRRK DSGDDNSTQD FMDVMQSVLD  300
GKNLGGYDAD TINKATCLTL ISGGSDTTVV SLTWALSLVL NNRDTLKKAQ EELDIQVGKE  360
RLVNEQDISK LVYLQAIVKE TLRLYPPGPL GGLRQFTEDC TLGGYHVSKG TRLIMNLSKI  420
QKDPRIWSDP TEFQPERFLT THKDVDPRGK HFEFIPFGAG RRACPGITFG LQVLHLTLAS  480
FLHAFEFSTP SNEQVNMRES LGLTNMKSTP LEVLISPRLS LNCFNLMKI              529

SEQ ID NO: 146          moltype = AA  length = 479
FEATURE                 Location/Qualifiers
source                  1..479
                        mol_type = protein
                        organism = Medicago trunculata
SEQUENCE: 146
MEPNFYLSLL LLFVTFISLS LFFIFYKQKS PLNLPPGKMG YPIIGESLEF LSTGWKGHPE  60
KFIFDRMRKY SSELFKTSIV GESTVVCCGA ASNKFLFSNE NKLVTAWWPD SVNKIFPTTS  120
LDSNLKEESI KMRKLLPQFF KPEALQRYVG VMDVIAQRHF VTHWDNKNEI TVYPLAKRYT  180
FLLACRLFMS VEDENHVAKF SDPFQLIAAG IISLPIDLPG TPFNKAIKAS NFIRKELIKI  240
IKQRRVDLAE GTASPTQDIL SHMLLTSDEN GKSMNELNIA DKILGLLIGG HDTASVACTF  300
LVKYLGELPH IYDKVYQEQM EIAKSKPAGE LLNWDDLKKM KYSWNVACEV MRLSPPLQGG  360
FREAITDFMF NGFSIPKGWK LYWSANSTHK NAECFPMPEK FDPTRFEGNG PAPYTFVPFG  420
GGPRMCPGKE YARLEILVFM HNLVKRFKWE KVIPDEKIIV DPFPIPAKDL PIRLYPHKA   479

SEQ ID NO: 147          moltype = AA  length = 710
FEATURE                 Location/Qualifiers
source                  1..710
                        mol_type = protein
                        organism = Stevia rebaudiana
SEQUENCE: 147
MQSDSVKVSP FDLVSAAMNG KAMEKLNASE SEDPTTLPAL KMLVENRELL TLFTTSFAVL  60
IGCLVFLMWR RSSSKKLVQD PVPQVIVVKK KEKESEVDDG KKKVSIFYGT QTGTAEGFAK  120
```

```
ALVEEAKVRY EKTSFKVIDL DDYAADDDEY EEKLKKESLA FFFLATYGDG EPTDNAANFY  180
KWFTEGDDKG EWLKKLQYGV FGLGNRQYEH FNKIAIVVDD KLTEMGAKRL VPVGLGDDDQ  240
CIEDDFTAWK ELVWPELDQL LRDEDDTSVT TPYTAAVLEY RVVYHDKPAD SYAEDQTHTN  300
GHVVHDAQHP SRSNVAFKKE LHTSQSDRSC THLEFDISHT GLSYETGDHV GVYSENLSEV  360
VDEALKLLGL SPDTYFSVHA DKEDGTPIGG ASLPPPFPPC TLRDALTRYA DVLSSPKKVA  420
LLALAAHASD PSEADRLKFL ASPAGKDEYA QWIVANQRSL LEVMQSFPSA KPPLGVFFAA  480
VAPRLQPRYY SISSSPKMSP NRIHVTCALV YETTPAGRIH RGLCSTWMKN AVPLTESPDC  540
SQASIFVRTS NFRLPVDPKV PVIMIGPGTG LAPFRGFLQE RLALKESGTE LGSSIFFFGC  600
RNRKVDFIYE DELNNFVETG ALSELIVAFS REGTAKEYVQ HKMSQKASDI WKLLSEGAYL  660
YVCGDAKGMA KDVHRTLHTI VQEQGSLDSS KAELYVKNLQ MSGRYLRDVW             710

SEQ ID NO: 148          moltype = AA  length = 692
FEATURE                 Location/Qualifiers
source                  1..692
                        mol_type = protein
                        organism = Arabidopsis thaliana
SEQUENCE: 148
MTSALYASDL FKQLKSIMGT DSLSDDVVLV IATTSLALVA GFVVLLWKKT TADRSGELKP  60
LMIPKSLMAK DEDDDLDLGS GKTRVSIFFG TQTGTAEGFA KALSEEIKAR YEKAAVKVID  120
LDDYAADDDQ YEEKLKKETL AFFCVATYGD GEPTDNAARF YKWFTEENER DIKLQQLAYG  180
VFALGNRQYE HFNKIGIVLD EELCKKGAKR LIEVGLGDDD QSIEDDFNAW KESLWSELDK  240
LLKDEDDKSV ATPYTAVIPE YRVVTHDPRF TTQKSMESNV ANGNTTIDIH HPCRVDVAVQ  300
KELHTHESDR SCIHLEFDIS RTGITYETGD HVGVYAENHV EIVEEAGKLL GHSLDLVFSI  360
HADKEDGSPL ESAVPPPFPG PCTLGTGLAR YADLLNPPRK SALVALAAYA TEPSEAEKLK  420
HLTSPDGKDE YSQWIVASQR SLLEVMAAFP SAKPPLGVFF AAIAPRLQPR YYSISSSPRL  480
APSRVHVTSA LVYGPTPTGR IHKGVCSTWM KNAVPAEKSH ECSGAPIFIR ASNFKLPSNP  540
STPIVMVGPG TGLAPFRGFL QERMALKEDG EELGSSLLFF GCRNRQMDFI YEDELNNFVD  600
QGVISELIMA FSREGAQKEY VQHKMMEKAA QVWDLIKEEG YLYVCGDAKG MARDVHRTLH  660
TIVQEQEGVS SSEAEAIVKK LQTEGRYLRD VW                                692

SEQ ID NO: 149          moltype = AA  length = 713
FEATURE                 Location/Qualifiers
source                  1..713
                        mol_type = protein
                        organism = Giberella fujikuroi
SEQUENCE: 149
MAELDTLDIV VLGVIFLGTV AYFTKGKLWG VTKDPYANGF AAGGASKPGR TRNIVEAMEE  60
SGKNCVVFYG SQTGTAEDYA SRLAKEGKSR FGLNTMIADL EDYDFDNLDT VPSDNIVMFV  120
LATYGEGEPT DNAVDFYEFI TGEDASFNEG NDPPLGNLNY VAFGLGNNTY EHYNSMVRNV  180
NKALEKLGAH RIGEAGEGDD GAGTMEEDFL AWKDPMWEAL AKKMGLEERE AVYEPIFAIN  240
ERDDLTPEAN EVYLGEPNKL HLEGTAKGPF NSHNPYIAPI AESYELFSAK DRNCLHMEID  300
ISGSNLKYET GDHIAIWPTN PGEEVNKFLD ILDLSGKQHS VVTVKALEPT AKVPFPNPTT  360
YDAILRYHLE ICAPVSRQFV STLAAFAPND DIKAEMNRLG SDKDYFHEKT GPHYYNIARF  420
LASVSKGEKW TKIPFSAFIE GLTKLQPRYY SISSSSLVQP KKISITAVVE SQQIPGRDDP  480
FRGVATNYLF ALKQKQNGDP NPAPFGQSYE LTGPRNKYDG IHVPVHVRHS NFKLPSDPGK  540
PIIMIGPGTG VAPFRGFVQE RAKQARDGVE VGKTLLFFGC RKSTEDFMYQ KEWQEYKEAL  600
GDKFEMITAF SREGSKKVYV QHRLKERSKE VSDLLSQKAY FYVCGDAAHM AREVNTVLAQ  660
IIAEGRGVSE AKGEEIVKNM RSANQYQVCS DFVTLHCKET TYANSELQED VWS         713

SEQ ID NO: 150          moltype = AA  length = 453
FEATURE                 Location/Qualifiers
source                  1..453
                        mol_type = protein
                        organism = Arabidopsis thaliana
SEQUENCE: 150
MGGLKFHVLM YPWFATGHMT PFLFLANKLA EKGHTVTFLL PKKSLKQLEH FNLFPHNIVF  60
RSVTVPHVDG LPVGTETASE IPVTSTDLLM SAMDLTRDQV EAVVRAVEPD LIFFDFAHWI  120
PEVARDFGLK TVKYVVVSAS TIASMLVPGG ELGVPPPGYP SSKVLLRKQD AYTMKKLEPT  180
NTIDVGPNLL ERVTTSLMNS DVIAIRTARE IEGNFCDYIE KHCRKKVLLT GPVFPEPDKT  240
RELEERWVKW LSGYEPDSVV FCALGSQVIL EKDQFQELCL GMELTGSPFL VAVKPPRGSS  300
TIQEALPEGF EERVKGRGLV WGGWVQQPLI LSHPSVGCFV SHCGFGSMWE SLLSDCQIVL  360
VPQLGDQVLN TRLLSDELKV SVEVAREETG WFSKESLCDA VNSVMKRDSE LGNLVRKNHT  420
KWRETVASPG LMTGYVDAFV ESLQDLVSGT THD                               453

SEQ ID NO: 151          moltype = DNA  length = 1362
FEATURE                 Location/Qualifiers
source                  1..1362
                        mol_type = other DNA
                        organism = Arabidopsis thaliana
SEQUENCE: 151
atgggtggtt tgaagtttca tgtacttatg tatccatggt tcgcaacagg ccatatgacc  60
ccgttccttt ttcttgccaa caaattggct gagaaaggtc atacggtcac tttcttgctt  120
cccaagaaat ctctgaaaca gttggaacat ttcaatctgt ttccacacaa cattgtcttt  180
cgctctgtca ccgtccctca tgtggatggt ctccccgttg gcacagagac agcctctgag  240
atccctgtga catcaactga tctcttgatg tctgctatgg atctcacacg tgatcaagtt  300
gaagctgtgg tccgagccgt tgaaccggac ctgatcttct ttgactttgc tcattggatt  360
ccagaagtag ctagggactt cggccttaag actgtaaagt acgtcgtggt gtctgcatcg  420
actatagcta gtatgcttgt cccaggtggt gagttaggtg ttcctccacc gggatatcca  480
tcatcaaagg tgctgcttcg taaacaagat gcttacacta tgaagaaact ggagcctaca  540
```

```
aatacaatcg atgtcggacc aaacctcttg gaacgagtca ctacaagtct tatgaactct  600
gatgtcattg cgataaggac agccagagaa atcgaaggaa acttttgcga ctatatagaa  660
aaacattgca ggaaaaaggt tctcttgaca ggtccggtgt tccctgagcc agacaagact  720
agagagctag aggaacgatg ggttaagtgg ctaagtgggt atgaaccaga ctcagtggtg  780
ttttgtgcac tgggctcaca agtcatttta gagaaagatc aattccaaga actctgctta  840
ggaatggagc taacaggttc accgtttctt gtagcggtta agccccctag aggctcatca  900
acgattcaag aagcacttcc tgaaggattc gaagagcggg ttaaaggaag aggccttgtt  960
tggggaggat gggttcaaca accattgata ttgtctcatc catcagtcgg gtgctttgtg  1020
agccattgtg ggtttggatc aatgtgggag tctttgctga gtgattgtca gatagtctta  1080
gtaccacagt tgggtgatca agtcctgaac acaagattgc tgagtgacga actcaaggtt  1140
tcggttgaag tggcaagaga ggaaacagga tggttctcga aagagagctt gtgcgatgct  1200
gtcaatagtg tgatgaaaag ggacagcgag ctcgggaacc tggtgaggaa gaatcacacc  1260
aagtggaggg agacagtagc tagtcctgga ctaatgactg gttatgtcga tgctttcgta  1320
gagtcattgc aggatcttgt ctctgggacc acccatgact ga                    1362

SEQ ID NO: 152         moltype = AA  length = 462
FEATURE                Location/Qualifiers
source                 1..462
                       mol_type = protein
                       organism = Oryza sativa
SEQUENCE: 152
MDSGYSSSYA AAAGMHVVIC PWLAFGHLLP CLDLAQRLAS RGHRVSFVST PRNISRLPPV  60
RPALAPLVAF VALPLPRVEG LPDGAESTND VPHDRPDMVE LHRRAFDGLA APFSEFLGTA  120
CADWVIVDVF HHWAAAAALE HKVPCAMMLL GSAHMIASIA DRRLERAETE SPAAAGQGRP  180
AAAPTFEVAR MKLIRTKGSS GMSLAERFSL TLSRSSLVVG RSCVEFEPET VPLLSTLRGK  240
PITFLGLMPP LHEGRREDGE DATVRWLDAQ PAKSVVYVAL GSEVPLGVEK VHELALGLEL  300
AGTRFLWALR KPTGVSDADL LPAGFEERTR GRGVVATRWV PQMSILAHAA VGAFLTHCGW  360
NSTIEGLMFG HPLIMLPIFG DQGPNARLIE AKNAGLQVAR NDGDGSFDRE GVAAAIRAVA  420
VEEESSKVFQ AKAKKLQEIV ADMACHERYI DGFIQQLRSY KD                    462

SEQ ID NO: 153         moltype = DNA  length = 1389
FEATURE                Location/Qualifiers
source                 1..1389
                       mol_type = other DNA
                       organism = Oryza sativa
SEQUENCE: 153
atggactccg gctactcctc ctcctacgcc gccgccgccg ggatgcacgt cgtgatctgc  60
ccgtggctcg ccttcggcca cctgctcccg tgcctcgacc tcgcccagcg cctcgcgtcg  120
cggggccacc gcgtgtcgtt cgtctccacg ccgcggaaca tatcccgcct cccgccggtg  180
cgccccgcgc tcgcgccgct cgtcgccttc gtggcgctgc cgctcccgcg cgtcgagggg  240
ctccccgacg gcgccgagtc caccaacgac gtcccccacg acaggccgga catggtcgag  300
ctccaccgga gggccttcga cggctcgcc gcgcccttct cggagttctt gggcaccgcg  360
tgcgccgact gggtcatcgt cgacgtcttc caccactggg ccgcagccgc cgctctcgag  420
cacaaggtgc catgtgcaat gatgttgttg ggctctgcac atatgatcgc ttccatagca  480
gacagacggc tcgagcgcgc ggagacagag tcgcctgcgg ctgccgggca gggacgccca  540
gcggcggcgc caacgttcga ggtggcgagg atgaagttga tacgaaccaa aggctcatcg  600
ggaatgtccc tcgccgagcg cttctccttg acgctctcga ggagcagcct cgtcgtcggg  660
cggagctgcg tggagttcga gccggagacc gtcccgctcc tgtcgacgct ccgcggtaag  720
cctattacct tccttggcct tatgccgccg ttgcatgaag gccgccgcga ggacggcgag  780
gatgccaccg tccgctggct cgacgcgcag ccggccaagt ccgtcgtgta cgtcgcgcta  840
ggcagcgagg tgccactggg agtggagaag gtccacgagc tcgcgctcgg gctggagctc  900
gccgggacgc gcttcctctg ggctcttagg aagcccactg gcgtctccga cgccgacctc  960
ctccccgccg gcttcgagga gcgcacgcgc ggccgcggcg tcgtggcgac gagatgggtt  1020
cctcagatga gcatactggc gcacgccgcc gtgggcgcgt tcctgaccca ctgcggctgg  1080
aactcgacca tcgaggggct catgttcggc cacccgctta tcatgctgcc gatcttcggc  1140
gaccagggac cgaacgcgcg gctaatcgag gcgaagaacg ccggattgca ggtggcaaga  1200
aacgacggcg atggatcgtt cgaccgagaa ggcgtcgcgg cggcgattcg tgcagtcgcg  1260
gtggaggaag aaagcagcaa agtgtttcaa gccaaagcca agaagctgca ggagatcgtc  1320
gcggacatgg cctgccatga gaggtacatc gacggattca ttcagcaatt gagatcttac  1380
aaggattga                                                         1389

SEQ ID NO: 154         moltype = DNA  length = 1389
FEATURE                Location/Qualifiers
misc_feature           1..1389
                       note = Oryza sativa sequence that has been codon optimized
                        for yeast
source                 1..1389
                       mol_type = other DNA
                       organism = synthetic construct
SEQUENCE: 154
atggatagtg gctactcctc atcttatgct gctgccgctg gtatgcacgt tgtgatctgc  60
ccttggttgg cctttggtca cctgttacca tgtctggatt tagcccaaag actggcctca  120
agaggccata gagtatcatt tgtgtctact cctagaaata tctctcgttt accaccagtc  180
agacctgctc tagctcctct agttgcattc gttgctcttc cacttccaag agtagaagga  240
ttgccagacg gcgctgaatc tactaatgac gtaccacatg atagacctga catggtcgaa  300
ttgcatagaa gagcctttga tggattggca gctccatttt ctgagttcct gggcacagca  360
tgtgcagact gggttatagt cgatgtattt catcactggg ctgctgcagc cgcattggaa  420
cataaggtgc cttgtgctat gatgttgtta gggtcagcac acatgatcgc atccatagct  480
gatagaagat tggaaagagc tgaaacagaa tccccagccg cagcaggaca aggtaggcca  540
```

```
gctgccgccc caacctttga agtggctaga atgaaattga ttcgtactaa aggtagttca  600
gggatgagtc ttgctgaaag gttttctctg acattatcta gatcatcatt agttgtaggt  660
agatcctgcg tcgagttcga acctgaaaca gtacctttac tatctacttt gagaggcaaa  720
cctattactt tccttggtct aatgcctcca ttacatgaag gaaggagaga agatggtgaa  780
gatgctactg ttaggtggtt agatgcccaa cctgctaagt ctgttgttta cgttgcattg  840
ggttctgagg taccactagg ggtggaaaag gtgcatgaat tagcattagg acttgagctg  900
gccggaacaa gattcctttg ggctttgaga aaaccaaccg gtgtttctga cgccgacttg  960
ctaccagctg ggttcgaaga gagaacaaga ggccgtggtg tcgttgctac tagatgggtc  1020
ccacaaatga gtattctagc tcatgcagct gtaggggcct ttctaaccca ttgcggttgg  1080
aactcaacaa tagaaggact gatgtttggt catccactta ttatgttacc aatctttggc  1140
gatcagggac ctaacgcaag attgattgag gcaaagaacg caggtctgca ggttgcacgt  1200
aatgatggtg atggttcctt tgatagagaa ggcgttgcag ctgccatcag agcagtcgcc  1260
gttgaggaag agtcatctaa agttttccaa gctaaggcca aaaaattaca agagattgtg  1320
gctgacatgg cttgtcacga aagatacatc gatggtttca tccaacaatt gagaagttat  1380
aaagactaa                                                        1389
```

```
SEQ ID NO: 155         moltype = DNA  length = 2506
FEATURE                Location/Qualifiers
source                 1..2506
                       mol_type = other DNA
                       organism = Arabidopsis thaliana
SEQUENCE: 155
cgtcagtcat caaggctaat tcgtcgcgag ttgctacgac gccgtttcgg ttgcttctgg  60
tttctttatg tctatcaacc ttcgctcctc cggttgttcg tctccgatct cagctacttt  120
ggaacgagga ttggactcag aagtacagac aagagctaac aatgtgagct ttgagcaaac  180
aaaggagaag attaggaaga tgttggagaa agtggagctt tctgtttcgg cctacgatac  240
tagttgggta gcaatggttc catcaccgag ctcccaaaat gctccacttt tcccacagtg  300
tgtgaaatgg ttattggata atcaacatga agatggatct tggggacttg ataaccatga  360
ccatcaatct cttaagaagg atgtgttatc atctacactg gctagtatcc tcgcgttaaa  420
gaagtgggga attggtgaaa gacaaataaa caagggtctc cagtttattg agctgaattc  480
tgcattagtc actgatgaaa ccatacagaa accaacaggg tttgatatta tatttcctgg  540
gatgattaaa tatgctagag atttgaatct gacgattcca ttgggctcag aagtggtgga  600
tgacatgata cgaaaaagag atctggatct taaatgtgat agtgaaaagt tttcaaaggg  660
aagagaagca tatctggcct atgttttaga ggggacaaga aacctaaaag attgggattt  720
gatagtcaaa tatcaaagga aaaatgggtc actgtttgat tctccagcca caacagcagc  780
tgcttttact cagtttggga atgatggttg tctccgttat ctctgttctc tccttcagaa  840
attcgaggct gcagttcctt cagtttatcc atttgatcaa tatgcacgcc ttagtataat  900
tgtcactctt gaaagcttag gaattgatag agatttcaaa accgaaatca aaagcatatt  960
ggatgaaacc tatagatatt ggcttcgtgg ggatgaagaa atatgtttgg acttggccac  1020
ttgtgctttg gctttccgat tattgcttgc tcatggctat gatgtgtctt acgatccgct  1080
aaaaccattt gcagaagaat ctggtttctc tgatactttg gaaggatatg ttaagaatac  1140
gttttctgtg ttagaattat ttaaggctgc tcaaagttat ccacatgaat cagctttgaa  1200
gaagcagtgt tgttggacta aacaatatct ggagatggaa ttgtccagct gggttaagac  1260
ctctgttcga gataaatacc tcaagaaaga ggtcgaggat gctcttgctt ttccctccta  1320
tgcaagccta gaaagatcag atcacaggag aaaaatactc aatggttctg ctgtggaaaa  1380
caccagagtt acaaaaacct catatcgttt gcacaatatt tgcacctctg atatcctgaa  1440
gttagctgtg gatgacttca atttctgcca gtccatacac cgtgaagaaa tggaacgtct  1500
tgataggtgg attgtggaga atagattgca ggaactgaaa tttgccagac agaagctggc  1560
ttactgttat ttctctgggg ctgcaacttt attttctcca gaactatctg atgctcgtat  1620
atcgtgggcc aaaggtggag tacttacaac ggttgtagac gacttctttg atgttggagg  1680
gtccaaagaa gaactggaaa acctcataca cttggtcgaa aagtgggatt tgaacggtgt  1740
tcctgagtac agctcagaac atgttgagat catattctca gttctaaggg acaccattct  1800
cgaaacagga gacaaagcat tcacctatca aggacgcaat gtgacacacc acattgtgaa  1860
aatttggttg gatctgctca agtctatgtt gagagaagcc gagtggtcca gtgacaagtc  1920
aacaccaagc ttggaggatt acatggaaaa tgcgtacata tcatttgcat taggaccaat  1980
tgtcctccca gctacctatc tgatcggacc tccacttcca gagaagacag tcgatagcca  2040
ccaatataat cagctctaca agctcgtgag cactatgggt cgtcttctaa atgacataca  2100
aggttttaag agagaaagcg cggaagggaa gctgaatgcg gtttcattgc acatgaaaca  2160
cgagagagac aatcgcagca aagaagtgat catagaatcg atgaaaggtt tagcagagag  2220
aaagagggaa gaattgcata agctagtttt ggaggagaaa ggaagtgtgg ttccaaggga  2280
atgcaaagaa gcgttcttga aaatgagcaa agtgttgaac ttattttaca ggaaggacga  2340
tggattcaca tcaaatgatc tgatgagtct tgttaaatca gtgatctacg agcctgttag  2400
cttacagaaa gaatctttaa cttgatccaa gttgatctgg caggtaaact cagtaaatga  2460
aaataagact ttggtcttct tctttgttgc ttcagaacaa gaagag              2506
```

```
SEQ ID NO: 156         moltype = AA  length = 785
FEATURE                Location/Qualifiers
source                 1..785
                       mol_type = protein
                       organism = Arabidopsis thaliana
SEQUENCE: 156
MSINLRSSGC SSPISATLER GLDSEVQTRA NNVSFEQTKE KIRKMLEKVE LSVSAYDTSW  60
VAMVPSPSSQ NAPLFPQCVK WLLDNQHEDG SWGLDNHDHQ SLKKDVLSST LASILALKKW  120
GIGERQINKG LQFIELNSAL VTDETIQKPT GFDIIFPGMI KYARDLNLTI PLGSEVVDDM  180
IRKRDLDLKC DSEKFSKGRE AYLAYVLEGT RNLKDWDLIV KYQRKNGSLF DSPATTAAAF  240
TQFGNDGCLR YLCSLLQKFE AAVPSVYPFD QYARLSIIVT LESLGIDRDF KTEIKSILDE  300
TYRYWLRGDE EICLDLATCA LAFRLLLAHG YDVSYDPLKP FAEESGFSDT LEGYVKNTFS  360
VLELFKAAQS YPHESALKKQ CCWTKQYLEM ELSSWVKTSV RDKYLKKEVE DALAFPSYAS  420
LERSDHRRKI LNGSAVENTR VTKTSYRLHN ICTSDILKLA VDDFNFCQSI HREEMERLDR  480
```

-continued

```
WIVENRLQEL KFARQKLAYC YFSGAATLFS PELSDARISW AKGGVLTTVV DDFFDVGGSK  540
EELENLIHLV EKWDLNGVPE YSSEHVEIIF SVLRDTILET GDKAFTYQGR NVTHHIVKIW  600
LDLLKSMLRE AEWSSDKSTP SLEDYMENAY ISFALGPIVL PATYLIGPPL PEKTVDSHQY  660
NQLYKLVSTM GRLLNDIQGF KRESAEGKLN AVSLHMKHER DNRSKEVIIE SMKGLAERKR  720
EELHKLVLEE KGSVVPRECK EAFLKMSKVL NLFYRKDDGF TSNDLMSLVK SVIYEPVSLQ  780
KESLT                                                             785

SEQ ID NO: 157         moltype = DNA  length = 2490
FEATURE                Location/Qualifiers
source                 1..2490
                       mol_type = other DNA
                       organism = Zea mays
SEQUENCE: 157
atggttttgt cttcttcttg tactacagta ccacacttat cttcattagc tgtcgtgcaa  60
cttggtcctt ggagcagtag gattaaaaag aaaaccgata ctgttgcagt accagccgct  120
gcaggaaggt ggagaagggc cttggctaga gcacagcaca catcagaatc cgcagctgtc  180
gcaaagggca gcagtttgac ccctatagtg agaactgacg ctgagtcaag gagaacaaga  240
tggccaaccg atgacgatga cgccgaacct ttagtggatg agatcagggc aatgcttact  300
tccatgtctg atggtgacat ttccgtgagc gcatacgata cagcctgggt cggattggtt  360
ccaagattag acggcggtga aggtcctcaa tttccagcag ctgtgagatg gataagaaat  420
aaccagttgc ctgacggaag ttggggcgat gccgcattat tctctgccta tgacaggctt  480
atcaataccc ttgcctgcgt tgtaactttg acaaggtggt ccctagaacc agagatgaga  540
ggtagaggac tatctttttt gggtaggaac atgtggaaat tagcaactga agatgaagag  600
tcaatgccta ttggcttcga attagcattt ccatctttga tagagcttgc taagagccta  660
ggtgtccatg acttccctta tgatcaccag gccctacaag gaatctactc ttcaagagag  720
atcaaaatga agaggattcc aaaagaagtg atgcataccg ttccaacatc aatattgcac  780
agtttggagg gtatgcctgg cctagattgg gctaaactac ttaaactaca gagcagcgac  840
ggaagttttt tgttctcacc agctgccact gcatatgctt taatgaatac cggagatgac  900
aggtgtttta gctacatcga tagaacagta aagaaattca acggcggcgt ccctaatgtt  960
tatccagtgg atctatttga acatatttgg gccgttgata gacttgaaag attaggaatc  1020
tccaggtact tccaaaagga gatcgaacaa tgcatggatt atgtaaacag gcattggact  1080
gaggacggta tttgttgggc aaggaactct gatgtcaaag aggtggacga cacagctatg  1140
gcctttagac ttcttaggtt gcacggctac agcgtcagtc ctgatgtgtt taaaaacttc  1200
gaaaaggacg gtgaattttt cgcatttgtc ggacagtcta atcaagctgt taccggtatg  1260
tacaacttaa acagagcaag ccagatatcc ttcccaggcg aggatgtgct tcatagagct  1320
ggtgccttct catatgagtt cttgaggaga aaagaagcag agggagcttt gagggacaag  1380
tggatcattt ctaaagatct acctggtgaa gttgtgtata ctttggattt tccatggtac  1440
ggcaacttac ctagagtcga ggccagagac tacctagagc aatacggagg tggtgatgac  1500
gtttggattg gcaagacatt gtataggatg ccacttgtaa acaatgatgt atatttggaa  1560
ttggcaagaa tggatttcaa ccactgccag gctttgcatc agttagagtg gcaaggacta  1620
aaaagatggt atactgaaaa taggttgatg gactttggtg tcgcccaaga agatgccctt  1680
agagcttatt ttcttgcagc cgcatctgtt tacgagcctt gtagagctgc cgagaggctt  1740
gcatgggcta gagccgcaat actagctaac gccgtgagca cccacttaag aaatagccca  1800
tcattcagag aaaggttaga gcattctctt aggtgtagac ctagtgaaga gacagatggc  1860
tcctggttta actcctcaag tggctctgat gcagttttag taaaggctgt cttaagactt  1920
actgattcat tagccaggga agcacagcca atccatggag gtgacccaga agatattata  1980
cacaagttgt taagatctgc ttgggccgag tgggttaggg aaaaggcaga cgctgccgat  2040
agcgtgtgca atggtagttc tgcagtagaa caagagggat caagaatggt ccatgataaa  2100
cagacctgtc tattattggc tagaatgatc gaaatttctg ccggtagggc agctggtgaa  2160
gcagccagtg aggacggcga tagaagaata attcaattaa caggctccat ctgcgacagt  2220
cttaagcaaa aaatgctagt ttcacaggac cctgaaaaaa atgaagagat gatgtctcac  2280
gtggatgacg aattgaagtt gaggattaga gagttcgttc aatatttgct tagactaggt  2340
gaaaaaaaga ctggatctag cgaaaccagg caaacatttt taagtatagt gaaatcatgt  2400
tactatgctg ctcattgccc acctcatgtc gttgatagac acattagtag agtgattttc  2460
gagccagtaa gtgccgcaaa gtaaccgcgg                                  2490

SEQ ID NO: 158         moltype = AA  length = 827
FEATURE                Location/Qualifiers
source                 1..827
                       mol_type = protein
                       organism = Zea mays
SEQUENCE: 158
MVLSSSCTTV PHLSSLAVVQ LGPWSSRIKK KTDTVAVPAA AGRWRRALAR AQHTSESAAV  60
AKGSSLTPIV RTDAESRRTR WPTDDDDAEP LVDEIRAMLT SMSDGDISVS AYDTAWVGLV  120
PRLDGGEGPQ FPAAVRWIRN NQLPDGSWGD AALFSAYDRL INTLACVVTL TRWSLEPEMR  180
GRGLSFLGRN MWKLATEDEE SMPIGFELAF PSLIELAKSL GVHDFPYDHQ ALQGIYSSRE  240
IKMKRIPKEV MHTVPTSILH SLEGMPGLDW AKLLKLQSSD GSFLFSPAAT AYALMNTGDD  300
RCFSYIDRTV KKFNGGVPNV YPVDLFEHIW AVDRLERLGI SRYFQKEIEQ CMDYVNRHWT  360
EDGICWARNS DVKEVDDTAM AFRLLRLHGY SVSPDVFKNF EKDGEFFAFV GQSNQAVTGM  420
YNLNRASQIS FPGEDVLHRA GAFSYEFLRR KEAEGALRDK WIISKDLPGE VVYTLDFPWY  480
GNLPRVEARD YLEQYGGGDD VWIGKTLYRM PLVNNDVYLE LARMDFNHCQ ALHQLEWQGL  540
KRWYTENRLM DFGVAQEDAL RAYFLAAASV YEPCRAAERL AWARAAILAN AVSTHLRNSP  600
SFRERLEHSL RCRPSEETDG SWFNSSSGSD AVLVKAVLRL TDSLAREAQP IHGGDPEDII  660
HKLLRSAWAE WVREKADAAD SVCNGSSAVE QEGSRMVHDK QTCLLLARMI EISAGRAAGE  720
AASEDGDRRI IQLTGSICDS LKQKMLVSQD PEKNEEMMSH VDDELKLRIR EFVQYLLRLG  780
EKKTGSSETR QTFLSIVKSC YYAAHCPPHV VDRHISRVIF EPVSAAK                827

SEQ ID NO: 159         moltype = DNA  length = 2570
FEATURE                Location/Qualifiers
```

-continued

```
source                  1..2570
                        mol_type = other DNA
                        organism = Arabidopsis thaliana
SEQUENCE: 159
cttcttcact aaatacttag acagagaaaa cagagctttt taaagccatg tctcttcagt  60
atcatgttct aaactccatt ccaagtacaa cctttctcag ttctactaaa acaacaatat  120
cttcttcttt ccttaccatc tcaggatctc ctctcaatgt cgctagagac aaatccagaa  180
gcggttccat acattgttca aagcttcgaa ctcaagaata cattaattct caagaggttc  240
aacatgattt gcctctaata catgagtggc aacagcttca aggagaagat gctcctcaga  300
ttagtgttgg aagtaatagt aatgcattca aagaagcagt gaagagtgtg aaaacgatct  360
tgagaaacct aacggacggg gaaattacga tatcggctta cgatacagct tgggttgcat  420
tgatcgatgc cggagataaa actccggcgt ttccctccgc cgtgaaatgg atcgccgaga  480
accaactttc cgatggttct tggggagatg cgtatctctt ctcttatcat gatcgtctca  540
tcaataccct tgcatgcgtc gttgctctaa gatcatggaa tctctttcct catcaatgca  600
acaaaggaat cacgtttttc cgggaaaata ttgggaagct agaagacgaa aatgatgagc  660
atatgccaat cggattcgaa gtagcattcc catcgttgct tgagatagct cgaggaataa  720
acattgatgt accgtacgat tctccggtct taaaagatat atacgccaag aaagagctaa  780
agcttacaag gataccaaaa gagataatgc acaagatacc aacaacattg ttgcatagtt  840
tggaggggat gcgtgattta gattgggaaa agctcttgaa acttcaatct caagacggat  900
ctttcctctt ctctccttcc tctaccgctt ttgcattcat gcagacccga gacagtaact  960
gcctcgagta tttgcgaaat gccgtcaaac gtttcaatgg aggagttccc aatgtctttc  1020
ccgtggatct tttcgagcac atatggatag tggatcggtt acaacgttta gggatatcga  1080
gatactttga agaagagatt aaagagtgtc ttgactatgt ccacagatat tggaccgaca  1140
atggcatatg ttgggctaga tgttcccatg tccaagacat cgatgataca gccatggcat  1200
ttaggctctt aagacaacat ggataccaag tgtccgcaga tgtattcaag aactttgaga  1260
aagagggaga gtttttctgc tttgtggggc aatcaaacca agcagtaacc ggtatgttca  1320
acctataccg ggcatcacaa ttggcgtttc caagggaaga gatattgaaa aacgccaaag  1380
agttttctta taattatctg ctagaaaaac gggagagaga ggagttgatt gataagtgga  1440
ttataatgaa agacttacct ggcgagattg ggtttgcgtt agagattcca tggtacgcaa  1500
gcttgcctcg agtagagacg agattctata ttgatcaata tggtggagaa aacgacgttt  1560
ggattggcaa gactctttat aggatgccat acgtgaacaa taatggatat ctggaattag  1620
caaaacaaga ttacaacaat tgccaagctc agcatcagct cgaatgggac atattccaaa  1680
agtggtatga agaaaatagg ttaagtgagt ggggtgtgcg cagaagtgag cttctcgagt  1740
gttactactt agcggctgca actatatttg aatcagaaag gtcacatgag agaatggttt  1800
gggctaagtc aagtgtattg gttaaagcca tttcttcttc ttttggggaa tcctctgact  1860
ccagaagaag cttctccgat cagtttcatg aatacattgc caatgctcga cgaagtgatc  1920
atcactttaa tgacaggaac atgagattgg accgaccagg atcggttcag gccagtcggc  1980
ttgccggagt gttaatcggg actttgaatc aaatgtcttt tgacctttttc atgtctcatg  2040
gccgtgacgt taacaatctc ctctatctat cgtggggaga ttggatggaa aaatggaaac  2100
tatatggaga tgaaggagaa ggagagctca tggtgaagat gataattcta atgaagaaca  2160
atgacctaac taacttcttc acccacactc acttcgttcg tctcgcggaa atcatcaatc  2220
gaatctgtct tcctcgccaa tacttaaagg caaggagaaa cgatgagaag gagaagacaa  2280
taaagagtat ggagaaggag atggggaaaa tggttgagtt agcattgtcg gagagtgaca  2340
catttcgtga cgtcagcatc acgtttcttg atgtagcaaa agcattttac tactttgctt  2400
tatgtggcga tcatctccaa actcacatct ccaaagtctt gtttcaaaaa gtctagtaac  2460
ctcatcatca tcatcgatcc attaacaatc agtggatcga tgtatccata gatgcgtgaa  2520
taatatttca tgtagagaag gagaacaaat tagatcatgt agggttatca              2570

SEQ ID NO: 160          moltype = AA  length = 802
FEATURE                 Location/Qualifiers
source                  1..802
                        mol_type = protein
                        organism = Arabidopsis thaliana
SEQUENCE: 160
MSLQYHVLNS IPSTTFLSST KTTISSSFLT ISGSPLNVAR DKSRSGSIHC SKLRTQEYIN  60
SQEVQHDLPL IHEWQQLQGE DAPQISVGSN SNAFKEAVKS VKTILRNLTD GEITISAYDT  120
AWVALIDAGD KTPAFPSAVK WIAENQLSDG SWGDAYLFSY HDRLINTLAC VVALRSWNLF  180
PHQCNKGITF FRENIGKLED ENDEHMPIGF EVAFPSLLEI ARGINIDVPY DSPVLKDIYA  240
KKELKLTRIP KEIMHKIPTT LLHSLEGMRD LDWEKLLKLQ SQDGSFLFSP SSTAFAFMQT  300
RDSNCLEYLR NAVKRFNGGV PNVFPVDLFE HIWIVDRLQR LGISRYFEEE IKECLDYVHR  360
YWTDNGICWA RCSHVQDIDD TAMAFRLLRQ HGYQVSADVF KNFEKEGEFF CFVGQSNQAV  420
TGMFNLYRAS QLAFPREEIL KNAKEFSYNY LLEKREREEL IDKWIIMKDL PGEIGFALEI  480
PWYASLPRVE TRFYIDQYGG ENDVWIGKTL YRMPYVNNNG YLELAKQDYN NCQAQHQLEW  540
DIFQKWYEEN RLSEWGVRRS ELLECYYLAA ATIFESERSH ERMVWAKSSV LVKAISSSFG  600
ESSDSRRSFS DQFHEYIANA RRSDHHFNDR NMRLDRPGSV QASRLAGVLI GTLNQMSFDL  660
FMSHGRDVNN LLYLSWGDWM EKWKLYGDEG EGELMVKMII LMKNNDLTNF FTHTHFVRLA  720
EIINRICLPR QYLKARRNDE KEKTIKSMEK EMGKMVELAL SESDTFRDVS ITFLDVAKAF  780
YYFALCGDHL QTHISKVLFQ KV                                          802

SEQ ID NO: 161          moltype = DNA  length = 2859
FEATURE                 Location/Qualifiers
source                  1..2859
                        mol_type = other DNA
                        organism = Gibberella fujikuroi
SEQUENCE: 161
atgcctggta aaattgaaaa tggtacccca aaggacctca agactggaaa tgattttgtt  60
tctgctgcta agagtttact agatcgagct ttcaaaagtc atcattccta ctacggatta  120
tgctcaactt catgtcaagt ttatgataca gcttgggttg caatgattcc aaaaacaaga  180
gataatgtaa aacagtggtt gtttccagaa tgtttccatt acctcttaaa aacacaagcc  240
```

```
gcagatggct catggggttc attgcctaca acacagacag cgggtatcct agatacagcc  300
tcagctgtgc tggcattatt gtgccacgca caagagcctt tacaaatatt ggatgtatct  360
ccagatgaaa tggggttgag aatagaacac ggtgtcacat ccttgaaacg tcaattagca  420
gtttggaatg atgtggagga caccaaccat attggcgtcg agtttatcat accagcctta  480
ctttccatgc tagaaaagga attagatgtt ccatcttttg aatttccatg taggtccatc  540
ttagagagaa tgcacgggga gaaattaggt catttcgacc tggaacaagt ttacggcaag  600
ccaagctcat tgttgcactc attggaagca tttctcggta agctagattt tgatcgacta  660
tcacatcacc tataccacgg cagtatgatg gcatctccat cttcaacggc tgcttatctt  720
attggggcta caaaatggga tgacgaagcc gaagattacc taagacatgt aatgcgtaat  780
ggtgcaggac atgggaatgg aggtatttct ggtacatttc caactactca tttcgaatgt  840
agctggatta tagcaacgtt gttaaaggtt ggctttactt tgaagcaaat tgacggcgat  900
ggcttaagag gtttatcaac catcttactt gaggcgcttc gtgatgagaa tggtgtcata  960
ggctttgccc ctagaacagc agatgtagat gacacagcca aagctctatt ggccttgtca  1020
ttggtaaacc agccagtgtc acctgatatc atgattaagg tctttgaggg caaagaccat  1080
tttaccactt ttggttcaga aagagatcca tcattgactt ccaacctgca cgtcctttta  1140
tctttactta aacaatctaa cttgtctcaa taccatcctc aaatcctcaa aacaacatta  1200
ttcacttgta gatggtggtg ggttccgat cattgtgtca aagacaaatg gaatttgagt  1260
cacctatatc caactatgtt gttggttgaa gccttcactg aagtgctcca tctcattgac  1320
ggtggtgaat tgtctagtct gtttgatgaa tcctttaagt gtaagattgg tcttagcatc  1380
tttcaagcgg tacttagaat aatcctcacc caagacaacg acggctcttg gagaggatac  1440
agagaacaga cgtgttacgc aatattggct ttagttcaag cgagacatgt atgctttttc  1500
actcacatgg ttgacagact gcaatcatgt gttgatcgag gtttctcatg gttgaaatct  1560
tgctcttttc attctcaaga cctgacttgg acctctaaaa cagcttatga agtgggtttc  1620
gtagctgaag catataaact agctgcttta caatctgctt ccctggaggt tcctgctgcc  1680
accattggac attctgtcac gtctgccgtt ccatcaagtg atcttgaaaa atacatgaga  1740
ttggtgagaa aaactgcgtt attctctcca ctggatgagt ggggtctaat ggcttctatc  1800
atcgaatctt catttttcgt accattactg caggcacaaa gagttgaaat ataccctaga  1860
gataatatca aggtggacga agataagtac ttgtctatta tcccattcac atgggtcgga  1920
tgcaataata ggtctagaac tttcgcaagt aacagatggc tatacgatat gatgtacctt  1980
tcattactcg gctatcaaac cgacgagtac atggaagctg tagctgggcc agtgtttggg  2040
gatgtttcct tgttacatca aacaattgat aaggtgattg ataatacaat gggtaacctt  2100
gcgagagcca atggaacagt acacagtggt aatggacatc agcacgaatc tcctaatata  2160
ggtcaagtcg aggacacctt gactcgtttc acaaattcag tcttgaatca caaagacgtc  2220
cttaactcta gctcatctga tcaagatact ttgagaagag agtttagaac attcatgcac  2280
gctcatataa cacaaatcga agataactca cgattcagta agcaagcctc atccgatgcg  2340
ttttcctctc ctgaacaatc ttactttcaa tgggtgaact caactggtgg ctcacatgtc  2400
gcttgcgcct attcatttgc cttctctaat tgcctcatgt ctgcaaattt gttgcagggt  2460
aaagacgcat ttccaagcgg aacgcaaaag tacttaatct cctctgttat gagacatgcc  2520
acaaacatgt gtagaatgta taacgacttt ggctctattg ccagagacaa cgctgagaga  2580
aatgttaata gtattcattt tcctgagttt actctctgta acggaacttc tcaaaaccta  2640
gatgaaagga aggaaagact tctgaaaatc gcaacttacg aacaagggta tttggataga  2700
gcactagagg ccttggaaag acagagtaga gatgatgccg gagacagagc tggatctaaa  2760
gatatgagaa agttgaaaat cgttaagtta ttctgtgatg ttacggactt atacgatcag  2820
ctctacgtta tcaaagattt gtcatcctct atgaagtaa                        2859
```

```
SEQ ID NO: 162          moltype = AA  length = 952
FEATURE                 Location/Qualifiers
source                  1..952
                        mol_type = protein
                        organism = Gibberella fujikuroi
SEQUENCE: 162
MPGKIENGTP KDLKTGNDFV SAAKSLLDRA FKSHHSYYGL CSTSCQVYDT AWVAMIPKTR  60
DNVKQWLFPE CFHYLLKTQA ADGSWGSLPT TQTAGILDTA SAVLALLCHA QEPLQILDVS  120
PDEMGLRIEH GVTSLKRQLA VWNDVEDTNH IGVEFIIPAL LSMLEKELDV PSFEFPCRSI  180
LERMHGEKLG HFDLEQVYGK PSSLLHSLEA FLGKLDFDRL SHHLYHGSMM ASPSSTAAYL  240
IGATKWDDEA EDYLRHVMRN GAGHGNGGIS GTFPTTHFEC SWIIATLLKV GFTLKQIDGD  300
GLRGLSTILL EALRDENGVI GFAPRTADVD DTAKALLALS LVNQPVSPDI MIKVFEGKDH  360
FTTFGSERDP SLTSNLHVLL SLLKQSNLSQ YHPQILKTTL FTCRWWWGSD HCVKDKWNLS  420
HLYPTMLLVE AFTEVLHLID GGELSSLFDE SFKCKIGLSI FQAVLRIILT QDNDGSWRGY  480
REQTCYAILA LVQARHVCFF THMVDRLQSC VDRGFSWLKS CSFHSQDLTW TSKTAYEVGF  540
VAEAYKLAAL QSASLEVPAA TIGHSVTSAV PSSDLEKYMR LVRKTALFSP LDEWGLMASI  600
IESSFFVPLL QAQRVEIYPR DNIKVDEDKY LSIIPFTWVG CNNRSRTFAS NRWLYDMMYL  660
SLLGYQTDEY MEAVAGPVFG DVSLLHQTID KVIDNTMGNL ARANGTVHSG NGHQHESPNI  720
GQVEDTLTRF TNSVLNHKDV LNSSSSDQDT LRREFRTFMH AHITQIEDNS RFSKQASSDA  780
FSSPEQSYFQ WVNSTGGSHV ACAYSFAFSN CLMSANLLQG KDAFPSGTQK YLISSVMRHA  840
TNMCRMYNDF GSIARDNAER NVNSIHFPEF TLCNGTSQNL DERKERLLKI ATYEQGYLDR  900
ALEALERQSR DDAGDRAGSK DMRKLKIVKL FCDVTDLYDQ LYVIKDLSSS MK          952
```

```
SEQ ID NO: 163          moltype = DNA  length = 1503
FEATURE                 Location/Qualifiers
source                  1..1503
                        mol_type = other DNA
                        organism = Stevia rebaudiana
SEQUENCE: 163
atggaggctt catatctata catttccatt cttctgcttc tagcttcgta cctcttcacc  60
acccaacttc gtcgtaaatc cgccaatcta ccgccgacgg tgttcccatc catccccata  120
atcggtcatc tctacctcct caaaaaacca ctctatagaa cactagccaa aattgccgcc  180
aaatacggcc ctatcctcca actccaacta gggtaccgcc gtgtcctcgt aatctcctcc  240
ccttccgccg ccgaagaatg cttcaccaac aacgacgtta tcttcgccaa ccgtccgaag  300
```

-continued

```
acgctattcg gaaaaattgt agggggtacc agcctcgggt cgctgtcgta cggcgaccag  360
tggcgcaacc tccgccgcgt tgcatccatc gagattctat cagtccaccg gctcaacgag  420
tttcacgaca tacgtgttga cgaaaaccgg cttctgatcc gtaaactaag atccagttct  480
tctccggtga ctctgataac ggtgttttac gcactaacgt taaatgtgat tatgagaatg  540
atctccggaa agaggtattt cgactcgggt gatcgggaat tggaggagga agggaagcga  600
ttccgggaga tactcgatga gacacttttg ctcgcgggtg cttctaatgt tggggattac  660
ttgccgattc tgaattggtt gggggtgaag agcttggaga agaagctaat cgcattgcag  720
aaaaagagag atgatttctt tcagggactg atcgagcaag ttcggaaatc tagaggggct  780
aaagtgggaa aaggaaggaa gacgatgatc gagttgttgt tatccctaca agaatctgaa  840
cctgagtatt acactgacgc catgatccga tcatttgtgc tgggtttatt agcagcaggg  900
agtgatacat cggctggaac tatggaatgg gcgatgtctc ttttggtaaa ccacccgcac  960
gtattaaaaa aggcacaggc tgaaattgat cgagtcatcg gcaacaaccg tctaattgat  1020
gagtccgaca tagggaatat accttacatt ggttgcatca taaacgagac gctcagattg  1080
taccctgcgg gcccgttgct atttccccat gagtcatcag cggactgtgt tatcagcggg  1140
tacaacatcc ctcgtgggac gatgcttatt gtcaaccaat gggcgataca tcatgaccca  1200
aaggtgtggg acgaccctga gacattcaaa ccggaaagat tccaagggct tgaagggaca  1260
cgagacgggt ttaagctgat gcctttgggt tccggaagga ggggttgtcc aggggaggga  1320
ttggcgattc gtttgcttgg gatgactctc gggtcggtta tccaatgctt tgattgggaa  1380
cgagtcggtg acgagatggt tgatatgacc gaaggtcttg ggtcacgtt gcctaaagct  1440
gtaccattag tcgccaagtg caagccgcgt tccgaaatga cgaatctact ctctgagcta  1500
tga                                                               1503
```

```
SEQ ID NO: 164         moltype = AA  length = 500
FEATURE                Location/Qualifiers
source                 1..500
                       mol_type = protein
                       organism = Stevia rebaudiana
SEQUENCE: 164
MEASYLYISI LLLLASYLFT TQLRRKSANL PPTVFPSIPI IGHLYLLKKP LYRTLAKIAA  60
KYGPILQLQL GYRRVLVISS PSAAEECFTN NDVIFANRPK TLFGKIVGGT SLGSLSYGDQ  120
WRNLRRVASI EILSVHRLNE FHDIRVDENR LLIRKLRSSS SPVTLITVFY ALTLNVIMRM  180
ISGKRYFDSG DRELEEEGKR FREILDETLL LAGASNVGDY LPILNWLGVK SLEKKLIALQ  240
KKRDDFFQGL IEQVRKSRGA KVGKGRKTMI ELLLSLQESE PEYYTDAMIR SFVLGLLAAG  300
SDTSAGTMEW AMSLLVNHPH VLKKAQAEID RVIGNNRLID ESDIGNIPYI GCIINETLRL  360
YPAGPLLFPH ESSADCVISG YNIPRGTMLI VNQWAIHHDP KVWDDPETFK PERFQGLEGT  420
RDGFKLMPFG SGRRGCPGEG LAIRLLGMTL GSVIQCFDWE RVGDEMVDMT EGLGVTLPKA  480
VPLVAKCKPR SEMTNLLSEL                                             500
```

```
SEQ ID NO: 165         moltype = DNA  length = 1503
FEATURE                Location/Qualifiers
source                 1..1503
                       mol_type = other DNA
                       organism = Stevia rebaudiana
SEQUENCE: 165
atggaagcct cttacctata catttctatt ttgcttttac tggcatcata cctgttcacc  60
actcaactta gaaggaagag cgctaatcta ccaccaaccg tgtttccatc aataccaatc  120
attggacact tatacttact caaaaagcct ctttatagaa ctttagcaaa aattgccgct  180
aagtacggac caatactgca attacaactc ggctacagac gtgttctggt gatttcctca  240
ccatcagcag cagaagagtg ctttaccaat aacgatgtaa tcttcgcaaa tagacctaag  300
acattgtttg gcaaaatagt gggtggaaca tcccttggca gtttatccta cggcgatcaa  360
tggcgtaatc taaggagagt agcttctatc gaaatcctat cagttcatag gttgaacgaa  420
tttcatgata tcagagtgga tgagaacaga ttgttaatta gaaaacttag aagttcatct  480
tctcctgtta ctcttataac agtcttttat gctctaacat tgaacgtcat tatgagaatg  540
atctctggca aaagatattt cgacagtggg gatagagaat tggaggagga aggtaagaga  600
tttcgagaaa tcttagacga aacgttgctt ctagccggtg cttctaatgt tggcgactac  660
ttaccaatat tgaactggtt gggagttaag tctcttgaaa agaaattgat cgctttgcag  720
aaaaagagag atgacttttt ccagggtttg attgaacagg ttagaaaatc tcgtggtgct  780
aaagtaggca aaggtagaaa aacgatgatc gaactcttat tatctttgca agagtcagaa  840
cctgagtact atacagatgc tatgataaga tcttttgtcc taggtctgct ggctgcaggt  900
agtgatactt cagcgggcac tatggaatgg gccatgagct tactggtcaa tcacccacat  960
gtattgaaga aagctcaagc tgaaatcgat agagttatcg gtaataacag attgattgac  1020
gagtcagaca ttggaaatat cccttacatc gggtgtatta tcaatgaaac tctaagactc  1080
tatccagcag ggccattgtt gttcccacat gaaagttctg ccgactgcgt tatttccggt  1140
tacaatatac ctagaggtac aatgttaatc gtaaaccaat gggcgattca tcacgatcct  1200
aaagtctggg atgatcctga aacctttaaa cctgaaagat ttcaaggatt agaaggaact  1260
agagatggtt tcaaacttat gccattcggt tctgggagaa gaggatgtcc aggtgaaggt  1320
ttggcaataa ggctgttagg gatgacacta ggctcagtga tccaatgttt tgattgggag  1380
agagtaggag atgagatggt tgacatgaca gaaggtttgg gtgtcacact tcctaaggcc  1440
gttccattag ttgccaaatg taagccacgt tccgaaatga ctaatctcct atccgaactt  1500
taa                                                               1503
```

```
SEQ ID NO: 166         moltype = AA  length = 691
FEATURE                Location/Qualifiers
source                 1..691
                       mol_type = protein
                       organism = Saccharomyces cerevisiae
SEQUENCE: 166
MPFGIDNTDF TVLAGLVLAV LLYVKRNSIK ELLMSDDGDI TAVSSGNRDI AQVVTENNKN  60
YLVLYASQTG TAEDYAKKFS KELVAKFNLN VMCADVENYD FESLNDVPVI VSIFISTYGE  120
```

-continued

```
GDFPDGAVNF EDFICNAEAG ALSNLRYNMF GLGNSTYEFF NGAAKKAEKH LSAAGAIRLG  180
KLGEADDGAG TTDEDYMAWK DSILEVLKDE LHLDEQEAKF TSQFQYTVLN EITDSMSLGE  240
PSAHYLPSHQ LNRNADGIQL GPFDLSQPYI APIVKSRELF SSNDRNCIHS EFDLSGSNIK  300
YSTGDHLAVW PSNPLEKVEQ FLSIFNLDPE TIFDLKPLDP TVKVPFPTPT TIGAAIKHYL  360
EITGPVSRQL FSSLIQFAPN ADVKEKLTLL SKDKDQFAVE ITSKYFNIAD ALKYLSDGAK  420
WDTVPMQFLV ESVPQMTPRY YSISSSSLSE KQTVHVTSIV ENFPNPELPD APPVVGVTTN  480
LLRNIQLAQN NVNIAETNLP VHYDLNGPRK LFANYKLPVH VRRSNFRLPS NPSTPVIMIG  540
PGTGVAPFRG FIRERVAFLE SQKKGGNNVS LGKHILFYGS RNTDDFLYQD EWPEYAKKLD  600
GSFEMVVAHS RLPNTKKVYV QDKLKDYEDQ VFEMINNGAF IYVCGDAKGM AKGVSTALVG  660
ILSRGKSITT DEATELIKML KTSGRYQEDV W                               691

SEQ ID NO: 167          moltype = AA  length = 335
FEATURE                 Location/Qualifiers
source                  1..335
                        mol_type = protein
                        organism = Saccharomyces cerevisiae
SEQUENCE: 167
MEAKIDELIN NDPVWSSQNE SLISKPYNHI LLKPGKNFRL NLIVQINRVM NLPKDQLAIV  60
SQIVELLHNS SLLIDDIEDN APLRRGQTTS HLIFGVPSTI NTANYMYFRA MQLVSQLTTK  120
EPLYHNLITI FNEELINLHR GQGLDIYWRD FLPEIIPTQE MYLNMVMNKT GGLFRLTLRL  180
MEALSPSSHH GHSLVPFINL LGIIYQIRDD YLNLKDFQMS SEKGFAEDIT EGKLSFPIVH  240
ALNFTKTKGQ TEQHNEILRI LLLRTSDKDI KLKLIQILEF DTNSLAYTKN FINQLVNMIK  300
NDNENKYLPD LASHSDTATN LHDELLYIID HLSEL                           335

SEQ ID NO: 168          moltype = AA  length = 712
FEATURE                 Location/Qualifiers
source                  1..712
                        mol_type = protein
                        organism = Arabidopsis thaliana
SEQUENCE: 168
MSSSSSSSTS MIDLMAAIIK GEPVIVSDPA NASAYESVAA ELSSMLIENR QFAMIVTTSI  60
AVLIGCIVML VWRRSGSGNS KRVEPLKPLV IKPREEEIDD GRKKVTIFFG TQTGTAEGFA  120
KALGEEAKAR YEKTRFKIVD LDDYAADDDE YEEKLKKEDV AFFFLATYGD GEPTDNAARF  180
YKWFTEGNDR GEWLKNLKYG VFGLGNRQYE HFNKVAKVVD DILVEQGAQR LVQVGLGDDD  240
QCIEDDFTAW REALWPELDT ILREEGDTAV ATPYTAAVLE YRVSIHDSED AKFNDITLAN  300
GNGYTVFDAQ HPYKANVAVK RELHTPESDR SCIHLEFDIA GSGLTMKLGD HVGVLCDNLS  360
ETVDEALRLL DMSPDTYFSL HAEKEDGTPI SSSLPPPFPP CNLRTALTRY ACLLSSPKKS  420
ALVALAAHAS DPTEAERLKH LASPAGKDEY SKWVVESQRS LLEVMAEFPS AKPPLGVFFA  480
GVAPRLQPRF YSISSSPKIA ETRIHVTCAL VYEKMPTGRI HKGVCSTWMK NAVPYEKSEK  540
LFLGRPIFVR QSNFKLPSDS KVPIIMIGPG TGLAPFRGFL QERLALVESG VELGPSVLFF  600
GCRNRRMDFI YEEELQRFVE SGALAELSVA FSREGPTKEY VQHKMMDKAS DIWNMISQGA  660
YLYVCGDAKG MARDVHRSLH TIAQEQGSMD STKAEGFVKN LQTSGRYLRD VW        712

SEQ ID NO: 169          moltype = AA  length = 709
FEATURE                 Location/Qualifiers
source                  1..709
                        mol_type = protein
                        organism = Stevia rebaudiana
SEQUENCE: 169
MQSESVEAST IDLMTAVLKD TVIDTANASD NGDSKMPPAL AMMFEIRDLL LILTTSVAVL  60
VGCFVVLVWK RSSGKKSGKE LEPPKIVVPK RRLEQEVDDG KKKVTIFFGT QTGTAEGFAK  120
ALFEEAKARY EKAAFKVIDL DDYAADLDEY AEKLKKETYA FFFLATYGDG EPTDNAAKFY  180
KWFTEGDEKG VWLQKLQYGV FGLGNRQYEH FNKIGIVVDD GLTEQGAKRI VPVGLGDDDQ  240
SIEDDFSAWK ELVWPELDLL LRDEDDKAAA TPYTAAIPEY RVVFHDKPDA FSDDHTQTNG  300
HAVHDAQHPC RSNVAVKKEL HTPESDRSCT HLEFDISHTG LSYETGDHVG VYCENLIEVV  360
EEAGKLLGLS TDTYFSLHID NEDGSPLGGP SLQPPFPPCT LRKALTNYAD LLSSPKKSTL  420
LALAAHASDP TEADRLRFLA SREGKDEYAE WVVANQRSLL EVMEAFPSAR PPLGVFFAAV  480
APRLQPRYYS ISSSPKMEPN RIHVTCALVY EKTPAGRIHK GICSTWMKNA VPLTESQDCS  540
WAPIFVRTSN FRLPIDPKVP VIMIGPGTGL APFRGFLQER LALKESGTEL GSSILFFGCR  600
NRKVDYIYEN ELNNFVENGA LSELDVAFSR DGPTKEYVQH KMTQKASEIW NMLSEGAYLY  660
VCGDAKGMAK DVHRTLHTIV QEQGSLDSSK AELYVKNLQM SGRYLRDVW           709

SEQ ID NO: 170          moltype = AA  length = 707
FEATURE                 Location/Qualifiers
source                  1..707
                        mol_type = protein
                        organism = Stevia rebaudiana
SEQUENCE: 170
MQSNSVKISP LDLVTALFSG KVLDTSNASE SGESAMLPTI AMIMENRELL MILTTSVAVL  60
IGCVVVLVWR RSSTKKSALE PPVIVVPKRV QEEEVDDGKK KVTVFFGTQT GTAEGFAKAL  120
VEEAKARYEK AVFKVIDLDD YAADDDEYEE KLKKESLAFF FLATYGDGEP TDNAARFYKW  180
FTEGDAKGEW LNKLQYGVFG LGNRQYEHFN KIAKVVDDGL VEQGAKRLVP VGLGDDDQCI  240
EDDFTAWKEL VWPELDQLLR DEDDTTVATP YTAAVAEYRV VFHEKPDALS EDYSYTNGHA  300
VHDAQHPCRS NVAVKKELHS PESDRSCTHL EFDISNTGLS YETGDHVGVY CENLSEVVND  360
AERLVGLPPD TYSSIHTDSE DGSPLGGASL PPPFPPCTLR KALTCYADVL SSPKKSALLA  420
LAAHATDPSE ADRLKFLASP AGKDEYSQWI VASQRSLLEV MEAFPSAKPS LGVFFASVAP  480
RLQPRYYSIS SSPKMAPDRI HVTCALVYEK TPAGRIHKGV CSTWMKNAVP MTESQDCSWA  540
PIYVRTSNFR LPSDPKVPVI MIGPGTGLAP FRGFLQERLA LKEAGTDLGL SILFFGCRNR  600
KVDFIYENEL NNFVETGALS ELIVAFSREG PTKEYVQHKM SEKASDIWNL LSEGAYLYVC  660
```

```
GDAKGMAKDV HRTLHTIVQE QGSLDSSKAE LYVKNLQMSG RYLRDVW              707

SEQ ID NO: 171         moltype = DNA  length = 2079
FEATURE                Location/Qualifiers
misc_feature           1..2079
                       note = Arabidopsis thaliana sequence that has been codon
                        optimized for yeast
source                 1..2079
                       mol_type = other DNA
                       organism = synthetic construct
SEQUENCE: 171
atgacttctg cactttatgc ctccgatctt ttcaaacaat tgaaaagtat catgggaacg  60
gattctttgt ccgatgatgt tgtattagtt attgctacaa cttctctggc actggttgct  120
ggtttcgttg tcttattgtg gaaaaagacc acggcagatc gttccggcga gctaaagcca  180
ctaatgatcc ctaagtctct gatggcgaaa gatgaggatg atgacttaga tctaggttct  240
ggaaaaacga gagtctctat cttcttcggc acacaaaccg gaacagccga aggattcgct  300
aaagcacttt cagaagagat caaagcaaga tacgaaaagg cggctgtaaa agtaatcgat  360
ttggatgatt acgctgccga tgatgaccaa tatgaggaaa agttgaaaaa ggaaacattg  420
gctttctttt gtgtagccac gtatggtgat ggtgaaccaa ccgataacgc cgcaagattc  480
tacaagtggt ttactgaaga gaacgaaaga gatatcaagt tgcagcaact tgcttacggc  540
gtttttgcct taggtaacag acaatacgag cactttaaca agataggtat tgtcttagat  600
gaagagttat gcaaaaaggg tgcgaagaga ttgattgaag tcggtttagg agatgatgat  660
caatctatcg aggatgactt taatgcatgg aaggaatctt tgtggtctga attagataag  720
ttacttaagg acgaagatga taaatccgtt gccactccat acacagccgt cattccagaa  780
tatagagtag ttactcatga tccaagattc acaacacaga aatcaatgga aagtaatgtg  840
gctaatggta atactaccat cgatattcat catccatgta gagtagacgt tgcagttcaa  900
aaggaattgc acactcatga atcagacaga tcttgcatac atcttgaatt tgatatatca  960
cgtactggta tcacttacga aacaggtgat cacgtgggtg tctacgctga aaaccatgtt  1020
gaaattgtag aggaagctgg aaagttgttg ggccatagtt tagatcttgt tttctcaatt  1080
catgccgata aagaggatgg ctcaccacta gaaagtgcag tgcctccacc atttccagga  1140
ccatgcaccc taggtaccgg tttagctcgt tacgcggatc tgttaaatcc tccacgtaaa  1200
tcagctctag tggccttggc tgcgtacgcc acagaacctt ctgaggcaga aaaactgaaa  1260
catctaactt caccagatgg taaggatgaa tactcacaat ggatagtagc tagtcaacgt  1320
tctttactag aagttatggc tgctttccca tccgctaaac ctcctttggg tgtttttcttc  1380
gccgcaatag cgcctagact gcaaccaaga tactattcaa tttcatcctc acctagactg  1440
gcaccatcaa gagttcatgt cacatccgct ttagtgtacg gtccaactcc tactggtaga  1500
atccataagg gcgtttgttc aacatggatg aaaaacgcgg ttccagcaga gaagtctcac  1560
gaatgttctg gtgctccaat ctttatcaga gcctccaact tcaaactgcc ttccaatcct  1620
tctactccta ttgtcatggt cggtcctggt acaggtcttg ctccattcag aggtttctta  1680
caagagagaa tggccttaaa ggaggatggt gaagagttgg gatcttcttt gttgtttttc  1740
ggctgtagaa acagacaaat ggatttcatc tacgaagatg aactgaataa ctttgtagat  1800
caaggagtta tttcagagtt gataatggct ttttctagag aaggtgctca gaaggagtac  1860
gtccaacaca aaatgatgga aaaggccgca caagtttggg acttaatcaa agaggaaggc  1920
tatctatatg tctgtggtga tgcaaagggt atggcaagag atgttcacag aacacttcat  1980
actatagtcc aggaacagga aggcgttagt tcttctgaag cggaagcaat tgtgaaaaag  2040
ttacaaacag agggaagata cttgagagat gtgtggtaa                        2079

SEQ ID NO: 172         moltype = DNA  length = 2139
FEATURE                Location/Qualifiers
misc_feature           1..2139
                       note = Arabidopsis thaliana sequence that has been codon
                        optimized for yeast
source                 1..2139
                       mol_type = other DNA
                       organism = synthetic construct
SEQUENCE: 172
atgtcttcct cttcctcttc cagtacctct atgattgatt tgatggctgc tattattaaa  60
ggtgaaccag ttatcgtctc cgacccagca aatgcctctg cttatgaatc agttgctgca  120
gaattgtctt caatgttgat cgaaaacaga caattcgcca tgatcgtaac tacatcaatc  180
gctgttttga tcggttgtat tgtcatgttg gtatggagaa gatccggtag tggtaattct  240
aaaagagtcg aacctttgaa accattagta attaagccaa gagaagaaga aatagatgac  300
ggtagaaaga aagttacaat atttttcggt acccaaactg gtacagctga aggttttgca  360
aaagccttag gtgaagaagc taaggcaaga tacgaaaaga ctagattcaa gatagtcgat  420
ttggatgact atgccgctga tgacgatgaa tacgaagaaa agttgaagaa agaagatgtt  480
gcatttttct ttttggcaac ctatggtgac ggtgaaccaa ctgacaatgc agccagattc  540
tacaaatggt ttacagaggg taatgatcgt ggtgaatggt tgaaaaactt aaagtacggt  600
gttttcggtt tgggtaacag acaatacgaa catttcaaca aagttgcaaa ggttgtcgac  660
gatattttgg tcgaacaagg tgctcaaaga ttagtccaag taggtttggg tgacgatgac  720
caatgtatag aagatgactt tactgcctgg agagaagctt tgtggcctga attagacaca  780
atcttgagag aagaaggtga caccgccgtt gctaccccat atactgctgc agtattagaa  840
tacagagttt ccatccatga tagtgaagac gcaaagttta atgatatcac tttggccaat  900
ggtaacggtt atacagtttt cgatgcacaa cacccttaca aagctaacgt tgcagtcaag  960
agagaattac atacaccaga atccgacaga agttgtatac acttggaatt tgatatcgct  1020
ggttccggtt taaccatgaa gttgggtgac catgtaggtg ttttatgcga caatttgtct  1080
gaaactgttg atgaagcatt gagattgttg gatatgtccc ctgacactta ttttagtttg  1140
cacgctgaaa aagaagatgg tacaccaatt tccagttctt taccacctcc attccctcca  1200
tgtaacttaa gaacagcctt gaccagatac gcttgcttgt tatcatcccc taaaaagtcc  1260
gccttggttg ctttagccgc tcatgctagt gatcctactg aagcagaaag attgaaacac  1320
ttagcatctc cagccggtaa agatgaatat tcaaagtggg tagttgaatc tcaaagatca  1380
```

-continued

```
ttgttagaag ttatggcaga atttccatct gccaagcctc cattaggtgt cttctttgct  1440
ggtgtagcac ctagattgca accaagattc tactcaatca gttcttcacc taagatcgct  1500
gaaactagaa ttcatgttac atgtgcatta gtctacgaaa agatgccaac cggtagaatt  1560
cacaagggtg tatgctctac ttggatgaaa aatgctgttc cttacgaaaa atcagaaaag  1620
ttgttcttag gtagaccaat cttcgtaaga caatcaaact tcaagttgcc ttctgattca  1680
aaggttccaa taatcatgat aggtcctggt acaggtttag ccccattcag aggtttcttg  1740
caagaaagat tggctttagt tgaatctggt gtcgaattag gtccttcagt tttgttcttt  1800
ggttgtagaa acagaagaat ggatttcatc tatgaagaag aattgcaaag attcgtcgaa  1860
tctggtgcat tggccgaatt atctgtagct tttcaagag aaggtccaac taaggaatac  1920
gttcaacata agatgatgga taaggcatcc gacatatgga acatgatcag tcaaggtgct  1980
tatttgtacg tttgcggtga cgcaaagggt atggccagag atgtccatag atctttgcac  2040
acaattgctc aagaacaagg ttccatggat agtaccaaag ctgaaggttt cgtaaagaac  2100
ttacaaactt ccggtagata cttgagagat gtctggtga                        2139
```

```
SEQ ID NO: 173         moltype = DNA  length = 2130
FEATURE                Location/Qualifiers
source                 1..2130
                       mol_type = other DNA
                       organism = Stevia rebaudiana
SEQUENCE: 173
atgcaatcgg aatccgttga agcatcgacg attgatttga tgactgctgt tttgaaggac  60
acagtgatcg atacagcgaa cgcatctgat aacggagact caaagatgcc gccggcgttg  120
gcgatgatgt tcgaaattcg tgatctgttg ctgattttga ctacgtcagt tgctgttttg  180
gtcggatgtt tcgttgtttt ggtgtggaag agatcgtccg ggaagaagtc cggcaaggaa  240
ttggagccgc cgaagatcgt tgtgccgaag aggcggctgg agcaggaggt tgatgatggt  300
aagaagaagg ttacgatttt cttcggaaca caaactggaa cggctgaagg tttcgctaag  360
gcacttttcg aagaagcgaa agcgcgatat gaaaaggcag cgtttaaagt gattgatttg  420
gatgattatg ctgctgattt ggatgagtat gcagagaagc tgaagaagga aacatatgct  480
ttcttcttct tggctacata tggagatggt gagccaactg ataatgctgc caaattttat  540
aaatggttta ctgagggaga cgagaaaggc gtttggcttc aaaaacttca atatggagta  600
tttggtcttg gcaacagaca atatgaacat ttcaacaaga ttggaatagt ggttgatgat  660
ggtctcaccg agcagggtgc aaaacgcatt gttcccgttg gtcttggaga cgacgatcaa  720
tcaattgaag acgatttttc ggcatggaaa gagttagtgt ggcccgaatt ggatctattg  780
cttcgcgatg aagatgacaa agctgctgca actccttaca cagctgcaat ccctgaatac  840
cgcgtcgtat ttcatgacaa acccgatgcg ttttctgatg atcatactca aaccaatggt  900
catgctgttc atgatgctca acatccatgc agatccaatg tggctgttaa aaaagagctt  960
catactcctg aatccgatcg ttcatgcaca catcttgaat ttgacatttc tcacactgga  1020
ttatcttatg aaactgggga tcatgttggt gtatactgtg aaaacctaat tgaagtagtg  1080
gaagaagctg ggaaattgtt aggattatca acagatactt atttctcgtt acatattgat  1140
aacgaagatg gttcaccact tggtggacct tcattacaac ctccttttcc tccttgtact  1200
ttaagaaaag cattgactaa ttatgcagat ctgttaagct ctcccaaaaa gtcaactttg  1260
cttgctctag ctgctcatgc ttccgatccc actgaagctg atcgtttaag atttcttgca  1320
tctcgcgagg gcaaggatga atatgctgaa tgggttgttg caaaccaaag aagtcttctt  1380
gaagtcatgg aagctttccc gtcagctaga ccgccacttg gtgttttctt tgcagcggtt  1440
gcaccgcgtt tacagcctcg ttactactct atttcttcct ccccaaagat ggaaccaaac  1500
aggattcatg ttacttgcgc gttggtttat gaaaaaactc ccgcaggtcg tatccacaaa  1560
ggaatctgct caacctggat gaagaacgct gtacctttga ccgaaagtca agattgcagt  1620
tgggcaccga tttttgttag aacatcaaac ttcagacttc caattgaccc gaaagtcccg  1680
gttatcatga ttggtcctgg aaccgggttg gctccattta ggggttttct tcaagaaaga  1740
ttggctctta aagaatccgg aaccgaactc gggtcatcta ttttattctt cggttgtaga  1800
aaccgcaaag tggattacat atatgagaat gaactcaaca actttgttga aaatggtgcg  1860
ctttctgagc ttgatgttgc tttctcccgc gatggcccga cgaaagaata cgtgcaacat  1920
aaaatgaccc aaaaggcttc tgaaatatgg aatatgcttt ctgagggagc atatttatat  1980
gtatgtggtg atgctaaagg catggctaaa gatgtacacc gtacacttca caccattgtg  2040
caagaacagg gaagtttgga ctcgtctaaa gcggagttgt atgtgaagaa tctacaaatg  2100
tcaggaagat acctccgtga tgtttggtaa                                  2130
```

```
SEQ ID NO: 174         moltype = DNA  length = 2124
FEATURE                Location/Qualifiers
source                 1..2124
                       mol_type = other DNA
                       organism = Stevia rebaudiana
SEQUENCE: 174
atgcaatcta actccgtgaa gatttcgccg cttgatctgg taactgcgct gtttagcggc  60
aaggttttgg acacatcgaa cgcatcggaa tcgggagaat ctgctatgct gccgactata  120
gcgatgatta tggagaatcg tgagctgttg atgatactca caacgtcggt tgctgtattg  180
atcggatgcg ttgtcgtttt ggtgtggcgg agatcgtcta cgaagaagtc ggcgttggag  240
ccaccggtga ttgtggttcc gaagagagtg caagaggagg aagttgatga tggtaagaag  300
aaagttacgg ttttcttcgg cacccaaact ggaacagctg aaggcttcgc taaggcactt  360
gttgaggaag ctaaagctcg atatgaaaag gctgtcttta aagtaattga tttggatgat  420
tatgctgctg atgacgatga gtatgaggag aaactaaaga aagaatcttt ggcctttttc  480
tttttggcta cgtatggaga tggtgagcca acagataatg ctgccagatt ttataaatgg  540
tttactgagg gagatgcgaa aggagaatgg cttaataagc ttcaatatgg agtatttggt  600
ttgggtaaca gacaatatga acattttaac aagatcgcaa aagtggttga tgatggtctt  660
gtagaacagg gtgcaaagcg tcttgttcct gttggacttg gagatgatga tcaatgtatt  720
gaagatgact tcaccgcatg gaaagagtta gtatggccgg agttggatca attacttcgt  780
gatgaggatg acacaactgt tgctactcca tacacagctg ctgttgcaga atatcgcgtt  840
gtttttcatg aaaaaccaga cgcgctttct gaagattata gttatacaaa tggccatgct  900
gttcatgatg ctcaacatcc atgcagatcc aacgtggctg tcaaaaagga acttcatagt  960
```

-continued

```
cctgaatctg accggtcttg cactcatctt gaatttgaca tctcgaacac cggactatca  1020
tatgaaactg ggaccatgt tggagtttac tgtgaaaact tgagtgaagt tgtgaatgat  1080
gctgaaagat tagtaggatt accaccagac acttactcct ccatccacac tgatagtgaa  1140
gacgggtcgc cacttggcgg agcctcattg ccgcctcctt tcccgccatg cactttaagg  1200
aaagcattga cgtgttatgc tgatgttttg agttctccca agaagtcggc tttgcttgca  1260
ctagctgctc atgccaccga tcccagtgaa gctgatagat tgaaatttct tgcatccccc  1320
gccggaaagg atgaatattc tcaatggata gttgcaagcc aaagaagtct ccttgaagtc  1380
atggaagcat tcccgtcagc taagccttca cttggtgttt tctttgcatc tgttgccccg  1440
cgcttacaac caagatacta ctctatttct tcctcaccca agatggcacc ggataggatt  1500
catgttacat gtgcattagt ctatgagaaa acacctgcag gccgcatcca caaaggagtt  1560
tgttcaactt ggatgaagaa cgcagtgcct atgaccgaga gtcaagattg cagttgggcc  1620
ccaatatacg tccgaacatc caatttcaga ctaccatctg accctaaggt cccggttatc  1680
atgattggac ctggcactgg tttggctcct tttagaggtt tccttcaaga gcggttagct  1740
ttaaaggaag ccggaactga cctcggttta tccattttat tcttcggatg taggaatcgc  1800
aaagtggatt tcatatatga aaacgagctt aacaactttg tggagactgg tgctctttct  1860
gagcttattg ttgctttctc ccgtgaaggc ccgactaagg aatatgtgca acacaagatg  1920
agtgagaagg cttcggatat ctggaacttg ctttctgaag gagcatattt atacgtatgt  1980
ggtgatgcca aaggcatggc caaagatgta catcgaaccc tccacacaat tgtgcaagaa  2040
cagggatctc ttgactcgtc aaaggcagaa ctctacgtga agaatctaca aatgtcagga  2100
agatacctcc gtgacgtttg gtaa                                        2124

SEQ ID NO: 175          moltype = DNA  length = 2427
FEATURE                 Location/Qualifiers
source                  1..2427
                        mol_type = other DNA
                        organism = Arabidopsis thaliana
SEQUENCE: 175
atggcaaacg ctgaacgtat gataacgcgc gtccacagcc aacgtgagcg tttgaacgaa  60
acgcttgttt ctgagagaaa cgaagtcctt gccttgcttt ccagggttga agccaaaggt  120
aaaggtattt tacaacaaaa ccagatcatt gctgaattcg aagctttgcc tgaacaaacc  180
cggaagaaac ttgaaggtgg tcctttcttt gaccttctca aatccactca ggaagcaatt  240
gtgttgccac catgggttgc tctagctgtg aggccaaggc ctggtgtttg ggaatactta  300
cgagtcaatc tccatgctct tgtcgttgaa gaactccaac ctgctgagtt tcttcatttc  360
aaggaagaac tcgttgatgg agttaagaat ggtaatttca ctcttgagct tgatttcgag  420
ccattcaatg cgtctatccc tcgtccaaca ctccacaaat acattggaaa tggtgttgac  480
ttccttaacc gtcatttatc ggctaagctc ttccatgaca aggagagttt gcttccattg  540
cttaagttcc ttcgtcttca cagccaccag ggcaagaacc tgatgttgag cgagaagatt  600
cagaacctca acactctgca acacaccttg aggaaagcag aagagtatct agcagagctt  660
aagtccgaaa cactgtatga agagtttgag gccaagtttg aggagattgg tcttgagagg  720
ggatggggag acaatgcaga gcgtgtcctt gacatgatac gtcttctttt ggaccttctt  780
gaggcgcctg atccttgcac tcttgagact tttcttggaa gagtaccaat ggtgttcaac  840
gttgtgatcc tctctccaca tggttacttt gctcaggaca atgttcttgg ttaccctgac  900
actggtggac aggttgttta cattcttgat caagttcgtg ctctggagat agagatgctt  960
caacgtatta agcaacaagg actcaacatt aaaccaagga ttctcattct aactcgactt  1020
ctacctgatg cggtaggaac tacatgcggt gaacgtctcg agagagttta tgattctgag  1080
tactgtgata ttcttcgtgt gcccttcaga acagagaagg gtattgttcg caaatggatc  1140
tcaaggttcg aagtctggcc atatctagag acttacaccg aggatgctgc ggttgagcta  1200
tcgaaagaat tgaatggcaa gcctgacctt atcattggta actacagtga tggaaatctt  1260
gttgcttctt tattggctca caaacttggt gtcactcagt gtaccattgc tcatgctctt  1320
gagaaaacaa agtacccgga ttctgatatc tactggaaga agcttgacga caagtaccat  1380
ttctcatgcc agttcactgc ggatattttc gcaatgaacc acactgattt catcatcact  1440
agtactttcc aagaaattgc tggaagcaaa gaaactgttg ggcagtatga aagccacaca  1500
gcctttactc ttcccggatt gtatcgagtt gttcacggga ttgatgtgtt tgatcccaag  1560
ttcaacattg tctctcctgg tgctgatatg agcatctact tcccttacac agaggagaag  1620
cgtagattga ctaagttcca ctctgagatc gaggagctcc tctacagcga tgttgagaac  1680
aaagagcact tatgtgtgct caaggacaag aagaagccga ttctcttcac aatggctagg  1740
cttgatcgtg tcaagaactt gtcaggtctt gttgagtggt acgggaagaa cacccgcttg  1800
cgtgagctag ctaacttggt tgttgttgga ggagacagga ggaaagagtc aaaggacaat  1860
gaagagaaag cagagatgaa gaaaatgtat gatctcattg aggaatacaa gctaaacggt  1920
cagttcaggt ggatctcctc tcagatggac cgggtaagga acggtgagct gtaccggtac  1980
atctgtgaca ccaagggtgc ttttgtccaa cctgcattat atgaagcctt tgggttaact  2040
gttgtggagg ctatgacttg tggtttaccg actttcgcca cttgcaaagg tggtccagct  2100
gagatcattg tgcacggtaa atcgggtttc cacattgacc cttaccatgg tgatcaggct  2160
gctgatactc ttgctgattt cttcaccaag tgtaaggagg atccatctca ctgggatgag  2220
atctcaaaag gagggcttca gaggattgag gagaaataca cttggcaaat ctattcacag  2280
aggctcttga cattgactgg tgtgtatgga ttctggaagc atgtctcgaa ccttgaccgt  2340
cttgaggctc gccgttacct tgaaatgttc tatgcattga agtatcgccc attggctcag  2400
gctgttcctc ttgcacaaga tgattga                                     2427

SEQ ID NO: 176          moltype = DNA  length = 2421
FEATURE                 Location/Qualifiers
source                  1..2421
                        mol_type = other DNA
                        organism = Stevia rebaudiana
SEQUENCE: 176
atggcggaac gtgtactcac tcgtgttcac gaacttcgtg agcgtctcga ttcaactctc  60
gcaactcatc gtaatgaaat cctcttgttt ctttcaagga ttgaaagcca tggaaaagga  120
atattgaagc ctcatcaagt tatgactgaa tttgaagcta tctgcaaaga agatcagagc  180
aaactctctg atggtgcttt ttatgaagtt cttaaatgca cacaggaagc aatagtgcaa  240
```

-continued

```
cctccatggg ttgcactcgc gatccgtctt cgacccggtg tttgggaata tgttagagtc  300
aatgttaatg ttttggtggt tgaagaatta agtgttcctg aatatcttca cttcaaagaa  360
gaattggtta atggaacatc gaatggcaac ttcgtgttgg aactggattt tgaacctttt  420
accgcatcgt ttcctcgacc aactttaacc aagtctattg gtaatggtgt tgagtttcta  480
aacagacatt tatctgctaa aatgtttcat gataaggata gcatgcaccc tcttcttgat  540
ttcctacgga ctcaccacta taagggaaag acaatgatgt tgaatgatag aatccaaaac  600
ctcaatgctc tacaatcggt gttgcgaaag gcgtcagagt acttatcaac actcgacgcg  660
gcaacaccgt actctcagtt tgaacataag tttcaagaaa tcgggttgga gagaggttgg  720
ggtgataaag cggaggtcgt aatggagatg atccacatgc ttctagacct tctagaagca  780
cccgacgcat gcacactcga gaagtttctc ggaagaatcc caatggtttt caatgttgtc  840
attctttcgc ctcatggcta cttcgcgcaa gaaaatgtgt tgggatatcc cgacactggc  900
ggtcaggttg tttacatctt ggatcaagtt cccgctctgg aacgcgagat gctcaaaagg  960
attaaggagc aaggactcga tatcattcct cgtatattga ttgttacgag gcttcttcct  1020
gacgcggttg ggaccacatg cggcaacgt ttagagaaag tgtttggagc cgaacactcg  1080
catattcttc gggtcccgtt tagaaccgaa aagggtattc ttcgtaaatg gatctctcgt  1140
tttgaggtgt ggccttacat cgagactttc accgaggatg ttgctaaaga agttacagca  1200
gagttgcaag caaaaccaga tttgatcatt ggaaactata gtgaaggaaa tttggttgca  1260
tctttgctag ctcacaagtt gggtgtcact cagtgtacca ttgctcatgc tttggagaaa  1320
actaaatacc cggattctga tatctactgg aagaactttg aggagaaata tcatttctct  1380
tcgcagttta ccgctgatct tatcgctatg aaccataccg acttcatcat caccagtact  1440
ttccaagaaa ttgctggaag taaggacacg gttggacagt acgagagtca taccgcgttc  1500
acaatgccgg gattgtatcg ggtggttcac gggatcgatg tttttgaccc caaattcaat  1560
attgtttcac ccggggccga tatgggaatt tactactcgt ataccgagaa agaaaagagg  1620
ctcactgcgc ttcaccctga aatcgatgaa cttctcttta gttccgtcga aaacgaagaa  1680
cacttatgtg tgttgaagga taagagtaaa ccaatcttgt tcacaatggc gcgattggat  1740
aatgtgaaga atttaaccgg actggttgaa tggtacgcta aaaacgaccg ccttcgtgag  1800
ctcgtgaacc tcgtggtcgt cggtggtgac cgaaggaaag agtcgaaaga tcttgaagag  1860
caagctcaga tgaagaagat gcatgaactt atcgaaacct acaaactcaa cggtcagttc  1920
aggtggatat cctcacaaat gaaccgcgtg aggaacggtg agttgtatcg cgttattgct  1980
gacacgcgag gtgcgtttat ccagcctgcg ttttacgagg cgtttgggtt gacggttgtg  2040
gaggccatga cttgtggcct gccgacattc gcgacacttc atggtgggcc cgctgagatt  2100
attgttcacg ggaaatccgg gttccatatt gacccgtatc acggtgacca ggtcaccgag  2160
ttgctggtca atttctttga gaaaactaaa caagacccgg gtcattggga ggccatttcc  2220
aagggtggtc tgcaacgtat tcaggagaaa tacacgtggc agatttattc agataggttg  2280
ttgacgcttg ccggagttta tggattctgg aagcatgtgt cgaagcttga caggctcgag  2340
atccgtcgtt atcttgaaat gttttacgcg ctcaagtatc gcaaactggc tgaatctgtt  2400
ccattggctg ttgatgagtg a                                           2421
```

```
SEQ ID NO: 177         moltype = DNA  length = 2421
FEATURE                Location/Qualifiers
source                 1..2421
                       mol_type = other DNA
                       organism = Coffea arabica
SEQUENCE: 177
atggccgaac gtgttctgac ccgtgttcac agcctccgcg aacgccttga tgctactttg  60
gctgcccacc gcaacgatgt tttgctgttt atgtcgaggc ttgaaaccca tgggaaaggg  120
atcctgaaac cccaccaact tttggctgag tttgaagaaa ttaacaagga tggtaaacaa  180
aaaattcatg atcatgcctt tgaagaagtc ctgaagtcca cacaggaagc aattgtgttg  240
ccccccctggg ttgcacttgc tattcgtctc agacctggtg tctgggagta tgttcgagtc  300
aatgtccatg cactcgttgt tgaggagtta accgtgccag agtacctgca tttcaaggaa  360
gaactcgttg atggaagcaa aaatgggaat tttgttttgg aactggactt cgaaccattt  420
acagcctctt ttcccaagcc aactctaact aagtacatag gcgacggagt tgagttcctc  480
aacaggcacc tctctgccaa aatgttccat gacaaggaga gcatggcccc tctccttgat  540
tttctccgtg ttcaccaata caagggcaag acaatgatgc ttaacgacag gatcaaggac  600
cttaacactc tccaagcagt tctgaggaag gcagaggagt acctaacaac actctctgca  660
gatacaccat actctgaatt cgagcacaaa ttccaagaaa ttggactgga gagaggttgg  720
ggtgatactg ctgagcgtgt cttggaaatg atctgcatgc ttctggatct tctgggggct  780
cctgactcgt gcacactaga gaaattccta gggagaatcc ctatggtatt caatgttgtt  840
attctttccc cccatggata ctttgcccag gaaaacgtat tgggttatcc tgataccggt  900
ggccaggttg tttacatatt ggatcaagtt cctgccttgg agcgtgagat gctgaagagg  960
ataaaggaac aaggacttga tgtcaagcca cgcattctaa ttataactag gctgcttcct  1020
gatgccccctg gaaccacttg tggtcaacgg cttgagaaag tatatggatc agagtactcc  1080
catatactca gagtcccctt cagaactgag aagggagttg ttcgcaaatg gatctctcgc  1140
tttgaagttt ggccctacat ggaaacattt actgaggatg ttgcaaaaga agtcactgca  1200
gaattacagg caaagccaga tttggttatt ggtaactaca gtgagggtaa ccttgttgcc  1260
tccttgcttg ctcacaagtt aggtgtaaca cagtgtacca ttgctcatgc tttggaaaaa  1320
accaagtatc ctgattctga tatttatttg agcaaatttg atgaaaagta ccacttctca  1380
tgtcagttca ctgcggatct tatcgcaatg aaccatacag atttcattat cactagcact  1440
ttccaagaaa tagctggaag caaggacact gttgggcaat atgaaagcca tatggccttc  1500
acaatgccag gattatacag agttgtacat ggcattgatg tttttgatcc aaaattcaac  1560
attgtctcac ctggagctga tacaaacctc tacttcccac acacagagaa ggaaaagaga  1620
ttgacatctt tccatcctga aattgaggag ttgcttttca gcgatgtgga gaatgaggaa  1680
cacctatgtg tgctaaaaga caaaaagaag cctatcttat tcaccatggc aagactggat  1740
cgcgtaaaga atttgacagg gcttgttgaa ttgtatgcta agaacccaaa actaagggaa  1800
ttggtcaatc ttgtcgtggt tggtggagac cgaaggaagg aatccaaaga tttggaagaa  1860
caagctgaga tgaagaaaat gtattcattg atagaaactt acaacttgaa cggccaattc  1920
agatggattt cttctcagat gaacagggtt agaaatggtg aactctatcg gtacattgct  1980
gacaccaggg gagcattcgt gcaacctgca ttttatgagg catttgggtt gactgtggtc  2040
gaggccatga catgtggttt gccaacattt gcaaccaacc atggtggtcc tgctgagatc  2100
```

-continued

```
attattcatg ggaaatctgg tttccacatt gatccatacc atggtgagca ggtcagcgag  2160
ctccttgcca atttctttga aaggtgcaag aaagagcctt cttactggga caccatttca  2220
gccggtggct tgaagcgtat ccaggaaaag tacacctggc aaatttactc agatcggttg  2280
ctgacgctgg ctggagttta tggattctgg aaatgtgttt ccaagcttga tcgccaggag  2340
atccgccgtt atctggaaat gttttatgct ctcaagtatc gcaagttggc tgaagctgtt  2400
ccattggctg ttgatcagta a                                            2421

SEQ ID NO: 178         moltype = AA  length = 481
FEATURE                Location/Qualifiers
source                 1..481
                       mol_type = protein
                       organism = Arabidopsis thaliana
SEQUENCE: 178
MHITKPHAAM FSSPGMGHVI PVIELGKRLS ANNGFHVTVF VLETDAASAQ SKFLNSTGVD  60
IVKLPSPDIY GLVDPDDHVV TKIGVIMRAA VPALRSKIAA MHQKPTALIV DLFGTDALCL  120
AKEFNMLSYV FIPTNARFLG VSIYYPNLDK DIKEEHTVQR NPLAIPGCEP VRFEDTLDAY  180
LVPDEPVYRD FVRHGLAYPK ADGILVNTWE EMEPKSLKSL LNPKLLGRVA RVPVYPIGPL  240
CRPIQSSETD HPVLDWLNEQ PNESVLYISF GSGGCLSAKQ LTELAWGLEQ SQQRFVWVVR  300
PPVDGSCCSE YVSANGGGTE DNTPEYLPEG FVSRTSDRGF VVPSWAPQAE ILSHRAVGGF  360
LTHCGWSSTL ESVVGGVPMI AWPLFAEQNM NAALLSDELG IAVRLDDPKE DISRWKIEAL  420
VRKVMTEKEG EAMRRKVKKL RDSAEMSLSI DGGGLAHESL CRVTKECQRF LERVVDLSRG  480
A                                                                  481

SEQ ID NO: 179         moltype = AA  length = 513
FEATURE                Location/Qualifiers
source                 1..513
                       mol_type = protein
                       organism = Arabidopsis thaliana
SEQUENCE: 179
MGAYETEKPT KDAAALETQS PEDFDQPSPL RKIISVASIA AGVQFGWALQ LSLLTPYVQL  60
LGIPHKWSSL IWLCGPVSGM IVQPIVGFHS DRCRSKFGRR RPFIATGAAL VAVAVFLIGY  120
AADFGYKMGD KLEEKVKVRA IGIFALGFWI LDVANNTLQG PCRAFLADLA AGDAKRTRVA  180
NAFFSFFMAV GNVLGYAAGS YTNLHKMFPF TMTKACDIYC ANLKTCFFLS ITLLLIVTVT  240
SLWYVNDKQW SPPPRNADDD EKTSSVPLFG EIFGAFKVMK RPMWMLLIVT ALNWIAWFPF  300
LLFDTDWMGR EVFGGDSDGN ERSKKLYSLG VQSGAMGLMF NSIVLGFMSL GVEWIGRKLG  360
GAKRLWGIVN FILAAGLAMT VLVTKFAEDH RKTAGDLAGP SASVKAGALS LFAVLGIPLA  420
ITFSTPFALA SIFSSCSGAG QGLSLGVLNL AIVIPQMIVS LGGGPFDALF GGGNLPAFIV  480
AAIAAAISGV LALTVLPSPP PDAPKATTMG GFH                               513

SEQ ID NO: 180         moltype = AA  length = 806
FEATURE                Location/Qualifiers
source                 1..806
                       mol_type = protein
                       organism = Coffea arabica
SEQUENCE: 180
MAERVLTRVH SLRERLDATL AAHRNDVLLF MSRLETHGKG ILKPHQLLAE FEEINKDGKQ  60
KIHDHAFEEV LKSTQEAIVL PPWVALAIRL RPGVWEYVRV NVHALVVEEL TVPEYLHFKE  120
ELVDGSKNGN FVLELDFEPF TASFPKPTLT KYIGDGVEFL NRHLSAKMFH DKESMAPLLD  180
FLRVHQYKGK TMMLNDRIKD LNTLQAVLRK AEEYLTTLSA DTPYSEFEHK FQEIGLERGW  240
GDTAERVLEM ICMLLDLLGA PDSCTLEKFL GRIPMVFNVV ILSPHGYFAQ ENVLGYPDTG  300
GQVVYILDQV PALEREMLKR IKEQGLDVKP RILIITRLLP DAPGTTCGQR LEKVYGSEYS  360
HILRVPFRTE KGVVRKWISR FEVWPYMETF TEDVAKEVTA ELQAKPDLVI GNYSEGNLVA  420
SLLAHKLGVT QCTIAHALEK TKYPDSDIYL SKFDEKYHFS CQFTADLIAM NHTDFIITST  480
FQEIAGSKDT VGQYESHMAF TMPGLYRVVH GIDVFDPKFN IVSPGADTNL YFPHTEKEKR  540
LTSFHPEIEE LLFSDVENEE HLCVLKDKKK PILFTMARLD RVKNLTGLVE LYAKNPKLRE  600
LVNLVVVGGD RRKESKDLEE QAEMKKMYSL IETYNLNGQF RWISSQMNRV RNGELYRYIA  660
DTRGAFVQPA FYEAFGLTVV EAMTCGLPTF ATNHGGPAEI IIHGKSGFHI DPYHGEQVSE  720
LLANFFERCK KEPSYWDTIS AGGLKRIQEK YTWQIYSDRL LTLAGVYGFW KCVSKLDRQE  780
IRRYLEMFYA LKYRKLAEAV PLAVDQ                                       806

SEQ ID NO: 181         moltype = DNA  length = 19
FEATURE                Location/Qualifiers
misc_feature           1..19
                       note = Hairpin loop forming sequence
source                 1..19
                       mol_type = other DNA
                       organism = synthetic construct
SEQUENCE: 181
tgaattcgtt aacgaattc                                               19

SEQ ID NO: 182         moltype = DNA  length = 19
FEATURE                Location/Qualifiers
misc_feature           1..19
                       note = Hairpin loop forming sequence
source                 1..19
                       mol_type = other DNA
                       organism = synthetic construct
SEQUENCE: 182
tgaattcgtt aacgaactc                                               19
```

```
SEQ ID NO: 183          moltype = DNA  length = 19
FEATURE                 Location/Qualifiers
misc_feature            1..19
                        note = Hairpin loop forming sequence
source                  1..19
                        mol_type = other DNA
                        organism = synthetic construct
SEQUENCE: 183
tgaattcgtt aacgaagtc                                              19

SEQ ID NO: 184          moltype = DNA  length = 19
FEATURE                 Location/Qualifiers
misc_feature            1..19
                        note = Hairpin loop forming sequence
source                  1..19
                        mol_type = other DNA
                        organism = synthetic construct
SEQUENCE: 184
tgaattcgtt aacgaaatt                                              19

SEQ ID NO: 185          moltype = DNA  length = 287
FEATURE                 Location/Qualifiers
source                  1..287
                        mol_type = other DNA
                        organism = Saccharomyces cerevisiae
SEQUENCE: 185
gcgttggttg gtggatcaag cccacgcgta ggcaatcctc gagcagatcc gccaggcgtg  60
tatatatagc gtggatggcc aggcaacttt agtgctgaca catacaggca tatatatatg  120
tgtgcgacga cacatgatca tatggcatgc atgtgctctg tatgtatata aaactcttgt  180
tttcttcttt tctctaaata ttctttcctt atacattagg acctttgcag cataaattac  240
tatacttcta tagacacaca aacacaaata cacacactaa attaata               287

SEQ ID NO: 186          moltype = DNA  length = 491
FEATURE                 Location/Qualifiers
source                  1..491
                        mol_type = other DNA
                        organism = Saccharomyces cerevisiae
SEQUENCE: 186
ggtcagcagc tctgatgtag atacacgtat ctcgacatgt tttattttta ctatacatac  60
ataaaagaaa taaaaaatga taacgtgtat attattattc atataatcaa tgagggtcat  120
tttctgaaac gcaaaaaacg gtaaatggaa aaaaaataaa gatagaaaaa gaaaacaaac  180
aaaggaaagg ttagcatatt aaataactga gctgatactt caacagcatc gctgaagaga  240
acagtattga aaccgaaaca ttttctaaag gcaaacaagg tactccatat ttgctggacg  300
tgttctttct ctcgtttcat atgcataatt ctgtcataag cctgttcttt ttcctggctt  360
aaacatcccg ttttgtaaaa gagaaatcta ttccacatat ttcattcatt cggctaccat  420
actaaggata aactaatccc gttgtttttt ggcctcgtca cataattata aactactaac  480
ccattatcag a                                                      491

SEQ ID NO: 187          moltype = DNA  length = 28
FEATURE                 Location/Qualifiers
misc_feature            1..28
                        note = Hairpin loop forming sequence
source                  1..28
                        mol_type = other DNA
                        organism = synthetic construct
SEQUENCE: 187
cacaaataca cacactaaat taataatg                                    28

SEQ ID NO: 188          moltype = DNA  length = 47
FEATURE                 Location/Qualifiers
misc_feature            1..47
                        note = Hairpin loop forming sequence
source                  1..47
                        mol_type = other DNA
                        organism = synthetic construct
SEQUENCE: 188
cacaaataca cacactaaat taatatgaat tcgttaacga attcatg               47

SEQ ID NO: 189          moltype = DNA  length = 47
FEATURE                 Location/Qualifiers
misc_feature            1..47
                        note = Hairpin loop forming sequence
source                  1..47
                        mol_type = other DNA
                        organism = synthetic construct
SEQUENCE: 189
cacaaataca cacactaaat taatatgaat tcgttaacga actcatg               47
```

-continued

```
SEQ ID NO: 190         moltype = DNA  length = 47
FEATURE                Location/Qualifiers
misc_feature           1..47
                       note = Hairpin loop forming sequence
source                 1..47
                       mol_type = other DNA
                       organism = synthetic construct
SEQUENCE: 190
cacaaataca cacactaaat taatatgaat tcgttaacga agtcatg              47

SEQ ID NO: 191         moltype = DNA  length = 47
FEATURE                Location/Qualifiers
misc_feature           1..47
                       note = Hairpin loop forming sequence
source                 1..47
                       mol_type = other DNA
                       organism = synthetic construct
SEQUENCE: 191
cacaaataca cacactaaat taatatgaat tcgttaacga aattatg              47

SEQ ID NO: 192         moltype = AA  length = 444
FEATURE                Location/Qualifiers
source                 1..444
                       mol_type = protein
                       organism = Saccharomyces cerevisiae
SEQUENCE: 192
MGKLLQLALH PVEMKAALKL KFCRTPLFSI YDQSTSPYLL HCFELLNLTS RSFAAVIREL  60
HPELRNCVTL FYLILRALDT IEDDMSIEHD LKIDLLRHFH EKLLLTKWSF DGNAPDVKDR  120
AVLTDFESIL IEFHKLKPEY QEVIKEITEK MGNGMADYIL DENYNLNGLQ TVHDYDVYCH  180
YVAGLVGDGL TRLIVIAKFA NESLYSNEQL YESMGLFLQK TNIIRDYNED LVDGRSFWPK  240
EIWSQYAPQL KDFMKPENEQ LGLDCINHLV LNALSHVIDV LTYLAGIHEQ STFQFCAIPQ  300
VMAIATLALV FNNREVLHGN VKIRKGTTCY LILKSRTLRG CVEIFDYYLR DIKSKLAVQD  360
PNFLKLNIQI SKIEQFMEEM YQDKLPPNVK PNETPIFLKV KERSRYDDEL VPTQQEEEYK  420
FNMVLSIILS VLLGFYYIYT LHRA                                       444

SEQ ID NO: 193         moltype = AA  length = 460
FEATURE                Location/Qualifiers
source                 1..460
                       mol_type = protein
                       organism = Schizosaccharomyces pombe
SEQUENCE: 193
MSLANRIEEI RCLCQYKLWN DLPSYGEDEN VPQNIRRCYQ LLDMTSRSFA VVIKELPNGI  60
REAVMIFYLV LRGLDTVEDD MTLPLDKKLP ILRDFYKTIE VEGWTFNESG PNEKDRQLLV  120
EFDVVIKEYL NLSEGYRNVI SNITKEMGDG MAYYASLAEK NDGFSVETIE DFNKYCHYVA  180
GLVGIGLSRL FAQSKLEDPD LAHSQAISNS LGLFLQKVNI IRDYREDFDD NRHFWPREIW  240
SKYTSSFGDL CLPDNSEKAL ECLSDMTANA LTHATDALVY LSQLKTQEIF NFCAIPQVMA  300
IATLAAVFRN PDVFQTNVKI RKGQAVQIIL HSVNLKNVCD LFLRYTRDIH YKNTPKDPNF  360
LKISIECGKI EQVSESLFPR RFREMYEKAY VSKLSEQKKG NGTQKAILND EQKELYRKDL  420
QKLGISILFV FFIILVCLAV IFYVFNIRIH WSDFKELNLF                       460

SEQ ID NO: 194         moltype = AA  length = 445
FEATURE                Location/Qualifiers
source                 1..445
                       mol_type = protein
                       organism = Yarrowia lipolytica
SEQUENCE: 194
MGKLIELLLH PSELSAAIHY KLWRQPLHPR DLSKESTELR RCYELLDVCS RSFAAVIREL  60
HPEVRDAVML FYLILRALDT IEDDMTLSRD IKIPILRDFT KCMKTPGWKF TDSDPNERDR  120
VVLQEFPVVM TEFNKLKPKY QEVIYDITDR MGNGMADYVI DDDFNNNGVD TIAAYDLYCH  180
HVAGIVGEGL TRITILAGFG TDVLHENPRL QESMGLFLQK VNIIRDYRED IDVNRAFWPR  240
EIWHKYAEEM RDFKDPKYSK KALHCTSDLV ANALGHATDC LDYLDNVTDP STFTFCAIPQ  300
VMAIATLDLV YRNPDVFQKN VKLRKGTTVS LILEASNVSG VCDIFTRYAR KVYKKSDPND  360
PNYFRVSVLC GKIEQHAALI KRQRGPPAKT IAQLEGERKE MALSLIVCLA VIFSMSGLMA  420
YIAYVSGFRW SPREIFDSKM FPLRD                                      445

SEQ ID NO: 195         moltype = AA  length = 443
FEATURE                Location/Qualifiers
source                 1..443
                       mol_type = protein
                       organism = Candida glabrata
SEQUENCE: 195
MGKVLDLALH PLELRAALKL KFIRQPLFST NDTRATPQLE RCYELLNLTS RSFAAVIMEL  60
HPELRNVIMV FYLILRALDT VEDDMTIDPQ LKVKVLREFD SKLDTTDWSF DGNDLKEKDR  120
VVLTEFPCIL GEYHKLKPEY QKVIKRITGL MGNGMADYIL DENFNLNGVQ TVKDYDKYCH  180
YVAGLVGDGL TELIVLAGFG SDDLYHGKNS FQLYESMGLF LQKTNIIRDY AEDLDDGRSF  240
WPKEIWSEYA TKLTDFRDPK NTQKGVDCIN HLVLNALTHV IDVLTYLSSI HEQSSFQFCA  300
IPQVMAIATL AKVFNNPEVL RKNVKIRKGT TCDLILNSRT LKGCVDIFQY YLRDMKQRLP  360
VEDPNYLKFN IQVAKIEQFI EEMFQDNLPA GVEPRETMIY LKVQERLKWD TQVIPRVQEE  420
DYKFNMALSV VFCVLLSFYF FTK                                        443
```

```
SEQ ID NO: 196          moltype = AA  length = 441
FEATURE                 Location/Qualifiers
source                  1..441
                        mol_type = protein
                        organism = Ashbya gossypii
SEQUENCE: 196
MGKVVQLFTH PLELKAALKL KFLREPLYPA DDTQGSAELK RCYQLLQRTS RSFAAVIMEL  60
HPELRNAVML FYLILRALDT VEDDMTISPK VKVPLLREFD QKLKLDTWSF DGNAKTEKDR  120
DVLVEFSTIL AEFHKLKPEY QQVIADITHK MGNGMADYIL DEKFNLSGLE TIQDYDRYCH  180
YVAGLVGDGL THLIMLAKFS SPGLYYDSPD LYESMGLFLQ KTNIIRDYAE DLADGRSFWP  240
KEIWSHYADD LASFSKPENA TAGVYCINHL VLNALGHVQH VLTYLASLRE QSSFQFCAIP  300
QVMAIATLAL VFGNERVLQT SVKIRKGTTC YLILKSRTFQ GCVEIFEHYL RDIRKRLTVA  360
DPNYLKLNIE IAKLDKFIEE MYQDKLPVGA KPQETEIYKK VRERSAYDLE VLPREQEEEF  420
KFNVLLSILF TVFGALYWYA K                                           441

SEQ ID NO: 197          moltype = AA  length = 443
FEATURE                 Location/Qualifiers
source                  1..443
                        mol_type = protein
                        organism = Cyberlindnera jadinii
SEQUENCE: 197
MGKLLQLALH PDELASIVQF KLFRKNENAR NPATESAELI RCYELLNLTS RSFAAVIEEL  60
HPELRNVIMV FYLVLRALDT VEVDMSIENS VKLPVLRQFH EKLDTKDWTF DGNSPNEKDR  120
CVLVEFDRIL GQYHELKPQY QKVIKEITEK MGNGMADYIE NENFNSNGLL TIEDYDLYCY  180
YVAGLVGDGL TQLIVLAKFG NSELSVNKQL FKSMGLFLQK TNIIRDYEED QVDGRAFWPK  240
EIWGKYANEL SDFMKPENQS QGLWCISELV CNALDHVIDV LQYLALVEEQ TSFNFCAIPQ  300
VMAIATLELV FQNPQVLTQH VKIRKGTTVS LILESRTLEG CARIFRRYLR KIHHKSHPSD  360
PNYLRLGITI GKIEQFLDGM YPHYVPKGIT PQTTSIRTQV VKRLQLDEPM KRDIDEEILK  420
TRILLLSLGV AVFGVVYGVV RII                                         443

SEQ ID NO: 198          moltype = AA  length = 448
FEATURE                 Location/Qualifiers
source                  1..448
                        mol_type = protein
                        organism = Candida albicans
SEQUENCE: 198
MGKFLQLLSH PTELKAVIQL FGFRQPLHPG KRDVNDKELG RCYELLNLTS RSFAAVIEEL  60
HPELRDAVMI FYLVLRALDT IEDDMTIKSS IKIPLLREFD TKLNTKNWTF DGYGPNEKDR  120
TVLVEFDKIL NVYHRLKPQY QDIIKSITFK MGNGMADYIL DEEFNVYGVA TVEDYNLYCH  180
YVAGLVGEGL TNLFVLANFG DKTLTENNFA KADSMGLFLQ KTNIIRDYHE DLQDGRSFWP  240
REIWSKYTEN LQDFHKVKTP AKEFAGVSCI NELVLNALGH VTDCLDYLSL VKDPSSFSFC  300
AIPQVMAVAT LAEVYNNPKV LHGVVKIRKG TTCRLILESR TLPGVVKIFK EYIQVINHKS  360
SVRDPNYLKI GIKCGEIEQY CEMIYPNKQA LPPSMKSLPE NKFTKIVASR ESIDLSVQRR  420
IEPGNFNCNV VLFGIGALIL SLIYFVLY                                    448

SEQ ID NO: 199          moltype = AA  length = 731
FEATURE                 Location/Qualifiers
source                  1..731
                        mol_type = protein
                        organism = Saccharomyces cerevisiae
SEQUENCE: 199
MTEFYSDTIG LPKTDPRLWR LRTDELGRES WEYLTPQQAA NDPPSTFTQW LLQDPKFPQP  60
HPERNKHSPD FSAFDACHNG ASFFKLLQEP DSGIFPCQYK GPMFMTIGYV AVNYIAGIEI  120
PEHERIELIR YIVNTAHPVD GGWGLHSVDK STVFGTVLNY VILRLLGLPK DHPVCAKARS  180
TLLRLGGAIG SPHWGKIWLS ALNLYKWEGV NPAPPETWLL PYSLPMHPGR WWVHTRGVYI  240
PVSYLSLVKF SCPMTPLLEE LRNEIYTKPF DKINFSKNRN TVCGVDLYYP HSTTLNIANS  300
LVVFYEKYLR NRFIYSLSKK KVYDLIKTEL QNTDSLCIAP VNQAFCALVT LIEEGVDSEA  360
FQRLQYRFKD ALFHGPQGMT IMGTNGVQTW DCAFAIQYFF VAGLAERPEF YNTIVSAYKF  420
LCHAQFDTEC VPGSYRDKRK GAWGFSTKTQ GYTVADCTAE AIKAIIMVKN SPVFSEVHHM  480
ISSERLFEGI DVLLNLQNIG SFEYGSFATY EKIKAPLAME TLNPAEVFGN IMVEYPYVEC  540
TDSSVLGLTY FHKYFDYRKE EIRTRIRIAI EFIKKSQLPD GSWYGSWGIC FTYAGMFALE  600
ALHTVGETYE NSSTVRKGCD FLVSKQMKDG GWGESMKSSE LHSYVDSEKS LVVQTAWALI  660
ALLFAEYPNK EVIDRGIDLL KNRQEESGEW KFESVEGVFN HSCAIEYPSY RFLFPIKALG  720
MYSRAYETHT L                                                      731

SEQ ID NO: 200          moltype = AA  length = 417
FEATURE                 Location/Qualifiers
source                  1..417
                        mol_type = protein
                        organism = Homo sapiens
SEQUENCE: 200
MEFVKCLGHP EEFYNLVRFR IGGKRKVMPK MDQDSLSSSL KTCYKYLNQT SRSFAAVIQA  60
LDGEMRNAVC IFYLVLRALD TLEDDMTISV EKKVPLLHNF HSFLYQPDWR FMESKEKDRQ  120
VLEDFPTISL EFRNLAEKYQ TVIADICRRM GIGMAEFLDK HVTSEQEWDK YCHYVAGLVG  180
IGLSRLFSAS EFEDPLVGED TERANSMGLF LQKTNIIRDY LEDQQGGREF WPQEVWSRYV  240
KKLGDFAKPE NIDLAVQCLN ELITNALHHI PDVITYLSRL RNQSVFNFCA IPQVMAIATL  300
AACYNNQQVF KGAVKIRKGQ AVTLMMDATN MPAVKAIIYQ YMEEIYHRIP DSDPSSSKTR  360
QIISTIRTQN LPNCQLISRS HYSPIYLSFV MLLAALSWQY LTTLSQVTED YVQTGEH     417
```

-continued

```
SEQ ID NO: 201         moltype = AA  length = 416
FEATURE                Location/Qualifiers
source                 1..416
                       mol_type = protein
                       organism = Mus musculus
SEQUENCE: 201
MEFVKCLGHP EEFYNLLRFR MGGRRNFIPK MDQDSLSSSL KTCYKYLNQT SRSFAAVIQA  60
LDGDIRHAIC VFYLVLRALD TVEDDMSISV EKKIPLLCNF HTFLYDPEWR FTESKEKDRQ  120
VLEDFPTISL EFRNLAEKYQ TVIDDICHRM GCGMAEFVDK DVTSKQDWDK YCHYVAGLVG  180
IGLSRLFSAS EFEDPIVGED IECANSMGLF LQKTNIIRDY LEDQQEGRKF WPQEVWGRYI  240
KKLEDFAKPE NVDVAVQCLN ELITNTLQHI PDVLTYLSRL RNQSVFNFCA IPQVMAIATL  300
AACYNNQQVF KGVVKIRKGQ AVTLMMDATN MPAVKAIIYQ YIEEIYHRIP NSDPSSSKTK  360
QVISKIRTQN LPNCQLISRS HYSPIYLSFI MLLAALSWQY LSTLSQVTED YVQREH      416

SEQ ID NO: 202         moltype = AA  length = 416
FEATURE                Location/Qualifiers
source                 1..416
                       mol_type = protein
                       organism = Rattus norvegicus
SEQUENCE: 202
MEFVKCLGHP EEFYNLLRFR MGGRRNFIPK MDRNSLSNSL KTCYKYLDQT SRSFAAVIQA  60
LDGDIRHAVC VFYLILRAMD TVEDDMAISV EKKIPLLRNF HTFLYEPEWR FTESKEKHRV  120
VLEDFPTISL EFRNLAEKYQ TVIADICHRM GCGMAEFLNK DVTSKQDWDK YCHYVAGLVG  180
IGLSRLFSAS EFEDPIVGED TECANSMGLF LQKTNIIRDY LEDQQEGRQF WPQEVWGKYV  240
KKLEDFVKPE NVDVAVKCLN ELITNALQHI PDVITYLSRL RNQSVFNFCA IPQVMAIATL  300
AACYNNHQVF KGVVKIRKGQ AVTLMMDATN MPAVKAIIYQ YIEEIYHRVP NSDPSASKAK  360
QLISNIRTQS LPNCQLISRS HYSPIYLSFI MLLAALSWQY LSTLSQVTED YVQREH      416

SEQ ID NO: 203         moltype = AA  length = 396
FEATURE                Location/Qualifiers
source                 1..396
                       mol_type = protein
                       organism = Aspergilus nidulans
SEQUENCE: 203
MTSDSHFHPP HAIPPRISSN RMSGASTRDK AALMGNFEKD WLSKGDKLQT NTDLSKRHTR  60
NQSSLDGTKY KDGKWSQENE EVIMGPYDYM LQHPGKDLRR QMINAFNVWL KVPSESLAII  120
TKVVAMLHTA SLLIDDVEDN SLLRRGIPVA HSIYGTAQTI NSANYVYFLA LQEVQKLKSP  180
AAIDIYVQEL LNLHRGQGMD LFWRDTLTCP SEDEYLEMVG NKTGGLFRLA VKLMQAESST  240
GKDCVALVNV LGLVFQICDD YLNLSDTTYT QNKGLCEDLT EGKFSFPIIH SIRSNPGNHQ  300
LINILRQRTK DEEVKRYALQ YMESTGSFKH TQDVVRQLRA RALQLIEEIE NSENGEQPEE  360
HNDGTMVRAI LDKITESTLA DTNTTTRDIN GNCATR                            396

SEQ ID NO: 204         moltype = AA  length = 485
FEATURE                Location/Qualifiers
source                 1..485
                       mol_type = protein
                       organism = Stevia rebaudiana
SEQUENCE: 204
MYNVTYHQNS KAMATSDSIV DDRKQLHVAT FPWLAFGHIL PFLQLSKLIA EKGHKVSFLS  60
TTRNIQRLSS HISPLINVVQ LTLPRVQELP EDAEATTDVH PEDIQYLKKA VDGLQPEVTR  120
FLEQHSPDWI IYDFTHYWLP SIAASLGISR AYFCVITPWT IAYLAPSSDA MINDSDGRTT  180
VEDLTTPPKW FPFPTKVCWR KHDLARMEPY EAPGISDGYR MGMVFKGSDC LLFKCYHEFG  240
TQWLPLLETL HQVPVVPVGL LPPEIPGDEK DETWVSIKKW LDGKQKGSVV YVALGSEALV  300
SQTEVVELAL GLELSGLPFV WAYRKPKGPA KSDSVELPDG FVERTRDRGL VWTSWAPQLR  360
ILSHESVCGF LTHCGSGSIV EGLMFGHPLI MLPIFCDQPL NARLLEDKQV GIEIPRNEED  420
GCLTKESVAR SLRSVVVENE GEIYKANARA LSKIYNDTKV EKEYVSQFVD YLEKNARAVA  480
IDHES                                                              485

SEQ ID NO: 205         moltype = DNA  length = 1673
FEATURE                Location/Qualifiers
source                 1..1673
                       mol_type = other DNA
                       organism = Stevia rebaudiana
SEQUENCE: 205
gctggccaaa tgtacaacgt tacttatcat caaaattcaa aagcaatggc taccagtgac  60
tccatagttg acgaccgtaa gcagcttcat gttgcgacgt tcccatggct tgctttcggt  120
cacatcctcc ctttccttca gctttcgaaa ttgatagctg aaaagggtca caaagtctcg  180
tttctttcta ccaccagaaa cattcaacgt ctctcttctc atatctcgcc actcataaat  240
gttgttcaac tcacacttcc acgtgtccaa gagctgccgg aggatgcaga ggcgaccact  300
gacgtccacc ctgaagatat tcaatatctc aagaaggctg ttgatggtct tcaaccggag  360
gtcacccggt ttctagaaca acactctccg gactggatta tttatgattt tactcactac  420
tggttgccat ccatcgcggc tagcctcggt atctcacgag cctacttctg cgtcatcact  480
ccatggacca ttgcttattt ggcaccctca tctgacgcca tgataaatga ttcagatggt  540
cgaaccacgg ttgaggatct cacgacaccg cccaagtggt ttcccttttcc gaccaaagta  600
tgctggcgga agcatgatct tgcccgaatg gagccttacg aagctccggg gatatctgat  660
ggataccgta tggggatggt ttttaaggga tctgattgtt tgcttttcaa atgttaccat  720
gagtttggaa ctcaatggct acctcttttg gagacactac accaagtacc ggtggttccg  780
gtgggattac tgccgccgga aatacccgga gacgagaaag atgaaacatg ggtgtcaatc  840
```

-continued

```
aagaaatggc tcgatggtaa acaaaaaggc agtgtggtgt acgttgcatt aggaagcgag    900
gctttggtga gccaaaccga ggttgttgag ttagcattgg gtctcgagct ttctgggttg    960
ccatttgttt gggcttatag aaaaccaaaa ggtcccgcga agtcagactc ggtggagttg   1020
ccagacgggt tcgtggaacg aactcgtgac cgtgggttgg tctggacgag ttgggcacct   1080
cagttacgaa tactgagcca cgagtcagtt tgtggtttct tgactcattg tggttctgga   1140
tcaattgtgg aagggctaat gtttggtcac cctctaatca tgctaccgat tttttgtgac   1200
caacctctga atgctcgatt actggaggac aaacaggtgg gaatcgagat accaagaaat   1260
gaggaagatg gttgcttgac caaggagtcg gttgctagat cactgaggtc cgttgttgtg   1320
gaaaacgaag gggagatcta caaggcgaac gcgagggcgc tgagtaaaat ctataacgac   1380
actaaggtgg aaaaagaata tgtaagccaa ttcgtagact atttggaaaa gaatgcgcgt   1440
gcggttgcca tcgatcatga gagttaacta tatcatcaag tatgtgtgag ttgttgggtt   1500
tcttttggaa agattcaaat gaaatgttgg aattgctaaa tatgttggta gaatcgatcg   1560
agtcttagga ggtgtcctag ttaattgttt taagctacta tattaataag ttgttattgt   1620
aaggctattt aaagccaaat tatgtgatga ataaagcaat tgattccagc cgt          1673
```

RECOMBINANT PRODUCTION OF STEVIOL GLYCOSIDES

CROSS-REFERENCE TO RELATED APPLICATIONS

This application is a continuation of U.S. application Ser. No. 17/471,615, filed on Sep. 10, 2021, which is a continuation of Ser. No. 16/535,373, filed on Aug. 8, 2019, which is a continuation of Ser. No. 15/439,660, filed on Feb. 22, 2017, now U.S. Pat. No. 10,435,730, which is a divisional of Ser. No. 14/237,540, filed on May 15, 2014, now U.S. Pat. No. 9,631,215, which is a U.S. national phase of International Application No. PCT/US2012/050021, filed on Aug. 8, 2012, which claims priority to U.S. Application Ser. No. 61/521,084, filed Aug. 8, 2011; U.S. Application Ser. No. 61/521,203, filed Aug. 8, 2011; U.S. Application Ser. No. 61/521,051, filed Aug. 8, 2011; U.S. Application Ser. No. 61/523,487, filed Aug. 15, 2011; U.S. Application Ser. No. 61/567,929, filed Dec. 7, 2011; and U.S. Application Ser. No. 61/603,639, filed Feb. 27, 2012. The entire disclosure contents of these applications are herewith incorporated by reference in their entirety into the present application.

INCORPORATION BY REFERENCE OF SEQUENCE LISTING PROVIDED ELECTRONICALLY

This application contains a Sequence Listing submitted as an electronic text file named "13-1234-US-CON3_SequenceListing_ST26.xml," having a size of 438,583 bytes, and created on Jun. 8, 2023. The information contained in this electronic file is hereby incorporated by reference in its entirety.

TECHNICAL FIELD

This disclosure relates to the recombinant production of steviol glycosides. In particular, this disclosure relates to the production of steviol glycosides such as rebaudioside D by recombinant hosts such as recombinant microorganisms, plants, or plant cells. This disclosure also provides compositions containing steviol glycosides. The disclosure also relates to tools and methods for producing terpenoids by modulating the biosynthesis of terpenoid precursors of the squalene pathway.

BACKGROUND

Sweeteners are well known as ingredients used most commonly in the food, beverage, or confectionary industries. The sweetener can either be incorporated into a final food product during production or for stand-alone use, when appropriately diluted, as a tabletop sweetener or an at-home replacement for sugars in baking. Sweeteners include natural sweeteners such as sucrose, high fructose corn syrup, molasses, maple syrup, and honey and artificial sweeteners such as aspartame, saccharine and sucralose. Stevia extract is a natural sweetener that can be isolated and extracted from a perennial shrub, *Stevia rebaudiana*. *Stevia* is commonly grown in South America and Asia for commercial production of stevia extract. Stevia extract, purified to various degrees, is used commercially as a high intensity sweetener in foods and in blends or alone as a tabletop sweetener.

Extracts of the Stevia plant contain rebaudiosides and other steviol glycosides that contribute to the sweet flavor, although the amount of each glycoside often varies among different production batches. Existing commercial products are predominantly rebaudioside A with lesser amounts of other glycosides such as rebaudioside C, D, and F. Stevia extracts may also contain contaminants such as plant-derived compounds that contribute to off-flavors. These off-flavors can be more or less problematic depending on the food system or application of choice. Potential contaminants include pigments, lipids, proteins, phenolics, saccharides, spathulenol and other sesquiterpenes, labdane diterpenes, monoterpenes, decanoic acid, 8,11,14-eicosatrienoic acid, 2-methyloctadecane, pentacosane, octacosane, tetracosane, octadecanol, stigmasterol, β-sitosterol, α- and β-amyrin, lupeol, β-amryin acetate, pentacyclic triterpenes, centauredin, quercitin, epi-alpha-cadinol, carophyllenes and derivatives, beta-pinene, beta-sitosterol, and gibberellin.

SUMMARY

Provided herein is a recombinant host, such as a microorganism, plant, or plant cell, comprising one or more biosynthesis genes whose expression results in production of steviol glycosides such as rebaudioside A, rebaudioside C, rebaudioside D, rebaudioside E, rebaudioside F, or dulcoside A. In particular, EUGT11, a uridine 5'-diphospho (UDP) glycosyl transferase described herein, can be used alone or in combination with one or more other UDP glycosyl transferases such as UGT74G1, UGT76G1, UGT85C2, and UGT91D2e, to allow the production and accumulation of rebaudioside D in recombinant hosts or using in vitro systems. As described herein, EUGT11 has a strong 1,2-19-O-glucose glycosylation activity, which is an important step for rebaudioside D production.

Typically, stevioside and rebaudioside A are the primary compounds in commercially-produced stevia extracts. Stevioside is reported to have a more bitter and less sweet taste than rebaudioside A. The composition of stevia extract can vary from lot to lot depending on the soil and climate in which the plants are grown. Depending upon the sourced plant, the climate conditions, and the extraction process, the amount of rebaudioside A in commercial preparations is reported to vary from 20 to 97% of the total steviol glycoside content. Other steviol glycosides are present in varying amounts in stevia extracts. For example, Rebaudioside B is typically present at less than 1-2%, whereas Rebaudioside C can be present at levels as high as 7-15%. Rebaudioside D is typically present in levels of 2% or less, and Rebaudioside F is typically present in compositions at 3.5% or less of the total steviol glycosides. The amount of the minor steviol glycosides affects the flavor profile of a Stevia extract. In addition, Rebaudioside D and other higher glycosylated steviol glycosides are thought to be higher quality sweeteners than Rebaudioside A. As such, the recombinant hosts and methods described herein are particularly useful for producing steviol glycoside compositions having an increased amount of Rebaudioside D for use, for example, as a non-caloric sweetener with functional and sensory properties superior to those of many high-potency sweeteners.

In one aspect, this document features a recombinant host that includes a recombinant gene encoding a polypeptide having at least 80% identity to the amino acid sequence set forth in SEQ ID NO:152.

This document also features a recombinant host that includes a recombinant gene encoding a polypeptide having the ability to transfer a second sugar moiety to the C-2' of a 19-O-glucose of rubusoside. This document also features a recombinant host that includes a recombinant gene encoding a polypeptide having the ability to transfer a second sugar moiety to the C-2' of a 19-O-glucose of stevioside.

In another aspect, this document features a recombinant host that includes a recombinant gene encoding a polypeptide having the ability to transfer a second sugar moiety to the C-2' of the 19-O-glucose of rubusoside and to the C-2' of the 13-O-glucose of rubusoside.

This document also features a recombinant host that includes a recombinant gene encoding a polypeptide having the ability to transfer a second sugar moiety to the C-2' of a 19-O-glucose of rebaudioside A to produce rebaudioside D, wherein the catalysis rate of the polypeptide is at least 20 times faster (e.g., 25 or 30 times faster) than a 91D2e polypeptide having the amino acid sequence set forth in SEQ ID NO: 5 when the reactions are performed under corresponding conditions.

In any of the recombinant hosts described herein, the polypeptide can have at least 85% sequence identity (e.g., 90%, 95%, 98%, or 99% sequence identity) to the amino acid sequence set forth in SEQ ID NO:152. The polypeptide can have the amino acid sequence set forth in SEQ ID NO: 152.

Any of the hosts described herein further can include a recombinant gene encoding a UGT85C polypeptide having at least 90% identity to the amino acid sequence set forth in SEQ ID NO:3. The UGT85C polypeptide can include one or more amino acid substitutions at residues 9, 10, 13, 15, 21, 27, 60, 65, 71, 87, 91, 220, 243, 270, 289, 298, 334, 336, 350, 368, 389, 394, 397, 418, 420, 440, 441, 444, and 471 of SEQ ID NO:3.

Any of the hosts described herein further can include a recombinant gene encoding a UGT76G polypeptide having at least 90% identity to the amino acid sequence set forth in SEQ ID NO:7. The UGT76G polypeptide can have one or more amino acid substitutions at residues 29, 74, 87, 91, 116, 123, 125, 126, 130, 145, 192, 193, 194, 196, 198, 199, 200, 203, 204, 205, 206, 207, 208, 266, 273, 274, 284, 285, 291, 330, 331, and 346 of SEQ ID NO:7.

Any of the hosts described herein further can include a gene (e.g., a recombinant gene) encoding a UGT74G1 polypeptide.

Any of the hosts described herein further can include a gene (e.g., a recombinant gene) encoding a functional UGT91D2 polypeptide. The UGT91D2 polypeptide can have at least 80% sequence identity to the amino acid sequence set forth in SEQ ID NO:5. The UGT91D2 polypeptide can have a mutation at position 206, 207, or 343 of SEQ ID NO:5. The UGT91D2 polypeptide also can have a mutation at positions 211 and 286 of SEQ ID NO:5 (e.g., L211M and V286A, referred to as UGT91D2e-b). The UGT91D2 polypeptide can have the amino acid sequence set forth in SEQ ID NOs: 5, 10, 12, 76, 78, or 95.

Any of the hosts described herein further can include one or more of (i) a gene encoding a geranylgeranyl diphosphate synthase;

(ii) a gene encoding a bifunctional copalyl diphosphate synthase and kaurene synthase, or a gene encoding a copalyl diphosphate synthase and a gene encoding a kaurene synthase;

(iii) a gene encoding a kaurene oxidase; and (iv) a gene encoding a steviol synthetase. Each of the genes of (i), (ii), (iii), and (iv) can be a recombinant gene.

Any of the hosts described herein further can include one or more of (v) a gene encoding a truncated HMG-CoA;

(vi) a gene encoding a CPR;

(vii) a gene encoding a rhamnose synthetase;

(viii) a gene encoding a UDP-glucose dehydrogenase; and (ix) a gene encoding a UDP-glucuronic acid decarboxylase. At least one of the genes of (i), (ii), (iii), (iv), (v), (vi), (vii), (viii), or (ix) can be a recombinant gene.

The geranylgeranyl diphosphate synthase can have greater than 90% sequence identity to one of the amino acid sequences set forth in SEQ ID NOs: 121-128. The copalyl diphosphate synthase can have greater than 90% sequence identity to the amino acid sequence set forth in SEQ ID NOs: 129-131. The kaurene synthase can have greater than 90% sequence identity to one of the amino acid sequences set forth in SEQ ID NOs: 132-135. The kaurene oxidase can have greater than 90% sequence identity to one of the amino acid sequences set forth in SEQ ID NOs: 138-141. The steviol synthetase can have greater than 90% sequence identity to one of the amino acid sequences set forth in SEQ ID NOs: 142-146.

Any of the recombinant hosts can produce at least one steviol glycoside when cultured under conditions in which each of the genes is expressed. The steviol glycoside can be selected from the group consisting of rubusoside, rebaudioside A, rebaudioside B, rebaudioside C, rebaudioside D, rebaudioside E, rebaudioside F, dulcoside A, stevioside, steviol-19-O-Glucoside, steviol-13-O-glucoside, steviol-1,2-bioside, steviol-1,3-bioside, 1,3-stevioside, as well as other rhamnosylated or xylosylated intermediates. The steviol glycoside (e.g., rebaudioside D) can accumulate to at least 1 mg/liter (e.g., at least 10 mg/liter, 20 mg/liter, 100 mg/liter, 200 mg/liter, 300 mg/liter, 400 mg/liter, 500 mg/liter, 600 mg/liter, or 700 mg/liter, or greater) of culture medium when cultured under said conditions.

This document also features a method of producing a steviol glycoside. The method includes growing any of the hosts described herein in a culture medium, under conditions in which the genes are expressed; and recovering the steviol glycoside produced by the host. The growing step can include inducing expression of one or more of the genes. The steviol glycoside can be a 13-O-1,2-diglycosylated and/or a 19-O-1,2-diglycosylated steviol glycoside (e.g., stevioside, steviol 1,2 bioside, rebaudioside D, or rebaudioside E). For example, the steviol glycoside can be rebaudioside D or rebaudioside E. Other examples of steviol glycosides can include rebaudioside A, rebaudioside B, rebaudioside C, rebaudioside F, and dulcoside A.

This document also features a recombinant host. The host includes (i) a gene encoding a UGT74G1; (ii) a gene encoding a UGT85C2; (iii) a gene encoding a UGT76G1; (iv) a gene encoding a glycosyltransferase having the ability to transfer a second sugar moiety to the C-2' of a 19-O-glucose of rubusoside or stevioside; and (v) optionally a gene encoding a UGT91D2e, wherein at least one of the genes is a recombinant gene. In some embodiments, each of the genes is a recombinant gene. The host can produce at least one steviol glycoside (e.g., rebaudioside D) when cultured under conditions in which each of the genes (e.g., recombinant genes) is expressed. The host further can include (a) a gene encoding a bifunctional copalyl diphosphate synthase and kaurene synthase, or a gene encoding a copalyl diphosphate synthase and a gene encoding a kaurene synthase; (b) a gene encoding a kaurene oxidase; (c) a gene encoding a steviol synthetase; (d) a gene encoding a geranylgeranyl diphosphate synthase.

This document also features a steviol glycoside composition produced by any of the hosts described herein. The composition has reduced levels of stevia plant-derived contaminants relative to a stevia extract.

In another aspect, this document features a steviol glycoside composition produced by any of the hosts described herein. The composition has a steviol glycoside composition enriched for rebaudioside D relative to the steviol glycoside composition of a wild-type Stevia plant.

In yet another aspect, this document features a method of producing a steviol glycoside composition. The method includes growing a host described herein in a culture medium, under conditions in which each of the genes is expressed; and recovering the steviol glycoside composition produced by the host (e.g., a microorganism). The composition is enriched for rebaudioside A, rebaudioside B, rebaudioside C, rebaudioside D, rebaudioside E, rebaudioside F or dulcoside A relative to the steviol glycoside composition of a wild-type Stevia plant. The steviol glycoside composition produced by the host (e.g., microorganism) can have a reduced level of stevia plant-derived contaminants relative to a stevia extract.

This document also features a method for transferring a second sugar moiety to the C-2' of a 19-O-glucose or the C-2' of a 13-O-glucose in a steviol glycoside. The method includes contacting the steviol glycoside with a EUGT11 polypeptide described herein or UGT91D2 polypeptide described herein (e.g., UGT91D2e-b) and a UDP-sugar under suitable reaction conditions for the transfer of the second sugar moiety to the steviol glycoside. The steviol glycoside can be rubusoside, wherein the second sugar moiety is glucose, and stevioside is produced upon transfer of the second glucose moiety. The steviol glycoside can be stevioside, wherein the second sugar moiety is glucose, and Rebaudioside E is produced upon transfer of the second glucose moiety. The steviol glycoside can be Rebaudioside A, and Rebaudioside D is produced upon transfer of the second glucose moiety.

In another embodiment of an improved downstream steviol glycoside pathway as disclosed herein, materials and methods are provided for the recombinant production of sucrose synthase, and to materials and methods for increasing production of UDP-glucose in a host, specifically for increasing the availability of UDP-glucose in vivo, with the purpose of promoting glycosylation reactions in the cells, and methods for reducing UDP concentrations in the cells are provided.

The document also provides a recombinant host comprising one or more exogenous nucleic acids encoding a sucrose transporter and a sucrose synthase, wherein expression of the one or more exogenous nucleic acids with a glucosyltransferase results in increased levels of UDP-glucose in the host. Optionally, the one or more exogenous nucleic acids comprise a SUS1 sequence. Optionally, the SUS1 sequence is from *Coffea arabica*, or encodes a functional homolog of the sucrose synthase encoded by the *Coffea arabica* SUS1 sequence, but equally an *Arabidopsis thaliana* or *Stevia rebaudiana* SUS may be used as described herein. In the recombinant host of the invention, the one or more exogenous nucleic acids may comprise a sequence encoding a polypeptide having the sequence set forth in SEQ ID NO:180, or an amino acid sequence at least 90 percent identical thereto, and optionally the one or more exogenous nucleic acids comprise a SUC1 sequence. In one embodiment, the SUC1 sequence is from *Arabidopsis thaliana*, or the SUC1 sequence encodes a functional homolog of the sucrose transporter encoded by the *Arabidopsis thaliana* SUC1 sequence. In the recombinant host, the one or more exogenous nucleic acids may comprise a sequence encoding a polypeptide having the sequence set forth in SEQ ID NO:179, or an amino acid sequence at least 90 percent identical thereto. The recombinant host has reduced ability to degrade external sucrose, as compared to a corresponding host that lacks the one or more exogenous nucleic acids.

The recombinant host may be a microorganism, such as a Saccharomycete, for example *Saccharomyces cerevisiae*. Alternatively, the microorganism is *Escherichia coli*. In an alternative embodiment, the recombinant host is a plant or plant cell.

The invention also provides a method for increasing the level of UDP-glucose and reducing the level of UDP in a cell, the method comprising expressing in the cell a recombinant sucrose synthase sequence and a recombinant sucrose transporter sequence, in a medium comprising sucrose, wherein the cell is deficient in sucrose degradation.

The invention additionally provides a method for promoting a glycosylation reaction in a cell, comprising expressing in the cell a recombinant sucrose synthase sequence and a recombinant sucrose transporter sequence, in a medium comprising sucrose, wherein the expressing results in a decreased level of UDP in the cell and an increased level of UDP-glucose in the cell, such that glycosylation in the cell is increased.

In either method for increasing the level of UDP-glucose or promoting glycosylation, the cell may produce vanillin glucoside, resulting in increased production of vanillin glucoside by the cell, or may produce steviol glucoside, resulting in increased production of steviol glucoside by the cell. Optionally, the SUS1 sequence is a *A. thaliana, S. rebaudiana*, or *Coffea arabica* SUS1 sequence (see e.g., FIG. 17, SEQ ID NOs. 175-177), or is a sequence that encodes a functional homolog of the sucrose synthase encoded by the *A. thaliana, S. rebaudiana*, or *Coffea arabica* SUS1 sequence. The recombinant sucrose synthase sequence optionally comprises a nucleic acid encoding a polypeptide having the sequence set forth in SEQ ID NO:180, or an amino acid sequence at least 90% identical thereto, wherein optionally the recombinant sucrose transporter sequence is a SUC1 sequence, or wherein optionally the SUC1 sequence is an *Arabidopsis thaliana* SUC1 sequence, or is a sequence that encodes a functional homolog of the sucrose transporter encoded by the *Arabidopsis thaliana* SUC1 sequence, or wherein optionally the recombinant sucrose transporter sequence comprises a nucleic acid encoding a polypeptide having the sequence set forth in SEQ ID NO:179, or an amino acid sequence at least 90% identical thereto. In either method, the host is a microorganism, for example a Saccharomycete, optionally such as *Saccharomyces cerevisiae*. Or the host may be *Escherichia coli*. Or the host may be a plant cell.

Also provided herein is a recombinant host, such as a microorganism, comprising one or more biosynthesis genes whose expression results in production of diterpenoids. Such genes include a gene encoding an ent-copalyl diphosphate synthase (CDPS) (EC 5.5.1.13), a gene encoding an ent-kaurene synthase, a gene encoding an ent-kaurene oxidase; or a gene encoding a steviol synthetase. At least one of the genes is a recombinant gene. The host can also be a plant cell. Expression of these gene(s) in a Stevia plant can result in increased steviol glycoside levels in the plant. In some embodiments the recombinant host further comprises a plurality of copies of a recombinant gene encoding a CDPS polypeptide (EC 5.5.1.13) lacking a chloroplast transit peptide sequence. The CDPS polypeptide can have at least 90%, 95%, 99%, or 100% identity to the truncated CDPS amino acid sequence set forth in FIG. 14. The host can further comprise a plurality of copies of a recombinant gene encoding a KAH polypeptide, e.g., a KAH polypeptide that has at least 90%, 95%, 99%, or 100% identity to the KAH amino acid sequence set forth in FIG. 12. The host can further comprise one or more of: (i) a gene encoding a geranylgeranyl diphosphate synthase; (ii) a gene encoding a ent-kaurene oxidase; and (iii) a gene encoding a ent-kaurene synthase. The host can further comprise one or more of (iv) a gene encoding a truncated HMG-CoA; (v) a gene encoding a CPR; (vi) a gene encoding a rhamnose synthetase; (vii) a gene encoding a UDP-glucose dehydrogenase; and (viii) a gene encoding a UDP-glucuronic acid decarboxylase. Two or more exogenous CPRs can be present, for example. The expression of one or more of such genes can be inducible. At least one of genes (i), (ii), (iii), (iv), (v), (vi), (vii), or (viii) can be a recombinant gene, and in some cases each of the genes of (i), (ii), (iii), (iv), (v), (vi), (vii), and (viii) is a recombinant gene. The geranylgeranyl diphosphate synthase can have greater than 90% sequence identity to the amino acid sequence set forth in SEQ ID NO:127; the kaurene oxidase can have greater than 90% sequence identity to the amino acid sequence set forth in SEQ ID NO:138; a CPR can have greater than 90% sequence identity to the amino acid sequence set forth in SEQ ID NO:168; a CPR can have greater than 90% sequence identity to the amino acid sequence set forth in SEQ ID NO:170, and a kaurene synthase can have greater than 90% sequence identity to the amino acid sequence set forth in SEQ ID NO: 156.

In one aspect, this document features an isolated nucleic acid encoding a polypeptide having the amino acid sequence set forth in SEQ ID NO:5, wherein the polypeptide contains substitutions position 211 and 286 of SEQ ID NO:5. For example, the polypeptide can include a methionine at position 211 and an alanine at position 286.

In one aspect, this document features an isolated nucleic acid encoding a polypeptide having at least 80% identity (e.g., at least 85%, 90%, 95%, or 99% identity) to the amino acid sequence set forth in FIG. 12C (SEQ ID NO:164). The polypeptide can have the amino acid sequence set forth in FIG. 12C.

In another aspect, this document features a nucleic acid construct that included a regulatory region operably linked to a nucleic acid encoding a polypeptide having at least 80% identity (e.g., at least 85%, 90%, 95%, or 99% identity) to the amino acid sequence set forth in FIG. 12C (SEQ ID NO:164). The polypeptide can have the amino acid sequence set forth in FIG. 12C.

This document also features a recombinant host that includes a recombinant gene (e.g., a plurality of copies of a recombinant gene) encoding a KAH polypeptide having at least 80% identity (e.g., at least 85%, 90%, 95%, or 99% identity) to the amino acid sequence set forth in FIG. 12C. The polypeptide can have the amino acid sequence set forth in FIG. 12C. The host can be a microorganism such as a saccharomycete (e.g., *Saccharomyces cerevisiae*) or *Escherichia coli*. The host can be a plant or plant cell (e.g., a *Stevia, Physcomitrella*, or tobacco plant or plant cell). The Stevia plant or plant cell is a *Stevia rebaudiana* plant or plant cell. The recombinant host can produce steviol when cultured under conditions in which each of the genes is expressed. The recombinant host can further comprise a gene encoding a UGT74G1 polypeptide; a gene encoding a UGT85C2 polypeptide; a gene encoding a UGT76G1 polypeptide; a gene encoding a UGT91D2 polypeptide; and/or a gene encoding a EUGT11 polypeptide. Such a host can produce at least one steviol glycoside when cultured under conditions in which each of the genes is expressed. The steviol glycoside can be steviol-13-O-glucoside, steviol-19-O-glucoside, rubusoside, rebaudioside A, rebaudioside B, rebaudioside C, rebaudioside D, rebaudioside E, rebaudioside F, and/or dulcoside A. The recombinant host can further comprise one or more of: a gene encoding a deoxyxylulose 5-phosphate synthase (DXS); a gene encoding a D-1-deoxyxylulose 5-phosphate reductoisomerase (DXR); a gene encoding a 4-diphosphocytidyl-2-C-methyl-D-erythritol synthase (CMS); a gene encoding a 4-diphosphocytidyl-2-C-methyl-D-erythritol kinase (CMK); a gene encoding a 4-diphosphocytidyl-2-C-methyl-D-erythritol 2,4-cyclodiphosphate synthase (MCS); a gene encoding a 1-hydroxy-2-methyl-2(E)-butenyl 4-diphosphate synthase (HDS); and a gene encoding a 1-hydroxy-2-methyl-2(E)-butenyl 4-diphosphate reductase (HDR). The recombinant host can further comprise one or more of: a gene encoding an acetoacetyl-CoA thiolase; a gene encoding a truncated HMG-CoA reductase; a gene encoding a mevalonate kinase; a gene encoding a phosphomevalonate kinase; and a gene encoding a mevalonate pyrophosphate decarboxylase. In another aspect, this document features a recombinant host that further comprises a gene encoding an ent-kaurene synthase (EC 4.2.3.19) and/or a gene encoding a gibberellin 20-oxidase (EC 1.14.11.12). Such a host produces gibberellin GA3 when cultured under conditions in which each of the genes is expressed.

This document also features an isolated nucleic acid encoding a CPR polypeptide having at least 80% sequence identity (e.g., at least 85%, 90%, 95%, or 99% sequence identity) to the *S. rebaudiana* CPR amino acid sequence set forth in FIG. 13. In some embodiments, the polypeptide has the *S. rebaudiana* CPR amino acid sequence set forth in FIG. 13 (SEQ ID NOs: 169 and 170).

In any of the hosts described herein, expression of one or more of the genes can be inducible.

In any of the hosts described herein, one or more genes encoding endogenous phosphatases can be deleted or disrupted such that endogenous phosphatase activity is reduced. For example, the yeast gene DPP1 and/or LPP1 can be disrupted or deleted such that the degradation of farnesyl pyrophosphate (FPP) to farnesol is reduced and the degradation of geranylgeranylpyrophosphate (GGPP)) to geranylgeraniol (GGOH) is reduced.

In another aspect, as described herein, ERG9 can be modified as defined below, resulting in the decreased production of squalene synthase (SQS) and an accumulation of terpenoid precursors. The precursors may or may not be secreted into the culture medium and can in turn be used as substrates to enzymes capable of metabolizing the terpenoid precursors into desired terpenoids.

Thus, in a main aspect the present invention relates to a cell comprising a nucleic acid sequence, said nucleic acid comprising i) a promoter sequence operably linked to
ii) a heterologous insert sequence operably linked to
iii) an open reading frame operably linked to
iv) a transcription termination signal, wherein the heterologous insert sequence has the general formula (I):

$$-X_1-X_2-X_3-X_4-X_5-$$

wherein $X_2$ comprises at least 4 consecutive nucleotides being complementary to, and forming a hairpin secondary structure element with at least 4 consecutive nucleotides of $X_4$, and wherein $X_3$ is optional and if present comprises unpaired nucleotides involved in forming a hairpin loop between $X_2$ and $X_4$, and wherein $X_1$ and $X_5$ individually and optionally comprises one or more nucleotides, and wherein the open reading frame upon expression encodes a polypeptide sequence having at least 70% identity to a squalene synthase (EC 2.5.1.21) or a biologically active fragment thereof, said fragment having at least 70% sequence identity to said squalene synthase in a range of overlap of at least 100 amino acids.

The cell of the present invention is useful in enhancing yield of industrially interesting terpenoids. Accordingly, in another aspect the present invention relates to a method for producing a terpenoid compound synthesized through the squalene pathway, in a cell culture, said method comprising the steps of (a) providing the cell as defined herein above, (b) culturing the cell of (a).

(c) recovering the terpenoid product compound.

By providing the cell comprising the genetically modified construct defined herein above, the accumulation of terpenoid precursors is enhanced (see e.g., FIG. 20).

Thus, in another aspect, the invention relates to a method for producing a terpenoid derived from a terpenoid precursor selected from the group consisting of Farnesyl-pyrophosphate (FPP), Isopentenyl-pyrophosphate (IPP), Dimethylallyl-pyrophosphate (DMAPP), Geranyl-pyrophosphate (GPP) and/or Geranylgeranyl-pyrophosphate (GGPP), said method comprising:

(a) contacting said precursor with an enzyme of the squalene synthase pathway, (b) recovering the terpenoid product.

The present invention may operate by at least partly, sterically hindering binding of the ribosome to the RNA thus reducing the translation of squalene synthase.

Accordingly, in one aspect the present invention relates to a method for reducing the translation rate of a functional squalene synthase (EC 2.5.1.21) said method comprising:

(a) providing the cell defined herein above, (b) culturing the cell of (a).

Similarly, the invention in another aspect relates to a method for decreasing turnover of farnesyl-pp to squalene, said method comprising:

(a) providing the cell defined herein above, (b) culturing the cell of (a).

As depicted in FIG. 20, the knocking down of the ERG9 results in build-up of precursors to squalene synthase. Thus in one aspect, the present invention relates to a method for enhancing accumulation of a compound selected from the group consisting of Farnesyl-pyrophosphate, Isopentenyl-pyrophosphate, Dimethylallyl-pyrophosphate, Geranyl-pyrophosphate and Geranylgeranyl-pyrophosphate, said method comprising the steps of:

(a) providing the cell defined herein above, and (b) culturing the cell of (a).

In one embodiment the invention relates to the production of Geranylgeranyl Pyrophosphate (GGPP) as well as other terpenoids, which can be prepared from Geranylgeranyl Pyrophosphate (GGPP).

In this embodiment of the invention the above described decrease of production of squalene synthase (SQS) may be combined with an increase in activity of Geranylgeranyl Pyrophosphate Synthase (GGPPS), which converts FPP to Geranylgeranyl Pyrophosphate (GGPP), leading to increased production of GGPP.

Thus, in one embodiment the invention relates to a microbial cell comprising a nucleic acid sequence, said nucleic acid comprising i) a promoter sequence operably linked to ii) a heterologous insert sequence operably linked to iii) an open reading frame operably linked to iv) a transcription termination signal, wherein the heterologous insert sequence and the open reading frame are as defined herein above, wherein said microbial cell furthermore comprises a heterologous nucleic acid encoding GGPPS operably linked to a nucleic acid sequence directing expression of GGPPS in said cell.

In addition, the document relates to a method for producing steviol or a steviol glycoside, wherein the method comprises use of any one of the above-mentioned microbial cells.

Any of the hosts described herein can be a microorganism (e.g., a Saccharomycete such as *Saccharomyces cerevisiae*, or *Escherichia coli*), or a plant or plant cell (e.g., a *Stevia* such as a *Stevia rebaudiana, Physcomitrella*, or tobacco plant or plant cell).

Unless otherwise defined, all technical and scientific terms used herein have the same meaning as commonly understood by one of ordinary skill in the art to which the invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and are not intended to be limiting. Other features and advantages of the invention will be apparent from the following detailed description. Applicants reserve the right to alternatively claim any disclosed invention using the transitional phrase "comprising," "consisting essentially of," or "consisting of," according to standard practice in patent law.

DESCRIPTION OF DRAWINGS

FIG. 1 is the chemical structure of various steviol glycosides.

FIG. 6 is an alignment of the amino acid sequence of EUGT11 (SEQ ID NO:152, top line) with the amino acid sequence of UGT91D2e (SEQ ID NO:5, bottom line).

FIG. 7 contains the amino acid sequence of EUGT11 (SEQ ID NO:152), the nucleotide sequence (SEQ ID NO:153) encoding EUGT11, and the nucleotide sequence encoding EUGTI1 that has been codon optimized for expression in yeast (SEQ ID NO: 154).

FIG. 9 is an alignment of the amino acid sequences of UGT91D1 and UGT91D2e (SEQ ID NO: 5).

FIG. 12A is the nucleotide sequence encoding the *Stevia rebaudiana* KAH (SEQ ID NO:163), designated SrKAHe1 herein.

FIG. 12B is the nucleotide sequence encoding the *Stevia rebaudiana* KAHe1 that has been codon-optimized for expression in yeast (SEQ ID NO:165).

FIG. 12C is the amino acid sequence of the *Stevia rebaudiana* KAHe1 (SEQ ID NO:164).

FIG. 13A contains the amino acid sequences of CPR polypeptides from *S. cerevisiae* (encoded by NCP1 gene) (SEQ ID NO:166), *A. thaliana* (encoded by ATR1 and encoded by ATR2) ((SEQ ID NOs: 148 and 168), and *S. rebaudiana* (encoded by CPR7 and encoded by CPR8) (SEQ ID NOs: 169 and 170).

FIG. 13B contains ATR1 nucleotide sequence (Accession No. CAA23011) that has been codon optimized for expression in yeast (SEQ ID NO:171); ATR2 nucleotide sequence that has been codon optimized for expression in yeast (SEQ ID NO:172); the *Stevia rebaudiana* CPR7 nucleotide sequence (SEQ ID NO:173); and the *Stevia rebaudiana* CPR8 nucleotide sequence (SEQ ID NO:174).

FIG. 14A contains the nucleotide sequence (SEQ ID NO:157) encoding a CDPS polypeptide (SEQ ID NO:158) from *Zea mays*. The sequence that is in bold and underlined can be deleted to remove the sequence encoding the chloroplast transit sequence.

FIG. 14B contains the amino acid sequence of the CDPS polypeptide (SEQ ID NO:158) from *Zea mays*. The sequence that is in bold and underlined can be deleted to remove the chloroplast transit sequence.

FIG. 15A contains a codon-optimized nucleotide sequence (SEQ ID NO:161) encoding a bifunctional CDPS-KS polypeptide (SEQ ID NO:162) from *Gibberella fujikuroi*. FIG. 15B contains the amino acid sequence of the bifunctional CDPS-KS polypeptide (SEQ ID NO:162) from *Gibberella fujikumoi*.

FIG. 17 contains the nucleic acid sequences encoding the *A. thaliana, S. rebaudiana* (from contig10573 selection_ORF S11E, with the mutation that changes S11 to glutamate (E) in bold, lowercase letters), and coffee (*Coffea arabica*) sucrose synthases, SEQ ID NOs:175, 176, and 177, respectively.

FIG. 19A is the amino acid sequence of the *A. thaliana* UDP-glycosyltransferase UGT72E2 (SEQ ID NO:178).

FIG. 19B is the amino acid sequence of the sucrose transporter SUC1 from *A. thaliana* (SEQ ID NO:179).

FIG. 19C is the amino acid sequence of the sucrose synthase from coffee (SEQ ID NO:180).

FIG. 21 contains the nucleotide sequence of the *Saccharomyces cerevisiae* Cycl promoter (SEQ ID NO:185) and *Saccharomyces cerevisiae* Kex2 promoter (SEQ ID NO:186).

FIG. 25 contains the amino acid sequence of squalene synthase polypeptides from *Saccharomyces cerevisiae, Schizosaccharomyces pombe, Yarrowia lipolytica, Candida glabrata, Ashbya gossypii, Cyberlindnera jadinii, Candida albicans, Saccharomyces cerevisiae, Homo sapiens, Mus musculus*, and *Rattus norvegicus* (SEQ ID NOs:192-202), and the amino acid sequence of a geranylgeranyl diphosphate synthase (GGPPS) from *Aspergillus nidulans* and *S. cerevisiae* (SEQ ID NOs. 203 and 167).

Like reference symbols in the various drawings indicate like elements.

DETAILED DESCRIPTION

Figure 2A:
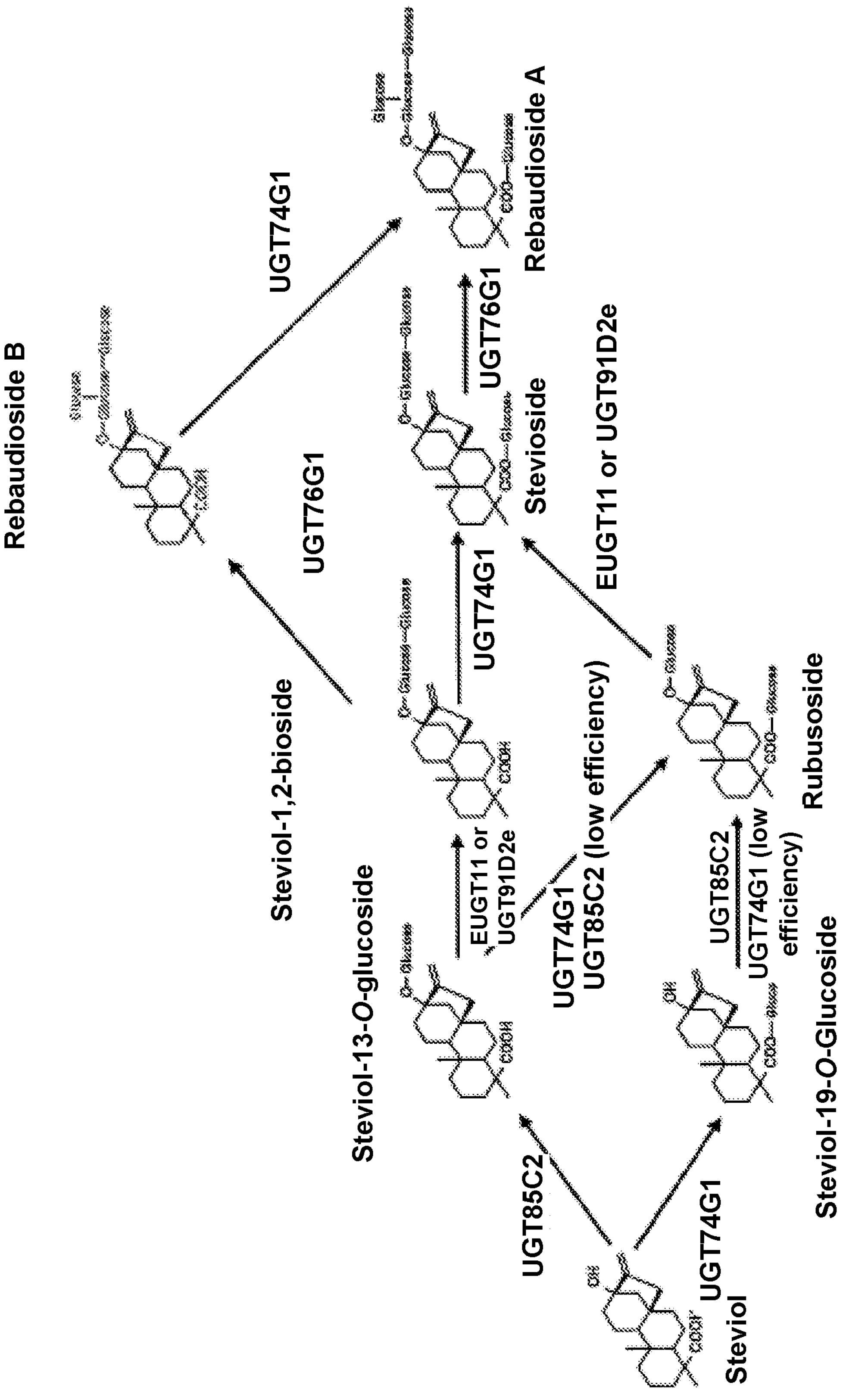
FIGS. 2A-D show representative pathways for the biosynthesis of steviol glycosides from steviol.
Figure 2B:
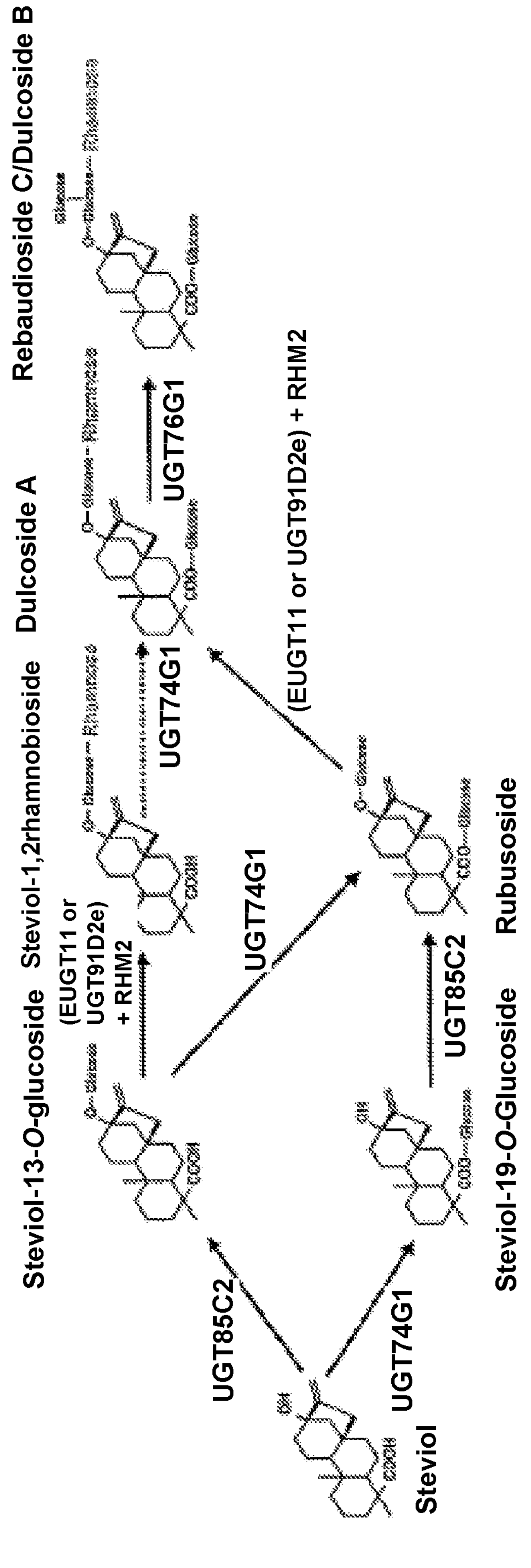

This document is based on the discovery that recombinant hosts such as plant cells, plants, or microorganisms can be developed that express polypeptides useful for the biosynthesis of steviol glycosides such as rebaudioside A, rebaudioside C, rebaudioside D, rebaudioside E, rebaudioside F, or dulcoside A. The recombinant hosts described herein are particularly useful for producing Rebaudioside D. Such hosts can express one or more Uridine 5'-diphospho (UDP) glycosyl transferases suitable for producing steviol glycosides. Expression of these biosynthetic polypeptides in various microbial chassis allows steviol glycosides to be produced in a consistent, reproducible manner from energy and carbon sources such as sugars, glycerol, $CO_2$, $H_2$, and sunlight. The proportion of each steviol glycoside produced by a recombinant host can be tailored by incorporating preselected biosynthetic enzymes into the hosts and expressing them at appropriate levels, to produce a sweetener composition with a consistent taste profile. Furthermore, the concentrations of steviol glycosides produced by recombinant hosts are expected to be higher than the levels of steviol glycosides produced in the *Stevia* plant, which improves the efficiency of the downstream purification. Such sweetener compositions contain little or no plant based contaminants, relative to the amount of contaminants present in Stevia extracts.

At least one of the genes is a recombinant gene, the particular recombinant gene(s) depending on the species or strain selected for use. Additional genes or biosynthetic modules can be included in order to increase steviol glycoside yield, improve efficiency with which energy and carbon sources are converted to steviol and its glycosides, and/or to enhance productivity from the cell culture or plant. Such additional biosynthetic modules include genes involved in the synthesis of the terpenoid precursors, isopentenyl diphosphate and dimethylallyl diphosphate. Additional biosynthetic modules include terpene synthase and terpene cyclase genes, such as genes encoding geranylgeranyl diphosphate synthase and copalyl diphosphate synthase; these genes may be endogenous genes or recombinant genes.

I. STEVIOL AND STEVIOL GLYCOSIDE BIOSYNTHESIS POLYPEPTIDES

A. Steviol Biosynthesis Polypeptides

Chemical structures for several of the compounds found in Stevia extracts are shown in FIG. 1, including the diterpene steviol and various steviol glycosides. CAS numbers are shown in Table A below. See also, *Steviol Glycosides Chemical and Technical Assessment 69th JECFA*, prepared by Harriet Wallin, Food Agric. Org. (2007).

TABLE A

| COMPOUND | CAS # |
|---|---|
| Steviol | 471-80-7 |
| Rebaudioside A | 58543-16-1 |
| Steviolbioside | 41093-60-1 |
| Stevioside | 57817-89-7 |
| Rebaudioside B | 58543-17-2 |
| Rebaudioside C | 63550-99-2 |
| Rebaudioside D | 63279-13-0 |
| Rebaudioside E | 63279-14-1 |
| Rebaudioside F | 438045-89-7 |
| Rubusoside | 63849-39-4 |
| Dulcoside A | 64432-06-0 |

It has been discovered that expression of certain genes in a host such as a microorganism confers the ability to synthesize steviol glycosides upon that host. As discussed in more detail below, one or more of such genes may be present naturally in a host. Typically, however, one or more of such genes are recombinant genes that have been transformed into a host that does not naturally possess them.

The biochemical pathway to produce steviol involves formation of geranylgeranyl diphosphate, cyclization to (−) copalyl diphosphate, followed by oxidation and hydroxylation to form steviol. Thus, conversion of geranylgeranyl diphosphate to steviol in a recombinant microorganism involves the expression of a gene encoding a kaurene synthase (KS), a gene encoding a kaurene oxidase (KO), and a gene encoding a steviol synthetase (KAH). Steviol synthetase also is known as kaurenoic acid 13-hydroxylase.

Suitable KS polypeptides are known. For example, suitable KS enzymes include those made by *Stevia rebaudiana, Zea mays, Populus trichocarpa*, and *Arabidopsis thaliana*. See, Table 1 and SEQ ID NOs: 132-135 and 156. Nucleotide sequences encoding these polypeptides are set forth in SEQ ID NOs: 40-47 and 155. The nucleotide sequences set forth in SEQ ID NOs:40-43 were modified for expression in yeast while the nucleotide sequences set forth in SEQ ID NOs: 44-47 are from the source organisms from which the KS polypeptides were identified.

TABLE 1

| KS Clones | | | | | | |
|---|---|---|---|---|---|---|
| Enzyme Source Organism | gi Number | Accession Number | Construct Name | Length (nts) | SEQ ID (DNA) | SEQ ID (protein) |
| *Stevia rebaudiana* | 4959241 | AAD34295 | MM-12 | 2355 | 40 | 132 |

TABLE 1-continued

| KS Clones | | | | | | |
|---|---|---|---|---|---|---|
| Enzyme Source Organism | gi Number | Accession Number | Construct Name | Length (nts) | SEQ ID (DNA) | SEQ ID (protein) |
| *Stevia rebaudiana* | 4959239 | AAD34294 | MM-13 | 2355 | 41 | 133 |
| *Zea mays* | 162458963 | NP_001105097 | MM-14 | 1773 | 42 | 134 |
| *Populus trichocarpa* | 224098838 | XP_002311286 | MM-15 | 2232 | 43 | 135 |
| *Arabidopsis thaliana* | 3056724 | AF034774 | EV-70 | 2358 | 155 | 156 |

Suitable KO polypeptides are known. For example, suitable KO enzymes include those made by *Stevia rebaudiana, Arabidopsis thaliana, Gibberella fujikori* and *Trametes versicolor*. See, Table 2 and SEQ ID NOs: 138-141. Nucleotide sequences encoding these polypeptides are set forth in in SEQ ID NOs: 52-59. The nucleotide sequences set forth in SEQ ID NOs: 52-55 were modified for expression in yeast. The nucleotide sequences set forth in SEQ ID NOs: 56-59 are from the source organisms from which the KO polypeptides were identified.

TABLE 2

| KO Clones | | | | | | |
|---|---|---|---|---|---|---|
| Enzyme Source Organism | gi Number | Accession Number | Construct Name | Length (nts) | SEQ ID (DNA) | SEQ ID (protein) |
| *Stevia rebaudiana* | 76446107 | ABA42921 | MM-18 | 1542 | 52 | 138 |
| *Arabidopsis thaliana* | 3342249 | AAC39505 | MM-19 | 1530 | 53 | 139 |
| *Gibberella fujikoroi* | 4127832 | CAA76703 | MM-20 | 1578 | 54 | 140 |
| *Trametes versicolor* | 14278967 | BAB59027 | MM-21 | 1500 | 55 | 141 |

Suitable KAH polypeptides are known. For example, suitable KAH enzymes include those made by *Stevia rebaudiana, Arabidopsis thaliana, Vitis vinifera* and *Medicago trunculata*. See, e.g., Table 3, SEQ ID NOs: 142-146; U.S. Patent Publication No. 2008-0271205; U.S. Patent Publication No. 2008-0064063 and Genbank Accession No. gi 189098312. The steviol synthetase from *Arabidopsis thaliana* is classified as a CYP714A2. Nucleotide sequences encoding these KAH enzymes are set forth in SEQ ID NOs: 60-69. The nucleotide sequences set forth in SEQ ID NOs: 60-64 were modified for expression in yeast while the nucleotide sequences from the source organisms from which the polypeptides were identified are set forth in SEQ ID NOs: 65-69.

TABLE 3

| KAH Clones | | | | | | | |
|---|---|---|---|---|---|---|---|
| Enzyme Source Organism | gi Number | Accession Number | Plasmid Name | Construct Name | Length (nts) | SEQ ID (DNA) | SEQ ID (protein) |
| *Stevia rebaudiana* | | —* | pMUS35 | MM-22 | 1578 | 60 | 142 |
| *Stevia rebaudiana* | 189418962 | ACD93722 | pMUS36 | MM-23 | 1431 | 61 | 143 |
| *Arabidopsis thaliana* | 15238644 | NP_197872 | pMUS37 | MM-24 | 1578 | 62 | 144 |
| *Vitis vinifera* | 225458454 | XP_002282091 | pMUS38 | MM-25 | 1590 | 63 | 145 |
| *Medicugo trunculata* | 84514135 | ABC59076 | pMUS39 | MM-26 | 1440 | 64 | 146 |

*= Sequence is shown in U.S. patent publication No. 2008-0064063.

In addition, a KAH polypeptide from *Stevia rebaudiana* that was identified herein is particularly useful in a recombinant host. The nucleotide sequence (SEQ ID NO:163) encoding the *S. rebaudiana* KAH (SrKAHe1) (SEQ ID NO:164) is set forth in FIG. 12A. A nucleotide sequence encoding the *S. rebaudiana* KAH that has been codon-optimized for expression in yeast (SEQ ID NO:165) is set forth in FIG. 12B. The amino acid sequence of the *S. rebaudiana* KAH is set forth in FIG. 12C. The *S. rebaudiana* KAH shows significantly higher steviol synthase activity as compared to the *Arabidopsis thaliana ent*-kaurenoic acid hydroxylase described by Yamaguchi et al. (U.S. Patent Publication No. 2008/0271205 A1) when expressed in *S. cerevisiae*. The *S. rebaudiana* KAH polypeptide set forth in FIG. 12C has less than 20% identity to the KAH from U.S. Patent Publication No. 2008/0271205, and less than 35% identity to the KAH from U.S. Patent Publication No. 2008/0064063.

In some embodiments, a recombinant microorganism contains a recombinant gene encoding a KO and/or a KAH polypeptide. Such microorganisms also typically contain a recombinant gene encoding a cytochrome P450 reductase (CPR) polypeptide, since certain combinations of KO and/or KAH polypeptides require expression of an exogenous CPR polypeptide. In particular, the activity of a KO and/or a KAH polypeptide of plant origin can be significantly increased by the inclusion of a recombinant gene encoding an exogenous CPR polypeptide. Suitable CPR polypeptides are known. For example, suitable CPR enzymes include those made by *Stevia rebaudiana* and *Arabidopsis thaliana*. See, e.g., Table 4 and SEQ ID NOs: 147 and 148. Nucleotide sequences encoding these polypeptides are set forth in SEQ ID NOs: 70, 71, 73, and 74. The nucleotide sequences set forth in SEQ ID NOs: 70-72 were modified for expression in yeast. The nucleotide sequences from the source organisms from which the polypeptides were identified are set forth in SEQ ID NOs:73-75.

TABLE 4

| CPR Clones | | | | | | | |
|---|---|---|---|---|---|---|---|
| Enzyme Source Organism | gi Number | Accession Number | Plasmid Name | Construct Name | Length (nts) | SEQ ID (DNA) | SEQ ID (protein) |
| *Stevia rebaudiana* | 93211213 | ABB88839 | pMUS40 | MM-27 | 2133 | 70 | 147 |
| *Arabidopsis thaliana* | 15233853 | NP_194183 | pMUS41 | MM-28 | 2079 | 71 | 148 |
| *Giberella fujikuroi* | 32562989 | CAE09055 | pMUS42 | MM-29 | 2142 | 72 | 149 |

For example, the steviol synthase encoded by SrKAHe1 is activated by the *S. cerevisiae* CPR encoded by gene NCP1 (YHR042W). Even better activation of the steviol synthase encoded by SrKAHe1 is observed when the *Arabidopsis thaliana* CPR encoded by the gene ATR2 or the *S. rebaudiana* CPR encoded by the gene CPR8 are co-expressed. FIG. 13A contains the amino acid sequence of the *S. cerevisiae, A. thaliana* (from ATR1 and ATR2 genes) and *S. rebaudiana* CPR polypeptides (from CPR7 and CPR8 genes) (SEQ ID NOs: 166-170). FIG. 13 B contains the nucleotide sequence encoding the *A. thaliana* and *S. rebaudiana* CPR polypeptides (SEQ ID NOs:171-174).

For example, the yeast gene DPP1 and/or the yeast gene LPP1 can be disrupted or deleted such that the degradation of farnesyl pyrophosphate (FPP) to farnesol is reduced and the degradation of geranylgeranylpyrophosphate (GGPP)) to geranylgeraniol (GGOH) is reduced. Alternatively, the promoter or enhancer elements of an endogenous gene encoding a phosphatase can be altered such that the expression of their encoded proteins is altered. Homologous recombination can be used to disrupt an endogenous gene. For example, a "gene replacement" vector can be constructed in such a way to include a selectable marker gene. The selectable marker gene can be operably linked, at both 5' and 3' end, to portions of the gene of sufficient length to mediate homologous recombination. The selectable marker can be one of any number of genes that complement host cell auxotrophy, provide antibiotic resistance, or result in a color change. Linearized DNA fragments of the gene replacement vector then are introduced into the cells using methods well known in the art (see below). Integration of the linear fragments into the genome and the disruption of the gene can be determined based on the selection marker and can be verified by, for example, Southern blot analysis. Subsequent to its use in selection, a selectable marker can be removed from the genome of the host cell by, e.g., Cre-loxP systems (see, e.g., Gossen et al. (2002) *Ann. Rev. Genetics* 36:153-173 and U.S. Application Publication No. 20060014264). Alternatively, a gene replacement vector can be constructed in such a way as to include a portion of the gene to be disrupted, where the portion is devoid of any endogenous gene promoter sequence and encodes none, or an inactive fragment of, the coding sequence of the gene. An "inactive fragment" is a fragment of the gene that encodes a protein having, e.g., less than about 10% (e.g., less than about 9%, less than about 8%, less than about 7%, less than about 6%, less than about 5%, less than about 4%, less than about 3%, less than about 2%, less than about 1%, or 0%) of the activity of the protein produced from the full-length coding sequence of the gene. Such a portion of the gene is inserted in a vector in such a way that no known promoter sequence is operably linked to the gene sequence, but that a stop codon and a transcription termination sequence are operably linked to the portion of the gene sequence. This vector can be subsequently linearized in the portion of the gene sequence and transformed into a cell. By way of single homologous recombination, this linearized vector is then integrated in the endogenous counterpart of the gene.

Expression in a recombinant microorganism of these genes results in the conversion of geranylgeranyl diphosphate to steviol.

B. Steviol Glycoside Biosynthesis Polypeptides

A recombinant host described herein can convert steviol to a steviol glycoside. Such a host (e.g., microorganism) contains genes encoding one or more UDP Glycosyl Transferases, also known as UGTs. UGTs transfer a monosaccharide unit from an activated nucleotide sugar to an acceptor moiety, in this case, an —OH or —COOH moiety on steviol or steviol derivative. UGTs have been classified into families and subfamilies based on sequence homology. Li et al. J. Biol. Chem. 276:4338-4343 (2001).

B. 1 Rubusoside Biosynthesis Polypeptides

The biosynthesis of rubusoside involves glycosylation of the 13-OH and the 19-COOH of steviol. See FIG. 2A. Conversion of steviol to rubusoside in a recombinant host such as a microorganism can be accomplished by the expression of gene(s) encoding UGTs 85C2 and 74G1, which transfer a glucose unit to the 13-OH or the 19-COOH, respectively, of steviol.

A suitable UGT85C2 functions as a uridine 5'-diphospho glucosyl:steviol 13-OH transferase, and a uridine 5'-diphospho glucosyl:steviol-19-O-glucoside 13-OH transferase. Functional UGT85C2 polypeptides also may catalyze glucosyl transferase reactions that utilize steviol glycoside substrates other than steviol and steviol-19-O-glucoside.

A suitable UGT74G1 polypeptide functions as a uridine 5'-diphospho glucosyl: steviol 19-COOH transferase and a uridine 5'-diphospho glucosyl: steviol-13-O-glucoside 19-COOH transferase. Functional UGT74G1 polypeptides also may catalyze glycosyl transferase reactions that utilize steviol glycoside substrates other than steviol and steviol-13-O-glucoside, or that transfer sugar moieties from donors other than uridine diphosphate glucose.

A recombinant microorganism expressing a functional UGT74G1 and a functional UGT85C2 can make rubusoside and both steviol monosides (i.e., steviol 13-O-monoglucoside and steviol 19-O-monoglucoside) when steviol is used as a feedstock in the medium. One or more of such genes may be present naturally in the host. Typically, however, such genes are recombinant genes that have been transformed into a host (e.g., microorganism) that does not naturally possess them.

As used herein, the term recombinant host is intended to refer to a host, the genome of which has been augmented by at least one incorporated DNA sequence. Such DNA sequences include but are not limited to genes that are not naturally present, DNA sequences that are not normally transcribed into RNA or translated into a protein ("expressed"), and other genes or DNA sequences which one desires to introduce into the non-recombinant host. It will be appreciated that typically the genome of a recombinant host described herein is augmented through the stable introduction of one or more recombinant genes. Generally, the introduced DNA is not originally resident in the host that is the recipient of the DNA, but it is within the scope of the invention to isolate a DNA segment from a given host, and to subsequently introduce one or more additional copies of that DNA into the same host, e.g., to enhance production of the product of a gene or alter the expression pattern of a gene. In some instances, the introduced DNA will modify or even replace an endogenous gene or DNA sequence by, e.g., homologous recombination or site-directed mutagenesis. Suitable recombinant hosts include microorganisms, plant cells, and plants.

The term "recombinant gene" refers to a gene or DNA sequence that is introduced into a recipient host, regardless of whether the same or a similar gene or DNA sequence may already be present in such a host. "Introduced," or "augmented" in this context, is known in the art to mean introduced or augmented by the hand of man. Thus, a recombinant gene may be a DNA sequence from another species, or may be a DNA sequence that originated from or is present in the same species, but has been incorporated into a host by recombinant methods to form a recombinant host. It will be appreciated that a recombinant gene that is introduced into a host can be identical to a DNA sequence that is normally present in the host being transformed, and is introduced to provide one or more additional copies of the DNA to thereby permit overexpression or modified expression of the gene product of that DNA.

Suitable UGT74G1 and UGT85C2 polypeptides include those made by *Stevia rebaudiana*. Genes encoding functional UGT74G1 and UGT85C2 polypeptides from *Stevia* are reported in Richman, et al. *Plant J.* 41: 56-67 (2005). Amino acid sequences of *S. rebaudiana* UGT74G1 and UGT85C2 polypeptides are set forth in SEQ ID NOs: 1 and 3, respectively. Nucleotide sequences encoding UGT74G1 and UGT85C2 that have been optimized for expression in yeast are set forth in SEQ ID NOs: 2 and 4, respectively. DNA 2.0 codon-optimized sequence for UGTs 85C2, 91D2e, 74G1 and 76G1 are set forth in SEQ ID NOs: 82, 84, 83, and 85, respectively. See also the UGT85C2 and UGT74G1 variants described below in the "Functional Homolog" section. For example, an UGT85C2 polypeptide containing substitutions at positions 65, 71, 270, 289, and 389 can be used (e.g., A65S, E71Q, T270M, Q289H, and A389V).

In some embodiments, the recombinant host is a microorganism. The recombinant microorganism can be grown on media containing steviol in order to produce rubusoside. In other embodiments, however, the recombinant microorganism expresses one or more recombinant genes involved in steviol biosynthesis, e.g., a CDPS gene, a KS gene, a KO gene and/or a KAH gene. Suitable CDPS polypeptides are known. For example, suitable CDPS enzymes include those made by *Stevia rebaudiana, Streptomyces clavuligerus, Bradyrhizobium japonicum, Zea mays*, and *Arabidopsis*. See, e.g., Table 5 and SEQ ID NOs: 129-131, 158, and 160. Nucleotide sequences encoding these polypeptides are set forth in SEQ ID NOs: 34-39, 157, and 159. The nucleotide sequences set forth in SEQ ID NOs: 34-36 were modified for expression in yeast. The nucleotide sequences from the source organisms from which the polypeptides were identified are set forth in SEQ ID NOs:37-39.

In some embodiments, CDPS polypeptides that lack a chloroplast transit peptide at the amino terminus of the unmodified polypeptide can be used. For example, the first 150 nucleotides from the 5' end of the *Zea mays* CDPS coding sequence shown in FIG. 14 (SEQ ID NO:157) can be removed. Doing so removes the amino terminal 50 residues of the amino acid sequence shown in FIG. 14 (SEQ ID NO:158), which encode a chloroplast transit peptide. The truncated CDPS gene can be fitted with a new ATG translation start site and operably linked to a promoter, typically a constitutive or highly expressing promoter. When a plurality of copies of the truncated coding sequence are introduced into a microorganism, expression of the CDPS polypeptide from the promoter results in an increased carbon flux towards ent-kaurene biosynthesis.

TABLE 5

| CDPS Clones | | | | | | | |
|---|---|---|---|---|---|---|---|
| Enzyme Source Organism | gi Number | Accession Number | Plasmid Name | Construct Name | Length (nts) | SEQ ID: (DNA) | SEQ ID (protein) |
| *Stevia rebaudiana* | 2642661 | AAB87091 | pMUS22 | MM-9 | 2364 | 34 | 129 |
| *Streptomyces clavuligerus* | 197705855 | EDY51667 | pMUS23 | MM-10 | 1584 | 35 | 130 |
| *Bradyrhizobium japonicum* | 529968 | AAC28895.1 | pMUS24 | MM-11 | 1551 | 36 | 131 |
| *Zea mays* | 50082774 | AY562490 | | EV65 | 2484 | 157 | 158 |
| *Arabidopsis thaliana* | 18412041 | NM_116512 | | EV64 | 2409 | 159 | 160 |

CDPS-KS bifunctional proteins (SEQ ID NOs: 136 and 137) also can be used. Nucleotide sequences encoding the CDPS-KS bifunctional enzymes shown in Table 6 were modified for expression in yeast (see SEQ ID NOs: 48 and 49). The nucleotide sequences from the source organisms from which the polypeptides were originally identified are set forth in SEQ ID NOs: 50 and 51. A bifunctional enzyme from *Gibberella fujikuroi* (SEQ ID NO:162) also can be used. A nucleotide sequence encoding the *Gibberella fujikuroi* bifunctional CDPS-KS enzyme was modified for expression in yeast (see FIG. 15A, SEQ ID NO: 161).

TABLE 6

| CDPS-KS Clones | | | | | | |
|---|---|---|---|---|---|---|
| Enzyme Source Organism | gi Number | Accession Number | Construct Name | Length (nts) | SEQ ID (DNA) | SEQ ID (protein) |
| *Phomopsis amygdali* | 186704306 | BAG30962 | MM-16 | 2952 | 48 | 136 |
| *Physcomitrella patens* | 146325986 | BAF61135 | MM-17 | 2646 | 49 | 137 |
| *Gibberella fujikuroi* | 62900107 | Q9UVY5.1 | | 2859 | 161 | 162 |

Thus, a microorganism containing a CDPS gene, a KS gene, a KO gene and a PG-7T KAH gene in addition to a UGT74G1 and a UGT85C2 gene is capable of producing both steviol monosides and rubusoside without the necessity for using steviol as a feedstock.

In some embodiments, the recombinant microorganism further expresses a recombinant gene encoding a geranylgeranyl diphosphate synthase (GGPPS). Suitable GGPPS polypeptides are known. For example, suitable GGPPS enzymes include those made by *Stevia rebaudiana, Gibberella fujikuroi, Mus musculus, Thalassiosira pseudonana, Streptomyces clavuligerus, Sulfolobus acidocaldarius, Synechococcus* sp. and *Arabidopsis thaliana*. See, Table 7 and SEQ ID NOs: 121-128. Nucleotide sequences encoding these polypeptides are set forth in SEQ ID NOs:18-33. The nucleotide sequences set forth in SEQ ID NOs: 18-25 were modified for expression in yeast while the nucleotide sequences from the source organisms from which the polypeptides were identified are set forth in SEQ ID NOs: 26-33.

TABLE 7

| GGPPS Clones | | | | | | | |
|---|---|---|---|---|---|---|---|
| Enzyme Source Organism | gi Number | Accession Number | Plasmid Name | Construct Name | Length (nts) | SEQ ID (DNA) | SEQ ID (protein) |
| *Stevia rebaudiana* | 90289577 | ABD92926 | pMUS14 | MM-1 | 1086 | 18 | 121 |
| *Gibberella fujikuroi* | 3549881 | CAA75568 | pMUS15 | MM-2 | 1029 | 19 | 122 |
| *Mus musculus* | 47124116 | AAH69913 | pMUS16 | MM-3 | 903 | 20 | 123 |
| *Thalassiosira pseudonana* | 223997332 | XP_002288339 | pMUS17 | MM-4 | 1020 | 21 | 124 |
| *Streptomyces clavuligerus* | 254389342 | ZP_05004570 | pMUS18 | MM-5 | 1068 | 22 | 125 |
| *Sulfulobus acidocaldarius* | 506371 | BAA43200 | pMUS19 | MM-6 | 993 | 23 | 126 |
| *Synechococcus* sp. | 86553638 | ABC98596 | pMUS20 | MM-7 | 894 | 24 | 127 |

TABLE 7-continued

| GGPPS Clones | | | | | | | |
|---|---|---|---|---|---|---|---|
| Enzyme Source Organism | gi Number | Accession Number | Plasmid Name | Construct Name | Length (nts) | SEQ ID (DNA) | SEQ ID (protein) |
| *Arabidopsis thaliana* | 15234534 | NP_195399 | pMUS21 | MM-8 | 1113 | 25 | 128 |

In some embodiments, the recombinant microorganism further can express recombinant genes involved in diterpene biosynthesis or production of terpenoid precursors, e.g., genes in the methylerythritol 4-phosphate (MEP) pathway or genes in the mevalonate (MEV) pathway discussed below, have reduced phosphatase activity, and/or express a sucrose synthase (SUS) as discussed herein.

B. 2 Rebaudioside A. Rebaudioside D. And Rebaudioside E Biosynthesis Polypeptides The biosynthesis of rebaudioside A involves glucosylation of the aglycone steviol. Specifically, rebaudioside A can be formed by glucosylation of the 13-OH of steviol which forms the 13-O-steviolmonoside, glucosylation of the C-2' of the 13-O-glucose of steviolmonoside which forms steviol-1,2-bioside, glucosylation of the C-19 carboxyl of steviol-1,2-bioside which forms stevioside, and glucosylation of the C-3' of the C-13-O-glucose of stevioside. The order in which each glucosylation reaction occurs can vary. See FIG. 2A.

Figure 2C:
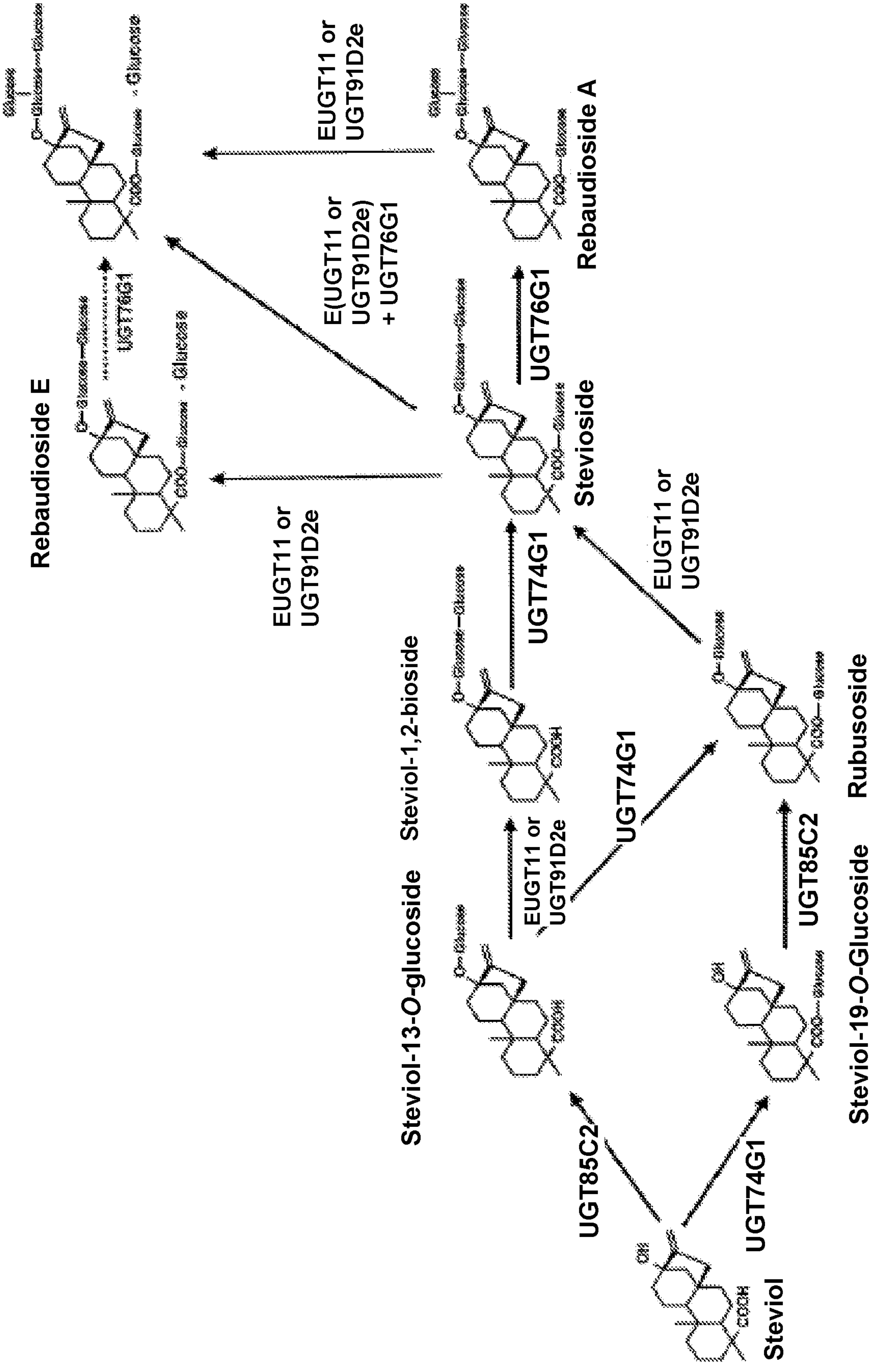
Figure 2D:
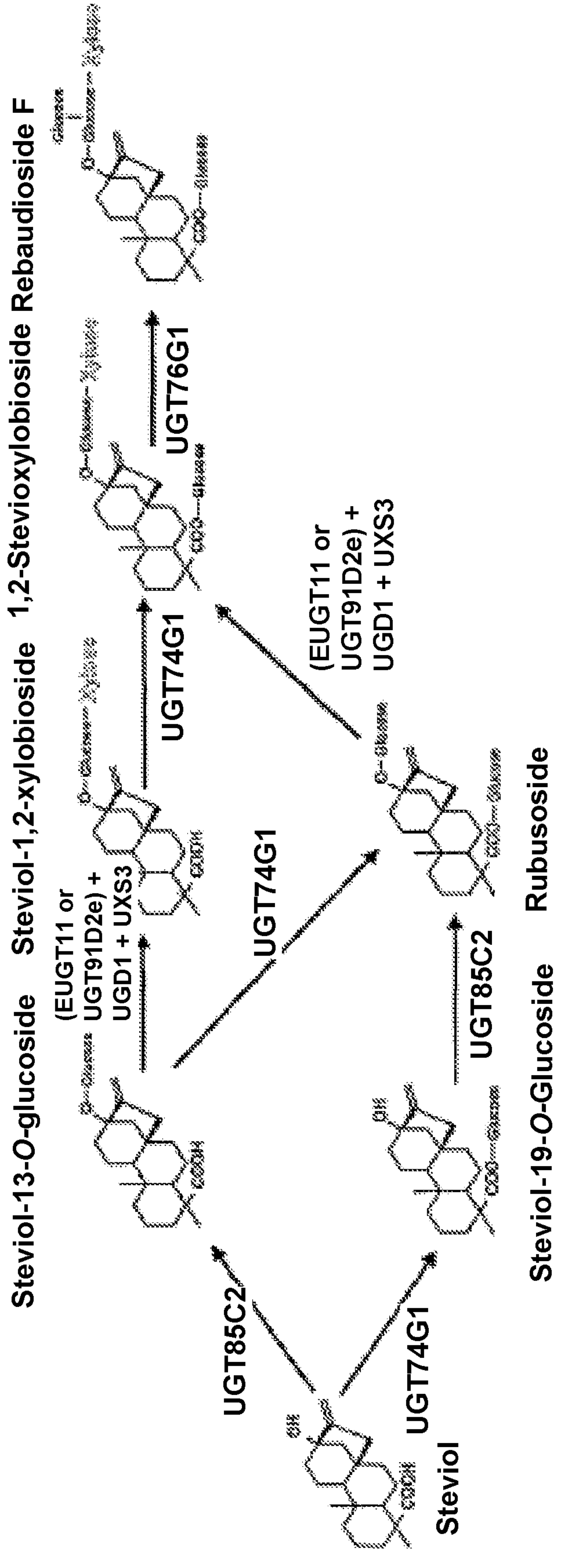

The biosynthesis of rebaudioside E and/or rebaudioside D involves glucosylation of the aglycone steviol. Specifically, rebaudioside E can be formed by glucosylation of the 13-OH of steviol which forms steviol-13-O-glucoside, glucosylation of the C-2' of the 13-O-glucose of steviol-13-O-glucoside which forms the steviol-1,2-bioside, glucosylation of the C-19 carboxyl of the 1,2-bioside to form 1,2-stevioside, and glucosylation of the C-2' of the 19-O-glucose of the 1,2-stevioside to form rebaudioside E. Rebaudioside D can be formed by glucosylation of the C-3' of the C-13-O-glucose of rebaudioside E. The order in which each glycosylation reaction occurs can vary. For example, the glucosylation of the C-2' of the 19-O-glucose may be the last step in the pathway, wherein Rebaudioside A is an intermediate in the pathway. See FIG. 2C.

It has been discovered that conversion of steviol to rebaudioside A, rebaudioside D, and/or rebaudioside E in a recombinant host can be accomplished by expressing the following functional UGTs: EUGT11, 74G1, 85C2, and 76G1, and optionally 91D2. Thus, a recombinant microorganism expressing combinations of these four or five UGTs can make rebaudioside A and rebaudioside D when steviol is used as a feedstock. Typically, one or more of these genes are recombinant genes that have been transformed into a microorganism that does not naturally possess them. It has also been discovered that UGTs designated herein as SM12UGT can be substituted for UGT91D2.

In some embodiments, less than five (e.g., one, two, three, or four) UGTs are expressed in a host. For example, a recombinant microorganism expressing a functional EUGT11 can make rebaudioside D when rebaudioside A is used as a feedstock. A recombinant microorganism expressing two functional UGTs, EUGT11 and 76G1, and optionally a functional 91D12, can make rebaudioside D when rubusoside or 1,2-stevioside is used as a feedstock. As another alternative, a recombinant microorganism expressing three functional UGTs, EUGT11, 74G1, 76G1, and optionally 91D2, can make rebaudioside D when fed the monoside, steviol-13-O-glucoside, in the medium. Similarly, conversion of steviol-19-O-glucoside to rebaudioside D in a recombinant microorganism can be accomplished by the expression of genes encoding UGTs EUGT11, 85C2, 76G1, and optionally 91D2, when fed steviol-19-O-glucoside. Typically, one or more of these genes are recombinant genes that have been transformed into a host that does not naturally possess them.

Suitable UGT74G1 and UGT85C2 polypeptides include those discussed above. A suitable UGT76G1 adds a glucose moiety to the C-3' of the C-13-O-glucose of the acceptor molecule, a steviol 1,2 glycoside. Thus, UGT76G1 functions, for example, as a uridine 5'-diphospho glucosyl: steviol 13-O-1,2 glucoside C-3' glucosyl transferase and a uridine 5'-diphospho glucosyl: steviol-19-O-glucose, 13-O-1,2 bioside C-3' glucosyl transferase. Functional UGT76G1 polypeptides may also catalyze glucosyl transferase reactions that utilize steviol glycoside substrates that contain sugars other than glucose, e.g., steviol rhamnosides and steviol xylosides. See, FIGS. 2A, 2B, 2C and 2D. Suitable UGT76G1 polypeptides include those made by *S. rebaudiana* and reported in Richman, et al. *Plant J.* 41: 56-67 (2005). The amino acid sequence of a *S. rebaudiana* UGT76G1 polypeptide is set forth in SEQ ID NO:7. The nucleotide sequence encoding the UGT76G1 polypeptide of SEQ ID NO:7 has been optimized for expression in yeast and is set forth in SEQ ID NO:8. See also the UGT76G1 variants set forth in the “Functional Homolog” section.

A suitable EUGT11 or UGT91D2 polypeptide functions as a uridine 5'-diphospho glucosyl: steviol-13-O-glucoside transferase (also referred to as a steviol-13-monoglucoside 1,2-glucosylase), transferring a glucose moiety to the C-2' of the 13-O-glucose of the acceptor molecule, steviol-13-O-glucoside.

A suitable EUGT11 or UGT91D2 polypeptide also functions as a uridine 5'-diphospho glucosyl: rubusoside transferase transferring a glucose moiety to the C-2' of the 13-O-glucose of the acceptor molecule, rubusoside, to produce stevioside. EUGT11 polypeptides also can transfer a glucose moiety to the C-2' of the 19-O-glucose of the acceptor molecule, rubusoside, to produce a 19-O-1,2-diglycosylated rubusoside (compound 2 in FIG. 3).

Functional EUGT11 or UGT91D2 polypeptides also can catalyze reactions that utilize steviol glycoside substrates other than steviol-13-O-glucoside and rubusoside. For example, a functional EUGT11 polypeptide may utilize stevioside as a substrate, transferring a glucose moiety to the C-2' of the 19-O-glucose residue to produce Rebaudioside E (see compound 3 in FIG. 3). Functional EUGT11 and UGT91D2 polypeptides may also utilize Rebaudioside A as a substrate, transferring a glucose moiety to the C-2' of the 19-O-glucose residue of Rebaudioside A to produce Rebaudioside D. As set forth in the Examples, EUGT11 can convert Rebaudioside A to Rebaudioside D at a rate that is least 20 times faster (e.g., as least 25 times or at least 30 times faster) than the corresponding rate of UGT91D2e (SEQ ID NO: 5) when the reactions are performed under similar conditions, i.e., similar time, temperature, purity, and substrate concentration. As such, EUGT11 produces greater amounts of RebD than UGT91D2e when incubated under similar conditions.

Figure 3:
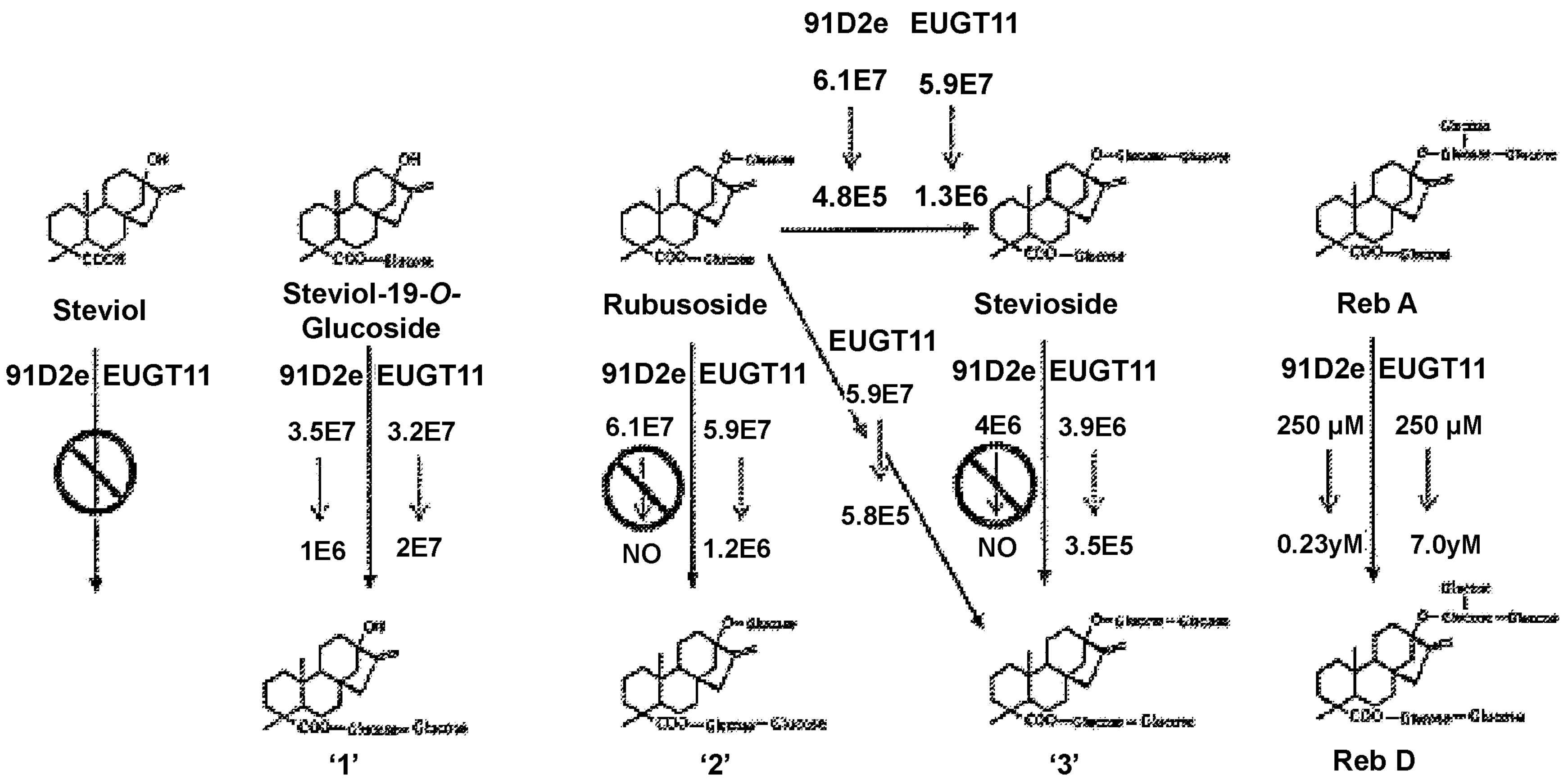
FIG. 3 is a schematic representation of 19-O-1,2-diglycosylation reactions by EUGT11 and UGT91D2e. The numbers are the average signal intensity for the substrates or the products of the reaction, from liquid chromatography-mass spectrometry (LC-MS) chromatograms FIG. 4 contains LC-MS chromatograms showing the production of rebaudioside D (RebD) from Rebaudioside A (RebA) using in vitro transcribed and translated UGT91D2e (SEQ ID NO:5) (left panel) or EUGT11 (SEQ ID NO:152) (right panel). The LC-MS was set to detect certain masses corresponding to steviol+5 glucoses (such as RebD), steviol+4 glucoses (such as RebA) etc. Each 'lane' is scaled according to the highest peak.

In addition, a functional EUGT11 exhibits significant C-2' 19-O-diglycosylation activity with rubusoside or stevioside as substrates, whereas UGT91D2e has no detectable diglycosylation activity with these substrates. Thus, a functional EUGT11 can be distinguished from UGT91D2e by the differences in steviol glycoside substrate-specificity. FIG. 3 provides a schematic overview of the 19-O-1,2 diglycosylation reactions that are performed by EUGT11 and UGT91D2e.

A functional EUGT11 or UGT91D2 polypeptide typically does not transfer a glucose moiety to steviol compounds having a 1,3-bound glucose at the C-13 position, i.e., transfer of a glucose moiety to steviol 1,3-bioside and 1,3-stevioside does not occur.

Functional EUGT11 and UGT91D2 polypeptides can transfer sugar moieties from donors other than uridine diphosphate glucose. For example, a functional EUGT11 or UGT91D2 polypeptide can act as a uridine 5'-diphospho D-xylosyl: steviol-13-O-glucoside transferase, transferring a xylose moiety to the C-2' of the 13-O-glucose of the acceptor molecule, steviol-13-O-glucoside. As another example, a functional EUGTI1 or UGT91D2 polypeptide can act as a uridine 5'-diphospho L-rhamnosyl: steviol-13-O-glucoside transferase, transferring a rhamnose moiety to the C-2' of the 13-O-glucose of the acceptor molecule, steviol-13-O-glucoside Suitable EUGTI1 polypeptides are described herein and can include the EUGTI1 polypeptide from *Oryza sativa* (GenBank Accession No. AC133334). For example, an EUGT11 polypeptide can have an amino acid sequence with at least 70% sequence identity (e.g., at least 75, 80, 85, 90, 95, 96, 97, 98, or 99% sequence identity) to the amino acid sequence set forth in SEQ ID NO: 152 (see FIG. 7). The nucleotide sequence encoding the amino acid sequence of SEQ ID NO: 152 is set forth in SEQ ID NO: 153. SEQ ID NO: 154 is a nucleotide sequence encoding the polypeptide of SEQ ID NO: 152 that has been codon optimized for expression in yeast.

Suitable functional UGT91D2 polypeptides include those disclosed herein, e.g., the polypeptides designated UGT91D2e and UGT91D2m. The amino acid sequence of an exemplary UGT91D2e polypeptide from *Stevia rebaudiana* is set forth in SEQ ID NO: 5. SEQ ID NO:6 is a nucleotide sequence encoding the polypeptide of SEQ ID NO:5 that has been codon optimized for expression in yeast. The *S. rebaudiana* nucleotide sequence encoding the polypeptide of SEQ ID NO:5 is set forth in SEQ ID NO:9. The amino acid sequences of exemplary UGT91D2m polypeptides from *S. rebaudiana* are set forth in SEQ ID NOs: 10 and 12, and are encoded by the nucleic acid sequences set forth in SEQ ID NOs: 11 and 13, respectively. In addition, UGT91D2 variants containing a substitution at amino acid residues 206, 207, and 343 of SEQ ID NO: 5 can be used. For example, the amino acid sequence set forth in SEQ ID NO:95 and having the following mutations with respect to wild-type UGT92D2e (SEQ ID NO:5) G206R, Y207C, and W343R can be used. In addition, a UGT91D2 variant containing substitutions at amino acid residues 211 and 286 can be used. For example, a UGT91D2 variant can include a substitution of a methionine for leucine at position 211 and a substitution of an alanine for valine at position 286 of SEQ ID NO:5 (UGT91D2e-b).

As indicated above, UGTs designated herein as SM12UGT can be substituted for UGT91D2. Suitable functional SM12UGT polypeptides include those made by *Ipomoea purpurea* (Japanese morning glory) and described in Morita et al. *Plant J.* 42, 353-363 (2005). The amino acid sequence encoding the *I. purpurea* IP3GGT polypeptide is set forth in SEQ ID NO:76. SEQ ID NO:77 is a nucleotide sequence encoding the polypeptide of SEQ ID NO:76 that has been codon optimized for expression in yeast. Another suitable SM12UGT polypeptide is a Bp94B1 polypeptide having an R25S mutation. See Osmani et al. *Plant Phys.* 148: 1295-1308 (2008) and Sawada et al. *J. Biol. Chem.* 280:899-906 (2005). The amino acid sequence of the *Bellis perennis* (red daisy) UGT94B1 polypeptide is set forth in SEQ ID NO:78. SEQ ID NO:79 is the nucleotide sequence encoding the polypeptide of SEQ ID NO:78 that has been codon optimized for expression in yeast.

In some embodiments, the recombinant microorganism is grown on media containing steviol-13-O-glucoside or steviol-19-O-glucoside in order to produce rebaudioside A and/or rebaudioside D. In such embodiments, the microorganism contains and expresses genes encoding a functional EUGT11, a functional UGT74G1, a functional UGT85C2, a functional UGT76G1, and an optional functional UGT91D2, and is capable of accumulating rebaudioside A and rebaudioside D when steviol, one or both of the steviolmonosides, or rubusoside is used as feedstock.

In other embodiments, the recombinant microorganism is grown on media containing rubusoside in order to produce rebaudioside A and/or rebaudioside D. In such embodiments, the microorganism contains and expresses genes encoding a functional EUGT11, a functional UGT76G1, and an optional functional UGT91D2, and is capable of producing rebaudioside A and/or rebaudioside D when rubusoside is used as feedstock.

In other embodiments the recombinant microorganism expresses one or more genes involved in steviol biosynthesis, e.g., a CDPS gene, a KS gene, a KO gene and/or a KAH gene. Thus, for example, a microorganism containing a CDPS gene, a KS gene, a KO gene and a KAH gene, in addition to a EUGT11, a UGT74G1, a UGT85C2, a UGT76G1, and optionally a functional UGT91D2 (e.g., UGT91D2e), is capable of producing rebaudioside A, rebaudioside D, and/or rebaudioside E without the necessity for including steviol in the culture media.

In some embodiments, the recombinant host further contains and expresses a recombinant GGPPS gene in order to provide increased levels of the diterpene precursor geranylgeranyl diphosphate, for increased flux through the steviol biosynthetic pathway. In some embodiments, the recombinant host further contains a construct to silence the expression of non-steviol pathways consuming geranylgeranyl diphosphate, ent-Kaurenoic acid or farnesyl pyrophosphate, thereby providing increased flux through the steviol and steviol glycosides biosynthetic pathways. For example, flux to sterol production pathways such as ergosterol may be reduced by downregulation of the ERG9 gene. See, the ERG9 section below and Examples 24-25. In cells that produce gibberellins, gibberellin synthesis may be downregulated to increase flux of ent-kaurenoic acid to steviol. In carotenoid-producing organisms, flux to steviol may be increased by downregulation of one or more carotenoid biosynthetic genes. In some embodiments, the recombinant microorganism further can express recombinant genes involved in diterpene biosynthesis or production of terpenoid precursors, e.g., genes in the MEP or MEV) pathways discussed below, have reduced phosphatase activity, and/or express a SUS as discussed herein.

One with skill in the art will recognize that by modulating relative expression levels of different UGT genes, a recombinant host can be tailored to specifically produce steviol glycoside products in a desired proportion. Transcriptional regulation of steviol biosynthesis genes and steviol glycoside biosynthesis genes can be achieved by a combination of transcriptional activation and repression using techniques known to those in the art. For in vitro reactions, one with skill in the art will recognize that addition of different levels of UGT enzymes in combination or under conditions which impact the relative activities of the different UGTS in combination will direct synthesis towards a desired proportion of each steviol glycoside. One with skill in the art will recognize that a higher proportion of rebaudioside D or E or more efficient conversion to rebaudioside D or E can be obtained with a diglycosylation enzyme that has a higher activity for the 19-O-glucoside reaction as compared to the 13-O-glucoside reaction (substrates rebaudioside A and stevioside).

In some embodiments, a recombinant host such as a microorganism produces rebaudioside D-enriched steviol glycoside compositions that have greater than at least 3% rebaudioside D by weight total steviol glycosides, e.g., at least 4% rebaudioside D at least 5% rebaudioside D, 10-20% rebaudioside D, 20-30% rebaudioside D, 30-40% rebaudioside D, 40-50% rebaudioside D, 50-60% rebaudioside D, 60-70% rebaudioside D, 70-80% rebaudioside D. In some embodiments, a recombinant host such as a microorganism produces steviol glycoside compositions that have at least 90% rebaudioside D, e.g., 90-99% rebaudioside D. Other steviol glycosides present may include those depicted in FIG. 2 C such as steviol monosides, steviol glucobiosides, rebaudioside A, rebaudioside E, and stevioside. In some embodiments, the rebaudioside D-enriched composition produced by the host (e.g., microorganism) can be further purified and the rebaudioside D or rebaudioside E so purified can then be mixed with other steviol glycosides, flavors, or sweeteners to obtain a desired flavor system or sweetening composition. For instance, a rebaudioside D-enriched composition produced by a recombinant host can be combined with a rebaudioside A, C, or F-enriched composition produced by a different recombinant host, with rebaudioside A, F, or C purified from a Stevia extract, or with rebaudioside A, F, or C produced in vitro.

In some embodiments, rebaudioside A, rebaudioside D, rebaudioside B, steviol monoglucosides, steviol-1,2-bioside, rubusoside, stevioside, or rebaudioside E can be produced using in vitro methods while supplying the appropriate UDP-sugar and/or a cell-free system for regeneration of UDP-sugars. See, for example, Jewett M C, et al. *Molecular Systems Biology, Vol.* 4, article 220 (2008); Masada S et al. *FEBS Letters*, Vol. 581, 2562-2566 (2007). In some embodiments, sucrose and a sucrose synthase may be provided in the reaction vessel in order to regenerate UDP-glucose from the UDP generated during glycosylation reactions. See FIG. 11. The sucrose synthase can be from any suitable organism. For example, a sucrose synthase coding sequence from *Arabidopsis thaliana, Stevia rebaudiana*, or *Coffea arabica* can be cloned into an expression plasmid under control of a suitable promoter, and expressed in a host such as a microorganism or a plant.

Conversions requiring multiple reactions may be carried out together, or stepwise. For example, rebaudioside D may be produced from rebaudioside A that is commercially available as an enriched extract or produced via biosynthesis, with the addition of stoichiometric or excess amounts of UDP-glucose and EUGT11. As an alternative, rebaudioside D may be produced from steviol glycoside extracts that are enriched for stevioside and rebaudioside A, using EUGT11 and a suitable UGT76G1 enzyme. In some embodiments, phosphatases are used to remove secondary products and improve the reaction yields. UGTs and other enzymes for in vitro reactions may be provided in soluble forms or in immobilized forms.

In some embodiments, rebaudioside A, rebaudioside D, or rebaudioside E can be produced using whole cells that are fed raw materials that contain precursor molecules such as steviol and/or steviol glycosides, including mixtures of steviol glycosides derived from plant extracts. The raw materials may be fed during cell growth or after cell growth. The whole cells may be in suspension or immobilized. The whole cells may be entrapped in beads, for example calcium or sodium alginate beads. The whole cells may be linked to a hollow fiber tube reactor system. The whole cells may be concentrated and entrapped within a membrane reactor system. The whole cells may be in fermentation broth or in a reaction buffer. In some embodiments, a permeabilizing agent is utilized for efficient transfer of substrate into the cells. In some embodiments, the cells are permeabilized with a solvent such as toluene, or with a detergent such as Triton-X or Tween. In some embodiments, the cells are permeabilized with a surfactant, for example a cationic surfactant such as cetyltrimethylammonium bromide (CTAB). In some embodiments, the cells are permeabilized with periodic mechanical shock such as electroporation or a slight osmotic shock. The cells can contain one recombinant UGT or multiple recombinant UGTs. For example, the cells can contain UGT 76G1 and EUGT11 such that mixtures of stevioside and RebA are efficiently converted to RebD. In some embodiments, the whole cells are the host cells described in section III A. In some embodiments, the whole cells are a Gram-negative bacterium such as *E. coli*. In some embodiments, the whole cell is a Gram-positive bacterium such as *Bacillus*. In some embodiments, the whole cell is a fungal species such as *Aspergillus*, or a yeast such as *Saccharomyces*. In some embodiments, the term "whole cell biocatalysis" is used to refer to the process in which the whole cells are grown as described above (e.g., in a medium and optionally permeabilized) and a substrate such as rebA or stevioside is provided and converted to the end product using the enzymes from the cells. The cells may or may not be viable, and may or may not be growing during the bioconversion reactions. In contrast, in fermentation, the cells are cultured in a growth medium and fed a carbon and energy source such as glucose and the end product is produced with viable cells.

B. 3 Dulcoside A and Rebaudioside C Biosynthesis Polypeptides

The biosynthesis of rebaudioside C and/or dulcoside A involves glucosylation and rhamnosylation of the aglycone steviol. Specifically, dulcoside A can be formed by glucosylation of the 13-OH of steviol which forms steviol-13-O-glucoside, rhamnosylation of the C-2' of the 13-O-glucose of steviol-13-O-glucoside which forms the 1,2 rhamnobioside, and glucosylation of the C-19 carboxyl of the 1,2 rhamnobioside. Rebaudioside C can be formed by glucosylation of the C-3' of the C-13-O-glucose of dulcoside A. The order in which each glycosylation reaction occurs can vary. See FIG. 2B.

It has been discovered that conversion of steviol to dulcoside A in a recombinant host can be accomplished by the expression of gene(s) encoding the following functional UGTs: 85C2, EUGT11 and/or 91D2e, and 74G1. Thus, a recombinant microorganism expressing these three or four UGTs and a rhamnose synthetase can make dulcoside A when fed steviol in the medium. Alternatively, a recombinant microorganism expressing two UGTs, EUGT11 and 74G1, and rhamnose synthetase can make dulcoside A when fed the monoside, steviol-13-O-glucoside or steviol-19-O-glucoside, in the medium. Similarly, conversion of steviol to rebaudioside C in a recombinant microorganism can be accomplished by the expression of gene(s) encoding UGTs 85C2, EUGT11, 74G1, 76G1, optionally 91D2e, and rhamnose synthetase when fed steviol, by the expression of genes encoding UGTs EUGT11 and/or 91D2e, 74G1, and 76G1, and rhamnose synthetase when fed steviol-13-O-glucoside, by the expression of genes encoding UGTs 85C2, EUGT11 and/or 91D2e, 76G1, and rhamnose synthetase when fed steviol-19-O-glucoside, or by the expression of genes encoding UGTs EUGT11 and/or 91D2e, 76G1, and rhamnose synthetase when fed rubusoside. Typically, one or more of these genes are recombinant genes that have been transformed into a microorganism that does not naturally possess them.

Suitable EUGT11, UGT91D2, UGT74G1, UGT76G1 and UGT85C2 polypeptides include the functional UGT polypeptides discussed herein. Rhamnose synthetase provides increased amounts of the UDP-rhamnose donor for rhamnosylation of the steviol compound acceptor. Suitable rhamnose synthetases include those made by *Arabidopsis thaliana*, such as the product of the *A. thaliana* RHM2 gene.

In some embodiments, a UGT79B3 polypeptide is substituted for a UGT91D2 polypeptide. Suitable UGT79B3 polypeptides include those made by *Arabidopsis thaliana*, which are capable of rhamnosylation of steviol 13-O-monoside in vitro. *A. thaliana* UGT79B3 can rhamnosylate glucosylated compounds to form 1,2-rhamnosides. The amino acid sequence of an *Arabidopsis thaliana* UGT79B3 is set forth in SEQ ID NO:150. The nucleotide sequence encoding the amino acid sequence of SEQ ID NO:150 is set forth in SEQ ID NO:151.

In some embodiments rebaudioside C can be produced using in vitro methods while supplying the appropriate UDP-sugar and/or a cell-free system for regeneration of UDP-sugars. See, for example, "An integrated cell-free metabolic platform for protein production and synthetic biology" by Jewett M C, Calhoun K A, Voloshin A, Wuu J J and Swartz J R in *Molecular Systems Biology* 4, article 220 (2008); Masada S et al. *FEBS Letters*, Vol. 581, 2562-2566 (2007). In some embodiments, sucrose and a sucrose synthase may be provided in the reaction vessel in order to regenerate UDP-glucose from UDP during the glycosylation reactions. See FIG. 11. The sucrose synthase can be from any suitable organism. For example, a sucrose synthase coding sequence from *Arabidopsis thaliana, Stevia rebaudiana*, or *Coffea arabica* can be cloned into an expression plasmid under control of a suitable promoter, and expressed in a host (e.g., a microorganism or a plant). In some embodiments a RHM2 enzyme (Rhamnose synthase) may also be provided, with NADPH, to generate UDP-rhamnose from UDP-glucose.

Reactions may be carried out together, or stepwise. For instance, rebaudioside C may be produced from rubusoside with the addition of stoichiometric amounts of UDP-rhamnose and EUGT11, followed by addition of UGT76G1 and an excess or stoichiometric supply of UDP-glucose. In some embodiments, phosphatases are used to remove secondary products and improve the reaction yields. UGTs and other enzymes for in vitro reactions may be provided in soluble forms or immobilized forms. In some embodiments, rebaudioside C, Dulcoside A, or other steviol rhamnosides can be produced using whole cells as discussed above. The cells can contain one recombinant UGT or multiple recombinant UGTs. For example, the cells can contain UGT 76G1 and EUGT11 such that mixtures of stevioside and RebA are efficiently converted to RebD. In some embodiments, the whole cells are the host cells described in section III A.

In other embodiments, the recombinant host expresses one or more genes involved in steviol biosynthesis, e.g., a CDPS gene, a KS gene, a KO gene and/or a KAH gene. Thus, for example, a microorganism containing a CDPS gene, a KS gene, a KO gene and a KAH gene, in addition to a UGT85C2, a UGT74G1, a EUGT11 gene, optionally a UGT91D2e gene, and a UGT76G1 gene, is capable of producing rebaudioside C without the necessity for including steviol in the culture media. In addition, the recombinant host typically expresses an endogenous or a recombinant gene encoding a rhamnose synthetase. Such a gene is useful in order to provide increased amounts of the UDP-rhamnose donor for rhamnosylation of the steviol compound acceptor. Suitable rhamnose synthetases include those made by *Arabidopsis thaliana*, such as the product of the *A. thaliana* RHM2 gene.

One with skill in the art will recognize that by modulating relative expression levels of different UGT genes as well as modulating the availability of UDP-rhamnose, a recombinant host can be tailored to specifically produce steviol and steviol glycoside products in a desired proportion. Transcriptional regulation of steviol biosynthesis genes, and steviol glycoside biosynthesis genes can be achieved by a combination of transcriptional activation and repression using techniques known to those in the art. For in vitro reactions, one with skill in the art will recognize that addition of different levels of UGT enzymes in combination or under conditions which impact the relative activities of the different UGTS in combination will direct synthesis towards a desired proportion of each steviol glycoside.

In some embodiments, the recombinant host further contains and expresses a recombinant GGPPS gene in order to provide increased levels of the diterpene precursor geranylgeranyl diphosphate, for increased flux through the rebaudioside A biosynthetic pathway. In some embodiments, the recombinant host further contains a construct to silence or reduce the expression of non-steviol pathways consuming geranylgeranyl diphosphate, ent-Kaurenoic acid or farnesyl pyrophosphate, thereby providing increased flux through the steviol and steviol glycosides biosynthetic pathways. For example, flux to sterol production pathways such as ergosterol may be reduced by downregulation of the ERG9 gene. See, the ERG9 section below and Examples 24-25. In cells that produce gibberellins, gibberellin synthesis may be downregulated to increase flux of ent-kaurenoic acid to steviol. In carotenoid-producing organisms, flux to steviol may be increased by downregulation of one or more carotenoid biosynthetic genes.

In some embodiments, the recombinant host further contains and expresses recombinant genes involved in diterpene biosynthesis or production of terpenoid precursors, e.g., genes in the MEP or MEV pathway, have reduced phosphatase activity, and/or express a SUS as discussed herein.

In some embodiments, a recombinant host such as a microorganism produces steviol glycoside compositions that have greater than at least 15% rebaudioside C of the total steviol glycosides, e.g., at least 20% rebaudioside C, 30-40% rebaudioside C, 40-50% rebaudioside C, 50-60% rebaudioside C, 60-70% rebaudioside C, 70-80% rebaudioside C, 80-90% rebaudioside C. In some embodiments, a recombinant host such as a microorganism produces steviol glycoside compositions that have at least 90% rebaudioside C, e.g., 90-99% rebaudioside C. Other steviol glycosides present may include those depicted in FIGS. 2 A and B such as steviol monosides, steviol glucobiosides, steviol rhamnobiosides, rebaudioside A, and Dulcoside A. In some embodiments, the rebaudioside C-enriched composition produced by the host can be further purified and the rebaudioside C or Dulcoside A so purified may then be mixed with other steviol glycosides, flavors, or sweeteners to obtain a desired flavor system or sweetening composition. For instance, a rebaudioside C-enriched composition produced by a recombinant microorganism can be combined with a rebaudioside A, F, or D-enriched composition produced by a different recombinant microorganism, with rebaudioside A, F, or D purified from a Stevia extract, or with rebaudioside A, F, or D produced in vitro.

B. 4 Rebaudioside F Biosynthesis Polypeptides

The biosynthesis of rebaudioside F involves glucosylation and xylosylation of the aglycone steviol. Specifically, rebaudioside F can be formed by glucosylation of the 13-OH of steviol which forms steviol-13-O-glucoside, xylosylation of the C-2' of the 13-O-glucose of steviol-13-O-glucoside which forms steviol-1,2-xylobioside, glucosylation of the C-19 carboxyl of the 1,2-xylobioside to form 1,2-stevioxyloside, and glucosylation of the C-3' of the C-13-O-glucose of 1,2-stevioxyloside to form rebaudioside F. The order in which each glycosylation reaction occurs can vary. See FIG. 2D.

It has been discovered that conversion of steviol to rebaudioside F in a recombinant host can be accomplished by the expression of genes encoding the following functional UGTs: 85C2, EUGT11 and/or 91D2e, 74G1, and 76G1, along with endogenous or recombinantly expressed UDP-glucose dehydrogenase and UDP-glucuronic acid decarboxylase. Thus, a recombinant microorganism expressing these four or five UGTs along with endogenous or recombinant UDP-glucose dehydrogenase and UDP-glucuronic acid decarboxylase can make rebaudioside F when fed steviol in the medium. Alternatively, a recombinant microorganism expressing two functional UGTs, EUGT11 or 91D2e, and 76G1, can make rebaudioside F when fed rubusoside in the medium. As another alternative, a recombinant microorganism expressing a functional UGT 76G1 can make rebaudioside F when fed 1,2 steviorhamnoside. As another alternative, a recombinant microorganism expressing 74G1, EUGT11 and/or 91D2e, 76G1, and can make rebaudioside F when fed the monoside, steviol-13-O-glucoside, in the medium. Similarly, conversion of steviol-19-O-glucoside to rebaudioside F in a recombinant microorganism can be accomplished by the expression of genes encoding UGTs 85C2, EUGT11 and/or 91D2e, and 76G1, when fed steviol-19-O-glucoside. Typically, one or more of these genes are recombinant genes that have been transformed into a host that does not naturally possess them.

Suitable EUGT11, UGT91D2, UGT74G1, UGT76G1 and UGT85C2 polypeptides include the functional UGT polypeptides discussed herein. In some embodiments, a UGT79B3 polypeptide is substituted for a UGT91, as discussed above. UDP-glucose dehydrogenase and UDP-glucuronic acid decarboxylase provide increased amounts of the UDP-xylose donor for xylosylation of the steviol compound acceptor. Suitable UDP-glucose dehydrogenases and UDP-glucuronic acid decarboxylases include those made by *Arabidopsis thaliana* or *Cryptococcus neoformans*. For example, suitable UDP-glucose dehydrogenase and UDP-glucuronic acid decarboxylases polypeptides can be encoded by the *A. thaliana* UGD1 gene and UXS3 gene, respectively. See, Oka and Jigami, *FEBS J.* 273:2645-2657 (2006).

In some embodiments rebaudioside F can be produced using in vitro methods while supplying the appropriate UDP-sugar and/or a cell-free system for regeneration of UDP-sugars. See, for example, Jewett M C, et al. *Molecular Systems Biology*, Vol. 4, article 220 (2008); Masada S et al. *FEBS Letters*, Vol. 581, 2562-2566 (2007). In some embodiments, sucrose and a sucrose synthase are provided in the reaction vessel in order to regenerate UDP-glucose from UDP during the glycosylation reactions. See FIG. 11. The sucrose synthase can be from any suitable organism. For example, a sucrose synthase coding sequence from *Arabidopsis thaliana, Stevia rebaudiana*, or *Coffea arabica* can be cloned into an expression plasmid under control of a suitable promoter, and expressed in a host, e.g., a microorganism or a plant. In some embodiments, UDP-xylose can be produced from UDP-glucose by supplying suitable enzymes, for example, the *Arabidopsis thaliana* UGD1 (UDP-glucose dehydrogenase) and UXS3 (UDP-glucuronic acid decarboxylase) enzymes along with NAD+ cofactor.

Reactions may be carried out together, or stepwise. For instance, rebaudioside F may be produced from rubusoside with the addition of stoichiometric amounts of UDP-xylose and EUGT11, followed by addition of UGT76G1 and an excess or stoichiometric supply of UDP-glucose. In some embodiments, phosphatases are used to remove secondary products and improve the reaction yields. UGTs and other enzymes for in vitro reactions may be provided in soluble forms or immobilized forms. In some embodiments, rebaudioside F or other steviol xylosides can be produced using whole cells as discussed above. For example, the cells may contain UGT 76G1 and EUGT11 such that mixtures of stevioside and RebA are efficiently converted to RebD. In some embodiments, the whole cells are the host cells described in section III A.

In other embodiments, the recombinant host expresses one or more genes involved in steviol biosynthesis, e.g., a CDPS gene, a KS gene, a KO gene and/or a KAH gene. Thus, for example, a microorganism containing a CDPS gene, a KS gene, a KO gene and a KAH gene, in addition to a EUGT11, UGT85C2, a UGT74G1, an optional UGT91D2 gene, and a UGT76G1 gene, is capable of producing rebaudioside F without the necessity for including steviol in the culture media. In addition, the recombinant host typically expresses an endogenous or a recombinant gene encoding a UDP-glucose dehydrogenase and a UDP-glucuronic acid decarboxylase. Such genes are useful in order to provide increased amounts of the UDP-xylose donor for xylosylation of the steviol compound acceptor. Suitable UDP-glucose dehydrogenases and UDP-glucuronic acid decarboxylases include those made by *Arabidopsis thaliana* or *Cryptococcus neoformans*. For example, suitable UDP-glucose dehydrogenase and UDP-glucuronic acid decarboxylases polypeptides can be encoded by the *A. thaliana* UGD1 gene and UXS3 gene, respectively. See, Oka and Jigami, *FEBS J.* 273:2645-2657 (2006).

One with skill in the art will recognize that by modulating relative expression levels of different UGT genes as well as modulating the availability of UDP-xylose, a recombinant microorganism can be tailored to specifically produce steviol and steviol glycoside products in a desired proportion. Transcriptional regulation of steviol biosynthesis genes can be achieved by a combination of transcriptional activation and repression using techniques known to those in the art. For in vitro reactions, one with skill in the art will recognize that addition of different levels of UGT enzymes in combination or under conditions which impact the relative activities of the different UGTS in combination will direct synthesis towards a desired proportion of each steviol glycosides.

In some embodiments, the recombinant host further contains and expresses a recombinant GGPPS gene in order to provide increased levels of the diterpene precursor geranylgeranyl diphosphate, for increased flux through the steviol biosynthetic pathway. In some embodiments, the recombinant host further contains a construct to silence the expression of non-steviol pathways consuming geranylgeranyl diphosphate, ent-Kaurenoic acid or farnesyl pyrophosphate, thereby providing increased flux through the steviol and steviol glycosides biosynthetic pathways. For example, flux to sterol production pathways such as ergosterol may be reduced by downregulation of the ERG9 gene. See, the ERG9 section below and Examples 24-25. In cells that produce gibberellins, gibberellin synthesis may be downregulated to increase flux of ent-kaurenoic acid to steviol. In carotenoid-producing organisms, flux to steviol may be increased by downregulation of one or more carotenoid biosynthetic genes. In some embodiments, the recombinant host further contains and expresses recombinant genes involved in diterpene biosynthesis, e.g., genes in the MEP pathway discussed below.

In some embodiments, a recombinant host such as a microorganism produces rebaudioside F-enriched steviol glycoside compositions that have greater than at least 4% rebaudioside F by weight total steviol glycosides, e.g., at least 5% rebaudioside F, at least 6% of rebaudioside F, 10-20% rebaudioside F, 20-30% rebaudioside F, 30-40% rebaudioside F, 40-50% rebaudioside F, 50-60% rebaudioside F, 60-70% rebaudioside F, 70-80% rebaudioside F. In some embodiments, a recombinant host such as a microorganism produces steviol glycoside compositions that have at least 90% rebaudioside F, e.g., 90-99% rebaudioside F. Other steviol glycosides present may include those depicted in FIGS. 2A and D such as steviol monosides, steviol glucobiosides, steviol xylobiosides, rebaudioside A, stevioxyloside, rubusoside and stevioside. In some embodiments, the rebaudioside F-enriched composition produced by the host can be mixed with other steviol glycosides, flavors, or sweeteners to obtain a desired flavor system or sweetening composition. For instance, a rebaudioside F-enriched composition produced by a recombinant microorganism can be combined with a rebaudioside A, C, or D-enriched composition produced by a different recombinant microorganism, with rebaudioside A, C, or D purified from a Stevia extract, or with rebaudioside A, C, or D produced in vitro.

C. Other Polypeptides

Genes for additional polypeptides whose expression facilitates more efficient or larger scale production of steviol or a steviol glycoside can also be introduced into a recombinant host. For example, a recombinant microorganism, plant, or plant cell can also contain one or more genes encoding a geranylgeranyl diphosphate synthase (GGPPS, also referred to as GGDPS). As another example, the recombinant host can contain one or more genes encoding a rhamnose synthetase, or one or more genes encoding a UDP-glucose dehydrogenase and/or a UDP-glucuronic acid decarboxylase. As another example, a recombinant host can also contain one or more genes encoding a cytochrome P450 reductase (CPR). Expression of a recombinant CPR facilitates the cycling of NADP+ to regenerate NADPH, which is utilized as a cofactor for terpenoid biosynthesis. Other methods can be used to regenerate NADHP levels as well. In circumstances where NADPH becomes limiting; strains can be further modified to include exogenous transhydrogenase genes. See, e.g., Sauer et al., *J. Biol. Chem.* 279: 6613-6619 (2004). Other methods are known to those with skill in the art to reduce or otherwise modify the ratio of NADH/NADPH such that the desired cofactor level is increased.

As another example, the recombinant host can contain one or more genes encoding one or more enzymes in the MEP pathway or the mevalonate pathway. Such genes are useful because they can increase the flux of carbon into the diterpene biosynthesis pathway, producing geranylgeranyl diphosphate from isopentenyl diphosphate and dimethylallyl diphosphate generated by the pathway. The geranylgeranyl diphosphate so produced can be directed towards steviol and steviol glycoside biosynthesis due to expression of steviol biosynthesis polypeptides and steviol glycoside biosynthesis polypeptides.

As another example the recombinant host can contain one or more genes encoding a sucrose synthase, and additionally can contain sucrose uptake genes if desired. The sucrose synthase reaction can be used to increase the UDP-glucose pool in a fermentation host, or in a whole cell bioconversion process. This regenerates UDP-glucose from UDP produced during glycosylation and sucrose, allowing for efficient glycosylation. In some organisms, disruption of the endogenous invertase is advantageous to prevent degradation of sucrose. For example, the *S. cerevisiae* SUC2 invertase may be disrupted. The sucrose synthase (SUS) can be from any suitable organism. For example, a sucrose synthase coding sequence from, without limitation, *Arabidopsis thaliana, Stevia rebaudiana*, or *Coffea arabica* can be cloned into an expression plasmid under control of a suitable promoter, and expressed in a host (e.g., a microorganism or a plant). The sucrose synthase can be expressed in such a strain in combination with a sucrose transporter (e.g., the *A. thaliana* SUC1 transporter or a functional homolog thereof) and one or more UGTs (e.g., one or more of UGT85C2, UGT74G1, UGT76G1, and UGT91D2e, EUGT11 or functional homologs thereof). Culturing the host in a medium that contains sucrose can promote production of UDP-glucose, as well as one or more glucosides (e.g., steviol glycosides).

In addition, a recombinant host can have reduced phosphatase activity as discussed herein.

C. 1 MEP Biosynthesis Polypeptides

In some embodiments, a recombinant host contains one or more genes encoding enzymes involved in the methylerythritol 4-phosphate (MEP) pathway for isoprenoid biosynthesis. Enzymes in the MEP pathway include deoxyxylulose 5-phosphate synthase (DXS), D-1-deoxyxylulose 5-phosphate reductoisomerase (DXR), 4-diphosphocytidyl-2-C-methyl-D-erythritol synthase (CMS), 4-diphosphocytidyl-2-C-methyl-D-erythritol kinase (CMK), 4-diphosphocytidyl-2-C-methyl-D-erythritol 2,4-cyclodiphosphate synthase (MCS), 1-hydroxy-2-methyl-2(E)-butenyl 4-diphosphate synthase (HDS) and 1-hydroxy-2-methyl-2(E)-butenyl 4-diphosphate reductase (HDR). One or more DXS genes, DXR genes, CMS genes, CMK genes, MCS genes, HDS genes and/or HDR genes can be incorporated into a recombinant microorganism. See, Rodriguez-Concepcion and Boronat, *Plant Phys.* 130: 1079-1089 (2002).

Suitable genes encoding DXS, DXR, CMS, CMK, MCS, HDS and/or HDR polypeptides include those made by *E. coli, Arabidopsis thaliana* and *Synechococcus leopoliensis*. Nucleotide sequences encoding DXR polypeptides are described, for example, in U.S. Pat. No. 7,335,815.

C. 2 Mevalonate Biosynthesis Polypeptides

In some embodiments, a recombinant host contains one or more genes encoding enzymes involved in the mevalonate pathway for isoprenoid biosynthesis. Genes suitable for transformation into a host encode enzymes in the mevalonate pathway such as a truncated 3-hydroxy-3-methyl-glutaryl (HMG)-CoA reductase (tHMG), and/or a gene encoding a mevalonate kinase (MK), and/or a gene encoding a phosphomevalonate kinase (PMK), and/or a gene encoding a mevalonate pyrophosphate decarboxylase (MPPD). Thus, one or more HMG-CoA reductase genes, MK genes, PMK genes, and/or MPPD genes can be incorporated into a recombinant host such as a microorganism.

Suitable genes encoding mevalonate pathway polypeptides are known. For example, suitable polypeptides include those made by *E. coli, Paracoccus denitrficans, Saccharomyces cerevisiae, Arabidopsis thaliana, Kitasatospora griseola, Homo sapiens, Drosophila melanogaster, Gallus gallus, Streptomyces* sp. KO-3988, *Nicotiana attenuata, Kitasatospora griseola, Hevea brasiliensis, Enterococcus faecium* and *Haematococcus pluvialis*. See, e.g., Table 8 and U.S. Pat. Nos. 7,183,089, 5,460,949, and 5,306,862.

TABLE 8

Sources of HMG CoA Reductases and other Mevalonate Genes

| Accession# | Organism | Enzyme | Size (nt) | Gene name | SEQ ID (codon optimized) | SEQ ID (protein) |
|---|---|---|---|---|---|---|
| XM_001467423 | *Leishmania infantum* | Acetyl-CoA C-acetyltransferase | 1323 | MEV-4 | 103 | 104 |
| YML075C | *Saccharomyces cerevisiae* | Truncated HMG (tHMG1) | 1584 | tHMG1 | 105 | 106 |
| EU263989 | *Ganoderma lucidum* | 3-HMG-CoA reductase | 3681 | MEV-11 | 107 | 108 |
| BC153262 | *Bos taurus* | 3-HMG-CoA reductase | 2667 | MEV-12 | 109 | 110 |
| AAD47596 | *Artemisia annua* | 3-HMG-CoA reductase | 1704 | MEV-13 | 111 | 112 |
| AAB62280 | *Trypanosoma cruzi* | 3-HMG-CoA reductase | 1308 | MEV-14 | 113 | 114 |
| CAG41604 | *Staph aureus* | 3-HMG-CoA reductase | 1281 | MEV-15 | 115 | 116 |
| DNA2.0 sequence | *Archaeoglobus fulgidus* | 3-HMG-CoA reductase | 1311 | HMG reductase | 117 | 118 |
| DNA2.0 sequence | *Pseudomonas mevalonii* | 3-HMG-CoA reductase | 1287 | HMG reductase | 119 | 120 |

C.3 Sucrose Synthase Polypeptides

Figure 11:
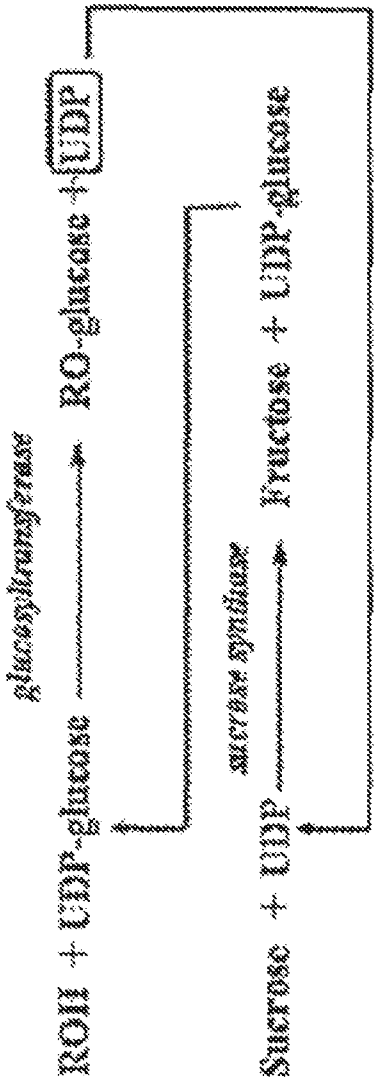
FIG. 11 is a schematic representation of UDP-glucose regeneration for the biosynthesis of steviol glycosides. SUS=sucrose synthase; Steviol=steviol or steviol glycoside substrate; UGT=UDP glycosyl transferase.

Sucrose synthase (SUS) can be used as a tool for generating UDP-sugar. SUS (EC 2.4.1.13) catalyzes the formation of UDP-glucose and fructose from sucrose and UDP (FIG. 11). UDP generated by the reaction of UGTs thus can be converted into UDP-glucose in the presence of sucrose. See, e.g., Chen et al. (2001) *J. Am. Chem. Soc.* 123:8866-8867; Shao et al. (2003) *Appl. Env. Microbiol.* 69:5238-5242; Masada et al. (2007) *FEBS Lett.* 581:2562-2566; and Son et al. (2009) *J. Microbiol. Biotechnol.* 19:709-712.

Sucrose synthases can be used to generate UDP-glucose and remove UDP, facilitating efficient glycosylation of compounds in various systems. For example, yeast deficient in the ability to utilize sucrose can be made to grow on sucrose by introducing a sucrose transporter and a SUS. For example, *Saccharomyces cerevisiae* does not have an efficient sucrose uptake system, and relies on extracellular SUC2 to utilize sucrose. The combination of disrupting the endogenous *S. cerevisiae* SUC2 invertase and expressing recombinant SUS resulted in a yeast strain that was able to metabolize intracellular but not extracellular sucrose (Riesmeier et al. ((1992) *EMBO J.* 11:4705-4713). The strain was used to isolate sucrose transporters by transformation with a cDNA expression library and selection of transformants that had gained the ability to take up sucrose.

As described herein, the combined expression of recombinant sucrose synthase and a sucrose transporter in vivo can lead to increased UDP-glucose availability and removal of unwanted UDP. For example, functional expression of a recombinant sucrose synthase, a sucrose transporter, and a glycosyltransferase, in combination with knockout of the natural sucrose degradation system (SUC2 in the case of *S. cerevisiae*) can be used to generate a cell that is capable of producing increased amounts of glycosylated compounds such as steviol glycosides. This higher glycosylation capability is due to at least (a) a higher capacity for producing UDP-glucose in a more energy efficient manner, and (b) removal of UDP from growth medium, as UDP can inhibit glycosylation reactions.

The sucrose synthase can be from any suitable organism. For example, a sucrose synthase coding sequence from, without limitation, *Arabidopsis thaliana, Stevia rebaudiana*, or *Coffea arabica* (see, e.g., FIGS. 19A-19C, SEQ ID NOs:178, 179, and 180) can be cloned into an expression plasmid under control of a suitable promoter, and expressed in a host (e.g., a microorganism or a plant). As described in the Examples herein, a SUS coding sequence may be expressed in a SUC2 (sucrose hydrolyzing enzyme) deficient *S. cerevisiae* strain, so as to avoid degradation of extracellular sucrose by the yeast. The sucrose synthase can be expressed in such a strain in combination with a sucrose transporter (e.g., the *A. thaliana* SUC1 transporter or a functional homolog thereof) and one or more UGTs (e.g., one or more of UGT85C2, UGT74G1, UGT76G1, EUGT11, and UGT91D2e, or functional homologs thereof). Culturing the host in a medium that contains sucrose can promote production of UDP-glucose, as well as one or more glucosides (e.g., steviol glucoside). It is to be noted that in some cases, a sucrose synthase and a sucrose transporter can be expressed along with a UGT in a host cell that also is recombinant for production of a particular compound (e.g., steviol).

C. 4 Modulation of ERG9 Activity

It is an object of the disclosure to produce terpenoids based on the concept of increasing the accumulation of terpenoid precursors of the squalene pathway. Non-limiting examples of terpenoids include Hemiterpenoids, 1 isoprene unit (5 carbons); Monoterpenoids, 2 isoprene units (10 C); Sesquiterpenoids, 3 isoprene units (15 C); Diterpenoids, 4 isoprene units (20 C) (e.g. ginkgolides); Triterpenoids, 6 isoprene units (30 C); Tetraterpenoids, 8 isoprene units (40 C) (e.g. carotenoids); and polyterpenoid with a larger number of isoprene units.

Hemiterpenoids include isoprene, prenol and isovaleric acid. Monoterpenoids include Geranyl pyrophosphate, Eucalyptol, Limonene and Pinene. Sesquiterpenoids include Farnesyl pyrophosphate, Artemisinin and Bisabolol. Diterpenoids include Geranylgeranyl pyrophosphate, steviol, Retinol, Retinal, Phytol, Taxol, Forskolin and Aphidicolin. Triterpenoids include Squalene and Lanosterol. Tetraterpenoids include Lycopene and Carotene.

Terpenes are hydrocarbons resulting from the combination of several isoprene units. Terpenoids can be thought of as terpene derivatives. The term terpene is sometimes used broadly to include the terpenoids. Just like terpenes, the terpenoids can be classified according to the number of isoprene units used. The present invention is focused on terpenoids and in particular terpenoids derived through the squalene pathway from the precursors Farnesyl-pyrophosphate (FPP), Isopentenyl-pyrophosphate (IPP), Dimethylallyl-pyrophosphate (DMAPP), Geranyl-pyrophosphate (GPP) and/or Geranylgeranyl-pyrophosphate (GGPP).

By terpenoids is understood terpenoids of the Hemiterpenoid class such as but not limited to isoprene, prenol and isovaleric acid; terpenoids of the Monoterpenoid class such as but not limited to geranyl pyrophosphate, eucalyptol, limonene and pinene; terpenoids of the Sesquiterpenoids class such as but not limited to farnesyl pyrophosphate, artemisinin and bisabolol; terpenoids of the diterpenoid class such as but not limited to geranylgeranyl pyrophosphate, steviol, retinol, retinal, phytol, taxol, forskolin and aphidicolin; terpenoids of the Triterpenoid class such as but not limited to lanosterol; terpenoids of the Tetraterpenoid class such as but not limited to lycopene and carotene.

In one embodiment the invention relates to production of terpenoids, which are biosynthesized from Geranylgeranyl-pyrophosphate (GGPP). In particular such terpenoids may be steviol.

In one embodiment the invention relates to production of terpenoids, which are biosynthesized from Geranylgeranyl-pyrophosphate (GGPP). In particular such terpenoids may be steviol.

The Cell

Figure 22:
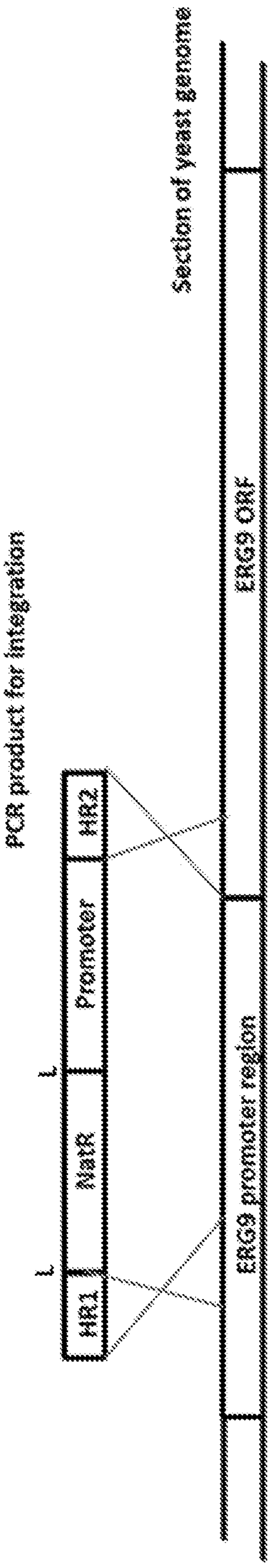
FIG. 22 is a schematic of the PCR product containing two regions, HR1 and HR2, which are homologous to parts of the genome sequence within the ERG9 promoter or 5' end of the ERG9 open reading frame (ORF), respectively. Also, on the PCR product is an antibiotic marker, NatR, which can be embedded between two Lox sites (L) for subsequent excision with Cre recombinase. The PCR product further can include a promoter, such as either the wild type ScKex2, wild type ScCyc1, and the promoter further can include a heterologous insert such as a hairpin (SEQ ID NO: 181-184) at its 3'-end (See FIG. 23).

The present invention relates to a cell, such as any of the hosts described in section III, modified to comprise the construct depicted in FIG. 22. Accordingly, in a main aspect, the present invention relates to a cell comprising a nucleic acid, said nucleic acid comprising i) a promoter sequence operably linked to
ii) a heterologous insert sequence operably linked to
iii) an open reading frame operably linked to
iv) a transcription termination signal, wherein the heterologous insert sequence has the general formula (I):

$$-X_1-X_2-X_3-X_4-X_5-$$

wherein $X_2$ comprises at least 4 consecutive nucleotides being complementary to, and forms a hairpin secondary structure element with at least 4 consecutive nucleotides of $X_4$, and wherein $X_3$ is optional and if present comprises nucleotides involved in forming a hairpin loop between $X_2$ and $X_4$, and wherein $X_1$ and $X_5$ individually and optionally comprise one or more nucleotides, and wherein the open reading frame upon expression encodes a squalene synthase (EC 2.5.1.21), e.g., a polypeptide sequence having at least 70% identity to a squalene synthase (EC 2.5.1.21) or a biologically active fragment thereof, said fragment having at least 70% sequence identity to said squalene synthase in a range of overlap of at least 100 amino acids.

In addition to above mentioned nucleic acid comprising a heterologous insert sequence, the cell may also comprise one or more additional heterologous nucleic acid sequences (e.g., nucleic acids encoding any of the steviol and steviol glycoside biosynthesis polypeptides of section I). In one preferred embodiment the cell comprises a heterologous nucleic acid encoding GGPPS operably linked to a nucleic acid sequence directing expression of GGPPS in said cell.

Heterologous Insert Sequence

The heterologous insert sequence can adapt the secondary structure element of a hairpin with a hairpin loop. The hairpin part comprises sections $X_2$ and $X_4$ which are complementary and hybridize to one another. Sections $X_2$ and $X_4$ flank section $X_3$, which comprises nucleotides that form a loop—the hairpin loop. The term complementary is understood by the person skilled in the art as meaning two sequences compared to each other, nucleotide by nucleotide counting from the 5' end to the 3' end, or vice versa.

The heterologous insert sequence is long enough to allow a hairpin to be completed, but short enough to allow limited translation of an ORF that is present in-frame and immediately 3' to the heterologous insert sequence. Thus, in one embodiment, the heterologous insert sequence comprises 10-50 nucleotides, preferably 10-30 nucleotides, more preferably 15-25 nucleotides, more preferably 17-22 nucleotides, more preferably 18-21 nucleotides, more preferably 18-20 nucleotides, more preferably 19 nucleotides.

$X_2$ and $X_4$ may individually consist of any suitable number of nucleotides, so long as a consecutive sequence of at least 4 nucleotides of $X_2$ is complementary to a consecutive sequence of at least 4 nucleotides of $X_4$. In a preferred embodiment $X_2$ and $X_4$ consist of the same number of nucleotides.

$X_2$ may for example consist of in the range of 4 to 25, such as in the range of 4 to 20, for example of in the range of 4 to 15, such as in the range of 6 to 12, for example in the range of 8 to 12, such as in the range of 9 to 11 nucleotides.

$X_4$ may for example consist of in the range of 4 to 25, such as in the range of 4 to 20, for example of in the range of 4 to 15, such as in the range of 6 to 12, for example in the range of 8 to 12, such as in the range of 9 to 11 nucleotides.

In one preferred embodiment, $X_2$ consists of a nucleotide sequence, which is complementary to the nucleotide sequence of $X_4$, i.e. it is preferred that all nucleotides of $X_2$ are complementary to the nucleotide sequence of $X_4$.

In one preferred embodiment $X_4$ consists of a nucleotide sequence, which is complementary to the nucleotide sequence of $X_2$, i.e. it is preferred that all nucleotides of $X_4$ are complementary to the nucleotide sequence of $X_2$. Very preferably, $X_2$ and $X_4$ consists of the same number of nucleotides, wherein $X_2$ is complementary to $X_4$ over the entire length of $X_2$ and $X_4$.

$X_3$ may be absent, i.e., $X_3$ may consist of zero nucleotides. It is also possible that $X_3$ consists of in the range of 1 to 5, such as in the range of 1 to 3 nucleotides.

$X_1$ may be absent, i.e., $X_1$ may consist of zero nucleotides. It is also possible that $X_1$ consists of in the range of 1 to 25, such as in the range of 1 to 20, for example in the range of 1 to 15, such as in the range of 1 to 10, for example in the range of 1 to 5, such as in the range of 1 to 3 nucleotides.

$X_5$ may be absent, i.e., $X_5$ may consist of zero nucleotides. It is also possible that $X_5$ may consist of in the range 1 to 5, such as in the range of 1 to 3 nucleotides.

The sequence may be any suitable sequence fulfilling the requirements defined herein above. Thus, the heterologous insert sequence may comprise a sequence selected from the group consisting of SEQ ID NO: 181, SEQ ID NO:182, SEQ ID NO:183, and SEQ ID NO:184. In a preferred embodiment the insert sequence is selected from the group consisting of SEQ ID NO: 181, SEQ ID NO:182, SEQ ID NO:183, and SEQ ID NO:184.

Squalene Synthase

Squalene synthase (SQS) is the first committed enzyme of the biosynthesis pathway that leads to the production of sterols. It catalyzes the synthesis of squalene from farnesyl pyrophosphate via the intermediate presqualene pyrophosphate. This enzyme is a critical branch point enzyme in the biosynthesis of terpenoids/isoprenoids and is thought to regulate the flux of isoprene intermediates through the sterol pathway. The enzyme is sometimes referred to as farnesyl-diphosphate farnesyltransferase (FDFT1).

The mechanism of SQS is to convert two units of farnesyl pyrophosphate into squalene.

SQS is considered to be an enzyme of eukaryotes or advanced organisms, although at least one prokaryote has been shown to possess a functionally similar enzyme.

In terms of structure and mechanics, squalene synthase most closely resembles phytoene synthase, which serves a similar role in many plants in the elaboration of phytoene, a precursor of many carotenoid compounds.

A high level of sequence identity indicates likelihood that the first sequence is derived from the second sequence. Amino acid sequence identity requires identical amino acid sequences between two aligned sequences. Thus, a candidate sequence sharing 70% amino acid identity with a reference sequence requires that, following alignment, 70% of the amino acids in the candidate sequence are identical to the corresponding amino acids in the reference sequence. Identity may be determined by aid of computer analysis, such as, without limitations, the ClustalW computer alignment program as described in section D. Using this program with its default settings, the mature (bioactive) part of a query and a reference polypeptide are aligned. The number of fully conserved residues are counted and divided by the length of the reference polypeptide. The ClustalW algorithm may similarly be used to align nucleotide sequences. Sequence identities may be calculated in a similar way as indicated for amino acid sequences.

In one important embodiment, the cell of the present invention comprises a nucleic acid sequence coding, as defined herein, upon expression for a squalene synthase wherein the squalene synthase is at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as at least 99.5%, such as at least 99.6%, such as at least 99.7%, such as at least 99.8%, such as at least 99.9%, such as 100% identical to a squalene synthase wherein the squalene synthase is selected from the group consisting of SEQ ID NO:192, SEQ ID NO:193, SEQ ID NO:194, SEQ ID NO:195, SEQ ID NO:196, SEQ ID NO:197, SEQ ID NO:198, SEQ ID NO:199, SEQ ID NO:200, SEQ ID NO:201, and SEQ ID NO:202.

Promoter

A promoter is a region of DNA that facilitates the transcription of a particular gene. Promoters are located near the genes they regulate, on the same strand and typically upstream (towards the 5' region of the sense strand). In order for the transcription to take place, the enzyme that synthesizes RNA, known as RNA polymerase, must attach to the DNA near a gene. Promoters contain specific DNA sequences and response elements which provide a secure initial binding site for RNA polymerase and for proteins called transcription factors that recruit RNA polymerase. These transcription factors have specific activator or repressor sequences of corresponding nucleotides that attach to specific promoters and regulate gene expressions.

In bacteria, the promoter is recognized by RNA polymerase and an associated sigma factor, which in turn are often brought to the promoter DNA by an activator protein binding to its own DNA binding site nearby. In eukaryotes the process is more complicated, and at least seven different factors are necessary for the binding of an RNA polymerase II to the promoter. Promoters represent critical elements that can work in concert with other regulatory regions (enhancers, silencers, boundary elements/insulators) to direct the level of transcription of a given gene.

As promoters are normally immediately adjacent to the open reading frame (ORF) in question, positions in the promoter are designated relative to the transcriptional start site, where transcription of RNA begins for a particular gene (i.e., positions upstream are negative numbers counting back from −1, for example −100 is a position 100 base pairs upstream).

Promoter Elements

- Core promoter—the minimal portion of the promoter required to properly initiate transcription
- Transcription Start Site (TSS)
- Approximately −35 bp upstream and/or downstream of the start site
- A binding site for RNA polymerase
  - RNA polymerase I: transcribes genes encoding ribosomal RNA
  - RNA polymerase II: transcribes genes encoding messenger RNA and certain small nuclear RNAs
  - RNA polymerase III: transcribes genes encoding tRNAs and other small RNAs
- General transcription factor binding sites
- Proximal promoter—the proximal sequence upstream of the gene that tends to contain primary regulatory elements
- Approximately −250 bp upstream of the start site
- Specific transcription factor binding sites
- Distal promoter—the distal sequence upstream of the gene that may contain additional regulatory elements, often with a weaker influence than the proximal promoter
- Anything further upstream (but not an enhancer or other regulatory region whose influence is positional/orientation independent)
- Specific transcription factor binding sites Prokaryotic Promoters In prokaryotes, the promoter consists of two short sequences at −10 and −35 positions upstream from the transcription start site. Sigma factors not only help in enhancing RNAP binding to the promoter but also help RNAP target specific genes to transcribe.

The sequence at −10 is called the Pribnow box, or the −10 element, and usually consists of the six nucleotides TATAAT. The Pribnow box is essential to start transcription in prokaryotes.

The other sequence at −35 (the −35 element) usually consists of the seven nucleotides TTGACAT. Its presence allows a very high transcription rate.

Both of the above consensus sequences, while conserved on average, are not found intact in most promoters. On average only 3 of the 6 base pairs in each consensus sequence is found in any given promoter. No promoter has been identified to date that has intact consensus sequences at both the −10 and −35; artificial promoters with complete conservation of the −10/−35 hexamers has been found to promote RNA chain initiation at very high efficiencies.

Some promoters contain a UP element (consensus sequence 5'-AAAWWTWTTTTNNNAAANNN-3'; W=A or T; N=any base) centered at −50; the presence of the −35 element appears to be unimportant for transcription from the UP element-containing promoters.

Eukaryotic Promoters

Eukaryotic promoters are typically located upstream of the gene (ORF) and can have regulatory elements several kilobases (kb) away from the transcriptional start site. In eukaryotes, the transcriptional complex can cause the DNA to fold back on itself, which allows for placement of regulatory sequences far from the actual site of transcription. Many eukaryotic promoters, contain a TATA box (sequence TATAAA), which in turn binds a TATA binding protein which assists in the formation of the RNA polymerase transcriptional complex. The TATA box typically lies very close to the transcriptional start site (often within 50 bases).

The cell of the present invention comprises a nucleic acid sequence which comprises a promoter sequence. The promoter sequence is not limiting for the invention and can be any promoter suitable for the host cell of choice.

In one embodiment of the present invention the promoter is a constitutive or inducible promoter.

In a further embodiment of the invention, the promoter is selected from the group consisting of an endogenous promoter, PGK-1, GPD1, PGK1, ADH1, ADH2, PYK1, TPI1, PDC1, TEF1, TEF2, FBA1, GAL1-10, CUP1, MET2, MET14, MET25, CYC1, GAL1-S, GAL1-L, TEF1, ADH1, CAG, CMV, human UbiC, RSV, EF-1alpha, SV40, Mt1, Tet-On, Tet-Off, Mo-MLV-LTR, Mx1, progesterone, RU486 and Rapamycin-inducible promoter.

Post-Transcriptional Regulation

Post-transcriptional regulation is the control of gene expression at the RNA level, therefore between the transcription and the translation of the gene.

The first instance of regulation is at transcription (transcriptional regulation) where due to the chromatin arrangement and due to the activity of transcription factors, genes are differentially transcribed.

After being produced, the stability and distribution of the different transcripts is regulated (post-transcriptional regulation) by means of RNA binding protein (RBP) that control the various steps and rates of the transcripts: events such as alternative splicing, nuclear degradation (exosome), processing, nuclear export (three alternative pathways), sequestration in DCP2-bodies for storage or degradation, and ultimately translation. These proteins achieve these events thanks to a RNA recognition motif (RRM) that binds a specific sequence or secondary structure of the transcripts, typically at the 5' and 3' UTR of the transcript.

Modulating the capping, splicing, addition of a Poly(A) tail, the sequence-specific nuclear export rates and in several contexts sequestration of the RNA transcript occurs in eukaryotes but not in prokaryotes. This modulation is a result of a protein or transcript which in turn is regulated and may have an affinity for certain sequences.

Capping

Capping changes the five prime end of the mRNA to a three prime end by 5'-5' linkage, which protects the mRNA from 5' exonuclease, which degrades foreign RNA. The cap also helps in ribosomal binding.

Splicing

Splicing removes the introns, noncoding regions that are transcribed into RNA, in order to make the mRNA able to create proteins. Cells do this by spliceosomes binding on either side of an intron, looping the intron into a circle and then cleaving it off. The two ends of the exons are then joined together.

Polyadenylation

Polyadenylation is the addition of a poly(A) tail to the 3' end, i.e. the poly(A) tail consists of multiple adenosine monophosphates. The poly-A sequence acts as a buffer to the 3' exonuclease and thus increases half-life of mRNA. In addition, a long poly(A) tail can increase translation. Thus the poly-A tail may be used to further modulate translation of the construct of the present invention, in order to arrive at the optimal translation rate.

In eukaryotes, polyadenylation is part of the process that produces mature messenger RNA (mRNA) for translation.

The poly(A) tail is also important for the nuclear export, translation, and stability of mRNA.

In one embodiment the nucleic acid sequence of the cell of the present invention, as defined herein above, further comprises a polyadenyl/polyadenylation sequence, preferably the 5' end of said polyadenyl 1/polyadenylation sequence is operably linked to the 3' end of the open reading frame, such as to the open reading frame encoding squalene synthase.

RNA Editing

RNA editing is a process which results in sequence variation in the RNA molecule, and is catalyzed by enzymes. These enzymes include the Adenosine Deaminase Acting on RNA (ADAR) enzymes, which convert specific adenosine residues to inosine in an mRNA molecule by hydrolytic deamination. Three ADAR enzymes have been cloned, ADAR1, ADAR2 and ADAR3, although only the first two subtypes have been shown to have RNA editing activity. Many mRNAs are vulnerable to the effects of RNA editing, including the glutamate receptor subunits GluR2, GluR3, GluR4, GluR5 and GluR6 (which are components of the AMPA and kainate receptors), the serotonin2C receptor, the GABA-alpha3 receptor subunit, the tryptophan hydroxlase enzyme TPH2, the hepatitis delta virus and more than 16% of microRNAs. In addition to ADAR enzymes, CDAR enzymes exist and these convert cytosines in specific RNA molecules, to uracil. These enzymes are termed 'APOBEC' and have genetic loci at 22q13, a region close to the chromosomal deletion which occurs in velocardiofacial syndrome (22q11) and which is linked to psychosis. RNA editing is extensively studied in relation to infectious diseases, because the editing process alters viral function.

Post-Transcriptional Regulatory Elements

Use of a post-transcriptional regulatory elements (PRE) is often necessary to obtain vectors with sufficient performance for certain applications. Schambach et al in Gene Ther. (2006) 13(7):641-5 reports that introduction of a post-transcriptional regulatory element (PRE) of woodchuck hepatitis virus (WHV) into the 3' untranslated region of retroviral and lentiviral gene transfer vectors enhances both titer and transgene expression. The enhancing activity of the PRE depends on the precise configuration of its sequence and the context of the vector and cell into which it is introduced.

Thus use of a PRE such as a woodchuck hepatitis virus post-transcriptional regulatory elements (WPRE) may be useful in the preparation of the cell of the present invention when using a gene therapeutic approach.

Accordingly, in one embodiment the nucleic acid sequence of the cell defined herein further comprises a post-transcriptional regulatory element.

In a further embodiment, the post-transcriptional regulatory element is a Woodchuck hepatitis virus post-transcriptional regulatory element (WPRE).

Terminal Repeats

To insert genetic sequences into host DNA, viruses often use sequences of DNA that repeats up to thousands of times, so called repeats, or terminal repeats including long terminal repeats (LTR) and inverted terminal repeats (ITR), wherein said repeat sequences may be both 5' and 3' terminal repeats. ITRs aid in concatamer formation in the nucleus after the single-stranded vector DNA is converted by host cell DNA polymerase complexes into double-stranded DNA. ITR sequences may be derived from viral vectors, such as AAV, e.g. AAV2.

In one embodiment, the nucleic acid sequence or the vector of the cell defined herein comprises a 5' terminal repeat and a 3' terminal repeat.

In one embodiment said 5' and 3' terminal repeats are selected from Inverted Terminal Repeats [ITR] and Long Terminal Repeats [LTR].

In one embodiment of said 5' and 3' terminal repeats are AAV Inverted Terminal Repeats [ITR].

Geranylgeranyl Pyrophosphate Synthase

The microbial cells of the present invention may in preferred embodiments contain a heterologous nucleic acid sequence encoding Geranylgeranyl Pyrophosphate Synthase (GGPPS). See, e.g., Table 7. GGPPS is an enzyme, which catalyzes the chemical reaction that turns one farnesyl pyrophosphate (FPP) molecule into one Geranylgeranyl Pyrophosphate (GGPP) molecule. Genes encoding GGPPS may for example be found in organisms that contain the mevalonate pathway.

The GGPPS to be used with the present invention may be any useful enzyme, which is capable of catalysing conversion of a farnesyl pyrophosphate (FPP) molecule into a Geranylgeranyl Pyrophosphate (GGPP) molecule. In particular, the GGPPS to be used with the present invention may be any enzyme capable of catalysing the following reaction:

(2E,6E)-farnesyl diphosphate+isopentenyl diphosphate->diphosphate+geranylgeranyl diphosphate.

It is preferred that the GGPPS used with the present invention is an enzyme categorised under EC 2.5.1.29.

The GGPPS may be GGPPS from a variety of sources, such as from bacteria, fungi or mammals. The GGPPS may be any kind of GGPPS, for example GGPPS-1, GGPPS-2, GGPPS-3 or GGPPS-4. The GGPPS may be wild type GGPPS or a functional homologue thereof.

For example, the GGPPS may be GGPPS-1 of *S. acidicaldarius* (SEQ ID NO: 126), GGPPS-2 of *A. nidulans* (SEQ ID NO: 203), GGPPS-3 of *S. cerevisiae* (SEQ ID NO: 167) or GGPPS-4 of *M. musculus* (SEQ ID NO:123) or a functional homologue of any of the aforementioned.

The heterologous nucleic acid encoding said GGPPS may be any nucleic acid sequence encoding said GGPPS. Thus, in embodiments of the invention where GGPPS is a wild type protein, the nucleic acid sequence may for example be a wild type cDNA sequence encoding said protein. However, it is frequently the case that the heterologous nucleic acid is nucleic acid sequence encoding any particular GGPPS, where said nucleic acid has been codon optimised for the particular microbial cell. Thus, by way of example, if the microbial cell is *S. cerevisiae*, then the nucleic acid encoding GGPPS has preferably been codon optimised for optimal expression in *S. cerevisiae*.

Functional homologues of GGPPS are preferably protein having above-mentioned activity and sharing at least 70% amino acid identity with the sequence of a reference GGPPS. Methods for determining sequence identity are described herein above in the section “Squalene synthase” and in section D.

In one embodiment, the cell, such as the microbial of the present invention comprises a nucleic acid sequence coding a GGPPS or a functional homologue thereof, where said functional homologue is at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as at least 99.5%, such as at least 99.6%, such as at least 99.7%, such as at least 99.8%, such as at least 99.9%, such as 100% identical to a GGPPS selected from the group consisting of SEQ ID NO:123, SEQ ID NO:126, SEQ ID NO:167 and SEQ ID NO:203.

Said heterologous nucleic acid sequence encoding a GGPPS is in general operably linked to a nucleic acid sequence directing expression of GGPPS in the microbial cell. The nucleic acid sequence directing expression of GGPPS in the microbial cell may be a promoter sequence, and preferably said promoter sequence is selected according the particular microbial cell. The promoter may for example be any of the promoters described herein above in the section “Promoter”

Vectors

A vector is a DNA molecule used as a vehicle to transfer foreign genetic material into another cell. The major types of vectors are plasmids, viruses, cosmids, and artificial chromosomes. Common to all engineered vectors is an origin of replication, a multicloning site, and a selectable marker.

The vector itself is generally a DNA sequence that consists of an insert (transgene) and a larger sequence that serves as the “backbone” of the vector. The purpose of a vector which transfers genetic information to another cell is typically to isolate, multiply, or express the insert in the target cell. Vectors called expression vectors (expression constructs) specifically are for the expression of the transgene in the target cell, and generally have a promoter sequence that drives expression of the transgene. Simpler vectors called transcription vectors are only capable of being transcribed but not translated: they can be replicated in a target cell but not expressed, unlike expression vectors. Transcription vectors are used to amplify their insert.

Insertion of a vector into the target cell is usually called transformation for bacterial cells, transfection for eukaryotic cells, although insertion of a viral vector is often called transduction.

Plasmids

Plasmid vectors are double-stranded generally circular DNA sequences that are capable of automatically replicating in a host cell. Plasmid vectors minimalistically consist of an origin of replication that allows for semi-independent replication of the plasmid in the host and also the transgene insert. Modern plasmids generally have many more features, notably including a "multiple cloning site" which includes nucleotide overhangs for insertion of an insert, and multiple restriction enzyme consensus sites to either side of the insert. In the case of plasmids utilized as transcription vectors, incubating bacteria with plasmids generates hundreds or thousands of copies of the vector within the bacteria in hours, and the vectors can be extracted from the bacteria, and the multiple cloning site can be cut by restriction enzymes to excise the hundredfold or thousandfold amplified insert. These plasmid transcription vectors characteristically lack crucial sequences that code for polyadenylation sequences and translation termination sequences in translated mRNAs, making protein expression from transcription vectors impossible. plasmids may be conjugative/transmissible and non-conjugative:

- conjugative: mediate DNA transfer through conjugation and therefore spread rapidly among the bacterial cells of a population; e.g., F plasmid, many R and some col plasmids.
- nonconjugative—do not mediate DNA through conjugation, e.g., many R and col plasmids.

Viral Vectors

Viral vectors are generally genetically-engineered viruses carrying modified viral DNA or RNA that has been rendered noninfectious, but still contain viral promoters and also the transgene, thus allowing for translation of the transgene through a viral promoter. However, because viral vectors frequently are lacking infectious sequences, they require helper viruses or packaging lines for large-scale transfection. Viral vectors are often designed for permanent incorporation of the insert into the host genome, and thus leave distinct genetic markers in the host genome after incorporating the transgene. For example, retroviruses leave a characteristic retroviral integration pattern after insertion that is detectable and indicates that the viral vector has incorporated into the host genome.

In one embodiment the invention concerns a viral vector capable of transfecting a host cell, such as a cell that can be cultured, e.g. a yeast cell or any other suitable eukaryotic cell. The vector is then capable of transfecting said cell with a nucleic acid that includes the heterologous insert sequence as described herein.

The viral vector can be any suitable viral vector such as a viral vector selected from the group consisting of vectors derived from the Retroviridae family including lentivirus, HIV, SIV, FIV, EAIV, CIV.

The viral vector may also be selected from the group consisting of alphavirus, adenovirus, adeno associated virus, baculovirus, HSV, coronavirus, Bovine papilloma virus, Mo-MLV and adeno associated virus.

In embodiments of the invention wherein the microbial cell comprises a heterologous nucleic acid encoding GGPPS, then said heterologous nucleic acid may be positioned on the vector also containing the nucleic acid encoding squalene synthase, or the heterologous nucleic acid encoding GGPPS may be positioned on a different vector. Said heterologous nucleic acid encoding GGPPS may be contained in any of the vectors described herein above.

In embodiments of the invention wherein the microbial cell comprises a heterologous nucleic acid encoding HMCR, then said heterologous nucleic acid may be positioned on the vector also containing the nucleic acid encoding squalene synthase, or the heterologous nucleic acid encoding HMCR may be positioned on a different vector. Said heterologous nucleic acid encoding HMCR may be contained in any of the vectors described herein above. It is also contained within the invention that the heterologous nucleic acid encoding GGPPS and the heterologous nucleic acid encoding HMCR may be positioned on the same or on individual vectors.

Transcription

Transcription is a necessary component in all vectors: the premise of a vector is to multiply the insert (although expression vectors later also drive the translation of the multiplied insert). Thus, even stable expression is determined by stable transcription, which generally depends on promoters in the vector. However, expression vectors have a variety of expression patterns: constitutive (consistent expression) or inducible (expression only under certain conditions or chemicals). This expression is based on different promoter activities, not post-transcriptional activities. Thus, these two different types of expression vectors depend on different types of promoters.

Viral promoters are often used for constitutive expression in plasmids and in viral vectors because they normally reliably force constant transcription in many cell lines and types.

Inducible expression depends on promoters that respond to the induction conditions: for example, the murine mammary tumor virus promoter only initiates transcription after dexamethasone application and the *Drosophila* heat shock promoter only initiates after high temperatures. transcription is the synthesis of mRNA. Genetic information is copied from DNA to RNA Expression Expression vectors require sequences that encode for e.g. polyadenylation tail (see herein above): Creates a polyadenylation tail at the end of the transcribed pre-mRNA that protects the mRNA from exonucleases and ensures transcriptional and translational termination: stabilizes mRNA production.

Minimal UTR length: UTRs contain specific characteristics that may impede transcription or translation, and thus the shortest UTRs or none at all are encoded for in optimal expression vectors.

Kozak sequence: Vectors should encode for a Kozak sequence in the mRNA, which assembles the ribosome for translation of the mRNA.

Above conditions are necessary for expression vectors in eukaryotes but not in prokaryotes.

Modern vectors may encompass additional features besides the transgene insert and a backbone such as a promoter (discussed above), genetic markers to e.g. allow for confirmation that the vector has integrated with the host genomic DNA, antibiotic resistance genes for antibiotic selection, and affinity tags for purification.

In one embodiment the cell of the present invention comprises a nucleic acid sequence integrated in a vector such as an expression vector.

In one embodiment the vector is selected from the group consisting of plasmid vectors, cosmids, artificial chromosomes and viral vectors.

The plasmid vector should be able to be maintained and replicated in bacteria, fungi and yeast.

The present invention also concerns cells comprising plasmid and cosmid vectors as well as artificial chromosome vectors.

The important factor is that the vector is functional and that the vector comprises at least the nucleic acid sequence comprising the heterologous insert sequence as described herein.

In one embodiment the vector is functional in fungi and in mammalian cells.

In one embodiment the invention concerns a cell transformed or transduced with the vector as defined herein above.

Methods for Producing Terpenoids

As mentioned herein above, the cell of the present invention (e.g., recombinant host cells) is useful in enhancing yield of industrially relevant terpenoids.

The cell of the invention may therefore be used in various set-ups in order to increase accumulation of terpenoid precursors and thus to increase yield of terpenoid products resulting from enzymatic conversion of said (upstream) terpenoid precursors.

Accordingly, in one aspect the present invention relates to a method for producing a terpenoid compound synthesized through the squalene pathway, in a cell culture, said method comprising the steps of (a) providing the cell as defined herein above, (b) culturing the cell of (a).

(c) recovering the terpenoid product compound.

Figure 20:
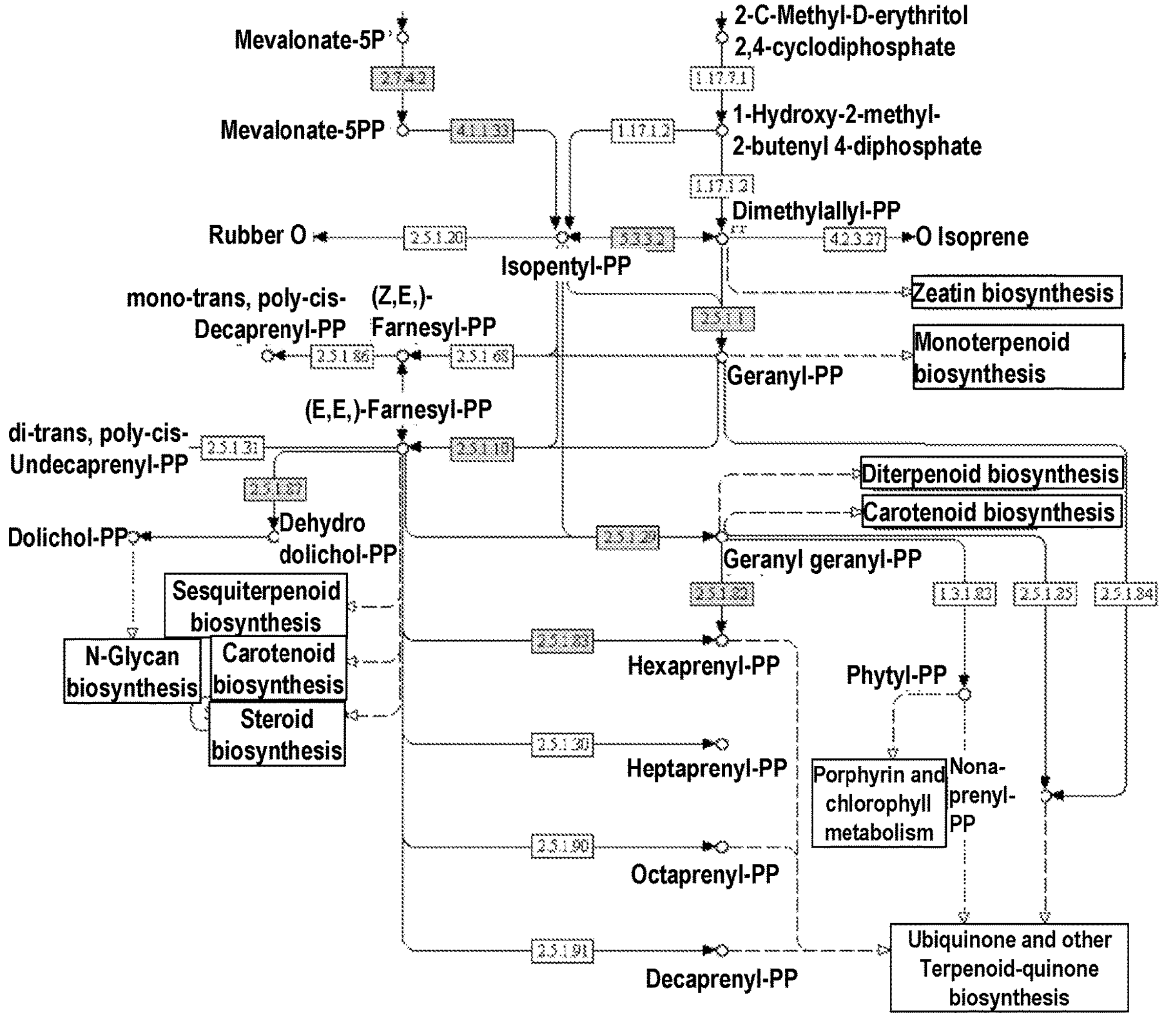
FIG. 20 is a schematic of the isoprenoid pathway in yeast, showing the position of ERG9.

By providing the cell comprising the genetically modified construct defined herein above, the accumulation of terpenoid precursors is enhanced (FIG. 20).

Thus, in another aspect, the invention relates to a method for producing a terpenoid derived from a terpenoid precursor selected from the group consisting of Farnesyl-pyrophosphate (FPP), Isopentenyl-pyrophosphate (IPP), Dimethylallyl-pyrophosphate (DMAPP), Geranyl-pyrophosphate (GPP) and/or Geranylgeranyl-pyrophosphate (GGPP), said method comprising:

(a) contacting said precursor with an enzyme of the squalene synthase pathway, (b) recovering the terpenoid product.

In one embodiment the terpenoid (product) of the method of the present invention as defined herein above, is selected from the group consisting of hemiterpenoids, monoterpenes, sesquiterpenoids, diterpenoids, sesterpenes, triterpenoids, tetraterpenoids and polyterpenoids.

In a further embodiment the terpenoid is selected from the group consisting of farnesyl phosphate, farnesol, geranylgeranyl, geranylgeraniol, isoprene, prenol, isovaleric acid, geranyl pyrophosphate, eucalyptol, limonene, pinene, farnesyl pyrophosphate, artemisinin, bisabolol, geranylgeranyl pyrophosphate, retinol, retinal, phytol, taxol, forskolin, aphidicolin, lanosterol, lycopene and carotene.

The terpenoid product can be used as starting point in an additional refining process. Thus, in one embodiment said method further comprises dephosphorylating the farnesyl phosphate to produce farnesol.

The enzyme or enzymes used in the process of preparing the target product terpenoid compound is preferably an enzyme "located downstream" of the terpenoid precursors Farnesyl-pyrophosphate, Isopentenyl-pyrophosphate, Dimethylallyl-pyrophosphate, Geranyl-pyrophosphate and Geranylgeranyl-pyrophosphate such as an enzyme located downstream of the terpenoid precursors Farnesyl-pyrophosphate, Isopentenyl-pyrophosphate, Dimethylallyl-pyrophosphate, Geranyl-pyrophosphate and Geranylgeranyl-pyrophosphate depicted in the squalene pathway of FIG. 20. The enzyme used in the process of preparing the target product terpenoid, based on the accumulation of precursors achieved through the present invention, may thus be selected from the group consisting of Dimethylallyltransferase (EC 2.5.1.1), Isoprene synthase (EC 4.2.3.27) and Geranyltranstransferase (EC 2.5.1.10).

The present invention may operate by at least partly, sterically hindering binding of the ribosome to the RNA thus reducing the translation of squalene synthase. Accordingly, in one aspect the present invention relates to a method for reducing the translation rate of a functional squalene synthase (EC 2.5.1.21) said method comprising:

(a) providing the cell defined herein above, (b) culturing the cell of (a).

Similarly, the invention in another aspect relates to a method for decreasing turnover of farnesyl-pp to squalene, said method comprising:

(a) providing the cell defined herein above, (b) culturing the cell of (a).

As depicted in FIG. 20, the knocking down of the ERG9 results in build-up of precursors to squalene synthase. Thus in one aspect, the present invention relates to a method for enhancing accumulation of a compound selected from the group consisting of Farnesyl-pyrophosphate, Isopentenyl-pyrophosphate, Dimethylallyl-pyrophosphate, Geranyl-pyrophosphate and Geranylgeranyl-pyrophosphate, said method comprising the steps of:

(a) providing the cell defined herein above, and (b) culturing the cell of (a).

In one embodiment the method of the invention as define herein above further comprises recovering the Farnesyl-pyrophosphate, Isopentenyl-pyrophosphate, Dimethylallyl-pyrophosphate, Geranyl-pyrophosphate or Geranylgeranyl-pyrophosphate compound. The recovered compound may be used in further processes for producing the desired terpenoid product compound. The further process may take place in the same cell culture as the process performed and defined herein above, such as the accumulation of the terpenoid precursors by the cell of the present invention. Alternatively, the recovered precursors may be added to another cell culture, or a cell free system, to produce the desired products.

As the precursors are intermediates, however mainly stable intermediates, a certain endogenous production of terpenoid products may occur based on the terpenoid precursor substrates. Also, the cells of the invention may have additional genetic modifications such that they are capable of performing both the accumulation of the terpenoid precursors (construct of the cell of the invention) and whole or substantially the whole subsequent biosynthesis process to the desired terpenoid product.

Thus, in one embodiment the method of the invention further comprises recovering a compound synthesized through the squalene pathway, said compound being derived from said Farnesyl-pyrophosphate, Isopentenyl-pyrophosphate, Dimethylallyl-pyrophosphate, Geranyl-pyrophosphate and/or Geranylgeranyl-pyrophosphate.

Occasionally it may be advantageous to include a squalene synthase inhibitor when culturing the cell of the present invention. Chemical inhibition of squalene synthase, e.g. by lapaquistat, is known in the art and is under investigation e.g. as a method of lowering cholesterol levels in the prevention of cardiovascular disease. It has also been suggested that variants in this enzyme may be part of a genetic association with hypercholesterolemia. Other squalene synthase inhibitors include Zaragozic acid and RPR 107393.

Thus, in one embodiment the culturing step of the method(s) defined herein above is performed in the presence of a squalene synthase inhibitor.

The cell of the invention may furthermore be genetically modified to further enhance production of certain key terpenoid precursors. In one embodiment the cell is additionally genetically modified to enhance activity of and/or overexpress one or more enzymes selected from the group consisting of Phosphomevalonate kinase (EC 2.7.4.2), Diphosphomevalonate decarboxylase (EC 4.1.1.33), 4-hydroxy-3-methylbut-2-en-1-yl diphosphate synthase (EC 1.17.7.1), 4-hydroxy-3-methylbut-2-enyl diphosphate reductase (EC 1.17.1.2), Isopentenyl-diphosphate Delta-isomerase 1 (EC 5.3.3.2), Short-chain Z-isoprenyl diphosphate synthase (EC 2.5.1.68), Dimethylallyltransferase (EC 2.5.1.1), Geranyltranstransferase (EC 2.5.1.10) and Geranylgeranyl pyrophosphate synthetase (EC 2.5.1.29).

As described herein above in one embodiment of the invention the microbial cell comprises both a nucleic acid encoding a sqalene synthase as described herein above as well as a heterologous nucleic acid encoding a GGPPS. Such microbial cells are particularly useful for the preparation of GGPP as well as terpenoids, wherein GGPP is an intermediate in their biosynthesis.

Accordingly, in one aspect the invention relates to a method for preparing GGPP, wherein the method comprises the steps of

- a. providing a microbial cell comprising a nucleic acid sequence, said nucleic acid comprising
  - i) a promoter sequence operably linked to
  - ii) a heterologous insert sequence operably linked to
  - iii) an open reading frame operably linked to
  - iv) a transcription termination signal, wherein the heterologous insert sequence and the open reading frame are as defined herein above, wherein said microbial cell furthermore comprises a heterologous nucleic acid encoding GGPPS operably linked to a nucleic acid sequence directing expression of GGPPS in said cell;
- b. Cultivating the microbial cell of a.;
- c. Recovering the GGPP.

In another aspect the invention relates to a method for preparing a terpenoid of which GGPP is an intermediate in the biosynthesis pathway, wherein the method comprises the steps of

- a. providing a microbial cell, wherein said microbial cell comprises a nucleic acid sequence, said nucleic acid comprising
  - i) a promoter sequence operably linked to
  - ii) a heterologous insert sequence operably linked to
  - iii) an open reading frame operably linked to
  - iv) a transcription termination signal, wherein the heterologous insert sequence and the open reading frame are as defined herein above, wherein said microbial cell furthermore comprises a heterologous nucleic acid encoding GGPPS operably linked to a nucleic acid sequence directing expression of GGPPS in said cell;
- b. Cultivating the microbial cell of a.; and
- c. Recovering the terpenoid, wherein said terpenoid may be any terpenoid described herein above in the section "Terpenoids" having GGPP as intermediate in its biosynthesises; and said microbial cell may be any of the microbial cells described herein above in the section "The cell"; and said promoter may be any promoter, such as any of the promoters described herein above in the section "Promoter"; and said heterologous insert sequence may be any of the heterologous insert sequences described herein above in the section "Heterologous insert sequence"; and said open reading frame encodes a squalene synthase, which may be any of the squalene synthases described herein above in the section "Squalene synthase"; and said GGPPS may be any of the GGPPS described herein above in the section "Geranylgeranyl Pyrophosphate Synthase".

In this embodiment said microbial cell may also optionally contain one or more additional heterologous nucleic acids encoding one or more enzymes involved in the biosynthesis pathway of said terpenoid.

In one particular aspect the invention relates to a method for preparing steviol, wherein the method comprises the steps of

- a. providing a microbial cell, wherein said microbial cell comprises a nucleic acid sequence, said nucleic acid comprising
  - i) a promoter sequence operably linked to
  - ii) a heterologous insert sequence operably linked to
  - iii) an open reading frame operably linked to
  - iv) a transcription termination signal, wherein the heterologous insert sequence and the open reading frame are as defined herein above, wherein said microbial cell furthermore comprises a heterologous nucleic acid encoding GGPPS operably linked to a nucleic acid sequence directing expression of GGPPS in said cell;
- b. Cultivating the microbial cell of a.;
- c. Recovering steviol, wherein said microbial cell may be any of the microbial cells described herein above in the section "The cell"; and said promoter may be any promoter, such as any of the promoters described herein above in the section "Promoter"; and said heterologous insert sequence may be any of the heterologous insert sequences described herein above in the section "Heterologous insert sequence"; and said open reading frame encodes a squalene synthase, which may be any of the squalene synthases described herein above in the section "Squalene synthase"; and said GGPPS may be any of the GGPPS described herein above in the section "Geranylgeranyl Pyrophosphate Synthase".

In this embodiment said microbial cell may also optionally contain one or more additional heterologous nucleic acids encoding one or more enzymes involved in the biosynthesis pathway of steviol.

In another aspect the invention relates to a method for preparing a terpenoid of which GGPP is an intermediate in the biosynthesis pathway, wherein the method comprises the steps of

- a. providing a microbial cell, wherein said microbial cell comprises a nucleic acid sequence, said nucleic acid comprising
  - i) a promoter sequence operably linked to
  - ii) a heterologous insert sequence operably linked to
  - iii) an open reading frame operably linked to
  - iv) a transcription termination signal, wherein the heterologous insert sequence and the open reading frame are as defined herein above, wherein said microbial cell furthermore comprises a heterologous nucleic acid encoding GGPPS operably linked to a nucleic acid sequence directing expression of GGPPS in said cell and wherein said microbial cell furthermore comprises a heterologous nucleic acid encoding HMCR operably linked to a nucleic acid sequence directing expression of HMCR in said cell;

b. Cultivating the microbial cell of a.;

c. Recovering the terpenoid, wherein said terpenoid may be any terpenoid described herein above in the section "Terpenoids" having GGPP as intermediate in its biosynthesises; and said microbial cell may be any of the microbial cells described herein above in the section "The cell"; and said promoter may be any promoter, such as any of the promoters described herein above in the section "Promoter"; and said heterologous insert sequence may be any of the heterologous insert sequences described herein above in the section "Heterologous insert sequence"; and said open reading frame encodes a squalene synthase, which may be any of the squalene synthases described herein above in the section "Squalene synthase"; and said GGPPS may be any of the GGPPS described herein above in the section "Geranylgeranyl Pyrophosphate Synthase"; and said HMCR may be any of the HMCR described herein above in the section "HMCR".

In this embodiment said microbial cell may also optionally contain one or more additional heterologous nucleic acids encoding one or more enzymes involved in the biosynthesis pathway of said terpenoid.

In one particular aspect the invention relates to a method for preparing steviol, wherein the method comprises the steps of a. providing a microbial cell, wherein said microbial cell comprises a nucleic acid sequence, said nucleic acid comprising
   i) a promoter sequence operably linked to
   ii) a heterologous insert sequence operably linked to
   iii) an open reading frame operably linked to
   iv) a transcription termination signal,
   wherein the heterologous insert sequence and the open reading frame are as defined herein above,
   wherein said microbial cell furthermore comprises a heterologous nucleic acid encoding GGPPS operably linked to a nucleic acid sequence directing expression of GGPPS in said cell;

b. Cultivating the microbial cell of a.;

c. Recovering steviol, wherein said microbial cell may be any of the microbial cells described herein above in the section "The cell"; and said promoter may be any promoter, such as any of the promoters described herein above in the section "Promoter"; and said heterologous insert sequence may be any of the heterologous insert sequences described herein above in the section "Heterologous insert sequence"; and said open reading frame encodes a squalene synthase, which may be any of the squalene synthases described herein above in the section "Squalene synthase"; and said GGPPS may be any of the GGPPS described herein above in the section "Geranylgeranyl Pyrophosphate Synthase" and said HMCR may be any of the HMCR described herein above in the section "HMCR".

In this embodiment said microbial cell may also optionally contain one or more additional heterologous nucleic acids encoding one or more enzymes involved in the biosynthesis pathway of steviol.

In one embodiment the cell is additionally genetically modified to enhance activity of and/or overexpress one or more enzymes selected from the group consisting of acetoacetyl CoA thiolose, HMG-CoA reductase or the catalytic domain thereof, HMG-CoA synthase, mevalonate kinase, phosphomevalonate kinase, phosphomevalonate decarboxylase, isopentenyl pyrophosphate isomerase, farnesyl pyrophosphate synthase, D-1-deoxyxylulose 5-phosphate synthase, and 1-deoxy-D-xylulose 5-phosphate reductoisomerase and farnesyl pyrophosphate synthase.

In one embodiment of the method of the present invention, the cell comprises a mutation in the ERG9 open reading frame.

In another embodiment of the method of the present invention the cell comprises an ERG9[Delta]::HIS3 deletion/insertion allele.

In yet another embodiment the step of recovering the compound in the method of the present invention further comprises purification of said compound from the cell culture media.

D. Functional Homologs

Functional homologs of the polypeptides described above are also suitable for use in producing steviol or steviol glycosides in a recombinant host. A functional homolog is a polypeptide that has sequence similarity to a reference polypeptide, and that carries out one or more of the biochemical or physiological function(s) of the reference polypeptide. A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, may themselves be functional homologs. Functional homologs can also be created via site-directed mutagenesis of the coding sequence for a polypeptide, or by combining domains from the coding sequences for different naturally-occurring polypeptides ("domain swapping"). Techniques for modifying genes encoding functional UGT polypeptides described herein are known and include, inter alia, directed evolution techniques, site-directed mutagenesis techniques and random mutagenesis techniques, and can be useful to increase specific activity of a polypeptide, alter substrate specificity, alter expression levels, alter subcellular location, or modify polypeptide:polypeptide interactions in a desired manner. Such modified polypeptides are considered functional homologs. The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of steviol or steviol glycoside biosynthesis polypeptides. Sequence analysis can involve BLAST, Reciprocal BLAST, or PSI-BLAST analysis of nonredundant databases using a GGPPS, a CDPS, a KS, a KO or a KAH amino acid sequence as the reference sequence. Amino acid sequence is, in some instances, deduced from the nucleotide sequence. Those polypeptides in the database that have greater than 40% sequence identity are candidates for further evaluation for suitability as a steviol or steviol glycoside biosynthesis polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in steviol biosynthesis polypeptides, e.g., conserved functional domains.

Conserved regions can be identified by locating a region within the primary amino acid sequence of a steviol or a steviol glycoside biosynthesis polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/ and pfam.janelia.org/. The information included at the Pfam database is described in Sonnhammer et al., *Nucl. Acids Res.,* 26:320-322 (1998); Sonnhammer et al., *Proteins,* 28:405-420 (1997); and Bateman et al., *Nucl. Acids Res.,* 27:260-262 (1999). Conserved regions also can be determined by aligning sequences of the same or related polypeptides from closely related species. Closely related species preferably are from the same family. In some embodiments, alignment of sequences from two different species is adequate.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

For example, polypeptides suitable for producing steviol glycosides in a recombinant host include functional homologs of EUGT11, UGT91D2e, UGT91D2m, UGT85C, and UGT76G. Such homologs have greater than 90% (e.g., at least 95% or 99%) sequence identity to the amino acid sequence of EUGT11 (SEQ ID NO: 152), UGT91D2e (SEQ ID NO:5), UGT91D2m (SEQ ID NO:10), UGT85C (SEQ ID NO:3), or UGT76G (SEQ ID NO:7). Variants of EUGT11, UGT91D2, UGT85C, and UGT76G polypeptides typically have 10 or fewer amino acid substitutions within the primary amino acid sequence, e.g., 7 or fewer amino acid substitutions, 5 or conservative amino acid substitutions, or between 1 and 5 substitutions. However, in some embodiments, variants of EUGT11, UGT91D2, UGT85C, and UGT76G polypeptides can have 10 or more amino acid substitutions (e.g., 10, 15, 20, 25, 30, 35, 10-20, 10-35, 20-30, or 25-35 amino acid substitutions). The substitutions may be conservative, or in some embodiments, non-conservative. Non-limiting examples of non-conservative changes in UGT91D2e polypeptides include glycine to arginine and tryptophan to arginine. Non-limiting examples of non-conservative substitutions in UGT76G polypeptides include valine to glutamic acid, glycine to glutamic acid, glutamine to alanine, and serine to proline. Non-limiting examples of changes to UGT85C polypeptides include histidine to aspartic acid, proline to serine, lysine to threonine, and threonine to arginine.

In some embodiments, a useful UGT91D2 homolog can have amino acid substitutions (e.g., conservative amino acid substitutions) in regions of the polypeptide that are outside of predicted loops, e.g., residues 20-26, 39-43, 88-95, 121-124, 142-158, 185-198, and 203-214 are predicted loops in the N-terminal domain and residues 381-386 are predicted loops in the C-terminal domain of SEQ ID NO:5. For example, a useful UGT91D2 homolog can include at least one amino acid substitution at residues 1-19, 27-38, 44-87, 96-120, 125-141, 159-184, 199-202, 215-380, or 387-473 of SEQ ID NO:5. In some embodiments, a UGT91D2 homolog can have an amino acid substitution at one or more residues selected from the group consisting of residues 30, 93, 99, 122, 140, 142, 148, 153, 156, 195, 196, 199, 206, 207, 211, 221, 286, 343, 427, and 438 of SEQ ID NO:5. For example, a UGT91D2 functional homolog can have an amino acid substitution at one or more of residues 206, 207, and 343, such as an arginine at residue 206, a cysteine at residue 207, and an arginine at residue 343 of SEQ ID NO:5. See, SEQ ID NO:95. Other functional homologs of UGT91D2 can have one or more of the following: a tyrosine or phenylalanine at residue 30, a proline or glutamine at residue 93, a serine or valine at residue 99, a tyrosine or a phenylalanine at residue 122, a histidine or tyrosine at residue 140, a serine or cysteine at residue 142, an alanine or threonine at residue 148, a methionine at residue 152, an alanine at residue 153, an alanine or serine at residue 156, a glycine at residue 162, a leucine or methionine at residue 195, a glutamic acid at residue 196, a lysine or glutamic acid at residue 199, a leucine or methionine at residue 211, a leucine at residue 213, a serine or phenylalanine at residue 221, a valine or isoleucine at residue 253, a valine or alanine at residue 286, a lysine or asparagine at residue 427, an alanine at residue 438, and either an alanine or threonine at residue 462 of SEQ ID NO:5. In another embodiment, a UGT91D2 functional homolog contains a methionine at residue 211 and an alanine at residue 286.

In some embodiments, a useful UGT85C homolog can have one or more amino acid substitutions at residues 9, 10, 13, 15, 21, 27, 60, 65, 71, 87, 91, 220, 243, 270, 289, 298, 334, 336, 350, 368, 389, 394, 397, 418, 420, 440, 441, 444, and 471 of SEQ ID NO:3. Non-limiting examples of useful UGT85C homologs include polypeptides having substitutions (with respect to SEQ ID NO:3) at residue 65 (e.g., a serine at residue 65), at residue 65 in combination with residue 15 (a leucine at residue 15), 270 (e.g., a methionine, arginine, or alanine at residue 270), 418 (e.g., a valine at residue 418), 440 (e.g., an aspartic acid at residue at residue 440), or 441 (e.g., an asparagine at residue 441); residues 13 (e.g., a phenylalanine at residue 13), 15, 60 (e.g., an aspartic acid at residue 60), 270, 289 (e.g., a histidine at residue 289), and 418; substitutions at residues 13, 60, and 270; substitutions at residues 60 and 87 (e.g., a phenylalanine at residue 87); substitutions at residues 65, 71 (e.g., a glutamine at residue 71), 220 (e.g., a threonine at residue 220), 243 (e.g., a tryptophan at residue 243), and 270; substitutions at residues 65, 71, 220, 243, 270, and 441; substitutions at residues 65, 71, 220, 389 (e.g., a valine at residue 389), and 394 (e.g., a valine at residue 394); substitutions at residues 65, 71, 270, and 289; substitutions at residues 220, 243, 270, and 334 (e.g., a serine at residue 334); or substitutions at residues 270 and 289. The following amino acid mutations did not result in a loss of activity in 85C2 polypeptides: V13F, F15L, H60D, A65S, E71Q, I87F, K220T, R243W, T270M, T270R, Q289H, L334S, A389V, I394V, P397S, E418V, G440D, and H441N. Additional mutations that were seen in active clones include K9E, K10R, Q21H, M27V, L91P, Y298C, K350T, H368R, G420R, L431P, R444G, and M471T. In some embodiments, an UGT85C2 contains substitutions at positions 65 (e.g., a serine), 71 (a glutamine), 270 (a methionine), 289 (a histidine), and 389 (a valine).

The amino acid sequence of *Stevia rebaudiana* UGTs 74G1,76G1 and 91D2e with N-terminal, in-frame fusions of the first 158 amino acids of human MDM2 protein, and *Stevia rebaudiana* UGT85C2 with an N-terminal in-frame fusion of 4 repeats of the synthetic PMI peptide (4 X TSFAEYWNLLSP, SEQ ID NO:86) are set forth in SEQ ID NOs: 90, 88, 94, and 92, respectively; see SEQ ID NOs: 89, 92, 93, and 95 for the nucleotide sequences encoding the fusion proteins.

In some embodiments, a useful UGT76G homolog can have one or more amino acid substitutions at residues 29, 74, 87, 91, 116, 123, 125, 126, 130, 145, 192, 193, 194, 196, 198, 199, 200, 203, 204, 205, 206, 207, 208, 266, 273, 274, 284, 285, 291, 330, 331, and 346 of SEQ ID NO:7. Non-limiting examples of useful UGT76G homologs include polypeptides having substitutions (with respect to SEQ ID NO:7) at residues 74, 87, 91, 116, 123, 125, 126, 130, 145, 192, 193, 194, 196, 198, 199, 200, 203, 204, 205, 206, 207, 208, and 291; residues 74, 87, 91, 116, 123, 125, 126, 130, 145, 192, 193, 194, 196, 198, 199, 200, 203, 204, 205, 206, 207, 208, 266, 273, 274, 284, 285, and 291; or residues 74, 87, 91, 116, 123, 125, 126, 130, 145, 192, 193, 194, 196, 198, 199, 200, 203, 204, 205, 206, 207, 208, 266, 273, 274, 284, 285, 291, 330, 331, and 346. See, Table 9.

TABLE 9

| Clone | Mutations |
|---|---|
| 76G_G7 | M29I, V74E, V87G, L91P, G116E, A123T, Q125A, I126L, T130A, V145M, C192S, S193A, F194Y, M196N, K198Q, K199I, Y200L, Y203I, F204L, E205G, N206K, I207M, T208I, P266Q, S273P, R274S, G284T, T285S, 287-3 bp deletion, L330V, G331A, L346I |
| 76G_H12 | M29I, V74E, V87G, L91P, G116E, A123T, Q125A, I126L, T130A, V145M, C192S, S193A, F194Y, M196N, K198Q, K199I, Y200L, Y203I, F204L, E205G, N206K, I207M, T208I, P266Q, S273P, R274S, G284T, T285S, 287-3 bp deletion |
| 76G_C4 | M29I, V74E, V87G, L91P, G116E, A123T, Q125A, I126L, T130A, V145M, C192S, S193A, F194Y, M196N, K198Q, K199I, Y200L, Y203I, F204L, E205G, N206K, I207M, T208I |

Methods to modify the substrate specificity of, for example, EUGT11 or UGT91D2e, are known to those skilled in the art, and include without limitation site-directed/rational mutagenesis approaches, random directed evolution approaches and combinations in which random mutagenesis/saturation techniques are performed near the active site of the enzyme. For example see Sarah A. Osmani, et al. *Phytochemistry* 70 (2009) 325-347.

A candidate sequence typically has a length that is from 80 percent to 200 percent of the length of the reference sequence, e.g., 82, 85, 87, 89, 90, 93, 95, 97, 99, 100, 105, 110, 115, 120, 130, 140, 150, 160, 170, 180, 190, or 200 percent of the length of the reference sequence. A functional homolog polypeptide typically has a length that is from 95 percent to 105 percent of the length of the reference sequence, e.g., 90, 93, 95, 97, 99, 100, 105, 110, 115, or 120 percent of the length of the reference sequence, or any range between. A percent identity for any candidate nucleic acid or polypeptide relative to a reference nucleic acid or polypeptide can be determined as follows. A reference sequence (e.g., a nucleic acid sequence or an amino acid sequence) is aligned to one or more candidate sequences using the computer program ClustalW (version 1.83, default parameters), which allows alignments of nucleic acid or polypeptide sequences to be carried out across their entire length (global alignment). Chenna et al., *Nucleic Acids Res.*, 31(13):3497-500 (2003).

ClustalW calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher site on the World Wide Web (searchlauncher.bcm.tmc.edu/multi-align/multi-align.html) and at the European Bioinformatics Institute site on the World Wide Web (ebi.ac.uk/clustalw).

To determine percent identity of a candidate nucleic acid or amino acid sequence to a reference sequence, the sequences are aligned using ClustalW, the number of identical matches in the alignment is divided by the length of the reference sequence, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

It will be appreciated that functional UGTs can include additional amino acids that are not involved in glucosylation or other enzymatic activities carried out by the enzyme, and thus such a polypeptide can be longer than would otherwise be the case. For example, a EUGT11 polypeptide can include a purification tag (e.g., HIS tag or GST tag), a chloroplast transit peptide, a mitochondrial transit peptide, an amyloplast peptide, signal peptide, or a secretion tag added to the amino or carboxy terminus. In some embodiments, a EUGT11 polypeptide includes an amino acid sequence that functions as a reporter, e.g., a green fluorescent protein or yellow fluorescent protein.

II. STEVIOL AND STEVIOL GLYCOSIDE BIOSYNTHESIS NUCLEIC ACIDS

A recombinant gene encoding a polypeptide described herein comprises the coding sequence for that polypeptide, operably linked in sense orientation to one or more regulatory regions suitable for expressing the polypeptide. Because many microorganisms are capable of expressing multiple gene products from a polycistronic mRNA, multiple polypeptides can be expressed under the control of a single regulatory region for those microorganisms, if desired. A coding sequence and a regulatory region are considered to be operably linked when the regulatory region and coding sequence are positioned so that the regulatory region is effective for regulating transcription or translation of the sequence. Typically, the translation initiation site of the translational reading frame of the coding sequence is positioned between one and about fifty nucleotides downstream of the regulatory region for a monocistronic gene.

In many cases, the coding sequence for a polypeptide described herein is identified in a species other than the recombinant host, i.e., is a heterologous nucleic acid. Thus, if the recombinant host is a microorganism, the coding sequence can be from other prokaryotic or eukaryotic microorganisms, from plants or from animals. In some case, however, the coding sequence is a sequence that is native to the host and is being reintroduced into that organism. A native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found.

"Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). A regulatory region is operably linked to a coding sequence by positioning the regulatory region and the coding sequence so that the regulatory region is effective for regulating transcription or translation of the sequence. For example, to operably link a coding sequence and a promoter sequence, the translation initiation site of the translational reading frame of the coding sequence is typically positioned between one and about fifty nucleotides downstream of the promoter. A regulatory region can, however, be positioned as much as about 5,000 nucleotides upstream of the translation initiation site, or about 2,000 nucleotides upstream of the transcription start site.

The choice of regulatory regions to be included depends upon several factors, including, but not limited to, efficiency, selectability, inducibility, desired expression level, and preferential expression during certain culture stages. It is a routine matter for one of skill in the art to modulate the expression of a coding sequence by appropriately selecting and positioning regulatory regions relative to the coding sequence. It will be understood that more than one regulatory region may be present, e.g., introns, enhancers, upstream activation regions, transcription terminators, and inducible elements.

One or more genes can be combined in a recombinant nucleic acid construct in "modules" useful for a discrete aspect of steviol and/or steviol glycoside production. Combining a plurality of genes in a module, particularly a polycistronic module, facilitates the use of the module in a variety of species. For example, a steviol biosynthesis gene cluster, or a UGT gene cluster, can be combined in a polycistronic module such that, after insertion of a suitable regulatory region, the module can be introduced into a wide variety of species. As another example, a UGT gene cluster can be combined such that each UGT coding sequence is operably linked to a separate regulatory region, to form a UGT module. Such a module can be used in those species for which monocistronic expression is necessary or desirable. In addition to genes useful for steviol or steviol glycoside production, a recombinant construct typically also contains an origin of replication, and one or more selectable markers for maintenance of the construct in appropriate species.

It will be appreciated that because of the degeneracy of the genetic code, a number of nucleic acids can encode a particular polypeptide; i.e., for many amino acids, there is more than one nucleotide triplet that serves as the codon for the amino acid. Thus, codons in the coding sequence for a given polypeptide can be modified such that optimal expression in a particular host is obtained, using appropriate codon bias tables for that host (e.g., microorganism). SEQ ID NOs:18-25, 34-36, 40-43, 48-49, 52-55, 60-64, 70-72, and 154 set forth nucleotide sequences encoding certain enzymes for steviol and steviol glycoside biosynthesis, modified for increased expression in yeast. As isolated nucleic acids, these modified sequences can exist as purified molecules and can be incorporated into a vector or a virus for use in constructing modules for recombinant nucleic acid constructs.

In some cases, it is desirable to inhibit one or more functions of an endogenous polypeptide in order to divert metabolic intermediates towards steviol or steviol glycoside biosynthesis. For example, it may be desirable to downregulate synthesis of sterols in a yeast strain in order to further increase steviol or steviol glycoside production, e.g., by downregulating squalene epoxidase. As another example, it may be desirable to inhibit degradative functions of certain endogenous gene products, e.g., glycohydrolases that remove glucose moieties from secondary metabolites or phosphatases as discussed herein. As another example, expression of membrane transporters involved in transport of steviol glycosides can be inhibited, such that secretion of glycosylated steviosides is inhibited. Such regulation can be beneficial in that secretion of steviol glycosides can be inhibited for a desired period of time during culture of the microorganism, thereby increasing the yield of glycoside product(s) at harvest. In such cases, a nucleic acid that inhibits expression of the polypeptide or gene product may be included in a recombinant construct that is transformed into the strain. Alternatively, mutagenesis can be used to generate mutants in genes for which it is desired to inhibit function.

III. HOSTS

A. Microorganisms

A number of prokaryotes and eukaryotes are suitable for use in constructing the recombinant microorganisms described herein, e.g., gram-negative bacteria, yeast and fungi. A species and strain selected for use as a steviol or steviol glycoside production strain is first analyzed to determine which production genes are endogenous to the strain and which genes are not present. Genes for which an endogenous counterpart is not present in the strain are assembled in one or more recombinant constructs, which are then transformed into the strain in order to supply the missing function(s).

Exemplary prokaryotic and eukaryotic species are described in more detail below. However, it will be appreciated that other species may be suitable. For example, suitable species may be in a genus selected from the group consisting of *Agaricus, Aspergillus, Bacillus, Candida, Corynebacterium, Escherichia, Fusarium/Gibberella, Kluyveromyces, Laetiporus, Lentinus, Phaffia, Phanerochaete, Pichia, Physcomitrella, Rhodoturula, Saccharomyces, Schizosaccharomyces, Sphaceloma, Xanthophyllomyces* and *Yarrowia*. Exemplary species from such genera include *Lentinus tigrinus, Laetiporus sulphureus, Phanerochaete chrysosporium, Pichia pastoris, Physcomitrella patens, Rhodoturula glutinis* 32, *Rhodoturula mucilaginosa,*

*Phaffia rhodozyma* UBV-AX, *Xanthophyllomyces dendrorhous, Fusarium fujikuroi/Gibberella fujikuroi, Candida utilis* and *Yarrowia lipolytica*. In some embodiments, a microorganism can be an Ascomycete such as *Gibberella fujikuroi, Kluyveromyces lactis, Schizosaccharomyces pombe, Aspergillus niger*, or *Saccharomyces cerevisiae*. In some embodiments, a microorganism can be a prokaryote such as *Escherichia coli, Rhodobacter sphaeroides*, or *Rhodobacter capsulatus*. It will be appreciated that certain microorganisms can be used to screen and test genes of interest in a high throughput manner, while other microorganisms with desired productivity or growth characteristics can be used for large-scale production of steviol glycosides.

*Saccharomyces cerevisiae*

*Saccharomyces cerevisiae* is a widely used chassis organism in synthetic biology, and can be used as the recombinant microorganism platform. There are libraries of mutants, plasmids, detailed computer models of metabolism and other information available for *S. cerevisiae*, allowing for rational design of various modules to enhance product yield. Methods are known for making recombinant microorganisms.

A steviol biosynthesis gene cluster can be expressed in yeast using any of a number of known promoters. Strains that overproduce terpenes are known and can be used to increase the amount of geranylgeranyl diphosphate available for steviol and steviol glycoside production.

*Aspergillus* spp.

*Aspergillus* species such as *A. oryzae, A. niger* and *A. sojae* are widely used microorganisms in food production, and can also be used as the recombinant microorganism platform. Nucleotide sequences are available for genomes of *A. nidulans, A. fumigatus, A. oryzae, A. clavatus, A. flavus, A. niger*, and *A. terreus*, allowing rational design and modification of endogenous pathways to enhance flux and increase product yield. Metabolic models have been developed for *Aspergillus*, as well as transcriptomic studies and proteomics studies. *A. niger* is cultured for the industrial production of a number of food ingredients such as citric acid and gluconic acid, and thus species such as *A. niger* are generally suitable for the production of food ingredients such as steviol and steviol glycosides.

*Escherichia coli*

*Escherichia coli*, another widely used platform organism in synthetic biology, can also be used as the recombinant microorganism platform. Similar to *Saccharomyces*, there are libraries of mutants, plasmids, detailed computer models of metabolism and other information available for *E. coli*, allowing for rational design of various modules to enhance product yield. Methods similar to those described above for *Saccharomyces* can be used to make recombinant *E. coli* microorganisms.

*Agaricus, Gibberella*, and *Phanerochaete* spp.

*Agaricus, Gibberella*, and *Phanerochaete* spp. can be useful because they are known to produce large amounts of gibberellin in culture. Thus, the terpene precursors for producing large amounts of steviol and steviol glycosides are already produced by endogenous genes. Thus, modules containing recombinant genes for steviol or steviol glycoside biosynthesis polypeptides can be introduced into species from such genera without the necessity of introducing mevalonate or MEP pathway genes.

*Arxula adeninivorans* (*Blastobotrys adeninivorans*)

*Arxula adeninivorans* is a dimorphic yeast (it grows as a budding yeast like the baker's yeast up to a temperature of 42° C., above this threshold it grows in a filamentous form) with unusual biochemical characteristics. It can grow on a wide range of substrates and can assimilate nitrate. It has successfully been applied to the generation of strains that can produce natural plastics or the development of a biosensor for estrogens in environmental samples.

*Yarrowia lipolytica*

*Yarrowia lipolytica* is a dimorphic yeast (see *Arxula adeninivorans*) that can grow on a wide range of substrates. It has a high potential for industrial applications but there are no recombinant products commercially available yet.

*Rhodobacter* spp.

*Rhodobacter* can be use as the recombinant microorganism platform. Similar to *E. coli*, there are libraries of mutants available as well as suitable plasmid vectors, allowing for rational design of various modules to enhance product yield. Isoprenoid pathways have been engineered in membranous bacterial species of *Rhodobacter* for increased production of carotenoid and CoQ10. See, U.S. Patent Publication Nos. 20050003474 and 20040078846. Methods similar to those described above for *E. coli* can be used to make recombinant *Rhodobacter* microorganisms.

*Candida boidinii*

*Candida boidinii* is a methylotrophic yeast (it can grow on methanol). Like other methylotrophic species such as *Hansenula polymorpha* and *Pichia pastoris*, it provides an excellent platform for the production of heterologous proteins. Yields in a multigram range of a secreted foreign protein have been reported. A computational method, IPRO, recently predicted mutations that experimentally switched the cofactor specificity of *Candida boidinii* xylose reductase from NADPH to NADH.

*Hansenula polymorpha* (*Pichia angusta*)

*Hansenula polymorpha* is another methylotrophic yeast (see *Candida boidinii*). It can furthermore grow on a wide range of other substrates; it is thermo-tolerant and can assimilate nitrate (see also *Kluyveromyces lactis*). It has been applied to the production of hepatitis B vaccines, insulin and interferon alpha-2a for the treatment of hepatitis C, furthermore to a range of technical enzymes.

*Kluyveromyces lactis*

*Kluyveromyces lactis* is a yeast regularly applied to the production of kefir. It can grow on several sugars, most importantly on lactose which is present in milk and whey. It has successfully been applied among others to the production of chymosin (an enzyme that is usually present in the stomach of calves) for the production of cheese. Production takes place in fermenters on a 40,000 L scale.

*Pichia pastoris*

*Pichia pastoris* is a methylotrophic yeast (see *Candida boidinii* and *Hansenula polymorpha*). It provides an efficient platform for the production of foreign proteins. Platform elements are available as a kit and it is worldwide used in academia for the production of proteins. Strains have been engineered that can produce complex human N-glycan (yeast glycans are similar but not identical to those found in humans).

*Physcomitrella* sp.

*Physcomitrella* mosses, when grown in suspension culture, have characteristics similar to yeast or other fungal cultures. This genera is becoming an important type of cell for production of plant secondary metabolites, which can be difficult to produce in other types of cells.

B. Plant Cells or Plants

In some embodiments, the nucleic acids and polypeptides described herein are introduced into plants or plant cells to increase overall steviol glycoside production or enrich for the production of specific steviol glycosides in proportion to others. Thus, a host can be a plant or a plant cell that includes at least one recombinant gene described herein. A plant or plant cell can be transformed by having a recombinant gene integrated into its genome, i.e., can be stably transformed. Stably transformed cells typically retain the introduced nucleic acid with each cell division. A plant or plant cell can also be transiently transformed such that the recombinant gene is not integrated into its genome. Transiently transformed cells typically lose all or some portion of the introduced nucleic acid with each cell division such that the introduced nucleic acid cannot be detected in daughter cells after a sufficient number of cell divisions. Both transiently transformed and stably transformed transgenic plants and plant cells can be useful in the methods described herein.

Transgenic plant cells used in methods described herein can constitute part or all of a whole plant. Such plants can be grown in a manner suitable for the species under consideration, either in a growth chamber, a greenhouse, or in a field. Transgenic plants can be bred as desired for a particular purpose, e.g., to introduce a recombinant nucleic acid into other lines, to transfer a recombinant nucleic acid to other species, or for further selection of other desirable traits. Alternatively, transgenic plants can be propagated vegetatively for those species amenable to such techniques. As used herein, a transgenic plant also refers to progeny of an initial transgenic plant provided the progeny inherits the transgene. Seeds produced by a transgenic plant can be grown and then selfed (or outcrossed and selfed) to obtain seeds homozygous for the nucleic acid construct.

Transgenic plants can be grown in suspension culture, or tissue or organ culture. For the purposes of this invention, solid and/or liquid tissue culture techniques can be used. When using solid medium, transgenic plant cells can be placed directly onto the medium or can be placed onto a filter that is then placed in contact with the medium. When using liquid medium, transgenic plant cells can be placed onto a flotation device, e.g., a porous membrane that contacts the liquid medium.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days, or about 1-3 days. The use of transient assays is particularly convenient for rapid analysis in different species, or to confirm expression of a heterologous polypeptide whose expression has not previously been confirmed in particular recipient cells.

Techniques for introducing nucleic acids into monocotyledonous and dicotyledonous plants are known in the art, and include, without limitation, *Agrobacterium*-mediated transformation, viral vector-mediated transformation, electroporation and particle gun transformation, U.S. Pat. Nos. 5,538,880; 5,204,253; 6,329,571; and 6,013,863. If a cell or cultured tissue is used as the recipient tissue for transformation, plants can be regenerated from transformed cultures if desired, by techniques known to those skilled in the art.

A population of transgenic plants can be screened and/or selected for those members of the population that have a trait or phenotype conferred by expression of the transgene. For example, a population of progeny of a single transformation event can be screened for those plants having a desired level of expression of a steviol or steviol glycoside biosynthesis polypeptide or nucleic acid. Physical and biochemical methods can be used to identify expression levels. These include Southern analysis or PCR amplification for detection of a polynucleotide; Northern blots, Si RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or nucleic acids. Methods for performing all of the referenced techniques are known. As an alternative, a population of plants comprising independent transformation events can be screened for those plants having a desired trait, such as production of a steviol glycoside or modulated biosynthesis of a steviol glycoside. Selection and/or screening can be carried out over one or more generations, and/or in more than one geographic location. In some cases, transgenic plants can be grown and selected under conditions which induce a desired phenotype or are otherwise necessary to produce a desired phenotype in a transgenic plant. In addition, selection and/or screening can be applied during a particular developmental stage in which the phenotype is expected to be exhibited by the plant. Selection and/or screening can be carried out to choose those transgenic plants having a statistically significant difference in a steviol glycoside level relative to a control plant that lacks the transgene.

The nucleic acids, recombinant genes, and constructs described herein can be used to transform a number of monocotyledonous and dicotyledonous plants and plant cell systems. Non-limiting examples of suitable monocots include, for example, cereal crops such as rice, rye, sorghum, millet, wheat, maize, and barley. The plant may be a non-cereal monocot such as asparagus, banana, or onion. The plant also may be a dicot such as stevia (*Stevia rebaudiana*), soybean, cotton, sunflower, pea, geranium, spinach, or tobacco. In some cases, the plant may contain the precursor pathways for phenyl phosphate production such as the mevalonate pathway, typically found in the cytoplasm and mitochondria. The non-mevalonate pathway is more often found in plant plastids [Dubey, et al., 2003 *J. Biosci.* 28 637-646]. One with skill in the art may target expression of steviol glycoside biosynthesis polypeptides to the appropriate organelle through the use of leader sequences, such that steviol glycoside biosynthesis occurs in the desired location of the plant cell. One with skill in the art will use appropriate promoters to direct synthesis, e.g., to the leaf of a plant, if so desired. Expression may also occur in tissue cultures such as callus culture or hairy root culture, if so desired.

In one embodiment, one or more nucleic acid or polypeptides described herein are introduced into Stevia (e.g., *Stevia rebaudiana*) such that overall steviol glycoside biosynthesis is increased or that the overall steviol glycoside composition is selectively enriched for one or more specific steviol glycosides (e.g., rebaudioside D). For example, one or more recombinant genes can be introduced into *Stevia* such that a EUGT11 enzyme (e.g., SEQ ID NO: 152 or a functional homolog thereof) is expressed alone or in combination with one or more of: a UGT91D enzyme such as UGT91D2e (e.g., SEQ ID NO:5 or a functional homolog thereof), UGT91D2m (e.g., SEQ ID NO:10); a UGT85C enzyme such as a variant described in the “Functional Homolog” section, a UGT76G1 enzyme such as a variant described in the “Functional Homolog” section, or a UGT74G1 enzyme. Nucleic acid constructs typically include a suitable promoter (e.g., 35S, e35S, or ssRUBISCO promoters) operably linked to a nucleic acid encoding the UGT polypeptide. Nucleic acids can be introduced into Stevia by *Agrobacterium*-mediated transformation; electroporation-mediated gene transfer to protoplasts; or by particle bombardment. See, e.g., Singh, et al., Compendium of Transgenic Crop Plants: Transgenic Sugar, Tuber and Fiber, Edited by Chittaranjan Kole and Timothy C. Hall, Blackwell Publishing Ltd. (2008), pp. 97-115. For particle bombardment of stevia leaf derived callus, the parameters can be as follows: 6 cm distance, 1100 psi He pressure, gold particles, and one bombardment.

Stevia plants can be regenerated by somatic embryogenesis as described by Singh et al., 2008, supra. In particular, leaf segments (approximately 1-2 cm long) can be removed from 5 to 6-week-old in vitro raised plants and incubated (adaxial side down) on MS medium supplemented with B5 vitamins, 30 g sucrose and 3 g Gelrite. 2,4-dichlorophenoxyacetic acid (2,4-D) can be used in combination with 6-benzyl adenine (BA), kinetin (KN), or zeatin. Proembryogenic masses appear after 8 weeks of subculture. Within 2-3 weeks of subcultures, somatic embryos will appear on the surface of cultures. Embryos can be matured in medium containing BA in combination with 2,4-D, a-naphthaleneacetic acid (NAA), or indolbutyric acid (IBA). Mature somatic embryos that germinate and form plantlets can be excised from calli. After plantlets reach 3-4 weeks, the plantlets can be transferred to pots with vermiculite and grown for 6-8 weeks in growth chambers for acclimatization and transferred to greenhouses.

In one embodiment, steviol glycosides are produced in rice. Rice and maize are readily transformable using techniques such as *Agrobacterium*-mediated transformation. Binary vector systems are commonly utilized for *Agrobacterium* exogenous gene introduction to monocots. See, for example, U.S. Pat. Nos. 6,215,051 and 6,329,571. In a binary vector system, one vector contains the T-DNA region, which includes a gene of interest (e.g., a UGT described herein) and the other vector is a disarmed Ti plasmid containing the vir region. Co-integrated vectors and mobilizable vectors also can be used. The types and pretreatment of tissues to be transformed, the strain of *Agrobacterium* used, the duration of the inoculation, the prevention of overgrowth and necrosis by the *Agrobacterium*, can be readily adjusted by one of skill in the art. Immature embryo cells of rice can be prepared for transformation with *Agrobacterium* using binary vectors. The culture medium used is supplemented with phenolic compounds. Alternatively, the transformation can be done in planta using vacuum infiltration. See, for example, WO 2000037663, WO 2000063400, and WO 2001012828.

IV. METHODS OF PRODUCING STEVIOL GLYCOSIDES

Recombinant hosts described herein can be used in methods to produce steviol or steviol glycosides. For example, if the recombinant host is a microorganism, the method can include growing the recombinant microorganism in a culture medium under conditions in which steviol and/or steviol glycoside biosynthesis genes are expressed. The recombinant microorganism may be grown in a fed batch or continuous process. Typically, the recombinant microorganism is grown in a fermentor at a defined temperature(s) for a desired period of time. Depending on the particular microorganism used in the method, other recombinant genes such as isopentenyl biosynthesis genes and terpene synthase and cyclase genes may also be present and expressed. Levels of substrates and intermediates, e.g., isopentenyl diphosphate, dimethylallyl diphosphate, geranylgeranyl diphosphate, kaurene and kaurenoic acid, can be determined by extracting samples from culture media for analysis according to published methods.

After the recombinant microorganism has been grown in culture for the desired period of time, steviol and/or one or more steviol glycosides can then be recovered from the culture using various techniques known in the art. In some embodiments, a permeabilizing agent can be added to aid the feedstock entering into the host and product getting out. If the recombinant host is a plant or plant cells, steviol or steviol glycosides can be extracted from the plant tissue using various techniques known in the art. For example, a crude lysate of the cultured microorganism or plant tissue can be centrifuged to obtain a supernatant. The resulting supernatant can then be applied to a chromatography column, e.g., a C-18 column, and washed with water to remove hydrophilic compounds, followed by elution of the compound(s) of interest with a solvent such as methanol. The compound(s) can then be further purified by preparative HPLC. See also WO 2009/140394.

The amount of steviol glycoside (e.g., rebaudioside D) produced can be from about 1 mg/L to about 1500 mg/L, e.g., about 1 to about 10 mg/L, about 3 to about 10 mg/L, about 5 to about 20 mg/L, about 10 to about 50 mg/L, about 10 to about 100 mg/L, about 25 to about 500 mg/L, about 100 to about 1,500 mg/L, or about 200 to about 1,000 mg/L. In general, longer culture times will lead to greater amounts of product. Thus, the recombinant microorganism can be cultured for from 1 day to 7 days, from 1 day to 5 days, from 3 days to 5 days, about 3 days, about 4 days, or about 5 days.

It will be appreciated that the various genes and modules discussed herein can be present in two or more recombinant microorganisms rather than a single microorganism. When a plurality of recombinant microorganisms is used, they can be grown in a mixed culture to produce steviol and/or steviol glycosides. For example, a first microorganism can comprise one or more biosynthesis genes for producing steviol while a second microorganism comprises steviol glycoside biosynthesis genes. Alternatively, the two or more microorganisms each can be grown in a separate culture medium and the product of the first culture medium, e.g., steviol, can be introduced into second culture medium to be converted into a subsequent intermediate, or into an end product such as rebaudioside A. The product produced by the second, or final microorganism is then recovered. It will also be appreciated that in some embodiments, a recombinant microorganism is grown using nutrient sources other than a culture medium and utilizing a system other than a fermentor.

Steviol glycosides do not necessarily have equivalent performance in different food systems. It is therefore desirable to have the ability to direct the synthesis to steviol glycoside compositions of choice. Recombinant hosts described herein can produce compositions that are selectively enriched for specific steviol glycosides (e.g., rebaudioside D) and have a consistent taste profile. Thus, the recombinant microorganisms, plants, and plant cells described herein can facilitate the production of compositions that are tailored to meet the sweetening profile desired for a given food product and that have a proportion of each steviol glycoside that is consistent from batch to batch. Microorganisms described herein do not produce the undesired plant byproducts found in Stevia extracts. Thus, steviol glycoside compositions produced by the recombinant microorganisms described herein are distinguishable from compositions derived from Stevia plants.

V. FOOD PRODUCTS

The steviol glycosides obtained by the methods disclosed herein can be used to make food products, dietary supplements and sweetener compositions. For example, substantially pure steviol or steviol glycoside such as rebaudioside A or rebaudioside D can be included in food products such as ice cream, carbonated beverages, fruit juices, yogurts, baked goods, chewing gums, hard and soft candies, and sauces. Substantially pure steviol or steviol glycoside can also be included in non-food products such as pharmaceutical products, medicinal products, dietary supplements and nutritional supplements. Substantially pure steviol or steviol glycosides may also be included in animal feed products for both the agriculture industry and the companion animal industry. Alternatively, a mixture of steviol and/or steviol glycosides can be made by culturing recombinant microorganisms separately or growing different plants/plant cells, each producing a specific steviol or steviol glycoside, recovering the steviol or steviol glycoside in substantially pure form from each microorganism or plant/plant cells and then combining the compounds to obtain a mixture containing each compound in the desired proportion. The recombinant microorganisms, plants, and plant cells described herein permit more precise and consistent mixtures to be obtained compared to current Stevia products. In another alternative, a substantially pure steviol or steviol glycoside can be incorporated into a food product along with other sweeteners, e.g. saccharin, dextrose, sucrose, fructose, erythritol, aspartame, sucralose, monatin, or acesulfame potassium. The weight ratio of steviol or steviol glycoside relative to other sweeteners can be varied as desired to achieve a satisfactory taste in the final food product. See, e.g., U.S. Patent Publication No. 2007/0128311. In some embodiments, the steviol or steviol glycoside may be provided with a flavor (e.g., citrus) as a flavor modulator. For example, Rebaudioside C can be used as a sweetness enhancer or sweetness modulator, in particular for carbohydrate based sweeteners, such that the amount of sugar can be reduced in the food product.

Compositions produced by a recombinant microorganism, plant, or plant cell described herein can be incorporated into food products. For example, a steviol glycoside composition produced by a recombinant microorganism, plant, or plant cell can be incorporated into a food product in an amount ranging from about 20 mg steviol glycoside/kg food product to about 1800 mg steviol glycoside/kg food product on a dry weight basis, depending on the type of steviol glycoside and food product. For example, a steviol glycoside composition produced by a recombinant microorganism, plant, or plant cell can be incorporated into a dessert, cold confectionary (e.g., ice cream), dairy product (e.g., yogurt), or beverage (e.g., a carbonated beverage) such that the food product has a maximum of 500 mg steviol glycoside/kg food on a dry weight basis. A steviol glycoside composition produced by a recombinant microorganism, plant, or plant cell can be incorporated into a baked good (e.g., a biscuit) such that the food product has a maximum of 300 mg steviol glycoside/kg food on a dry weight basis. A steviol glycoside composition produced by a recombinant microorganism, plant, or plant cell can be incorporated into a sauce (e.g., chocolate syrup) or vegetable product (e.g., pickles) such that the food product has a maximum of 1000 mg steviol glycoside/kg food on a dry weight basis. A steviol glycoside composition produced by a recombinant microorganism, plant, or plant cell can be incorporated into a bread such that the food product has a maximum of 160 mg steviol glycoside/kg food on a dry weight basis. A steviol glycoside composition produced by a recombinant microorganism, plant, or plant cell can be incorporated into a hard or soft candy such that the food product has a maximum of 1600 mg steviol glycoside/kg food on a dry weight basis. A steviol glycoside composition produced by a recombinant microorganism, plant, or plant cell can be incorporated into a processed fruit product (e.g., fruit juices, fruit filling, jams, and jellies) such that the food product has a maximum of 1000 mg steviol glycoside/kg food on a dry weight basis.

For example, such a steviol glycoside composition can have from 90-99% rebaudioside A and an undetectable amount of stevia plant-derived contaminants, and be incorporated into a food product at from 25-1600 mg/kg, e.g., 100-500 mg/kg, 25-100 mg/kg, 250-1000 mg/kg, 50-500 mg/kg or 500-1000 mg/kg on a dry weight basis.

Such a steviol glycoside composition can be a rebaudioside B-enriched composition having greater than 3% rebaudioside B and be incorporated into the food product such that the amount of rebaudioside B in the product is from 25-1600 mg/kg, e.g., 100-500 mg/kg, 25-100 mg/kg, 250-1000 mg/kg, 50-500 mg/kg or 500-1000 mg/kg on a dry weight basis. Typically, the rebaudioside B-enriched composition has an undetectable amount of stevia plant-derived contaminants.

Such a steviol glycoside composition can be a rebaudioside C-enriched composition having greater than 15% rebaudioside C and be incorporated into the food product such that the amount of rebaudioside C in the product is from 20-600 mg/kg, e.g., 100-600 mg/kg, 20-100 mg/kg, 20-95 mg/kg, 20-250 mg/kg, 50-75 mg/kg or 50-95 mg/kg on a dry weight basis. Typically, the rebaudioside C-enriched composition has an undetectable amount of stevia plant-derived contaminants.

Such a steviol glycoside composition can be a rebaudioside D-enriched composition having greater than 3% rebaudioside D and be incorporated into the food product such that the amount of rebaudioside D in the product is from 25-1600 mg/kg, e.g., 100-500 mg/kg, 25-100 mg/kg, 250-1000 mg/kg, 50-500 mg/kg or 500-1000 mg/kg on a dry weight basis. Typically, the rebaudioside D-enriched composition has an undetectable amount of stevia plant-derived contaminants.

Such a steviol glycoside composition can be a rebaudioside E-enriched composition having greater than 3% rebaudioside E and be incorporated into the food product such that the amount of rebaudioside E in the product is from 25-1600 mg/kg, e.g., 100-500 mg/kg, 25-100 mg/kg, 250-1000 mg/kg, 50-500 mg/kg or 500-1000 mg/kg on a dry weight basis. Typically, the rebaudioside E-enriched composition has an undetectable amount of stevia plant-derived contaminants.

Such a steviol glycoside composition can be a rebaudioside F-enriched composition having greater than 4% rebaudioside F and be incorporated into the food product such that the amount of rebaudioside F in the product is from 25-1000 mg/kg, e.g., 100-600 mg/kg, 25-100 mg/kg, 25-95 mg/kg, 50-75 mg/kg or 50-95 mg/kg on a dry weight basis. Typically, the rebaudioside F-enriched composition has an undetectable amount of stevia plant-derived contaminants.

Such a steviol glycoside composition can be a dulcoside A-enriched composition having greater than 4% dulcoside A and be incorporated into the food product such that the amount of dulcoside A in the product is from 25-1000 mg/kg, e.g., 100-600 mg/kg, 25-100 mg/kg, 25-95 mg/kg, 50-75 mg/kg or 50-95 mg/kg on a dry weight basis. Typically, the dulcoside A-enriched composition has an undetectable amount of stevia plant-derived contaminants.

Such a steviol glycoside composition can be a composition enriched for rubusoside xylosylated on either of the two positions—the 13-O-glucose or the 19-O-glucose. Such a composition can have greater than 4% of the xylosylated rubusoside compound, and can be incorporated into the food product such that the amount of xylosylated rubusoside compound in the product is from 25-1000 mg/kg, e.g., 100-600 mg/kg, 25-100 mg/kg, 25-95 mg/kg, 50-75 mg/kg or 50-95 mg/kg on a dry weight basis. Typically, the xylosylated rubusoside enriched composition has an undetectable amount of stevia plant-derived contaminants.

Such a steviol glycoside composition can be a composition enriched for compounds rhamnosylated on either of the two positions—the 13-O-glucose or the 19-O-glucose, or compounds containing one rhamnose and multiple glucoses (e.g., steviol 13-O-1,3-diglycoside-1,2-rhamnoside). Such a composition can have greater than 4% of the rhamnosylated compound, and can be incorporated into the food product such that the amount of rhamnosylated compound in the product is from 25-1000 mg/kg, e.g., 100-600 mg/kg, 25-100 mg/kg, 25-95 mg/kg, 50-75 mg/kg or 50-95 mg/kg on a dry weight basis. Typically, the composition enriched for rhamnosylated compounds has as an undetectable amount of stevia plant-derived contaminants.

In some embodiments, a substantially pure steviol or steviol glycoside is incorporated into a tabletop sweetener or "cup-for-cup" product. Such products typically are diluted to the appropriate sweetness level with one or more bulking agents, e.g., maltodextrins, known to those skilled in the art. Steviol glycoside compositions enriched for rebaudioside A, rebaudioside C, rebaudioside D, rebaudioside E, rebaudioside F, dulcoside A, or rhamnosylated or xylosylated compounds, can be package in a sachet, for example, at from 10,000 to 30,000 mg steviol glycoside/kg product on a dry weight basis, for tabletop use.

In some embodiments, this disclosure relates to the following items:

1. A recombinant host cell comprising a nucleic acid sequence, said nucleic acid comprising a heterologous insert sequence operably linked to an open reading frame, wherein the heterologous insert sequence has the general formula (I):

$$-X_1-X_2-X_3-X_4-X_5-$$

wherein $X_2$ comprises at least 4 consecutive nucleotides complementary to at least 4 consecutive nucleotides of $X_4$, wherein $X_3$ comprises zero nucleotides, or one or more nucleotides forming a hairpin loop, wherein $X_1$ and $X_5$ each individually consists of zero nucleotides, or one or more nucleotides, wherein the open reading frame encodes a squalene synthase (EC 2.5.1.21).

2. The recombinant cell according to item 1, said nucleic acid comprises in 5' to 3' order, a promoter sequence operably linked to a heterologous insert sequence operably linked to an open reading frame, wherein the heterologous insert sequence and the open reading frame are as defined in item 1.

3. A cell comprising a nucleic acid sequence, said nucleic acid comprising i) a promoter sequence operably linked to ii) a heterologous insert sequence operably linked to iii) an open reading frame operably linked to iv) a transcription termination signal, wherein the heterologous insert sequence has the general formula (I):

$$-X_1-X_2-X_3-X_4-X_5-$$

wherein $X_2$ comprises at least 4 consecutive nucleic acids being complementary to, and forms a hairpin secondary structure element with at least 4 consecutive nucleic acids of $X_4$, and wherein $X_3$ comprises unpaired nucleic acids thus forming a hairpin loop between $X_2$ and $X_4$, and wherein $X_1$ and $X_5$ individually and optionally comprises one or more nucleic acids, and wherein the open reading frame upon expression encodes a polypeptide sequence having at least 70% identity to a squalene synthase (EC 2.5.1.21) or a biologically active fragment thereof, said fragment having at least 70% sequence identity to said squalene synthase in a range of overlap of at least 100 amino acids.

4. The cell according to any one of items 1 to 3, wherein the heterologous insert sequence comprises 10-50 nucleotides, preferably 10-30 nucleotides, more preferably 15-25 nucleotides, more preferably 17-22 nucleotides, more preferably 18-21 nucleotides, more preferably 18-20 nucleotides, more preferably 19 nucleotides.

5. The cell according to any one of items 1 to 4, wherein $X_2$ and $X_4$ consists of the same number of nucleotides.

6. The cell according to any one of items 1 to 5, wherein all $X_2$ consists of in the range of 4 to 25, such as in the range of 4 to 20, for example of in the range of 4 to 15, such as in the range of 6 to 12, for example in the range of 8 to 12, such as in the range of 9 to 11 nucleotides.

7. The cell according to any one of items 1 to 6, wherein all $X_4$ consists of in the range of 4 to 25, such as in the range of 4 to 20, for example of in the range of 4 to 15, such as in the range of 6 to 12, for example in the range of 8 to 12, such as in the range of 9 to 11 nucleotides.

8. The cell according to any one of items 1 to 7, wherein $X_2$ consists of a nucleotide sequence, which is complementary to the nucleotide sequence of $X_4$.

9. The cell according to any one of items 1 to 8, wherein $X_4$ consists of a nucleotide sequence, which is complementary to the nucleotide sequence of $X_2$.

10. The cell according to any one of items 1 to 9, wherein $X_3$ is absent, i.e. $X_3$ consists of zero nucleotides.

11. The cell according to any one of items 1 to 9, wherein $X_3$ consists of in the range of 1 to 5, such as in the range of 1 to 3 nucleotides.

12. The cell according to any one of items 1 to 11, wherein $X_1$ is absent, i.e. $X_1$ consists of zero nucleotides.

13. The cell according to any one of items 1 to 11, wherein $X_1$ consists of in the range of 1 to 25, such as in the range of 1 to 20, for example in the range of 1 to 15, such as in the range of 1 to 10, for example in the range of 1 to 5, such as in the range of 1 to 3 nucleotides.

14. The cell according to any one items 1 to 13, wherein $X_5$ is absent, i.e. $X_5$ consists of zero nucleotides.

15. The cell according to any one of items 1 to 11, wherein $X_5$ consists of in the range 1 to 5, such as in the range of 1 to 3 nucleotides.

16. The cell according to any one of items 1 to 15, wherein the heterologous insert sequence comprises a sequence selected from the group consisting of SEQ ID NO: 181, SEQ ID NO: 182, SEQ ID NO: 183 and SEQ ID NO: 184.

17. The cell according to any one of items 1 to 16, wherein the heterologous insert sequence is selected from the group consisting of SEQ ID NO: 181, SEQ ID NO: 182, SEQ ID NO: 183 and SEQ ID NO: 184.

18. The cell according to any one of items 1 to 17, wherein the squalene synthase is at least 75%, such as at least 80%, such as at least 85%, such as at least 87%, such as at least 90%, such as at least 91%, such as at least 92%, such as at least 93%, such as at least 94%, such as at least 95%, such as at least 96%, such as at least 97%, such as at least 98%, such as at least 99%, such as 100% identical to a squalene synthase selected from the group consisting of SEQ ID NO: 192, SEQ ID NO:193, SEQ ID NO:194, SEQ ID NO:194, SEQ ID NO:195, SEQ ID NO:196, SEQ ID NO:197, SEQ ID NO:198, SEQ ID NO:199, SEQ ID NO:200, SEQ ID NO:201, and SEQ ID NO:202.

19. The cell according to any one of items 1 to 18, wherein said promoter is a constitutive or inducible promoter.

20. The cell according to any one of items 1 to 19, wherein said promoter is selected from the group consisting of an endogenous promoter, GPD1, PGK1, ADH1, ADH2, PYK1, TPI1, PDC1, TEF1, TEF2, FBA1, GAL1-10, CUP1, MET2, MET14, MET25, CYC1, GAL1-S, GAL1-L, TEF1, ADH1, CAG, CMV, human UbiC, RSV, EF-1alpha, SV40, Mt1, Tet-On, Tet-Off, Mo-MLV-LTR, Mx1, progesterone, RU486 and Rapamycin-inducible promoter.

21. The cell according to any one of items 1 to 20, wherein the nucleic acid sequence further comprises a polyadenyl sequence.

22. The cell according to item 21, wherein the 5' end of said polyadenyl sequence is operably linked to the 3' end of the nucleic acid of item 1.

23. The cell according to any one of items 1 to 22, wherein the nucleic acid sequence further comprises a post-transcriptional regulatory element.

24. The cell of item 23, wherein said post-transcriptional regulatory element is a Woodchuck hepatitis virus post-transcriptional regulatory element (WPRE).

25. The cell of any of items 1 to 24, wherein the nucleic acid comprises a 5' terminal repeat and a 3' terminal repeat.

26. The cell of item 25, wherein the 5' and 3' terminal repeats are selected from Inverted Terminal Repeats [ITR] and Long Terminal Repeats [LTR].

27. The cell according to any one of items 1 to 26, wherein the nucleic acid sequence is integrated in a vector.

28. The cell of item 27, wherein the vector is an expression vector.

29. The cell of item 27, wherein the vector is selected from the group consisting of plasmid vectors, cosmids, artificial chromosomes and viral vectors.

30. The cell of item 29 wherein the plasmid vector can be maintained and replicated in bacteria, fungi and yeast.

31. The cell of item 29, wherein the viral vector is selected from the group consisting of vectors derived from the Retroviridae family including lentivirus, HIV, SIV, FIV, EAIV, CIV.

32. The cell of item 31, wherein the viral vector is selected from the group consisting of alphavirus, adenovirus, adeno associated virus, baculovirus, HSV, coronavirus, Bovine papilloma virus, Mo-MLV and adeno associated virus.

33. The cell of any of items 27 to 32, wherein said vector is functional in mammalian cells.

34. The cell of any of the preceding items wherein the cell is transformed or transduced with the vector of any of the items 27 to 33.

35. The cell of any of items 1 to 34, wherein said cell is a eukaryotic cell.

36. The cell of any of items 1 to 34, wherein said cell is a prokaryotic cell.

37. The cell of item 35, wherein said cell is selected from the group consisting of fungi cells such as yeast and *aspergillus*; microalgae such as *Chlorella* and *Prototheca*; plant cells; and mammalian cells, such as human, feline, porcine, simian, canine, murine, rat, mouse and rabbit cells.

38. The cell of item 37, wherein the yeast is selected from the group consisting of *Saccharomyces cerevisiae, Schizosaccharomyces pombe, Yarrowia lipolytica, Candida glabrata, Ashbya gossypii, Cyberlindnera jadinii*, and *Candida albicans*.

39. The cell of item 37, wherein the cell is selected from the group consisting of CHO, CHO-K1, HEI193T, HEK293, COS, PC12, HiB5, RN33b, BHK cells.

40. The cell of item 36, wherein said cell is *E. coli, Corynebacterium, Bacillus, Pseudomonas* or *Streptomyces*.

41. The cell of any of items 35 to 40, wherein said prokaryotic cell, or said fungi cell, has been genetically modified to express at least a portion of the enzymes of the mevalonate independent pathway.

42. The cell according to any one of items 1 to 41, wherein the cell furthermore comprises a heterologous nucleic acid encoding GGPPS operably linked to a nucleic acid sequence directing expression of GGPPS in said cell.

43. The cell according to item 42, wherein said GGPPS is selected from the groups consisting of SEQ ID NO: 126, SEQ ID NO:123, SEQ ID NO:203, SEQ ID NO:167, and functional homologues thereof sharing at least 75% sequence identity with any of the aforementioned.

43. A method for producing a terpenoid compound synthesized through the squalene pathway, in a cell culture, said method comprising the steps of (a) providing the cell of any one of items 1 to 42, (b) culturing the cell of (a).

(c) recovering the terpenoid product compound.

44. A method for producing a terpenoid derived from a terpenoid precursor selected from the group consisting of Farnesyl-pyrophosphate (FPP), Isopentenyl-pyrophosphate (IPP), Dimethylallyl-pyrophosphate (DMAPP), Geranyl-pyrophosphate (GPP) and/or Geranylgeranyl-pyrophosphate (GGPP), said method comprising:

(a) contacting said precursor with an enzyme of the squalene synthase pathway, (b) recovering the terpenoid product.

45. The method of any of items 44 and 45, wherein the terpenoid product is selected from the group consisting of hemiterpenoids, monoterpenes, sesquiterpenoids, diterpenoids, sesterpenes, triterpenoids, tetraterpenoids and polyterpenoids.

46. The method of item 44, wherein the terpenoid is selected from the group consisting of farnesyl phosphate, farnesol, geranylgeranyl, geranylgeraniol, isoprene, prenol, isovaleric acid, geranyl pyrophosphate, eucalyptol, limonene, pinene, farnesyl pyrophosphate, artemisinin, bisabolol, geranylgeranyl pyrophosphate, retinol, retinal, phytol, taxol, forskolin, aphidicolin, lanosterol, lycopene and carotene.

47. The method of item 46, wherein said method further comprises dephosphorylating the farnesyl phosphate to produce farnesol.

48. The method of item 44, wherein the enzyme of the squalene synthase pathway is selected from the group consisting of Dimethylallyltransferase (EC 2.5.1.1), Isoprene synthase (EC 4.2.3.27) and Geranyltranstransferase (EC 2.5.1.10).

49. A method for reducing the translation rate of a functional squalene synthase (EC 2.5.1.21) said method comprising:

(a) providing the cell of any one of items 1 to 42, (b) culturing the cell of (a).

50. A method for decreasing turnover of farnesyl-pp to squalene, said method comprising:

(d) providing the cell of any one of items 1 to 42, (e) culturing the cell of (a).

51. A method for enhancing accumulation of a compound selected from the group consisting of Farnesyl-pyrophosphate, Isopentenyl-pyrophosphate, Dimethylallyl-pyrophosphate, Geranyl-pyrophosphate and Geranylgeranyl-pyrophosphate, said method comprising the steps of:

(a) providing the cell of any one of items 1 to 42, and (b) culturing the cell of (a).

52. The method of item 51, further comprising recovering the Farnesyl-pyrophosphate, Isopentenyl-pyrophosphate, Dimethylallyl-pyrophosphate, Geranyl-pyrophosphate or Geranylgeranyl-pyrophosphate compound.

53. The method of any one of items 51 and 52, further comprising recovering a compound synthesized through the squalene pathway, said compound being derived from said Farnesyl-pyrophosphate, Isopentenyl-pyrophosphate, Dimethylallyl-pyrophosphate, Geranyl-pyrophosphate and/or Geranylgeranyl-pyrophosphate.

54. The method of any of items 43 to 53, wherein the step of culturing the cell is performed in the presence of a squalene synthase inhibitor.

55. The method of any of items 43 to 54, wherein the cell additionally is genetically modified to enhance activity of and/or overexpress one or more enzymes selected from the group consisting of Phosphomevalonate kinase (EC 2.7.4.2), Diphosphomevalonate decarboxylase (EC 4.1.1.33), 4-hydroxy-3-methylbut-2-en-1-yl diphosphate synthase (EC 1.17.7.1), 4-hydroxy-3-methylbut-2-enyl diphosphate reductase (EC 1.17.1.2), Isopentenyl-diphosphate Delta-isomerase 1 (EC 5.3.3.2), Short-chain Z-isoprenyl diphosphate synthase (EC 2.5.1.68), Dimethylallyltransferase (EC 2.5.1.1), Geranyltranstransferase (EC 2.5.1.10) and Geranylgeranyl pyrophosphate synthetase (EC 2.5.1.29).

56. The method of any of items 43 to 55, wherein the cell additionally is genetically modified to enhance activity of and/or overexpress one or more enzymes selected from the group consisting of acetoacetyl CoA thiolose, HMG-CoA reductase or the catalytic domain thereof, HMG-CoA synthase, mevalonate kinase, phosphomevalonate kinase, phosphomevalonate decarboxylase, isopentenyl pyrophosphate isomerase, farnesyl pyrophosphate synthase, D-1-deoxyxylulose 5-phosphate synthase, and 1-deoxy-D-xylulose 5-phosphate reductoisomerase and farnesyl pyrophosphate synthase.

57. The method of any of items 43 to 56, wherein the cell comprises a mutation in the ERG9 open reading frame.

58. The method of any of items 43 to 57, wherein the cell comprises an ERG9[Delta]::HIS3 deletion/insertion allele.

59. The method of any of items 43 to 58, wherein the step of recovering the compound comprises purification of said compound from the cell culture media.

VI. EXAMPLES

The invention will be further described in the following examples, which do not limit the scope of the invention described in the claims. In the examples described herein, the following LC-MS methodology was used to analyze steviol glycosides and steviol pathway intermediates unless otherwise indicated.

1) Analyses of Steviol Glycosides

LC-MS analyses were performed using an Agilent 1200 Series HPLC system (Agilent Technologies, Wilmington, DE, USA) fitted with a Phenomenex® kinetex C18 column (150×2.1 mm, 2.6 μm particles, 100 Å pore size) connected to a TSQ Quantum Access (ThermoFisher Scientific) triple quadropole mass spectrometer with a heated electrospray ion (HESI) source. Elution was carried out using a mobile phase of eluent B (MeCN with 0.1% Formic acid) and eluent A (water with 0.1% Formic acid) by increasing the gradient from 10->40% B from min 0.0 to 1.0, increasing 40->50% B in min 1.0 to 6.5, 50->100/o B from min 6.5 to 7.0 and finally washing and re-equilibration. The flow rate was 0.4 ml/min and the column temperature 30° C. The steviol glycosides were detected using SIM (Single Ion Monitoring) in positive mode with the following m/z-traces.

| Description | Exact Mass | m/z trace | compound (typical $t_R$ in min) |
|---|---|---|---|
| Steviol + 1 Glucose | $[M + H]^+$ 481.2796 | 481.2 ± 0.5 | 19-SMG (6.1), 13-SMG (6.4) |
| | $[M + Na]^+$ 503.2615 | 503.1 ± 0.5 | |
| Steviol + 2 Glucose | $[M + Na]^+$ 665.3149 | 665 ± 0.5 | Rubusoside (4.7) Steviol-1,2-bioside (5.2) Steviol-1,3-bioside (5.8) |
| Steviol + 3 Glucose | $[M + Na]^+$ 827.3677 | 827.4 ± 0.5 | 1,2-Stevioside (4.0) 1,3-Stevioside (4.4) Rebaudioside B (5.0) |
| Steviol + 4 Glucose | $[M + Na]^+$ 989.4200 | 989.4 ± 0.5 | Rebaudioside A (3.9) |
| Steviol + 5 Glucose | $[M + Na]^+$ 1151.4728 | 1151.4 ± 0.5 | Rebaudioside D (3.3) |

The level of steviol glycosides were quantified by comparing with calibration curves obtained with authentic standards from LGC Standards. For example, standard solutions of 0.5 to 100 μM Rebaudioside A were typically utilized to construct a calibration curve.

2) Analyses of Steviol and Ent-Kaurenoic Acid

LC-MS analyses of steviol and ent-kaurenoic acid were performed on the system described above. For the separation, a Thermo Science Hypersil Gold (C-18, 3 μm, 100×2.1 mm) column was used and a 20 mM ammonium acetate aqueous solution was used as eluent A and acetonitrile as eluent B. The gradient conditions were: 20->55% B in min 0.0 to 1.0, 55->100 in min 1.0-7.0 and finally washing and re-equilibration. The flow rate was 0.5 mL/min and the column temperature 30° C. Steviol and ent-kaurenoic acid were detected using SIM (Single Ion Monitoring) in negative mode with the following m/z-traces.

| Description | Exact Mass | m/z trace | typical $t_R$ in min |
|---|---|---|---|
| Steviol | $[M - H]^-$ 317.2122 | 317.4 ± 0.5 | 3.3 |
| Ent-kaurenoic acid | $[M - H]^-$ 301.2173 | 301.4 ± 0.5 | 5.5 |

3) HPLC Quantification of UDP-Glucose

For the quantification of UDP-glucose, an Agilent 1200 Series HPLC system was used, with a Waters XBridge BEH amide (2.5 μm, 3.0×50 mm) column. Eluent A was a 10 mM ammonium acetate aqueous solution (pH 9.0) and Eluent B acetonitrile. The gradient conditions were: 95% B holding from min 0.0-0.5, decreasing from 95-50% B in min 0.5-4.5, holding 50% B from min 4.5-6.8 and finally re-equilibrating to 95% B. The flow rate was 0.9 mL/min and the column temperature 20° C. UDP-glucose was detected by $UV_{262nm}$ absorbance.

The amount of UDP-glucose was quantified by comparing with a calibration curve obtained with a commercially available standard (e.g., from Sigma Aldrich).

Example 1—Identification of EUGT11

Fifteen genes were tested for RebA 1,2-glycosylation activity. See Table 10.

TABLE 10

| Name | Source | GenBank Accession No. |
|---|---|---|
| EUGT2 | *Oryza sativa* UGT91 homolog | AP003270 |
| EUGT3 | *Oryza sativa* UGT91 homolog | AP005171 |
| EUGT4 | *Oryza sativa* UGT91 homolog | AP005643 |
| EUGT6 | *Oryza sativa* UGT91 homolog | AP005259 |
| EUGT7 | *Oryza sativa* UGT91 homolog | AP005171 |
| EUGT8 | *Oryza sativa* UGT91 homolog | XM_470006 |
| EUGT9 | *Oryza sativa* UGT91 homolog | AP005643 |
| EUGT10 | *Oryza sativa* UGT91 homolog | AC133334 |
| EUGT11 | *Oryza sativa* UGT91 homolog | AC133334 |
| EUGT12 | *Oryza sativa* UGT91 homolog | AC133334 |
| EUGT15 | *Petunia* × hybrid UGT79 homolog | Z25802 |
| EUGT16 | *Arabidopsis thaliana* UGT79 homolog | AC004786 |
| EUGT17 | *Dianthus caryophyllus* UGT79 homolog | AB294391 |
| EUGT18 | *Ipomoea nil* UGT79 homolog | AB192314 |
| EUGT19 | *Oryza sativa* UGT79 homolog | NM_001074394 |

Figure 4:
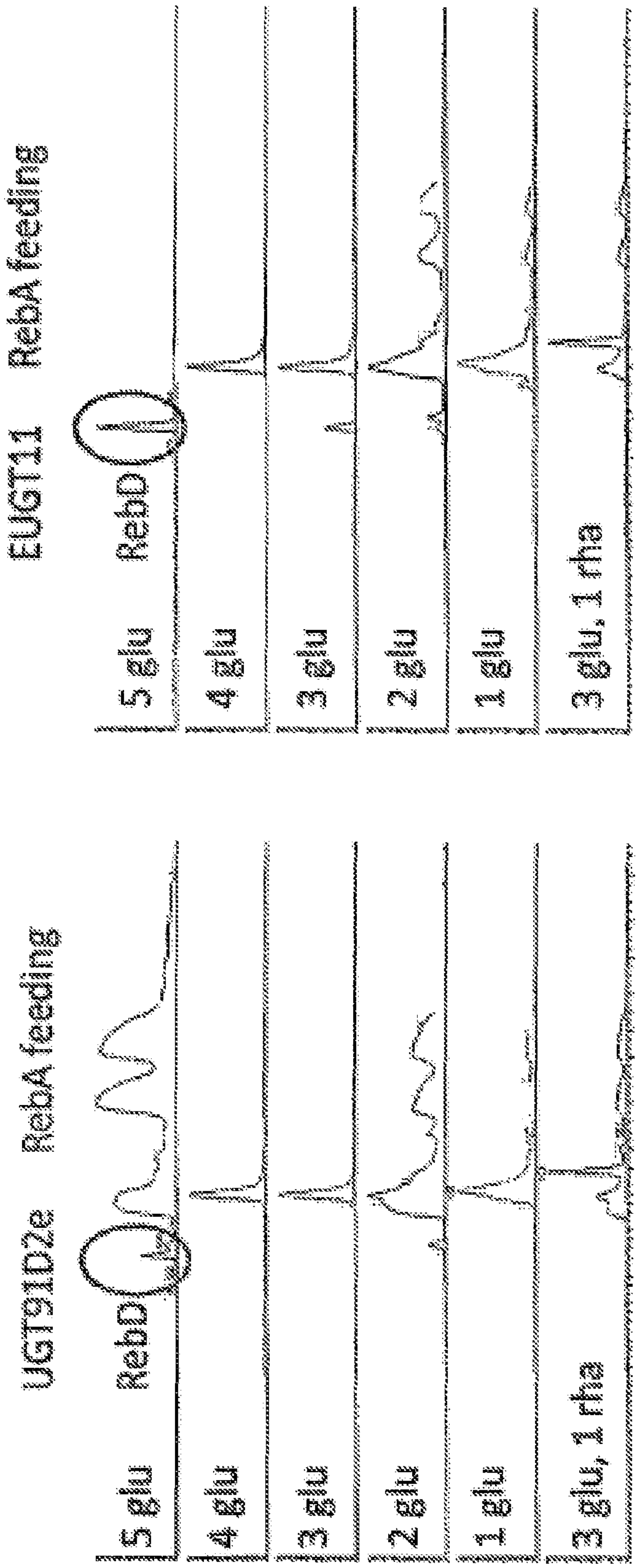

In vitro transcription and translation of these genes was performed, and the resulting UGTs incubated with RebA and UDP-glucose. Following incubation, the reactions were analyzed by LC-MS. The reaction mixture containing EUGT11 (Rice, AC133334, SEQ ID NO:152) was shown to convert significant quantities of RebA to RebD. See LC-MS chromatograms in FIG. 4. As shown in the left panel of FIG. 4, UGT91D2e produced a trace amount of RebD when RebA was used as the feedstock. As shown in the right panel of FIG. 4, EUGT11 produced a significant amount of RebD when RebA was used as the feedstock. Preliminary quantification of the amount of RebD that was produced indicated that EUGT11 was approximately 30 times more efficient than UGT91D2e at converting RebA to RebD.

To further characterize EUGT11 and for quantitative comparison to UGT91D2e, the nucleotide sequence encoding EUGT11 (SEQ ID NO: 153, non-codon optimized, FIG. 7) was cloned into two *E. coli* expression vectors, one containing an N-terminal HIS-tag and one containing an N-terminal GST-tag. EUGT11 was expressed using both systems and purified. When the purified enzymes were incubated with UDP-glucose and RebA, RebD was produced.

Example 2—Identification of EUGT11 Reactions

EUGT11 was produced by in vitro transcription and translation, and incubated with various substrates in the RebD pathway. Similar experiments were carried out using in vitro transcribed and translated UGT91D2e. FIG. 3 shows a schematic overview of 19-O-1,2-diglycosylation reactions performed by EUGT11 and UGT91D2e. Compounds 1-3 were identified solely by mass and expected retention time. The numbers shown in FIG. 3 are the average peak height of the indicated steviol glycoside obtained from a LC-MS chromatogram, and, although not quantitative, can be used to compare the activity of the two enzymes. EUGT11 and UGT91D2e were not able to use steviol as a substrate. Both enzymes were able to convert steviol 19-O-monoglucoside (SMG) to compound 1, with EUGT11 being about ten times more efficient than UGT91D2e at converting 19-SMG to compound 1.

Figure 5:
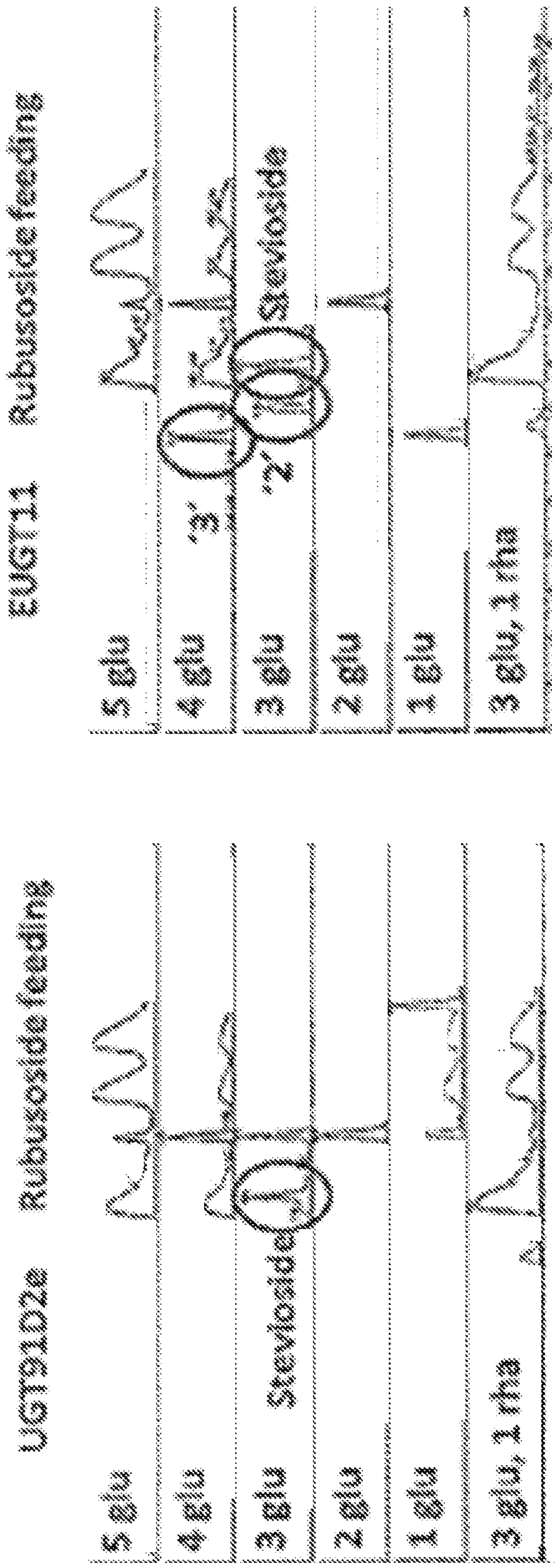
FIG. 5 contains LC-MS chromatograms showing the conversion of rubusoside to stevioside and compounds '2' and '3' (RebE) by UGT91D2e (left panel) and EUGT11 (right panel).

Both enzymes were able to convert rubusoside to stevioside with comparable activity but only EUGT11 was able to convert rubusoside to compound 2 and compound 3 (RebE). See FIG. 5. The left panel of FIG. 5 contains LC-MS chromatograms of the conversion of rubusoside to stevioside. The right panel of FIG. 5 contains chromatograms of the conversion of rubusoside to stevioside, to compound 2, and to compound 3 (RebE). Conversion of rubusoside to compound 3 requires two consecutive 1, 2-O-glycosylations at the 19- and 13-positions of steviol. UGT91D2e was able to produce a trace amount of compound 3 (RebE) in one experiment whereas EUGT11 produced a significant amount of compound 3.

Both enzymes were able to convert RebA to RebD. However, EUGT11 was approximately 30 times better at converting RebA to RebD. Overall, it appears that EUGT11 produces more product than UGT91D2e in all reactions (with similar time, concentrations, temperature, and purity of enzyme) except the conversion of rubusoside to stevioside.

Example 3—Expression of EUGT11 in Yeast

The nucleotide sequence encoding EUGT11 was codon-optimized (SEQ ID NO:154) and transformed into yeast along with nucleic acids encoding all four UGTs (UGT91D2e, UGT74G1, UGT76G1, and UGT85C2). The resulting yeast strain was grown in medium containing steviol and steviol glycosides that accumulated were analyzed by LC-MS. EUGT11 was required for the production of RebD. In other experiments, RebD production has been observed with UGT91D2e, UGT74G1, UGT76G1, and UGT85C2.

Example 4—UGT Activity on 19-O-1,2-Diglycosylated Steviol Glycosides

The 19-O-1,2-diglycosylated steviol glycosides produced by EUGT11 need further glycosylation to be converted to RebD. The following experiments were performed to determine if other UGTs could use these intermediates as substrates.

In one experiment, compound 1 was produced in vitro from 19-SMG by either EUGT11 or UGT91D2e in the presence of UDP-glucose. After boiling the sample, UGT85C2 and UDP-glucose were added. The sample was analyzed by LC-MS and compound 2 was detected. This experiment indicated that UGT85C2 can use compound 1 as a substrate.

In another experiment, compound 2 was incubated with UGT91D2e and UDP-glucose. The reaction was analyzed by LC-MS. UGT91D2e was not able to convert compound 2 to compound 3 (RebE). Incubation of compound 2 with EUGT11 and UDP-glucose results in the production of compound 3. UGT76G1 was able to use RebE as a substrate to produce RebD.

This shows that the 19-O-1,2-diglycosylation of the steviol glycosides is able to take place at any time during production of RebD as the downstream enzymes are able to metabolize the 19-O-1,2-diglycosylated intermediates.

Example 5—Comparison of EUGT11 and UGT91D2e Sequence

The amino acid sequence of EUGT11 (SEQ ID NO:152, FIG. 7) and the amino acid sequence of UGT91D2e (SEQ ID NO:5) were aligned using the FASTA algorithm (Pearson and Lipman, Proc. Natl. Acad. Sci., 85:2444-2448 (1998)). See FIG. 6. EUGT11 and UGT91D2e are 42.7% identical over 457 amino acids.

Example 6—Modification of 19-1,2-Diglycosylating Activity of UGT91D2e

Crystal structures are available for a number of UGTs. Generally, the N-terminal half of a UGT is primarily involved with substrate binding whereas the C-terminal half is involved in binding the UDP-sugar donor.

Figure 8:
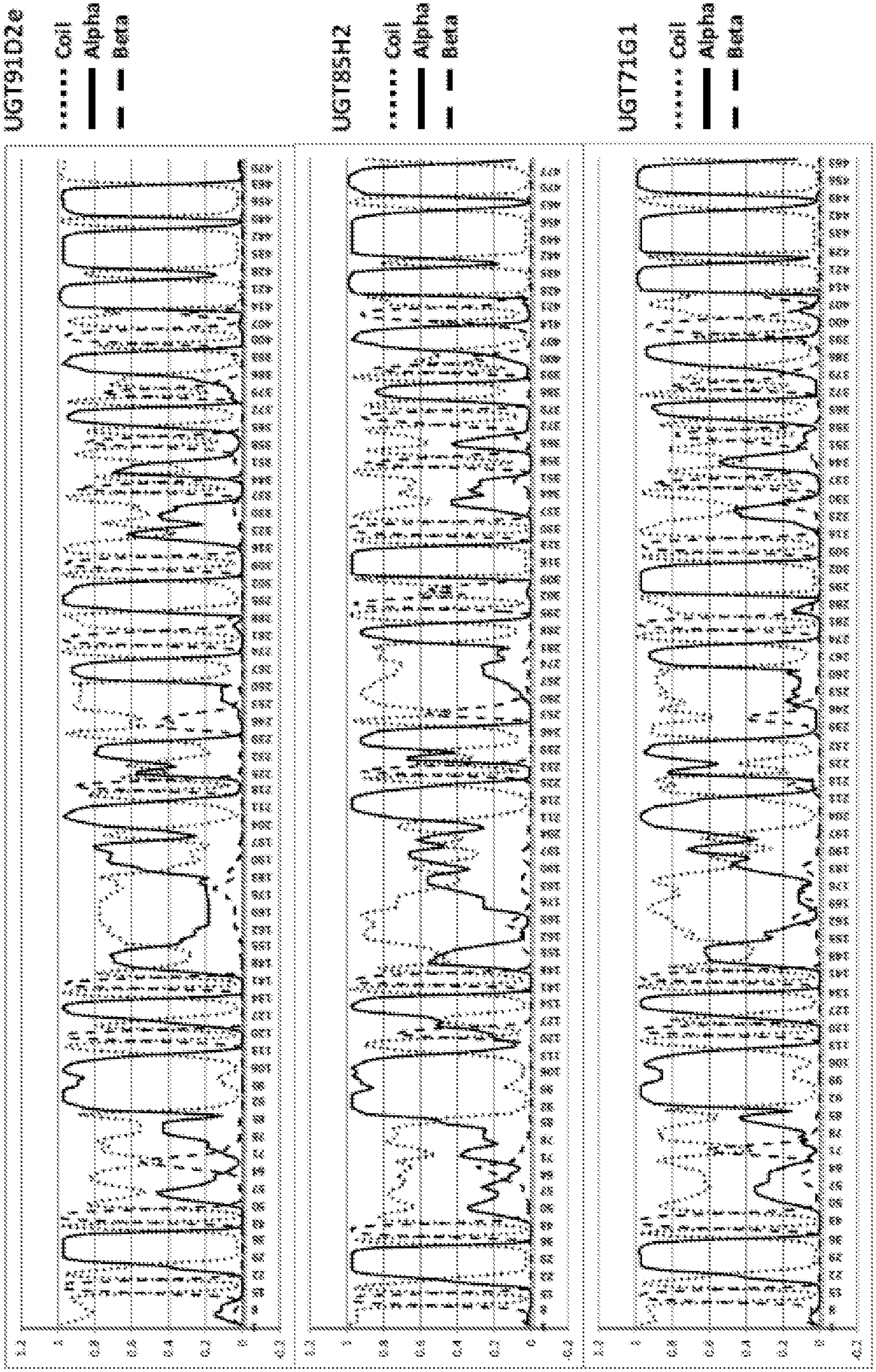
FIG. 8 is an alignment of the secondary structure predictions of UGT91D2e with UGT85H2 and UGT71G1. Secondary structure predictions were made by subjecting the amino acid sequences of the three UGTs to NetSurfP ver. 1.1—Protein Surface Accessibility and Secondary Structure Predictions, at the world wide web at cbs.dtu.dk/services/NetSurfP/. This predicted the presence and location of alpha helices, beta sheets and coils in the proteins. These were subsequently labeled as shown for UGT91D2e. For example, the first N-terminal beta-sheet was labeled Nβ1. The y-axis represents the certainty of the prediction, the higher the more confident and the x-axis represents amino acid position. Although the primary sequence identity between these UGTs is very low, the secondary structures show a very high degree of conservation.

Modeling the secondary structure of UGT91D2e onto the secondary structure of the UGTs that have been crystalized revealed a conserved pattern of secondary structure, despite a highly diverged primary sequence as shown in FIG. 8. The crystal structures of UGT71G1 and UGT85H2 (see, for example H. Shao et al, *The Plant Cell* November 2005 vol. 17 no 11 3141-3154 and L. Li et al., *J Mol Biol.* 2007 370(5):951-63) have been reported. Known loops, alpha-helices and beta-sheets are indicated on UGT91D2e in FIG. 8. Although the homology at the primary structure level of these UGTs is fairly low, the secondary structure appears to be conserved, allowing predictions regarding the locations of amino acids involved in substrate binding on UGT91D2e based on the location of such amino acids in UGT85H2 and UGT71G1.

Regions commonly involved in substrate binding were superimposed on UGT91D2e and largely shown to coincide with the 22 amino acid differences from UGT91D1 (GenBank Accession No. Protein Accession number AAR06918, GI:37993665). UGT91D1 is highly expressed in *Stevia* and thought to be a functional UGT. However, its substrate is not a steviol glycoside. This suggests that UGT91D1 has a different substrate, which may be defined by the 22 amino acids with which it differs from UGT91D2e. FIG. 9 is an alignment of the amino acid sequences of UGT91D1 and UGT91D2e. The boxes represent areas that are reported to be involved in substrate binding. The amino acids highlighted in dark grey show the 22 amino acid differences between UGT91D1 and UGT91D2e. Stars denote amino acids that have been shown to be involved in substrate binding in UGTs that have had their crystal structure resolved (more stars under one particular amino acids means substrate binding has been shown with more than one structure-resolved UGTs). There is a strong correlation between the 22 amino acid differences between the two UGT91s, the regions known to be involved in substrate binding, and the actual amino acids involved in substrate binding in the crystal structure-resolved UGTs. This suggests that the 22 amino acid differences between the two UGT91s are involved in substrate binding.

All 22 altered 91D2es were expressed in a XJb Autolysis *E. coli* strain from a pGEX-4T1 vector. In order to assess the activity of the enzymes, two substrate feeding experiments were performed—in vivo and in vitro. Most mutants had lower activity than wild type, however, 5 mutants showed increased activity. This was reproduced by in vitro transcription and translation (IVT) and showed that C583A, C631A and T857C have approximately 3-fold higher stevioside-forming activity than the wild-type UGT91D2e, whereas C662t and A1313C had approximately twice the stevioside-forming activity (nucleotide numbering). These changes result in amino acid mutations corresponding to L195M, L211M, V286A; and S221F and E438A, respectively. The increased activity differed depending on substrate, with C583A and C631A showing almost a 10-fold increase using 13-SMG as substrate and about a 3-fold increase using rubusoside as substrate, whereas T857C showed a 3-fold increase when using either 13-SMG or rubusoside as substrate.

Figure 10:
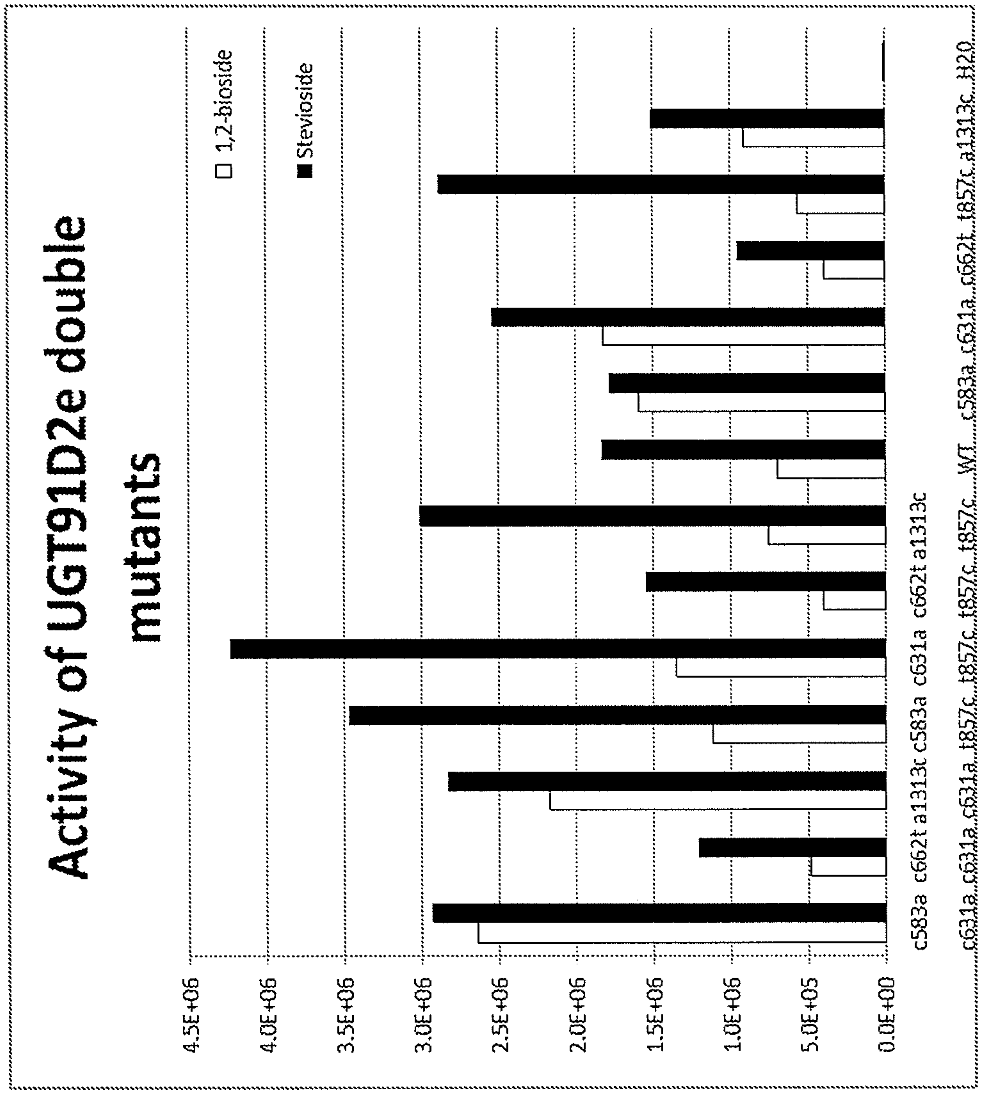
FIG. 10 is a bar graph of the activity of double amino acid substitution mutants of UGT91D2e. The filled bars represent stevioside production and the open bars represent 1,2-bioside production.

To investigate if these mutations were additive, a range of double mutants were made and analyzed for activity (FIG. 10). In this particular experiment, a higher wild type level of activity was observed than the previous four experiments; however, the relative activities of the mutations remain the same. As rubusoside accumulates in many of the *S. cerevisiae* strains expressing the 4 UGTs (UGT74G1, UGT85C2, UGT76G1, and UGT91D2e), the stevioside-forming activity may be more important for increasing steviol glycoside production. As such, the double mutant C631A/T857C (nucleotide numbering) may be useful. This mutant has been named UGT91D2e-b, which contains the amino acid modifications L211M and V286A. The experiments have been reproduced in vitro using *S. cerevisiae*-expressed UGT91D2e-mutants.

To improve 19-1,2-diglycosylating activity of UGT91D2e, a directed saturated mutagenic screen of UGT91D2e of the 22 amino acid differences between UGT91D2e and UGT91D1 was performed. GeneArt's® (Life Technologies, Carlsbad, CA) site-saturation mutagenesis was used to obtain a library containing each of the mutations. The library was cloned into the BamHI and NotI sites of pGEX4T1 bacterial expression plasmid expressing the mutated versions of 91D2e as GST fusion proteins, resulting in a new library (Lib #116). Lib #116 was transformed into XJbAutolysis *E. coli* strain (ZymoResearch, Orange, CA) to produce approximately 1600 clones containing the 418 expected mutations (i.e., 22 positions with 19 different amino acids at each position). Other plasmids expressing GST-tagged versions of 91D2e (EPCS1314), 91D2e-b (EPSC1888) or EUGT11 (EPSC1744) as well as the empty pGEX4T1 (PSB12) were transformed as well.

Screening by LC-MS

To analyze the approximately 1600 mutant clones of UGT91D2e, the *E. coli* transformants were grown overnight at 30° C. in 1 ml of NZCYM containing ampicillin (100 mg/1) and chloramphenicol (33 mg/1), in 96-well format. The next day, 150 μl of each culture was inoculated into 3 ml NZCYM containing ampicillin (100 mg/1), chloramphenicol (33 mg/1), arabinose 3 mM, IPTG 0.1 mM and ethanol 2% v/v, in 24-well format, and incubated at 20° C. and 200 rpm for ~20 h. The following day, cells were spun down and pellets were resuspended in 100 μl of lysis buffer containing 10 mM Tris-HCl pH 8, 5 mM $MgCl_2$, 1 mM $CaCl_2$) and complete mini protease inhibitor EDTA-free (3 tablets/100 ml) (Hoffmann-La Roche, Basel, Switzerland) and frozen −80° C. for at least 15 minutes to promote cell lysis. Pellets were thawed at room temperature and 50 μl of DNase mix (1 μl of 1.4 mg/ml DNase in H2O (~80000 u/ml), 1.2 μl of $MgCl_2$ 500 mM and 47.8 μl of 4×PBS buffer solution) was added to each well. Plates were shaken at 500 rpm for 5 min at room temperature to allow degradation of genomic DNA. Plates were spun down at 4000 rpm for 30 min at 4° C. and six μl of the lysates were used in UGT in vitro reactions as described for GST-91D2e-b, using rubusoside or rebaudioside A as substrates. In each case, the resulting compounds, stevioside or rebaudioside D (rebD), were measured by LC-MS. Results were analyzed in comparison with the stevioside or rebD produced by the lysates expressing the corresponding controls (91D2e, 91D2e-b, EUGT11 and the empty plasmid). Clones showing activity similar to or higher than the ones expressing 91D2e-b were selected as primary hits.

Half of the 1600 clones and the corresponding controls were assayed for their capacity to glycosylate rubusoside and rebaudiosideA. Stevioside and RebD were quantified by LC-MS. Under the conditions used, lysates from clones expressing the native UGT91D2e show activity just around background with both substrates (approximately 0.5 μM stevioside and 1 μM RebD), while clones expressing UGT91D2e-b show consistently improved product formation (>10 μM Stevioside; >1.5 μM RebD). Clones expressing EUGT11 consistently display a higher level of activity, especially using RebA as substrate. Cutoff for considering clones as primary hits in the screening was generally set at 1.5 μM for both products, but in some cases was adjusted for each independent assay.

Example 7—EUGT11 Homologs

A Blastp search of the NCBI nr database using the EUGT11 protein sequence revealed approximately 79 potential UGT homologs from 14 plant species (one of which is the Stevia UGT91D1, approximately 67% identical to EUGT11 in conserved UGT regions but less than 45% overall). Homologs with greater than 90% identity in conserved regions were identified from corn, soybean, *Arabidopsis*, grape, and Sorghum. The overall homology of the full-length EUGT11 homologs, at the amino acid level, was only 28-68%.

RNA was extracted from plant material by the method described by Iandolino et al. (Iandolino et al., *Plant Mol Biol Reporter* 22, 269-278, 2004), the RNeasy Plant mini Kit (Qiagen) according to the manufacturer's instructions, or using the Fast RNA Pro Green Kit (MP Biomedicals) according to the manufacturer's instructions. cDNA was produced by AffinityScript QPCR cDNA Synthesis Kit (Agilent) according to the manufacturer's instructions. Genomic DNA was extracted using the FastDNA kit (MP biomedicals) according to the manufacturer's instructions. PCR was performed on cDNA using either the Dream Taq polymerase (Fermentas) or the Phusion polymerase (New England Biolabs) and a series of primers designed to amplify the homologs.

PCR-reactions were analyzed by electrophoresis in SyberSafe-containing agarose-TAE gels. DNA was visualized by UV-irradiation in a trans illuminator. Bands of the correct size were cut out, purified through spin columns according to the manufacturer's specifications, and cloned into TOPO-Zero blunt (for Phusion polymerase-generated products) or TOPO-TA (for Dream Taq-generated products). The TOPO-vectors containing the PCR-products were transformed into *E. coli* DH5Bα and plated on LB-agar plates containing the appropriate selective antibiotics. DNA was extracted from surviving colonies and sequenced. The genes with the correct sequence were cut out by restriction digest with SbfI and AscI, cloned into similarly digested IVT8 vector and transformed into *E. coli*. PCRs were performed on all cloned genes to amplify the gene and flanking regions required for in vitro transcription and translation. Proteins were produced from the PCR products by in vitro transcription and translation using the Promega L5540, TNT T7 Quick for PCR DNA Kit according to the manufacturer's instructions. Production of protein was evaluated by incorporation of $^{35}$S-methionine followed by separation by SDS-PAGE and visualization on a Typhoon phosphor-imager.

Activity assays were set up totaling 20% (by volume) of each in vitro reaction, 0.1 mM rubusoside or RebA, 5% DMSO, 100 mM Tris-HCl pH 7.0, 0.01 units Fast alkaline phosphatase (Fermentas), and 0.3 mM UDP-glucose (final concentrations). Following incubation at 30° C. for one hour, the samples were analyzed by LC-MS for production of stevioside and RebD as described above. The UGT91D2e and UGT91D2e-b (double mutant described in Example 6) were used as positive controls, along with EUGT11. Under the initial assay conditions, clone P 64B (see Table 11) produced a trace amount of product using rubusoside and RebA. Table 11 lists the percent identity at the amino acid level compared to EUGT11 for the whole length of the UGTs, which ranges from 28-58%. High amounts of homology (96-100%) were observed over shorter stretches of sequences, which may indicate highly conserved domains of plant UGTs.

TABLE 11

List of cloned EUGT11 homologs and their amino acid percent identity to EUGT11.

| UGT | Accession | % identity to EUGT11 |
|---|---|---|
| P44G | XP_002297733.1 | 32.16 |
| P54A | XP_002532392.1 | 34.20 |
| P51H | XP_002325254.1 | 32.53 |
| P55D | XP_002533517.1 | 31.90 |
| P5F | AAM12787.1 | 31.73 |
| P48G | XP_002318358.1 | 33.20 |
| P52F | XP_002334090.1 | 32.80 |
| P48F | XP_002318358.1 | 33.00 |
| T4B-b | NP_565540.4 | 31.19 |
| P56C | XP_002533518.1 | 32.60 |
| T67H | XP_002270294.1 | 34.06 |
| T65E | CAN80742.1 | 34.98 |
| T74G | XP_002270331.1 | 35.48 |
| T65D | CAN80742.1 | 34.98 |
| T69F1 | XP_003635103.1 | 34.69 |
| P6B | Q66PF2.1 | 33.20 |
| P6D variant | Q66PF2.1 | 33.60 |
| P64B | ACE87855.1 | 34.64 |
| T3F | AT5G65550 | 34.94 |
| P53H | XP_002527371.1 | 33.40 |
| P53F | XP_002527371.1 | 33.40 |
| P46H | XP_002303861.1 | 32.40 |
| 2-b | NP_199780.1 | 35.79 |
| T70F | XP_002275802.1 | 36.67 |
| T72A | XP_002275850.1 | 36.42 |
| T71G | XP_002275824.1 | 37.25 |
| P49G | XP_002320817.1 | 35.15 |
| P57H | XP_002511902.1 | 36.23 |
| 45 Pop | XP_002302598.1 | 34.21 |
| P50G | XP_002323718.1 | 32.86 |
| P50H | XP_002323718.1 | 32.66 |
| T73G | XP_002281094.1 | 32.05 |
| 63 | XP_002458816.1 | 37.25 |
| P78B | NP_001147674.1 | 35.33 |
| 62 | XP_002458815.1 | 34.06 |
| P9F | BAJ84800.1 | 37.92 |
| T7H | NP_001240857.1 | 31.30 |
| 16-1 | BAJ93155.1 | 58.03 |
| T16H | BAJ93155.1 | 58.03 |
| 31TA | BAD35324.1 | 51.81 |
| P41G | NP_001174664.1 | 35.40 |
| P37G | NP_001051010.1 | 56.71 |
| P60aH | XP_002466606.1 | 57.35 |
| 12 | BAJ89368.1 | 44.35 |
| P12A | BAJ89368.1 | 44.35 |
| P12H | BAJ89368.1 | 44.35 |
| P10B | BAJ86656.1 | 45.16 |
| P58aF | XP_002463702.1 | 43.71 |

TABLE 11-continued

List of cloned EUGT11 homologs and their amino acid percent identity to EUGT11.

| UGT | Accession | % identity to EUGT11 |
|---|---|---|
| P59aG | XP_002463705.1 | 43.51 |
| P76H | NP_001140711.1 | 28.81 |

Example 8—Cell-Free Biocatalytic Production of Reb-D

The cell-free approach is an in vitro system where RebA, stevioside or a steviol glycoside mixture is enzymatically converted to RebD. The system requires stoichiometric amounts of UDP-glucose and therefore UDP-glucose regeneration from UDP and sucrose using sucrose synthase can be used. Additionally, sucrose synthase removes UDP produced during the reaction, which improves conversion to glycosylated products by alleviated product inhibition observed for glycosylation reactions. See, WO 2011/153378.

Enzyme Expression and Purification

UGT91D2e-b (described in Example 6) and EUGT11 are key enzymes that catalyze the glycosylation of RebA yielding RebD. These UGTs were expressed in bacteria (*E. coli*) but one of ordinary skill in the art will appreciate that such proteins also can be prepared using different methods and hosts (e.g., other bacteria such as *Bacillus* sp., yeast such as *Pichia* sp. or *Saccharomyces* sp., other fungi (e.g., *Aspergillus*), or other organisms). For example, the proteins can be produced by in vitro transcription and translation or by protein synthesis.

The UGT91D2e-b and EUGT11 genes were cloned in pET30a or pGEX4T1 plasmids. Resulting vectors were transformed into an XJb (DE3) Autolysis *E. coli* strain (ZymoResearch, Orange, CA). Initially, *E. coli* transformants were grown overnight at 30° C. in NZCYM medium, followed by induction with 3 mM arabinose and 0.1 mM IPTG, and further incubation overnight at 30° C. The corresponding fusion proteins were purified by affinity chromatography using included 6HIS- or GST-tags and standard methods. One skilled in the art will appreciate that other protein purification methods such as gel filtration or other chromatography techniques also can be used, along with precipitation/crystallization or fractionation with e.g., ammonium sulfate. While EUGT11 was expressed well using the initial conditions, UGT91D2e-b required several modifications to the base protocol to increase protein solubility, including lowering the temperature of the overnight expression from 30° C. to 20° C. and adding 2% ethanol to the expression medium. Generally 2-4 mg/L of soluble GST-EUGT11 and 400-800 µg/l of GST-UGT91D2e-b were purified with this method.

Stability of EUGT11

Reactions were conducted to explore the stability of EUGT11 under various RebA to RebD reaction conditions. Omitting the substrate from the reaction mixture, EUGT11 was pre-incubated for various periods of time before substrate was added. Following a pre-incubation of the enzyme in 100 mM Tris-HCl buffer, substrate (100 µM RebA) and other reaction components (300 µM UDP-glucose, and 10 U/mL Alkaline Phosphatase (Fermentas/Thermo Fisher, Waltham, MA)) were added (0, 1, 4 or 24 hours after the incubation was started). The reaction was then allowed to proceed for 20 h, after which the reactions were stopped and RebD product-formation measured. Experiments were repeated at different temperatures: 30° C., 32.7° C., 35.8° C. and 37° C.

The activity of EUGT11 was reduced rapidly when the enzyme was pre-incubated at 37° C., reaching approximately half activity after 1 hour, and having almost no activity after 4 hours. At 30° C., the activity was not significantly reduced after 4 hours and after 24 hours, approximately one-third of the activity remained. This suggests that EUGT11 is heat-labile.

To assess the thermal stability of EUGT11 and to compare it with the other UGTs in the steviol glycosylation pathway, denaturation temperatures of the proteins were determined using differential scanning calorimetry (DSC). Use of DSC thermograms to estimate denaturation temperatures, TD, is described, for example, by E. Freire in *Methods in Molecular Biology* 1995, Vol. 40 191-218. DSC was performed (using 6HIS-purified EUGT11, yielding an apparent TD of 39° C.; while when GST-purified 91D2e-b was used, the measured TD was 79° C. For reference, the measured TD when using 6HIS-purified UGT74G1, UGT76G1 and UGT85C2 was 86° C. in all cases. One of skill in the art will recognize that enzyme immobilization or addition of thermal protectants can be added to the reactions to improve stability of the protein. Non-limiting examples of thermal protectants include trehalose, glycerol, ammonium sulphate, betaine, trimethylamine oxide, and proteins.

Enzyme Kinetics

A series of experiments were performed to determine kinetic parameters of EUGT11 and 91D2e-b. For both enzymes, 100 µM RebA, 300 µM UDP-glucose, and 10 U/mL Alkaline Phosphatase (Fermentas/Thermo Fisher, Waltham, MA) were used in the reactions. For EUGT11, the reactions were performed at 37° C. using 100 mM Tris-HCl, pH 7, and 2% enzyme. For 91D2e-b, the reactions were performed at 30° C. using 20 mM Hepes-NaOH, pH 7.6, 20% (by volume) enzyme. The initial velocities ($V_0$) were calculated in the linear range of a product versus time plot.

To first investigate the linearity intervals, initial time-courses were done for each enzyme. EUGT11 was assayed at 37° C. for 48 h at initial concentrations of 100 µM RebA and 300 µM UDP-glucose. UGT91D2e-b was assayed at 37° C. for 24 h at initial concentrations of 200 µM RebA and 600 µM UDP-glucose. Based on these range-finding studies, it was determined that the initial 10 minutes in the case of EUGT11, and the initial 20 minutes in UGT91D2e-b would be in the linear range with respect to product formation, and therefore initial velocities of each reaction were calculated in those intervals. In the case of EUGT11, RebA concentrations assayed were 30 µM, 50 µM, 100 µM, 200 µM, 300 µM and 500 µM. Concentration of UDP-glucose was always three times the concentration of RebA and incubation was performed at 37° C. By plotting the calculated $V_0$ as a function of the substrate concentrations, Michaelis-Menten curves were generated. By plotting the reciprocal of $V_0$ and the reciprocal of [S], a Lineweaver-Burk graphic was obtained, with $y=339.85x+1.8644$; $R^2=0.9759$.

$V_{max}$ and $K_M$ parameters were determined from the curve-fit Lineweaver-Burk data, calculated from the x- and y intercepts ($x=0$, $y=1/V_{max}$) and ($y=0$, $x=-1/K_M$). Additionally, the same parameters also were calculated by a non-linear least squares regression, using the SOLVER function in Excel. The results obtained with both methods for EUGT11 and RebA are presented in Table 12, along with all the kinetic parameters of this example. Results from both Nonlinear Least Square Fit method and Lineweaver-Burk plot are presented in Table 12. $K_{cat}$ is calculated based on $V_{max}$ divided by the approximate amount of protein in the assay.

TABLE 12

Comparison of kinetic parameters for EUGT11 and UGT 91D2e-b, with RebA or UDP-glucose as substrate.

| | Nonlinear Least Square Fit | | | | Lineweaver-Burk plot | | | |
|---|---|---|---|---|---|---|---|---|
| | Reb A | | UDP-glucose | | Reb A | | UDP-glucose | |
| | EUGT11 | 91D2e-b | EUGT11 | 91D2e-b | EUGT11 | 91D2e-b | EUGT11 | 91D2e-b |
| $V_{max}$ (μM · $min^{-1}$) | 0.52 | 0.34 | 0.79 | 0.19 | 0.54 | 0.44 | 0.78 | 0.18 |
| $K_{cat}$ ($min^{-1}$) | 8.11 | 0.32 | 12.32 | 0.2 | 8.42 | 0.41 | 12.1 | 0.19 |
| $K_M$ (μM) | 162.5 | 1150 | 130 | 45.1 | 182.3 | 1580 | 118 | 41.9 |
| $K_{cat}/K_M$ ($min^{-1}$ · $\mu M^{-4}$) | 0.05 | 0.000275 | 0.095 | 0.00454 | 0.046 | 0.000258 | 0.102 | 0.00463 |

In order to investigate the influence of UDP-glucose concentration in the glycosylation reaction, as well as the affinity of EUGT11 for UDP-glucose, similar kinetics analysis were performed. EUGT11 was incubated with increasing amounts of UDP-glucose (20 μM, 50 μM, 100 μM, and 200 μM), maintaining an excess of RebA (500 μM). The kinetic parameters were calculated as described above, and shown in Table 12.

In the case of UGT91D2e-b, RebA concentrations assayed were 50 μM, 100 μM, 200 μM, 300 μM, 400 μM and 500 μM. Concentration of UDP-glucose was always three times the concentration of RebA and incubation was performed at 30° C., in the reaction conditions described above for UGT91D2e-b. The kinetic parameters were calculated as previously described; and the resulting kinetic parameters are shown in Table 12. Additionally, kinetic parameters of UGT91D2e-b towards UDP-glucose were determined. UGT91D2e-b was incubated with increasing amounts of UDP-glucose (30 μM, 50 μM, 100 μM, and 200 μM), maintaining an excess of RebA (1500 μM). incubation was performed at 30° C., in optimal conditions for UGT91D2e-b. The kinetic parameters were calculated as previously described and results are presented in Table 12.

By comparison of the kinetics parameters for EUGT11 and 91D2e-b, it was concluded that 91D2e-b has a lower K and has lower affinity for RebA (higher $K_M$) although the $K_M$ for UDP-glucose of 91D2e-b is lower than EUGT11. UGT91D2e-b has a lower $K_{cat}/K_M$ which is a measure of catalytic efficiency, combining information on rate of catalysis with a particular substrate (Kcat) and the strength of enzyme-substrate binding ($K_M$).

Determining the Limiting Factor in Reactions

Under the conditions described above for EUGT11, approximately 25% of the RebA administered was converted to RebD. The limiting factor in these conditions could be either the enzyme, UDP-glucose or RebA. Experiments were set up to distinguish between these possibilities. A standard assay was allowed to run its course during 4 hours. This was followed by addition of either extra RebA substrate, extra enzyme, extra UDP-glucose or extra enzyme and UDP-glucose. Addition of extra enzyme resulted in a relative increase of the conversion of around 50%, adding extra RebA or UDP-glucose alone did not increase the conversion significantly, but the simultaneous addition of enzyme and UDP-glucose increased the conversion approximately 2-fold.

Experiments were conducted to examine the limit to this benefit of adding bolus amounts of UDP-glucose and fresh enzyme in the conversion of RebA to RebD reaction. Additional enzyme or enzyme and UDP-glucose were added after 1, 6, 24 and 28 hours. In the case of the addition of both extra EUGT11 and UDP-glucose, a conversion of more than 70% was achieved. No other components had a significant effect on the conversion. This indicates that EUGT11 is a primary limiting factor for the reaction but UDP-glucose also is limiting. As UDP-glucose is present at 3-fold higher concentration than RebA, this indicates that UDP-glucose may be somewhat unstable in the reaction mixture, at least in the presence of EUGT11. Alternatively, as explained below, EUGT11 may be metabolizing the UDP-glucose.

Inhibition Studies

Experiments were conducted to determine if factors such as sucrose, fructose, UDP, product (RebD) and impurities in the less pure Stevia extracts raw materials inhibited the extent of the conversion of steviol glycoside substrates to RebD. In a standard reaction mixture, excess of the potential inhibitors (sucrose, fructose, UDP, RebD, or a commercial blend of steviol glycosides (*Steviva*, Steviva Brands, Inc., Portland, OR)) were added. Following incubation, RebD-production was quantified. Addition of 500 μg/ml of the commercial Steviva mix (approximately 60% 1,2-stevioside, 30% RebA, 5% Rubusoside, 2% 1,2-bioside, less than 1% of RebD, RebC and others, as evaluated by LC-MS) was not found to be inhibitory, but rather increased the overall RebD production (to around 60 μM from around 30 μM without any addition) well beyond the RebD originally added with the blend (around 5 μM). From the molecules tested, only UDP was shown to have an inhibitory effect on RebD-production at the concentration used (500 μM), as measured by LC-MS. The RebD that was produced was less than 7 μM. This inhibition can be alleviated in the in vivo or in vitro reactions for RebD production, by including an UDP recycling system to UDP-glucose, either by yeast or by an added SUS (sucrose synthase enzyme) in conjunction with sucrose. Moreover, when working with lower amounts of UDP-glucose (300 μM), the addition of alkaline phosphatase to remove UDP-G does not increase the amount of RebD produced in the in vitro glycosylations substantially, suggesting that the UDP produced may not be inhibitory at these concentrations.

RebA Vs Crude Steviol Glycoside Mix

In some experiments, a crude steviol glycoside mix was used as a source of RebA instead of purified RebA. As such a crude steviol glycoside mix contains a high percentage of stevioside along with RebA, UGT76G1 was included in the reactions. In vitro reactions were performed as described above using 0.5 g/l of the *Steviva*® mix as substrate and enzyme (UGT76G1 and/or EUGT11) and incubated at 30° C. The presence of steviol glycosides was analyzed by LC-MS.

When only UGT76G1 was added to the reactions, stevioside was converted to RebA quite efficiently. An unknown penta-glycoside (with a retention time peak at 4.02 min) also was detected. When only EUTG11 was added to the reaction, large amounts of RebE, RebA, RebD and an unknown steviol-pentaglycoside (with a retention time peak at 3.15 min) were found. When both EUGT11 and UGT76G1 were added to the reactions, the stevioside peak was reduced, and almost entirely converted to RebA and RebD. There were trace amounts of the unknown steviol-pentaglycoside (peak at 4.02 min). No RebE was detected nor was the second unknown steviol-pentaglycoside (peak at 3.15 min). This result indicated that the use of stevia extracts as a substrate to produce RebD in vitro is possible when EUGT11 and UGT76G1 are used in combination.

Non-Specific UDP-Glucose Metabolism

To determine if EUGT11 can metabolize UDP-glucose independently of the conversion of RebA to RebD, GST-purified EUGT11 was incubated in the presence or absence of RebA substrate, and UDP-glucose usage was measured as UDP-release, using the TR-FRET Transcreener® kit (BellBrook Labs). The Transcreener® kit is based on a tracer molecule bound to an antibody. The tracer molecule is displaced by UDP or ADP in a highly sensitive and quantitative manner. The FP kit includes an Alexa633 tracer bound to an antibody. The tracer is displaced by UDP/ADP. The displaced tracer freely rotates leading to a decrease in fluorescence polarization. Therefore, UDP production is proportional to a decrease in polarization. The FI kit includes a quenched Alexa594 Tracer bound to an antibody, which is conjugated to an IRDye® QC-1 quencher. The tracer is displaced by UDP/ADP, whereby the displaced tracer is un-quenched, leading to a positive increase in fluorescence intensity. Therefore, UDP production is proportional to an increase in fluorescence. A TR-FRET kit includes a HiLyte647 Tracer bound to an Antibody-Tb conjugate. Excitation of the terbium complex in the UV range (ca. 330 nm) results in energy transfer to the tracer and emission at a higher wavelength (665 nm) after a time delay. The tracer is displaced by UDP/ADP causing a decrease in TR-FRET.

It was observed that UDP-glucose measured was the same independent of the presence of RebA substrate. UDP release was not detectable in the absence of enzyme. This indicates a non-specific degradation of UDP-glucose by EUGT11. Nevertheless, RebD was still produced when RebA was added, suggesting that EUGT11 would preferentially catalyze RebA glycosylation over the non-specific UDP-glucose degradation.

Experiments were set up to find out the destiny of the glucose molecule in the absence of RebA or other obvious glycosylation substrates. One common factor in all previous reactions was the presence of Tris buffer and/or trace amounts of glutathione, which both contain potential glycosylation sites. The effect of these molecules on the non-specific UDP-glucose consumption was assayed using GST-purified EUGT11 (with glutathione) and HIS-purified enzyme (without glutathione) in in vitro reactions, in the presence or absence of RebA. UDP-glucose usage was measured as UDP-release, using the TR-FRET Transcreener® kit. UDP release occurred in all cases and was independent of the presence of RebA. UDP release was slower when the HIS-purified enzyme was used, but the overall catalytic activity of the enzyme in conversion of RebA to RebD was also lower, suggesting a lower amount of active soluble enzyme present in the assay. Therefore, it appears that the UDP-glucose metabolism by EUGT11 is independent of the presence of substrate and independent of the presence of glutathione in the reaction, under the conditions tested.

To test the effect of Tris on the metabolism of UDP-glucose by EUGT11, GST-EUGT11 was purified using a Tris- or a PBS-based buffer for the elution, obtaining similar amounts of protein in both cases. Tris- and PBS-purified enzymes were used in in vitro reactions using Tris and HEPES as buffers respectively, in the presence or absence of RebA in a similar manner as above. In both conditions, the UDP release was the same in the reactions whether RebA was added or not, indicating that the metabolism of UDP-glucose by EUGT11 is independent of both the presence of RebA and Tris in the reaction. This suggests that the UDP-release detected may somehow be an artifact caused by a property of EUGT11 or, alternatively, EUGT11 may be hydrolyzing UDP-glucose. EUGT11 is still efficient at converting RebA to RebD preferentially and the loss of UDP-G can be compensated by addition of the sucrose synthase recycling system described below.

RebA Solubility

The solubility of RebA determines the concentration that can be used both for the whole-cell approach and for the cell-free approach. Several different solutions of RebA in water were made and left at room temperature for several days. After 24 hours of storage, RebA precipitated at concentrations of 50 mM or higher. Twenty-five mM RebA started to precipitate after 4-5 days, while 10 mM or lower concentrations remained in solution, even when stored at 4° C.

RebD Solubility

The solubility of RebD was assessed by making several different solutions of RebD in water were made and incubated at 30° C. for 72 hours. RebD was found to be soluble in water initially in concentrations of 1 mM or lower while concentrations of 0.5 mM or less were found to be stable for longer periods of time. One with skill in the art will recognize that the solubility can be influenced by any number of conditions such as pH, temperature, or different matrices.

Sucrose Synthase

Sucrose synthase (SUS) has been used to regenerate UDP-glucose from UDP and sucrose (FIG. 11) for other small molecule glycosylations (Masada Sayaka et al. *FEBS Letters* 581 (2007) 2562-2566). Three SUS1 genes from *A. thaliana, S. rebaudiana* and coffee (*Coffea arabica*) were cloned into pGEX4T1 *E. coli* expression vectors (see FIG. 17 for the sequences). Using methods similar to those described for EUGT11, around 0.8 mg/l of GST-AtSUS1 (*A. thaliana* SUS1) was purified. Initial expression of CaSUS1 (*Coffea arabica* SUS1) and SrSUS1 (*S. rebaudiana* SUS1) followed by GST-purification did not produce significant amounts of protein although, when analyzed by western blot, the presence of GST-SrSUS1 was verified. When GST-SrSUS1 was expressed at 20° C. in the presence of 2% ethanol, approximately 50 μg/l of enzyme was produced.

Experiments were performed to evaluate the UDP-glucose regenerating activity of the purified GST-AtSUS1 and GST-SrSUS1. In vitro assays were conducted in 100 mM Tris-HCl pH=7.5 and 1 mM UDP (final concentration). Either ~2.4 μg of purified GST-AtSUS1, ~0.15 μg of GST-SrSUS1, or ~1.5 μg commercial BSA (New England Biolabs, Ipswich, MA) were also added. Reactions were done in presence or absence of ~200 mM sucrose and incubated at 37° C. for 24 h. Product UDP-glucose was measured by HPLC as described in the analytical section. AtSUS1 produced ~0.8 mM UDP-glucose when sucrose was present. No UDP-glucose was observed when SrSUS1 or the negative control (BSA) was used. The lack of activity observed for SrSUS1 could be explained by the poor quality and concentration of the purified enzyme. UDP-glucose production by AtSUS1 was sucrose dependent and, therefore, it was concluded that AtSUS1 can be used in a coupled reaction to regenerate the UDP-glucose used by EUGT1 or other UGTs for small molecule glycosylation (FIG. 11, above).

SUS catalyzes the formation of UDP-glucose and fructose from sucrose and from UDP as depicted in FIG. 11. This UDP-glucose then can be used by EUGT11 for glycosylation of RebA to produce RebD. In vitro assays as described above were performed, adding ~200 mM sucrose, 1 mM UDP, 100 μM RebA, ~1.6 μg purified GST-AtSUS1 and ~0.8 μg GST-EUGT11. Formation of product, RebD, was evaluated by LC-MS. When AtSUS, EUGT11, sucrose and UDP were mixed with RebA, 81±5 μM of RebD was formed. The reaction was dependent on the presence of AtSUS, EUGT11 and sucrose. The conversion rate was similar to what has been observed previously using UDP-glucose provided extraneously. This shows that AtSUS can be used to regenerate UDP-glucose for RebD-formation by EUGT11.

Example 9: Whole-Cell Biocatalytic Production of RebD

In this example, several parameters were studied that are factors for using whole cell biocatalytic systems in the production of RebD from RebA or other steviol glycosides. The ability of raw materials to cross the cell membrane and availability of UDP-glucose are two such factors. Permeabilizing agents were studied as well as different cell types to ascertain which systems may be the most beneficial for RebD production.

Permeabilizing Agents

Several different permeabilization agents have previously been shown to allow intracellular enzymatic conversion of various compounds that are normally not able to cross a cell membrane (Chow and Palecek, *Biotechnol Prog.* 2004 March-April; 20(2):449-56). In several cases, the approaches resemble a partial lysis of the cells and, in yeast, often rely on the removal of the cell membrane by a detergent and the encapsulation of the enzymes inside of the remaining cell wall, which is permeable to smaller molecules. Common to these methods is the exposure to the permeabilizing agent followed by a centrifugation step to pellet cells before the addition of the substrate. See, for example, Flores et al., *Enzyme Microb. Technol.*, 16, pp. 340-346 (1994); Presecki & Vasic-Racki, *Biotechnology Letters*, 27, pp. 1835-1839 (2005); Yu et al., *J Ind Microbiol Biotechnol*, 34, 151-156 (2007); Chow and Palecek, Cells. *Biotechol. Prog.*, 20, pp. 449-456 (2004); Fernandez et al., *Journal of Bacteriology*, 152, pp. 1255-1264 (1982); Kondo et al., *Enzyme and microbial technology*, 27, pp. 806-811 (2000); Abraham and Bhat, *J Ind Microbiol Biotechnol*, 35, pp. 799-804 (2008); Liu et al.; *Journal of bioscience and bioengineering*, 89, pp. 554-558 (2000); and Gietz and Schiestl, *Nature Protocols*, 2, pp. 31-34 (2007) regarding permeabilization of yeast. See, Naglak and Wang, *Biotechnology and Bioengineering*, 39, pp. 732-740 (1991); Alakomi et al., *Applied and environmental Microbiology*, 66, pp. 2001-2005 (2000); and Fowler and Zabin, *Journal of bacteriology*, 92, pp. 353-357 (1966) regarding permeabilization of bacteria. As described in this example, it was determined if cells could remain viable and therefore could retain de novo UDP-glucose biosynthesis.

Experiments were done to establish conditions for permeabilization in *E. coli* and in yeast. Growing cells (*S. cerevisiae* or *E. coli*) were treated with different concentrations/combinations of permeabilization agents: toluene, chloroform and ethanol for permeabilization of *S. cerevisiae*, and guanidine, lactic acid, DMSO and/or Triton X-100 for permeabilization of *E. coli*. Tolerance of both model organisms to high concentrations of RebA and other potential substrates also was evaluated. The permeabilization was measured by the amount of RebD produced from a EUGT11-expressing organism after incubation in a RebA containing medium (feeding experiment). Enzyme activity was monitored before and after exposure to the permeabilizing agents by lysing the cells and analyzing the activity of the released UGTs in an in vitro assay.

In yeast, none of the permeabilization conditions tested resulted in an increase on RebD above the detected background (i.e., contaminating RebD levels present in the RebA stock used for feeding). This indicates that, under the tested conditions, yeast cells remain impermeable to RebA and/or the reduced cell viability caused by the solvents results in a decrease of EUGT11 activity as well.

In *E. coli*, none of the conditions tested resulted in permeabilization of the cells and subsequent production of RebD above background levels. Detectable levels of RebD were measured when lysates from strains expressing EUGT11 were used in the in vitro reactions (data not shown), indicating that EUGT11 enzyme is present and active even after all permeabilization treatments (though the level of activity varies). The permeabilization treatments had little or no effect on cell viability, except treating cultures with 0.2 M guanidine and 0.5% TritonX-100, which severely decreased viability.

*S. cerevisiae* also was subjected to permeabilization assays not allowing further growth of the cells using Triton X-100, N-lauryl sarcosine (LS), or Lithium acetate+polyethylene glycol (LiAc+PEG). That is, under these conditions, permeabilization renders the cells unviable by removing the cell membrane altogether while retaining the cell-wall as a barrier to keep enzymes and gDNA inside. In such methods, UDP-glucose can be supplemental or recycled as described above. The advantage of permeabilization versus the purely in vitro approach is that individual enzymes do not need to be separately produced and isolated.

Figure 18:
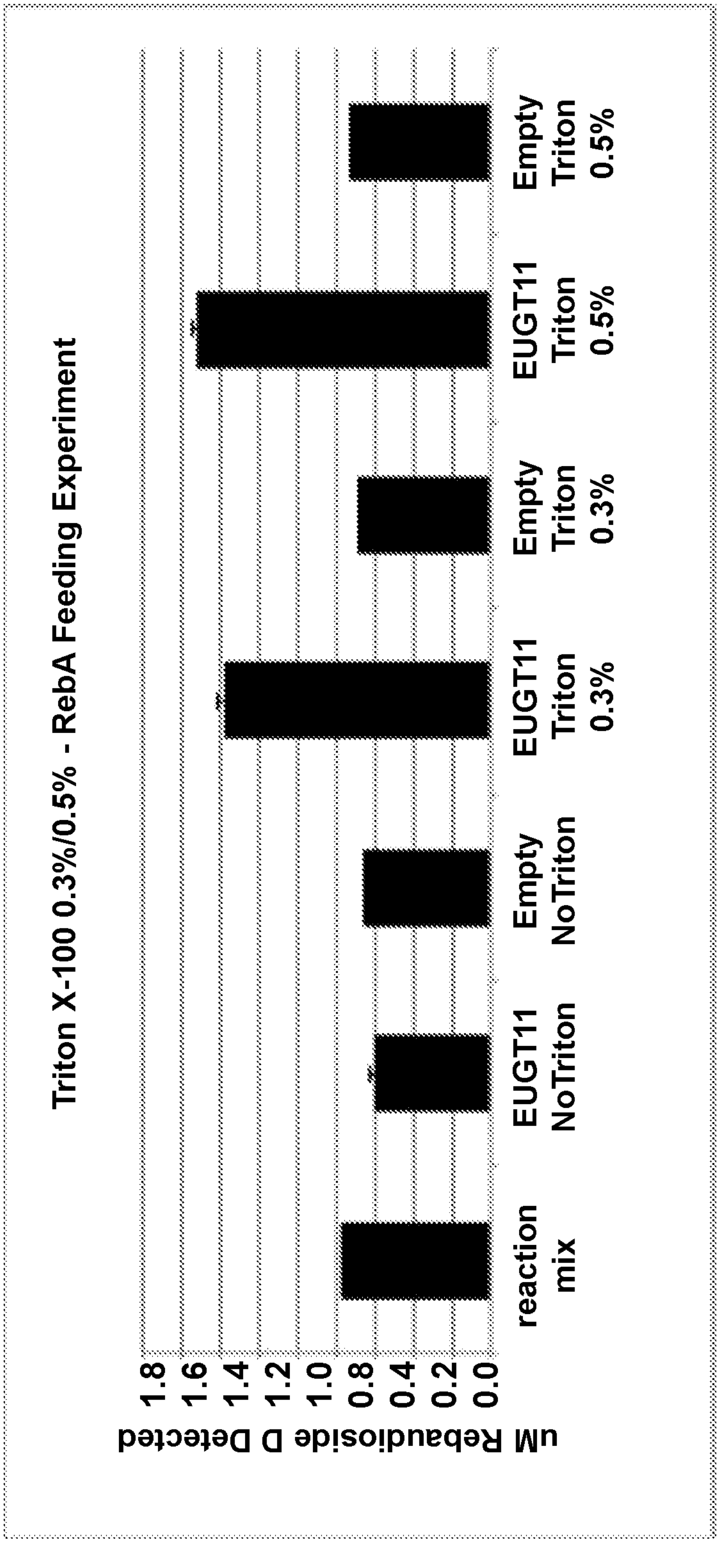
FIG. 18 is a bar graph of rebD production in permeabilized *S. cerevisiae*, which had been transformed with EUGT11 or an empty plasmid ("Empty"). Cells were grown to exponential growth phase, washed in PBS buffer and subsequently treated with Triton X-100 (0.3% or 0.5% in PBS) 30° C., 30 min. After permeabilization cells were washed in PBS and resuspended in reaction mix containing 100 μM RebA and 300 μM UDP-glucose. Reactions proceeded for 20 h, 30° C.

N-Lauryl sarcosine treatment resulted in inactivation of EUGT11 and only a minor increase in RebD was detected when LiAc/PEG was applied (data not shown). Treatment with Triton X-100 0.3% or 0.5%, however, increased the amount of RebD above background levels (see FIG. 18) while sustaining the activity of EUGT11. For Triton X-100 assays, overnight cultures were washed three times in PBS buffer. Cells corresponding to 6 $OD_{600}$ units were resuspended in PBS containing 0.3% or 0.5% Triton X-100 respectively. Treated cells were vortexed and incubated 30 minutes at 30° C. After treatment, cells were washed in PBS buffer. Cells corresponding to 5 $OD_{600}$ units were used in an in vitro assay, as described for GST-EUGT11 and 0.6 $OD_{600}$ units were resuspended in reaction buffer and incubated overnight at 30° C. as described for the LS treated samples. Untreated samples were used as controls.

Lysates from transformants expressing EUGT11 were able to convert some RebA into RebD (8 to 50 μM were measured in the reactions) when cells were untreated or after treatment with LiAC/PEG or Triton X100. However, no RebD was measured in lysates of cell pellets treated with LS. Permeabilized but non-lysed cells were able to produce some RebD (1.4 to 1.5 μM measured) when treated with 0.3% or 0.5% Triton X100 (FIG. 18) while no RebD was found on the samples treated with LS or LiAC/PEG. These results show that RebD can be produced from RebA biocatalytically using whole cells and using Triton X100 as the permeabilizing agent.

Example 10—Assessment of Codon Optimized UGT Sequences

Optimal coding sequences for UGT 91d2e, 74G1, 76G1, and 85C2 were designed and synthesized for yeast expression using two methodologies, supplied by GeneArt (Regensburg, Germany) (SEQ ID NOs: 6, 2, 8, and 4, respectively) or DNA 2.0 (Menlo Park, CA) (SEQ ID NOs: 84, 83, 85, and 82, respectively). The amino acid sequences of UGT 91d2e, 74G1, 76G1, and 85C2 (SEQ ID NOs: 5, 1, 7, and 3, respectively) were not changed.

The wild-type, DNA 2.0, and GeneArt sequences were assayed for in vitro activity to compare reactivity on substrates in the steviol glycosides pathway. UGTs were inserted in high copy (2p) vectors and expressed from a strong constitutive promoter (GPD1) (vectors P423-GPD, P424-GPD, P425-GPD, and P426-GPD). The plasmids were transformed individually into the universal Watchmaker strain, EFSC301 (described in Example 3 of WO2011/153378) and assays were carried out using cell lysates prepared from equal amount of cells (8 OD units). For the enzymatic reactions, 6 µL of each cell lysate were incubated in a 30 µL reaction with 0.25 mM steviol (final concentration) to test UGT74G1 and UGT85C2 clones, and with 0.25 mM 13-SMG (13SMG) (final concentration) to test 76G1 and 91D2e UGTs. Assays were carried out for 24 hours at 30° C. Prior to LC-MS analysis, one volume of 100% DMSO was added to each reaction, samples were centrifuged at 16000 g, and the supernatants analysed.

The lysates expressing the GeneArt-optimized genes provided higher levels of UGT activity under the conditions tested. Expressed as a percentage of the wild-type enzyme, the GeneArt lysates showed equivalent activity to the wild-type for UGT74G1, 170% activity for UGT76G1, 340% activity for UGT85C2 and 130% activity for UGT91D2e. Using UGT85C2 may improve the overall flux and productivity of cells for production of Reb-A and Reb-D when expressed in *S. cerevisiae*.

Further experiments were conducted to determine if the codon-optimized UGT85C2 could reduce 19-SMG accumulation and increase rubusoside and higher glycosylated steviol glycosides production. The production of 19-SMG and rubusoside were analysed in a steviol-feeding experiment of *S. cerevisiae* strain BY4741 expressing the wild type UGT74G1 as well as the codon-optimized UGT85C2 from high copy (2p) vectors under strong constitutive promoter (GPD1) (vectors P426-GPD and P423-GPD, respectively). Whole culture samples (without cell removal) were taken and boiled in an equal volume of DMSO for total glycosides levels. Intracellular concentrations reported were obtained by pelleting cells, and resuspending in 50% DMSO to the volume of the original culture sample taken, followed by boiling. The "total" glycosides level and the normalized intracellular level then were measured using LC-MS. Using wild type UGT74G1 and wild type UGT85C2, approximately 13.5 µM rubusoside was produced in total with a maximum normalized intracellular concentration of about 7 µM. In contrast, when wild type UGT74G1 and codon-optimized UGT85C2 were used, a maximum of 26 µM rubusoside was produced, or approximately double of what was produced using the wild type UGT85C2. Additionally, the maximum normalized intracellular concentration of rubusoside was 13 µM, again an approximate doubling of what was produced using wild type UGT85C2. Intracellular concentration of 19-SMG was significantly reduced from a maximum of 35 µM using the wild type UGT85C2 to 19 µM using the codon-optimized UGT85C2. Consequently, about 10 µM less total 19-SMG was measured for the codon-optimized UGT85C2. This shows that more 19-SMG is converted into rubusoside and confirms that the wild type UGT85C2 is a bottleneck.

During diversity screening, another homolog of UGT85C2 was discovered during *Stevia rebaudiana* cDNA cloning. The homolog has the following combination of conserved amino acid polymorphisms (with respect to the amino acid numbering of the wild-type *S. rebaudiana* UGT85C coding sequence set forth in Accession No. AY345978.1): A65S, E71Q, T270M, Q289H, and A389V. This clone, termed UGT85C2 D37, was expressed through coupled in vitro transcription-translation of PCR products (TNT*T7 Quick for PCR DNA kit, Promega). The expression product was assayed for glycosylation activity using steviol (0.5 mM) as the sugar acceptor, as described in WO/2011/153378 with the exception that assays were allowed to incubate for 24 hours. As compared to the wildtype UGT85C2 control assay, the D37 enzyme appears to have approximately 30% higher glycosylation activity.

Example 11—Identification of a Novel & Rebaudiana KAH

A partial sequence (GenBank Accession No. BG521726) was identified in the *Stevia rebaudiana* EST data base that had some homology to a *Stevia* KAH. The partial sequence was blasted against raw *Stevia rebaudiana* pyrosequencing reads using CLC main workbench software. Reads that partially overlapped with the ends of the partial sequence were identified and used to increase the length of the partial sequence. This was done several times until the sequence encompassed both the start- and the stop codons. The complete sequence was analyzed for frameshift mutations and nucleotide substitutions that may have been introduced by blasting the complete sequence against the raw pyrosequencing reads. The resulting sequence was designated SrKAHe1. See FIG. 12.

Activity of the KAH encoded by SrKAHe1 was assessed in vivo in *S. cerevisiae* background strain CEN.PK 111-61A, which expresses genes encoding enzymes constituting the entire biosynthetic pathway from the yeast secondary metabolites isopentenyl pyrophosphate (IPP) and farnesyl pyrophosphate (FPP) to steviol-19-O-monoside, except the steviol synthase enzyme that converts ent-kaurenoic acid to steviol.

Briefly, the *S. cerevisiae* strain CEN.PK 111-61A was modified to express an *Aspergillus nidulans* GGPPS, a 150 nt truncated *Zea mays* CDPS (with a new start codon, see below), a *S. rebaudiana* KS, a *S. rebaudiana* KO and the *S. rebaudiana* UGT74G1 from chromosomally integrated gene copies, with TPI1 and GPD1 yeast promoters driving transcription. The CEN.PK 111-61A yeast strain that expresses all of these genes was designated EFSC2386. Thus, strain EFSC2386 contained the following integrated genes: *Aspergillus nidulans* Geranyl geranyl pyrophosphate synthase (GGPPS); *Zea mays* ent-Copalyl diphosphate synthase (CDPS); *Stevia rebaudiana* ent-Kaurene synthase (KS); *Stevia rebaudiana* ent-kaurene oxidase (KO); and *Stevia*

*rebaudiana* UGT74G1; in combination with the pathway from IPP and FPP to steviol-19-O-monoside, without a steviol synthase (KAH).

Expression of different steviol synthases (from episomal expression plasmids) was tested in strain EFSC2386 in combination with the expression of various CPRs (from episomal expression plasmids), and production of steviol-19-O-monoside was detected by LC-MS analysis of culture sample extracts. The nucleic acids encoding the CPRs were inserted in the multi cloning site of the p426 GPD basic plasmid while the nucleic acids encoding the steviol synthases were inserted in the multi cloning site the p415 TEF basic plasmid (p4XX basic plasmid series by Mumberg et al., *Gene* 156 (1995), 119-122). Production of steviol-19-O-monoside occurs when a functional steviol synthase enzyme is present.

The KAHs that were expressed from episomal expression plasmids in strain EFSC2386 were "indKAH" (Kumar et al, Accession no. DQ398871; Reeja et al., Accession No. EU722415); "KAH1" (*S. rebaudiana* steviol synthase from Brandle et al., U.S. Patent Publication No. 2008/0064063 A1); "KAH3" (*A. thaliana* steviol synthase from Yamaguchi et al., U.S. Patent Publication No. 2008/0271205 A1); "SrKAHe1" (*S. rebaudiana* steviol synthase cloned from *S. rebaudiana* cDNA as described above); and "DNA2.0.SrKAHe1" (codon optimized sequence (DNA2.0) encoding *S. rebaudiana* steviol synthase, see FIG. 12B).

The CPRs that were expressed from episomal expression plasmids in strain EFSC2386 were "CPR1" (*S. rebaudiana* NADPH dependent cytochrome P450 reductase (Kumar et al., Accession no. DQ269454); "ATR1" (*A. thaliana* CPR, Accession No. CAA23011, see also FIG. 13); "ATR2" (*A. thaliana* CPR, Accession No. CAA46815, see also FIG. 13); "CPR7" (*S. rebaudiana* CPR, see FIG. 13, CPR7 is similar to "CPR1"); "CPR8" (*S. rebaudiana* CPR, similar to *Artemisia annua* CPR, see FIG. 13); and "CPR4" (*S. cerevisiae* NCP1 (Accession No. YHR042W, see also FIG. 13).

Table 13 provides the levels of steviol-19-O-monoside (μM) in strain EFSC2386 with the various combination of steviol synthases and CPRs.

TABLE 13

19-SMG Production

| Strain | 19-SMG production (μM) |
|---|---|
| "indKAH" CPR1 | 0.000 |
| "indKAH" ATR1 | 0.000 |
| "indKAH" ATR2 | 0.000 |
| "indKAH" CPR7 | 0.000 |
| "indKAH" CPR8 | 0.000 |
| "indKAH" CPR4 | 0.000 |
| "KAH1" CPR1 | 0.000 |
| "KAH1" ATR1 | 0.000 |
| "KAH1" ATR2 | 0.000 |
| "KAH1" CPR7 | 0.000 |
| "KAH1" CPR8 | 0.000 |
| "KAH1" CPR4 | 0.000 |
| "KAH3" CPR1 | 5.300 |
| "KAH3" ATR1 | 5.921 |
| "KAH3" ATR2 | 0.000 |
| "KAH3" CPR7 | 5.693 |
| "KAH3" CPR8 | 0.000 |
| "KAH3" CPR4 | 0.000 |
| "SrKAHe1" CPR1 | 20.129 |
| "SrKAHe1" ATR1 | 15.613 |
| "SrKAHe1" ATR2 | 40.407 |
| "SrKAHe1" CPR7 | 33.724 |
| "SrKAHe1" CPR8 | 41.695 |
| "SrKAHe1" CPR4 | 28.949 |

TABLE 13-continued

19-SMG Production

| Strain | 19-SMG production (μM) |
|---|---|
| "DNA2.0.SrKAHe1" CPR1 | 26.065 |
| "DNA2.0.SrKAHe1" ATR1 | 26.974 |
| "DNA2.0.SrKAHe1" ATR2 | 54.354 |
| "DNA2.0.SrKAHe1" CPR7 | 30.797 |
| "DNA2.0.SrKAHe1" CPR8 | 50.956 |
| "DNA2.0.SrKAHe1" CPR4 | 30.368 |

Only KAH3 and the steviol synthase encoded by SrKAHe1 had activity when expressed in *S. cerevisiae*. The DNA 2.0. codon optimized SrKAHe1 sequence encoding steviol synthase resulted in a level of steviol-19-O-monoside accumulation that was approximately one order of magnitude higher as compared with a codon optimized KAH3 when each were co-expressed with optimal CPRs. In the experiments presented in this example, the combination of KAH1 and ATR2 CPR did not result in the production of steviol-19-O-monoside.

Example 12—Pairings of CPRs and KO

The CEN.PK S. *Cerevisiae* EFSC2386 strain and the CPRs referred to in this Example are described in the Example 11 ("Identification of *S. rebaudiana* KAH"). EFSC2386 contained the following integrated genes: *Aspergillus nidulans* Geranyl geranyl pyrophosphate synthase (GGPPS); *Zea mays* ent-copalyl diphosphate synthase (CDPS); *Stevia rebaudiana* ent-kaurene synthase (KS); and *Stevia rebaudiana* ent-kaurene oxidase (KO). This strain produces ent-kaurenoic acid that was detected by LC-MS analysis.

A collection of cytochrome P450 reductases (CPRs) were expressed and tested in strain EFSC2386; "CPR1" (*S. rebaudiana* NADPH dependent cytochrome P450 reductase, Kumar et al., Accession no. DQ269454); "ATR1" (*A. thaliana* CPR, Accession No. CAA23011); "ATR2" (*A. thaliana* CPR, Accession No. CAA46815); "CPR7" (*S. rebaudiana* CPR, CPR7 is similar to "CPR1"); "CPR8" (*S. rebaudiana* CPR, similar to *Artemisia annua* CPR; and "CPR4" (*S. cerevisiae* NCP1, Accession No. YHR042W).

Overexpression of the *S. cerevisiae* endogenous native CPR (referred to as CPR4 in Table 14), and especially overexpression of one of the *A. thaliana* CPRs namely ATR2, gives good activation of the *Stevia rebaudiana* kaurene oxidase (the latter called KO1 in Table 14) and results in increased accumulation of ent-kaurenoic acid. See Table 14, which presents the area under curve (AUC) of the ent-kaurenoic acid peak in the LC-MS chromatograms. KO1 is an ent-kaurenoic acid producing yeast control strain without additional overexpression of CPRs.

TABLE 14

Effect of Different Cytochrome P450 Reductase Enzymes with KO-1

| Cytochrome P450 Reductase | Ent-Kaurenoic Acid (AUC) |
|---|---|
| CPR-1 | 14113 |
| ATR-1 | 13558 |
| ATR-2 | 29412 |
| CPR-7 | 18918 |
| CPR-8 | 12590 |

TABLE 14-continued

| Effect of Different Cytochrome P450 Reductase Enzymes with KO-1 | |
|---|---|
| Cytochrome P450 Reductase | Ent-Kaurenoic Acid (AUC) |
| CPR-4 | 25103 |
| Control | 16593 |

Example 13—Evaluating KS-5 and KS-1 in Steviol Pathways

The yeast strain EFSC1972 is a CEN.PK 111-61A *S. cerevisiae* strain that has the biosynthetic pathway from IPP/FPP to rubusoside expressed by integrated gene copies encoding the *Aspergillus nidulans* GGPPS (internal name GGPPS-10), the *Stevia rebaudiana* KS (KS1, SEQ ID NO:133), the *Arabidopsis thaliana* KAH (KAH-3, SEQ ID NO:144), the *Stevia rebaudiana* KO (KO1, SEQ ID NO:138), the *Stevia rebaudiana* CPR (CPR-1, SEQ ID NO:147), the full length *Zea mays* CDPS (CDPS-5, SEQ ID NO:158), the *Stevia rebaudiana* UGT74G1 (SEQ ID NO:1) and *Stevia rebaudiana* UGT85C2 (SEQ ID NO:3). Furthermore EFSC1972 has down regulation of the ERG9 gene expression by displacement of the endogenous promoter with the cupper inducible promoter CUP1.

When EFSC1972 is transformed with a CEN/ARS-based plasmid that expresses the *Stevia rebaudiana* SrKAHe1 from a TEF1 promoter, and simultaneously transformed with 2μ-based plasmids that express the *Synechococcus* sp GGPPS (GGPPS-7) and a truncated version of the *Zea mays* CDPS (truncated CDPS-5) from a GPD promoter, the result is growth-impaired *S. cerevisiae* producer of rubusoside (and 19-SMG). This strain is referred to as the "enhanced EFSC1972" in the following text. To determine whether the slow growth rate is caused by accumulation of the toxic pathway intermediate ent-copalyl diphosphate, a collection of kaurene synthase (KS) genes was expressed in the "enhanced EFSC1972" strain then growth and steviol glycoside production was assessed.

Figure 16:
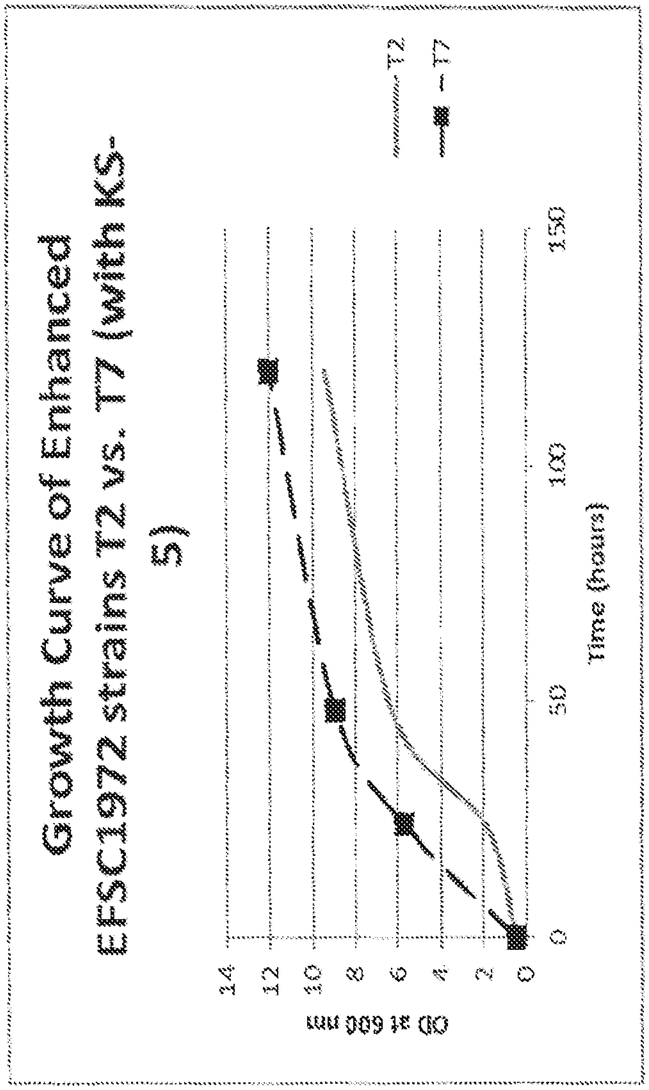
FIG. 16 is a graph of the growth of two strains of *S. cerevisiae*, enhanced EFSC1972 (designated T2) and enhanced EFSC1972 with further overexpression of the *Arabidopsis thaliana* kaurene synthase (KS-5) (designated T7, squares). Numbers on the y-axis are OD600 values of the cell culture, while numbers on the x-axis represent hours of growth in synthetic complete based medium at 30° C.

Expression of the *A. thaliana* KS (KS5) results in improved growth and steviol glycoside production of the "enhanced EFSC1972" strain. See FIG. 16. The same positive effect on growth cannot be achieved by further overexpression of the *Stevia rebaudiana* kaurene synthase (KS-1) in the enhanced EFSC1972 (data not shown).

Example 14—Yeast Strain EFSC1859

*Saccharomyces cerevisiae* strain EFSC1859 contains GGPPS-10, CDPS-5, KS-1, KO-1, KAH-3, CPR-1 and UGT74G1 coding sequences integrated into the genome and expressed from the strong constitutive GPD1 and TPI promoters. See Table 15. In addition, the endogenous promoter for the yeast ERG9 gene was replaced with the copper inducible promoter CUP1 for downregulation of the ERG9 squalene synthase. In standard yeast growth medium, the ERG9 gene is transcribed at very low levels, since the concentration of copper in such medium is low. The decrease in ergosterol production in this strain results in increased amounts of isoprene units available for isoprenoid biosynthesis. In addition, strain EFSC1859 also expresses UGT85C2 from a 2 micron multicopy vector using a GPD1 promoter. EFSC1859 produces rubusoside and steviol 19-O-glycoside.

*Zea mays* CDPS DNA, with and without the chloroplast signal peptide, was expressed from a 2 micron multicopy plasmid using the GPD promoter. The nucleotide sequence and amino acid sequence of the *Zea mays* CDPS are forth in FIG. 14. The chloroplast signal peptide is encoded by nucleotides 1-150 and corresponds to residues 1 to 50 of the amino acid sequence.

TABLE 15

| Gene Source | Enzyme | Designation | gi Number | Accession No. |
|---|---|---|---|---|
| *Aspergillus nidulans* | GGPP synthase | GGPPS-10 (C301) | 29468175 | AF479566 |
| *Zea mays* | CDP synthase | CDPS-5 (EV65) | 50082774 | AY562490 |
| *Stevia rebaudiana* | Kaurene synthase | KS-1 | 4959241 | AAD34295 |
| *Stevia rebaudiana* | KO | KO-1 | 76446107 | ABA42921 |
| *Arabidopsis thaliana* | KAH | KAH-3 | 15238644 | NP_197872 |
| *Stevia rebaudiana* | UGT74G1 | | | |
| *Stevia rebaudiana* | UGT85C2 | | | |
| *Stevia rebaudiana* | CPR | CPR-1 | 93211213 | ABB88839 |

EFSC1859+maize full-length CDPS plasmid, and EFSC+ maize truncated CDPS plasmid were grown in selective yeast medium with 4% glucose. Rubusoside and 19-SMG production were measured by LC-MS to estimate the production level. The removal of the plastid leader sequence did not appear to increase steviol glycoside production as compared to the wild-type sequence, and demonstrates that the CDPS transit peptide can be removed without causing a loss of steviol glycoside biosynthesis.

Example 15—Yeast Strain EFSC1923

*Saccharomyces cerevisiae* strain CEN.PK 111-61A was modified to produce steviol glycosides by introduction of steviol glycoside pathway enzymes from various organisms. The modified strain was designated EFSC1923.

Strain EFSC1923 contains an *Aspergillus nidulans* GGPP synthase gene expression cassette in the *S. cerevisiae* PRP5-YBR238C intergenic region, a *Zea mays* full-length CDPS and *Stevia rebaudiana* CPR gene expression cassette in the MPT5-YGL176C intergenic region, a *Stevia rebaudiana* kaurene synthase and CDPS-1 gene expression cassette in the ECM3-YOR093C intergenic region, an *Arabidopsis thaliana* KAH and *Stevia rebaudiana* KO gene expression cassette in the KIN1-INO2 intergenic region, a *Stevia rebaudiana* UGT74G1 gene expression cassette in the MGA1-YGR250C intergenic region and a *Stevia rebaudiana* UGT85C2 gene expression cassette integrated by displacing the TRP1 gene ORF. See Table 15. In addition, the endogenous promoter for the yeast ERG9 gene was replaced with the copper inducible promoter CUP1.

Strain EFSC1923 produced approximately 5 μM of the steviol glycoside, steviol 19-O-monoside, on selective yeast medium with 4% glucose.

Example 16—Expression of a Truncated Maize CDPS in Yeast Strain EFSC1923

The 150 nucleotides at the 5' end of the *Zea mays* CDP synthase coding sequence in Table 15 (SEQ ID NO:157, see FIG. 14) was deleted, the remainder of the coding sequence was provided with a new translation start ATG, and the truncated sequence was operably linked to the GPD1 promoter in the multicopy plasmid p423GPD in *Saccharomyces cerevisiae* EFSC1923. Plasmid p423GPD is described in Mumberg, D et al, *Gene,* 156: 119-122(1995). EFSC1923 and EFSC1923 plus p423GPD-Z.m.tCDPS were grown in for 96 hours in selective yeast medium containing 4% glucose. The amount of steviol 19-O-monoside produced by EFSC1923+p423GPD-Z.m.tCDPS (the truncated *Zea mays* CDPS) under these conditions was approximately 2.5 fold more than that produced by EFSC1923 without the plasmid.

The *Arabidopsis thaliana* KAH coding sequence from Table 15 was inserted in a multicopy plasmid designated p426GPD, under the control of the GPD1 promoter. Plasmid p426GPD is described in Mumberg, D et al, *Gene.* 156: 119-122(1995). No significant difference was observed between the amount of steviol 19-O-monoside produced by EFSC1923+p426GPD-A.t.KAH, and EFSC1923 lacking the plasmid.

EFSC1923 was transformed with both p423GPD-Z.m.tCDPS and p426 p426GPD-A.t.KAH. Surprisingly, the amount of steviol 19-O-monoside produced under these conditions by EFSC1923 harboring both plasmids (i.e., the truncated *Zea mays* CDPS and *Arabidopsis* KAH) was more than 6 fold greater than the amount produced by EFSC1923 alone.

A bifunctional CDPS-KS from *Gibberella fujikuroi* (NCBI Accession no: Q9UVY5.1, FIG. 15) was cloned and compared to the truncated CDPS-5. The bifunctional *Gibberella* CDPS-KS was cloned into a 2p plasmid with a GPD promoter and transformed with a plasmid expressing the *Arabidopsis thaliana* KAH-3 from a 2μ based-plasmid from a GPD promoter into EFSC1923. In shake flask studies, this bifunctional CDPS-KS was about 5.8 times more active in producing steviol 19-O-monoside than strain EFSC1923 with the KAH-3 alone. However, it was found to be less optimal than the KAH-3 and truncated CDPS combination under the conditions tested. Therefore, further strains were constructed with KS-5 and truncated CDPS.

Example 17—Toxicity of Intermediates

The effect on *S. cerevisiae* vitality of geranyl geranyl pyrophosphate (GGPP), ent-copalyl diphosphate (CDP) or ent-kaurene production was investigated by expression of *Synechococcus* sp GGPPS alone (GGPP production), the GGPPS and the 50 amino acid N-terminally truncated *Zea mays* CDPS (see Example 16) together (CDP production), or the GGPPS, truncated CDPS and the *Arabidopsis thaliana* kaurene synthase (KS5) together (ent kaurene production) in the laboratory *S. cerevisiae* strain CEN.PK background. Genes were expressed from 2μ plasmids with GPD promoters driving transcription of truncated CDPS and KS5, while transcription of the GGPPS was driven by the ADH1 promoter. The growth of *S. cerevisiae* CEN.PK transformed with various combinations of these plasmids (GGPPS alone; GGPPS+truncated CDPS; or GGPPS+truncated CDPS+KS5) or plasmids without gene insertions was observed. GGPP production, and especially CDP production, was toxic to *S. cerevisiae* when produced as end products. Interestingly, ent-kaurene appeared to not be toxic to yeast in the amounts produced in this experiment.

Example 18—Disruption of Endogenous Phosphatase Activity

The yeast genes DPP1 and LPP1 encode phosphatases that can degrade FPP and GGPP to farnesol and geranylgeraniol, respectively. The gene-encoding DPP1 was deleted in strain EFSC1923 (described in Example 15) to determine if there was an effect on steviol glycoside production. When this dpp1 mutant strain was further transformed with a plasmid expressing the *Z. mays* CDPS lacking the chloroplast transit sequence (Example 16), both small and large transformants emerged. Strains of the “large colony” type produced ~40% more 19-SMG as compared to “small colony” type and the non-DPP1 deleted strain, under the conditions tested. These results indicate that deletion of DPP1 can have a positive effect on steviol glycoside production and that the degradation of prenyl pyrophosphates in yeast therefore could influence steviol glycoside production negatively.

Example 19—Construction of a Genetically Stable Yeast Reporter Strain Producing Vanillin Glucoside from Glucose with a Disrupted SUC2 Gene A yeast strain producing vanillin glucoside from glucose was created basically as described in Brochado et al. ((2010) *Microbial Cell Factories* 9:84-98) (strain VG4), but with additional integration into the ECM3 inter-locus region in the yeast genome of an expression cassette with *E. coli* EntD PPTase controlled by the yeast TPI1 promoter (as described in Hansen et al. (2009) *Appl. Environ. Microbiol.* 75(9): 2765-2774), disruption of SUC2 by replacing coding sequence with a MET15 expression cassette, and disruption of LEU2 by replacing coding sequence with a Tn5ble expression cassette conferring resistance to phleomycin. The resulting yeast strain was called V28. This strain also encodes a recombinant *A. thaliana* UDP-glycosyltransferase (UGT72E2, GenBank Accession No. Q9LVR1) having the amino acid sequence set forth in FIG. 19 (SEQ ID NO:178).

Example 20—Expression of Sucrose Transporter and Sucrose Synthase in Yeast Already Biosynthesizing Vanillin Glucoside A sucrose transporter SUC1 from *Arabidopsis thaliana* was isolated by PCR amplification from cDNA prepared from *A. thaliana*, using proof-reading PCR polymerase. The resulting PCR fragment was transferred by restriction digestion with SpeI and EcoRI and inserted into the corresponding in the low copy number yeast expression vector p416-TEF (a CEN-ARS based vector), from which the gene can be expressed from the strong TEF promoter. The resulting plasmid was named pVAN192. The sequence of the encoded sucrose transporter is set forth in FIG. 19B (GenBank Accession No. AEE35247, SEQ ID NO:179).

A sucrose synthase SUS1 from *Coffea arabica* (Accession No. CAJ32596) from was isolated by PCR amplification from cDNA prepared from *C. arabica*, using proof-reading PCR polymerase. The PCR fragment was transferred by restriction digestion with SpeI and Sa/I and inserted into the corresponding position in the high copy number yeast expression vector p425-GPD (a 2 μm based vector), from which the gene can be expressed from the strong GPD promoter. The resulting plasmid was named pMUS55. The sequence of the encoded sucrose synthase is set forth in FIG. 19C (GenBank Accession No. CAJ32596; SEQ ID NO:180).

pVAN192 and pMUS55 were introduced into the yeast strain V28 by genetic transformation, using a lithium acetate transformation protocol, creating the yeast strain V28::

pVAN192::pMUS55. A control strain was made by transforming V28 with the empty plasmids P146-TEF and P425-GPD.

These two yeast strains were grown in 200 ml cultures in 500 ml Erlenmeyer shake flasks using SC (synthetic complete) growth medium without aromatic amino acids supplemented with 2% glucose and 2% sucrose and adjusted to pH 5.0. Cultures were incubated at moderate revolution (150 rpm), at 30° C. for 72 hours. Samples were taken at 72 hours, and the content of vanillin glucoside determined. As can be seen from the table below, VG production in the control strain (containing empty plasmids p416-TEF and p425-GPD) was 330 mg/L VG, while the yeast strain V28::pVAN192::pMUS55 expressing sucrose synthase and sucrose transporter produced 445 mg/l VG, corresponding to a 34.8% increase in VG production.

| Strain | Vanillin glucoside (g/L after 72 h) |
|---|---|
| V28 (p416-TEF + P425-GPD) | 330 |
| V28::pVAN192::pMUS55 | 445 |

This indicates that co-expression of a sucrose synthase and a sucrose transporter together with a glucosyltransferase increased the ability to glycosylate a small molecule aglycon, and concentration of the glycosylated aglycon was significantly increased. In this case, a significant improvement in vanillin glucosylation was achieved, resulting in a significant increase in titer of the end product, vanillin-O-β-glucoside.

Example 21—Improved Steviol Glycoside Producing Strains

Strain Construction of *Saccharomyces cerevisiae* EFSC2763

EFSC2763 yeast strain is derived from a wild type *Saccharomyces cerevisiae* strain containing three auxotrophic modifications, namely the deletions of URA3, LEU2 and HIS3. The genetics of the strain have been stabilized and can be used as a regular diploid or haploid yeast strain. EFSC2763 has been converted to a steviol glycoside producing yeast by genomic-integration of four DNA constructs. Each construct contains multiple genes that were introduced into the yeast genome by homologous recombination. Furthermore, construct one and two were assembled by homologous recombination.

The first construct contains eight genes and is inserted in the DPP1 locus and disrupts and partially deletes DPP1 (see Example 18). The DNA inserted contains: the *A. gossypii* TEF promoter expressing the NatMX gene (selectable marker) followed by the TEF terminator from *A. gossypii*; Gene Art codon optimized *S. rebaudiana* UGT85C2 (see Example 10) expressed from the native yeast GPD1 promoter and followed by the native yeast CYC1 terminator; *S. rebaudiana* CPR-8 (see FIG. 13) expressed using the TPI1 promoter followed by the native yeast TDH1 terminator; *A. thaliana* Kaurene synthase (KS-5, see Example 13, SEQ ID NO:156) expressed from the PDC1 promoter and followed by the native yeast FBA1 terminator; *Synechococcus* sp. GGPPS (GGPPS-7) expressed using the TEF2 promoter and followed by the native yeast PFI1 terminator; DNA2.0 codon-optimized *S. rebaudiana* KAHe1 (see Example 11, SEQ ID NO:165), expressed from the TEF1 promoter and followed by the ENO2 terminator; *S. rebaudiana* KO-1 expressed using the FBA1 promoter and followed by the native yeast TDH2 terminator; and *Zea mays* truncated CDPS (see Example 14) expressed using the PGK1 promoter and followed by the native yeast ADH2 terminator.

The second construct was inserted at the YPRCΔ15 locus and contains the native yeast TEF promoter from *A. gossypii* in front expressing the KanMX gene (selectable marker) followed by the TEF terminator from *A. gossypii*, the Gene Art codon optimized *A. thaliana* ATR2 (see FIG. 13B) expressed from the PGK1 promoter followed by the yeast ADH2 terminator, *S. rebaudiana* UGT74G1 expressed from the TPI1 promoter followed by the yeast TDH1 terminator, Gene Art codon-optimized *S. rebaudiana* UGT76G1 expressed from the TEF1 promoter followed by the yeast ENO2 terminator, and GeneArt codon-optimized *S. rebaudiana* UGT91D2e-b (see Example 6) expressed from the GPD1 promoter and followed by the yeast CYC1 terminator.

The first and the second construct were combined in the same spore clone by mating and dissection. This yeast strain was subsequently transformed with construct three and four in two successive events.

Construct three was integrated between genes PRP5 and YBR238C and contained the TEF promoter from *A. gossypii* in expressing the *K. lactis* LEU2 gene followed by the TEF terminator from *A. gossypii*, the GPD1 promoter expressing the DNA2.0-optimized *S. rebaudiana* KAHe1 followed by the CYC1 terminator, and the TPI1 promoter expressing the *Zea mays* truncated CDPS. Construct four was integrated in the genome between genes ECM3 and YOR093C with an expression cassette containing the TEF promoter from *A. gossypii* expressing the *K. pneumoniae* hph gene followed by the TEF terminator from *A. gossypii, Synechococcus* sp. GGPPS expressed from the GPD1 promoter followed by the CYC1 terminator, and the TPI1 promoter expressing the *A. thaliana* Kaurene synthase. The four utilized genetic markers were subsequently removed.

As analyzed by LC-MS following the DMSO-extraction of total steviol glycosides from cells and broth, EFSC2772 produces between 40-50 μM or 2-3 μM/OD600 Rebaudioside A, after growth for four days in 3 ml SC (Synthetic Complete) media at 30° C. with 320 RPM shaking in deep-well plates.

Strain Construction of *Saccharomyces cerevisiae* EFSC2772

EFSC2772 is very similar to strain 2763 with the exception that the genetic markers were not removed, and the strain was made prototrophic by introduction of the two plasmids p413TEF (public domain CEN/ARS shuttle plasmid with HIS3 marker) and p416-TEF (public domain CEN/ARS shuttle plasmid with URA3 marker) by transformation, and designated EFSC2772.

As analyzed by LC-MS following the DMSO-extraction of total steviol glycosides from cells and broth, EFSC2772 produces similar levels of Rebaudioside A as 2763, after growth in deep-well plates. Higher optical densities and higher titers were obtained through aerobic fed-batch growth in 2 L (working volume) fermentors which included a ~16 hour growth phase in the base medium (Synthetic Complete media) followed by ~100 hours of feeding with glucose utilized as the carbon and energy source combined with trace metals, vitamins, salts, and Yeast Nitrogen Base (YNB) and/or amino acid supplementation. The pH was kept near pH 5 and the temperature setpoint was 30° C. As evidenced by LC-MS, combined cellular and extracellular product concentrations were between 920-1660 mg/L of Reb-A and approximately 300-320 mg/L of Reb-D in the two different experiments, approximately 700 mg/L of Reb-A was detected in the broth when the higher titer results were obtained. Additionally a large peak was seen for Reb-B, and one skilled in the art will recognize that additional copies of UGT74G1 or upregulation of UGT74G1 will further increase the conversion of RebB to RebA.

Strain EFSC2743 was made in a similar manner as above, but without the two plasmids conferring prototrophy and with the addition of a p416 (CEN/ARS)-based plasmid expressing EUGT11 from the TEF promoter. This strain was grown in a fed-batch fermentation as above. This strain produced a total amount of RebD of 920 mg/L and furthermore approximately a 9:1 ratio of RebD to RebA was seen. Approximately 360 mg/L of RebD was found in the broth.

Example 22—UDP-Glucose Capacity

In Example 21, it was shown that yeast can fully glycosylate over 1 mM steviol e.g., to RebD, RebB, and RebA. Similarly, *Saccharomyces* strains are able to glycosylate as much as 60 mM of other small molecule products (data not shown). However, the glycosylation limit of the yeast native UDP-glucose regenerating system is unknown, or the rate at which it replenishes the UDP-glucose pool needed for cell wall synthesis. Therefore, experiments were designed to investigate if an increase in UDP-glucose production would increase the glycosylation rate in yeast. A suc2 deletion mutant was transformed with plasmids harboring the *A. thaliana* suc1 gene encoding a sucrose transporter, UGT74G1 and *A. thaliana* SUS. UGT74G1 can rapidly glycosylate steviol to steviol 19-O-monoglucoside (19-SMG). Transformants were pre-grown overnight in 13-ml culture tubes containing 4 ml of SC medium lacking leucine, histidine and uracil. The next day, cells corresponding to 2 $OD_{600}$ units were spun down and resuspended in 2 ml of fresh media was containing 2% sucrose and or 100 μM steviol. Cultures were shaken at 30° C. for 3 days in culture tubes. After 1 h, 3 h, 6 h, 21 h and 46 h, aliquots were taken. Aliquots of 100 μl of culture were spun down and an equal volume of DMSO was added. Samples were vortexed, heated at 80° C. for 15 minutes, centrifuged, and the 19-SMG content analyzed by LC-MS. No difference in the rate of glycosylation of steviol was observed between wild-type and SUS1-augmented strains at the time points tested. This suggests that glycosylation of steviol by UGT74G1 proceeds at a slower rate than UDP-glucose is regenerated by the yeast and that extra UDP-glucose may not be needed to achieve high titers of small molecule glycosylation in vivo. Nevertheless, the use of a SUS to recycle UDP-glucose in vitro is shown in Example 8 and therefore its use in an in vivo system is expected to increase the rate of production of steviol glycosides, if UDP-glucose should become limiting.

Example 23—Reb-C and Reb-F Production In Vivo from Glucose

Production of RebC from Steviol

Previous experiments (Publication No. WO/2011/153378) have shown that recombinantly expressed *Arabidopsis thaliana* RHM2 (rhamnose synthetase, locus tag AT1G53500) is able to convert UDP-glucose to UDP-rhamnose. This UDP-rhamnose can be used to produce steviol-13-O-glucopyranosyl-1,2-rhamnoside, when incubated with UGT91D2e and steviol-13-O-monoglucoside in vitro.

Further experiments were conducted to confirm production of RebC from steviol by expressing all 4 UGTs and the RHM2 in yeast in vivo, followed by steviol feeding. EFSC301 strain (MAT alpha, lys2ADE8 his3ura3leu2trp1) was transformed with the following plasmids expressing wild type gene sequences: p424GPD expressing wild type UGT74G1 (Accession no: AY345982); p423GPD expressing wild type 85C2 (Accession no.: AY345978.1); and a p426GPD derived-plasmid expressing wildtype UGT76G1 (Accession no: AY345974) and UGT91D2e under GPD promoters. Plasmid p425GPD expressing either RHM2 or an empty p425GPD control plasmid was cotransformed with the UGTs. Transformants were pre-grown overnight in 13 mL culture tubes containing 2-3 ml of SC medium lacking leucine, histidine, tryptophan and uracil. The next day, after growth had reached 0.4 $OD_{600}$ units, cells were spun down, resuspended in fresh medium containing 25 μM steviol and shaken at 30° C. for 3 days in culture tubes. An aliquot of 100 μL of culture was spun down. An equal volume of DMSO was added to the supernatant of this sample while 200 μL of 50% DMSO was added to the pellet. Samples were vortexed, heated at 80° C. for 15 minutes, centrifuged, and the steviol glycoside content analyzed by LC-MS. RebC was detected in growth media and cellular extracts only when the RHM2 gene was coexpressed with the UGTs. Quantification showed that approximately equal amounts of RebA and RebC were produced. This shows that RHM2 is able to produce significant quantities of UDP-rhamnose in vivo and that UGT91D2e is capable of efficient rhamnosylation in vivo. Two other compounds were observed via LC-MS with retention times of 5.64 and 5.33 minutes and m/z ratios corresponding to steviol with 1 glucose- and 1 rhamnose (steviol-1,2 rhamnobioside), and 2 glucoses- and 1 rhamnose (Dulcoside A), respectively. This suggests that the remaining UGTs in the steviol glycoside pathway are capable of accepting rhamnosylated intermediates, i.e, the rhamnosylation step does not need to occur last.

In addition, a series of sequential in vitro experiments were conducted to determine whether any dead-end reactions occur in the rebaudioside C pathway. See FIG. 2B. For example, the rhamnosylation activity of UGT91D2e on rubusoside and subsequent conversion of the product to RebC by UGT76G1 was demonstrated using in vitro reactions. In this experiment, UGT91D2e and RHM2 recombinantly expressed in *E. coli* and purified were incubated overnight with rubusoside, NADPH, $NAD^+$ and UDP-glucose. The reaction mixture was subsequently boiled to denature the enzymes. An aliquot of the reaction was added to an enzyme preparation of UGT76G1 with UDP-glucose. The rubusoside was converted in the presence of UGT91D2e and RHM2 to a compound with m/z corresponding to steviol with 2-glucoses and 1-rhamnose. Subsequently, this compound was converted in the presence of UGT76G1 to RebC, which indicates that the intermediate is Dulcoside A. This experiment therefore demonstrates that UGT91D2e is able to rhamnosylate rubusoside and that UGT76G1 is able to convert the product to RebC.

Similarly, it was shown through in vitro reactions that rhamnosylation of 13-SMG by UGT91D2e (forming a steviol compound with one glucose and one rhamnose) and subsequent formation of a compound with 2 glucoses and 1 rhamnose by UGT76G1. This compound has a unique retention time (4.56 min) and is thought to be steviol 13-O-1,3-diglycoside-1,2-rhamnoside. This compound also was observed when steviol was fed to yeast expressing the four UGTs and RHM2.

From the current data, it is shown that UGT91D2e is able to rhamnosylate 13-SMG and rubusoside. It is also shown that UGT74G1 and UGT76G1 are able to metabolize the rhamnosylated compound produced by UGT91D2e from 13-SMG. When these compounds are incubated with the remaining UGT (UGT74G1 or UGT76G1 depending on which UGT was used for the previous step), RebC is formed. This indicates that the order of glycosylation is of little importance as UGT74G1 and UGT76G1 are able to glycosylate rhamnosylated substrates.

Production of RebC from Glucose

Plasmids expressing RHM2 and UGTs 76G1 and 91D2e were transformed into a stable rubusoside producer, the EFSC1923 strain (see Example 15). This yeast is a *Saccharomyces cerevisiae* CEN.PK 111-61A derivative with the UGTs 85C2 (Accession no.: AY345978.1) and 74G1 (Accession no: AY345982) integrated into the genome as well as auxotrophic modifications. In strain EFSC1923 (see Example 15), expression of squalene synthase, which is encoded by ERG9, was downregulated by displacement of the endogenous promoter with the CUP1 copper-inducible promoter. Strain EFSC1923 also contains an *Aspergillus nidulans* GGPP synthase (GGPPS-10) expression cassette in the *S. cerevisiae* PRP5-YBR238C intergenic region, a *Zea mays* full-length CDPS (CDPS-5) and *Stevia rebaudiana* CPR (CPR-1) gene expression cassette in the MPT5-YGL176C intergenic region, a *Stevia rebaudiana* Kaurene synthase and CDPS (KS-1/CDPS-1) gene expression cassette in the ECM3-YOR093C intergenic region, an *Arabidopsis thaliana* KAH (KAH-3) and *Stevia rebaudiana* KO (KO-1) gene expression cassette in the KIN1-INO2 intergenic region, a *Stevia rebaudiana* UGT74G1 gene expression cassette in the MGA1-YGR250C intergenic region and a *Stevia rebaudiana* UGT85C2 gene expression cassette integrated by displacing the TRP1 gene ORF20. Inserted steviol pathway genes are described in Table 11 of published PCT WO/2011/153378.

EFSC1923 strain was transformed with a p423GPD-derived plasmid expressing wildtype UGT74G1 and UGT85C2 sequences using GPD promoters and a p426GPD-derived plasmid expressing wildtype UGT76G1 (Accession no: AY345974) and UGT91D2e (see SEQ ID NO:5) under the control of GPD promoters. Plasmid p425GPD expressing *Arabidopsis thaliana* RHM2 (enzyme locus tag AT1G53500) or an empty p425GPD control plasmid was co-transformed. Transformants were pre-grown overnight in 13-ml culture tubes containing 2-3 ml of SC medium lacking leucine, histidine and uracil. The next day, when the culture reached an $OD_{600}$ of 0.4 units it was centrifuged, resuspended in fresh medium, and shaken at 30° C. for 3 days in culture tubes. One hundred μL of culture were spun down; to this an equivalent volume of DMSO was added to the supernatant while 200 μL of 50% DMSO was added to the pellet. Samples were vortexed, heated at 80° C. for 15 minutes, spun down and the steviol glycoside content analyzed by LC-MS.

Analyses of the medium and normalized intracellular content of this strain showed production of RebC. Approximately 8 μM RebC and 4 μM RebA was produced as determined by LC-MS. Furthermore, the intermediates produced following steviol feeding were not detected in this experiment. Accumulation of RebC was strictly dependent on expression of RHM2. This example demonstrates de novo biosynthesis of RebC from glucose.

Production of Additional Steviol Glycosides from Steviol and Glucose

Using the same GPD-based plasmids described above, the stable steviol-producing strain EFSC1923 containing UGT74G1 and UGT85C2 was transformed with the UGTs required to produce RebB (UGT76G1 and UGT91D2e/EUGT11), RebE (UGT91D2e/EUGT11) and dulcoside A (RHM2, UGT91D2e/EUGT11). Wildtype EUGT11 (NCBI: NP_001051007), which was found to have higher diglycosylation activity, was cloned into p424GPD for this experiment. Transformants were pre-grown overnight in 13-ml culture tubes containing 2-3 ml of SC medium lacking leucine, histidine, tryptophan and uracil. The next day, after growth had reached 0.4 $OD_{600}$ units, cells were spun down, resuspended in fresh medium containing 25 μM steviol (except for glucose experiments) and shaken at 30° C. for 3 days in culture tubes. An aliquot of 100 μL of culture was spun down. An equal volume of DMSO was added to the supernatant of this sample while 200 μL of 50% DMSO was added to the pellet. Samples were vortexed, heated at 80° C. for 15 minutes, centrifuged, and the steviol glycoside content analyzed by LC-MS. LC-MS analyses confirmed in vivo production of RebB, RebE, and Dulcoside A in *S. cerevisiae* from glucose or steviol. See, e.g., FIGS. 2A and 2B. A higher concentration of steviol-glycosides was observed following steviol-feeding (as judged by chromatograms).

Characterization of RebF Pathway Intermediates Using EUGT11.

The xylosylating properties of UGT91D2e and EUGT11 were compared in vitro. By using UDP-xylose as the sugar-donor, UGT91D2e was previously shown to xylosylate steviol-13-O-monoglucoside forming a key intermediate in RebF biosynthesis (Publication No. WO/2011/153378). Similar in vitro experiments using EUGT11 and UGT91D2e have shown that these UGTs are capable of xylosylating rubusoside. When UGT91D2e is used, the LC-MS analysis shows a new peak with an m/z ratio corresponding to steviol with 2 glucose molecules and 1 xylose. See, FIG. 26. Because of the shift in the retention time this peak is thought to correspond to rubusoside xylosylated on the 13-O-glucose. When EUGT11 is used, the LC-MS analysis shows two new, similar sized peaks at retention time 3.99 and 4.39 minutes with m/z ratios corresponding to steviol with 2 glucoses and 1 xylose. These products most likely correspond to rubusoside xylosylated on either of the two positions—the 13-O-glucose or the 19-O-glucose.

Production of RebF from Glucose

In vivo production of RebF requires cloning of UGD1 (UDP-glucose dehydrogenase) and USX3 (UDP-glucoronic acid decarboxylase) from *Arabidopsis* for production of UDP-xylose. UGD1 and UXS3 were inserted in a high copy (2μ) vector, derived from P425-GPD, containing two expression cassettes, and expressed from strong constitutive promoters (TPI1 and GPD1, respectively). The plasmid was transformed into the RebA producer strain EFSC2763 (described in Example 21) and cultivated during 3 days in selection medium (SC-leu). The LC-MS results clearly show the appearance of a new peak at retention time 4.13 minutes with m/z ratios corresponding to steviol with 3 glucoses and 1 xylose and identified as RebF (based on a commercial RebF standard), as well as other new peaks with m/z ratios corresponding to steviol with 2 glucoses and 1 xylose (as above), indicating that UGT91D2e was capable of carrying out xylosylation in vivo. These peaks were not seen in the negative controls.

Example 24—Effect of Squalene Synthase (ERG9) Down Regulation Using a Heterologous Insert In yeast such as *Saccharomyces cerevisiae*, the mevalonate pathway produces a number of isoprenoid phosphate intermediates in the biosynthetic pathway to squalene (See FIG. 20). The squalene synthase in yeast is ERG9. See GenBank Accession No. P29704.2 for the *Saccharomyces cerevisiae* squalene synthase; P36596 for the *Schizosaccha-*

*romyces pombe* squalene synthase; Q9Y753 for the *Yarrowia lipolytica* squalene synthase; Q9HGZ6 for the *Candida glabrata* squalene synthase; Q752X9 for the *Ashbya gossypii* squalene synthase; 074165 for the *Cyberlindnera jadinii* squalene synthase; P78589 for the *Candida albicans* squalene synthase; P38604 for the *Saccharomyces cerevisiae* lanosterol synthase; P37268 for the *Homo sapiens* squalene synthase; P53798 for the *Mus musculus* squalene synthase; and Q02769 for the *Rattus norvegicus* squalene synthase. See FIG. 25 (SEQ ID NOs:192-202).

Introduction of Stemloop Structure in 5'UTR of ERG9 Gene

The wild-type ERG9 promoter region was replaced with the CYC1 promoter sequence and a 5'UTR sequence by homologous recombination. The 5'UTR region contains a sequence that can form a stemloop structure. See SEQ ID NOs. 181-183. SEQ ID NO:184 is another sequence that also can be used.

```
(heterologous insert 1):
                                    SEQ ID NO: 181
TGAATTCGTTAACGAATTC

(heterologous insert 2):
                                    SEQ ID NO: 182
TGAATTCGTTAACGAACTC

(heterologous insert 3):
                                    SEQ ID NO: 183
TGAATTCGTTAACGAAGTC

(heterologous insert 4):
                                    SEQ ID NO: 184
TGAATTCGTTAACGAAATT
```

Without being bound to a particular mechanism, the stemloop may partially block the 5'-3' directed ribosomal scanning for the AUG and reduce the translation of the transcript. Stemloops with different degree of basepairing were tested to find stemloops that reduced the ERG9 transcript translation sufficiently to boost FPP levels without affecting the growth of the yeast strain.

Figure 23:
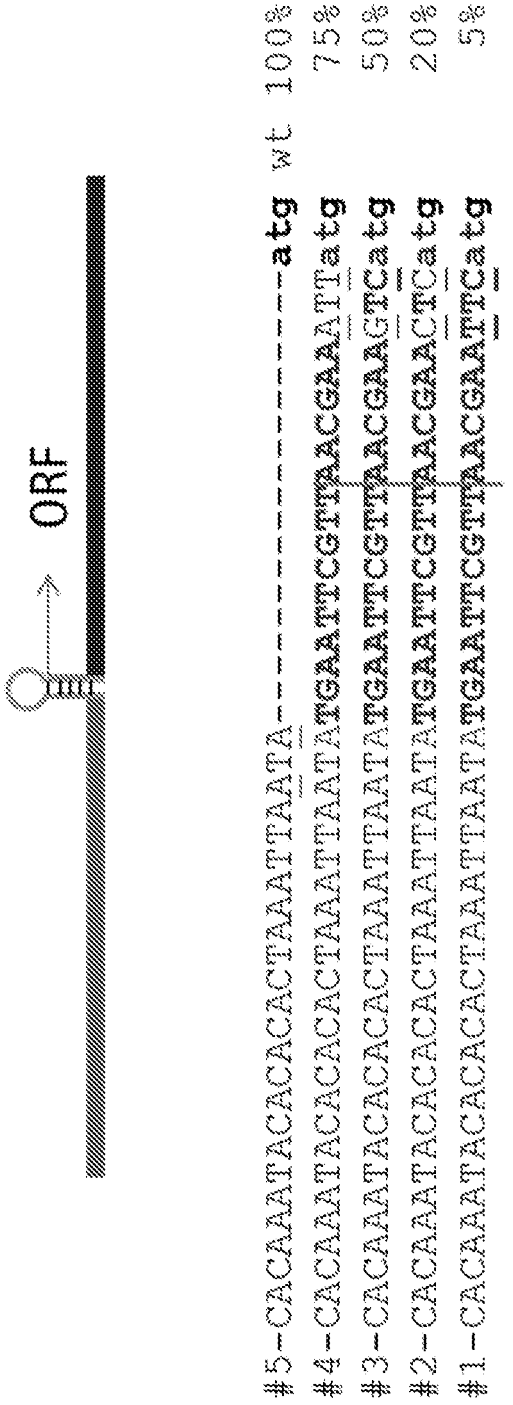
FIG. 23 is a schematic of promoter and ORF with a hairpin stemloop immediately upstream of the translation startsite (arrow) and an alignment of a portion of the wild-type *S. cerevisiae* Cycl promoter sequence and initial ATG of the ERG9 OPR without a heterologous insert (SEQ ID NO:187) and with four different heterologous inserts (SEQ ID NOs. 188-191). 75% refers to construct comprising the ScCyc1 promoter followed by SEQ ID NO: 184 (SEQ ID NO:191); 50% refers to construct comprising the ScCycl promoter followed by SEQ ID NO: 183 (SEQ ID NO:190); 20% refers to construct comprising the ScCyc1 promoter followed by SEQ ID NO: 182 (SEQ ID NO:189); 5% refers to construct comprising the ScCyc1 promoter followed by SEQ ID NO: 181 (SEQ ID NO:188).

DNA fragments encompassing an ERG9 promoter upstream sequence (for homologous recombination), an expression cassette for the gene (NatR) that confers resistance to Nourseothricin, a CYC1 promoter (SEQ ID NO: 185, FIG. 21), a 5' UTR sequence with a stemloop structure, and an ERG9 ORF sequence (for homologous recombination) were generated by PCR. DNA fragments that contained either the CYC1 promoter or the KEX2 promoter (SEQ ID NO: 186) but no stemloops were also generated as controls. The flanking ERG9 sequences for recombination as well as the stemloop structure were introduced via the PCR oligos. An overview of the construct for homologous recombination is shown in FIG. 22. The DNA fragments were transformed into an *S. cerevisiae* host strain that subsequently was selected on nourseothricin containing growth plates. Clones with successful exchange of the native ERG9 promoter with the CYC1 promoter and stemloop-containing 5'UTR sequence were identified. Overview and sequence of the stem-loop region is provided in FIG. 23. The sequence identified as 5% corresponds with the heterologous insert having SEQ ID NO:181; the sequence identified as 20% corresponds with the heterologous insert having SEQ ID NO:182; and the sequence identified as 50% corresponds with the heterologous insert having SEQ ID NO:183.

Assessment of FPP Accumulation (Boosting Effect)

The *Amorpha*-4,11-diene Synthase (ADS) gene catalyzes the chemical reaction that turns one FPP molecule into *Amorpha*-4,11-diene in the plant *Artemisia annua*. The gene is functional and efficient in *S. cerevisiae* and can be used to indirectly assess the accumulation of FPP in the strains with the stemloop structure introduced in the heterologous 5'UTR of the ERG9 gene. An *S. cerevisiae* codon optimized nucleic acid encoding ADS (GenBank Accession No. AAF61439) was cloned on a multicopy plasmid (2μ) under the control of the PGK1 promoter and transformed in the wild type and engineered *S. cerevisiae* strains. *Amorpha*-4,11-diene production was measured and compared to the standard compound caryophyllene, as described by (Ro et al. 2006. *Nature* 440(7086):940-943; Paradise et al. *Biotechnol Bioeng*. 2008 Jun. 1; 100(2):371-8; Newman et al. *Biotechnol Bioeng* 95(4):684-691).

Chemicals

Dodecane and caryophyllene were purchased from Sigma-Aldrich (St. Louis, MO). Complete Supplement Mixtures for formulation of Synthetic Complete (SC) media were purchased from Formedium (UK). All others chemical were purchased from Sigma-Aldrich.

Yeast Cultivation

Engineered yeast strains were grown in SC 2% glucose with uracil dropped out. Cultures were grown at 30° C. overnight and then used to inoculate main cultures in 250 mL shake flasks containing 25 mL SC medium, and grown to an optical density of 0.1 at 600 nm. The main cultures were grown for 72 h at 30° C. Because amorphadiene at very low concentrations is volatile from aqueous cultures, 2.5 mL dodecane was added to each culture flask in order to trap and retain the amorphadiene produced. 10 μl of the dodecane layer was sampled and diluted 100 fold in ethyl acetate for quantification by GC-MS GC-MS Analysis of Amorphadiene GC-MS was used to measure amorphadiene production from yeast cultures. Samples were analysed using the method as follow: The GC oven temperature program used 80° C. for 2 min, followed by a ramping of 30° C./min to 160° C., then 3° C./min up to 170° C., and finally 30° C./min up to 300° C. with a 2 min final hold. Injector and MS quadrupole detector temperatures were 250° C. and 150° C., respectively. 1 μL was injected in split less mode. The MS was operated in full scan mode. Amorphadiene concentration was calculated in (−)-tran-caryophyllene equivalents using a caryophyllene standard curve using the total ions.

Figure 24:
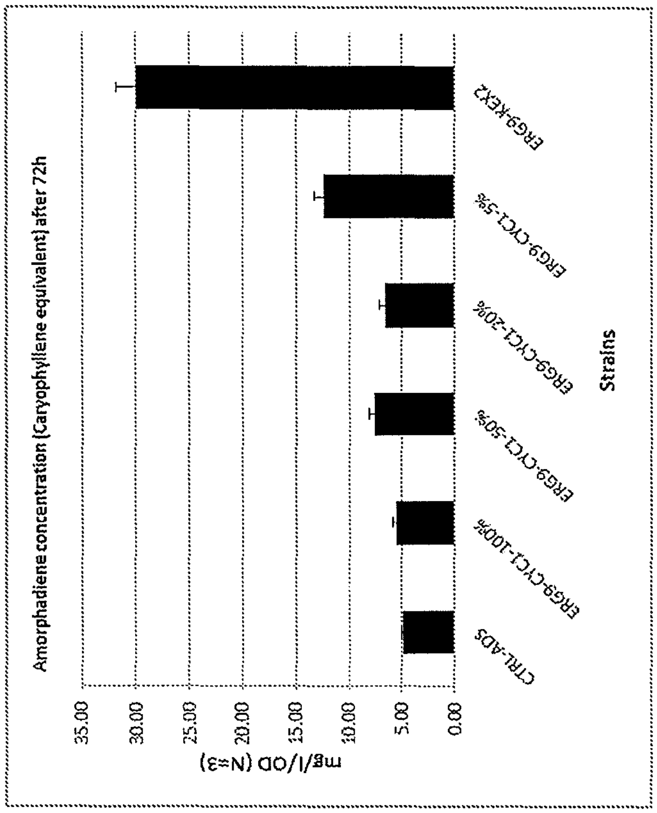
FIG. 24 is a bar graph showing amorphadiene produced in yeast strains with different promoter constructs inserted in front of the ERG9 gene of the host genome. CTRL-ADS refers to control strain with no modification; ERG9-CYC1-100% refers to construct comprising the ScCycl promoter and no insert; ERG9-CYC1-50% refers to construct comprising the ScCycl promoter followed by SEQ ID NO: 183 (SEQ ID NO:190); ERG9-CYC1-20% refers to construct comprising the ScCyc1 promoter followed by SEQ ID NO: 182 (SEQ ID NO:189); ERG9-CYC1-5% refers to construct comprising the ScCyc1 promoter followed by SEQ ID NO: 181 (SEQ ID NO:188); ERG9-KEX2-100% refers to construct comprising the ScKex2 promoter.

The analysis of the different strains, including the different promoter constructs, showed an increased production of amorphadiene ((2.5×) when using the heterologous insert having the nucleotide sequence set forth in SEQ ID NO: 181 compared to either no insert or the inserts having the nucleotide sequences set forth in SEQ ID NO:182 and 183. See FIG. 24. The heterologous insert set forth in SEQ ID NO:181 has the most stable secondary structure. For comparison the wild type yeast, with unmodified ERG9, was also analyzed (FIG. 24: CTRL-ADS) and this strain showed even lower production of amorphadiene. Conversely, the construct that comprised the very weak promoter ScKex2 showed an even higher level of amorphadiene (6×).

Example 25—Analysis of the Effect of Squalene Synthase (ERG9) Down Regulation and GGPPS Overexpression on GGPP Production Assessment of GGPP Accumulation

*S. cerevisiae* contains a GGPPS (BTS1). In addition to BTS1 there are several heterologous GGPPS enzymes that are functional and efficient in *S. cerevisiae*. When a functional GGPPS is overexpressed in *S. cerevisiae*, it leads to accumulation of GGPP, which may be converted to geranylgeraniol (GGOH) by the *S. cerevisiae* enzymes DPP1 and LPP1. The GGOH is partly exported to the yeast culture medium. GGOH can be measured by GC-MS and its accumulation can indirectly be used to assess the potential pool of GGPP that is available for enzymes that use GGPP as substrate.

Four different GGPPSs (GGPPS-1 (*S. acidicaldarius*, see Table 7), GGPPS-2 (*A. nidulans*, FIG. 25, SEQ ID NO:203), GGPPS-3 (*S. cerevisiae*, BTS1, FIG. 25, SEQ ID NO:167), and GGPPS-4 (*M. musculus*, see Table 7)) were assessed. The nucleotide sequences encoding GGPPS-1, GGPPS-2, and GGPPS-4 were *S. cerevisiae* codon optimized. All nucleic acids encoding the GGPPS polypeptides were cloned on a multitcopy plasmid (2p) under the control of the PGK1 promoter and transformed in two different ERG9 down regulated strains: KEX2-ERG9 and CYC1(5%)-ERG9 (see Example 24).

Engineered yeast strains were grown in SC 2% glucose with uracil dropped out. Complete Supplement Mixtures for formulation of Synthetic Complete (SC) media were purchased from Formedium (UK). All others chemical were purchased from Sigma-Aldrich (St. Louis, MO). All optical density measurements were done at OD 600 nm. Cultures were grown at 30° C. overnight and then used to inoculate 250 ml unbaffled culture flasks containing 25 ml SC medium at an OD600 of 0.1. The main cultures were grown for 72 h at 30° C.

To measure GGOH accumulation, yeast cells (pellet) and yeast culture medium (supernatant) were extracted separately and then combined before analysis by GC-MS. The supernatant was extracted with Hexane in a 1:1 ratio. The pellet was first subjected to a saponification in solution containing 20% KOH and 50% Ethanol and the lysed cells were finally extracted with Hexane in a 1:1 ratio. The GC oven temperature program used was 80° C. for 2 min, followed by a ramp to 160° C. at 30° C./min, then to 170° C. at 3° C./min and finally to 300° C. at 30° C./min with a 2 min hold. Injector and MS quadrupole detector temperatures were 250° C. and 150° C., respectively. 2 ul was injected in split less mode. The MS was operated in full scan mode.

Figure 26:
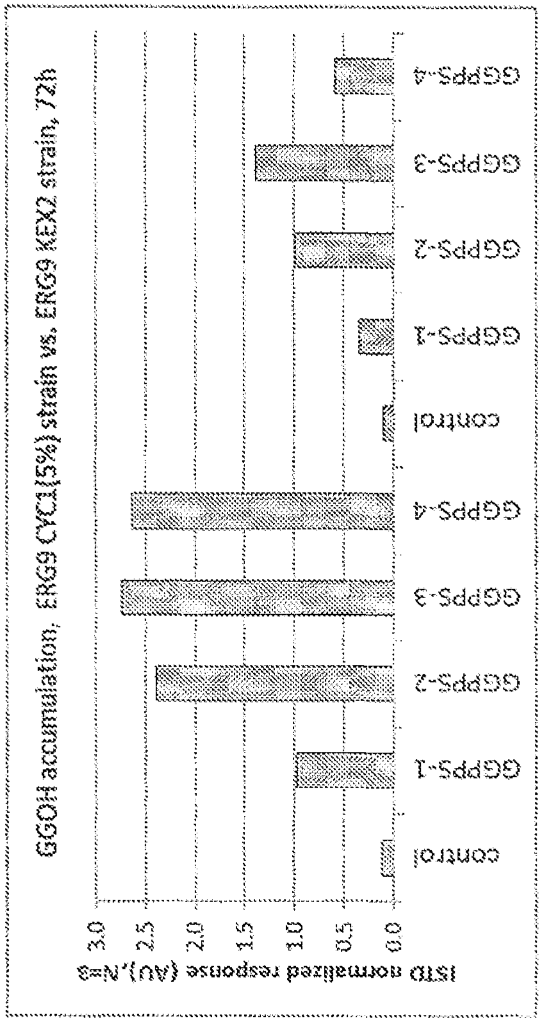
FIG. 26 is a bar graph of geranylgeraniol (GGOH) accumulation in the ERG9-CYC1-5% strain and ERG9-KEX2 strain after 72 hours.
Figure 27:
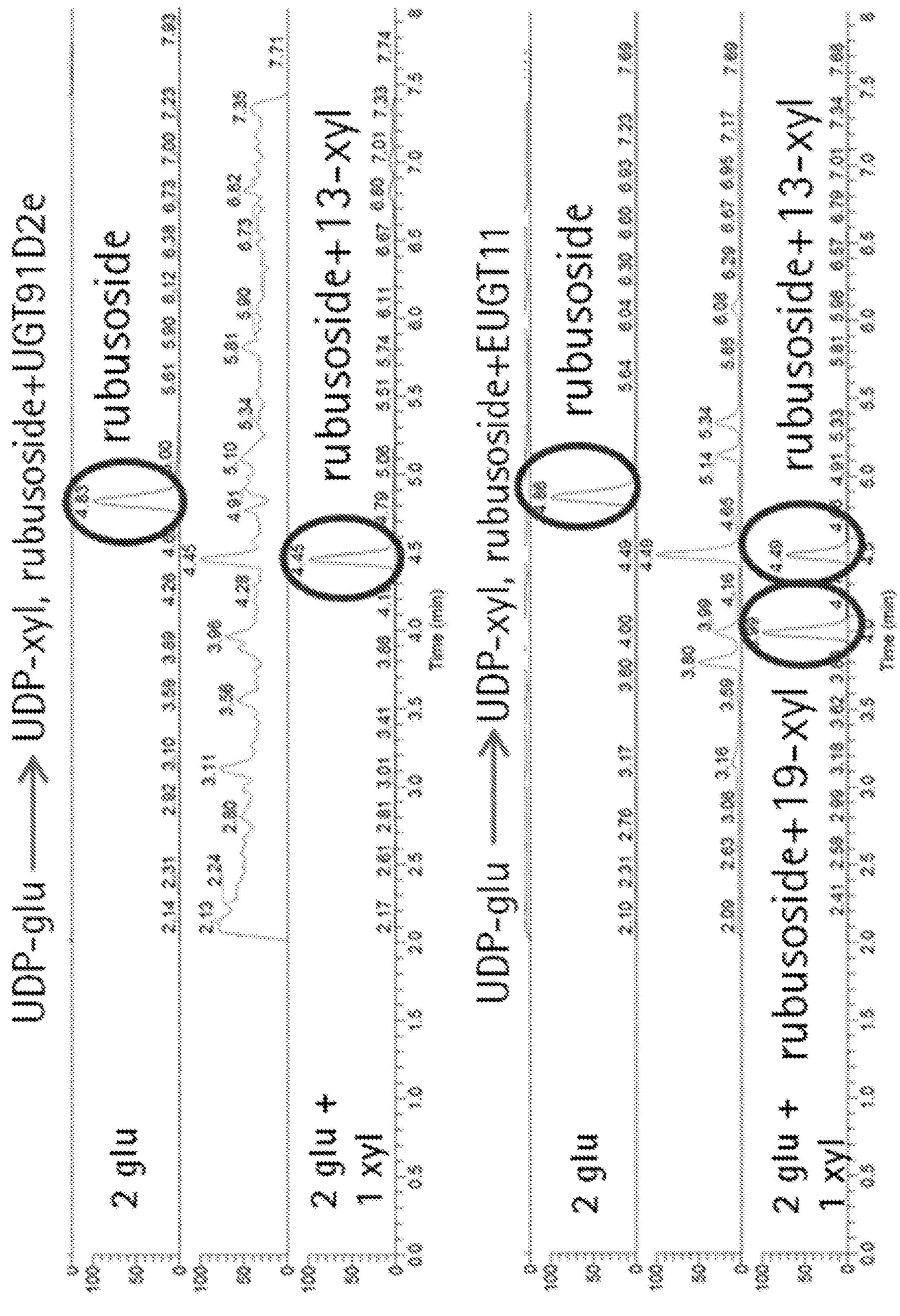
FIG. 27 is a representative chromatograph showing the conversion of rubusoside to xylosylated intermediates for RebF production by UGT91D2e and EUGT11.

When the GGPPS were overexpressed in the CYC1(5%)-ERG9 strain or KEX2-ERG9 strain, there was a significant increase in GGOH (GGPP) production observed with all four GGPPS polypeptides compared to the control where no GGPPS was expressed. Notably, the CYC1(5%)-ERG9 strain showed a 2-4 fold higher GGOH (GGPP) accumulation than the KEX2-ERG9 strain. The results are shown in FIG. 26.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for producing a target steviol glycoside or a target steviol glycoside composition, comprising contacting a starting composition comprising a precursor steviol glycoside having a 13-O-glucose, a 19-O-glucose, or both a 13-O-glucose and a 19-O-glucose, and/or a mixture thereof with a first recombinant uridine 5'-diphospho (UDP) glycosyl transferase polypeptide capable of beta 1,2 glycosylation of a C2' of the 13-O-glucose, the 19-O-glucose, or both the 13-O-glucose and the 19-O-glucose of the precursor steviol glycoside and having at least 80% identity to the amino acid sequence set forth in SEQ ID NO: 152 and one or more sugar moiety donor, under suitable reaction conditions to transfer one or more sugar moieties from the one or more sugar moiety donor to the precursor steviol glycoside, thereby producing the target steviol glycoside or the target steviol glycoside composition;
   wherein the precursor steviol glycoside is steviol-13-O-glucoside, rubusoside, stevioside or rebaudioside A;
   wherein the target steviol glycoside is or the target steviol glycoside composition comprises stevioside, rebaudioside E, rebaudioside D, steviol-1,2 bioside, steviol-1,2-xylobioside, steviol-1,2-rhamnobioside, or an isomer thereof;
   wherein the first recombinant 5'-UDP glycosyl transferase polypeptide is capable of converting Rebaudioside A (RebA) to Rebaudioside D (RebD) at a rate that is at least 20 times faster than the rate at which a UDP glycosyl transferase polypeptide having the amino acid sequence set forth in SEQ ID NO:5 is capable of converting RebA to RebD under corresponding reaction conditions; and/or
   wherein the first recombinant 5'-UDP glycosyl transferase polypeptide is capable of converting higher amounts of RebA to RebD compared to the UDP glycosyl transferase polypeptide having the amino acid sequence set forth in SEQ ID NO:5 under corresponding reaction conditions.

2. The method of claim 1, wherein:
   (a) the precursor steviol glycoside is rubusoside, wherein the additional sugar moiety is glucose, and stevioside is produced upon transfer of the additional glucose moiety;
   (b) the precursor steviol glycoside is stevioside, the additional sugar moiety is glucose, and rebaudioside E is produced upon transfer of the additional glucose moiety;
   (c) the precursor steviol glycoside is stevioside, the additional sugar moiety is glucose, the stevioside is contacted with the polypeptide capable of beta 1,2 glycosylation of the C2' of the 13-O-glucose, 19-O-glucose, or both 13-O-glucose and 19-O-glucose of a steviol glycoside and a polypeptide capable of beta 1,3 glycosylation of the C3' of the 13-O-glucose of a steviol glycoside, and rebaudioside D is produced upon transfer of the additional glucose moiety;
   (d) the precursor steviol glycoside is steviol-13-O-glucoside, the additional sugar moiety is glucose, and steviol-1,2 bioside is produced upon transfer of the additional glucose moiety;
   (e) the precursor steviol glycoside is steviol-13-O-glucoside, the additional sugar moiety is xylose, and steviol-1,2-xylobioside is produced upon transfer of the additional sugar moiety;
   (f) the precursor steviol glycoside is steviol-13-O-glucoside, the additional sugar moiety is rhamnose, and steviol-1,2-rhamnobioside is produced upon transfer of the additional sugar moiety;
   (g) the precursor steviol glycoside is rebaudioside A, the additional sugar moiety is glucose, and rebaudioside D is produced upon transfer of the additional glucose moiety; or
   (h) the precursor steviol glycoside is rubusoside, the additional sugar moiety is xylose, and 1,2-stevioxyloside is produced upon transfer of the sugar moiety.

3. The method of claim 1, wherein the starting composition is further contacted with:
   (a) a second 5'-UDP glycosyl transferase polypeptide capable of beta 1,2 glycosylation of the C2' of the 13-O-glucose, 19-O-glucose, or both 13-O-glucose and 19-O-glucose of the precursor steviol glycoside;
   (b) a 5'-UDP glycosyl transferase polypeptide capable of glycosylating steviol or the precursor steviol glycoside at its C-19 carboxyl group;
   (c) a 5'-UDP glycosyl transferase polypeptide capable of glycosylating steviol or the precursor steviol glycoside at its C-13 hydroxyl group; and/or
   (d) a 5'-UDP glycosyl transferase polypeptide capable of beta 1,3 glycosylation of the C3' of the 13-O-glucose, 19-O-glucose, or both 13-O-glucose and 19-O-glucose of the precursor steviol glycoside.

4. The method of claim 3, wherein at least one of the polypeptides is expressed in a recombinant host comprising one or more genes encoding the one or more polypeptides.

5. The method of claim 4, wherein the sugar moiety donor comprises ADP-sugar, CDP-sugar, GDP-sugar, and/or UDP-sugar.

6. The method of claim 3, wherein:
   (a) the second 5'-UDP glycosyl transferase polypeptide comprises a polypeptide having at least 80% sequence identity to the amino acid sequence set forth in SEQ ID NO:5 or the amino acid sequence set forth in SEQ ID NO:76 or 78;

(b) the 5'-UDP glycosyl transferase polypeptide capable of glycosylating the steviol or the precursor steviol glycoside at its C-19 carboxyl group comprises a polypeptide having at least 90% sequence identity to the amino acid sequence set forth in SEQ ID NO: 1;

(c) the 5'-UDP glycosyl transferase polypeptide capable of glycosylating the steviol or the precursor steviol glycoside at its C-13 hydroxyl group comprises a polypeptide having at least 90% sequence identity to the amino acid sequence set forth in SEQ ID NO:3; and/or (d) the 5'-UDP glycosyl transferase polypeptide capable of beta 1,3 glycosylation of the C3' of the 13-O-glucose, 19-O-glucose, or both 13-O-glucose and 19-O-glucose of the precursor steviol glycoside comprises a polypeptide having at least 90% sequence identity to the amino acid sequence set forth in SEQ ID NO:7.

7. The method of claim 1, wherein the first recombinant 5'-UDP glycosyl transferase polypeptide is expressed by a recombinant host comprising a recombinant gene encoding the first recombinant 5'-UDP glycosyl transferase polypeptide.

8. The method of claim 1, wherein the method is an in vitro method, further comprising supplying the sugar moiety donor or a cell-free system for regeneration of the sugar moiety donor.

9. The method of claim 8, wherein the target steviol glycoside is or the target steviol glycoside composition comprises RebD, the starting composition comprises RebA as the precursor steviol glycoside, wherein the starting composition is contacted with the first recombinant 5'-UDP glycosyl transferase polypeptide in stoichiometric or excess amount relative to RebD.

10. The method of claim 8, wherein the target steviol glycoside is or the target steviol glycoside composition comprises RebD, the starting composition comprises a *stevia* extract having at least one of RebA and stevioside as the precursor steviol glycoside, wherein the starting composition is contacted with the first recombinant 5'-UDP glycosyl transferase polypeptide, a 5'-UDP glycosyl transferase polypeptide capable of beta 1,3 glycosylation of the C3' of the 13-O-glucose, 19-O-glucose, or both 13-O-glucose and 19-O-glucose of the precursor steviol glycoside and UDP-glucose in stoichiometric or excess amount relative to the steviol glycoside.

11. The method of claim 8, wherein the target steviol glycoside is RebA, RebD, rebaudioside B (RebB), steviol-1,2-bioside, stevioside, rebaudioside E (RebE), dulcoside A, rebaudioside C (RebC), rebaudioside F (RebF), or a mixture of two or more of these compounds.

12. The method of claim 8, wherein the first recombinant 5'-UDP glycosyl transferase polypeptide is provided in soluble form or in immobilized form.

13. The method of claim 8, wherein the in vitro method is a whole cell in vitro method, wherein the whole cells are fed raw materials comprising the steviol and/or the precursor steviol glycoside.

14. The method of claim 13, wherein the whole cells are fed raw materials comprising the steviol and/or the precursor steviol glycoside is derived from plant extract.

15. The method of claim 13, wherein the whole cell used in the whole cell in vitro method is:

(a) in suspension or immobilized;

(b) entrapped in a calcium or sodium alginate bead;

(c) linked to a hollow fiber tube reactor system;

(d) concentrated and entrapped within a membrane reactor system; or (d)

(e) in fermentation broth or in a reaction buffer.

16. The method of claim 13, further comprising permeabilizing the whole cell by using a permeabilizing agent, wherein the permeabilizing agent is a solvent, a detergent, or a surfactant, by a mechanical shock, an electroporation, or an osmotic shock.

17. The method of claim 13, wherein the whole cell is microorganism being a prokaryote or a eukaryote.

18. The method of claim 13, wherein the whole cell is an *Escherichia coli* cell, a *Saccharomyces cerevisiae* cell, or a *Yarrowia lipolytica* cell.

19. The method of claim 13, wherein the starting composition further comprises steviol that is converted to RebA, RebD and/or RebE and the whole cell is a recombinant cell expressing:

(a) the first recombinant 5'-UDP glycosyl transferase polypeptide;

(b) a 5'-UDP glycosyl transferase polypeptide capable of glycosylating steviol or the precursor steviol glycoside at its C-19 carboxyl group;

(c) a 5'-UDP glycosyl transferase polypeptide capable of glycosylating steviol or the precursor steviol glycoside at its C-13 hydroxyl group; and (d) a 5'-UDP glycosyl transferase polypeptide capable of beta 1,3 glycosylation of the C3' of the 13-O-glucose, 19-O-glucose, or both 13-O-glucose and 19-O-glucose of the precursor steviol glycoside.

20. The method of claim 19, wherein the recombinant cell further expresses a second 5'-UDP glycosyl transferase polypeptide capable of beta 1,2 glycosylation of the C2' of the 13-O-glucose, 19-O-glucose, or both 13-O-glucose and 19-O-glucose of the precursor steviol glycoside.

21. The method of claim 13, wherein RebA as the precursor steviol glycoside is converted to RebD as the target steviol glycoside and the whole cell is the recombinant cell expressing the first recombinant 5'-UDP glycosyl transferase polypeptide.

22. The method of claim 13, wherein rubusoside or stevioside RebA as the precursor steviol glycoside is converted to RebD as the target steviol glycoside and the whole cell is a recombinant cell expressing:

(a) the first recombinant 5'-UDP glycosyl transferase polypeptide; and (b) a 5'-UDP glycosyl transferase polypeptide capable of beta 1,3 glycosylation of the C3' of the 13-O-glucose, 19-O-glucose, or both 13-O-glucose and 19-O-glucose of the precursor steviol glycoside.

23. The method of claim 22, wherein the recombinant cell further expresses a second 5'-UDP glycosyl transferase polypeptide capable of beta 1,2 glycosylation of the C2' of the 13-O-glucose, 19-O-glucose, or both 13-O-glucose and 19-O-glucose of the precursor steviol glycoside.

24. The method of claim 13, wherein steviol-13-O-glucoside (13-SMG) is converted to RebD and the whole cell is a recombinant cell expressing:

(a) the first recombinant 5'-UDP glycosyl transferase polypeptide;

(b) a 5'-UDP glycosyl transferase polypeptide capable of glycosylating steviol or the precursor steviol glycoside at its C-19 carboxyl group; and (c) a 5'-UDP glycosyl transferase polypeptide capable of beta 1,3 glycosylation of the C3' of the 13-O-glucose, 19-O-glucose, or both 13-O-glucose and 19-O-glucose of the precursor steviol glycoside.

25. The method of claim 24, wherein the recombinant cell further expresses a second 5'-UDP glycosyl transferase polypeptide capable of beta 1,2 glycosylation of the C2' of the 13-O-glucose, 19-O-glucose, or both 13-O-glucose and 19-O-glucose of the precursor steviol glycoside.

26. The method of claim 13, wherein steviol-19-O-glucoside (19-SMG) is converted to RebD and the whole cell is a recombinant cell expressing:

(a) the first recombinant 5'-UDP glycosyl transferase polypeptide;

(b) a 5'-UDP glycosyl transferase polypeptide capable of glycosylating steviol or the precursor steviol glycoside at its C-13 hydroxyl group; and (c) a 5'-UDP glycosyl transferase polypeptide capable of beta 1,3 glycosylation of the C3' of the 13-O-glucose, 19-O-glucose, or both 13-O-glucose and 19-O-glucose of the precursor steviol glycoside.

27. The method of claim 26, wherein the recombinant cell further expresses a second 5'-UDP glycosyl transferase polypeptide capable of beta 1,2 glycosylation of the C2' of the 13-O-glucose, 19-O-glucose, or both 13-O-glucose and 19-O-glucose of the precursor steviol glycoside.

28. A method of transferring an additional sugar moiety to a C2' of the 13-O-glucose, the 19-O-glucose, or both the 13-O-glucose and the 19-O-glucose of a precursor steviol glycoside having a 13-O-glucose, a 19-O-glucose, or both a 13-O-glucose and a 19-O-glucose, comprising contacting the precursor steviol glycoside with a first recombinant uridine 5'-diphospho (UDP) glycosyl transferase polypeptide capable of beta 1,2 glycosylation of a C2' of the 13-O-glucose, the 19-O-glucose, or both the 13-O-glucose and the 19-O-glucose of the precursor steviol glycoside and having at least 80% identity to the amino acid sequence set forth in SEQ ID NO:152 and one or more sugar moiety donor, under suitable reaction conditions to transfer of the additional sugar moiety to the precursor steviol glycoside;

wherein the precursor steviol glycoside is steviol-13-O-glucoside, rubusoside, stevioside or rebaudioside A; and wherein stevioside, rebaudioside E, rebaudioside D, steviol-1,2 bioside, steviol-1,2-xylobioside, steviol-1,2-rhamnobioside, an isomer thereof, and/or a steviol glycoside composition thereof is produced upon transfer of the additional sugar moiety.

29. The method of claim 28, wherein:

(a) the precursor steviol glycoside is rubusoside, the second additional sugar moiety is glucose, and stevioside is produced upon transfer of the additional second glucose moiety;

(b) the precursor steviol glycoside is stevioside, the second additional sugar moiety is glucose, and RebE is produced upon transfer of the additional second glucose moiety; and/or (c) the steviol glycoside is RebA, the additional second sugar moiety is glucose and RebD is produced upon transfer of the additional second glucose moiety.

30. The method of claim 28, wherein the starting composition comprising the precursor steviol glycoside is further contacted with:

(a) a second 5'-UDP glycosyltransferase polypeptide having at least 80% sequence identity to the amino acid sequence set forth in SEQ ID NO:5 or the amino acid sequence set forth in SEQ ID NO:76 or 78;

(b) a 5'-UDP glycosyltransferase polypeptide capable of glycosylating the steviol or the precursor steviol glycoside at its C-19 carboxyl group has the amino acid sequence having at least 90% sequence identity to the amino acid sequence set forth in SEQ ID NO:1;

(c) a 5'-UDP glycosyltransferase polypeptide capable of glycosylating the steviol or the precursor steviol glycoside at its C-13 hydroxyl group has the amino acid sequence having at least 90% sequence identity to the amino acid sequence set forth in SEQ ID NO:3; and/or (d) a 5'-UDP glycosyltransferase polypeptide capable of beta 1,3 glycosylation of the C3' of the 13-O-glucose, 19-O-glucose, or both 13-O-glucose and 19-O-glucose of the precursor steviol glycoside has the amino acid sequence having at least 90% sequence identity to the amino acid sequence set forth in SEQ ID NO: 7.

* * * * *